United States Patent
Duan et al.

(10) Patent No.: US 10,711,020 B2
(45) Date of Patent: Jul. 14, 2020

(54) TRICYCLIC SULFONES AS RORγ MODULATORS

(71) Applicant: BRISTOL-MYERS SQUIBB COMPANY, Princeton, NJ (US)

(72) Inventors: Jingwu Duan, Yardley, PA (US); T. G. Murali Dhar, Newtown, PA (US); David Marcoux, Pennington, NJ (US); Robert J. Cherney, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/295,378

(22) Filed: Mar. 7, 2019

(65) Prior Publication Data

US 2019/0241588 A1 Aug. 8, 2019

Related U.S. Application Data

(63) Continuation of application No. 15/701,818, filed on Sep. 12, 2017, now Pat. No. 10,273,259, which is a
(Continued)

(51) Int. Cl.
*C07F 9/6574* (2006.01)
*C07D 215/36* (2006.01)
(Continued)

(52) U.S. Cl.
CPC ........ *C07F 9/65742* (2013.01); *C07D 209/30* (2013.01); *C07D 209/60* (2013.01); *C07D 209/70* (2013.01); *C07D 215/36* (2013.01); *C07D 221/10* (2013.01); *C07D 401/06* (2013.01); *C07D 401/12* (2013.01); *C07D 403/06* (2013.01); *C07D 403/12* (2013.01); *C07D 405/06* (2013.01); *C07D 409/04* (2013.01); *C07D 409/06* (2013.01); *C07D 413/06* (2013.01); *C07D 413/10* (2013.01); *C07D 413/12* (2013.01); *C07D 417/04* (2013.01); *C07D 417/06* (2013.01); *C07D 417/12* (2013.01); *C07D 417/14* (2013.01);
(Continued)

(58) Field of Classification Search
CPC ....... A61K 35/17; A61K 35/74; A61K 9/0053
See application file for complete search history.

(56) References Cited

U.S. PATENT DOCUMENTS 9,815,859 B2 * 11/2017 Duan .................... C07D 403/12
10,273,259 B2 * 4/2019 Duan .................... C07D 413/06
(Continued)

FOREIGN PATENT DOCUMENTS

WO WO2007/084595 7/2007
WO WO2014/062938 4/2014
(Continued)

OTHER PUBLICATIONS

Hawkes, Jason E., et al., "Psoriasis pathogenesis and the development of novel targeted immune therapies", Mechanisms of allergic diseases, J Allergy Clin Immunol, Sep. 2017, vol. 140, No. 3, pp. 645-653.
(Continued)

*Primary Examiner* — Pancham Bakshi
(74) *Attorney, Agent, or Firm* — Elliott Korsen

(57) ABSTRACT

There are described RORγ modulators of the formula (I),

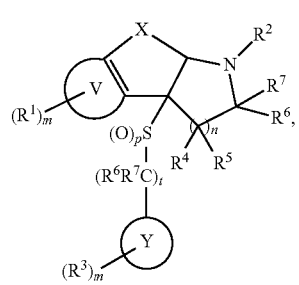

and formula (II)

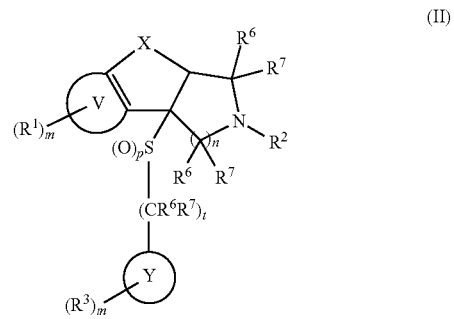

or stereoisomers, tautomers, pharmaceutically acceptable salts, solvates, or prodrugs thereof, wherein all substituents are defined herein. Also provided are pharmaceutical compositions comprising the same. Such compounds and compositions are useful in methods for modulating RORγ activity in a cell and methods for treating a subject suffering from a disease or disorder in which the subject would therapeutically benefit from modulation of RORγ activity, for example, autoimmune and/or inflammatory disorders.

1 Claim, No Drawings

Related U.S. Application Data continuation of application No. 15/148,209, filed on May 6, 2016, now Pat. No. 9,815,859.

(60) Provisional application No. 62/158,178, filed on May 7, 2015.

(51) Int. Cl.

| | | |
|---|---|---|
| *C07D 409/04* | (2006.01) | |
| *C07D 417/04* | (2006.01) | |
| *C07D 209/30* | (2006.01) | |
| *C07D 209/60* | (2006.01) | |
| *C07D 209/70* | (2006.01) | |
| *C07D 221/10* | (2006.01) | |
| *C07D 401/06* | (2006.01) | |
| *C07D 401/12* | (2006.01) | |
| *C07D 403/06* | (2006.01) | |
| *C07D 403/12* | (2006.01) | |
| *C07D 405/06* | (2006.01) | |
| *C07D 409/06* | (2006.01) | |
| *C07D 413/06* | (2006.01) | |
| *C07D 413/10* | (2006.01) | |
| *C07D 413/12* | (2006.01) | |
| *C07D 417/06* | (2006.01) | |
| *C07D 417/12* | (2006.01) | |
| *C07D 417/14* | (2006.01) | |
| *C07D 471/04* | (2006.01) | |
| *C07D 491/052* | (2006.01) | |
| *C07D 491/107* | (2006.01) | |
| *C07D 493/08* | (2006.01) | |
| *C07D 495/04* | (2006.01) | |
| *C07D 495/08* | (2006.01) | |

(52) U.S. Cl.
CPC ....... *C07D 471/04* (2013.01); *C07D 491/052* (2013.01); *C07D 491/107* (2013.01); *C07D 493/08* (2013.01); *C07D 495/04* (2013.01); *C07D 495/08* (2013.01)

(56) References Cited

U.S. PATENT DOCUMENTS

2007/0197581 A1* 8/2007 Asberom ............... C07C 317/14
514/291
2015/0191483 A1 7/2015 Duan et al.

FOREIGN PATENT DOCUMENTS

| WO | WO2015/035278 | 3/2015 |
|---|---|---|
| WO | WO2015/042212 | 3/2015 |
| WO | WO2015/103507 | 7/2015 |
| WO | WO2015/103508 | 7/2015 |
| WO | WO2015/103509 | 7/2015 |
| WO | WO2015/103510 | 7/2015 |

OTHER PUBLICATIONS

Takaishi, Mikiro, et al., "Oral administration of a novel RORγt antagonist attenuates psoriasis-like skin lesion of two independent mouse models through neutralization of IL-17", Journal of Dermatological Science, 2017, vol. 85, pp. 12-19.

Xue, Xiaohua, et al., "Pharmacologic modulation of RORγt translates to efficacy in preclinical and translational models of psoriasis and inflammatory arthritis", Scientific Reports, 2016, 6:37977, pp. 1-17.

Ruo, et al., "SAR of tricyclic sulfones as γ-secretase inhibitors", Science China Chemistry, Nov. 2011, vol. 54, No. 11, pp. 1688-1701.

Article in Press, "RoRyt inhibitors suppress TH17 responses in inflammatory arthritis and inflammatory bowel disease", Letter to the Editor, J. Allergy Clin. Immunol, 2015, pp. 1-4.

Bassolas-Molina, Helena, et al., "An RORγt Oral Inhibitor Modulates IL-17 Responses in Peripheral Blood and Intestinal Mucosa of Crohn's Disease Patients", Frontiers in Immunology, 2018, vol. 9, Art. 2307, pp. 1-12.

Withers, David R., et al., "Transient inhibition of ROR-γt therapeutically limits intestinal inflammation by reducing TH17 cells and preserving group 3 innate lymphoid cells", Nature Medicine, 2016, pp. 1-7.

* cited by examiner

TRICYCLIC SULFONES AS RORγ MODULATORS

CROSS-REFERENCE TO RELATED APPLICATIONS

This application is a continuation of U.S. patent application Ser. No. 15/701,818 filed on Sep. 12, 2017, which is a continuation of U.S. patent application Ser. No. 15/148,209 filed on May 6, 2016, now U.S. Pat. No. 9,851,859, which claims priority from U.S. Provisional Application No. 62/158,178 filed May 7, 2015, the disclosures of which are incorporated herein by reference in their entirety.

FIELD OF THE INVENTION

This invention relates to modulators of the retinoid-related orphan receptor RORγ and methods for using said modulators. The compounds described herein can be particularly useful for diagnosing, preventing, or treating a variety of diseases and disorders in humans and animals. Exemplary disorders include, but are not limited to, psoriasis, rheumatoid arthritis, inflammatory bowel disease, Crohn's disease, ulcerative colitis, acute graft-versus-host disease, psoriatic arthritis, ankylosing spondylitis and multiple sclerosis.

BACKGROUND OF THE INVENTION

The retinoid-related orphan receptors, RORα, RORβ, and RORγ, play an important role in numerous biological processes including organ development, immunity, metabolism, and circadian rhythms. See, for example, Dussault et al. in Mech. Dev. (1998) vol. 70, 147-153; Andre et al. in EMBO J. (1998) vol. 17, 3867-3877; Sun et al. in Science (2000) vol. 288, 2369-2373; and Jetten in Nucl. Recept. Signal. (2009) vol. 7, 1-32.

RORγ is expressed in several tissues including the thymus, kidney, liver, and muscle. Two isoforms of RORγ have been identified: RORγ1 and RORγ2 (also known, respectively, as RORγ and RORγt). See, for example, Hirose et al. in Biochem. Biophys. Res. Commun. (1994) vol. 205, 1976-1983; Oritz et al. in Mol. Endocrinol. (1995) vol. 9, 1679-1691; and He et al. in Immunity (1998) vol. 9, 797-806. Expression of RORγt is restricted to lymphoid cell types including CD4+CD8+ thymocytes, IL-17 producing T helper (Th17) cells, lymphoid tissue inducer (LTi) cells, and γδ cells. RORγt is essential for the development of lymph nodes and Peyer's patches and for the normal differentiation of Th17, γδ, and LTi cells. See, for example, Sun et al. in Science (2000) vol. 288, 2369-2373; Ivanov et al. in Cell (2006) vol. 126, 1121-1133; Eberl et al. in Nat. Immunol. (2004) vol. 5, 64-73; Ivanov et al. in Semin. Immunol. (2007) vol. 19, 409-417; and Cua and Tato in Nat. Rev. Immunol. (2010) vol. 10, 479-489.

Proinflammatory cytokines such as IL-17A (also referred to as IL-17), IL-17F, and IL-22 produced by Th17 cells and other RORγ+ lymphocytes activate and direct the immune response to extracellular pathogens. See, for example, Ivanov et al. in Semin. Immunol. (2007) vol. 19: 409-417; and Marks and Craft in Semin. Immunol. (2009) vol. 21, 164-171. RORγ directly regulates IL-17 transcription and disruption of RORγ in mice attenuates IL-17 production. See, for example, Ivanov et al. in Cell (2006) vol. 126, 1121-1133.

Dysregulated production of IL-17 has been implicated in several human autoimmune and inflammatory diseases including multiple sclerosis, rheumatoid arthritis, psoriasis, inflammatory bowel disease (IBD), and asthma. See, for example, Lock et al. in Nat. Med. (2002) vol. 8, 500-508; Tzartos et al. in Am. J. Pathol. (2008) vol. 172, 146-155; Kotake et al. in J. Clin. Invest. (1999) vol. 103, 1345-1352; Kirkham et al. in Arthritis Rheum. (2006) vol. 54, 1122-1131; Lowes et al. in J. Invest. Dermatol. (2008) vol. 128, 1207-1211; Leonardi et al. in N. Engl. J. Med. (2012) vol. 366, 1190-1199; Fujino et al. in Gut (2003) vol. 52, 65-70; Seiderer et al. in Inflamm. Bowel Dis. (2008) vol. 14, 437-445; Wong et al. in Clin. Exp. Immunol. (2001) vol. 125, 177-183; and Agache et al. in Respir. Med. (2010) 104: 1131-1137. In murine models of these diseases, inhibition of IL-17 function by neutralizing antibodies or genetic disruption of IL-17 or IL-17 receptor ameliorates the disease course or clinical symptoms. See, for example, Hu et al. in Ann. N.Y. Acad. Sci. (2011) vol. 1217, 60-76.

Disruption of RORγ in mice also attenuates disease progression or severity in animal models of autoimmunity and inflammation including experimental autoimmune encephalomyelitis (EAE), imiquimod induced psoriasis, colitis, and allergic airway disease. See, for example, Ivanov et al. in Cell (2006) vol. 126, 1121-1133; Yang et al. in Immunity (2008) vol. 28, 29-39; Pantelyushin et al. in J. Clin. Invest. (2012) vol. 122, 2252-2256; Leppkes et al. in Gastroenterology (2009) vol. 136, 257-267; and Tilley et al. in J. Immunol. (2007) vol. 178, 3208-3218.

Each of the references in this Background section is hereby incorporated herein by reference in its entirety for all purposes.

Therapeutic agents exist to treat a variety of inflammatory and autoimmune diseases, but there still remains a significant unmet medical need in these therapeutic areas. Given the role of IL-17 in human disease and the validation of IL-17 and RORγ as targets in murine disease models, compounds capable of modulating RORγt activity are contemplated to provide a therapeutic benefit in the treatment of multiple immune and inflammatory disorders.

SUMMARY OF THE INVENTION

In one aspect, the invention comprises compounds of the formula (I),

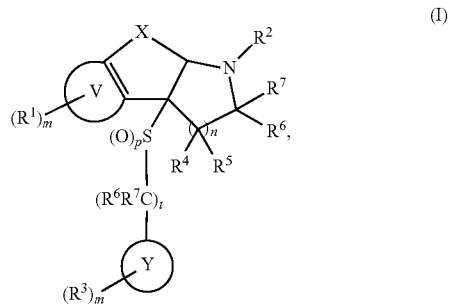

or pharmaceutically acceptable salts thereof, wherein all substituents are defined herein. The invention includes stereoisomers, tautomers, solvates, or prodrugs thereof.

In another aspect, the invention comprises compounds of the formula (II),

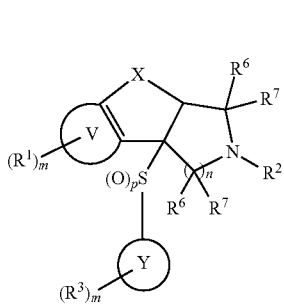

(II)

or pharmaceutically acceptable salts thereof, wherein all substituents are defined herein. The invention includes stereoisomers, tautomers, solvates, or prodrugs thereof.

In another aspect, the invention comprises pharmaceutical compositions comprising a compound according to formula (I), stereoisomeric form or pharmaceutically acceptable salt, as described herein, and a pharmaceutically acceptable carrier, excipient, or diluent.

In another aspect, the invention comprises methods for modulating RORγ in a cell comprising contacting the cell with an effective amount of a compound according to formula (I), stereoisomeric form or pharmaceutically acceptable salt, as described herein. This aspect may be conducted in vitro or in vivo.

In another aspect, the invention comprises methods for treating a subject suffering from a disease or disorder modulated by RORγ, the method comprising administering to a subject a therapeutically effective amount of a compound according to formula (I), stereoisomeric form, pharmaceutically acceptable salt or pharmaceutical composition as described herein.

In another aspect, the invention comprises a method for treating a disease or disorder selected from an inflammatory disease or disorder, an autoimmune disease or disorder, an allergic disease or disorder, a metabolic disease or disorder, and/or cancer in a subject, the method comprising administering to the subject a therapeutically effective amount of a compound according to formula (I), or a stereoisomeric form, pharmaceutically acceptable salt or pharmaceutical composition as described herein.

DETAILED DESCRIPTION OF THE INVENTION

In one aspect, the invention comprises compounds of formula (I),

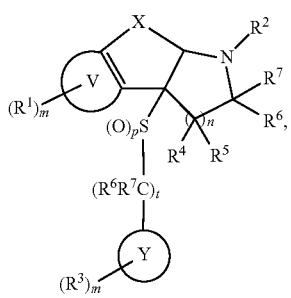

(I)

or a stereoisomer or pharmaceutically acceptable salt thereof, wherein

X is $-CR^4R^5-$, $-(CR^4R^5)_2-$, $-OCR^6R^7-$, $-S(O)_pCR^6R^7-$ or $-NR^6CR^6R^7-$; wherein when X is $-OCR^6R^7-$, $-S(O)_pCR^6R^7-$ or $-NR^6CR^6R^7-$; the structure contemplated, for e.g. when X is $-OCR^6R^7-$, would be

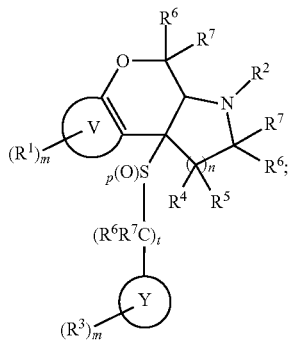

V and Y are independently 5 or 6-membered aromatic or heteroaromatic rings;

$R^1$ is, independently at each occurrence, selected from hydrogen, $CD_3$, halo, $OCF_3$, CN, $-O(C_1-C_6)$alkyl, $-O(C_1-C_6)$alkyl-OH, -alkoxyalkoxy (e.g. $-O-CH_2CH_2OCH_3$), $S(O)_p(C_1-C_6)$alkyl, $-S(O)_p(C_1-C_6)$alkyl-OH, -thioalkoxyalkoxy (e.g. $-SCH_2CH_2OCH_3$), $NR^{11}R^{11}$, $C_{1-6}$ alkyl substituted with 0-3 $R^{1a}$, $-(CR^{2e}R^{2f})_r$-3-14 membered carbocycle substituted with 0-3 $R^{1a}$ and $-(CR^{2e}R^{2f})_r$-5-10 membered heterocycle comprising carbon atoms, and 1-4 heteroatoms selected from N, O, and $S(O)_p$ substituted with 0-3 $R^{1a}$;

$R^{1a}$ is, independently at each occurrence, hydrogen, =O, halo, $CF_3$, $OCF_3$, CN, $NO_2$, $-(CR^{2e}R^{2f})_r-OR^b$, $-(CR^{2e}R^{2f})_r-S(O)_pR^b$, $-(CR^{2e}R^{2f})_r-C(O)R^b$, $-(CR^{2e}R^{2f})_r-C(O)OR^b$, $-(CR^{2e}R^{2f})_r-OC(O)R^b$, $-(CR^{2e}R^{2f})_r-NR^{11}R^{11}$, $-(CR^{2e}R^{2f})_r-C(O)NR^{11}R^{11}$, $-(CR^{2e}R^{2f})_r-NR^bC(O)R^c$, $-(CR^{2e}R^{2f})_r-NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, $-(CR^{2e}R^{2f})_r$-3-14 membered carbocycle substituted with 0-3 $R^a$, or $-(CR^{2e}R^{2f})_r$-5-7 membered heterocycle comprising carbon atoms, and 1-4 heteroatoms selected from N, O, and $S(O)_p$ substituted with 0-3 $R^a$;

$R^2$ is selected from hydrogen, CN, $-(CR^{2e}R^{2f})_r-C(O)R^{2d}$, $-(CR^{2e}R^{2f})_r-C(O)OR^{2b}$, $-(CR^{2e}R^{2f})_r-C(O)NR^{11}R^{11}$, $-(CR^{2e}R^{2f})_r-S(O)_2R^{2c}$, $C_{1-6}$ alkyl substituted with 0-3 $R^{2a}$, $C_{2-6}$ alkenyl substituted with 0-3 $R^{2a}$, $-(CR^{2e}R^{2f})_r$-3-10 membered carbocycle substituted with 0-4 $R^a$, and $-(CR^{2e}R^{2f})_r$-4-7 membered heterocycle comprising carbon atoms, and 1-4 heteroatoms selected from N, O, P(=O) and $S(O)_p$ substituted with 0-4 $R^a$;

$R^{2a}$ is, independently at each occurrence, hydrogen, =O, halo, $OCF_3$, CN, $NO_2$, $-(CR^{2e}R^{2f})r-OR^b$, $-(CR^{2e}R^{2f})r-S(O)_pR^b$, $-(CR^{2e}R^{2f})r-C(O)R^b$, $-(CR^{2e}R^{2f})r-C(O)OR^b$, $-(CR^{2e}R^{2f})r-OC(O)R^b$, $-(CR^{2e}R^{2f})r-OC(O)NR^{11}R^{11}$, $-(CR^{2e}R^{2f})r-OC(O)OR^c$, $-(CR^{2e}R^{2f})r-NR^{11}R^{11}$, $-(CR^{2e}R^{2f})r-C(O)NR^{11}R^{11}$, $-(CR^{2e}R^{2f})r-NR^bC(O)R^c$, $-(CR^{2e}R^{2f})r-NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^d$, $C_{1-6}$ haloalkyl, $C_{2-6}$ alkenyl substituted with 0-3 $R^a$, $C_{2-6}$ alkynyl substituted with 0-3 $R^a$, $-(CR^{2e}R^{2f})r$-3-14 membered carbocycle substituted with 0-3 $R^a$, or $-(CR^{2e}R^{2f})r$-

4-7 membered heterocycle comprising carbon atoms, and 1-4 heteroatoms selected from N, O, P(=O) and S(O)$_p$ substituted with 0-4 R$^a$;

R$^{2b}$ is, independently at each occurrence, hydrogen, CF$_3$, —(CR$^{2e}$R$^{2f}$)$_q$OR$^b$, —(CR$^{2e}$R$^{2f}$)$_q$S(O)$_p$R$^b$, —(CR$^{2e}$R$^{2f}$)r-C(O)R$^{1d}$, —(CR$^{2e}$R$^{2f}$)r-C(O)OR$^b$, —(CR$^{2e}$R$^{2f}$)$_q$OC(O)R$^b$, —(CR$^{2e}$R$^{2f}$)$_q$NR$^{11}$R$^{11}$, —(CR$^{2e}$R$^{2f}$)r-C(O)NR$^{11}$R$^{11}$, —(CR$^{2e}$R$^{2f}$)$_q$NR$^b$C(O)R$^c$, —(CR$^{2e}$R$^{2f}$)$_q$NR$^b$C(O)OR$^c$, —(CR$^{2e}$R$^{2f}$)$_q$NR$^b$C(O)NR$^{11}$R$^{11}$, —(CR$^{2e}$R$^{2f}$)$_q$S(O)$_2$NR$^{11}$R$^{11}$, —(CR$^{2e}$R$^{2f}$)$_q$NR$^b$S(O)$_2$R$^c$, C$_{1-6}$ alkyl substituted with 0-2 R$^a$, C$_{1-6}$ haloalkyl, —(CR$^{2e}$R$^{2f}$)r-3-14 membered carbocycle substituted with 0-3 R$^a$, or —(CR$^{2e}$R$^{2f}$)r-5-7 membered heterocycle comprising carbon atoms and 1-4 heteroatoms selected from N, O, P(=O) and S(O), substituted with 0-4 R$^a$;

R$^{2c}$ is, independently at each occurrence, hydrogen, C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or —(CR$^{2e}$R$^{2f}$)r-5-10 membered heterocycle containing 1-4 heteroatoms selected from N, O, P(=O) and S(O)$_p$, substituted with 0-4 R$^a$;

R$^{2d}$ is, independently at each occurrence, hydrogen, C$_{1-6}$ alkyl substituted with 0-2 R$^d$, C$_{1-6}$ haloalkyl, C(O)NR$^{11}$R$^{11}$, —(CR$^{2e}$R$^{2f}$)r-C$_{3-10}$ cycloalkyl substituted with 0-3 R$^d$, where the cycloalkyl ring may be fused, bridged or spirocyclic, —(CR$^{2e}$R$^{2f}$)r-phenyl substituted with 0-2 R$^a$, or a —(CR$^{2e}$R$^{2f}$)r-4-10 membered heterocycle where the heterocycle may be fused, bridged or spirocyclic, containing 1-4 heteroatoms selected from N, O, P(=O) and S(O)$_p$, substituted with 0-4 R$^a$;

R$^{2e}$ and R$^{2f}$ are, independently at each occurrence, hydrogen, halogen or C$_{1-6}$ alkyl;

R$^3$ is, independently at each occurrence, selected from hydrogen, halo, N$_3$, CN, —(CR$^{2e}$R$^{2f}$)r-OR$^{3b}$, —(CR$^{2e}$R$^{2f}$)r-NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, and S(O)$_p$, substituted with 0-3 R$^{3a}$, or two R$^3$ located on adjacent carbon atoms link to form a 5-7 membered carbocycle or a 5-7 membered heterocycle comprising carbon atoms and 1-4 heteroatom selected from N, O and S(O)$_p$, both optionally substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CR$^{2e}$R$^{2f}$)r-OR$^b$, —(CR$^{2e}$R$^{2f}$)r-S(O)$_p$R$^b$, —(CR$^{2e}$R$^{2f}$)r-C(O)R$^b$, —(CR$^{2e}$R$^{2f}$)r-C(O)OR$^b$, —(CR$^{2e}$R$^{2f}$)r-OC(O)R$^b$, —(CR$^{2e}$R$^{2f}$)r-NR$^{11}$R$^{11}$, —(CR$^{2e}$R$^{2f}$)r-C(O)NR$^{11}$R$^{11}$, —(CR$^{2e}$R$^{2f}$)r-NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{2e}$R$^{2f}$)r-3-14 membered carbocycle substituted with 0-3 R$^a$, or —(CR$^{2e}$R$^{2f}$)r-5-10 membered heterocycle comprising carbon atoms and 1-4 heteroatoms selected from N, O, and S(O)$_p$ substituted with 0-3 R$^a$;

R$^{3b}$ is, independently at each occurrence, hydrogen, CF$_3$, —(CR$^{2e}$R$^{2f}$)$_q$OR$^b$, (CR$^{2e}$R$^{2f}$)$_q$S(O)$_p$R$^b$, —(CR$^{2e}$R$^{2f}$)r-C(O)R$^d$, —(CR$^{2e}$R$^{2f}$)r-C(O)OR$^b$, —(CR$^{2e}$R$^{2f}$)$_q$OC(O)R$^b$, —(CR$^{2e}$R$^{2f}$)$_q$NR$^{11}$R$^{11}$, —(CR$^{2e}$R$^{2f}$)r-C(O)NR$^{11}$R$^{11}$, (CR$^{2e}$R$^{2f}$)$_q$NR$^b$C(O)R$^{1c}$, —(CR$^{2e}$R$^{2f}$)$_q$NR$^b$C(O)OR$^c$, —(CR$^{2e}$R$^{2f}$)$_q$NR$^b$C(O)NR$^{11}$R$^{11}$, —(CR$^{2e}$R$^{2f}$)$_q$S(O)$_2$NR$^{11}$R$^{11}$, —(CR$^{2e}$R$^{2f}$)$_q$NR$^b$S(O)$_2$R$^c$, C$_{1-6}$ alkyl substituted with 0-3 R$^a$, C$_{1-6}$ haloalkyl, —(CR$^{2e}$R$^{2f}$)r-3-14 membered carbocycle substituted with 0-3 R$^a$, or —(CR$^{2e}$R$^{2f}$)r-5-7 membered heterocycle comprising carbon atoms and 1-4 heteroatoms selected from N, O, and S(O)$_p$ substituted with 0-3 R$^a$;

R$^4$ and R$^5$ are independently hydrogen, halo, C$_{1-6}$ alkyl or C$_{1-6}$ haloalkyl, or R$^4$ and R$^5$ together with the carbon atom to which they are attached form a 3- to 6-membered spirocarbocyclyl ring or a spiroheterocyclyl ring;

R$^6$ and R$^7$ are independently hydrogen, C(=O)C$_{1-4}$ alkyl, C(=O)OC$_{1-4}$ alkyl, C$_{1-6}$ alkyl or C$_{1-6}$ haloalkyl; or R$^6$ and R$^7$ taken together are =O;

R$^{11}$ is, independently at each occurrence, hydrogen, C$_{1-6}$ alkyl substituted with 0-3 R$^f$, CF$_3$, C$_{3-10}$ cycloalkyl substituted with 0-3 R$^f$, —(CR$^{2e}$R$^{2f}$)r-phenyl substituted with 0-3 R$^d$, or —(CR$^{2e}$R$^{2f}$)r-5-7 membered heterocycle comprising carbon atoms and 1-4 heteroatoms selected from N, O, P(=O) and S(O)$_p$ substituted with 0-4 R$^d$;

or one R$^{11}$ and a second R$^{11}$, both attached to the same nitrogen atom, combine to form a heterocycle comprising carbon atoms and 1-4 heteroatoms selected from N, O, P(=O) and S(O)$_p$ substituted with 0-4 R$^d$;

R$^a$ is, independently at each occurrence, hydrogen, =O, halo, OCF$_3$, CF$_3$, CHF$_2$, CN, NO$_2$, —(CR$^{2e}$R$^{2f}$)r-OR$^b$, —(CR$^{2e}$R$^{2f}$)r-S(O)$_p$R$^b$, —(CR$^{2e}$R$^{2f}$)r-C(O)R$^b$, —(CR$^{2e}$R$^{2f}$)r-C(O)OR$^b$, —(CR$^{2e}$R$^{2f}$)r-OC(O)R$^b$, —(CR$^{2e}$R$^{2f}$)r-NR$^{11}$R$^{11}$, —(CR$^{2e}$R$^{2f}$)r-C(O)NR$^{11}$R$^{11}$, —(CR$^{2e}$R$^{2f}$)r-NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{2e}$R$^{2f}$)r-3-14 membered carbocycle, or —(CR$^{2e}$R$^{2f}$)r-5-7 membered heterocycle comprising carbon atoms and 1-4 heteroatoms selected from N, O, P(=O) and S(O)$_p$ substituted with 0-4 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{2e}$R$^{2f}$)r-5-7 membered heterocycle comprising carbon atoms and 1-4 heteroatoms selected from N, O, P(=O) and S(O)$_p$ substituted with 0-4 R$^f$, or —(CR$^{2e}$R$^{2f}$)r-6-10 membered carbocycle substituted with 0-3 R$^d$;

R$^c$ is, independently at each occurrence, C$_{1-6}$ alkyl substituted with 0-3 R$^f$, —(CR$^{2e}$R$^{2f}$)r-C$_{3-6}$ cycloalkyl substituted with 0-3 R$^f$, or —(CR$^{2e}$R$^{2f}$)r-phenyl substituted with 0-3 R$^f$;

R$^d$ is, independently at each occurrence, hydrogen, =O, halo, OCF$_3$, CF$_3$, CN, NO$_2$, —OR$^e$, —(CR$^{2e}$R$^{2f}$)r-C(O)R$^e$, —NR$^e$R$^e$, —NR$^e$C(O)OR$^e$, C(O)NR$^e$R$^e$, —NR$^e$C(O)R$^e$, CO$_2$H, CO$_2$R$^e$, —NR$^e$SO$_2$R$^e$, SO$_2$R$^e$, C$_{1-6}$ alkyl substituted with 0-3 R$^f$, C$_{3-6}$ cycloalkyl substituted with 0-3 R$^f$, —(CR$^{2e}$R$^{2f}$)r-phenyl substituted with 0-3 R$^f$ or —(CR$^{2e}$R$^{2f}$)r-5-7 membered heterocycle comprising carbon atoms and 1-4 heteroatoms selected from N, O, P(=O) and S(O)$_p$ substituted with 0-4 R$^f$;

R$^e$ is, independently at each occurrence, selected from hydrogen, C(O)NR$^f$R$^f$, C$_{1-6}$ alkyl, C$_{3-6}$ cycloalkyl, -5-7 membered heterocycle or —(CR$^{2e}$R$^{2f}$)r-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$(C$_{1-6}$ alkyl), CO$_2$H, CO$_2$(C$_{1-6}$ alkyl), OH, C$_{3-6}$ cycloalkyl, CF$_3$, O(C$_{1-6}$ alkyl), or an optionally substituted —(CR$^{2e}$R$^{2f}$)r-5-10 membered heterocycle comprising carbon atoms and 1-4 heteroatoms selected from N, O, P(=O) and S(O)$_p$, phenyl or C$_{3-6}$ cycloalkyl, each group optionally substituted with halo, CN, CF$_3$, C$_{1-6}$ alkyl or O(C$_{1-6}$ alkyl);

m is 0, 1, 2 or 3 n is 0, 1 or 2;

p and q are, independently at each occurrence, 0, 1, or 2;

r is 0, 1, 2, 3, or 4; and t is 0 or 1.

In a second aspect, the invention comprises compounds of formula Ia

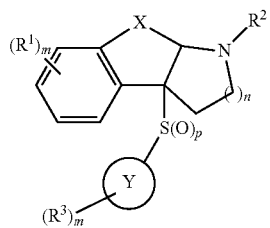

(Ia)

wherein

X is $-CR^4R^5-$, $-(CR^4R^5)_2-$, $-OCR^6R^7-$, $-S(O)_pCR^6R^7-$ or $-NR^6CR^6R^7-$;

Y is a 5 or 6-membered aromatic or heteroaromatic ring;

$R^1$ is, independently at each occurrence, selected from hydrogen, $CD_3$, halo, $C_{1-6}$ alkyl substituted with 0-3 $R^{1a}$, $-(CR^{2e}R^{2f})_r$-3-14 membered carbocycle substituted with 0-3 $R^{1a}$ and $-(CR^{2e}R^{2f})_r$-5-10 membered heterocycle comprising carbon atoms, and 1-4 heteroatoms selected from N, O, and $S(O)_p$ substituted with 0-3 $R^{1a}$;

$R^{1a}$ is, independently at each occurrence, hydrogen, =O, halo, $CF_3$, $OCF_3$, CN, $NO_2$, $-(CR^{2e}R^{2f})_r-OR^b$, $-(CR^{2e}R^{2f})_r-S(O)_pR^b$, $-(CR^{2e}R^{2f})_r-C(O)R^b$, $-(CR^{2e}R^{2f})_r-C(O)OR^b$, $-(CR^{2e}R^{2f})_r-OC(O)R^b$, $-(CR^{2e}R^{2f})_r-NR^{11}R^{11}$, $-(CR^{2e}R^{2f})_r-C(O)NR^{11}R^{11}$, $-(CR^{2e}R^{2f})_r-NR^bC(O)R^c$, $-(CR^{2e}R^{2f})_r-NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, $-(CR^{2e}R^{2f})_r$-3-14 membered carbocycle substituted with 0-3 $R^a$, or $-(CR^{2e}R^{2f})_r$-5-7 membered heterocycle comprising carbon atoms, and 1-4 heteroatoms selected from N, O, and $S(O)_p$ substituted with 0-3 $R^a$;

$R^2$ is selected from hydrogen, $-(CR^{2e}R^{2f})_r-C(O)R^{2d}$, $-(CR^{2e}R^{2f})_r-C(O)OR^2b$, $-(CR^{2e}R^{2f})_r-C(O)NR^{11}R^{11}$, $-(CR^{2e}R^{2f})_r-S(O)_2R^{2c}$, $C_{1-6}$ alkyl substituted with 0-3 $R^{2a}$, $C_{2-6}$ alkenyl substituted with 0-3 $R^{2a}$, $-(CR^{2e}R^{2f})_r$-3-10 membered carbocycle substituted with 0-3 $R^a$, and $-(CR^{2e}R^{2f})_r$-4-7 membered heterocycle comprising carbon atoms, and 1-4 heteroatoms selected from N, O, P(=O) and S(O), substituted with 0-4 $R^a$;

$R^{2a}$ is, independently at each occurrence, hydrogen, =O, halo, $OCF_3$, CN, $NO_2$, $-(CR^{2e}R^{2f})_r-OR^b$, $-(CR^{2e}R^{2f})_r-S(O)_pR^b$, $-(CR^{2e}R^{2f})_r-C(O)R^b$, $-(CR^{2e}R^{2f})_r-C(O)OR^b$, $-(CR^{2e}R^{2f})_r-OC(O)R^b$, $-(CR^{2e}R^{2f})_r-OC(O)NR^{11}R^{11}$, $-(CR^{2e}R^{2f})_r-OC(O)OR^c$, $-(CR^{2e}R^{2f})_r-NR^{11}R^{11}$, $-(CR^{2e}R^{2f})_r-C(O)NR^{11}R^{11}$, $-(CR^{2e}R^{2f})_r-NR^bC(O)R^c$, $-(CR^{2e}R^{2f})_r-NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, $-(CR^{2e}R^{2f})_r$-3-14 membered carbocycle substituted with 0-3 $R^a$, or $-(CR^{2e}R^{2f})_r$-4-7 membered heterocycle comprising carbon atoms, and 1-4 heteroatoms selected from N, O, P(=O) and $S(O)_p$ substituted with 0-4 $R^a$;

$R^{2b}$ is, independently at each occurrence, hydrogen, $CF_3$, $-(CR^{2e}R^{2f})_qOR^b$, $-(CR^{2e}R^{2f})_qS(O)_pR^b$, $-(CR^{2e}R^{2f})_r-C(O)R^{1d}$, $-(CR^{2e}R^{2f})_r-C(O)OR^b$, $-(CR^{2e}R^{2f})_qOC(O)R^b$, $-(CR^{2e}R^{2f})_qNR^{11}R^{11}$, $-(CR^{2e}R^{2f})_r-C(O)NR^{11}R^{11}$, $-(CR^{2e}R^{2f})_qNR^bC(O)R^{1c}$, $-(CR^{2e}R^{2f})_qNR^bC(O)OR^c$, $-(CR^{2e}R^{2f})_qNR^bC(O)NR^{11}R^{11}$, $-(CR^{2e}R^{2f})_qS(O)_2NR^{11}R^{11}$, $-(CR^{2e}R^{2f})_qNR^bS(O)_2R^c$, $C_{1-6}$ alkyl substituted with 0-2 $R^a$, $C_{1-6}$ haloalkyl, $-(CR^{2e}R^{2f})_r$-3-14 membered carbocycle substituted with 0-3 $R^a$, or $-(CR^{2e}R^{2f})_r$-5-7 membered heterocycle comprising carbon atoms and 1-4 heteroatoms selected from N, O, P(=O) and $S(O)_p$ substituted with 0-4 $R^a$;

$R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or $-(CR^{2e}R^{2f})_r$-5-10 membered heterocycle containing 1-4 heteroatoms selected from N, O, P(=O) and $S(O)_p$, substituted with 0-4 $R^a$;

$R^{2d}$ is, independently at each occurrence, hydrogen, $C_{1-6}$ alkyl substituted with 0-2 $R^d$, $C_{1-6}$ haloalkyl, $C(O)NR^{11}R^{11}$, $-(CR^{2e}R^{2f})_r-C_{3-10}$ cycloalkyl substituted with 0-3 $R^d$, where the cycloalkyl ring may be fused, bridged or spirocyclic, $-(CR^{2e}R^{2f})_r$-phenyl substituted with 0-2 $R^a$, or a $-(CR^{2e}R^{2f})_r$-4-10 membered heterocycle where the heterocycle may be fused, bridged or spirocyclic, containing 1-4 heteroatoms selected from N, O, P(=O) and $S(O)_p$, substituted with 0-4 $R^a$;

$R^{2e}$ and $R^{2f}$ are, independently at each occurrence, hydrogen, halogen or $C_{1-6}$ alkyl;

$R^3$ is, independently at each occurrence, selected from hydrogen, halo, $N_3$, CN, $-(CR^{2e}R^{2f})_r-OR^3b$, $-(CR^{2e}R^2)_r-NR^{11}R^{11}$, $C_{1-6}$ alkyl substituted with 0-3 $R^{3a}$, $C_{3-10}$ cycloalkyl substituted with 0-3 $R^{3a}$; and phenyl substituted with 0-3 $R^{3a}$, or 4-10 membered heterocycle containing 1-4 heteroatoms selected from N, O, and $S(O)_p$, substituted with 0-3 $R^{3a}$, or two $R^3$ located on adjacent carbon atoms link to form a 5-7 membered carbocycle or a 5-7 membered heterocycle comprising carbon atoms and 1-4 heteroatom selected from N, O and $S(O)_p$, both optionally substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, $-(CR^{2e}R^{2f})_r-OR^b$, $-(CR^{2e}R^{2f})_r-S(O)_pR^b$, $-(CR^{2e}R^{2f})_r-C(O)R^b$, $-(CR^{2e}R^{2f})_r-C(O)OR^b$, $-(CR^{2e}R^{2f})_r-OC(O)R^b$, $-(CR^{2e}R^{2f})_r-NR^{11}R^{11}$, $-(CR^{2e}R^{2f})_r-C(O)NR^{11}R^{11}$, $-(CR^{2e}R^{2f})_r-NR^bC(O)R^c$, $-(CR^{2e}R^{2f})_r-NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, $-(CR^{2e}R^{2f})_r$-3-14 membered carbocycle substituted with 0-3 $R^a$, or $-(CR^{2e}R^{2f})_r$-5-10 membered heterocycle comprising carbon atoms and 1-4 heteroatoms selected from N, O, and $S(O)_p$ substituted with 0-3 $R^a$;

$R^{3b}$ is, independently at each occurrence, hydrogen, $CF_3$, $-(CR^{2e}R^{2f})_qOR^b$, $(CR^{2e}R^{2f})_qS(O)_pR^b$, $-(CR^{2e}R^{2f})_r-C(O)R^{1d}$, $-(CR^{2e}R^{2f})_r-C(O)OR^b$, $-(CR^{2e}R^{2f})_qOC(O)R^b$, $-(CR^{2e}R^{2f})_qNR^{11}R^{11}$, $-(CR^{2e}R^{2f})_r-C(O)NR^{11}R^{11}$, $-(CR^{2e}R^{2f})_qNR^bC(O)R^{1c}$, $-(CR^{2e}R^{2f})_qNR^bC(O)OR^c$, $-(CR^{2e}R^{2f})_qNR^bC(O)NR^{11}R^{11}$, $-(CR^{2e}R^{2f})_qS(O)_2NR^{11}R^{11}$, $-(CR^{2e}R^{2f})_qNR^bS(O)_2R^c$, $C_{1-6}$ alkyl substituted with 0-3 $R^a$, $C_{1-6}$ haloalkyl, $-(CR^{2e}R^{2f})_r$-3-14 membered carbocycle substituted with 0-3 $R^a$, or $-(CR^{2e}R^{2f})_r$-5-7 membered heterocycle comprising carbon atoms and 1-4 heteroatoms selected from N, O, and $S(O)_p$ substituted with 0-3 $R^a$;

$R^4$ and $R^5$ are independently hydrogen, halo, $C_{1-6}$ alkyl or $C_{1-6}$ haloalkyl, or $R^4$ and $R^5$ together with the carbon atom to which they are attached form a 3- to 6-membered spirocarbocyclyl ring or a spiroheterocyclyl ring;

$R^6$ and $R^7$ are independently hydrogen, $C_{1-6}$ alkyl or $C_{1-6}$ haloalkyl;

$R^{11}$ is, independently at each occurrence, hydrogen, $C_{1-6}$ alkyl substituted with 0-3 $R^f$, $CF_3$, $C_{3-10}$ cycloalkyl substituted with 0-3 $R^f$, —$(CR^{2e}R^{2f})$r-phenyl substituted with 0-3 $R^d$, or —$(CR^{2e}R^{2f})$r-5-7 membered heterocycle comprising carbon atoms and 1-4 heteroatoms selected from N, O, P(=O) and S(O)$_p$ substituted with 0-4 $R^d$;

or one $R^{11}$ and a second $R^{11}$, both attached to the same nitrogen atom, combine to form a heterocycle comprising carbon atoms and 1-4 heteroatoms selected from N, O, P(=O) and S(O)$_p$ substituted with 0-4 $R^d$;

$R^a$ is, independently at each occurrence, hydrogen, =O, halo, $OCF_3$, $CF_3$, $CHF_2$, CN, $NO_2$, —$(CR^{2e}R^{2f})$r-OR$^b$, —$(CR^{2e}R^{2f})$r-S(O)$_p$R$^b$, —$(CR^{2e}R^{2f})$r-C(O)R$^b$, —$(CR^{2e}R^{2f})$r-C(O)OR$^b$, —$(CR^{2e}R^{2f})$r-OC(O)R$^b$, —$(CR^{2e}R^{2f})$r-NR$^{11}$R$^{11}$, —$(CR^{2e}R^{2f})$r-C(O)NR$^{11}$R$^{11}$, —$(CR^{2e}R^{2f})$r-NR$^b$C(O)R$^c$, —$(CR^{2e}R^{2f})$r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, $C_{1-6}$ alkyl substituted with 0-3 $R^f$, $C_{1-6}$ haloalkyl, $C_{2-6}$ alkenyl substituted with 0-3 $R^e$, $C_{2-6}$ alkynyl substituted with 0-3 $R^e$, —$(CR^{2e}R^{2f})$r-3-14 membered carbocycle, or —$(CR^{2e}R^{2f})$r-5-7 membered heterocycle comprising carbon atoms and 1-4 heteroatoms selected from N, O, P(=O) and S(O)$_p$ substituted with 0-4 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, —$(CR^{2e}R^{2f})$r-5-7 membered heterocycle comprising carbon atoms and 1-4 heteroatoms selected from N, O, P(=O) and S(O)$_p$ substituted with 0-4 $R^f$, or —$(CR^{2e}R^{2f})$r-6-10 membered carbocycle substituted with 0-3 $R^d$;

$R^c$ is, independently at each occurrence, $C_{1-6}$ alkyl substituted with 0-3 $R^f$, —$(CR^{2e}R^{2f})$r-$C_{3-6}$ cycloalkyl substituted with 0-3 $R^f$, or —$(CR^{2e}R^{2f})$r-phenyl substituted with 0-3 $R^f$;

$R^d$ is, independently at each occurrence, hydrogen, =O, halo, $OCF_3$, $CF_3$, CN, $NO_2$, —OR$^e$, —$(CR^{2e}R^{2f})$r-C(O)R$^c$, —NR$^e$R$^e$, —NR$^e$C(O)OR$^c$, C(O)NR$^e$R$^e$, —NR$^e$C(O)R$^c$, $CO_2$H, $CO_2$R$^c$, —NR$^e$SO$_2$R$^c$, SO$_2$R$^c$, $C_{1-6}$ alkyl substituted with 0-3 $R^f$, $C_{3-6}$ cycloalkyl substituted with 0-3 $R^f$, —$(CR^{2e}R^{2f})$r-phenyl substituted with 0-3 $R^f$ or —$(CR^{2e}R^{2f})$r-5-7 membered heterocycle comprising carbon atoms and 1-4 heteroatoms selected from N, O, P(=O) and S(O)$_p$ substituted with 0-4 $R^f$;

$R^e$ is, independently at each occurrence, selected from hydrogen, C(O)NR$^f$R$^f$, $C_{1-6}$ alkyl, $C_{3-6}$ cycloalkyl, -5-7 membered heterocycle or —$(CR^{2e}R^{2f})$r-phenyl substituted with 0-3 $R^f$;

$R^f$ is, independently at each occurrence, hydrogen, =O, halo, CN, $NH_2$, NH($C_{1-6}$ alkyl), N($C_{1-6}$ alkyl)$_2$, SO$_2$($C_{1-6}$ alkyl), $CO_2$H, $CO_2$($C_{1-6}$ alkyl), OH, $C_{3-6}$ cycloalkyl, $CF_3$, O($C_{1-6}$ alkyl); or an optionally substituted —$(CR^{2e}R^{2f})$r-5-10 membered heterocycle comprising carbon atoms and 1-4 heteroatoms selected from N, O, P(=O) and S(O)$_p$, phenyl or $C_{3-6}$ cycloalkyl, each group optionally substituted with halo, CN, $CF_3$, $C_{1-6}$ alkyl or O($C_{1-6}$ alkyl);

m is 0, 1, 2 or 3 n is 0, 1 or 2;

p and q are, independently at each occurrence, 0, 1, or 2; and r is 0, 1, 2, 3, or 4;

or a stereoisomer or pharmaceutically-acceptable salt thereof.

In a third aspect, the invention comprises compounds of the formula

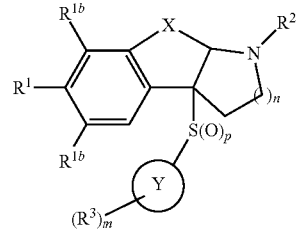

wherein

X is —$CR^4R^5$—, —$(CR^4R^5)_2$—, —$OCR^6R^7$—, —$S(O)_pCR^6R^7$— or —$NR^6CR^6R^7$—;

Y is a 5 or 6-membered aromatic or heteroaromatic ring;

$R^1$ is selected from halo, $C_{1-6}$ alkyl substituted with 0-3 $R^{1a}$, —$(CR^{2e}R^{2f})$r-3-14 membered carbocycle substituted with 0-3 $R^{1a}$ and —$(CR^{2e}R^{2f})$r-5-10 membered heterocycle comprising carbon atoms, and 1-4 heteroatoms selected from N, O, and S(O)$_p$ substituted with 0-3 $R^{1a}$;

$R^{1a}$ is, independently at each occurrence, hydrogen, =O, halo, $CF_3$, $OCF_3$, CN, $NO_2$, —$(CR^{2e}R^{2f})_r$—OR$^b$, —$(CR^{2e}R^{2f})_r$—S(O)$_p$R$^b$, —$(CR^{2e}R^{2f})_r$—C(O)R$^b$, —$(CR^{2e}R^{2f})_r$—C(O)OR$^b$, —$(CR^{2e}R^{2f})$r-OC(O)R$^b$, —$(CR^{2e}R^{2f})$r-NR$^{11}$R$^{11}$, $(CR^{2e}R^{2f})$r-C(O)NR$^{11}$R$^{11}$, —$(CR^{2e}R^{2f})$r-NR$^b$C(O)R$^c$, —$(CR^{2e}R^{2f})$r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CR^{2e}R^{2f})_r$-3-14 membered carbocycle substituted with 0-3 $R^a$, or —$(CR^{2e}R^{2f})$r-5-7 membered heterocycle comprising carbon atoms, and 1-4 heteroatoms selected from N, O, and S(O)$_p$ substituted with 0-3 $R^a$;

$R^{1b}$ is, independently at each occurrence, hydrogen, $CD_3$, halo, $CF_3$, and $C_1$-$C_4$ alkyl;

$R^2$ is selected from hydrogen, —$(CR^{2e}R^{2f})$r-C(O)R$^{2d}$, —$(CR^{2e}R^{2f})$r-C(O)OR$^2$b, —$(CR^{2e}R^{2f})$r-C(O)NR$^{11}$R$^{11}$, —$(CR^{2e}R^{2f})$r-S(O)$_2$R$^{2c}$, $C_{1-6}$ alkyl substituted with 0-3 $R^{2a}$, $C_{2-6}$ alkenyl substituted with 0-3 $R^{2a}$, —$(CR^{2e}R^{2f})$r-3-10 membered carbocycle substituted with 0-3 $R^a$, and —$(CR^{2e}R^{2f})$r-4-7 membered heterocycle comprising carbon atoms, and 1-4 heteroatoms selected from N, O, P(=O) and S(O), substituted with 0-4 $R^a$;

$R^{2a}$ is, independently at each occurrence, hydrogen, =O, halo, $OCF_3$, CN, $NO_2$, —$(CR^{2e}R^{2f})$r-OR$^b$, —$(CR^{2e}R^{2f})$r-S(O)$_p$R$^b$, —$(CR^{2e}R^{2f})$r-C(O)R$^b$, —$(CR^{2e}R^{2f})$r-C(O)OR$^b$, —$(CR^{2e}R^{2f})$r-OC(O)R$^b$, —$(CR^{2e}R^{2f})$r-OC(O)NR$^{11}$R$^{11}$, —$(CR^{2e}R^{2f})$r-OC(O)OR$^c$, —$(CR^{2e}R^{2f})$r-NR$^{11}$R$^{11}$, —$(CR^{2e}R^{2f})$r-C(O)NR$^{11}$R$^{11}$, —$(CR^{2e}R^{2f})$r-NR$^b$C(O)R$^c$, —$(CR^{2e}R^{2f})$r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CR^{2e}R^{2f})$r-3-14 membered carbocycle substituted with 0-3 $R^a$, or —$(CR^{2e}R^{2f})$r-4-7 membered heterocycle comprising carbon atoms, and 1-4 heteroatoms selected from N, O, P(=O) and S(O)$_p$ substituted with 0-4 $R^a$;

$R^{2b}$ is, independently at each occurrence, hydrogen, $CF_3$, —$(CR^{2e}R^{2f})_q$OR$^b$, —$(CR^{2e}R^{2f})_q$S(O)$_p$R$^b$, —$(CR^{2e}R^{2f})$r-C(O)R$^{1d}$, —$(CR^{2e}R^{2f})$r-C(O)OR$^b$, —$(CR^{2e}R^{2f})_q$OC(O)R$^b$, —$(CR^{2e}R^{2f})_q$NR$^{11}$R$^{11}$, —$(CR^{2e}R^{2f})$r-C(O)NR$^{11}$R$^{11}$, —(CR$^{2e}$R$^{2f}$)$_q$NR$^b$C(O)R$^{1c}$, —(CR$^{2e}$R$^{2f}$)$_q$NR$^b$C(O)OR$^c$, —(CR$^{2e}$R$^{2f}$)$_q$NR$^b$C(O)NR$^{11}$R$^{11}$, —(CR$^{2e}$R$^{2f}$)$_q$S(O)$_2$NR$^{11}$R$^{11}$, —(CR$^{2e}$R$^{2f}$)$_q$NR$^b$S(O)$_2$R$^c$, C$_{1-6}$ alkyl substituted with 0-2 R$^a$, C$_{1-6}$ haloalkyl, —(CR$^{2e}$R$^{2f}$)r-3-14 membered carbocycle substituted with 0-3 R$^a$, or —(CR$^{2e}$R$^{2f}$)r-5-7 membered heterocycle comprising carbon atoms and 1-4 heteroatoms selected from N, O, P(=O) and S(O)$_p$ substituted with 0-4 R$^a$;

R$^{2c}$ is, independently at each occurrence, hydrogen, C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or —(CR$^{2e}$R$^{2f}$)r-5-10 membered heterocycle containing 1-4 heteroatoms selected from N, O, P(=O) and S(O)$_p$, substituted with 0-4 R$^a$;

R$^{2d}$ is, independently at each occurrence, hydrogen, C$_{1-6}$ alkyl substituted with 0-2 R$^d$, C$_{1-6}$ haloalkyl, C(O)NR$^{11}$R$^{11}$, —(CR$^{2e}$R$^{2f}$)r-C$_{3-10}$ cycloalkyl substituted with 0-3 R$^d$, where the cycloalkyl ring may be fused, bridged or spirocyclic, —(CR$^{2e}$R$^{2f}$)r-phenyl substituted with 0-2 R$^a$, or a —(CR$^{2e}$R$^{2f}$)r-4-10 membered heterocycle where the heterocycle may be fused, bridged or spirocyclic, containing 1-4 heteroatoms selected from N, O, P(=O) and S(O)$_p$, substituted with 0-4 R$^a$;

R$^{2e}$ and R$^{2f}$ are, independently at each occurrence, hydrogen, halogen or C$_{1-6}$ alkyl;

R$^3$ is, independently at each occurrence, selected from hydrogen, halo, N$_3$, CN, —(CR$^{2e}$R$^{2f}$)r-OR$^{3b}$, —(CR$^{2e}$R$^{2f}$)r-NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, and S(O)$_p$, substituted with 0-3 R$^{3a}$, or two R$^3$ located on adjacent carbon atoms link to form a 5-7 membered carbocycle or a 5-7 membered heterocycle comprising carbon atoms and 1-4 heteroatom selected from N, O and S(O)$_p$, both optionally substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CR$^{2e}$R$^{2f}$)r-OR$^b$, —(CR$^{2e}$R$^{2f}$)r-S(O)$_p$R$^b$, —(CR$^{2e}$R$^{2f}$)r-C(O)R$^b$, —(CR$^{2e}$R$^{2f}$)r-C(O)OR$^b$, —(CR$^{2e}$R$^{2f}$)r-OC(O)R$^b$, —(CR$^{2e}$R$^{2f}$)r-NR$^{11}$R$^{11}$, —(CR$^{2e}$R$^{2f}$)r-C(O)NR$^{11}$R$^{11}$, —(CR$^{2e}$R$^{2f}$)r-NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{2e}$R$^{2f}$)r-3-14 membered carbocycle substituted with 0-3 R$^a$, or —(CR$^{2e}$R$^{2f}$)r-5-10 membered heterocycle comprising carbon atoms and 1-4 heteroatoms selected from N, O, and S(O)$_p$ substituted with 0-3 R$^a$;

R$^{3b}$ is, independently at each occurrence, hydrogen, CF$_3$, —(CR$^{2e}$R$^{2f}$)$_q$OR$^b$, (CR$^{2e}$R$^{2f}$)$_q$S(O)$_p$R$^b$, —(CR$^{2e}$R$^{2f}$)r-C(O)R$^{1d}$, —(CR$^{2e}$R$^{2f}$)r-C(O)OR$^b$, —(CR$^{2e}$R$^{2f}$)$_q$OC(O)R$^b$, —(CR$^{2e}$R$^{2f}$)$_q$NR$^{11}$R$^{11}$, —(CR$^{2e}$R$^{2f}$)r-C(O)NR$^{11}$R$^{11}$, —(CR$^{2e}$R$^{2f}$)$_q$NR$^b$C(O)R$^{1c}$, (CR$^{2e}$R$^{2f}$)$_q$NR$^b$C(O)OR$^c$, —(CR$^{2e}$R$^{2f}$)$_q$NR$^b$C(O)NR$^{11}$R$^{11}$, —(CR$^{2e}$R$^{2f}$)$_q$S(O)$_2$NR$^{11}$R$^{11}$, —(CR$^{2e}$R$^{2f}$)$_q$NR$^b$S(O)$_2$R$^c$, C$_{1-6}$ alkyl substituted with 0-3 R$^a$, C$_{1-6}$ haloalkyl, —(CR$^{2e}$R$^{2f}$)r-3-14 membered carbocycle substituted with 0-3 R$^a$, or —(CR$^{2e}$R$^{2f}$)r-5-7 membered heterocycle comprising carbon atoms and 1-4 heteroatoms selected from N, O, and S(O), substituted with 0-3 R$^a$;

R$^4$ and R$^5$ are independently hydrogen, halo, C$_{1-6}$ alkyl or C$_{1-6}$ haloalkyl, or R$^4$ and R$^5$ together with the carbon atom to which they are attached form a 3- to 6-membered spirocarbocyclyl ring or a spiroheterocyclyl ring;

R$^6$ and R$^7$ are independently hydrogen, C$_{1-6}$ alkyl or C$_{1-6}$ haloalkyl;

R$^{11}$ is, independently at each occurrence, hydrogen, C$_{1-6}$ alkyl substituted with 0-3 R$^f$, CF$_3$, C$_{3-10}$ cycloalkyl substituted with 0-3 R$^f$, —(CR$^{2e}$R$^{2f}$)r-phenyl substituted with 0-3 R$^d$, or —(CR$^{2e}$R$^{2f}$)r-5-7 membered heterocycle comprising carbon atoms and 1-4 heteroatoms selected from N, O, P(=O) and S(O)$_p$ substituted with 0-4 R$^d$;

or one R$^{11}$ and a second R$^{11}$, both attached to the same nitrogen atom, combine to form a heterocycle comprising carbon atoms and 1-4 heteroatoms selected from N, O, P(=O) and S(O)$_p$ substituted with 0-4 R$^d$;

R$^a$ is, independently at each occurrence, hydrogen, =O, halo, OCF$_3$, CF$_3$, CHF$_2$, CN, NO$_2$, —(CR$^{2e}$R$^{2f}$)r-OR$^b$, —(CR$^{2e}$R$^{2f}$)r-S(O)$_p$R$^b$, —(CR$^{2e}$R$^{2f}$)r-C(O)R$^b$, —(CR$^{2e}$R$^{2f}$)r-C(O)OR$^b$, —(CR$^{2e}$R$^{2f}$)r-OC(O)R$^b$, —(CR$^{2e}$R$^{2f}$)r-NR$^{11}$R$^{11}$, —(CR$^{2e}$R$^{2f}$)r-C(O)NR$^{11}$R$^{11}$, —(CR$^{2e}$R$^{2f}$)r-NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{2e}$R$^{2f}$)r-3-14 membered carbocycle, or —(CR$^{2e}$R$^{2f}$)r-5-7 membered heterocycle comprising carbon atoms and 1-4 heteroatoms selected from N, O, P(=O) and S(O)$_p$ substituted with 0-4 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{2e}$R$^{2f}$)r-5-7 membered heterocycle comprising carbon atoms and 1-4 heteroatoms selected from N, O, P(=O) and S(O)$_p$ substituted with 0-4 R$^f$, or —(CR$^{2e}$R$^{2f}$)r-6-10 membered carbocycle substituted with 0-3 R$^d$;

R$^c$ is, independently at each occurrence, C$_{1-6}$ alkyl substituted with 0-3 R$^f$, —(CR$^{2e}$R$^{2f}$)r-C$_{3-6}$ cycloalkyl substituted with 0-3 R$^f$, or —(CR$^{2e}$R$^{2f}$)r-phenyl substituted with 0-3 R$^f$;

R$^d$ is, independently at each occurrence, hydrogen, =O, halo, OCF$_3$, CF$_3$, CN, NO$_2$, —OR$^e$, —(CR$^{2e}$R$^{2f}$)r-C(O)R$^c$, —NR$^e$R$^e$, —NR$^e$C(O)OR$^c$, C(O)NR$^e$R$^e$, —NR$^e$C(O)R$^c$, CO$_2$H, CO$_2$R$^c$, —NR$^e$SO$_2$R$^c$, SO$_2$R$^c$, C$_{1-6}$ alkyl substituted with 0-3 R$^f$, C$_{3-6}$ cycloalkyl substituted with 0-3 R$^f$, —(CR$^{2e}$R$^{2f}$)r-phenyl substituted with 0-3 R$^f$ or —(CR$^{2e}$R$^{2f}$)r-5-7 membered heterocycle comprising carbon atoms and 1-4 heteroatoms selected from N, O, P(=O) and S(O)$_p$ substituted with 0-4 R$^f$;

R$^e$ is, independently at each occurrence, selected from hydrogen, C(O)NR$^f$R$^f$, C$_{1-6}$ alkyl, C$_{3-6}$ cycloalkyl, -5-7 membered heterocycle or —(CR$^{2e}$R$^{2f}$)r-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$(C$_{1-6}$ alkyl), CO$_2$H, CO$_2$(C$_{1-6}$ alkyl), OH, C$_{3-6}$ cycloalkyl, CF$_3$, O(C$_{1-6}$ alkyl); or an optionally substituted —(CR$^{2e}$R$^{2f}$)r-5-10 membered heterocycle comprising carbon atoms and 1-4 heteroatoms selected from N, O, P(=O) and S(O)$_p$, phenyl or C$_{3-6}$ cycloalkyl, each group optionally substituted with halo, CN, CF$_3$, C$_{1-6}$ alkyl or O(C$_{1-6}$ alkyl);

m is 0, 1, 2 or 3 n is 0, 1 or 2;

p and q are, independently at each occurrence, 0, 1, or 2; and r is 0, 1, 2, 3, or 4;

or a stereoisomer or pharmaceutically-acceptable salt thereof.

In a 4$^{th}$ aspect, the invention comprises compounds of the formula

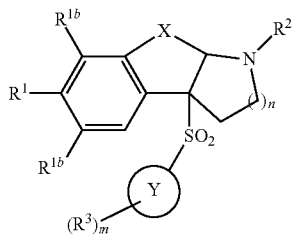

wherein

X is —CR⁴R⁵—, —(CR⁴R⁵)₂, —OCR⁶R⁷—, —S(O)$_p$CR⁶R⁷— or —NR⁶CR⁶R⁷—;

Y is a 5 or 6-membered aromatic or heteroaromatic ring;

R¹ is selected from halo, C$_{1-6}$ alkyl substituted with 0-3 R$^{1a}$, —(CR$^{2e}$R$^{2f}$)r-3-14 membered carbocycle substituted with 0-3 R$^{1a}$ and —(CR$^{2e}$R$^{2f}$)r-5-10 membered heterocycle comprising carbon atoms, and 1-4 heteroatoms selected from N, O, and S(O)$_p$ substituted with 0-3 R$^{1a}$;

R$^{1a}$ is, independently at each occurrence, hydrogen, =O, halo, CF₃, OCF₃, CN, NO₂, —(CR$^{2e}$R$^{2f}$)$_r$—OR$^b$, —(CR$^{2e}$R$^{2f}$)$_r$—S(O)$_p$R$^b$, —(CR$^{2e}$R$^{2f}$)$_r$—C(O)R$^b$, —(CR$^{2e}$R$^{2f}$)$_r$—C(O)OR$^b$, —(CR$^{2e}$R$^{2f}$)r-OC(O)R$^b$, —(CR$^{2e}$R$^{2f}$)r-NR$^{11}$R$^{11}$, —(CR$^{2e}$R$^{2f}$)r-C(O)NR$^{11}$R$^{11}$, —(CR$^{2e}$R$^{2f}$)$_r$—NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{2e}$R$^{2f}$)$_r$-3-14 membered carbocycle substituted with 0-3 R$^a$, or —(CR$^{2e}$R$^{2f}$)r-5-7 membered heterocycle comprising carbon atoms, and 1-4 heteroatoms selected from N, O, and S(O)$_p$ substituted with 0-3 R$^a$;

R$^{1b}$ is, independently at each occurrence, hydrogen, CD₃, halo, CF₃, and C$_1$-C$_4$ alkyl;

R² is selected from hydrogen, —(CR$^{2e}$R$^{2f}$)r-C(O)R$^{2d}$, —(CR$^{2e}$R$^{2f}$)r-C(O)OR$^{2b}$, —(CR$^{2e}$R$^{2f}$)r-C(O)NR$^{11}$R$^{11}$, —(CR$^{2e}$R$^{2f}$)r-S(O)₂R$^{2c}$, C$_{1-6}$ alkyl substituted with 0-3 R$^{2a}$, C$_{2-6}$ alkenyl substituted with 0-3 R$^{2a}$, —(CR$^{2e}$R$^{2f}$)r-3-10 membered carbocycle substituted with 0-3 R$^a$, and —(CR$^{2e}$R$^{2f}$)r-4-7 membered heterocycle comprising carbon atoms, and 1-4 heteroatoms selected from N, O, P(=O) and S(O)$_p$ substituted with 0-4 R$^a$;

R$^{2a}$ is, independently at each occurrence, hydrogen, =O, halo, OCF₃, CN, NO₂, —(CR$^{2e}$R$^{2f}$)r-OR$^b$, —(CR$^{2e}$R$^{2f}$)r-S(O)$_p$R$^b$, —(CR$^{2e}$R$^{2f}$)r-C(O)R$^b$, —(CR$^{2e}$R$^{2f}$)r-C(O)OR$^b$, —(CR$^{2e}$R$^{2f}$)r-OC(O)R$^b$, —(CR$^{2e}$R$^{2f}$)r-OC(O)NR$^{11}$R$^{11}$, —(CR$^{2e}$R$^{2f}$)r-OC(O)OR$^c$, —(CR$^{2e}$R$^{2f}$)r-NR$^{11}$R$^{11}$, —(CR$^{2e}$R$^{2f}$)r-C(O)NR$^{11}$R$^{11}$, —(CR$^{2e}$R$^{2f}$)r-NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{2e}$R$^{2f}$)r-3-14 membered carbocycle substituted with 0-3 R$^a$, or —(CR$^{2e}$R$^{2f}$)r-4-7 membered heterocycle comprising carbon atoms, and 1-4 heteroatoms selected from N, O, P(=O) and S(O)$_p$ substituted with 0-4 R$^a$;

R$^{2b}$ is, independently at each occurrence, hydrogen, CF₃, —(CR$^{2e}$R$^{2f}$)$_q$OR$^b$, —(CR$^{2e}$R$^{2f}$)$_q$S(O)$_p$R$^b$, —(CR$^{2e}$R$^{2f}$)r-C(O)R$^{1d}$, —(CR$^{2e}$R$^{2f}$)r-C(O)OR$^b$, —(CR$^{2e}$R$^{2f}$)$_q$OC(O)R$^b$, —(CR$^{2e}$R$^{2f}$)$_q$NR$^{11}$R$^{11}$, —(CR$^{2e}$R$^{2f}$)r-C(O)NR$^{11}$R$^{11}$, —(CR$^{2e}$R$^{2f}$)$_q$NR$^b$C(O)R$^{1c}$, —(CR$^{2e}$R$^{2f}$)$_q$NR$^b$C(O)OR$^c$, —(CR$^{2e}$R$^{2f}$)$_q$NR$^b$C(O)NR$^{11}$R$^{11}$, —(CR$^{2e}$R$^{2f}$)$_q$S(O)₂NR$^{11}$R$^{11}$, —(CR$^{2e}$R$^{2f}$)$_q$NR$^b$S(O)₂R$^c$, C$_{1-6}$ alkyl substituted with 0-2 R$^a$, C$_{1-6}$ haloalkyl, —(CR$^{2e}$R$^{2f}$)r-3-14 membered carbocycle substituted with 0-3 R$^a$, or —(CR$^{2e}$R$^{2f}$)r-5-7 membered heterocycle comprising carbon atoms and 1-4 heteroatoms selected from N, O, P(=O) and S(O), substituted with 0-4 R$^a$;

R$^{2c}$ is, independently at each occurrence, hydrogen, C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or —(CR$^{2e}$R$^{2f}$)r-5-10 membered heterocycle containing 1-4 heteroatoms selected from N, O, P(=O) and S(O)$_p$, substituted with 0-4 R$^a$;

R$^{2d}$ is, independently at each occurrence, hydrogen, C$_{1-6}$ alkyl substituted with 0-2 R$^d$, C$_{1-6}$ haloalkyl, C(O)NR$^{11}$R$^{11}$, —(CR$^{2e}$R$^{2f}$)r-C$_{3-10}$ cycloalkyl substituted with 0-3 R$^d$, where the cycloalkyl ring may be fused, bridged or spirocyclic, —(CR$^{2e}$R$^{2f}$)r-phenyl substituted with 0-2 R$^a$, or a —(CR$^{2e}$R$^{2f}$)r-4-10 membered heterocycle where the heterocycle may be fused, bridged or spirocyclic, containing 1-4 heteroatoms selected from N, O, P(=O) and S(O)$_p$, substituted with 0-4 R$^a$;

R$^{2e}$ and R$^{2f}$ are, independently at each occurrence, hydrogen, halogen or C$_{1-6}$ alkyl;

R³ is, independently at each occurrence, selected from hydrogen, halo, N₃, CN, —(CR$^{2e}$R$^{2f}$)r-OR$^{3b}$, —(CR$^{2e}$R$^{2f}$)r-NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, and S(O)$_p$, substituted with 0-3 R$^{3a}$, or two R³ located on adjacent carbon atoms link to form a 5-7 membered carbocycle or a 5-7 membered heterocycle comprising carbon atoms and 1-4 heteroatom selected from N, O and S(O)$_p$, both optionally substituted with 0-3 R$^{3a}$;

R$^{3a}$ is, independently at each occurrence, hydrogen, =O, halo, OCF₃, OCHF₂, CF₃, CHF₂, CN, NO₂, —(CR$^{2e}$R$^{2f}$)r-OR$^b$, —(CR$^{2e}$R$^{2f}$)r-S(O)$_p$R$^b$, —(CR$^{2e}$R$^{2f}$)r-C(O)R$^b$, —(CR$^{2e}$R$^{2f}$)r-C(O)OR$^b$, —(CR$^{2e}$R$^{2f}$)r-OC(O)R$^b$, —(CR$^{2e}$R$^{2f}$)r-NR$^{11}$R$^{11}$, —(CR$^{2e}$R$^{2f}$)r-C(O)NR$^{11}$R$^{11}$, —(CR$^{2e}$R$^{2f}$)r-NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{2e}$R$^{2f}$)r-3-14 membered carbocycle substituted with 0-3 R$^a$, or —(CR$^{2e}$R$^{2f}$)r-5-10 membered heterocycle comprising carbon atoms and 1-4 heteroatoms selected from N, O, and S(O)$_p$ substituted with 0-3 R$^a$;

R$^{3b}$ is, independently at each occurrence, hydrogen, CF₃, —(CR$^{2e}$R$^{2f}$)$_q$OR$^b$, (CR$^{2e}$R$^{2f}$)$_q$S(O)$_p$R$^b$, —(CR$^{2e}$R$^{2f}$)r-C(O)R$^{1d}$, —(CR$^{2e}$R$^{2f}$)r-C(O)OR$^b$, —(CR$^{2e}$R$^{2f}$)$_q$OC(O)R$^b$, —(CR$^{2e}$R$^{2f}$)$_q$NR$^{11}$R$^{11}$, (CR$^{2e}$R$^{2f}$)r-C(O)NR$^{11}$R$^{11}$, —(CR$^{2e}$R$^{2f}$)$_q$NR$^b$C(O)R$^{1c}$, —(CR$^{2e}$R$^{2f}$)$_q$NR$^b$C(O)OR$^c$, —(CR$^{2e}$R$^{2f}$)$_q$NR$^b$C(O)NR$^{11}$R$^{11}$, —(CR$^{2e}$R$^{2f}$)$_q$S(O)₂NR$^{11}$R$^{11}$, —(CR$^{2e}$R$^{2f}$)$_q$NR$^b$S(O)₂R$^c$, C$_{1-6}$ alkyl substituted with 0-3 R$^a$, C$_{1-6}$ haloalkyl, —(CR$^{2e}$R$^{2f}$)r-3-14 membered carbocycle substituted with 0-3 R$^a$, or —(CR$^{2e}$R$^{2f}$)r-5-7 membered heterocycle comprising carbon atoms and 1-4 heteroatoms selected from N, O, and S(O)$_p$ substituted with 0-3 R$^a$;

R⁴ and R⁵ are independently hydrogen, halo, C$_{1-6}$ alkyl or C$_{1-6}$ haloalkyl, or R⁴ and R⁵ together with the carbon atom to which they are attached form a 3- to 6-membered spirocarbocyclyl ring or a spiroheterocyclyl ring;

R⁶ and R⁷ are independently hydrogen, C$_{1-6}$ alkyl or C$_{1-6}$ haloalkyl;

R$^{11}$ is, independently at each occurrence, hydrogen, C$_{1-6}$ alkyl substituted with 0-3 R$^f$, CF₃, C$_{3-10}$ cycloalkyl substituted with 0-3 R$^f$, —(CR$^{2e}$R$^{2f}$)r-phenyl substituted with 0-3 R$^d$, or —(CR$^{2e}$R$^{2f}$)r-5-7 membered heterocycle comprising carbon atoms and 1-4 heteroatoms selected from N, O, P(=O) and S(O)$_p$ substituted with 0-4 R$^d$;

or one R$^{11}$ and a second R$^{11}$, both attached to the same nitrogen atom, combine to form a heterocycle comprising carbon atoms and 1-4 heteroatoms selected from N, O, P(=O) and S(O)$_p$ substituted with 0-4 R$^d$;

R$^a$ is, independently at each occurrence, hydrogen, =O, halo, OCF$_3$, CF$_3$, CHF$_2$, CN, NO$_2$, —(CR$^{2e}$R$^{2f}$)r-OR$^b$, —(CR$^{2e}$R$^{2f}$)r-S(O)$_p$R$^b$, —(CR$^{2e}$R$^{2f}$)r-C(O)R$^b$, —(CR$^{2e}$R$^{2f}$)r-C(O)OR$^b$, —(CR$^{2e}$R$^{2f}$)r-OC(O)R$^b$, —(CR$^{2e}$R$^{2f}$)r-NR$^{11}$R$^{11}$, —(CR$^{2e}$R$^{2f}$)r-C(O)NR$^{11}$R$^{11}$, —(CR$^{2e}$R$^{2f}$)r-NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{2e}$R$^{2f}$)r-3-14 membered carbocycle, or —(CR$^{2e}$R$^{2f}$)r-5-7 membered heterocycle comprising carbon atoms and 1-4 heteroatoms selected from N, O, P(=O) and S(O)$_p$ substituted with 0-4 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{2e}$R$^{2f}$)r-5-7 membered heterocycle comprising carbon atoms and 1-4 heteroatoms selected from N, O, P(=O) and S(O)$_p$ substituted with 0-4 R$^f$, or —(CR$^{2e}$R$^{2f}$)r-6-10 membered carbocycle substituted with 0-3 R$^d$;

R$^c$ is, independently at each occurrence, C$_{1-6}$ alkyl substituted with 0-3 R$^f$, —(CR$^{2e}$R$^{2f}$)r-C$_{3-6}$ cycloalkyl substituted with 0-3 R$^f$, or —(CR$^{2e}$R$^{2f}$)r-phenyl substituted with 0-3 R$^f$;

R$^d$ is, independently at each occurrence, hydrogen, =O, halo, OCF$_3$, CF$_3$, CN, NO$_2$, —OR$^e$, —(CR$^{2e}$R$^{2f}$)r-C(O)R$^c$, —NR$^e$R$^e$, —NR$^e$C(O)OR$^c$, C(O)NR$^e$R$^e$, —NR$^e$C(O)R$^c$, CO$_2$H, CO$_2$R$^c$, —NR$^e$SO$_2$R$^c$, SO$_2$R$^c$, C$_{1-6}$ alkyl substituted with 0-3 R$^f$, C$_{3-6}$ cycloalkyl substituted with 0-3 R$^f$, —(CR$^{2e}$R$^{2f}$)r-phenyl substituted with 0-3 R$^f$ or —(CR$^{2e}$R$^{2f}$)r-5-7 membered heterocycle comprising carbon atoms and 1-4 heteroatoms selected from N, O, P(=O) and S(O)$_p$ substituted with 0-4 R$^f$;

R$^e$ is, independently at each occurrence, selected from hydrogen, C(O)NR$^f$R$^f$, C$_{1-6}$ alkyl, C$_{3-6}$ cycloalkyl, -5-7 membered heterocycle or —(CR$^{2e}$R$^{2f}$)r-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$(C$_{1-6}$ alkyl), CO$_2$H, CO$_2$(C$_{1-6}$ alkyl), OH, C$_{3-6}$ cycloalkyl, CF$_3$, O(C$_{1-6}$ alkyl), or an optionally substituted —(CR$^{2e}$R$^{2f}$)r-5-10 membered heterocycle comprising carbon atoms and 1-4 heteroatoms selected from N, O, P(=O) and S(O)$_p$, phenyl or C$_{3-6}$ cycloalkyl, each group optionally substituted with halo, CN, CF$_3$, C$_{1-6}$ alkyl or O(C$_{1-6}$ alkyl);

m is 0, 1, 2 or 3 n is 0, 1 or 2;

p and q are, independently at each occurrence, 0, 1, or 2; and r is 0, 1, 2, 3, or 4, or a stereoisomer or pharmaceutically-acceptable salt thereof.

In a 5$^{th}$ aspect, the invention comprises compounds of the formula

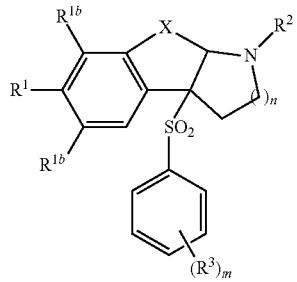

wherein

X is —CR$^4$R$^5$—, —(CR$^4$R$^5$)$_2$, —OCR$^6$R$^7$—, —S(O)$_p$CR$^6$R$^7$— or —NR$^6$CR$^6$R$^7$—;

R$^1$ is selected from halo, C$_{1-6}$ alkyl substituted with 0-3 R$^{1a}$, —(CR$^{2e}$R$^{2f}$)r-3-14 membered carbocycle substituted with 0-3 R$^{1a}$ and —(CR$^{2e}$R$^{2f}$)r-5-10 membered heterocycle comprising carbon atoms, and 1-4 heteroatoms selected from N, O, and S(O)$_p$ substituted with 0-3 R$^{1a}$;

R$^{1a}$ is, independently at each occurrence, hydrogen, =O, halo, CF$_3$, OCF$_3$, CN, NO$_2$, —(CR$^{2e}$R$^{2f}$)$_r$—OR$^b$, —(CR$^{2e}$R$^{2f}$)$_r$—S(O)$_p$R$^b$, —(CR$^{2e}$R$^{2f}$)$_r$—C(O)R$^b$, —(CR$^{2e}$R$^{2f}$)$_r$—C(O)OR$^b$, —(CR$^{2e}$R$^{2f}$)r-OC(O)R$^b$, —(CR$^{2e}$R$^{2f}$)r-NR$^{11}$R$^{11}$, (CR$^{2e}$R$^{2f}$)r-C(O)NR$^{11}$R$^{11}$, (CR$^{2e}$R$^{2f}$)$_r$—NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{2e}$R$^{2f}$)$_r$-3-14 membered carbocycle substituted with 0-3 R$^a$, or —(CR$^{2e}$R$^{2f}$)r-5-7 membered heterocycle comprising carbon atoms, and 1-4 heteroatoms selected from N, O, and S(O)$_p$ substituted with 0-3 R$^a$;

R$^{1b}$ is, independently at each occurrence, hydrogen, CD$_3$, halo, CF$_3$, and C$_1$-C$_4$ alkyl;

R$^2$ is selected from hydrogen, —(CR$^{2e}$R$^{2f}$)r-C(O)R$^{2d}$, —(CR$^{2e}$R$^{2f}$)r-C(O)OR$^2$b, —(CR$^{2e}$R$^{2f}$)r-C(O)NR$^{11}$R$^{11}$, —(CR$^{2e}$R$^{2f}$)r-S(O)$_2$R$^{2c}$, C$_{1-6}$ alkyl substituted with 0-3 R$^{2a}$, C$_{2-6}$ alkenyl substituted with 0-3 R$^{2a}$, —(CR$^{2e}$R$^{2f}$)r-3-10 membered carbocycle substituted with 0-3 R$^a$, and —(CR$^{2e}$R$^{2f}$)r-4-7 membered heterocycle comprising carbon atoms, and 1-4 heteroatoms selected from N, O, P(=O) and S(O)$_p$ substituted with 0-4 R$^a$;

R$^{2a}$ is, independently at each occurrence, hydrogen, =O, halo, OCF$_3$, CN, NO$_2$, —(CR$^{2e}$R$^{2f}$)r-OR$^b$, —(CR$^{2e}$R$^{2f}$)r-S(O)$_p$R$^b$, —(CR$^{2e}$R$^{2f}$)r-C(O)R$^b$, —(CR$^{2e}$R$^{2f}$)r-C(O)OR$^b$, —(CR$^{2e}$R$^{2f}$)r-OC(O)R$^b$, —(CR$^{2e}$R$^{2f}$)r-OC(O)NR$^{11}$R$^{11}$, —(CR$^{2e}$R$^{2f}$)r-OC(O)OR$^c$, —(CR$^{2e}$R$^{2f}$)r-NR$^{11}$R$^{11}$, —(CR$^{2e}$R$^{2f}$)r-C(O)NR$^{11}$R$^{11}$, —(CR$^{2e}$R$^{2f}$)r-NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{2e}$R$^{2f}$)r-3-14 membered carbocycle substituted with 0-3 R$^a$, or —(CR$^{2e}$R$^{2f}$)r-4-7 membered heterocycle comprising carbon atoms, and 1-4 heteroatoms selected from N, O, P(=O) and S(O)$_p$ substituted with 0-4 R$^a$;

R$^{2b}$ is, independently at each occurrence, hydrogen, CF$_3$, —(CR$^{2e}$R$^{2f}$)$_q$OR$^b$, —(CR$^{2e}$R$^{2f}$)$_q$S(O)$_p$R$^b$, —(CR$^{2e}$R$^{2f}$)r-C(O)R$^{1d}$, —(CR$^{2e}$R$^{2f}$)r-C(O)OR$^b$, —(CR$^{2e}$R$^{2f}$)$_q$OC(O)R$^b$, —(CR$^{2e}$R$^{2f}$)$_q$NR$^{11}$R$^{11}$, —(CR$^{2e}$R$^{2f}$)r-C(O)NR$^{11}$R$^{11}$, —(CR$^{2e}$R$^{2f}$)$_q$NR$^b$C(O)R$^{1c}$, —(CR$^{2e}$R$^{2f}$)$_q$NR$^b$C(O)OR$^c$, —(CR$^{2e}$R$^{2f}$)$_q$NR$^b$C(O)NR$^{11}$R$^{11}$, —(CR$^{2e}$R$^{2f}$)$_q$S(O)$_2$NR$^{11}$R$^{11}$, —(CR$^{2e}$R$^{2f}$)$_q$NR$^b$S(O)$_2$R$^c$, C$_{1-6}$ alkyl substituted with 0-2 R$^a$, C$_{1-6}$ haloalkyl, —(CR$^{2e}$R$^{2f}$)r-3-14 membered carbocycle substituted with 0-3 $R^a$, or —$(CR^{2e}R^{2f})$r-5-7 membered heterocycle comprising carbon atoms and 1-4 heteroatoms selected from N, O, P(=O) and S(O), substituted with 0-4 $R^a$;

$R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CR^{2e}R^{2f})$r-5-10 membered heterocycle containing 1-4 heteroatoms selected from N, O, P(=O) and S(O)$_p$, substituted with 0-4 $R^a$;

$R^{2d}$ is, independently at each occurrence, hydrogen, $C_{1-6}$ alkyl substituted with 0-2 $R^d$, $C_{1-6}$ haloalkyl, C(O)NR$^{11}$R$^{11}$, —$(CR^{2e}R^{2f})$r-$C_{3-10}$ cycloalkyl substituted with 0-3 $R^d$, where the cycloalkyl ring may be fused, bridged or spirocyclic, —$(CR^{2e}R^{2f})$r-phenyl substituted with 0-2 $R^a$, or a —$(CR^{2e}R^{2f})$r-4-10 membered heterocycle where the heterocycle may be fused, bridged or spirocyclic, containing 1-4 heteroatoms selected from N, O, P(=O) and S(O)$_p$, substituted with 0-4 $R^a$;

$R^{2e}$ and $R^{2f}$ are, independently at each occurrence, hydrogen, halogen or $C_{1-6}$ alkyl;

$R^3$ is, independently at each occurrence, selected from hydrogen, halo, $N_3$, CN, —$(CR^{2e}R^{2f})$r-OR$^3$b, —$(CR^{2e}R^{2f})$r-NR$^{11}$R$^{11}$, $C_{1-6}$ alkyl substituted with 0-3 $R^{3a}$, $C_{3-10}$ cycloalkyl substituted with 0-3 $R^{3a}$; and phenyl substituted with 0-3 $R^{3a}$, or 4-10 membered heterocycle containing 1-4 heteroatoms selected from N, O, and S(O)$_p$, substituted with 0-3 $R^{3a}$, or two $R^3$ located on adjacent carbon atoms link to form a 5-7 membered carbocycle or a 5-7 membered heterocycle comprising carbon atoms and 1-4 heteroatom selected from N, O and S(O)$_p$, both optionally substituted with 0-3 $R^{3a}$;

$R^{3a}$ is, independently at each occurrence, hydrogen, =O, halo, OCF$_3$, OCHF$_2$, CF$_3$, CHF$_2$, CN, NO$_2$, —$(CR^{2e}R^{2f})$r-OR$^b$, —$(CR^{2e}R^{2f})$r-S(O)$_p$R$^b$, —$(CR^{2e}R^{2f})$r-C(O)R$^b$, —$(CR^{2e}R^{2f})$r-C(O)OR$^b$, —$(CR^{2e}R^{2f})$r-OC(O)R$^b$, —$(CR^{2e}R^{2f})$r-NR$^{11}$R$^{11}$, —$(CR^{2e}R^{2f})$r-C(O)NR$^{11}$R$^{11}$, —$(CR^{2e}R^{2f})$r-NR$^b$C(O)R$^c$, —$(CR^{2e}R^{2f})$r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{2e}R^{2f})$r-3-14 membered carbocycle substituted with 0-3 $R^a$, or —$(CR^{2e}R^{2f})$r-5-10 membered heterocycle comprising carbon atoms and 1-4 heteroatoms selected from N, O, and S(O)$_p$ substituted with 0-3 $R^a$;

$R^{3b}$ is, independently at each occurrence, hydrogen, CF$_3$, —$(CR^{2e}R^{2f})_q$OR$^b$, $(CR^{2e}R^{2f})_q$S(O)$_p$R$^b$, —$(CR^{2e}R^{2f})$r-C(O)R$^{1d}$, —$(CR^{2e}R^{2f})$r-C(O)OR$^b$, —$(CR^{2e}R^{2f})_q$OC(O)R$^b$, —$(CR^{2e}R^{2f})_q$NR$^{11}$R$^{11}$, $(CR^{2e}R^{2f})$r-C(O)NR$^{11}$R$^{11}$, $(CR^{2e}R^{2f})_q$NR$^b$C(O)R$^{1c}$, $(CR^{2e}R^{2f})_q$NR$^b$C(O)OR$^c$, —$(CR^{2e}R^{2f})_q$NR$^b$C(O)NR$^{11}$R$^{11}$, —$(CR^{2e}R^{2f})_q$S(O)$_2$NR$^{11}$R$^{11}$, —$(CR^{2e}R^{2f})_q$NR$^b$S(O)$_2$R$^c$, $C_{1-6}$ alkyl substituted with 0-3 $R^a$, $C_{1-6}$ haloalkyl, —$(CR^{2e}R^{2f})$r-3-14 membered carbocycle substituted with 0-3 $R^a$, or —$(CR^{2e}R^{2f})$r-5-7 membered heterocycle comprising carbon atoms and 1-4 heteroatoms selected from N, O, and S(O), substituted with 0-3 $R^a$;

$R^4$ and $R^5$ are independently hydrogen, halo, $C_{1-6}$ alkyl or $C_{1-6}$ haloalkyl, or $R^4$ and $R^5$ together with the carbon atom to which they are attached form a 3- to 6-membered spirocarbocyclyl ring or a spiroheterocyclyl ring;

$R^6$ and $R^7$ are independently hydrogen, $C_{1-6}$ alkyl or $C_{1-6}$ haloalkyl;

$R^{11}$ is, independently at each occurrence, hydrogen, $C_{1-6}$ alkyl substituted with 0-3 $R^f$, CF$_3$, $C_{3-10}$ cycloalkyl substituted with 0-3 $R^f$, —$(CR^{2e}R^{2f})$r-phenyl substituted with 0-3 $R^d$, or —$(CR^{2e}R^{2f})$r-5-7 membered heterocycle comprising carbon atoms and 1-4 heteroatoms selected from N, O, P(=O) and S(O)$_p$ substituted with 0-4 $R^d$;

or one $R^{11}$ and a second $R^{11}$, both attached to the same nitrogen atom, combine to form a heterocycle comprising carbon atoms and 1-4 heteroatoms selected from N, O, P(=O) and S(O)$_p$ substituted with 0-4 $R^d$;

$R^a$ is, independently at each occurrence, hydrogen, =O, halo, OCF$_3$, CF$_3$, CHF$_2$, CN, NO$_2$, —$(CR^{2e}R^{2f})$r-OR$^b$, —$(CR^{2e}R^{2f})$r-S(O)$_p$R$^b$, —$(CR^{2e}R^{2f})$r-C(O)R$^b$, —$(CR^{2e}R^{2f})$r-C(O)OR$^b$, —$(CR^{2e}R^{2f})$r-OC(O)R$^b$, —$(CR^{2e}R^{2f})$r-NR$^{11}$R$^{11}$, —$(CR^{2e}R^{2f})$r-C(O)NR$^{11}$R$^{11}$, —$(CR^{2e}R^{2f})$r-NR$^b$C(O)R$^c$, —$(CR^{2e}R^{2f})$r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, $C_{1-6}$ alkyl substituted with 0-3 $R^f$, $C_{1-6}$ haloalkyl, $C_{2-6}$ alkenyl substituted with 0-3 $R^e$, $C_{2-6}$ alkynyl substituted with 0-3 $R^e$, —$(CR^{2e}R^{2f})$r-3-14 membered carbocycle, or —$(CR^{2e}R^{2f})$r-5-7 membered heterocycle comprising carbon atoms and 1-4 heteroatoms selected from N, O, P(=O) and S(O)$_p$ substituted with 0-4 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, —$(CR^{2e}R^{2f})$r-5-7 membered heterocycle comprising carbon atoms and 1-4 heteroatoms selected from N, O, P(=O) and S(O)$_p$ substituted with 0-4 $R^f$, or —$(CR^{2e}R^{2f})$r-6-10 membered carbocycle substituted with 0-3 $R^d$;

$R^c$ is, independently at each occurrence, $C_{1-6}$ alkyl substituted with 0-3 $R^f$, —$(CR^{2e}R^{2f})$r-$C_{3-6}$ cycloalkyl substituted with 0-3 $R^f$, or —$(CR^{2e}R^{2f})$r-phenyl substituted with 0-3 $R^f$;

$R^d$ is, independently at each occurrence, hydrogen, =O, halo, OCF$_3$, CF$_3$, CN, NO$_2$, —OR$^e$, —$(CR^{2e}R^{2f})$r-C(O)R$^c$, —NR$^e$R$^e$, —NR$^e$C(O)OR$^c$, C(O)NR$^e$R$^e$, —NR$^e$C(O)R$^c$, CO$_2$H, CO$_2$R$^c$, —NR$^e$SO$_2$R$^c$, SO$_2$R$^c$, $C_{1-6}$ alkyl substituted with 0-3 $R^f$, $C_{3-6}$ cycloalkyl substituted with 0-3 $R^f$, —$(CR^{2e}R^{2f})$r-phenyl substituted with 0-3 $R^f$ or —$(CR^{2e}R^{2f})$r-5-7 membered heterocycle comprising carbon atoms and 1-4 heteroatoms selected from N, O, P(=O) and S(O)$_p$ substituted with 0-4 $R^f$;

$R^e$ is, independently at each occurrence, selected from hydrogen, C(O)NR$^f$R$^f$, $C_{1-6}$ alkyl, $C_{3-6}$ cycloalkyl, -5-7 membered heterocycle or —$(CR^{2e}R^{2f})$r-phenyl substituted with 0-3 $R^f$;

$R^f$ is, independently at each occurrence, hydrogen, =O, halo, CN, NH$_2$, NH($C_{1-6}$ alkyl), N($C_{1-6}$ alkyl)$_2$, SO$_2$($C_{1-6}$ alkyl), CO$_2$H, CO$_2$($C_{1-6}$ alkyl), OH, $C_{3-6}$ cycloalkyl, CF$_3$; O($C_{1-6}$ alkyl), or an optionally substituted —$(CR^{2e}R^{2f})$r-5-10 membered heterocycle comprising carbon atoms and 1-4 heteroatoms selected from N, O, P(=O) and S(O)$_p$, phenyl or $C_{3-6}$ cycloalkyl, each group optionally substituted with halo, CN, CF$_3$, $C_{1-6}$ alkyl or O($C_{1-6}$ alkyl);

m is 0, 1, 2 or 3 n is 0, 1 or 2;

p and q are, independently at each occurrence, 0, 1, or 2; and r is 0, 1, 2, 3, or 4, or a stereoisomer or pharmaceutically-acceptable salt thereof.

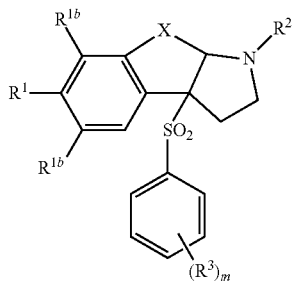

or a stereoisomer or pharmaceutically-acceptable salt thereof.

In a 7th aspect, the invention comprises compounds of the formula

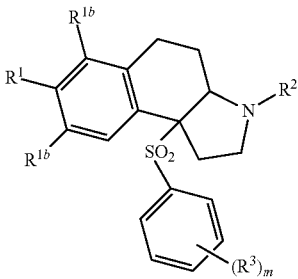

or a stereoisomer or pharmaceutically-acceptable salt thereof.

In an 8th aspect, the invention comprises compounds of the formula

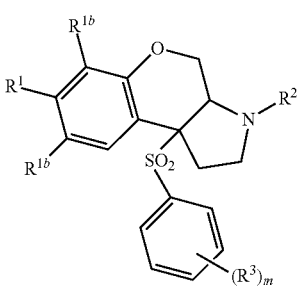

or a stereoisomer or pharmaceutically-acceptable salt thereof.

In a 9th aspect, the invention comprises compounds of the formula

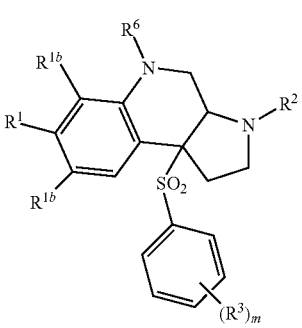

or a stereoisomer or pharmaceutically-acceptable salt thereof.

In a 10th aspect, the invention comprises compounds within the 7th aspect, wherein $R^1$ is halo, phenyl substituted with 0-3 $R^{1a}$, or $C_{1-6}$ alkyl substituted with 0-3 $R^{1a}$;

$R^{1a}$ is, independently at each occurrence, hydrogen, $CF_3$, halo, $C_{1-6}$ alkyl substituted with 0-3 $R^a$, —$(CR^{2e}R^{2f})$r-$OR^b$, and —$(CR^{2e}R^{2f})$r-phenyl substituted with 0-3 $R^a$, $R^2$ is hydrogen, $SO_2R^{2c}$, $C_{1-6}$ alkyl substituted with 0-3 $R^{2a}$, $CO_2R^{2b}$, —$C(O)R^{2d}$, —$C(O)NR^{11}R^{11}$; or a 5-7 membered heterocycle comprising carbon atoms, and 1-4 heteroatoms selected from N, O, P(=O) and $S(O)_p$ substituted with 0-4 $R^a$, $R^{2a}$ is hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})$r-5-7 membered heterocycle comprising carbon atoms and 1-4 heteroatoms selected from N, O, P(=O) and $S(O)_p$ substituted with 0-4 $R^a$, or —$(CR^{2e}R^{2f})$r-phenyl substituted with 0-3 $R^a$;

$R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CR^{2e}R^{2f})$r-5-10-membered heterocycle containing 1-4 heteroatoms selected from N, O, P(=O) and $S(O)_p$, substituted with 0-4 $R^a$;

$R^{2d}$ is, independently at each occurrence, hydrogen, $C_{1-6}$ alkyl substituted with 0-3 $R^d$, $C_{1-6}$ haloalkyl, $C(O)NR^{11}R^{11}$, $C_{3-10}$ cycloalkyl substituted with 0-2 $R^d$, $(CR^{2e}R^{2f})$r-phenyl substituted with 0-2 $R^a$, or a 4-10 membered heterocycle containing 1-4 heteroatoms selected from N, O, P(=O) and $S(O)_p$, substituted with 0-4 $R^a$;

$R^3$ is, independently at each occurrence, hydrogen, halo, $N_3$, CN, $OR^{3b}$, —$NH_2$, $NH(C_{1-6}$ alkyl), $N(C_{1-6}$ alkyl)$_2$, $C_{1-6}$ alkyl substituted with 0-3 $R^{3a}$ or $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{2e}R^{2f})$r-$OR^b$, —$(CR^{2e}R^{2f})$r-$S(O)_pR^b$, —$(CR^{2e}R^{2f})$r-$C(O)R^b$, —$(CR^{2e}R^{2f})$r-$C(O)OR^b$, —$(CR^{2e}R^{2f})$r-$OC(O)R^b$, —$(CR^{2e}R^{2f})$r-$NR^{11}R^{11}$, —$(CR^{2e}R^2)$r-$C(O)NR^{11}R^{11}$, —$(CR^{2e}R^{2f})$r-$NR^bC(O)R^c$, —$(CR^{2e}R^{2f})$r-$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{2e}R^{2f})$r-3-14 membered carbocycle substituted with 0-3 $R^a$, or —$(CR^{2e}R^{2f})$r-5-10 membered heterocycle comprising carbon atoms and 1-4 heteroatoms selected from N, O, and $S(O)_p$ substituted with 0-3 $R^a$; and $R^{3b}$ is, independently at each occurrence, hydrogen, $C_{1-6}$ alkyl substituted with 0-3 $R^a$ or phenyl substituted with 0-3 $R^a$;

or a stereoisomer or pharmaceutically-acceptable salt thereof.

In an 11th aspect, the invention comprises compounds within the 8th aspect, wherein $R^1$ is halo, phenyl substituted with 0-3 $R^{1a}$, or $C_{1-6}$ alkyl substituted with 0-3 $R^{1a}$;

$R^{1a}$ is, independently at each occurrence, hydrogen, $CF_3$, halo, $C_{1-6}$ alkyl substituted with 0-3 $R^a$, —$(CR^{2e}R^{2f})$r-$OR^b$, and —$(CR^{2e}R^{2f})$r-phenyl substituted with 0-3 $R^a$, $R^2$ is hydrogen, $SO_2R^{2c}$, $C_{1-6}$ alkyl substituted with 0-3 $R^{2a}$, $CO_2R^{2b}$, —$C(O)R^{2d}$, —$C(O)NR^{11}R^{11}$; or a 5-7 membered heterocycle comprising carbon atoms, and 1-4 heteroatoms selected from N, O, and $S(O)_p$ substituted with 0-3 $R^a$, $R^{2a}$ is hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})$r-5-7 membered heterocycle comprising carbon atoms and 1-4 heteroatoms selected from N, O, P(=O) and S(O)$_p$ substituted with 0-4 $R^a$, or —$(CR^{2e}R^{2f})$r-phenyl substituted with 0-3 $R^a$;

$R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CR^{2e}R^{2f})$r-5-10-membered heterocycle containing 1-4 heteroatoms selected from N, O, P(=O) and S(O)$_p$, substituted with 0-4 $R^a$;

$R^{2d}$ is, independently at each occurrence, hydrogen, $C_{1-6}$ alkyl substituted with 0-3 $R^d$, $C_{1-6}$ haloalkyl, C(O)NR$^{11}$R$^{11}$, $C_{3-10}$ cycloalkyl substituted with 0-2 $R^d$, $(CR^{2e}R^{2f})$r-phenyl substituted with 0-2 $R^a$, or a 4-10 membered heterocycle containing 1-4 heteroatoms selected from N, O, P(=O) and S(O)$_p$, substituted with 0-4 $R^a$;

$R^3$ is, independently at each occurrence, hydrogen, halo, N$_3$, CN, OR$^{3b}$, —NH$_2$, NH(C$_{1-6}$ alkyl), N(C$_{1-6}$ alkyl)$_2$, C$_{1-6}$ alkyl substituted with 0-3 $R^{3a}$ or $C_{3-10}$ cycloalkyl substituted with 0-3 $R^{3a}$;

$R^{3a}$ is, independently at each occurrence, hydrogen, =O, halo, OCHF$_2$, OCHF$_2$, CF$_3$, CHF$_2$, CN, NO$_2$, —$(CR^{2e}R^{2f})$r-OR$^b$, —$(CR^{2e}R^{2f})$r-S(O)$_p$R$^b$, —$(CR^{2e}R^{2f})$r-C(O)R$^b$, —$(CR^{2e}R^{2f})$r-C(O)OR$^b$, —$(CR^{2e}R^{2f})$r-OC(O)R$^b$, —$(CR^{2e}R^{2f})$r-NR$^{11}$R$^{11}$, —$(CR^{2e}R^{2f})$r-C(O)NR$^{11}$R$^{11}$, —$(CR^{2e}R^{2f})$r-NR$^b$C(O)R$^c$, —$(CR^{2e}R^{2f})$r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{2e}R^{2f})$r-3-14 membered carbocycle substituted with 0-3 $R^a$, or —$(CR^{2e}R^{2f})$r-5-10 membered heterocycle comprising carbon atoms and 1-4 heteroatoms selected from N, O, and S(O)$_p$ substituted with 0-3 $R^a$; and $R^{3b}$ is, independently at each occurrence, hydrogen, $C_{1-6}$ alkyl substituted with 0-3 $R^a$ or phenyl substituted with 0-3 $R^a$;

or a stereoisomer or pharmaceutically-acceptable salt thereof.

In a 12$^{th}$ aspect, the invention comprises compounds within the 10$^{th}$ aspect, wherein $R^1$ is $C_{1-6}$ alkyl substituted with 0-3 $R^{1a}$;

$R^{1a}$ is, independently at each occurrence, hydrogen, CF$_3$, halo or $C_{1-6}$ alkyl substituted with 0-3 $R^a$, $R^2$ is $C_{1-6}$ alkyl substituted with 0-3 $R^{2a}$, CO$_2$R$^{2b}$, —C(O)R$^{2d}$ or —C(O)NR$^{11}$R$^{11}$;

$R^{2a}$ is hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})$r-5-7 membered heterocycle comprising carbon atoms and 1-4 heteroatoms selected from N, O, P(=O) and S(O)$_p$ substituted with 0-4 $R^a$, or —$(CR^{2e}R^{2f})$r-phenyl substituted with 0-3 $R^a$;

$R^{2d}$ is, independently at each occurrence, $C_{3-10}$ cycloalkyl substituted with 0-2 $R^d$, or a 4-10 membered heterocycle containing 1-4 heteroatoms selected from N, O, P(=O) and S(O)$_2$, substituted with 0-4 $R^a$;

$R^3$ is hydrogen, halo, cyclopropyl or $C_{1-6}$ alkyl;

or a stereoisomer or pharmaceutically-acceptable salt thereof.

In a 13$^{th}$ aspect, the invention comprises compounds within the 11$^{th}$ aspect, wherein $R^1$ is $C_{1-6}$ alkyl substituted with 0-3 $R^{1a}$;

$R^{1a}$ is, independently at each occurrence, hydrogen, CF$_3$, halo or $C_{1-6}$ alkyl substituted with 0-3 $R^a$;

$R^2$ is $C_{1-6}$ alkyl substituted with 0-3 $R^{2a}$, CO$_2$R$^{2b}$, —C(O)R$^{2d}$ or —C(O)NR$^{11}$R$^{11}$;

$R^{2a}$ is hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})$r-5-7 membered heterocycle comprising carbon atoms and 1-4 heteroatoms selected from N, O, P(=O) and S(O)$_p$ substituted with 0-4 $R^a$, or —$(CR^{2e}R^{2f})$r-phenyl substituted with 0-3 $R^a$;

$R^{2d}$ is, independently at each occurrence, $C_{3-10}$ cycloalkyl substituted with 0-2 $R^d$, or a 4-10 membered heterocycle containing 1-4 heteroatoms selected from N, O, P(=O) and S(O)$_2$, substituted with 0-4 $R^a$;

$R^3$ is hydrogen, halo, cyclopropyl or $C_{1-6}$ alkyl;

or a stereoisomer or pharmaceutically-acceptable salt thereof.

In a further aspect, the invention comprises compounds according to the 12th aspect, wherein $R^1$ is

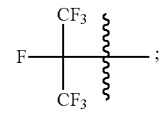

$R^2$ is —C(O)R$^{2d}$;

$R^{2d}$ is, independently at each occurrence, $C_{3-10}$ cycloalkyl substituted with 0-2 $R^d$, or a 4-10 membered heterocycle containing 1-4 heteroatoms selected from N, O, P(=O) and S(O)$_2$, substituted with 0-4 $R^a$;

$R^3$ is F, Cl, cyclopropyl or methyl;

or a stereoisomer or pharmaceutically-acceptable salt thereof.

In a further aspect, the invention comprises compounds according to the 12th aspect, wherein $R^1$ is

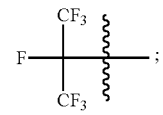

$R^2$ is —C(O)R$^{2d}$;

$R^{2d}$ is, independently at each occurrence, $C_{3-10}$ cycloalkyl substituted with 0-2 $R^d$, or a 4-10 membered heterocycle containing 1-4 heteroatoms selected from N, O, P(=O) and S(O)$_2$, substituted with 0-4 $R^a$;

$R^3$ is F, Cl, cyclopropyl or methyl;

or a stereoisomer or pharmaceutically-acceptable salt thereof.

In another aspect, there is provided a compound of Formula (II), or stereoisomers, tautomers, pharmaceutically acceptable salts, solvates, or prodrugs thereof, wherein:

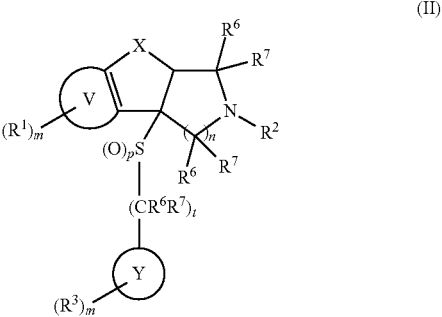

X is —CR$^4$R$^5$—, —O—, —NR$^6$—, —S(O)$_p$—, —(CR$^4$R$^5$)$_2$—, —OCR$^6$R$^7$—, —CR$^6$R$^7$O—, —S(O)$_p$CR$^6$R$^7$—, —CR$^6$R$^7$S(O)$_p$—, —NR$^6$CR$^6$R$^7$— or —CR$^6$R$^7$NR$^6$—;

V and Y are independently 5 or 6-membered aromatic or heteroaromatic rings;

R$^1$ is, independently at each occurrence, selected from halo, C$_{1-6}$ alkyl substituted with 0-3 R$^{1a}$, —(CR$^{2e}$R$^{2f}$)r-3-14 membered carbocycle substituted with 0-3 R$^{1a}$ and —(CR$^{2e}$R$^{2f}$)r-5-10 membered heterocycle comprising carbon atoms, and 1-4 heteroatoms selected from N, O, and S(O)$_p$ substituted with 0-3 R$^{1a}$;

R$^{1a}$ is, independently at each occurrence, hydrogen, =O, halo, CF$_3$, OCF$_3$, CN, NO$_2$, —(CR$^{2e}$R$^{2f}$)$_r$—OR$^b$, —(CR$^{2e}$R$^{2f}$)$_r$—S(O)$_p$R$^b$, —(CR$^{2e}$R$^{2f}$)$_r$—C(O)R$^b$, —(CR$^{2e}$R$^{2f}$)$_r$—C(O)OR$^b$, —(CR$^{2e}$R$^{2f}$)r-OC(O)R$^b$, —(CR$^{2e}$R$^{2f}$)r-NR$^{11}$R$^{11}$, (CR$^{2e}$R$^{2f}$)r-C(O)NR$^{11}$R$^{11}$, —(CR$^{2e}$R$^{2f}$)$_r$—NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{2e}$R$^{2f}$)r-3-14 membered carbocycle substituted with 0-3 R$^a$, or —(CR$^{2e}$R$^{2f}$)r-5-7 membered heterocycle comprising carbon atoms, and 1-4 heteroatoms selected from N, O, and S(O)$_p$ substituted with 0-3 R$^a$;

R$^2$ is selected from hydrogen, —(CR$^{2e}$R$^{2f}$)r-C(O)R$^{2d}$, —(CR$^{2e}$R$^{2f}$)r-C(O)OR$^{2b}$, —(CR$^{2e}$R$^{2f}$)r-C(O)NR$^{11}$R$^{11}$, —(CR$^{2e}$R$^{2f}$)r-S(O)$_2$R$^{2c}$, C$_{1-6}$ alkyl substituted with 0-3 R$^{2a}$, C$_{2-6}$ alkenyl substituted with 0-3 R$^{2a}$, —(CR$^{2e}$R$^{2f}$)r-3-10 membered carbocycle substituted with 0-3 R$^a$, and —(CR$^{2e}$R$^{2f}$)r-4-7 membered heterocycle comprising carbon atoms, and 1-4 heteroatoms selected from N, O, P(=O) and S(O), substituted with 0-4 R$^a$;

R$^{2a}$ is, independently at each occurrence, hydrogen, =O, halo, OCF$_3$, CN, NO$_2$, —(CR$^{2e}$R$^{2f}$)r-OR$^b$, —(CR$^{2e}$R$^{2f}$)r-S(O)$_p$R$^b$, —(CR$^{2e}$R$^{2f}$)r-C(O)R$^b$, —(CR$^{2e}$R$^{2f}$)r-C(O)OR$^b$, —(CR$^{2e}$R$^{2f}$)r-OC(O)R$^b$, —(CR$^{2e}$R$^{2f}$)r-OC(O)NR$^{11}$R$^{11}$, —(CR$^{2e}$R$^{2f}$)r-OC(O)R$^c$, —(CR$^{2e}$R$^{2f}$)r-NR$^{11}$R$^{11}$, (CR$^{2e}$R$^{2f}$)r-C(O)NR$^{11}$R$^{11}$, —(CR$^{2e}$R$^{2f}$)r-NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{2e}$R$^{2f}$)r-3-14 membered carbocycle substituted with 0-3 R$^a$, or —(CR$^{2e}$R$^{2f}$)r-4-7 membered heterocycle comprising carbon atoms, and 1-4 heteroatoms selected from N, O, P(=O) and S(O)$_p$ substituted with 0-4 R$^a$;

R$^{2b}$ is, independently at each occurrence, hydrogen, CF$_3$, —(CR$^{2e}$R$^{2f}$)$_q$OR$^b$, —(CR$^{2e}$R$^{2f}$)$_q$S(O)$_p$R$^b$, —(CR$^{2e}$R$^{2f}$)r-C(O)R$^{1d}$, —(CR$^{2e}$R$^{2f}$)r-C(O)OR$^b$, —(CR$^{2e}$R$^{2f}$)$_q$OC(O)R$^b$, —(CR$^{2e}$R$^{2f}$)NR$^{11}$R$^{11}$, —(CR$^{2e}$R$^{2f}$)r-C(O)NR$^{11}$R$^{11}$, —(CR$^{2e}$R$^{2f}$)$_q$NR$^b$C(O)R$^c$, —(CR$^{2e}$R$^{2f}$)$_q$NR$^b$C(O)OR$^c$, —(CR$^{2e}$R$^{2f}$)$_q$NR$^b$C(O)NR$^{11}$R$^{11}$, —(CR$^{2e}$R$^{2f}$)$_q$S(O)$_2$NR$^{11}$R$^{11}$, —(CR$^{2e}$R$^{2f}$)$_q$NR$^b$S(O)$_2$R$^c$, C$_{1-6}$ alkyl substituted with 0-2 R$^a$, C$_{1-6}$ haloalkyl, —(CR$^{2e}$R$^{2f}$)r-3-14 membered carbocycle substituted with 0-3 R$^a$, or —(CR$^{2e}$R$^{2f}$)r-5-7 membered heterocycle comprising carbon atoms and 1-4 heteroatoms selected from N, O, P(=O) and S(O)$_p$ substituted with 0-4 R$^a$;

R$^{2c}$ is, independently at each occurrence, hydrogen, C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or —(CR$^{2e}$R$^{2f}$)r-5-10 membered heterocycle containing 1-4 heteroatoms selected from N, O, P(=O) and S(O)$_p$, substituted with 0-4 R$^a$;

R$^{2d}$ is, independently at each occurrence, hydrogen, C$_{1-6}$ alkyl substituted with 0-2 R$^d$, C$_{1-6}$ haloalkyl, C(O)NR$^{11}$R$^{11}$, —(CR$^{2e}$R$^{2f}$)r-C$_{3-10}$ cycloalkyl substituted with 0-3 R$^d$, where the cycloalkyl ring may be fused, bridged or spirocyclic, —(CR$^{2e}$R$^{2f}$)r-phenyl substituted with 0-2 R$^a$, or a —(CR$^{2e}$R$^{2f}$)r-4-10 membered heterocycle where the heterocycle may be fused, bridged or spirocyclic, containing 1-4 heteroatoms selected from N, O, P(=O) and S(O)$_p$, substituted with 0-3 R$^a$;

R$^{2e}$ and R$^{2f}$ are, independently at each occurrence, hydrogen, halogen or C$_{1-6}$ alkyl;

R$^3$ is, independently at each occurrence, selected from hydrogen, halo, N$_3$, CN, —(CR$^{2e}$R$^{2f}$)r-OR$^3$b, —(CR$^{2e}$R$^{2f}$)r-NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, and S(O)$_p$, substituted with 0-3 R$^{3a}$, or two R$^3$ located on adjacent carbon atoms link to form a 5-7 membered carbocycle or a 5-7 membered heterocycle comprising carbon atoms and 1-4 heteroatom selected from N, O and S(O)$_p$, both optionally substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CR$^{2e}$R$^{2f}$)r-OR$^b$, —(CR$^{2e}$R$^{2f}$)r-S(O)$_p$R$^b$, —(CR$^{2e}$R$^{2f}$)r-C(O)R$^b$, —(CR$^{2e}$R$^{2f}$)r-C(O)OR$^b$, —(CR$^{2e}$R$^{2f}$)r-OC(O)R$^b$, —(CR$^{2e}$R$^{2f}$)r-NR$^{11}$R$^{11}$, —(CR$^{2e}$R$^2$)r-C(O)NR$^{11}$R$^{11}$, —(CR$^{2e}$R$^{2f}$)r-NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{2e}$R$^{2f}$)r-3-14 membered carbocycle substituted with 0-3 R$^a$, or —(CR$^{2e}$R$^{2f}$)r-5-10 membered heterocycle comprising carbon atoms and 1-4 heteroatoms selected from N, O, and S(O)$_p$ substituted with 0-3 R$^a$;

R$^{3b}$ is, independently at each occurrence, hydrogen, CF$_3$, —(CR$^{2e}$R$^{2f}$)$_q$OR$^b$, (CR$^{2e}$R$^{2f}$)$_q$S(O)$_p$R$^b$, —(CR$^{2e}$R$^{2f}$)r-C(O)R$^{1d}$, —(CR$^{2e}$R$^{2f}$)r-C(O)OR$^b$, —(CR$^{2e}$R$^{2f}$)$_q$OC(O)R$^b$, —(CR$^{2e}$R$^{2f}$)$_q$NR$^{11}$R$^{11}$, —(CR$^{2e}$R$^{2f}$)r-C(O)NR$^{11}$R$^{11}$, —(CR$^{2e}$R$^{2f}$)$_q$NR$^b$C(O)R$^{1c}$, (CR$^{2e}$R$^{2f}$)$_q$NR$^b$C(O)OR$^c$, —(CR$^{2e}$R$^{2f}$)$_q$NR$^b$C(O)NR$^{11}$R$^{11}$, —(CR$^{2e}$R$^{2f}$)$_q$S(O)$_2$NR$^{11}$R$^{11}$, —(CR$^{2e}$R$^{2f}$)$_q$NR$^b$S(O)$_2$R$^c$, C$_{1-6}$ alkyl substituted with 0-3 R$^a$, C$_{1-6}$ haloalkyl, —(CR$^{2e}$R$^{2f}$)r-3-14 membered carbocycle substituted with 0-3 R$^a$, or —(CR$^{2e}$R$^{2f}$)r-5-7 membered heterocycle comprising carbon atoms and 1-4 heteroatoms selected from N, O, and S(O)$_p$ substituted with 0-3 R$^a$;

R$^4$ and R$^5$ are independently hydrogen, halo, C$_{1-6}$ alkyl or C$_{1-6}$ haloalkyl, or R$^4$ and R$^5$ together with the carbon atom to which they are attached form a 3- to 6-membered spirocarbocyclyl ring or a spiroheterocyclyl ring;

R$^6$ and R$^7$ are independently hydrogen, C$_{1-6}$ alkyl or C$_{1-6}$ haloalkyl;

R$^{11}$ is, independently at each occurrence, hydrogen, C$_{1-6}$ alkyl substituted with 0-3 R$^f$, CF$_3$, C$_{3-10}$ cycloalkyl substituted with 0-3 R$^f$, —(CR$^{2e}$R$^{2f}$)r-phenyl substituted with 0-3 R$^d$, or —(CR$^{2e}$R$^{2f}$)r-5-7 membered heterocycle comprising carbon atoms and 1-4 heteroatoms selected from N, O, P(=O) and S(O)$_p$ substituted with 0-4 R$^d$;

or one R$^{11}$ and a second R$^{11}$, both attached to the same nitrogen atom, combine to form a heterocycle comprising carbon atoms and 1-4 heteroatoms selected from N, O, P(=O) and S(O)$_p$ substituted with 0-4 R$^d$;

R$^a$ is, independently at each occurrence, hydrogen, =O, halo, OCF$_3$, CF$_3$, CHF$_2$, CN, NO$_2$, —(CR$^{2e}$R$^{2f}$)r-OR$^b$, —(CR$^{2e}$R$^{2f}$)r-S(O)$_p$R$^b$, —(CR$^{2e}$R$^{2f}$)r-C(O)R$^b$, —(CR$^{2e}$R$^{2f}$)r-C(O)OR$^b$, —(CR$^{2e}$R$^{2f}$)r-OC(O)R$^b$, —(CR$^{2e}$R$^{2f}$)r-NR$^{11}$R$^{11}$, —(CR$^{2e}$R$^{2f}$)r-C(O)NR$^{11}$R$^{11}$, —(CR$^{2e}$R$^{2f}$)r-NR$^b$C (O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{2e}$R$^{2f}$)r-3-14 membered carbocycle, or —(CR$^{2e}$R$^{2f}$)r-5-7 membered heterocycle comprising carbon atoms and 1-4 heteroatoms selected from N, O, P(=O) and S(O)$_p$ substituted with 0-4 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{2e}$R$^{2f}$)r-5-7 membered heterocycle comprising carbon atoms and 1-4 heteroatoms selected from N, O, P(=O) and S(O)$_p$ substituted with 0-4 R$^f$, or —(CR$^{2e}$R$^{2f}$)r-6-10 membered carbocycle substituted with 0-3 R$^d$;

R$^c$ is, independently at each occurrence, C$_{1-6}$ alkyl substituted with 0-3 R$^f$, —(CR$^{2e}$R$^{2f}$)r-C$_{3-6}$ cycloalkyl substituted with 0-3 R$^f$, or —(CR$^{2e}$R$^{2f}$)r-phenyl substituted with 0-3 R$^f$;

R$^d$ is, independently at each occurrence, hydrogen, =O, halo, OCF$_3$, CF$_3$, CN, NO$_2$, —OR$^e$, —(CR$^{2e}$R$^{2f}$)r-C(O)R$^c$, —NR$^e$R$^e$, —NR$^e$C(O)OR$^c$, C(O)NR$^e$R$^e$, —NR$^e$C(O)R$^c$, CO$_2$H, CO$_2$R$^c$, —NR$^e$SO$_2$R$^c$, SO$_2$R$^c$, C$_{1-6}$ alkyl substituted with 0-3 R$^f$, C$_{3-6}$ cycloalkyl substituted with 0-3 R$^f$, —(CR$^{2e}$R$^{2f}$)r-phenyl substituted with 0-3 R$^f$ or —(CR$^{2e}$R$^{2f}$)r-5-7 membered heterocycle comprising carbon atoms and 1-4 heteroatoms selected from N, O, P(=O) and S(O)$_p$ substituted with 0-3 R$^f$;

R$^e$ is, independently at each occurrence, selected from hydrogen, C(O)NR$^f$R$^f$, C$_{1-6}$ alkyl, C$_{3-6}$ cycloalkyl, -5-7 membered heterocycle or —(CR$^{2e}$R$^{2f}$)r-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$(C$_{1-6}$ alkyl), CO$_2$H, CO$_2$(C$_{1-6}$ alkyl), OH, C$_{3-6}$ cycloalkyl, CF$_3$, O(C$_{1-6}$ alkyl), or an optionally substituted —(CR$^{2e}$R$^{2f}$)r-5-10 membered heterocycle comprising carbon atoms and 1-4 heteroatoms selected from N, O, P(=O) and S(O)$_p$, phenyl or C$_{3-6}$ cycloalkyl, each group optionally substituted with halo, CN, CF$_3$, C$_{1-6}$ alkyl or O(C$_{1-6}$ alkyl);

m is 0, 1, 2 or 3 n is 1 or 2;

p and q are, independently at each occurrence, 0, 1, or 2;

r is 0, 1, 2, 3, or 4; and t is 0 or 1.

In another aspect, the invention comprises compounds of formula IIa

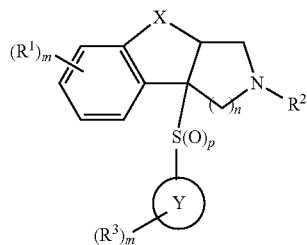

(IIa)

wherein

X is —CR$^4$R$^5$—, —O—, —NR$^6$—, —S(O)$_p$—, —(CR$^4$R$^5$)$_2$—, —OCR$^6$R$^7$—, —CR$^6$R$^7$O—, —S(O)$_p$CR$^6$R$^7$—, —CR$^6$R$^7$S(O)$_p$—, —NR$^6$CR$^6$R$^7$— or —CR$^6$R$^7$NR$^6$—;

Y is a 5 or 6-membered aromatic or heteroaromatic ring;

R$^1$ is, independently at each occurrence, selected from halo, C$_{1-6}$ alkyl substituted with 0-3 R$^{1a}$, —(CR$^{2e}$R$^{2f}$)r-3-14 membered carbocycle substituted with 0-3 R$^{1a}$ and —(CR$^{2e}$R$^{2f}$)r-5-10 membered heterocycle comprising carbon atoms, and 1-4 heteroatoms selected from N, O, and S(O)$_p$ substituted with 0-3 R$^{1a}$;

R$^{1a}$ is, independently at each occurrence, hydrogen, =O, halo, CF$_3$, OCF$_3$, CN, NO$_2$, —(CR$^{2e}$R$^{2f}$)$_r$—OR$^b$, —(CR$^{2e}$R$^{2f}$)$_r$—S(O)$_p$R$^b$, —(CR$^{2e}$R$^{2f}$)$_r$—C(O)R$^b$, —(CR$^{2e}$R$^{2f}$)$_r$—C(O)OR$^b$, —(CR$^{2e}$R$^{2f}$)r-OC(O)R$^b$, —(CR$^{2e}$R$^{2f}$)r-NR$^{11}$R$^{11}$, (CR$^{2e}$R$^{2f}$)r-C(O)NR$^{11}$R$^{11}$, —(CR$^{2e}$R$^{2f}$)$_r$—NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{2e}$R$^{2f}$)r-3-14 membered carbocycle substituted with 0-3 R$^a$, or —(CR$^{2e}$R$^{2f}$)r-5-7 membered heterocycle comprising carbon atoms, and 1-4 heteroatoms selected from N, O, and S(O)$_p$ substituted with 0-3 R$^a$;

R$^2$ is selected from hydrogen, —(CR$^{2e}$R$^{2f}$)r-C(O)R$^{2d}$, —(CR$^{2e}$R$^{2f}$)r-C(O)OR$^2$b, —(CR$^{2e}$R$^{2f}$)r-C(O)NR$^{11}$R$^{11}$, —(CR$^{2e}$R$^{2f}$)r-S(O)$_2$R$^{2c}$, C$_{1-6}$ alkyl substituted with 0-3 R$^{2a}$, C$_{2-6}$ alkenyl substituted with 0-3 R$^{2a}$, —(CR$^{2e}$R$^{2f}$)r-3-10 membered carbocycle substituted with 0-3 R$^a$, and —(CR$^{2e}$R$^{2f}$)r-4-7 membered heterocycle comprising carbon atoms, and 1-4 heteroatoms selected from N, O, P(=O) and S(O), substituted with 0-4 R$^a$;

R$^{2a}$ is, independently at each occurrence, hydrogen, =O, halo, OCF$_3$, CN, NO$_2$, —(CR$^{2e}$R$^{2f}$)r-OR$^b$, —(CR$^{2e}$R$^{2f}$)r-S(O)$_p$R$^b$, —(CR$^{2e}$R$^{2f}$)r-C(O)R$^b$, —(CR$^{2e}$R$^{2f}$)r-C(O)OR$^b$, —(CR$^{2e}$R$^{2f}$)r-OC(O)R$^b$, —(CR$^{2e}$R$^{2f}$)r-OC(O)NR$^{11}$R$^{11}$, —(CR$^{2e}$R$^{2f}$)r-OC(O)OR$^c$, —(CR$^{2e}$R$^{2f}$)r-NR$^{11}$R$^{11}$, —(CR$^{2e}$R$^{2f}$)r-C(O)NR$^{11}$R$^{11}$, —(CR$^{2e}$R$^{2f}$)r-NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CR$^{2e}$R$^{2f}$)r-3-14 membered carbocycle substituted with 0-3 R$^a$, or —(CR$^{2e}$R$^{2f}$)r-4-7 membered heterocycle comprising carbon atoms, and 1-4 heteroatoms selected from N, O, P(=O) and S(O)$_p$ substituted with 0-4 R$^a$;

R$^{2b}$ is, independently at each occurrence, hydrogen, CF$_3$, —(CR$^{2e}$R$^{2f}$)$_q$OR$^b$, —(CR$^{2e}$R$^{2f}$)$_q$S(O)$_p$R$^b$, —(CR$^{2e}$R$^{2f}$)r-C(O)R$^{1d}$, —(CR$^{2e}$R$^{2f}$)r-C(O)OR$^b$, —(CR$^{2e}$R$^{2f}$)$_q$OC(O)R$^b$, —(CR$^{2e}$R$^{2f}$)$_q$NR$^{11}$R$^{11}$, —(CR$^{2e}$R$^{2f}$)r-C(O)NR$^{11}$R$^{11}$, —(CR$^{2e}$R$^{2f}$)$_q$NR$^b$C(O)R$^{1c}$, —(CR$^{2e}$R$^{2f}$)$_q$NR$^b$C(O)OR$^c$, —(CR$^{2e}$R$^{2f}$)$_q$NR$^b$C(O)NR$^{11}$R$^{11}$, —(CR$^{2e}$R$^{2f}$)$_q$S(O)$_2$NR$^{11}$R$^{11}$, —(CR$^{2e}$R$^{2f}$)$_q$NR$^b$S(O)$_2$R$^c$, C$_{1-6}$ alkyl substituted with 0-2 R$^a$, C$_{1-6}$ haloalkyl, —(CR$^{2e}$R$^{2f}$)r-3-14 membered carbocycle substituted with 0-3 R$^a$, or —(CR$^{2e}$R$^{2f}$)r-5-7 membered heterocycle comprising carbon atoms and 1-4 heteroatoms selected from N, O, P(=O) and S(O)$_p$ substituted with 0-4 R$^a$;

R$^{2c}$ is, independently at each occurrence, hydrogen, C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or —(CR$^{2e}$R$^{2f}$)r-5-10 membered heterocycle containing 1-4 heteroatoms selected from N, O, P(=O) and S(O)$_p$, substituted with 0-4 R$^a$;

R$^{2d}$ is, independently at each occurrence, hydrogen, C$_{1-6}$ alkyl substituted with 0-2 R$^d$, C$_{1-6}$ haloalkyl, C(O)NR$^{11}$R$^{11}$, —(CR$^{2e}$R$^{2f}$)r-C$_{3-10}$ cycloalkyl substituted with 0-3 R$^d$, where the cycloalkyl ring may be fused, bridged or spirocyclic, —(CR$^{2e}$R$^{2f}$)r-phenyl substituted with 0-2 R$^a$, or a —(CR$^{2e}$R$^{2f}$)r-4-10 membered heterocycle where the heterocycle may be fused, bridged or spirocyclic, containing 1-4 heteroatoms selected from N, O, P(=O) and S(O)$_p$, substituted with 0-4 R$^a$;

R$^{2e}$ and R$^{2f}$ are, independently at each occurrence, hydrogen, halogen or C$_{1-6}$ alkyl;

R$^3$ is, independently at each occurrence, selected from hydrogen, halo, N$_3$, CN, —(CR$^{2e}$R$^{2f}$)r-OR$^{3b}$, —(CR$^{2e}$R$^{2f}$)r-NR$^{11}$R$^{11}$, C$_{1-6}$ alkyl substituted with 0-3 R$^{3a}$, C$_{3-10}$ cycloalkyl substituted with 0-3 R$^{3a}$; and phenyl substituted with 0-3 R$^{3a}$, or 4-10 membered heterocycle containing 1-4 heteroatoms selected from N, O, and S(O)$_p$, substituted with 0-3 R$^{3a}$, or two R$^3$ located on adjacent carbon atoms link to form a 5-7 membered carbocycle or a 5-7 membered heterocycle comprising carbon atoms and 1-4 heteroatom selected from N, O and S(O)$_p$, both optionally substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CR$^{2e}$R$^{2f}$)r-OR$^b$, —(CR$^{2e}$R$^{2f}$)r-S(O)$_p$R$^b$, —(CR$^{2e}$R$^{2f}$)r-C(O)R$^b$, —(CR$^{2e}$R$^{2f}$)r-C(O)OR$^b$, —(CR$^{2e}$R$^{2f}$)r-OC(O)R$^b$, —(CR$^{2e}$R$^{2f}$)r-NR$^{11}$R$^{11}$, —(CR$^{2e}$R$^{2f}$)r-C(O)NR$^{11}$R$^{11}$, —(CR$^{2e}$R$^{2f}$)r-NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CR$^{2e}$R$^{2f}$)r-3-14 membered carbocycle substituted with 0-3 R$^a$, or —(CR$^{2e}$R$^{2f}$)r-5-10 membered heterocycle comprising carbon atoms and 1-4 heteroatoms selected from N, O, and S(O)$_p$ substituted with 0-3 R$^a$;

R$^{3b}$ is, independently at each occurrence, hydrogen, CF$_3$, —(CR$^{2e}$R$^{2f}$)$_q$OR$^b$, (CR$^{2e}$R$^{2f}$)$_q$S(O)$_p$R$^b$, —(CR$^{2e}$R$^{2f}$)r-C(O)R$^{1d}$, —(CR$^{2e}$R$^{2f}$)r-C(O)OR$^b$, —(CR$^{2e}$R$^{2f}$)$_q$OC(O)R$^b$, —(CR$^{2e}$R$^{2f}$)$_q$NR$^{11}$R$^{11}$, —(CR$^{2e}$R$^{2f}$)r-C(O)NR$^{11}$R$^{11}$, —(CR$^{2e}$R$^{2f}$)$_q$NR$^b$C(O)R$^b$, —(CR$^{2e}$R$^{2f}$)$_q$NR$^b$C(O)OR$^c$, —(CR$^{2e}$R$^{2f}$)$_q$NR$^b$C(O)NR$^{11}$R$^{11}$, —(CR$^{2e}$R$^{2f}$)$_q$S(O)$_2$NR$^{11}$R$^{11}$, —(CR$^{2e}$R$^{2f}$)$_q$NR$^b$S(O)$_2$R$^c$, C$_{1-6}$ alkyl substituted with 0-3 R$^a$, C$_{1-6}$ haloalkyl, —(CR$^{2e}$R$^{2f}$)r-3-14 membered carbocycle substituted with 0-3 R$^a$, or —(CR$^{2e}$R$^{2f}$)r-5-7 membered heterocycle comprising carbon atoms and 1-4 heteroatoms selected from N, O, and S(O)$_p$ substituted with 0-3 R$^a$;

R$^4$ and R$^5$ are independently hydrogen, halo, C$_{1-6}$ alkyl or C$_{1-6}$ haloalkyl, or R$^4$ and R$^5$ together with the carbon atom to which they are attached form a 3- to 6-membered spirocarbocyclyl ring or a spiroheterocyclyl ring;

R$^6$ and R$^7$ are independently hydrogen, C$_{1-6}$ alkyl or C$_{1-6}$ haloalkyl;

R$^{11}$ is, independently at each occurrence, hydrogen, C$_{1-6}$ alkyl substituted with 0-3 R$^f$, CF$_3$, C$_{3-10}$ cycloalkyl substituted with 0-3 R$^f$, —(CR$^{2e}$R$^{2f}$)r-phenyl substituted with 0-3 R$^d$, or —(CR$^{2e}$R$^{2f}$)r-5-7 membered heterocycle comprising carbon atoms and 1-4 heteroatoms selected from N, O, P(=O) and S(O)$_p$ substituted with 0-4 R$^d$;

or one R$^{11}$ and a second R$^{11}$, both attached to the same nitrogen atom, combine to form a heterocycle comprising carbon atoms and 1-4 heteroatoms selected from N, O, P(=O) and S(O)$_p$ substituted with 0-4 R$^d$;

R$^a$ is, independently at each occurrence, hydrogen, =O, halo, OCF$_3$, CF$_3$, CHF$_2$, CN, NO$_2$, —(CR$^{2e}$R$^{2f}$)r-OR$^b$, —(CR$^{2e}$R$^{2f}$)r-S(O)$_p$R$^b$, —(CR$^{2e}$R$^{2f}$)r-C(O)R$^b$, —(CR$^{2e}$R$^{2f}$)r-C(O)OR$^b$, —(CR$^{2e}$R$^{2f}$)r-OC(O)R$^b$, —(CR$^{2e}$R$^{2f}$)r-NR$^{11}$R$^{11}$, —(CR$^{2e}$R$^{2f}$)r-C(O)NR$^{11}$R$^{11}$, —(CR$^{2e}$R$^{2f}$)r-NR$^b$C(O)R$^c$, —(CR$^{2e}$R$^{2f}$)r-NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^e$, C$_{2-6}$ alkynyl substituted with 0-3 R$^e$, —(CR$^{2e}$R$^{2f}$)r-3-14 membered carbocycle, or —(CR$^{2e}$R$^{2f}$)r-5-7 membered heterocycle comprising carbon atoms and 1-4 heteroatoms selected from N, O, and S(O)$_p$ substituted with 0-3 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CR$^{2e}$R$^{2f}$)r-5-7 membered heterocycle comprising carbon atoms and 1-4 heteroatoms selected from N, O, P(=O) and S(O)$_p$ substituted with 0-4 R$^f$, or —(CR$^{2e}$R$^{2f}$)r-6-10 membered carbocycle substituted with 0-3 R$^d$;

R$^c$ is, independently at each occurrence, C$_{1-6}$ alkyl substituted with 0-3 R$^f$, —(CR$^{2e}$R$^{2f}$)r-C$_{3-6}$ cycloalkyl substituted with 0-3 R$^f$, or —(CR$^{2e}$R$^{2f}$)r-phenyl substituted with 0-3 R$^f$;

R$^d$ is, independently at each occurrence, hydrogen, =O, halo, OCF$_3$, CF$_3$, CN, NO$_2$, —OR$^e$, —(CR$^{2e}$R$^{2f}$)r-C(O)R$^c$, —NR$^e$R$^e$, —NR$^e$C(O)OR$^c$, C(O)NR$^e$R$^e$, —NR$^e$C(O)R$^c$, CO$_2$H, CO$_2$R$^c$, —NR$^e$SO$_2$R$^c$, SO$_2$R$^c$, C$_{1-6}$ alkyl substituted with 0-3 R$^f$, C$_{3-6}$ cycloalkyl substituted with 0-3 R$^f$, —(CR$^{2e}$R$^{2f}$)r-phenyl substituted with 0-3 R$^f$ or —(CR$^{2e}$R$^{2f}$)r-5-7 membered heterocycle comprising carbon atoms and 1-4 heteroatoms selected from N, O, P(=O) and S(O)$_p$ substituted with 0-4 R$^f$;

R$^e$ is, independently at each occurrence, selected from hydrogen, C(O)NR$^f$R$^f$, C$_{1-6}$ alkyl, C$_{3-6}$ cycloalkyl, -5-7 membered heterocycle or —(CR$^{2e}$R$^{2f}$)r-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$(C$_{1-6}$ alkyl), CO$_2$H, CO$_2$(C$_{1-6}$ alkyl), OH, C$_{3-6}$ cycloalkyl, CF$_3$, O(C$_{1-6}$ alkyl), or an optionally substituted —(CR$^{2e}$R$^{2f}$)r-5-10 membered heterocycle comprising carbon atoms and 1-4 heteroatoms selected from N, O, P(=O) and S(O)$_p$, phenyl or C$_{3-6}$ cycloalkyl, each group optionally substituted with halo, CN, CF$_3$, C$_{1-6}$ alkyl or O(C$_{1-6}$ alkyl);

m is 0, 1, 2 or 3 n is 1 or 2;

p and q are, independently at each occurrence, 0, 1, or 2; and r is 0, 1, 2, 3, or 4;

or a stereoisomer or pharmaceutically-acceptable salt thereof.

In another aspect, the invention comprises compounds of the formula

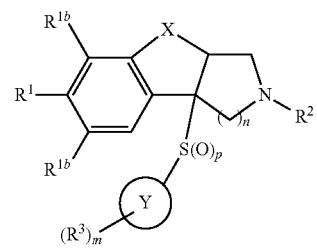

wherein

X is —CR$^4$R$^5$—, —O—, —NR$^6$—, —S(O)$_p$—, —(CR$^4$R$^5$)$_2$—, —OCR$^6$R$^7$—, —CR$^6$R$^7$O—, —S(O)$_p$CR$^6$R$^7$—, —CR$^6$R$^7$S(O)$_p$—, —NR$^6$CR$^6$R$^7$— or —CR$^6$R$^7$NR$^6$—;

Y is a 5 or 6-membered aromatic or heteroaromatic ring;

R$^1$ is selected from halo, C$_{1-6}$ alkyl substituted with 0-3 R$^{1a}$, —(CR$^{2e}$R$^{2f}$)r-3-14 membered carbocycle substituted with 0-3 R$^{1a}$ and —(CR$^{2e}$R$^{2f}$)r-5-10 membered heterocycle comprising carbon atoms, and 1-4 heteroatoms selected from N, O, and $S(O)_p$ substituted with 0-3 $R^{1a}$;

$R^{1a}$ is, independently at each occurrence, hydrogen, =O, halo, $CF_3$, $OCF_3$, CN, $NO_2$, $-(CR^{2e}R^{2f})_r-OR^b$, $-(CR^{2e}R^{2f})_r-S(O)_pR^b$, $-(CR^{2e}R^{2f})_r-C(O)R^b$, $-(CR^{2e}R^{2f})_r-C(O)OR^b$, $-(CR^{2e}R^{2f})r-OC(O)R^b$, $-(CR^{2e}R^{2f})r-NR^{11}R^{11}$, $(CR^{2e}R^{2f})r-C(O)NR^{11}R^{11}$, $-(CR^{2e}R^{2f})_r-NR^bC(O)R^c$, $-(CR^{2e}R^{2f})r-NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, $-(CR^{2e}R^{2f})r$-3-14 membered carbocycle substituted with 0-3 $R^a$, or $-(CR^{2e}R^{2f})r$-5-7 membered heterocycle comprising carbon atoms, and 1-4 heteroatoms selected from N, O, and $S(O)_p$ substituted with 0-3 $R^a$;

$R^{1b}$ is, independently at each occurrence, hydrogen, $CD_3$, halo, $CF_3$, and $C_1$-$C_4$ alkyl;

$R^2$ is selected from hydrogen, $-(CR^{2e}R^{2f})r-C(O)R^{2d}$, $-(CR^{2e}R^{2f})r-C(O)OR^{2b}$, $-(CR^{2e}R^{2f})r-C(O)NR^{11}R^{11}$, $-(CR^{2e}R^{2f}r-S(O)_2R^{2c}$, $C_{1-6}$ alkyl substituted with 0-3 $R^{2a}$, $C_{2-6}$ alkenyl substituted with 0-3 $R^{2a}$, $-(CR^{2e}R^{2f})r$-3-10 membered carbocycle substituted with 0-3 $R^a$, and $-(CR^{2e}R^{2f})r$-4-7 membered heterocycle comprising carbon atoms, and 1-4 heteroatoms selected from N, O, P(=O) and $S(O)_p$ substituted with 0-4 $R^a$;

$R^{2a}$ is, independently at each occurrence, hydrogen, =O, halo, $OCF_3$, CN, $NO_2$, $-(CR^{2e}R^{2f})r-OR^b$, $-(CR^{2e}R^{2f})r-S(O)_pR^b$, $-(CR^{2e}R^{2f})r-C(O)R^b$, $-(CR^{2e}R^{2f})r-C(O)OR^b$, $-(CR^{2e}R^{2f})r-OC(O)R^b$, $-(CR^{2e}R^{2f})r-OC(O)NR^{11}R^{11}$, $-(CR^{2e}R^{2f})r-OC(O)OR^c$, $-(CR^{2e}R^{2f})r-NR^{11}R^{11}$, $-(CR^{2e}R^{2f})r-C(O)NR^{11}R^{11}$, $-(CR^{2e}R^{2f})r-NR^bC(O)R^c$, $-(CR^{2e}R^{2f})r-NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, $-(CR^{2e}R^{2f})r$-3-14 membered carbocycle substituted with 0-3 $R^a$, or $-(CR^{2e}R^{2f})r$-4-7 membered heterocycle comprising carbon atoms, and 1-4 heteroatoms selected from N, O, P(=O) and $S(O)_p$ substituted with 0-4 $R^a$;

$R^{2b}$ is, independently at each occurrence, hydrogen, $CF_3$, $-(CR^{2e}R^{2f})_qOR^b$, $-(CR^{2e}R^{2f})_qS(O)_pR^b$, $-(CR^{2e}R^{2f})r-C(O)R^{1d}$, $-(CR^{2e}R^{2f})r-C(O)OR^b$, $-(CR^{2e}R^{2f})_qOC(O)R^b$, $-(CR^{2e}R^{2f})_qNR^{11}R^{11}$, $-(CR^{2e}R^{2f})r-C(O)NR^{11}R^{11}$, $-(CR^{2e}R^{2f})_qNR^bC(O)R^{1c}$, $-(CR^{2e}R^{2f})_qNR^bC(O)OR^c$, $-(CR^{2e}R^{2f})_qNR^bC(O)NR^{11}R^{11}$, $-(CR^{2e}R^{2f})_qS(O)_2NR^{11}R^{11}$, $-(CR^{2e}R^{2f})_qNR^bS(O)_2R^c$, $C_{1-6}$ alkyl substituted with 0-2 $R^a$, $C_{1-6}$ haloalkyl, $-(CR^{2e}R^{2f})r$-3-14 membered carbocycle substituted with 0-3 $R^a$, or $-(CR^{2e}R^{2f})r$-5-7 membered heterocycle comprising carbon atoms and 1-4 heteroatoms selected from N, O, P(=O) and S(O), substituted with 0-4 $R^a$;

$R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or $-(CR^{2e}R^{2f})r$-5-10 membered heterocycle containing 1-4 heteroatoms selected from N, O, P(=O) and $S(O)_p$, substituted with 0-4 $R^a$;

$R^{2d}$ is, independently at each occurrence, hydrogen, $C_{1-6}$ alkyl substituted with 0-2 $R^d$, $C_{1-6}$ haloalkyl, $C(O)NR^{11}R^{11}$, $-(CR^{2e}R^{2f})r-C_{3-10}$ cycloalkyl substituted with 0-3 $R^d$, where the cycloalkyl ring may be fused, bridged or spirocyclic, $-(CR^{2e}R^{2f})r$-phenyl substituted with 0-2 $R^a$, or a $-(CR^{2e}R^{2f})r$-4-10 membered heterocycle where the heterocycle may be fused, bridged or spirocyclic, containing 1-4 heteroatoms selected from N, O, P(=O) and $S(O)_p$, substituted with 0-4 $R^a$;

$R^{2e}$ and $R^{2f}$ are, independently at each occurrence, hydrogen, halogen or $C_{1-6}$ alkyl;

$R^3$ is, independently at each occurrence, selected from hydrogen, halo, $N_3$, CN, $-(CR^{2e}R^{2f})r-OR^{3b}$, $-(CR^{2e}R^{2f})r-NR^{11}R^{11}$, $C_{1-6}$ alkyl substituted with 0-3 $R^{3a}$, $C_{3-10}$ cycloalkyl substituted with 0-3 $R^{3a}$; and phenyl substituted with 0-3 $R^{3a}$, or 4-10 membered heterocycle containing 1-4 heteroatoms selected from N, O, and $S(O)_p$, substituted with 0-3 $R^{3a}$, or two $R^3$ located on adjacent carbon atoms link to form a 5-7 membered carbocycle or a 5-7 membered heterocycle comprising carbon atoms and 1-4 heteroatom selected from N, O and $S(O)_p$, both optionally substituted with 0-3 $R^{3a}$; $R^{3a}$ is, independently at each occurrence, hydrogen, =O, halo, $OCF_3$, $OCHF_2$, $CF_3$, $CHF_2$, CN, $NO_2$, $-(CR^{2e}R^{2f})r-OR^b$, $-(CR^{2e}R^{2f})r-S(O)_pR^b$, $-(CR^{2e}R^{2f})r-C(O)R^b$, $-(CR^{2e}R^{2f})r-C(O)OR^b$, $-(CR^{2e}R^{2f})r-OC(O)R^b$, $-(CR^{2e}R^{2f})r-NR^{11}R^{11}$, $-(CR^{2e}R^{2f})r-C(O)NR^{11}R^{11}$, $-(CR^{2e}R^{2f})r-NR^bC(O)R^c$, $-(CR^{2e}R^{2f})r-NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, $-(CR^{2e}R^{2f})r$-3-14 membered carbocycle substituted with 0-3 $R^a$, or $-(CR^{2e}R^{2f})r$-5-10 membered heterocycle comprising carbon atoms and 1-4 heteroatoms selected from N, O, and $S(O)_p$ substituted with 0-3 $R^a$;

$R^{3b}$ is, independently at each occurrence, hydrogen, $CF_3$, $-(CR^{2e}R^{2f})_qOR^b$, $(CR^{2e}R^{2f})_qS(O)_pR^b$, $-(CR^{2e}R^{2f})r-C(O)R^d$, $-(CR^{2e}R^{2f})r-C(O)OR^b$, $-(CR^{2e}R^{2f})_qOC(O)R^b$, $-(CR^{2e}R^{2f})_qNR^{11}R^{11}$, $-(CR^{2e}R^{2f})r-C(O)NR^{11}R^{11}$, $-(CR^{2e}R^{2f})_qNR^bC(O)R^{1c}$, $-(CR^{2e}R^{2f})_qNR^bC(O)OR^c$, $-(CR^{2e}R^{2f})_qNR^bC(O)NR^{11}R^{11}$, $-(CR^{2e}R^{2f})_qS(O)_2NR^{11}R^{11}$, $-(CR^{2e}R^{2f})_qNR^bS(O)_2R^c$, $C_{1-6}$ alkyl substituted with 0-3 $R^a$, $C_{1-6}$ haloalkyl, $-(CR^{2e}R^{2f})r$-3-14 membered carbocycle substituted with 0-3 $R^a$, or $-(CR^{2e}R^{2f})r$-5-7 membered heterocycle comprising carbon atoms and 1-4 heteroatoms selected from N, O, and $S(O)_p$ substituted with 0-3 $R^a$;

$R^4$ and $R^5$ are independently hydrogen, halo, $C_{1-6}$ alkyl or $C_{1-6}$ haloalkyl, or $R^4$ and $R^5$ together with the carbon atom to which they are attached form a 3- to 6-membered spirocarbocyclyl ring or a spiroheterocyclyl ring;

$R^6$ and $R^7$ are independently H, $C_{1-6}$ alkyl or $C_{1-6}$ haloalkyl;

$R^{11}$ is, independently at each occurrence, hydrogen, $C_{1-6}$ alkyl substituted with 0-3 $R^f$, $CF_3$, $C_{3-10}$ cycloalkyl substituted with 0-3 $R^f$, $-(CR^{2e}R^{2f})r$-phenyl substituted with 0-3 $R^d$, or $-(CR^{2e}R^{2f})r$-5-7 membered heterocycle comprising carbon atoms and 1-4 heteroatoms selected from N, O, P(=O) and $S(O)_p$ substituted with 0-4 $R^d$;

or one $R^{11}$ and a second $R^{11}$, both attached to the same nitrogen atom, combine to form a heterocycle comprising carbon atoms and 1-4 heteroatoms selected from N, O, P(=O) and $S(O)_p$ substituted with 0-4 $R^d$;

$R^a$ is, independently at each occurrence, hydrogen, =O, halo, $OCF_3$, $CF_3$, $CHF_2$, CN, $NO_2$, $-(CR^{2e}R^{2f})r-OR^b$, $-(CR^{2e}R^{2f})r-S(O)_pR^b$, $-(CR^{2e}R^{2f})r-C(O)R^b$, $-(CR^{2e}R^{2f})r-C(O)OR^b$, $-(CR^{2e}R^{2f})r-OC(O)R^b$, $-(CR^{2e}R^{2f})r-NR^{11}R^{11}$, $-(CR^{2e}R^{2f})r-C(O)NR^{11}R^{11}$, $-(CR^{2e}R^{2f})r-NR^bC(O)R^c$, $-(CR^{2e}R^{2f})r-NR^bC(O)OR^c$, $-NR^bC(O)NR^{11}R^{11}$, $-S(O)_pNR^{11}R^{11}$, $-NR^bS(O)_pR^c$, $C_{1-6}$ alkyl substituted with 0-3 $R^f$, $C_{1-6}$ haloalkyl, $C_{2-6}$ alkenyl substituted with 0-3 $R^e$, $C_{2-6}$ alkynyl substituted with 0-3 $R^e$, $-(CR^{2e}R^{2f})r$-3-14 membered carbocycle, or $-(CR^{2e}R^{2f})r$-5-7 membered heterocycle comprising carbon atoms and 1-4 heteroatoms selected from N, O, P(=O) and $S(O)_p$ substituted with 0-4 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, —$(CR^{2e}R^{2f})_r$-5-7 membered heterocycle comprising carbon atoms and 1-4 heteroatoms selected from N, O, P(=O) and $S(O)_p$ substituted with 0-4 $R^f$, or —$(CR^{2e}R^{2f})_r$-6-10 membered carbocycle substituted with 0-3 $R^d$;

$R^c$ is, independently at each occurrence, $C_{1-6}$ alkyl substituted with 0-3 $R^f$, —$(CR^{2e}R^{2f})_r$-$C_{3-6}$ cycloalkyl substituted with 0-3 $R^f$, or —$(CR^{2e}R^{2f})_r$-phenyl substituted with 0-3 $R^f$;

$R^d$ is, independently at each occurrence, hydrogen, =O, halo, $OCF_3$, $CF_3$, CN, $NO_2$, —$OR^e$, —$(CR^{2e}R^{2f})_r$-$C(O)R^c$, —$NR^eR^e$, —$NR^eC(O)OR^c$, $C(O)NR^eR^e$, —$NR^eC(O)R^c$, $CO_2H$, $CO_2R^c$, —$NR^eSO_2R^c$, $SO_2R^c$, $C_{1-6}$ alkyl substituted with 0-3 $R^f$, $C_{3-6}$ cycloalkyl substituted with 0-3 $R^f$, —$(CR^{2e}R^{2f})_r$-phenyl substituted with 0-3 $R^f$ or —$(CR^{2e}R^{2f})_r$-5-7 membered heterocycle comprising carbon atoms and 1-4 heteroatoms selected from N, O, P(=O) and $S(O)_p$ substituted with 0-4 $R^f$;

$R^e$ is, independently at each occurrence, selected from hydrogen, $C(O)NR^fR^f$, $C_{1-6}$ alkyl, $C_{3-6}$ cycloalkyl, -5-7 membered heterocycle or —$(CR^{2e}R^{2f})_r$-phenyl substituted with 0-3 $R^f$;

$R^f$ is, independently at each occurrence, hydrogen, =O, halo, CN, $NH_2$, $NH(C_{1-6}$ alkyl), $N(C_{1-6}$ alkyl$)_2$, $SO_2(C_{1-6}$ alkyl), $CO_2H$, $CO_2(C_{1-6}$ alkyl), OH, $C_{3-6}$ cycloalkyl, $CF_3$, $O(C_{1-6}$ alkyl), or an optionally substituted —$(CR^{2e}R^{2f})_r$-5-10 membered heterocycle comprising carbon atoms and 1-4 heteroatoms selected from N, O, P(=O) and $S(O)_p$, phenyl or $C_{3-6}$ cycloalkyl, each group optionally substituted with halo, CN, $CF_3$, $C_{1-6}$ alkyl or $O(C_{1-6}$ alkyl);

m is 0, 1, 2 or 3 n is 1 or 2;

p and q are, independently at each occurrence, 0, 1, or 2; and r is 0, 1, 2, 3, or 4;

or a stereoisomer or pharmaceutically-acceptable salt thereof.

In another aspect, the invention comprises compounds of the formula

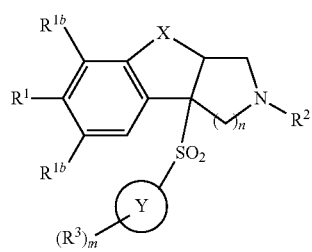

or a stereoisomer or pharmaceutically-acceptable salt thereof.

In another aspect, the invention comprises compounds of the formula

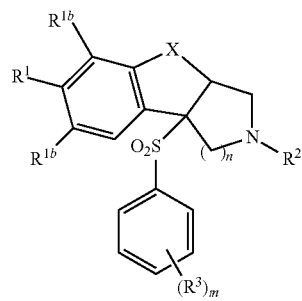

or a stereoisomer or pharmaceutically acceptable salt thereof.

In another aspect, the invention comprises compounds of the formula

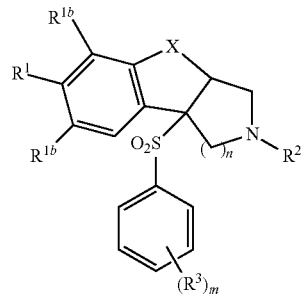

or a stereoisomer or pharmaceutically acceptable salt thereof.

In another aspect, the invention comprises compounds of the formula

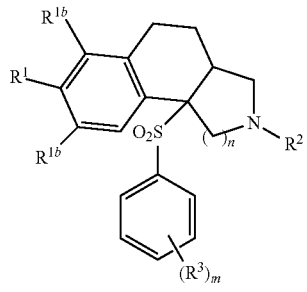

or a stereoisomer or pharmaceutically-acceptable salt thereof.

In another aspect, the invention comprises compounds of the formula

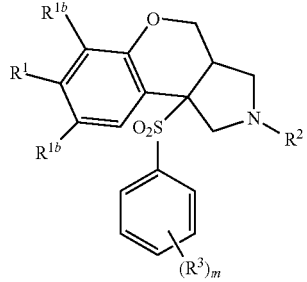

or a stereoisomer or pharmaceutically-acceptable salt thereof.

In another aspect, the invention comprises compounds of the formula

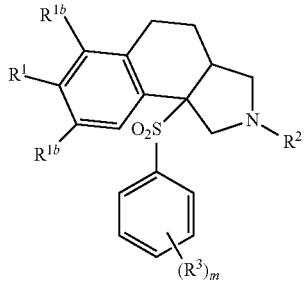

wherein $R^1$ is halo, phenyl substituted with 0-3 $R^{1a}$, or $C_{1-6}$ alkyl substituted with 0-3 $R^{1a}$;

$R^{1a}$ is, independently at each occurrence, hydrogen, $CF_3$, halo, $C_{1-6}$ alkyl substituted with 0-3 $R^a$, —$(CR^{2e}R^{2f})_r$-$OR^b$, and —$(CR^{2e}R^{2f})_r$-phenyl substituted with 0-3 $R^a$, $R^{1b}$ is, independently at each occurrence, hydrogen, $CD_3$, halo, $CF_3$, and $C_1$-$C_4$ alkyl;

$R^2$ is hydrogen, $SO_2R^{2c}$, $C_{1-6}$ alkyl substituted with 0-3 $R^{2a}$, $CO_2R^{2b}$, —$C(O)R^{2d}$, —$C(O)NR^{11}R^{11}$; or a 5-7 membered heterocycle comprising carbon atoms, and 1-4 heteroatoms selected from N, O, P(=O) and $S(O)_p$ substituted with 0-4 $R^a$, $R^{2a}$ is hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})_r$-5-7 membered heterocycle comprising carbon atoms and 1-4 heteroatoms selected from N, O, P(=O) and $S(O)_p$ substituted with 0-4 $R^a$, or —$(CR^{2e}R^{2f})_r$-phenyl substituted with 0-3 $R^a$;

$R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CR^{2e}R^{2f})_r$-5-10-membered heterocycle containing 1-4 heteroatoms selected from N, O, P(=O) and $S(O)_p$, substituted with 0-4 $R^a$;

$R^{2d}$ is, independently at each occurrence, hydrogen, $C_{1-6}$ alkyl substituted with 0-3 $R^d$, $C_{1-6}$ haloalkyl, $C(O)NR^{11}R^{11}$, $C_{3-10}$ cycloalkyl substituted with 0-2 $R^d$, $(CR^{2e}R^{2f})_r$-phenyl substituted with 0-2 $R^a$, or a 4-10 membered heterocycle containing 1-4 heteroatoms selected from N, O, P(=O) and $S(O)_p$, substituted with 0-4 $R^a$;

$R^3$ is, independently at each occurrence, hydrogen, halo, $N_3$, CN, $OR^{3b}$, —$NH_2$, $NH(C_{1-6}$ alkyl), $N(C_{1-6}$ alkyl$)_2$, $C_{1-6}$ alkyl substituted with 0-3 $R^{3a}$ or $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{2e}R^{2f})_r$-$OR^b$, —$(CR^{2e}R^{2f})_r$-$S(O)_pR^b$, —$(CR^{2e}R^{2f})_r$-$C(O)R^b$, —$(CR^{2e}R^{2f})_r$-$C(O)OR^b$, —$(CR^{2e}R^{2f})_r$-$OC(O)R^b$, —$(CR^{2e}R^{2f})_r$-$NR^{11}R^{11}$, —$(CR^{2e}R^{2f})_r$-$C(O)NR^{11}R^{11}$, —$(CR^{2e}R^{2f})_r$-$NR^bC(O)R^c$, —$(CR^{2e}R^{2f})_r$-$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{2e}R^{2f})_r$-3-14 membered carbocycle substituted with 0-3 $R^a$, or —$(CR^{2e}R^{2f})_r$-5-10 membered heterocycle comprising carbon atoms and 1-4 heteroatoms selected from N, O, and $S(O)_p$ substituted with 0-3 $R^a$; and $R^{3b}$ is, independently at each occurrence, hydrogen, $C_{1-6}$ alkyl substituted with 0-3 $R^a$ or phenyl substituted with 0-3 $R^a$;

or a stereoisomer or pharmaceutically-acceptable salt thereof.

In another aspect, the invention comprises compounds of the formula

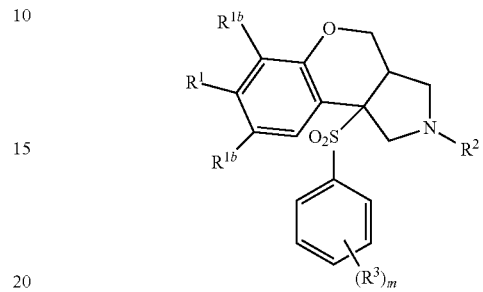

wherein $R^1$ is halo, phenyl substituted with 0-3 $R^{1a}$, or $C_{1-6}$ alkyl substituted with 0-3 $R^{1a}$;

$R^{1a}$ is, independently at each occurrence, hydrogen, $CF_3$, halo, $C_{1-6}$ alkyl substituted with 0-3 $R^a$, —$(CR^{2e}R^{2f})_r$-$OR^b$, and —$(CR^{2e}R^{2f})_r$-phenyl substituted with 0-3 $R^a$, $R^{1b}$ is, independently at each occurrence, hydrogen, $CD_3$, halo, $CF_3$, and $C_1$-$C_4$ alkyl;

$R^2$ is hydrogen, $SO_2R^{2c}$, $C_{1-6}$ alkyl substituted with 0-3 $R^{2a}$, $CO_2R^{2b}$, —$C(O)R^{2d}$, —$C(O)NR^{11}R^{11}$; or a 5-7 membered heterocycle comprising carbon atoms, and 1-4 heteroatoms selected from N, O, P(=O) and $S(O)_p$ substituted with 0-4 $R^a$, $R^{2a}$ is hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})_r$-5-7 membered heterocycle comprising carbon atoms and 1-4 heteroatoms selected from N, O, P(=O) and $S(O)_p$ substituted with 0-4 $R^a$, or —$(CR^{2e}R^{2f})_r$-phenyl substituted with 0-3 $R^a$;

$R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CR^{2e}R^{2f})_r$-5-10-membered heterocycle containing 1-4 heteroatoms selected from N, O, P(=O) and $S(O)_p$, substituted with 0-4 $R^a$;

$R^{2d}$ is, independently at each occurrence, hydrogen, $C_{1-6}$ alkyl substituted with 0-3 $R^d$, $C_{1-6}$ haloalkyl, $C(O)NR^{11}R^{11}$, $C_{3-10}$ cycloalkyl substituted with 0-2 $R^d$, $(CR^{2e}R^{2f})_r$-phenyl substituted with 0-2 $R^a$, or a 4-10 membered heterocycle containing 1-4 heteroatoms selected from N, O, P(=O) and $S(O)_p$, substituted with 0-4 $R^a$;

$R^3$ is, independently at each occurrence, hydrogen, halo, $N_3$, CN, $OR^{3b}$, —$NH_2$, $NH(C_{1-6}$ alkyl), $N(C_{1-6}$ alkyl$)_2$, $C_{1-6}$ alkyl substituted with 0-3 $R^{3a}$ or $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CR^{2e}R^{2f})_r$-$OR^b$, —$(CR^{2e}R^{2f})_r$-$S(O)_pR^b$, —$(CR^{2e}R^{2f})_r$-$C(O)R^b$, —$(CR^{2e}R^{2f})_r$-$C(O)OR^b$, —$(CR^{2e}R^{2f})_r$-$OC(O)R^b$, —$(CR^{2e}R^{2f})_r$-$NR^{11}R^{11}$, —$(CR^{2e}R^{2f})_r$-$C(O)NR^{11}R^{11}$, —$(CR^{2e}R^{2f})_r$-$NR^bC(O)R^c$, —$(CR^{2e}R^{2f})_r$-$NR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CR^{2e}R^{2f})_r$-3-14 membered carbocycle substituted with 0-3 $R^a$, or —$(CR^{2e}R^{2f})$r-5-10 membered heterocycle comprising carbon atoms and 1-4 heteroatoms selected from N, O, and $S(O)_p$ substituted with 0-3 $R^a$; and $R^{3b}$ is, independently at each occurrence, hydrogen, $C_{1-6}$ alkyl substituted with 0-3 $R^a$ or phenyl substituted with 0-3 $R^a$;

or a stereoisomer or pharmaceutically-acceptable salt thereof.

In another aspect, the invention comprises compounds of the formula

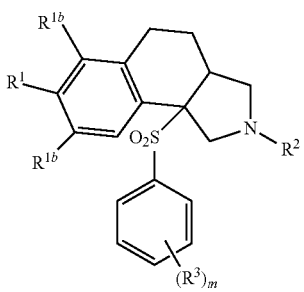

wherein $R^1$ is $C_{1-6}$ alkyl substituted with 0-3 $R^{1a}$;

$R^{1a}$ is, independently at each occurrence, hydrogen, $CF_3$, halo or $C_{1-6}$ alkyl substituted with 0-3 $R^a$;

$R^{1b}$ is, independently at each occurrence, hydrogen, $CD_3$, halo, $CF_3$, and $C_1$-$C_4$ alkyl;

$R^2$ is $C_{1-6}$ alkyl substituted with 0-3 $R^{2a}$, $CO_2R^{2b}$, —C(O)$R^{2d}$ or —C(O)$NR^{11}R^{11}$;

$R^{2a}$ is hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})$r-5-7 membered heterocycle comprising carbon atoms and 1-4 heteroatoms selected from N, O, P(=O) and $S(O)_p$ substituted with 0-4 $R^a$, or —$(CR^{2e}R^{2f})$r-phenyl substituted with 0-3 $R^a$;

$R^{2d}$ is, independently at each occurrence, $C_{3-10}$ cycloalkyl substituted with 0-2 $R^d$, or a 4-10 membered heterocycle containing 1-4 heteroatoms selected from N, O, P(=O) and $S(O)_2$, substituted with 0-4 $R^a$;

$R^3$ is hydrogen, halo or $C_{1-6}$ alkyl;

or a stereoisomer or pharmaceutically-acceptable salt thereof.

In another aspect, the invention comprises compounds of the formula

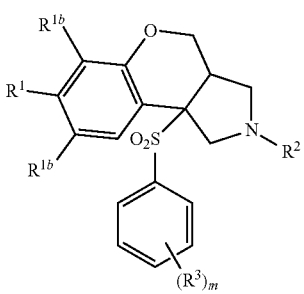

wherein $R^1$ is $C_{1-6}$ alkyl substituted with 0-3 $R^{1a}$;

$R^{1a}$ is, independently at each occurrence, hydrogen, $CF_3$, halo or $C_{1-6}$ alkyl substituted with 0-3 $R^a$;

$R^{1b}$ is, independently at each occurrence, hydrogen, $CD_3$, halo, $CF_3$, and $C_1$-$C_4$ alkyl;

$R^2$ is $C_{1-6}$ alkyl substituted with 0-3 $R^{2a}$, $CO_2R^{2b}$, —C(O)$R^{2d}$ or —C(O)$NR^{11}R^{11}$;

$R^{2a}$ is hydrogen or $C_{1-6}$ alkyl substituted with 0-3 $R^a$;

$R^{2b}$ is hydrogen, $C_{1-6}$ alkyl substituted with 0-2 $R^a$, $C_{3-6}$ cycloalkyl substituted with 0-3 $R^a$, —$(CR^{2e}R^{2f})$r-5-7 membered heterocycle comprising carbon atoms and 1-4 heteroatoms selected from N, O, P(=O) and $S(O)_p$ substituted with 0-4 $R^a$, or —$(CR^{2e}R^{2f})$r-phenyl substituted with 0-3 $R^a$;

$R^{2d}$ is, independently at each occurrence, $C_{3-10}$ cycloalkyl substituted with 0-2 $R^d$, or a 4-10 membered heterocycle containing 1-4 heteroatoms selected from N, O, P(=O) and $S(O)_2$, substituted with 0-4 $R^a$;

$R^3$ is hydrogen, halo or $C_{1-6}$ alkyl;

or a stereoisomer or pharmaceutically-acceptable salt thereof.

In another aspect, the invention comprises compounds of the formula

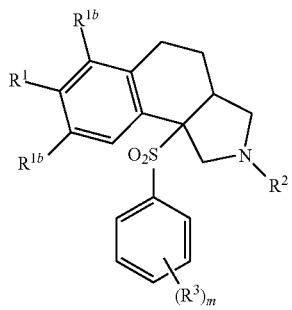

wherein $R^1$ is

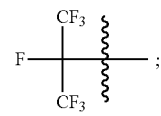

$R^{1b}$ is, independently at each occurrence, hydrogen, $CD_3$, halo, $CF_3$, and $C_1$-$C_4$ alkyl;

$R^2$ is —C(O)$R^{2d}$;

$R^{2d}$ is, independently at each occurrence, $C_{3-10}$ cycloalkyl substituted with 0-2 $R^d$, or a 4-10 membered heterocycle containing 1-4 heteroatoms selected from N, O, P(=O) and $S(O)_2$, substituted with 0-4 $R^a$;

$R^3$ is F, Cl or methyl;

or a stereoisomer or pharmaceutically-acceptable salt thereof.

In another aspect, the invention comprises compounds of the formula

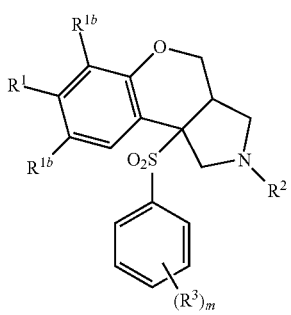

wherein
R¹ is

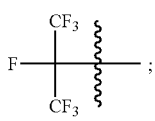

$R^{1b}$ is, independently at each occurrence, hydrogen, $CD_3$, halo, $CF_3$, and $C_1$-$C_4$ alkyl;

$R^2$ is —$C(O)R^{2d}$;

$R^{2d}$ is, independently at each occurrence, $C_{3-10}$ cycloalkyl substituted with 0-2 $R^d$, or a 4-10 membered heterocycle containing 1-4 heteroatoms selected from N, O, P(=O) and $S(O)_2$, substituted with 0-4 $R^a$;

$R^3$ is F, Cl or methyl;

or a stereoisomer or pharmaceutically-acceptable salt thereof.

In another aspect, there is provided a compound of Formula (I), or stereoisomers, tautomers, pharmaceutically acceptable salts, solvates, or prodrugs thereof, wherein $R^2$ is:

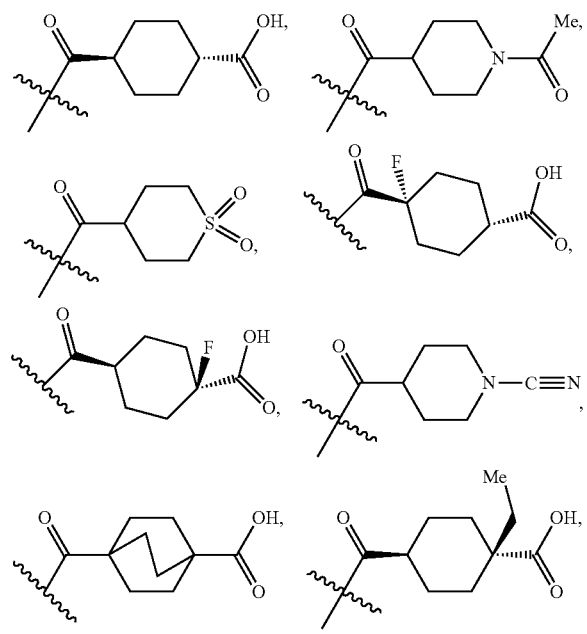

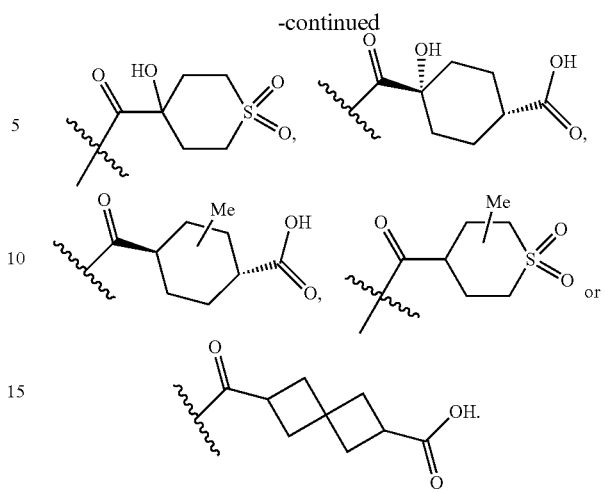

In another aspect, there is provided a compound selected from the exemplified examples within the scope of the first aspect, or a pharmaceutically acceptable salt, tautomer or stereoisomer thereof.

In another aspect, there is provided a compound selected from the exemplified examples within the scope of formula II, or a pharmaceutically acceptable salt, tautomer or stereoisomer thereof.

In another aspect, there is provided a compound selected from any subset list of compounds within the scope of any of the above aspects.

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof In another embodiment, the invention provides a compound of the present invention for use in therapy.

In another embodiment, the invention provides a combined preparation of a compound of the present invention and additional therapeutic agent(s) for simultaneous, separate or sequential use in therapy.

In another embodiment, the invention provides a compound of the present invention for use in treating diseases (or a method of treating diseases) in which inflammation is a component including, without limitation, diseases such as psoriasis, rheumatoid arthritis, inflammatory bowel disease, Crohn's disease, ulcerative colitis, acute graft-versus-host disease, psoriatic arthritis, ankylosing spondylitis and multiple sclerosis.

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

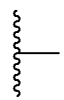

is used in structural formulas herein to depict the bond that is the point of attachment of the moiety or substituent to the core or backbone structure.

A dash "-" that is not between two letters or symbols is used to indicate a point of attachment for a substituent. For example, —$CONH_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound."

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group, for example, aryl or heteroaryl groups which are optionally substituted for example with alkyl, halo or haloalkyl. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "$CO_2$" is used herein, this is intended to refer to the group

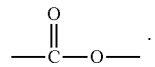

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, S(O)$_2$H, or S(O)H group.

The term "cycloalkyl" refers to cyclized alkyl groups, including mono-, bi- or poly-cyclic ring systems. C$_{3-7}$ cycloalkyl is intended to include C$_3$, C$_4$, C$_5$, C$_6$, and C$_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Thus, examples of aryl groups include:

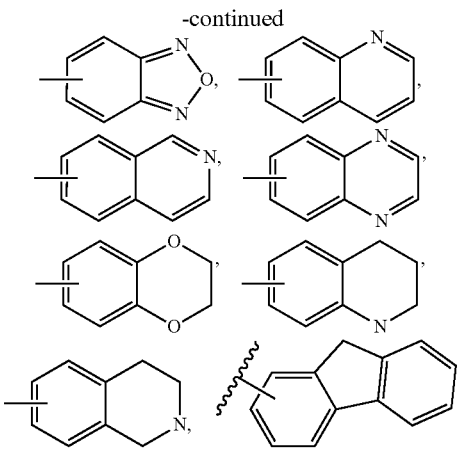

-continued

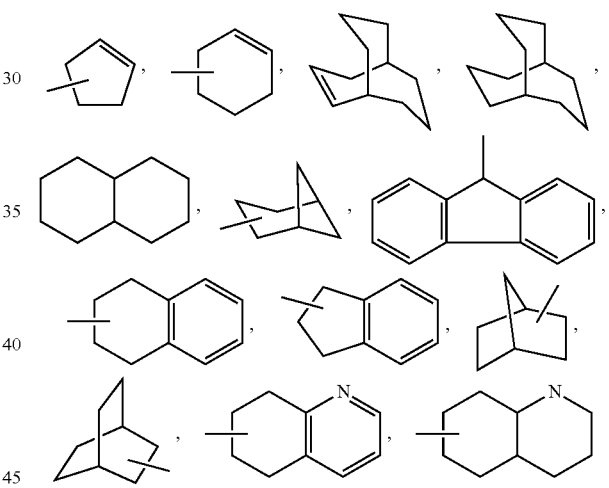

(fluorenyl) and the like, which optionally may be substituted at any available carbon or nitrogen atom. A preferred aryl group is optionally-substituted phenyl.

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems:

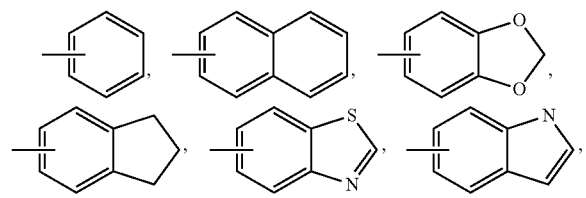

and the like, which optionally may be substituted at any available atoms of the ring(s). Preferred cycloalkyl groups include cyclopropyl, cyclopentyl, cyclohexyl, and

The term "halo" or "halogen" refers to chloro, bromo, fluoro and iodo.

The term "haloalkyl" means a substituted alkyl having one or more halo substituents. For example, "haloalkyl" includes mono, di, and trifluoromethyl.

The term "haloalkoxy" means an alkoxy group having one or more halo substituents. For example, "haloalkoxy" includes OCF$_3$.

The terms "heterocycle", "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocycle groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

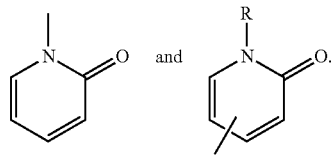

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrolinyl, acridinyl, phenanthridinyl, xanthenyl and the like.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The terms "carbocycle, carbocyclyl or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, hydrogen sulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogen sulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization. One enantiomer of a compound of Formulas I and II may display superior activity compared with the other.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:
a) Bundgaard, H., ed., *Design of Prodrugs*, Elsevier (1985), and Widder, K. et al., eds., Methods in Enzymology, 112:309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and
c) Bundgaard, H., *Adv. Drug Deliv. Rev.*, 8:1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers.

It should further be understood that solvates (e.g., hydrates) of the compounds of Formula I are also with the scope of the present invention. Methods of solvation are generally known in the art.

Another aspect of the invention is a pharmaceutical composition including a compound, stereoisomeric form, pharmaceutical salt, solvate or hydrate as described herein. The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by U.S. regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the subject by employing procedures known in the art.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former.

The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a subject will vary depending upon what is being administered, the purpose of the administration, such as prophylaxis or therapy, the state of the subject, the manner of administration, and the like. In therapeutic applications, compositions can be administered to a subject already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the subject, and the like.

The compositions administered to a subject can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the subject, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular subject, the relative biological efficacy of the compound selected, formulation of the excipient, and its route of administration. Effective doses can be extrapolated from dose-response curves derived from in vitro or animal model test systems.

The compounds of the present invention are useful to prevent, diagnose, and treat various medical disorders in humans or animals. The compounds are used to inhibit or reduce one or more activities associated with RORγ receptors, relative to RORγ receptors in the absence of the same compounds. Thus, in one aspect of the invention, a method for treating a disease or disorder selected from an autoimmune disease or disorder, asthma, an allergic disease or disorder, a metabolic disease or disorder, and cancer in a subject comprises administering to the subject a therapeutically effective amount of compound according to formula (I), stereoisomeric form, N-oxide, pharmaceutically acceptable salt, solvate, hydrate or pharmaceutical composition as described herein. See, e.g., L. A. Solt et al., "Action of RORs and their ligands in (patho)physiology," *Trends Endocrinol. Metab.* 2012, 23 (12): 619-627; M. S. Maddur et al., "Th17 cells: biology, pathogenesis of autoimmune and inflammatory diseases, and therapeutic strategies," *Am. J. Pathol.* 2012 July; 181(1):8-18; and A. M. Jetten, "Retinoid-related orphan receptors (RORs): critical roles in development, immunity, circadian rhythm, and cellular metabolism," *Nucl. Recept. Signal.* 2009; 7:e003, each of which is hereby incorporated herein by reference in its entirety, as well as the references discussed in the Background section. In certain embodiments, the autoimmune disease or disorder is selected from rheumatoid arthritis, ankylosing spondylitis, psoriasis and psoriatic arthritis, multiple sclerosis, inflammatory bowel diseases and lupus. In certain embodiments, the allergic disease or disorder is selected from allergic rhinitis and dermatitis. In certain embodiments, the metabolic disease or disorder is selected from obesity, obesity-induced insulin resistance and type II diabetes.

In certain embodiments, the disease or disorder is rheumatoid arthritis. See, e.g., L. A. Solt et al., referenced above, as well as the references discussed in the Background section.

In other embodiments, the disease or disorder is multiple sclerosis. See, e.g., L. Codarri et al., "RORγt drives production of the cytokine GM-CSF in helper T cells, which is essential for the effector phase of autoimmune neuroinflammation," *Nat. Immunol.,* 2011 June; 12(6):560-7, which is hereby incorporated herein by reference in its entirety, as well as the references discussed in the Background section.

In other embodiments, the disease or disorder is ankylosing spondylitis. See, e.g., E. Toussirot, "The IL23/Th17 pathway as a therapeutic target in chronic inflammatory diseases," *Inflamm. Allergy Drug Targets,* 2012 April; 11(2): 159-68, which is hereby incorporated herein by reference in its entirety, as well as the references discussed in the Background section.

In other embodiments, the disease or disorder is inflammatory bowel disease. See, e.g., M. Leppkes et al., "ROR-gamma-expressing Th17 cells induce murine chronic intestinal inflammation via redundant effects of IL-17A and IL-17F," *Gastroenterology,* 2009 January; 136(1):257-67, which is hereby incorporated herein by reference in its entirety, as well as the references discussed in the Background section.

In other embodiments, the disease or disorder is lupus. See, e.g., K. Yoh et al., "Overexpression of RORγt under control of the CD2 promoter induces polyclonal plasmacytosis and autoantibody production in transgenic mice," *Eur. J. Immunol.*, 2012 August; 42(8): 1999-2009, which is hereby incorporated herein by reference in its entirety, as well as the references discussed in the Background section.

In other embodiments, the disease or disorder is psoriasis. See, e.g., S. Pantelyushin et al., "RORγt+ innate lymphocytes and γδ T cells initiate psoriasiform plaque formation in mice," *J. Clin. Invest.*, 2012 Jun. 1; 122(6):2252-6; and S. P. Raychaudhri, "Role of IL-17 in Psoriasis and Psoriatic Arthritis," Clin. Rev. Allergy Immunol., 2013; 44(2): 183-193, each of which is hereby incorporated herein by reference in its entirety, as well as the references discussed in the Background section.

In other embodiments, the disease or disorder is psoriatic arthritis. See, e.g., S. P. Raychaudhri, referenced above, as well as the references discussed in the Background section.

In other embodiments, the disease or disorder is graft-vs.-host disease (GVHD). Y. Yu et al., "Prevention of GVHD while sparing GVL effect by targeting Th1 and Th17 transcription factor T-bet and RORγt in mice," *Blood,* 2011 Nov. 3; 118(18):5011-20, which is hereby incorporated by reference in its entirety, as well as the references discussed in the Background section.

In other embodiments, the disease or disorder is autoimmune uveitis. See, e.g., R. Horai et al., "Cytokines in autoimmune uveitis," *J. Interferon Cytokine Res.,* 2011 October; 31(10):733-44, which is hereby incorporated herein by reference in its entirety, as well as the references discussed in the Background section.

In other embodiments, the disease or disorder is obesity and/or insulin resistance. See, e.g., B. Meissburger et al., "Adipogenesis and insulin sensitivity in obesity are regulated by retinoid-related orphan receptor gamma," *EMBO Mol. Med.,* 2011 November; 3(11):637-51, which is hereby incorporated herein by reference in its entirety, as well as the references discussed in the Background section.

In other embodiments, the disease or disorder is melanoma. See, e.g., Purwar R, et al. Robust tumor immunity to melanoma mediated by interleukin-9-producing T cells. Nat. Med., 2012 July: 18:1248-53, which is hereby incorporated herein by reference in its entirety, as well as the references discussed in the Background section.

In certain aspects, the medical disorder being diagnosed, treated, or prevented by use of the presently disclosed compounds can be, for example, an autoimmune disorder. In other embodiments, the disorder being diagnosed, treated or prevented by use of the presently disclosed compounds can be an inflammatory disorder. For example, in certain embodiments, the disorder is selected from arthritis, diabetes, multiple sclerosis, uveitis, rheumatoid arthritis, psoriasis, asthma, bronchitis, allergic rhinitis, chronic obstructive pulmonary disease, atherosclerosis, *H. pylori* infection and inflammatory bowel disease. In other embodiments, the disorder is selected from Crohn's disease, ulcerative colitis, sprue and food allergies. In other embodiments, the disorder is experimental autoimmune encephalomyelitis, imiquimod-induced psoriasis, colitis or allergic airway disease.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; (ii) eliciting the biological or medicinal response that is being sought in a tissue, system, animal, individual or human by a researcher, veterinarian, medical doctor or other clinician; or (iii) inhibiting the referenced disease state; for example, inhibiting a disease, condition or disorder in an individual who is experiencing or displaying the pathology or symptomatology of the disease, condition or disorder.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Examples of compounds of the present invention prepared by methods described in the general schemes are given in the Examples section set out hereinafter. Preparation of homochiral examples may be carried out by techniques known to one skilled in the art. For example, homochiral compounds may be prepared by separation of racemic products or diastereomers by chiral phase preparative HPLC. Alternatively, the example compounds may be prepared by methods known to give enantiomerically or diastereomerically enriched products.

The reactions and techniques described in this section are performed in solvents appropriate to the reagents and materials employed and are suitable for the transformations being effected. Also, in the description of the synthetic methods given below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art, with alternatives required when incompatible substituents are present. This will sometimes require a judgment to modify the order of the synthetic steps or to select one particular process scheme over another in order to obtain a desired compound of the invention. It will also be recognized that another major consideration in the planning of any synthetic route in this field is the judicious choice of a protecting group used for protection of reactive functional groups present in the compounds described in this invention. An authoritative account describing the many alternatives to the trained practitioner is Wuts and Greene, *Greene's Protective Groups in Organic Synthesis*, Fourth Edition, Wiley and Sons (2007).

Scheme 1 illustrates a method for the preparation of compounds 7. An appropriately functionalized carbonyl compound 1 (which can be purchased or synthesized using typical conditions; see, for example: *Eur. J. Med. Chem.* 2015, 90, 834; *Science of Synthesis* 2077, 31a, 1097; PCT Int. Appl. 2014/138484; *Bioorg. Med. Chem. Lett.* 2012, 22, 240; *Eur. J. Med. Chem.* 2013, 69, 490; or PCT Int. Appl. 2013/178322) may be reacted with an appropriate thiol in the presence of an acid such as HCl or $TiCl_4$ to afford a vinyl sulfide 2a, a thioketal 2b, or a mixture of 2a and 2b. Oxidation of sulfide 2a, thioketal 2b, or a mixture of 2a and 2b can be accomplished using a reagent such as m-chloroperoxybenzoic acid to afford sulfone 3. A nucleophile such as an amino alcohol 4 can then be added, yielding an alcohol 5. This compound could be converted to the corresponding methanesulfonate 6 using methanesulfonyl chloride and triethylamine, followed by treatment with a base such as potassium tert-butoxide, to give tricyclic amine 7.

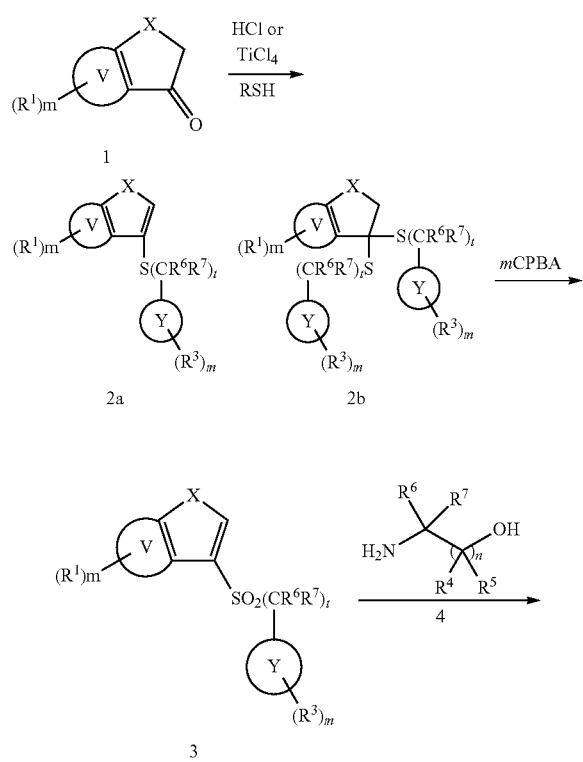

SCHEME 1

An alternative method for the preparation of compounds 7 is shown in Scheme 2. An appropriately substituted olefin 8 (which can be purchased, or prepared using typical methods; see for example US Pat. Appl. 2007/0155738 and US Pat. Appl. 2005/261310) can be converted to the epoxide 9, for example by treatment with a reagent such as m-chloroperoxybenzoic acid. The epoxide may be treated with a nucleophile such as a protected amino alcohol 10 (where P is, for example, tert-butyldimethylsilyl) to provide alcohol 11. Treatment of 11 with a suitable reagent such as triphenylphosphine and diethyl azodicarboxylate can provide the substituted aziridine 12. Treatment of the aziridine with an appropriate thiol can give 13. Protection of the amino group with a suitable protecting group P' such as tert-butoxycarbonyl (Boc) or benzyloxycarbonyl (Cbz), followed by oxidation of the thiol with a reagent such as m-chloroperoxybenzoic acid, can provide the sulfone 14. Selective removal of the alcohol protecting group, followed by conversion to the corresponding methanesulfonate and treatment with a base such as potassium tert-butoxide (as in Scheme 1) can provide 15, which can be deprotected to provide the tricyclic amine 7.

SCHEME 2

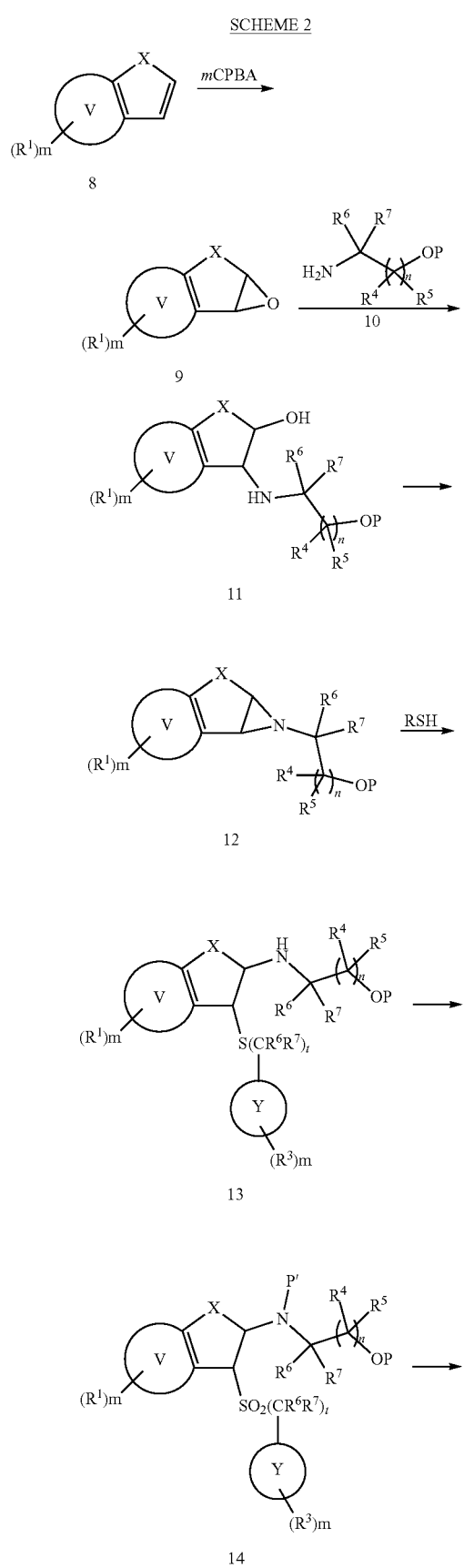

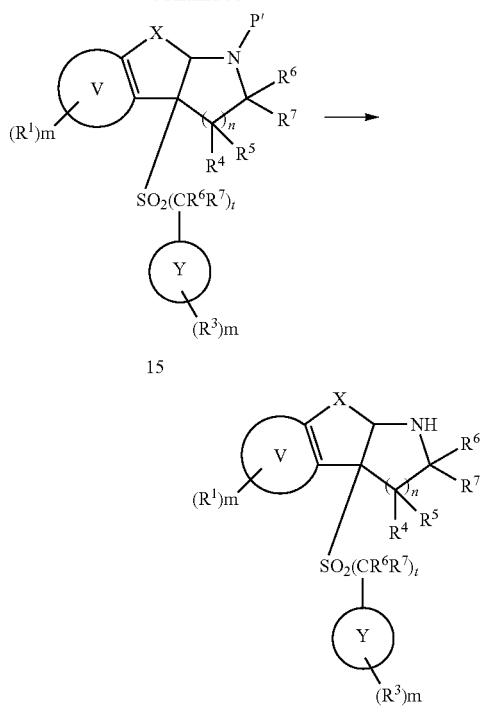

Scheme 3 illustrates an approach to the synthesis of compounds of type 17. Appropriately functionalized vinyl sulfone 3 may undergo cycloaddition reactions with a variety of reagents. For example, reaction with N-benzyl-1-methoxy-N-((trimethylsilyl)methyl)-methanamine in the presence of a catalytic amount of trifluoroacetic acid can provide pyrrolidine 16. Deprotection using hydrogen with catalytic palladium on carbon can give rise to pyrrolidine 17.

SCHEME 3

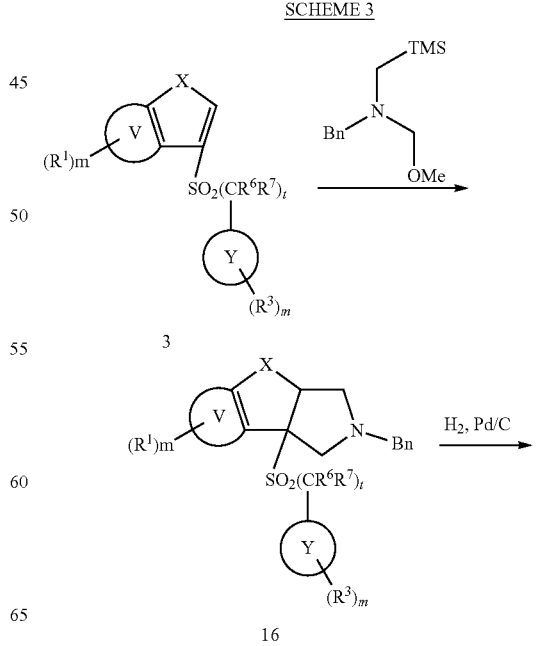

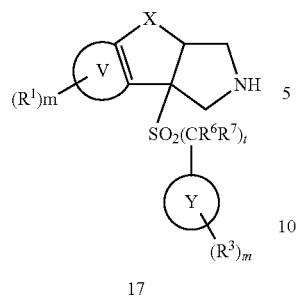

17

An approach to the synthesis of compounds of type 27 is shown in Scheme 4. An appropriate fluoro-substituted aldehyde 18 can be condensed with dimethyl malonate in the presence of an acid and base such as benzoic acid and piperidine to provide 19. This compound can be reacted with an appropriate thiol to provide 20. The ester groups of 20 can be reduced, for example with diisobutylaluminum hydride, to provide the diol 21, which can be treated with a base such as sodium hydride to provide 22. The sulfide can be converted to the corresponding sulfone 23 by treatment with a reagent such as m-chloroperoxybenzoic acid. Oxidation of the carbinol of 23, for example using 1,1,1-tris(acetyloxy)-11-dihydro-1,2-benziodoxol-3-(1H)-one (Dess-Martin periodinane) can provide the aldehyde 24. This material can be reacted with an amino alcohol 4 in the presence of a reducing agent such as sodium triacetoxyborohydride to give 25. Protection of the nitrogen, for example as the Boc or Cbz derivative, followed by conversion to the methanesulfonate and treatment with a base such as potassium tert-butoxide (as in Scheme 1) can provide the tricyclic compound 26. Deprotection of the amine can then provide 27.

SCHEME 4

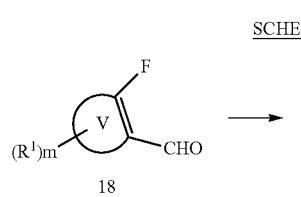

18

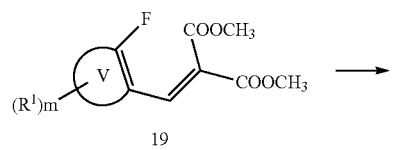

19

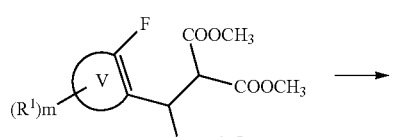

20

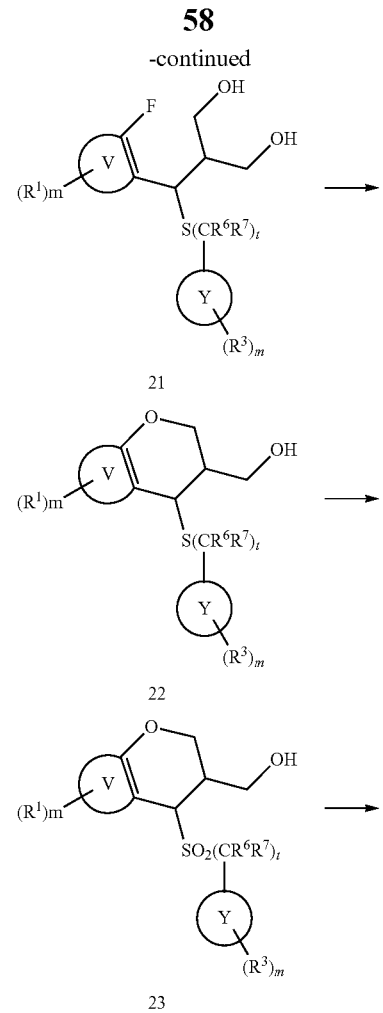

21

22

23

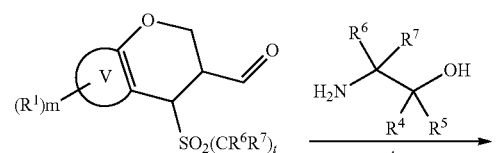

24

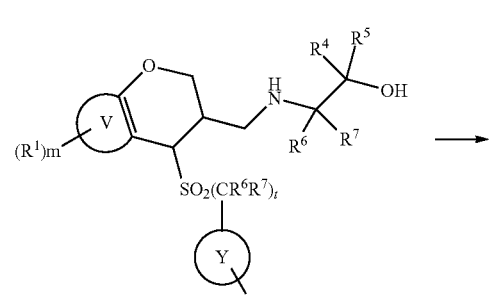

25

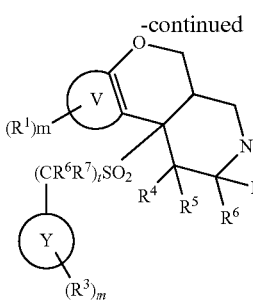

26

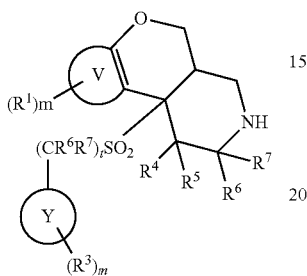

27

Scheme 5 illustrates methods which can provide access to amine intermediates through modification of compounds 7. (The same method can be applied to other intermediates, such as amines 17 or 27.) Amine 7, wherein $R^1$ is a halide such as Cl, Br or I, can be treated with di-tert-butyl dicarbonate to provide the protected amine 28. Any of a number of well-known methods for converting an aromatic halide to a different group can then be applied to convert 28 into 29, where $R^{1'}$ is a different substituent. Some examples, not meant to be limiting, are: (1) treatment with an aryl or alkenyl boronic acid or boronate ester in the presence of a suitable palladium catalyst, commonly known as the Suzuki coupling (see, for example, *Chem. Rev.* 1979, 95, 2457; *J. Organometallic Chem.* 1999, 576, 147), to give 29 where $R^{1'}$ can be aryl, heteroaryl or alkenyl (the latter of which can be further converted to the corresponding alkyl by catalytic reduction); (2) treatment with a zinc reagent such as zinc(II) cyanide or an alkyl- or cycloalkylzinc halide in the presence of a suitable palladium catalyst, commonly known as the Negishi coupling (see, for example, *Metal-Catalyzed Cross-Coupling Reactions* ($2^{nd}$ edition), 2004, 815), to give 29 where $R^{1'}$ can be, for example, alkyl, cycloalkyl or cyano; (3) treatment with an amine or amide in the presence of a suitable palladium catalyst, commonly known as the Buchwald-Hartwig coupling (see, for example, *Chem. Sci.* 2011, 2, 27; *Acc. Chem. Res.* 1998, 31, 805; *Angew. Chem. Int. Ed.* 2008, 47, 6338), to give 29 where $R^{1'}$ can be, for example, dialkylamino; (4) treatment with an organomagnesium halide in the presence of a suitable iron catalyst (see, for example, *Org. React.* 2014, 83, 1; *J. Am. Chem. Soc.,* 2002, 13856), to give 29 where $R^{1'}$ can be, for example, methyl or trideuteromethyl; (5) treatment with a fluorinated alkyl halide in the presence of a copper catalyst (see, for example, *Tetrahedron* 1969, 25, 5921; *Angew. Chem. Int. Ed.* 2011, 50, 3793), to give 29 where $R^{1'}$ can be, for example, trifluoromethyl, heptafluoropropyl, heptafluoroisopropyl, or the like; or (6) treatment with copper(I) halide to give 29 where $R^{1'}$ is a different halide from $R^1$ in 28. Removal of the Boc protecting group can be achieved by treatment with a strong acid such as HCl or trifluoroacetic acid. The same or similar methods can also be applied to a protected amine 30 (or a protected amine derived from amines 17 or 27) wherein $R^3$ is a halide such as Cl, Br or I to give the corresponding 31 where $R^{3'}$ is a different group, as described above.

SCHEME 5

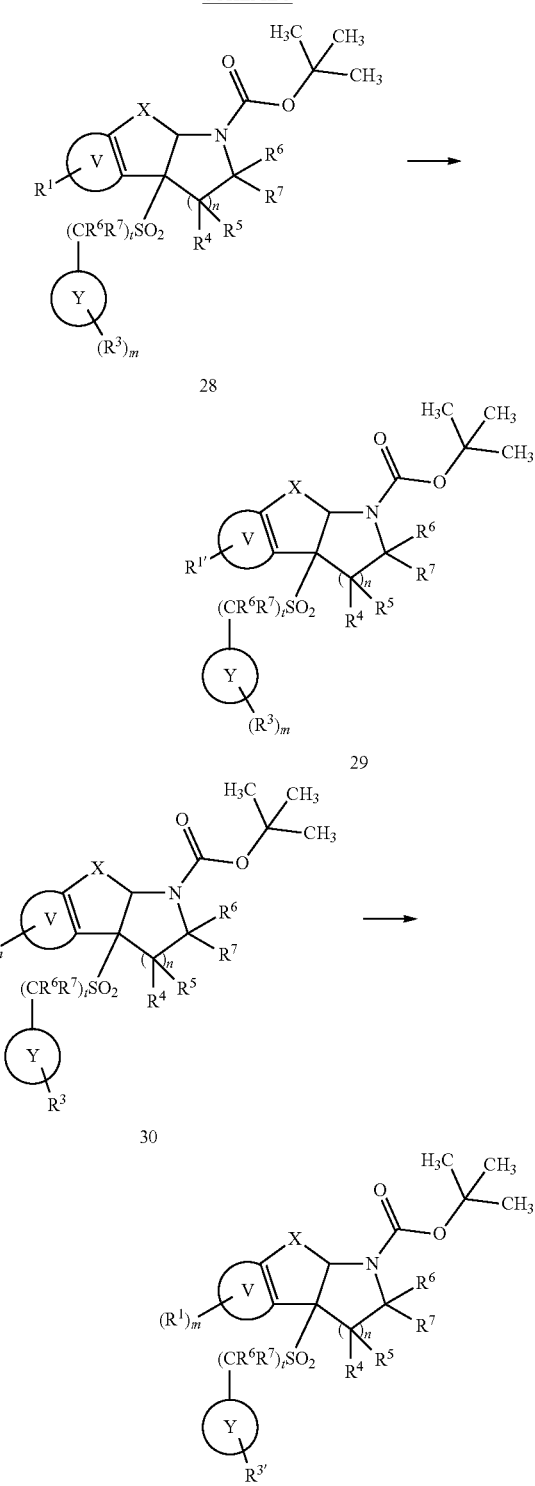

An alternative method for the conversion of a compound 28 where $R^1$ is Br or I to a compound 32 or 33 is shown in Scheme 6. Compound 28 can be treated with an organometallic reagent such as n-butyllithium, and then reacted with a carbonyl containing compound RC(=O)R' to provide alcohol 32. Optionally, alcohol 32 may be treated with a fluorinating agent such as (diethylamino)sulfur trifluoride, affording a fluorinated analog such as 33. Treatment of 32 or 33 with a strong acid such as HCl or trifluoroacetic acid would then remove the Boc protecting group.

SCHEME 6

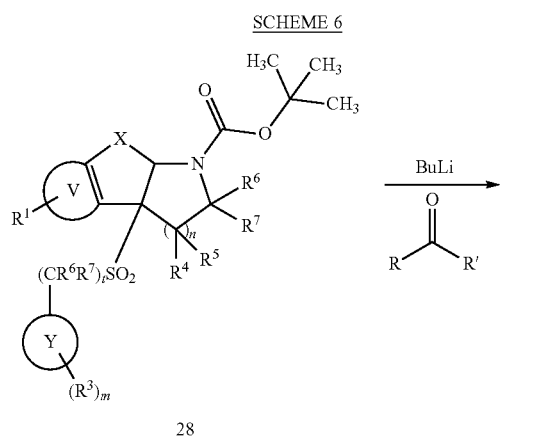

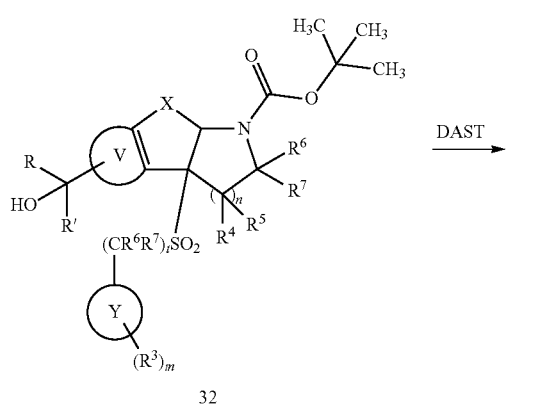

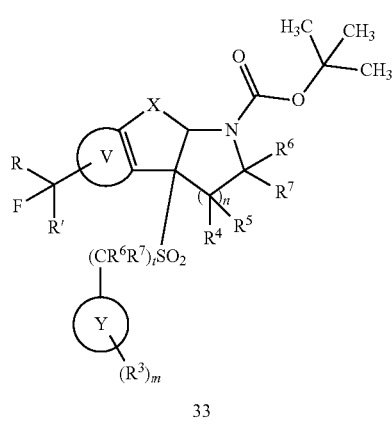

A variety of methods well known in the literature can be used for conversion of amines 7 to compounds of the present invention. (Such methods can also be used for similar conversions of amines 17 and 27 to compounds of the present invention.) Some examples are shown in Scheme 7. An amine 7 can be treated with an acid anhydride (RC(=O))$_2$P or an acid chloride RC(=O)Cl in the presence of a base such as triethylamine or pyridine to provide an amide 34. Alternatively, an amine 7 can be treated with an acid RC(=O)OH in the presence of a suitable base and a coupling reagent such as (benzotriazol-1-yloxy)tris(dimethylamino)phosphonium hexafluorophosphate (BOP), O-(7-azabenzotriazol-1-yl)-1,1,3,3-tetramethyluronium hexafluorophosphate (HATU), benzotriazol-1-yl-oxytripyrrolidinophosphonium hexafluorophosphate (PyBOP), or a combination of 1-hydroxybenzotriazole (HOBT) and N-(3-dimethylaminopropyl)-N'-ethylcarbodiimide (EDC) to provide an amide 34. An amine 7 can also be treated with a sulfonyl chloride RSO$_2$Cl in the presence of a suitable base to provide a sulfonamide 35. An amine 7 can also be treated with an isocyanate RN=C=O to provide a urea 36 (where R' is H), or with an aminocarbonyl chloride RN(R')C(=O)Cl to provide a urea 36. Alternatively, an amine 7 can be treated with phosgene or triphosgene to provide the intermediate N-chlorocarbonyl derivative, which can then be treated with an amine RN(R')H to provide a urea 36. An amine 7 can be treated with a sulfamyl chloride RN(R')SO$_2$Cl to provide a sulfamide 37. An amine 7 can be treated with an appropriate substituted or unsubstituted alkyl halide, cycloalkyl halide, or arylalkyl halide RC(R')(H)X' where X' is Br, I or Cl, or with a related alkyl group containing another leaving group X' such as methanesulfonate or trifluoromethanesulfonate, in the presence of a suitable base, to provide an alkylated amine 38. Alternatively, an amine 7 can be treated with an aldehyde RCHO or a ketone RC(=O)R', in the presence of a reducing agent such as sodium cyanoborohydride or sodium triacetoxyborohydride, to provide an alkylated amine 38 (where R' is H if an aldehyde is used). An amine 7 can be treated with an aryl or heteroaryl iodide ArI, an aryl or heteroaryl bromide ArBr, an aryl or heteroaryl chloride ArCl, or an aryl or heteroaryl trifluoromethanesulfonate ArOS(=O)$_2$CF$_3$ in the presence of a suitable palladium catalyst to provide an arylamine 39 (a reaction commonly known as the Buchwald-Hartwig coupling; see, for example, *Chem. Sci.* 2011, 2, 27; *Acc. Chem. Res.* 1998, 31, 805; *Angew. Chem. Int. Ed.* 2008, 47, 6338).

SCHEME 7

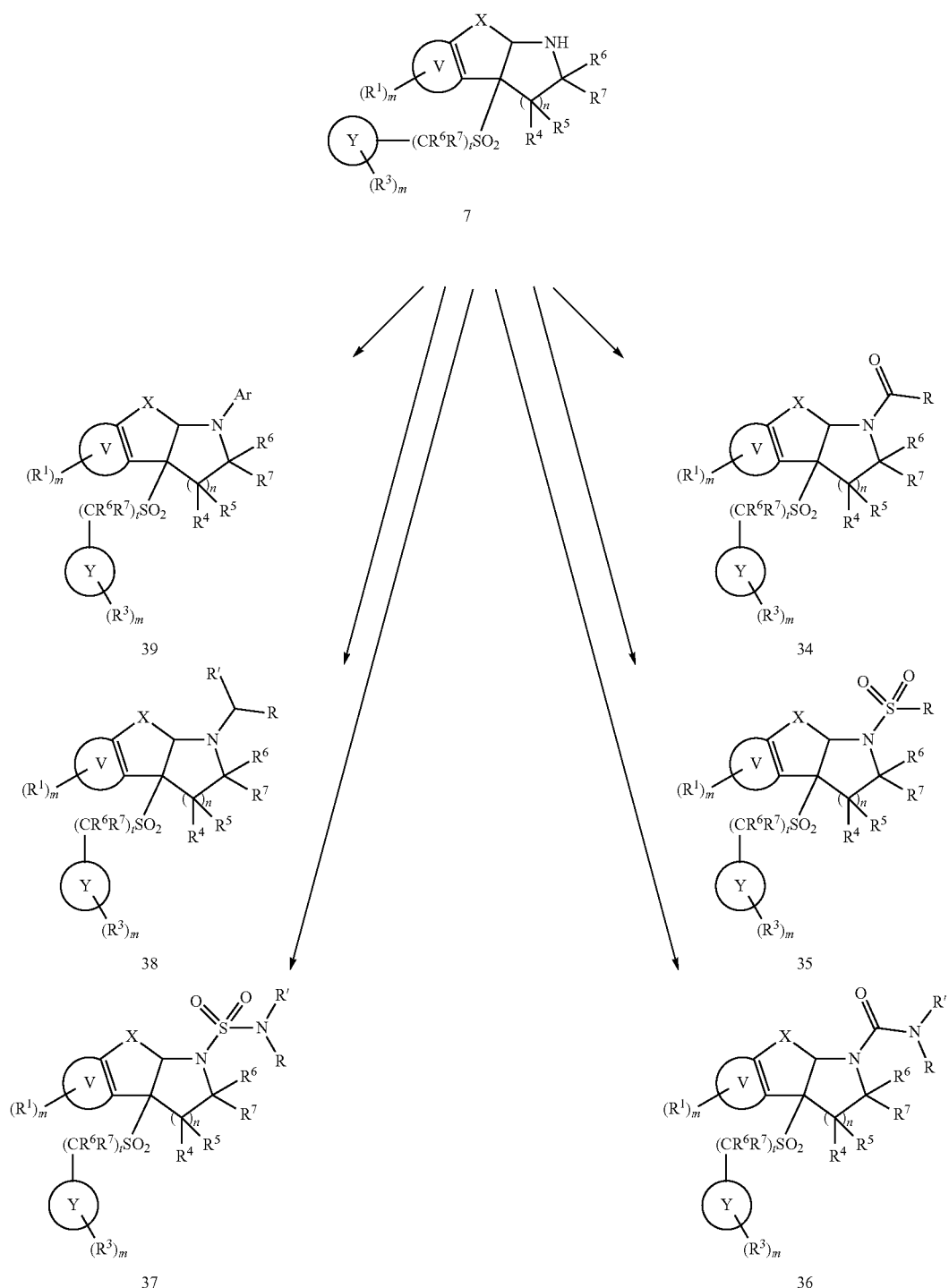

A method for preparing certain compounds 41 is shown in Scheme 8. An amine 40 can be treated with an aldehyde RCHO or a ketone RC(=O)R' in the presence of a reducing agent such as sodium triacetoxyborohydride or sodium cyanoborohydride to provide the alkylated amine 41. Alternatively, an amine 40 can be treated with an alkyl chloride, alkyl bromide, alkyl iodide or other activated alkyl derivatives such as an alkyl methanesulfonate or alkyl trifluoromethanesulfonate, in the presence of a suitable base, to provide the alkylated amine 41. If $R^a$ in 41 is a protecting group such as Boc, it can be removed using standard methods and the resulting amine reacted as desired, for example as shown in Scheme 7.

SCHEME 8

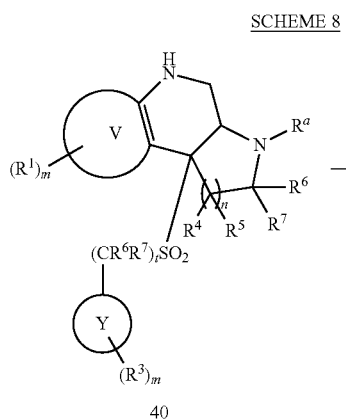

40

41

A variety of available methods may be used for conversion of intermediates or compounds of the invention to other intermediates or compounds of the invention. Some examples, well known to those skilled in the art of organic chemistry, include but are not limited to: conversion of a carboxylic acid ester to a carboxylic acid; conversion of a carboxylic acid to an amide; conversion of an amine to an amide, a urea, or a sulfonamide; alkylation or arylation of an amine; replacement of an aryl halide by an alkyl group, an aryl group or an amino group; and electrophilic substitution of an aromatic ring.

It will be appreciated by one skilled in the art of organic chemistry that various steps in a synthesis may be performed in an alternative sequence from that described in order to give a desired compound or compounds.

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined below. Common Intermediates are generally useful for the preparation of more than one Example and are identified sequentially by the Intermediate number and step in which they were prepared (e.g., Intermediate 1, Step A), or by the Intermediate number only where the compound is the title compound. Compounds of the Examples are identified by the Example number and step in which they were prepared (e.g., Example 1, Step A) if the compound is an intermediate, or by the Example number only where the compound is the title compound of the Example. In some instances alternative preparations of Intermediates or Examples are described. Frequently chemists skilled in the art of synthesis may devise alternative preparations which may be desirable based on one or more considerations such as shorter reaction time, less expensive starting materials, ease of operation or isolation, improved yield, suitability to catalysis, avoidance of toxic reagents, accessibility of specialized instrumentation, decreased number of linear steps, etc. The intent of describing alternative preparations is to further enable the preparation of the Examples of this invention. In some instances some functional groups in the outlined Examples and claims may be replaced by well known bioisosteric replacements known in the art, for example, replacement of a carboxylic acid group with a tetrazole or a phosphate moiety. Starting materials and intermediates for which no preparation is explicitly shown are available commercially, are known in the literature, or may be prepared by analogy to similar compounds which are known in the literature.

Heating of a reaction mixture via microwave irradiation was done in sealed vials using a Biotage® Initiator Microwave Synthesizer. Solvent removal was performed by concentration under reduced pressure. Column chromatography was generally performed using the flash chromatography technique (J. Org. Chem. 1978, 43, 2923), or with prepacked silica gel cartridges using a CombiFlash® automated chromatography apparatus (Teledyne Isco), eluting with the solvent or solvent mixture indicated. Analytical and preparative high performance liquid chromatography (HPLC) was generally performed using a reverse phase column of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chiral super-critical fluid chromatographic (SFC) separation of enantiomers or diastereomers was performed using conditions described for the individual cases. Mass spectral data were obtained by liquid chromatography mass spectroscopy (LCMS) using electrospray ionization.

Many Intermediates and Examples are homochiral (entirely or mostly a single enantiomer), but in some cases the absolute configuration has not been proven. In those cases, a text notation to the left of the structure will indicate that the compound is homochiral, and indicates whether the compound was obtained from (or is derived from an intermediate which was obtained from) the specified peak eluting during chiral SFC separation. However, in all cases, the stereochemistry within the tricyclic ring system is cis. Thus, for example, the structure 42 shown below indicates that, while the material is homochiral, the absolute stereochemistry of the material, which was derived from the second-eluting peak during SFC separation, is not known, but is either the absolute stereochemistry shown in 42a or that shown in 42b.

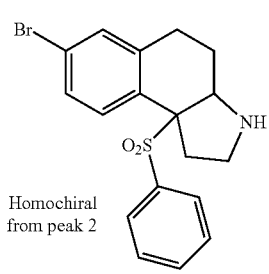

42

Homochiral from peak 2

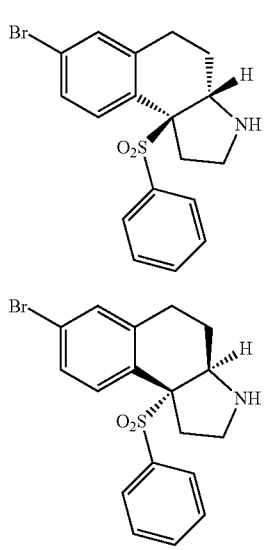

42a

42b

Structure 44 below, which indicates that the tricyclic moiety is derived from peak 2 eluting during chiral separation of a tricyclic intermediate used to prepare 43, while the final product 44 is derived from peak 1 eluting during chiral separation of the diastereomeric mixture 43.

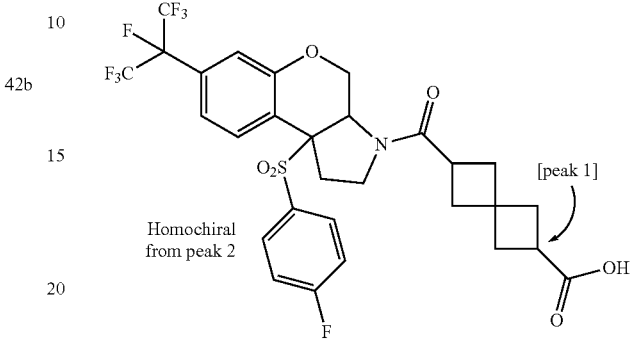

44

Homochiral from peak 2 [peak 1]

In some cases, an Intermediate or Example is derived from combining a homochiral starting material with a non-homochiral or racemic starting material, yielding a mixture of two or more diastereomers. In such cases, if the absolute stereochemistry of the homochiral starting material is not known, a text notation to the left of the structure will indicate that the chiral centers of the tricyclic moiety are those of the homochiral tricyclic intermediate derived from the indicated peak eluting during chiral SFC separation (as above), while the non-homochiral asymmetric center or centers are indicated by a wavy line, for example as shown in structure 43 below.

If the absolute configuration at an asymmetric center of an Intermediate or Example is known, or that asymmetric center is derived from a precursor whose absolute configuration is known, this is explicitly shown in the structure of the Intermediate or Example. If no absolute configuration is explicitly shown at an asymmetric center in a structure, and no text notation is present with the structure (as above), that chiral center is either racemic or of undefined stereochemistry.

Chemical names were determined using ChemBioDraw Ultra, version 14.0.0.126 (PerkinElmer Inc.). The following abbreviations are used:

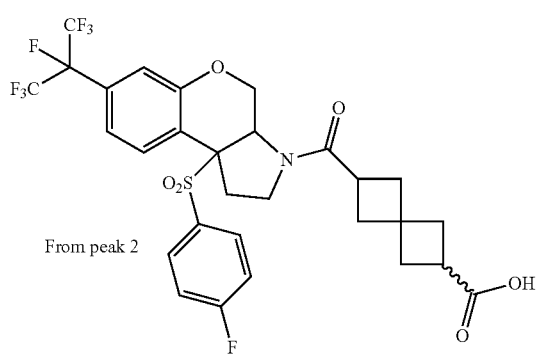

43

From peak 2

In some cases, a diastereomeric mixture resulting from combining a homochiral starting material with a non-homochiral starting material (such as structure 43 above) has been separated by a method such as chiral SFC to give a homochiral product wherein the absolute stereochemistry at none of the asymmetric centers is known. In such cases, a text notation to the left of the structure (as above) will indicate that the chiral centers of the tricyclic moiety are those of the tricyclic intermediate derived from the indicated peak eluting during chiral SFC separation of the intermediate, and a text notation in brackets to the right of the structure will indicate the peak (from the separation of the diastereomeric mixture such as structure 43 above) from which the product was isolated. An example is shown in

| ABBREVIATION | NAME |
|---|---|
| BINAP | 2,2'-bis(diphenylphosphino)-1,1'-binaphthalene |
| Boc | tert-butyloxycarbonyl |
| BOP | (benzotriazol-1-yloxy)tris(dimethylamino)phosphonium hexafluorophosphate |
| $CDCl_3$ | deuterated chloroform |
| DAST | diethylaminosulfur trifluoride |
| DCM | dichloromethane |
| DIBAL-H | diisobutylaluminum hydride |
| DIPEA | diisopropylethylamine |
| DMF | N,N-dimethylformamide |
| DMSO | dimethyl sulfoxide |
| DMSO-$d_6$ | deuterated dimethyl sulfoxide |
| $Et_3N$ | triethylamine |
| EtOAc | ethyl acetate |
| h | hours |
| HATU | O-(7-azabenzotriazol-1-yl)-1,1,3,3-tetramethyluronium hexafluorophosphate |
| HPLC | high performance liquid chromatography |
| LCMS | liquid chromatography—mass spectrometry |
| MeCN | acetonitrile |
| MeOH | methanol |
| MeOH-$d_4$ | deuterated methanol |
| mCPBA | meta-chloroperoxybenzoic acid |
| min | minutes |
| MsCl | methanesulfonyl chloride |
| PyBOP | benzotriazol-1-yl-oxytripyrrolidinophosphonium hexafluorophosphate |
| rt | room temperature |

-continued

| ABBREVIATION | NAME |
|---|---|
| SFC | super-critical fluid chromatography |
| TFA | trifluoroacetic acid |
| THF | tetrahydrofuran |
| TLC | thin layer chromatography |
| $t_R$ | chromatographic retention time |
| Xantphos | 4,5-bis(diphenylphosphino)-9,9-dimethylxanthene |

HPLC Methods

Method A: (Analytical)

Column: Kinetex® XB-$C_{18}$ 3×75 mm, 2.6 m (Phenomenex Inc.); mobile phase A: 10 mM ammonium acetate in water-MeCN (98:2); mobile phase B: 10 mM ammonium acetate in water-MeCN (2:98); flow rate lmL/min; gradient 4.7 min.

Method B: (Analytical)

Column: Acquity UPLC® BEH $C_{18}$ 2.1×50 mm, 1.7 m (Waters Corp.); mobile phase A: water with 0.05% TFA; mobile phase B: MeCN with 0.05% TFA; temperature: 50° C.; flow rate 0.80 mL/min; gradient: 2-98% B over 1 min, then 0.5 min isocratic at 98% B.

Method C: (Analytical)

Column: Acquity UPLC® BEH $C_{18}$ 2.1×50 mm, 1.7 μm (Waters Corp.); mobile phase A: 5:95 MeCN-water with 10 mM ammonium acetate; mobile phase B: 95:5 MeCN-water with 10 mM ammonium acetate; temperature: 50° C.; flow rate 1.0 mL/min; gradient: 0-100% B over 3 min, then 0.75 min isocratic at 100% B.

Method D: (Analytical)

Column: Acquity UPLC® BEH $C_{18}$ 2.1×50 mm, 1.7 μm (Waters Corp.); mobile phase A: 5:95 MeCN-water with 0.1% TFA; mobile phase B: 95:5 MeCN-water with 0.1% TFA; temperature: 50° C.; flow rate 1.0 mL/min; gradient: 0-100% B over 3 min, then 0.75 min isocratic at 100% B.

Method E: (Preparative)

Column: XBridge™ $C_{18}$ 19×200 mm, 5 m (Waters Corp.); mobile phase A: 5:95 MeCN-water with 10 mM ammonium acetate; mobile phase B: 95:5 MeCN-water with 10 mM ammonium acetate; flow rate 20 mL/min; gradient: increasing B, then isocratic.

Method F: (Preparative)

Column: XBridge™ $C_{18}$ 19×200 mm, 5 m (Waters Corp.); mobile phase A: 5:95 MeCN-water with 0.1% TFA; mobile phase B: 95:5 MeCN-water with 0.1% TFA; flow rate 20 mL/min; gradient: increasing B, then isocratic.

Method G: (Preparative)

Column: Luna® $C_{18}$ 30×100 mm, 5 m (Phenomenex Inc.); mobile phase A: water with 0.1% TFA; mobile phase B: MeCN with 0.1% TFA; flow rate 30 mL/min; gradient: increasing B, then isocratic.

Intermediate 1

4-((4-fluorophenyl)sulfonyl)-7-iodo-1,2-dihydronaphthalene

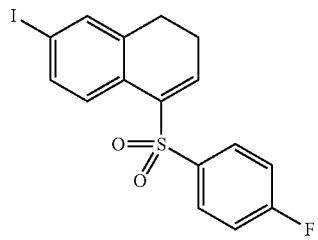 [SMILES: O=S(=O)(C1=CCCc2cc(I)ccc21)c1ccc(F)cc1]

A solution of 6-iodo-3,4-dihydronaphthalen-1(2H)-one (13.3 g, 48.9 mmol) and $TiCl_4$ (1 M in DCM, 48.9 mL, 48.9 mmol) in THF (326 mL) in an ice-water bath was treated with a solution of 4-fluorobenzenethiol (6.3 mL, 58.7 mmol) and $Et_3N$ (13.6 mL, 98 mmol) in THF (25 mL) at a rate such that the temperature remained below 10° C. The solution was stirred at rt for 60 min, then was treated with water (200 mL) and concentrated to remove the bulk of the organic solvents. The aqueous residue was extracted with diethyl ether (2×250 mL). The combined organic layers were dried over $Na_2SO_4$, filtered and concentrated under reduced pressure to provide crude (4-fluorophenyl)(6-iodo-3,4-dihydronaphthalen-1-yl)sulfane (20 g) as a mixture with the corresponding thioketal, which was used directly. HPLC $t_R$ 1.36 min (method B).

A solution of (4-fluorophenyl)(6-iodo-3,4-dihydronaphthalen-1-yl)sulfane and its thioketal (the mixture from the above reaction, 18.69 g) in DCM (978 mL) in an ice-water bath was treated portionwise with mCPBA (21.92 g, 98 mmol). The mixture was allowed to reach rt and was stirred for 1 h, when LCMS showed consumption of the starting material and 4-((4-fluorophenyl)sulfinyl)-7-iodo-1,2-dihydronaphthalene as the major product. Additional mCPBA (10.96 g, 48.9 mmol) was added at rt. The reaction was stirred for 30 min, when LCMS showed very little sulfoxide ($t_R$ 1.00 min, method B). The mixture was washed twice with saturated aqueous $NaHCO_3$, and the organic phase was dried over $Na_2SO_4$ and concentrated. The residue was purified by column chromatography, eluting with EtOAc-hexanes (gradient from 0-10%). The resulting material was dissolved in EtOAc and washed twice with saturated aqueous $NaHCO_3$. The organic phase was dried over $Na_2SO_4$ and concentrated to provide 4-((4-fluorophenyl)sulfonyl)-7-iodo-1,2-dihydronaphthalene as a white foamy solid (12 g, 59% yield over two steps). LCMS m/z 455.9 $(M+H+MeCN)^+$, HPLC $t_R$ 1.09 min (method B). $^1$H NMR (400 MHz, $CDCl_3$) δ 7.97-7.89 (m, 2H), 7.64 (d, J=8.8 Hz, 1H), 7.57-7.47 (m, 3H), 7.22-7.13 (m, 2H), 2.79-2.68 (m, 2H), 2.61-2.50 (m, 2H). $^{19}$F NMR (376 MHz, $CDCl_3$) δ −102.7 (s, 1F).

Alternative Procedure:

A solution of 6-iodo-3,4-dihydronaphthalen-1(2H)-one (5.0 g, 18.38 mmol), 4-fluorobenzenethiol (4.11 mL, 38.6 mmol) and absolute ethanol (20 mL) was cooled with an ice-water bath and bubbled with HCl gas until saturation was reached (observed by the formation of a white precipitate). The mixture was allowed to warm to rt and stirred overnight. The mixture was dissolved in ether (250 mL) and washed sequentially with water (2×125 mL), 0.5 M aqueous $Na_2CO_3$ (3×100 mL) and brine (100 mL). The organic layer was dried over Na$_2$SO$_4$ and concentrated to provide a solid (9.2 g) which was a mixture of thioketal and vinyl sulfide. The solid was dissolved in chloroform (150 mL) and cooled in an ice-water bath. A solution of mCPBA (35 g, 156 mmol) in DCM (200 mL) was washed with brine (50 mL), dried over Na$_2$SO$_4$, filtered, and the filter cake was washed with DCM (50 mL). The combined filtrates were added dropwise in portions to the chloroform solution of the products from above until the reaction was completed as judged by LCMS (175 mL of the mCPBA solution was needed). The mixture was cooled in an ice bath, filtered to remove the insoluble material, and the filtrate was stirred with 10% aqueous Na$_2$S$_2$O$_3$ (120 mL) for 5 min. The organic phase was separated, washed sequentially with 10% aqueous Na$_2$S$_2$O$_3$ (2×120 mL), 10% aqueous Na$_2$CO$_3$ (3×200 mL) and brine (150 mL), dried over Na$_2$SO$_4$ and concentrated. The residue was purified by column chromatography on silica gel, eluting with EtOAc-hexanes (gradient from 0-20%) to give 4-((4-fluorophenyl)sulfonyl)-7-iodo-1,2-dihydronaphthalene (5.3 g, 70% yield) as a white foamy solid.

Intermediate 2

4-((4-fluorophenyl)sulfonyl)-7-(perfluoropropan-2-yl)-1,2-dihydronaphthalene

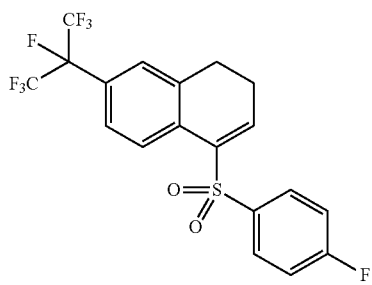 [SMILES: O=S(=O)(C1=CCCc2cc(C(F)(C(F)(F)F)C(F)(F)F)ccc21)c1ccc(F)cc1]

Step A: 6-(perfluoropropan-2-yl)-3,4-dihydronaphthalen-1(2H)-one

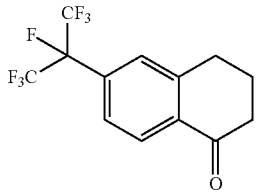 [SMILES: O=C1CCCc2cc(C(F)(C(F)(F)F)C(F)(F)F)ccc21]

Activated copper was prepared by adding zinc dust (24.57 g, 376 mmol) portionwise with stirring to a solution of copper(II) sulfate (45.09 g, 283 mmol) in water (250 mL) over 10 min. The mixture was stirred 10 min longer, then the supernatant was decanted from the red precipitate. This was washed twice with water by decantation, then was stirred with 1 M aqueous HCl (400 mL) for 2.5 h. The supernatant was decanted and the precipitate was washed with water by decantation until the pH of the supernatant was about 7. The solid was stored under water and an inert atmosphere (nitrogen or argon). For use the solid was washed twice by decantation with MeOH, then twice with diethyl ether, and dried under vacuum.

Dried activated copper (10.13 g, 159 mmol) was combined with 6-iodo-3,4-dihydronaphthalen-1(2H)-one (4.20 g, 15.44 mmol) and dry DMF (85 mL), bubbled with argon, and treated with 1,1,1,2,3,3,3-heptafluoro-2-iodopropane (8.78 mL, 61.7 mmol). The reaction vessel was sealed under argon and heated at 120° C. for 3 h. The mixture was cooled to rt, diluted with EtOAc and filtered through Celite. The solids were washed with additional EtOAc and the combined filtrates were concentrated. The residue was dissolved in EtOAc, shaken with water, and the mixture was filtered through Celite. The solids were washed with additional EtOAc, and the organic phase of the combined filtrates was separated, washed twice with 5% aqueous LiCl, then with brine, dried over Na$_2$SO$_4$ and concentrated. The residue was purified by column chromatography on silica gel (330 g), eluting with EtOAc-hexanes (gradient from 5-30%), to provide 6-(perfluoropropan-2-yl)-3,4-dihydronaphthalen-1(2H)-one as an orange oil (3.32 g, 68% yield). LCMS m/z 356.0 (M+H+MeCN)$^+$, HPLC t$_R$ 1.13 min (method B). $^1$H NMR (400 MHz, CDCl$_3$) δ 8.17 (d, J=8.4 Hz, 1H), 7.58 (d, J=8.6 Hz, 1H), 7.55 (s, 1H), 3.07 (t, J=6.1 Hz, 2H), 2.77-2.71 (t, J=6.6 Hz, 2H), 2.22 (quintet, 6.4 Hz, 2H). $^{19}$F NMR (376 MHz, CDCl$_3$) δ −75.38 (d, J=7.2 Hz, 6F), −182.41 (septet, J=7.2 Hz, 1F).

Step B: 4-((4-fluorophenyl)sulfonyl)-7-(perfluoropropan-2-yl)-1,2-dihydronaphthalene

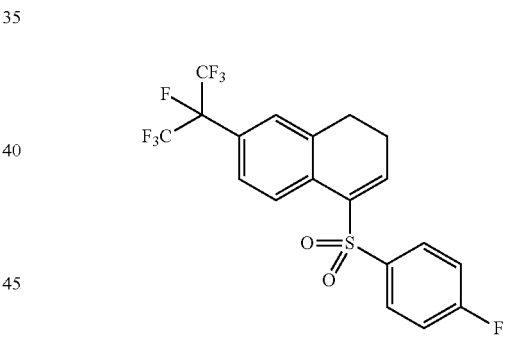

Following the alternative procedure used to prepare Intermediate 1, 6-(perfluoropropan-2-yl)-3,4-dihydronaphthalen-1(2H)-one was converted into 4-((4-fluorophenyl)sulfonyl)-7-(perfluoropropan-2-yl)-1,2-dihydronaphthalene in quantitative yield, with minor impurities present, and was used without further purification. LCMS m/z 457.3 (M+H)$^+$, HPLC t$_R$ 1.12 min (method B). $^1$H NMR (400 MHz, CDCl$_3$) δ 7.99 (dt, J=8.9, 4.3 Hz, 3H), 7.58 (t, J=4.8 Hz, 1H), 7.44 (d, J=8.6 Hz, 1H), 7.39 (s, 1H), 7.22 (t, J=8.6 Hz, 2H), 2.92-2.84 (m, 2H), 2.65 (td, J=8.0, 5.0 Hz, 2H).

The Intermediates in Table 1 were prepared using the same methods or similar methods used to prepare Intermediates 1 and 2, by employing the appropriate ketone and substituted thiophenol.

TABLE 1

| Intermediate number | Structure | LCMS m/z observed | HPLC $t_R$ (min) | HPLC method |
|---|---|---|---|---|
| 3 | 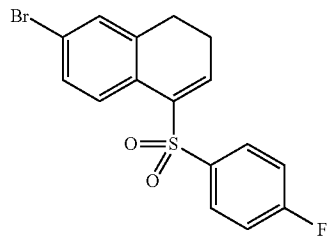 [SMILES: O=S(=O)(C1=CCCc2cc(Br)ccc21)c1ccc(F)cc1] | 364.8 (M + H + MeCN)⁺ | 1.09 | B |
| 4 | 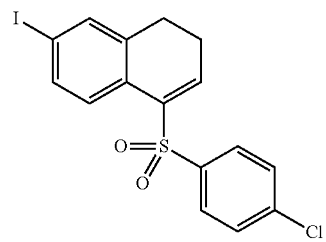 [SMILES: O=S(=O)(C1=CCCc2cc(I)ccc21)c1ccc(Cl)cc1] | 493.8 (M + Na + MeCN)⁺ | 1.13 | B |
| 5 | 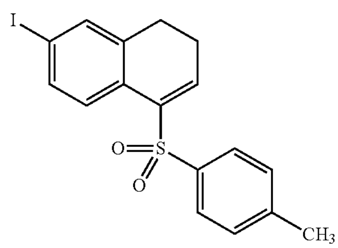 | 451.9 (M + H + MeCN)⁺ | 1.12 | B |
| 6 | 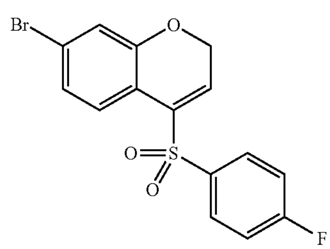 [SMILES: O=S(=O)(C1=CCOc2cc(Br)ccc21)c1ccc(F)cc1] | 410.0 (M + H + MeCN)⁺ | 1.08 | B |
| 7 | 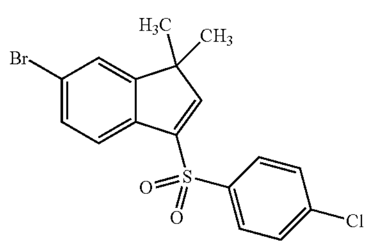 | 438.0 (M + H + MeCN)⁺ | 1.18 | B |
| 8 | 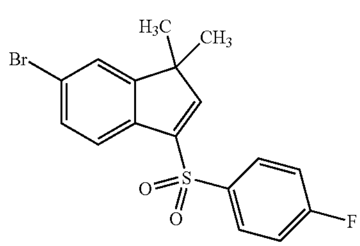 | 422.1 (M + H + MeCN)⁺ | 1.13 | B |

TABLE 1-continued

| Intermediate number | Structure | LCMS m/z observed | HPLC $t_R$ (min) | HPLC method |
|---|---|---|---|---|
| 9 | 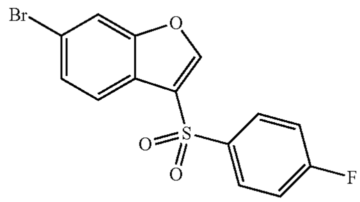 [SMILES: O=S(=O)(c1ccc(F)cc1)c1coc2cc(Br)ccc12] | 396.1 (M + H + MeCN)+ | 1.08 | B |
| 10 | 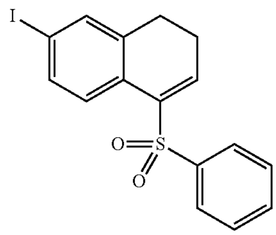 [SMILES: O=S(=O)(C1=CCCc2cc(I)ccc21)c1ccccc1] | 438.0 (M + H + MeCN)+ | 1.11 | B |
| 11 | 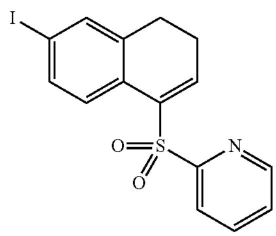 [SMILES: O=S(=O)(C1=CCCc2cc(I)ccc21)c1ccccn1] | 398.4 (M + H)+ | 1.01 | B |
| 12 | 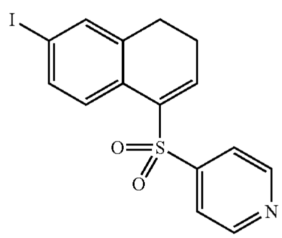 [SMILES: O=S(=O)(C1=CCCc2cc(I)ccc21)c1ccncc1] | 398.0 (M + H)+ | 1.01 | B |
| 13 | 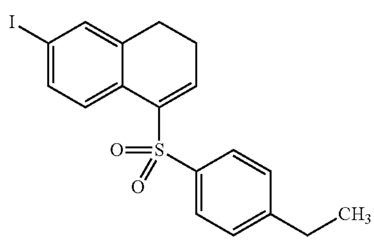 | 466.0 (M + H + MeCN)+ | 1.17 | B |
| 14 | 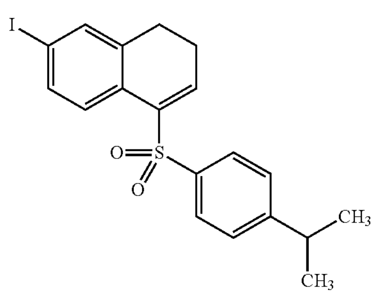 | 480.0 (M + H + MeCN)+ | 1.20 | B |

TABLE 1-continued

| Intermediate number | Structure | LCMS m/z observed | HPLC $t_R$ (min) | HPLC method |
|---|---|---|---|---|
| 15 | 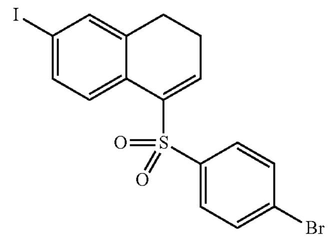 [SMILES: O=S(=O)(C1=CCCc2cc(I)ccc21)c1ccc(Br)cc1] | 516.0 (M + H + MeCN)⁺ | 1.19 | B |
| 16 | 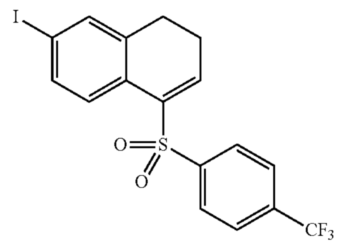 [SMILES: O=S(=O)(C1=CCCc2cc(I)ccc21)c1ccc(C(F)(F)F)cc1] | 506.0 (M + H + MeCN)⁺ | 1.17 | B |
| 17 | 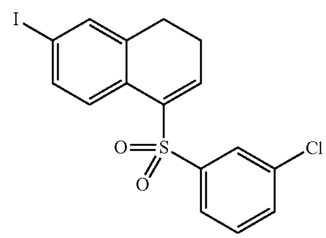 [SMILES: O=S(=O)(C1=CCCc2cc(I)ccc21)c1cccc(Cl)c1] | 472.1 (M + H + MeCN)⁺ | 1.13 | B |
| 18 | 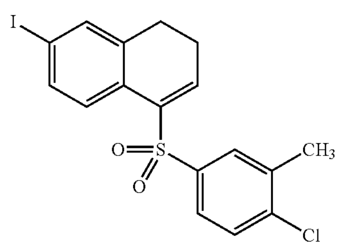 | 486.0 (M + H + MeCN)⁺ | 1.21 | B |
| 19 | 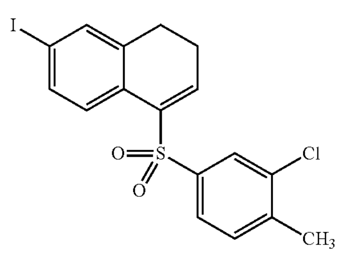 | 486.0 (M + H + MeCN)⁺ | 1.21 | B |
| 20 | 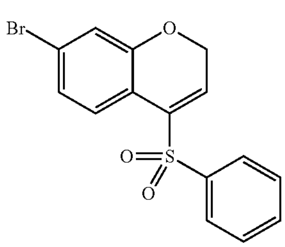 [SMILES: O=S(=O)(C1=CCOc2cc(Br)ccc21)c1ccccc1] | 350.9 (M + H)⁺ | 1.06 | B |

TABLE 1-continued

| Intermediate number | Structure | LCMS m/z observed | HPLC $t_R$ (min) | HPLC method |
|---|---|---|---|---|
| 21 | 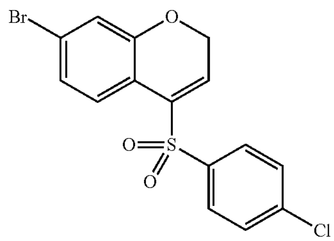 [SMILES: O=S(=O)(C1=CCOc2cc(Br)ccc21)c1ccc(Cl)cc1] | 447.9 (M + Na + MeCN)$^+$ | 1.10 | B |
| 22 | 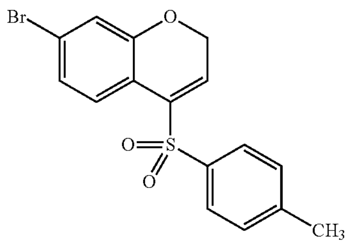 [SMILES: Cc1ccc(S(=O)(=O)C2=CCOc3cc(Br)ccc32)cc1] | 365.0 (M + H)$^+$ | 1.06 | B |
| 23 | 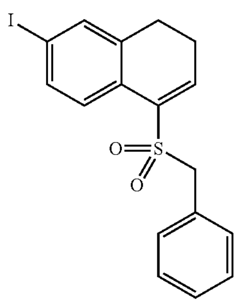 [SMILES: O=S(=O)(Cc1ccccc1)C1=CCCc2cc(I)ccc21] | 452.0 (M + H + MeCN)$^+$ | 1.11 | B |
| 24 | 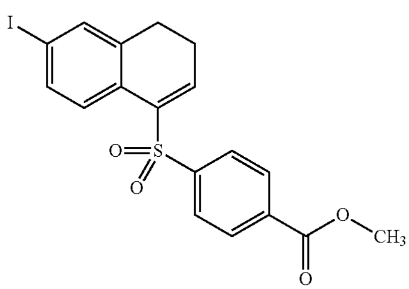 | 496.1 (M + H + MeCN)$^+$ | 1.12 | B |
| 25 | 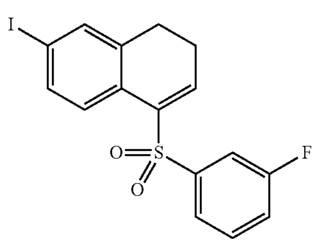 [SMILES: O=S(=O)(C1=CCCc2cc(I)ccc21)c1cccc(F)c1] | 455.9 (M + H + MeCN)$^+$ | 1.09 | B |
| 26 | 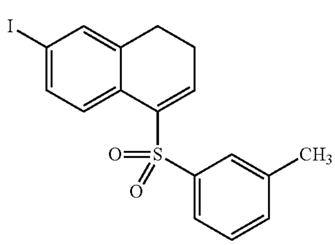 [SMILES: Cc1cccc(S(=O)(=O)C2=CCCc3cc(I)ccc32)c1] | 411.0 (M + H)$^+$ | 1.10 | B |

TABLE 1-continued

| Intermediate number | Structure | LCMS m/z observed | HPLC $t_R$ (min) | HPLC method |
|---|---|---|---|---|
| 27 | (6-iodo-3,4-dihydronaphthalen-1-yl) 4-fluoro-3-methylphenyl sulfone | 428.9 (M + H)+ | 1.10 | B |
| 28 | (6-bromo-3,4-dihydronaphthalen-1-yl) 3-fluorophenyl sulfone | 407.8 (M + H + MeCN)+ | 1.11 | B |
| 29 | (6-iodo-3,4-dihydronaphthalen-1-yl) 3,4-dichlorophenyl sulfone | 465.1 (M + H)+ | 1.18 | B |
| 30 | (6-(perfluoroethyl)-3,4-dihydronaphthalen-1-yl) 3-bromo-4-fluorophenyl sulfone | 576.2 (M + H + MeCN)+ | 1.16 | B |
| 31 | (6-iodo-3,4-dihydronaphthalen-1-yl) 3,4-difluorophenyl sulfone | 474.0 (M + H + MeCN)+ | 1.09 | B |

Intermediate 32

(3aR,9bR)-9b-((4-fluorophenyl)sulfonyl)-7-(perfluoropropan-2-yl)-2,3,3a,4,5,9b-hexahydro-1H-benzo[e]indole hydrochloride

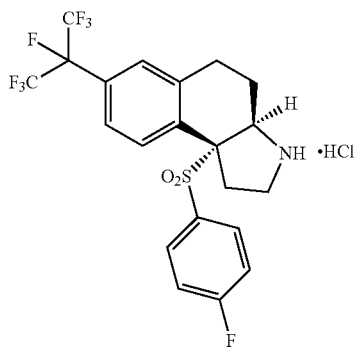 [SMILES: O=S(=O)(c1ccc(F)cc1)[C@@]12CCN[C@@H]1CCc1cc(C(F)(C(F)(F)F)C(F)(F)F)ccc12 ; Cl]

Step A: 2-((6-bromo-1-((4-fluorophenyl)sulfonyl)-1,2,3,4-tetrahydronaphthalen-2-yl)amino)ethan-1-ol

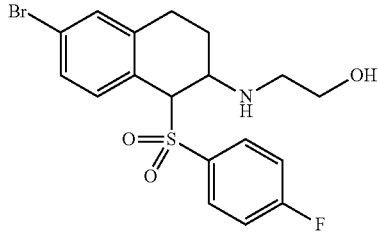 [SMILES: O=S(=O)(c1ccc(F)cc1)C1c2ccc(Br)cc2CCC1NCCO]

A solution of 7-bromo-4-((4-fluorophenyl)sulfonyl)-1,2-dihydronaphthalene (Intermediate 3; 5.7 g, 15.52 mmol) in THF (259 mL) in an ice-water bath was treated with 2-aminoethanol (13.42 mL, 233 mmol). The mixture was stirred at about 5° C. for 30 min, when LCMS showed complete consumption of the starting material. The mixture was concentrated and the resulting oil was dissolved in EtOAc (250 mL), washed with saturated aqueous NaHCO$_3$, then twice with brine, dried over Na$_2$SO$_4$, filtered and concentrated. The residue was purified by column chromatography on silica gel, eluting with EtOAc, to provide 2-((6-bromo-1-((4-fluorophenyl)sulfonyl)-1,2,3,4-tetrahydronaphthalen-2-yl)amino)ethanol (2.8 g, 42% yield. LCMS m/z 427.8 (M+H)$^+$, HPLC t$_R$ 0.71 min (method B).

Step B: 2-((6-bromo-1-((4-fluorophenyl)sulfonyl)-1,2,34-tetrahydronaphthalen-2-yl)amino)ethyl Methanesulfonate

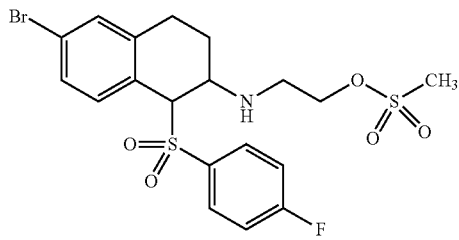 [SMILES: CS(=O)(=O)OCCNC1CCc2cc(Br)ccc2C1S(=O)(=O)c1ccc(F)cc1]

A solution of 2-((6-bromo-1-((4-fluorophenyl)sulfonyl)-1,2,3,4-tetrahydronaphthalen-2-yl)amino)ethanol (2.8 g, 6.54 mmol) in DCM (654 mL) was treated at rt with MsCl (0.611 mL, 7.84 mmol) followed by Et$_3$N (1.093 mL, 7.84 mmol). The mixture was stirred for 1 h, when LCMS showed complete consumption of the starting material. The mixture was washed with a 1:1 mixture of brine and water, and the organic layer was dried over Na$_2$SO$_4$, filtered and concentrated to provide 2-((6-bromo-1-((4-fluorophenyl)sulfonyl)-1,2,3,4-tetrahydronaphthalen-2-yl)amino)ethyl methanesulfonate (2.9 g, 88% yield), used without further purification. LCMS m/z 505.9 (M+H)$^+$, HPLC t$_R$ 0.76 min (method B).

Step C: 7-bromo-9b-((4-fluorophenyl)sulfonyl)-2,3,3a,4,5,9b-hexahydro-1H-benzo[e]indole

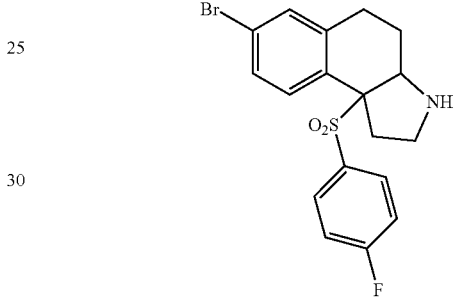

A solution of 2-((6-bromo-1-((4-fluorophenyl)sulfonyl)-1,2,3,4-tetrahydronaphthalen-2-yl)amino)ethyl methanesulfonate (2.9 g, 5.73 mmol) in THF (286 mL) was treated portionwise with potassium tert-butoxide ((3.21 g, 28.6 mmol) at rt, such that the temperature of the reaction mixture did not exceed 25.5° C. The mixture was stirred for 1 h, when LCMS showed complete consumption of starting material. The mixture was treated with 100 mL of a 1:1 mixture of water and brine and partially concentrated. The aqueous residue was extracted with EtOAc (2×125 mL), and the combined organic layers were dried over Na$_2$SO$_4$, filtered and concentrated to provide crude 7-bromo-9b-((4-fluorophenyl)sulfonyl)-2,3,3a,4,5,9b-hexahydro-1H-benzo[e]indole (2.1 g), used without further purification. LCMS m/z 409.9 (M+H)$^+$, HPLC t$_R$ 0.76 min (method B). $^1$H NMR (400 MHz, CDCl$_3$) δ 7.51-7.43 (m, 1H), 7.42-7.35 (m, 1H), 7.32-7.27 (m, 2H), 7.11 (s, 1H), 7.02 (t, J=8.78 Hz, 2H), 3.97 (dd, J=12.0, 6.0 Hz, 1H), 3.32 (dd, J=11.5, 4.0 Hz, 1H), 3.27-3.13 (m, 1H), 3.02 (d, J=12.0 Hz, 1H), 2.50-2.30 (m, 2H), 2.05-1.95 (m, 1H), 1.77-1.56 (m, 1H), 1.34-1.20 (m, 1H).

Step D: tert-butyl 7-bromo-9b-((4-fluorophenyl)sulfonyl)-1,2,3a,4,5,9b-hexahydro-3H-benzo[e]indole-3-carboxylate

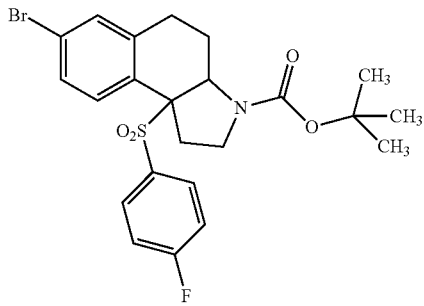 [SMILES: CC(C)(C)OC(=O)N1CCC2(S(=O)(=O)c3ccc(F)cc3)c3ccc(Br)cc3CCC12]

A solution of 7-bromo-9b-((4-fluorophenyl)sulfonyl)-2,3,3a,4,5,9b-hexahydro-1H-benzo[e]indole (2.1 g, 5.12 mmol) in DCM (50 mL) was treated with di-tert-butyl dicarbonate (1.426 mL, 6.14 mmol) and Et₃N (1.427 mL, 10.24 mmol). The mixture was stirred at rt for 1 h, when LCMS showed complete consumption of starting material. The mixture was diluted with DCM (100 mL) and washed sequentially with 1 M aqueous HCl and 1 M aqueous NaOH. The organic layer was dried over Na₂SO₄, filtered and concentrated. The residue was purified by column chromatography on silica gel, eluting with EtOAc-hexanes, to afford tert-butyl 7-bromo-9b-((4-fluorophenyl)sulfonyl)-1,2,3a,4,5,9b-hexahydro-3H-benzo[e]indole-3-carboxylate (1.6 g, 61% yield for 3 steps). LCMS m/z 453.9 (M+H—C₄H₈)⁺, HPLC $t_R$ 1.15 min (method B). ¹H NMR (400 MHz, CDCl₃) δ 7.70-7.51 (m, 1H), 7.46-7.32 (m, 3H), 7.16-6.91 (m, 3H), 4.49-4.45 (m, 1H), 3.76-3.73 (m, 1H), 3.59-3.38 (m, 2H), 2.43-2.34 (m, 3H), 1.73 (t, J=14.8 Hz, 1H), 1.49 (s, 9H), 1.34-1.12 (m, 1H). ¹⁹F NMR (376 MHz) δ −102.6.

Step E: (3aS,9bS)-tert-butyl 7-bromo-9b-((4-fluorophenyl)sulfonyl)-3a,4,5,9b-tetrahydro-1H-benzo[e]indole-3-carboxylate and (3aR,9bR)-tert-butyl 9b-((4-fluorophenyl)sulfonyl)-7-bromo-3a,4,5,9b-tetrahydro-1H-benzo[e]indole-3-carboxylate Peak 1

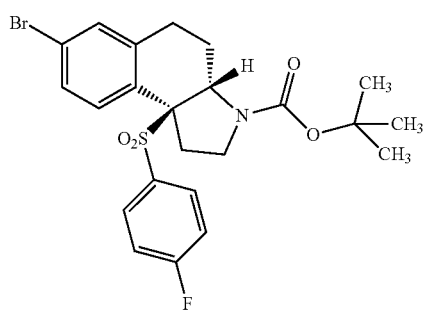

Peak 2

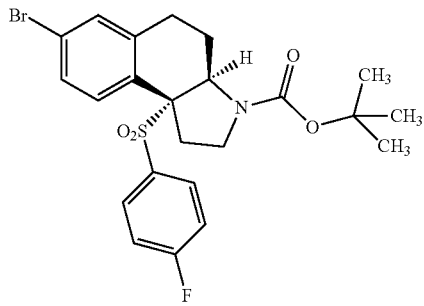

A sample of tert-butyl 9b-((4-fluorophenyl)sulfonyl)-7-bromo-3a,4,5,9b-tetrahydro-1H-benzo[e]indole-3-carboxylate (1.6 g, 3.13 mmol) was separated by chiral SFC using the following conditions: Column: Lux® Cellulose-4 (4.6× 250) mm, 5 μm (Phenomenex Inc.); column temperature 24.9° C.; CO₂ flow rate: 2.10 mL/min; co-solvent: 30% of 0.2% diethylamine in MeOH, flow rate 0.9 mL/min; injection volume: 10 mL. Peak 1 ((3aS,9bS)-tert-butyl 7-bromo-9b-((4-fluorophenyl)sulfonyl)-3a,4,5,9b-tetrahydro-1H-benzo[e]indole-3-carboxylate) was eluted with $t_R$ 2.79 min. Peak 2 ((3aR,9bR)-tert-butyl 9b-((4-fluorophenyl)sulfonyl)-7-bromo-3a,4,5,9b-tetrahydro-1H-benzo[e]indole-3-carboxylate, 0.7 g) was eluted with $t_R$ 3.92 min (100%). The absolute configurations of peaks 1 and 2 were determined based on single crystal X-ray analysis from the anomalous dispersion signal using the FLACK method. Analytical data for Peak 2: LCMS m/z 453.9 (M+H—C₄H₈)⁺, HPLC $t_R$ 1.15 min (method B); ¹H NMR (400 MHz, CDCl₃) δ 7.70-7.51 (m, 1H), 7.46-7.32 (m, 3H), 7.16-6.91 (m, 3H), 4.49-4.45 (m, 1H), 3.76-3.73 (m, 1H), 3.59-3.38 (m, 2H), 2.43-2.34 (m, 3H), 1.73 (t, J=14.8 Hz, 1H), 1.49 (s, 9H), 1.34-1.12 (m, 1H). ¹⁹F NMR (376 MHz) δ −102.6.

Step F: (3aR,9bR)-tert-butyl 9b-((4-fluorophenyl)sulfonyl)-7-(1,1,1,3,3,3-hexafluoro-2-hydroxypropan-2-yl)-3a,4,5,9b-tetrahydro-1H-benzo[e]indole-3-carboxylate

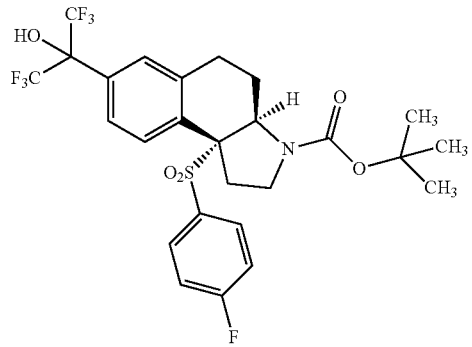 [SMILES: CC(C)(C)OC(=O)N1CC[C@@]2(S(=O)(=O)c3ccc(F)cc3)c3ccc(C(O)(C(F)(F)F)C(F)(F)F)cc3CC[C@@H]12]

tert-Butyllithium (3 M in heptane, 376 μL, 0.940 mmol) was added dropwise to a stirred solution of (3aR,9bR)-tert-butyl 7-bromo-9b-((4-fluorophenyl)sulfonyl)-3a,4,5,9b-tetrahydro-1H-benzo[e]indole-3-carboxylate (240 mg, 0.470 mmol) (which had been dried by concentration from toluene three times) in diethyl ether (8.2 mL) under nitrogen in a dry ice acetone bath. The resulting brownish solution was stirred for 15 min at −78° C. Gaseous CF₃C(O)CF₃ (3.28 g. 19.73 mmol) was slowly added via a needle by placing the tip of the needle just above the cold solution to allow the gas to condense (about 2 min; the weight of reagent added was estimated by weighing the gas cylinder before and after the addition). The resulting mixture was stirred under nitrogen for 30 min at −78° C., then at rt for 30 min. The mixture was treated with saturated aqueous NH₄Cl (15 mL) and diluted with EtOAc (100 mL). The layers were separated and the aqueous layer was extracted with EtOAc (50 mL). The combined organic layers were dried over Na₂SO₄ and concentrated, and the residue was purified by column chromatography on silica gel, eluting with hexanes followed by a gradient to 30% EtOAc-hexanes, to provide (3aR,9bR)-tert-butyl 9b-((4-fluorophenyl)sulfonyl)-7-(1,1,1,3,3,3-hexafluoro-2-hydroxypropan-2-yl)-3a,4,5,9b-tetrahydro-1H-benzo[e]indole-3-carboxylate (200 mg, 71% yield, about 75% purity). LCMS m/z 541.8 (M+H—$C_4H_8$)⁺, HPLC $t_R$ 1.08 min (method B). ¹H NMR (400 MHz, CDCl₃) δ 7.75 (d, J=8.4 Hz, 1H), 7.61 (d, J=8.1 Hz, 1H), 7.41 (dd, J=8.3, 5.2 Hz, 2H), 7.38-7.32 (m, 1H), 7.04 (t, J=8.3 Hz, 2H), 4.55-4.38 (m, 1H), 3.81-3.66 (m, 1H), 3.57-3.32 (m, 2H), 2.52-2.29 (m, 3H), 1.74 (t, J=13.2 Hz, 1H), 1.52 (br. s., 9H). ¹⁹F NMR (376 MHz, CDCl₃) δ −102.5 (s, 1F), −75.5 (s, 6F).

Alternative Preparation of (3aR,9bR)-tert-butyl 9b-((4-fluorophenyl)sulfonyl)-7-(1,1,1,3,3,3-hexafluoro-2-hydroxypropan-2-yl)-3a,4,5,9b-tetrahydro-1H-benzo[e]indole-3-carboxylate The same procedure was used, but starting with (3aR,9bR)-tert-butyl 9b-((4-fluorophenyl)sulfonyl)-7-iodo-3a,4,5,9b-tetrahydro-1H-benzo[e]indole-3-carboxylate (prepared by following the procedures of Steps A through E above, but starting from Intermediate 1 instead of Intermediate 3; 1.1 g, 1.973 mmol) to provide (3aR,9bR)-tert-butyl 9b-((4-fluorophenyl)sulfonyl)-7-(1,1,1,3,3,3-hexafluoro-2-hydroxypropan-2-yl)-3a,4,5,9b-tetrahydro-1H-benzo[e]indole-3-carboxylate (0.7 g, 70% yield, about 80% purity).

Step G: (3aR,9bR)-tert-butyl 9b-((4-fluorophenyl)sulfonyl)-7-(perfluoropropan-2-yl)-3a,4,5,9b-tetrahydro-1H-benzo[e]indole-3-carboxylate

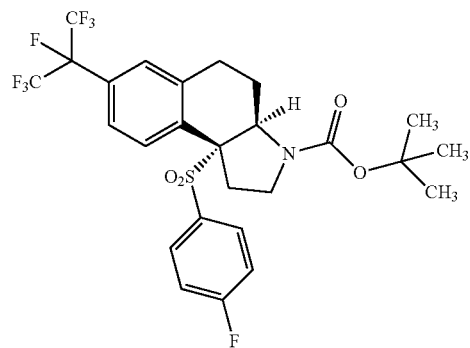 [SMILES: CC(C)(C)OC(=O)N1CC[C@@]2(S(=O)(=O)c3ccc(F)cc3)c3ccc(C(F)(C(F)(F)F)C(F)(F)F)cc3CC[C@@H]12]

DAST (2.92 mL, 22.09 mmol) was added to a stirred solution of (3aR,9bR)-tert-butyl 9b-((4-fluorophenyl)sulfonyl)-7-(1,1,1,3,3,3-hexafluoro-2-hydroxypropan-2-yl)-3a,4,5,9b-tetrahydro-1H-benzo[e]indole-3-carboxylate (1.1 g, 1.841 mmol) in 1,2-dichloroethane (18.41 mL) under N₂ at rt. The reaction vessel was sealed and heated with stirring at 60° C. After 15 h, LCMS showed only partial consumption of the starting material. Additional DAST (2.92 mL, 22.09 mmol) was added and the mixture was stirred at 60° C. for 4 h more. The mixture was cooled to rt, carefully quenched with MeOH (1 mL), diluted with EtOAc (160 mL) and washed with saturated aqueous NaHCO₃. The aqueous phase was separated and extracted with EtOAc (100 mL). The combined organic phases were washed with brine (50 mL), dried over Na₂SO₄, filtered and concentrated. The residue was purified by column chromatography on silica gel, eluting with EtOAc-hexanes (gradient from 5-40%), to provide (3aR,9bR)-tert-butyl 9b-((4-fluorophenyl)sulfonyl)-7-(perfluoropropan-2-yl)-3a,4,5,9b-tetrahydro-1H-benzo[e]indole-3-carboxylate (800 mg, 72.5% yield). LCMS m/z 544.0 (M+H—$C_4H_8$)⁺, HPLC $t_R$ 1.21 min (method B).

Alternative Preparation of (3aR,9bR)-tert-butyl 9b-((4-fluorophenyl)sulfonyl)-7-(perfluoropropan-2-yl)-3a,4,5,9b-tetrahydro-1H-benzo[e]indole-3-carboxylate A mixture of activated copper (prepared as outlined in Step A of the preparation of Intermediate 2; 3.5 g, 55 mmol) and (3aR,9bR)-tert-butyl 9b-((4-fluorophenyl)sulfonyl)-7-iodo-3a,4,5,9b-tetrahydro-1H-benzo[e]indole-3-carboxylate (prepared by following the procedures of Steps A through E above, but starting from Intermediate 1 instead of Intermediate 3; 4 g, 7.2 mmol) in dry DMF (18 mL) was purged with nitrogen, treated with 1,1,1,2,3,3,3-heptafluoro-2-iodopropane (4.6 mL, 32 mmol) and heated at 120° C. in a sealed reaction vessel. After 4 h the mixture was cooled to rt, diluted with EtOAc and filtered through Celite. The filtrate was washed 4 times with brine, dried with Na₂SO₄ and concentrated. The residue was purified by column chromatography on silica, eluting with EtOAc-hexanes, to provide (3aR,9bR)-tert-butyl 9b-((4-fluorophenyl)sulfonyl)-7-(perfluoropropan-2-yl)-3a,4,5,9b-tetrahydro-1H-benzo[e]indole-3-carboxylate (3.6 g, 84% yield).

Step H: (3aR,9bR)-9b-((4-fluorophenyl)sulfonyl)-7-(perfluoropropan-2-yl)-2,3,3a,4,5,9b-hexahydro-1H-benzo[e]indole hydrochloride

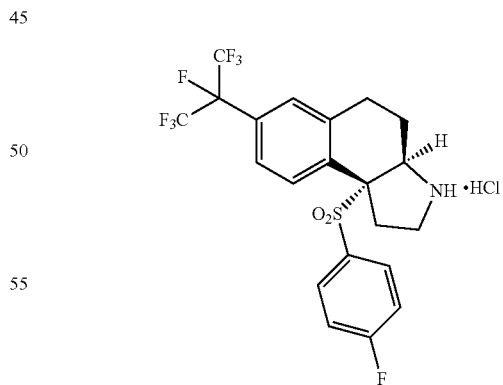

A solution of (3aR,9bR)-tert-butyl 9b-((4-fluorophenyl)sulfonyl)-7-(perfluoropropan-2-yl)-3a,4,5,9b-tetrahydro-1H-benzo[e]indole-3-carboxylate (250 mg, 0.417 mmol) in DCM (4.2 mL) was treated with HCl (4 M in 1,4-dioxane, 4.2 mL, 16.68 mmol). After 1 h at rt, the mixture was concentrated to provide (3aR,9bR)-9b-((4-fluorophenyl)sulfonyl)-7-(perfluoropropan-2-yl)-2,3,3a,4,5,9b-hexahydro- 1H-benzo[e]indole, HCl (225 mg). LCMS m/z 500.0 (M+H)+, HPLC $t_R$: 0.88 min (method B).

The Intermediates in Table 2 were prepared using procedures (or similar procedures) used in the preparation of Intermediate 32, starting from an appropriate vinylic sulfone, an appropriate aminocarbinol, and other appropriate reagents. In the preparation of some of the Intermediates in Table 2, one or more steps used in the preparation of Intermediate 32 were omitted, or applied in a different order, as appropriate.

TABLE 2

| Intermediate number | Structure | LCMS m/z observed | HPLC $t_R$ (min) | HPLC method |
|---|---|---|---|---|
| 33 | 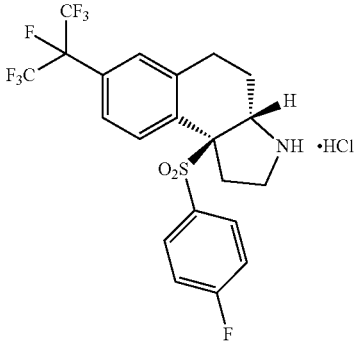 [SMILES: O=S(=O)(c1ccc(F)cc1)[C@]12CCN[C@H]1CCc1cc(C(F)(C(F)(F)F)C(F)(F)F)ccc12 ; Cl] | 500.0 (M + H)+ | 0.88 | B |
| 34 | 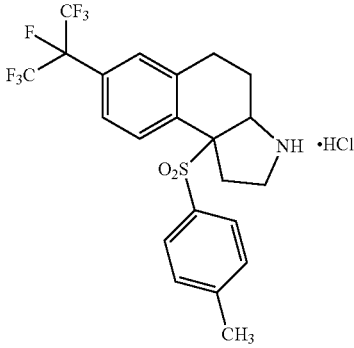  Homochiral from peak 2 | 496.1 (M + H)+ | 0.92 | B |
| 35 | 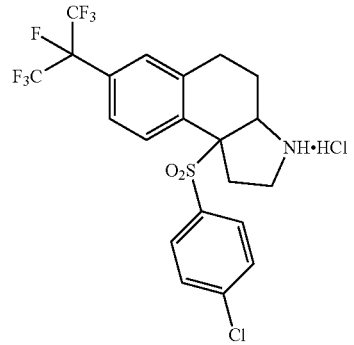  Homochiral from peak 2 | 516.0 (M + H)+ | 0.94 | B |

TABLE 2-continued
| Intermediate number | Structure | LCMS m/z observed | HPLC $t_R$ (min) | HPLC method |
|---|---|---|---|---|
| 36 | 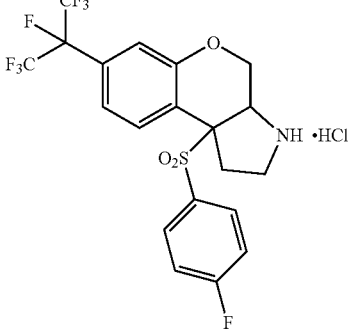<br>Homochiral from peak 2 | 502.1 (M + H)+ | 0.84 | B |
| 37 | 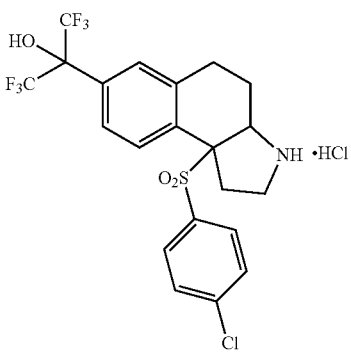<br>Homochiral from peak 2 | 513.3 (M + H)+ | 0.81 | B |
| 38 | <br>Homochiral from peak 2 | 500.5 (M + H)+ | 0.78 | B |
| 39 | 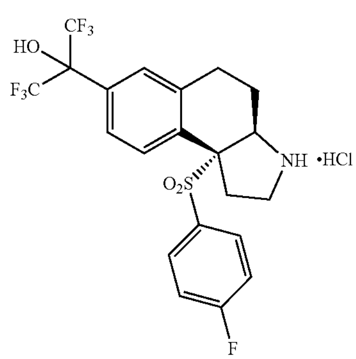 [SMILES: O=S(=O)(c1ccc(F)cc1)[C@@]12CCN[C@@H]1CCc1cc(C(O)(C(F)(F)F)C(F)(F)F)ccc12 ; Cl] | 498.0 (M + H)+ | 0.85 | B |

TABLE 2-continued

| Intermediate number | Structure | LCMS m/z observed | HPLC $t_R$ (min) | HPLC method |
|---|---|---|---|---|
| 40 | ![structure] Homochiral from peak 2 | 516.0 (M + H)+ | 0.79 | B |
| 41 | ![structure] Homochiral from peak 2 | 514.0 (M + H)+ | 0.80 | B |
| 42 | ![structure] Homochiral from peak 2 | 516.2 (M + H)+ | 0.88 | B |
| 43 | ![structure] Homochiral from peak 2 | 500.0 (M + H)+ | 0.82 | B |

TABLE 2-continued
| Intermediate number | Structure | LCMS m/z observed | HPLC $t_R$ (min) | HPLC method |
|---|---|---|---|---|
| 44 | 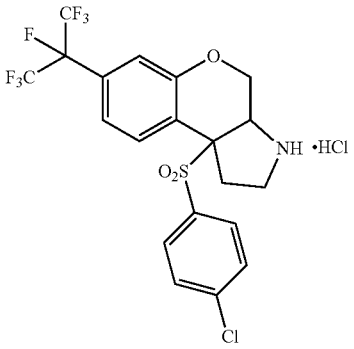<br>Homochiral from peak 2 | 518.0 $(M + H)^+$ | 0.92 | B |
| 45 | 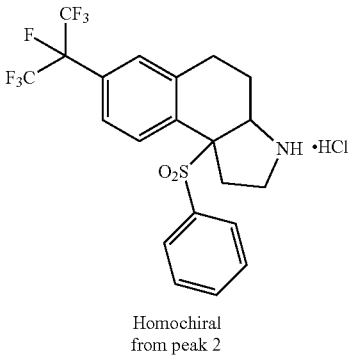 [SMILES: O=S(=O)(c1ccccc1)C12CCNC1COc1cc(C(F)(C(F)(F)F)C(F)(F)F)ccc12 ; Cl]<br>Homochiral from peak 2 | 482.0 $(M + H)^+$ | 0.87 | B |
| 46 | 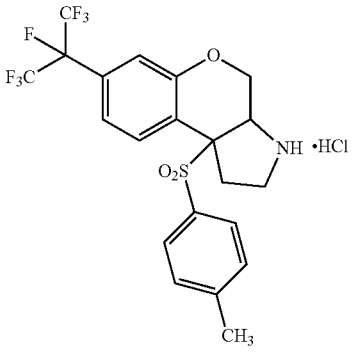<br>Homochiral from peak 2 | 498.0 $(M + H)^+$ | 0.89 | B |
| 47 | 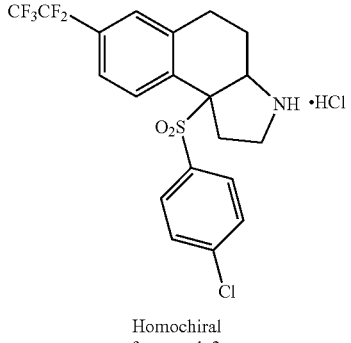<br>Homochiral from peak 2 | 466.0 $(M + H)^+$ | 0.87 | B |

TABLE 2-continued
| Intermediate number | Structure | LCMS m/z observed | HPLC $t_R$ (min) | HPLC method |
|---|---|---|---|---|
| 48 | 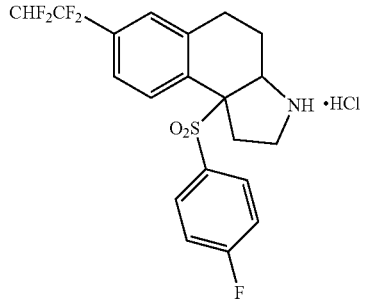<br>Homochiral from peak 2 | 432.1 (M + H)+ | 0.77 | B |
| 49 | 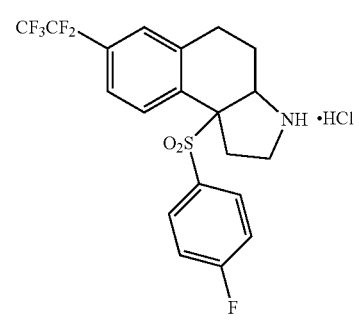<br>Homochiral from peak 2 | 450.1 (M + H)+ | 0.83 | B |
| 50 | 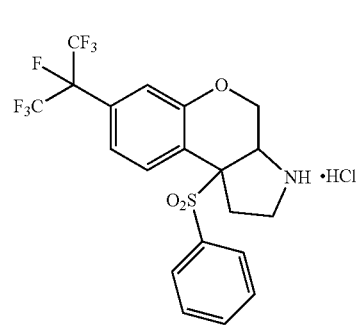<br>Homochiral from peak 2 | 484.0 (M + H)+ | 0.85 | B |
| 51 | 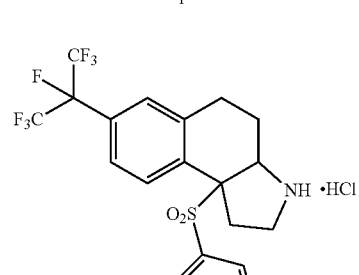<br>Homochiral from peak 2 | 514.0 (M + H)+ | 0.87 | B |

TABLE 2-continued

| Intermediate number | Structure | LCMS m/z observed | HPLC $t_R$ (min) | HPLC method |
|---|---|---|---|---|
| 52 | (structure) Homochiral from peak 2 | 530.2 (M + H)⁺ | 0.97 | B |
| 53 | (structure) Homochiral from peak 2 | 488.0 (M + H)⁺ | 0.84 | B |
| 54 | (structure) Homochiral from peak 2 | 500.0 (M + H)⁺ | 0.88 | B |
| 55 | (structure) Homochiral from peak 2 | 496.1 (M + H)⁺ | 0.87 | B |

TABLE 2-continued

| Intermediate number | Structure | LCMS m/z observed | HPLC $t_R$ (min) | HPLC method |
|---|---|---|---|---|
| 56 | (structure) Homochiral from peak 2 | 483.2 (M + H)⁺ | 0.77 | B |
| 57 | (structure) Homochiral from peak 2 | 483.3 (M + H)⁺ | 0.76 | B |
| 58 | (structure) Homochiral from peak 2 | 524.1 (M + H)⁺ | 0.96 | B |
| 59 | (structure) Homochiral from peak 2 | 510.3 (M + H)⁺ | 0.90 | B |

TABLE 2-continued
| Intermediate number | Structure | LCMS m/z observed | HPLC $t_R$ (min) | HPLC method |
|---|---|---|---|---|
| 60 | 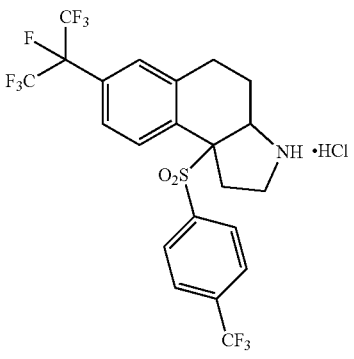<br>Homochiral from peak 2 | 550.3 (M + H)⁺ | 1.01 | B |
| 61 | 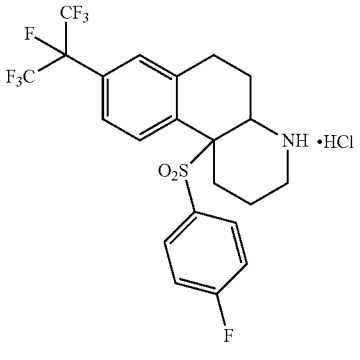<br>Homochiral from peak 2 | 514.5 (M + H)⁺ | 0.86 | B |
| 62 | 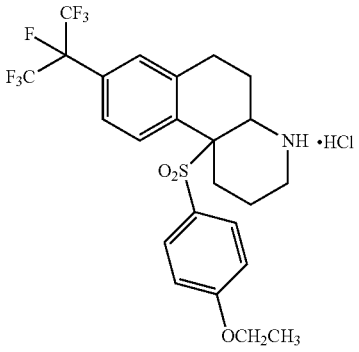<br>Homochiral from peak 2 | 540.4 (M + H)⁺ | 0.88 | B |
| 63 | 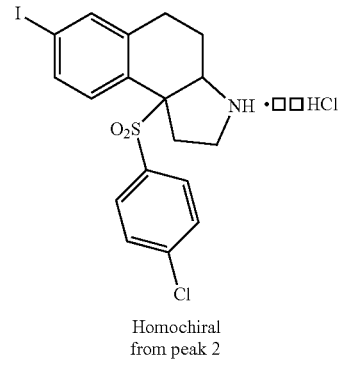<br>Homochiral from peak 2 | 473.9 (M + H)⁺ | 0.83 | B |

TABLE 2-continued
| Intermediate number | Structure | LCMS m/z observed | HPLC $t_R$ (min) | HPLC method |
|---|---|---|---|---|
| 64 | 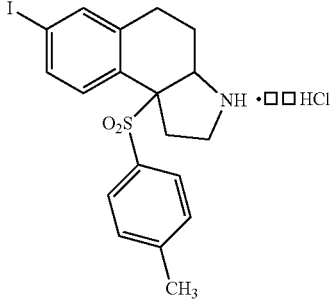<br>Homochiral from peak 2 | 453.8 (M + H)+ | 0.76 | B |
| 65 | 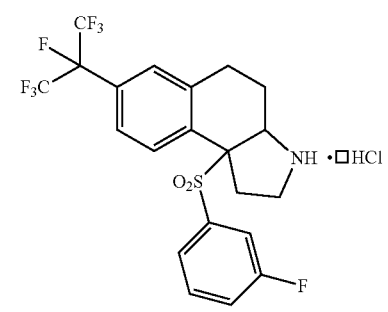<br>Homochiral from peak 2 | 500.0 (M + H)+ | 0.89 | B |
| 66 | 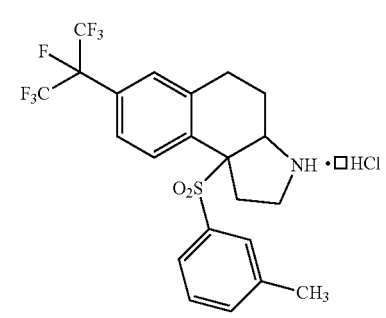<br>Homochiral from peak 2 | 496.2 (M + H)+ | 0.86 | B |
| 67 | 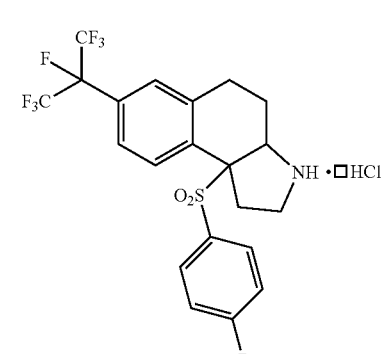<br>Homochiral from peak 2 | 558.4 (M + H + MeCN)+ | 1.22 | B |

TABLE 2-continued
| Intermediate number | Structure | LCMS m/z observed | HPLC $t_R$ (min) | HPLC method |
|---|---|---|---|---|
| 68 | 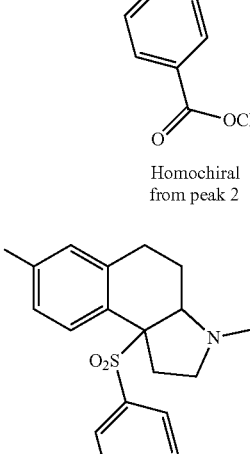<br>Homochiral from peak 2 | 584.4 $(M + H - C_4H_8)^+$ | 1.17 | B |
| 69 | 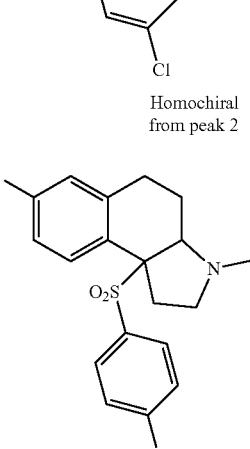<br>Homochiral from peak 2 | 517.8 $(M + H - C_4H_8)^+$ | 1.22 | B |
| 70 | <br>Homochiral from peak 2 | 497.7 $(M + H - C_4H_8)^+$ | 1.18 | B |
| 71 | 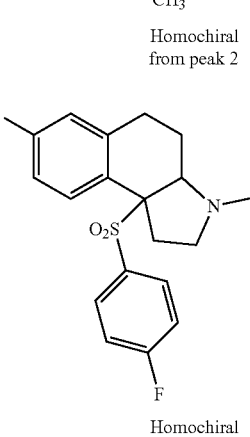<br>Homochiral from peak 2 | 501.8 $(M + H - C_4H_8)^+$ | 2.45 | C |

TABLE 2-continued
| Intermediate number | Structure | LCMS m/z observed | HPLC $t_R$ (min) | HPLC method |
|---|---|---|---|---|
| 72 | 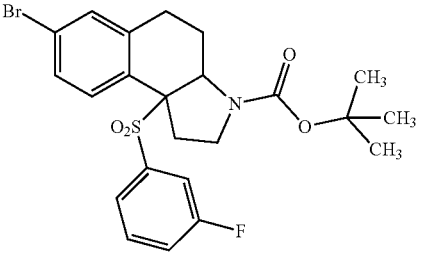<br>Homochiral from peak 1 | 495.0 $(M + H - C_4H_8)^+$ | 1.19 | B |
| 73 | 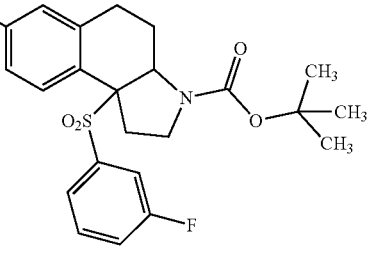<br>Homochiral from peak 2 | 495.0 $(M + H - C_4H_8)^+$ | 1.19 | B |
| 74 | 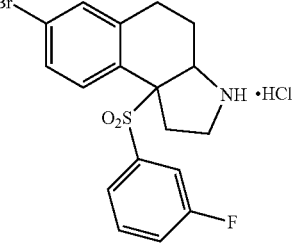<br>Homochiral from peak 2 | 409.9 $(M + H)^+$ | 0.73 | B |
| 75 | 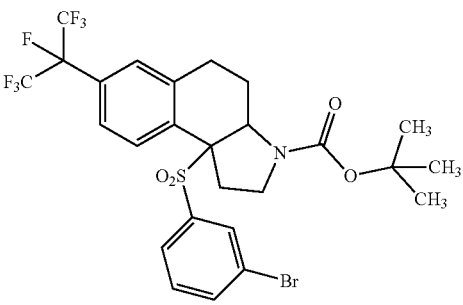<br>Homochiral from peak 2 | 645.0 $(M + H + MeCN - C_4H_8)^+$ | 1.27 | B |

TABLE 2-continued
| Intermediate number | Structure | LCMS m/z observed | HPLC $t_R$ (min) | HPLC method |
|---|---|---|---|---|
| 76 | 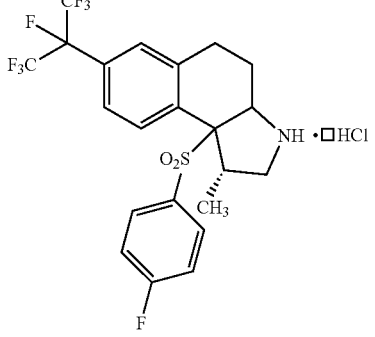<br>Homochiral from peak 1 | 514.1 (M + H)⁺ | 0.90 | B |
| 77 | 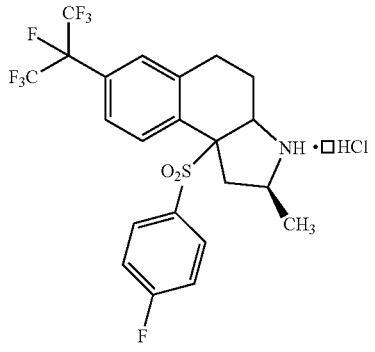<br>Homochiral from peak 1 | 514.0 (M + H)⁺ | 0.88 | B |
| 78 | 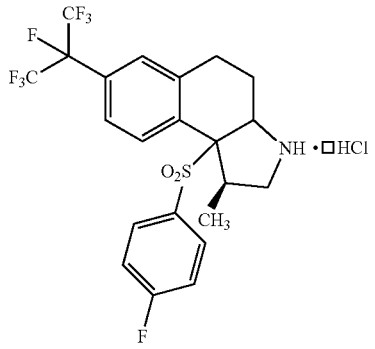<br>Homochiral from peak 1 | 514.1 (M + H)⁺ | 0.90 | B |

TABLE 2-continued
| Intermediate number | Structure | LCMS m/z observed | HPLC $t_R$ (min) | HPLC method |
|---|---|---|---|---|
| 79 | 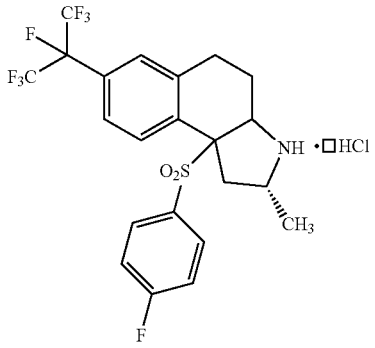 Homochiral from peak 2 | 514.0 (M + H)+ | 0.89 | B |
| 80 | 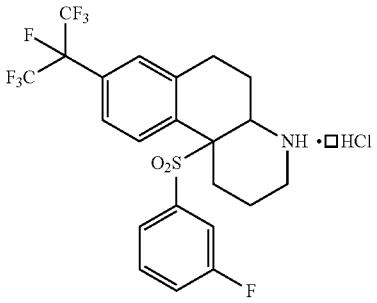 Homochiral from peak 2 | 514.1 (M + H)+ | 0.92 | B |
| 81 | 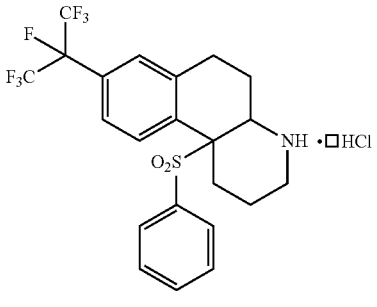 Homochiral from peak 2 | 496.1 (M + H)+ | 0.89 | B |
| 82 | 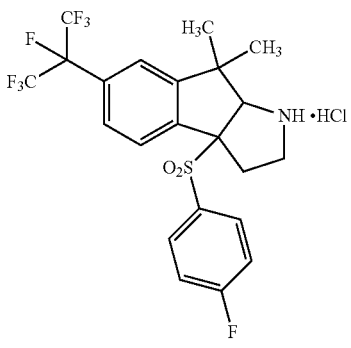 Homochiral from peak 1 | 514.2 (M + H)+ | 0.90 | B |

TABLE 2-continued
| Intermediate number | Structure | LCMS m/z observed | HPLC $t_R$ (min) | HPLC method |
|---|---|---|---|---|
| 83 | 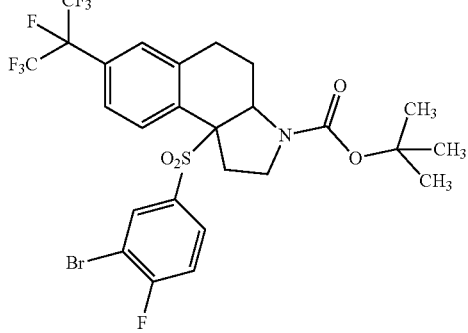<br>Homochiral from peak 1 | 663.2 $(M + H + MeCN - C_4H_8)^+$ | 1.22 | B |
| 84 | 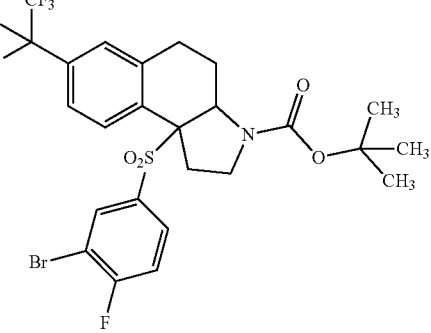<br>Homochiral from peak 2 | 663.2 $(M + H + MeCN - C_4H_8)^+$ | 1.22 | B |
| 85 | 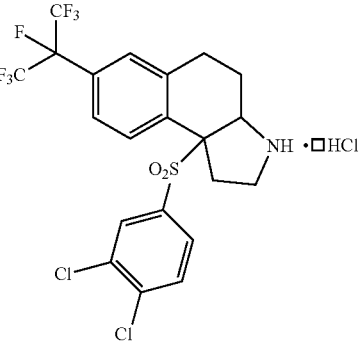<br>Homochiral from peak 2 | 550.0 $(M + H)^+$ | 0.91 | B |
| 86 | 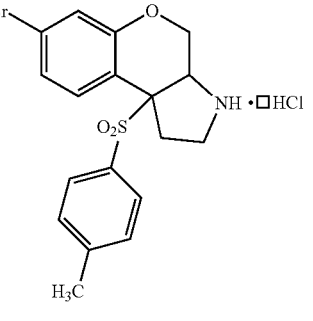<br>Homochiral from peak 2 | 408.0 $(M + H)^+$ | 0.73 | B |

TABLE 2-continued

| Intermediate number | Structure | LCMS m/z observed | HPLC $t_R$ (min) | HPLC method |
|---|---|---|---|---|
| 87 | 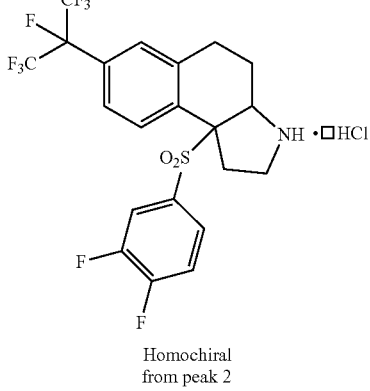<br>Homochiral from peak 2 | 518.0 (M + H)⁺ | 0.88 | B |

Intermediate 88

9b-((4-fluorophenyl)sulfonyl)-7-(perfluoropropan-2-yl)-2,3,3a,4,5,9b-hexahydro-1H-pyrrolo[2,3-c]quinoline Dihydrochloride

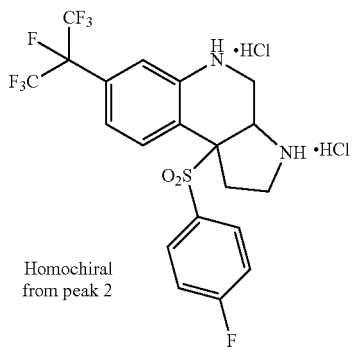 [SMILES: O=S(=O)(c1ccc(F)cc1)C12CCNC1CNc1cc(C(F)(C(F)(F)F)C(F)(F)F)ccc12 ; Cl ; Cl]

Homochiral from peak 2

Step A: Tert-butyl 7-bromo-4-((4-fluorophenyl)sulfonyl)quinoline-1 (2H)-carboxylate

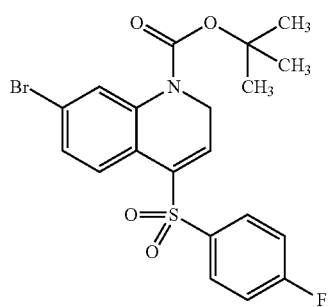 [SMILES: CC(C)(C)OC(=O)N1CC=C(S(=O)(=O)c2ccc(F)cc2)c2ccc(Br)cc21]

A solution of 7-bromo-2,3-dihydroquinolin-4(1H)-one (8 g, 35 mmol), 4-fluorobenzenethiol (7.9 mL, 74 mmol) and absolute ethanol (44 mL) was cooled with an ice-water bath. HCl gas was bubbled through the mixture until saturation was reached (as indicated by the formation of a white precipitate). The mixture was stirred on the ice-water bath for 1 h and at rt for 1 h more. The mixture was concentrated and the resulting oil was dissolved in DCM (250 mL) and washed with 1 M aqueous NaOH. The organic phase was dried over $Na_2SO_4$ and concentrated to give crude 7-bromo-4,4-bis((4-fluorophenyl)thio)-1,2,3,4-tetrahydroquinoline as a solid (16.4 g, 100% yield). HPLC $t_R$ 1.27 min (method B).

This material was dissolved in 1,4-dioxane (180 mL) and treated with 4-dimethylaminopyridine (13 g, 106 mmol) and di-tert-butyl dicarbonate (25 mL, 106 mmol). The mixture was stirred at rt for 16, then was diluted with EtOAc and washed twice with 1 M aqueous HCl. The organic phase was dried over $Na_2SO_4$ and concentrated to afford tert-butyl 7-bromo-4,4-bis((4-fluorophenyl)thio)-3,4-dihydroquinoline-1(2H)-carboxylate (20 g, 100% yield). HPLC $t_R$ 1.37 min (method B).

This material was dissolved in DCM (350 mL) and cooled with an ice-water bath. mCPBA (22 g, 172 mmol) was added and the mixture was stirred for 1 h. Additional mCPBA (22 g, 172 mmol) was added, and stirring was continued for 1 h more. The mixture was filtered to remove the insoluble material, and the filtrate was treated with 10% aqueous $Na_2S_2O_3$ (120 mL) and stirred for 5 min. The organic phase was separated, washed sequentially with 10% aqueous $Na_2S_2O_3$ (2×120 mL), 10% aqueous $Na_2CO_3$ (3×200 mL) and brine (150 mL), dried over $Na_2SO_4$ and concentrated to give crude tert-butyl 7-bromo-4-((4-fluorophenyl)sulfonyl)quinoline-1(2H)-carboxylate (17 g) which was used without further purification. LCMS m/z 468.0 (M+H+MeCN)⁺, HPLC $t_R$ 1.16 min (method B).

Step B: Tert-butyl 7-bromo-4-((4-fluorophenyl)sulfonyl)-3-((2-hydroxyethyl)amino)-3,4-dihydroquinoline-1 (2H)-carboxylate

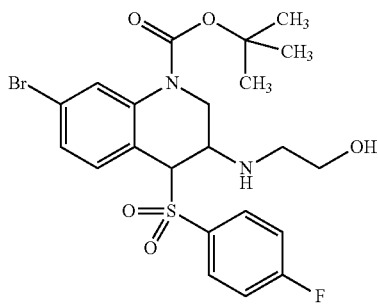 [SMILES: CC(C)(C)OC(=O)N1CC(NCCO)C(S(=O)(=O)c2ccc(F)cc2)c2ccc(Br)cc21]

A solution of tert-butyl 7-bromo-4-((4-fluorophenyl)sulfonyl)quinoline-1(2H)-carboxylate (16.6 g, 35 mmol) in THF (700 mL) was stirred on an ice-water bath and treated with 2-aminoethanol (11 mL, 177 mmol). The mixture was stirred at about 5° C. for 30 min, then was concentrated. The resulting oil was dissolved in EtOAc (750 mL) and the solution washed three times with brine, dried over $Na_2SO_4$ and concentrated to provide tert-butyl 7-bromo-4-((4-fluorophenyl)sulfonyl)-3-((2-hydroxyethyl)amino)-3,4-dihydroquinoline-1(2H)-carboxylate (19.5 g) which was used without further purification. LCMS m/z 529.0 $(M+H)^+$, HPLC $t_R$ 0.89 min (method B).

Step C: Tert-butyl 7-bromo-9b-((4-fluorophenyl)sulfonyl)-1,2,3,3a,4,9b-hexahydro-5H-pyrrolo[2,3-c]quinoline-5-carboxylate

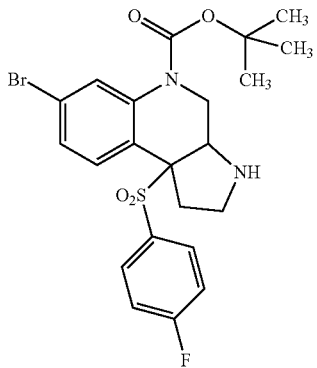 [SMILES: CC(C)(C)OC(=O)N1CC2NCCC2(S(=O)(=O)c2ccc(F)cc2)c2ccc(Br)cc21]

A solution of tert-butyl 7-bromo-4-((4-fluorophenyl)sulfonyl)-3-((2-hydroxyethyl)amino)-3,4-dihydroquinoline-1 (2H)-carboxylate (19 g, 35 mmol) in DCM (650 mL) was treated with MsCl (3.3 mL, 43 mmol), then with $Et_3N$ (5.9 mL, 43 mmol) at rt. The mixture was stirred for 30 min, when LCMS showed complete conversion to the methanesulfonate derivative; LCMS m/z 607.0 $(M+1)^+$, HPLC $t_R$ 0.94 min (method B). The mixture was treated with a solution of potassium tert-butoxide (20 g, 180 mmol) in THF (150 mL) and stirred for 30 min. The mixture was then treated with a 1:1 mixture of water and saturated brine (100 mL) and diluted with EtOAc (1 L). The organic phase was separated and washed 3 times with brine, dried over $Na_2SO_4$ and concentrated to give crude tert-butyl 7-bromo-9b-((4-fluorophenyl)sulfonyl)-2,3,3a,4-tetrahydro-1H-pyrrolo[2,3-c]quinoline-5-carboxylate (19 g), used without further purification. LCMS m/z 511.0 $(M+1)^+$, HPLC $t_R$ 0.85 min (method B).

Step D: Di-tert-butyl 7-bromo-9b-((4-fluorophenyl)sulfonyl)-1,3a,4,9b-tetrahydro-3H-pyrrolo[2,3-c]quinoline-3,5(2H)-dicarboxylate, Two Homochiral Enantiomers

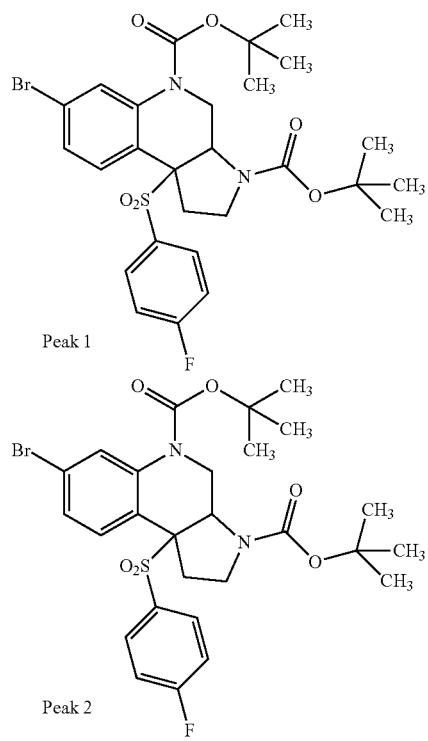

Peak 1

Peak 2

A solution of tert-butyl 7-bromo-9b-((4-fluorophenyl)sulfonyl)-2,3,3a,4-tetrahydro-1H-pyrrolo[2,3-c]quinoline-5-carboxylate (18 g, 35 mmol) in DCM (350 mL) was treated with di-tert-butyl dicarbonate (12 mL, 53 mmol) and diisopropylethylamine (18.5 mL, 106 mmol). The mixture was stirred at rt for 1 h, then was diluted with DCM (100 mL) and washed sequentially with 1 M aqueous HCl and 1 M aqueous NaOH. The organic phase was dried over $Na_2SO_4$ and concentrated. The residue was purified by column chromatography on silica gel, eluting with EtOAc-hexanes, to provide di-tert-butyl 7-bromo-9b-((4-fluorophenyl)sulfonyl)-1,3a,4,9b-tetrahydro-3H-pyrrolo[2,3-c]quinoline-3,5 (2H)-dicarboxylate (7.6 g, 35% overall yield from 7-bromo-2,3-dihydroquinolin-4(1H)-one).

This material was separated by chiral SFC using the following conditions: Column: Chiralcel® OD-H 50×250 mm, 5 m (Chiral Technologies Inc.); column temperature 35° C.; pressure 100 bars; mobile phase $CO_2$-MeOH (90:10); flow rate 300 mL/min; injection volume 0.9 mL. Peak 1 was eluted with $t_R$ 3.51 min. Peak 2 (2.6 g) was eluted with $t_R$ 4.01 min. LCMS m/z 454.9 $(M+2H-CO_2C_4H_9-C_4H_9)^+$, HPLC $t_R$ 1.22 min (method B).

Step E: Di-tert-butyl 9b-((4-fluorophenyl)sulfonyl)-7-(perfluoropropan-2-yl)-1,3a,4,9b-tetrahydro-3H-pyrrolo[2,3-c]quinoline-3,5(2H)-dicarboxylate (Homochiral)

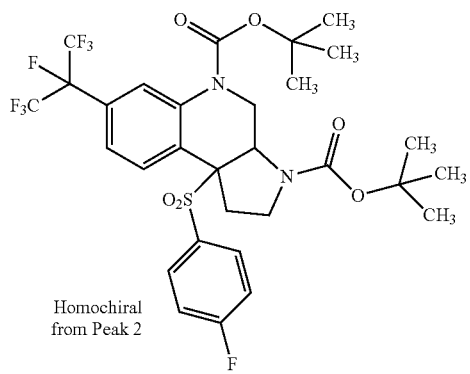 [SMILES: CC(C)(C)OC(=O)N1CC2N(C(=O)OC(C)(C)C)CCC2(S(=O)(=O)c2ccc(F)cc2)c2ccc(C(F)(C(F)(F)F)C(F)(F)F)cc21]

Homochiral from Peak 2

A sealable reaction vessel was charged with activated copper powder (prepared as outlined in Step A of the preparation of Intermediate 2; 3.5 g, 55 mmol), homochiral di-tert-butyl 7-bromo-9b-((4-fluorophenyl)sulfonyl)-3a,4-dihydro-1H-pyrrolo[2,3-c]quinoline-3,5(2H)-dicarboxylate (from Peak 2; 2.9 g, 4.7 mmol) DMF (16 mL) and 1,1,1,2,3,3,3-heptafluoro-2-iodopropane (5.4 mL, 38 mmol). The sealed vial was purged with nitrogen and heated at 120° C. After 4 h, the mixture was cooled to rt, diluted with EtOAc and filtered through Celite. The filtrate was washed 4 times with brine, dried over $Na_2SO_4$ and concentrated. The residue was purified by column chromatography on silica gel, eluting with EtOAc-hexanes, to provide homochiral di-tert-butyl 9b-((4-fluorophenyl)sulfonyl)-7-(perfluoropropan-2-yl)-3a,4-dihydro-1H-pyrrolo[2,3-c]quinoline-3,5(2H)-dicarboxylate (712 mg, 22% yield) along with recovered starting material (1.1 g). LCMS m/z 545.0 $(M+2H—CO_2C_4H_9—C_4H_9)^+$, HPLC $t_R$ 1.27 min (method B).

Step F: 9b-((4-fluorophenyl)sulfonyl)-7-(perfluoropropan-2-yl)-2,3,3a,4,5,9b-hexahydro-1H-pyrrolo[2,3-c]quinoline Dihydrochloride Homochiral from Peak 2

A solution of di-tert-butyl 9b-((4-fluorophenyl)sulfonyl)-7-(perfluoropropan-2-yl)-3a,4-dihydro-1H-pyrrolo[2,3-c]quinoline-3,5(2H)-dicarboxylate (from Peak 2; 358 mg, 0.511 mmol) in DCM (2.5 mL) was treated with HCl (4 M in 1,4-dioxane; 2.5 mL, 10 mmol). The mixture was allowed to stand at rt for 1 h, then was concentrated to provide 9b-((4-fluorophenyl)sulfonyl)-7-(perfluoropropan-2-yl)-2,3,3a,4,5,9b-hexahydro-1H-pyrrolo[2,3-c]quinoline dihydrochloride (290 mg, 99% yield). LCMS m/z 501.1 $(M+1)^+$, HPLC $t_R$ 0.89 min (method B). $^1H$ NMR (500 MHz, DMSO-$d_6$) δ 7.52 (d, J=8.3 Hz, 1H), 7.44 (dd, J=8.3, 5.1 Hz, 2H), 7.26 (t, J=8.6 Hz, 2H), 6.85 (d, J=8.2 Hz, 1H), 6.74 (s, 1H), 6.27 (br. s., 1H), 3.77 (t, J=5.5 Hz, 1H), 3.13-3.05 (m, 1H), 3.01-2.91 (m, 1H), 2.91-2.74 (m, 3H), 2.55 (s, 1H), 2.46-2.32 (m, 1H). $^{19}F$ NMR (376 MHz, DMSO-$d_6$) δ −104.9 (s, 1F), −77.3 (m, 1F), −77.0 (s, 6F).

The Intermediates in Table 3 were prepared using the same methods or similar methods used to prepare Intermediate 88, by employing the appropriate substituted thiophenol.

TABLE 3

| Intermediate number | Structure | LCMS m/z observed | HPLC $t_R$ (min) | HPLC method |
|---|---|---|---|---|
| 89 | (structure shown; Homochiral from peak 1) | 501.0 $(M + H)^+$ | 0.89 | B |

TABLE 3-continued
| Intermediate number | Structure | LCMS m/z observed | HPLC $t_R$ (min) | HPLC method |
|---|---|---|---|---|
| 90 | 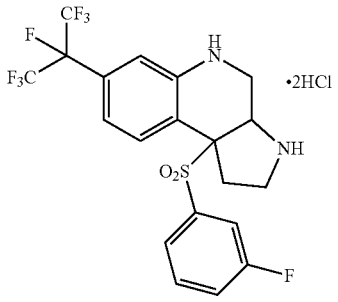<br>Homochiral from peak 1 | 501.0 (M + H)⁺ | 0.86 | B |
| 91 | 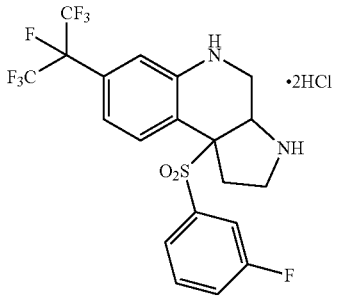<br>Homochiral from peak 2 | 501.0 (M + H)⁺ | 0.86 | B |
| 92 | 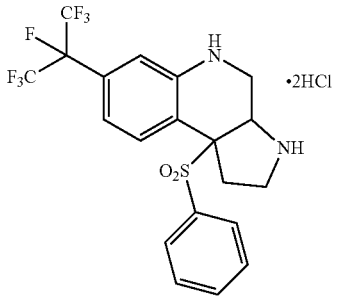<br>Homochiral from peak 2 | 483.1 (M + H)⁺ | 0.86 | B |
| 93 | 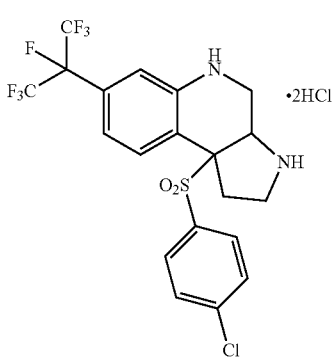<br>Homochiral from peak 2 | 517.0 (M + H)⁺ | 0.88 | B |

Intermediates 94 and 95

3a-((4-fluorophenyl)sulfonyl)-6-(perfluoropropan-2-yl)-1,2,3,3a,8,8a-hexahydroindeno[2,1-b]pyrrole Hydrochloride (Two Homochiral Enantiomers)

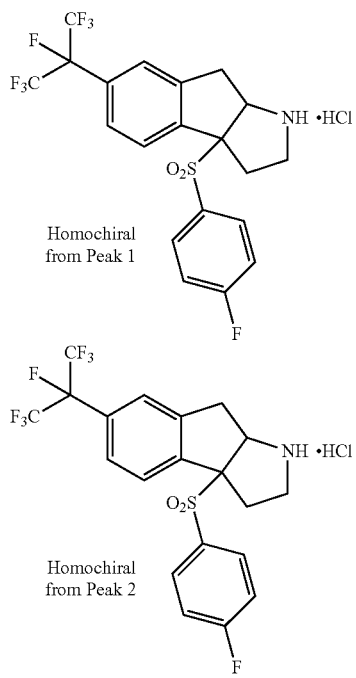

Homochiral from Peak 1

Homochiral from Peak 2

Step A: 4-bromo-1a,6a-dihydro-6H-indeno[1,2-b]oxirene

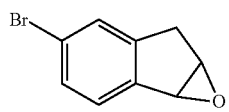 [SMILES: Brc1ccc2c(c1)CC1OC21]

A solution of 6-bromo-1H-indene (prepared according to the procedure in U.S. Pat. No. 7,678,798; 5.30 g, 27.2 mmol) in DCM (125 mL) was treated with NaHCO$_3$ (6.85 g, 82 mmol) and stirred vigorously on an ice-water bath. The mixture was treated portionwise over 20 min with mCPBA (9.38 g, 38.0 mmol). After 3.75 h, additional mCPBA (1.675 g, 6.79 mmol) was added, and the reaction flask was stirred on an ice-water bath for 19.75 h more. The mixture was diluted with DCM (125 mL) and shaken with 10% aqueous Na$_2$S$_2$O$_3$ (100 mL). Additional DCM (250 mL), 1.5 M aqueous K$_2$HPO$_4$ (200 mL) and water (100 mL) were added, and the layers were mixed and separated. The aqueous phase was extracted twice more with DCM, and the combined organic phases were washed sequentially with 1.5 M aqueous K$_2$HPO$_4$, 10% aqueous Na$_2$S$_2$O$_3$, 1.5 M aqueous K$_2$HPO$_4$, water and brine, then dried over Na$_2$SO$_4$ and concentrated. The residue was purified by column chromatography on silica gel (330 g), eluting with EtOAc-hexanes (gradient from 5-40%), to provide 4-bromo-1a,6a-dihydro-6H-indeno[1,2-b]oxirene as a white solid (4.324 g, 74%), contaminated with about 2% by weight of 5-bromo-1H-inden-2(3H)-one. $^1$H NMR (400 MHz, CDCl$_3$) δ 7.42-7.33 (m, 3H), 4.29-4.23 (m, 1H), 4.15 (t, J=2.9 Hz, 1H), 3.23 (d, J=18.3 Hz, 1H), 2.99 (dd, J=18.2, 3.0 Hz, 1H).

Step B: (1RS,2RS)-5-bromo-1-((2-((tert-butyldimethylsilyl)oxy)ethyl)amino)-2,3-dihydro-1H-inden-2-ol (Racemic)

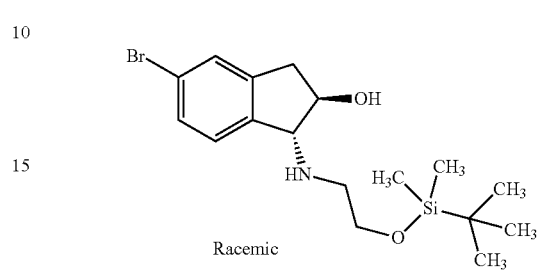

Racemic

A solution of 4-bromo-1a,6a-dihydro-6H-indeno[1,2-b]oxirene (4.32 g, 20.06 mmol) in MeCN (90 mL) at rt was treated with LiClO$_4$ (2.77 g, 26.1 mmol) and 2-((tert-butyldimethylsilyl)oxy)ethanamine (prepared according to *J. Org. Chem.* 2009, 74 (4), 1791 suppl.; 4.57 g, 26.1 mmol). The mixture was heated to 55° C. and stirred for 22.5 h. The mixture was cooled to rt and concentrated, and the residue was partitioned between water and EtOAc. The aqueous phase was extracted twice more with EtOAc, and the combined organic layers were washed with saturated brine, dried over Na$_2$SO$_4$ and concentrated to provide a dark brown viscous syrup. The material was purified by column chromatography on silica gel (330 g), eluting with EtOAc-hexanes (gradient from 30-100%, then isocratic) to provide (1RS,2RS)-5-bromo-1-((2-((tert-butyldimethylsilyl)oxy)ethyl)amino)-2,3-dihydro-1H-inden-2-ol (racemic) as a tan waxy solid (5.842 g, 75% yield). LCMS m/z 386.0 (M+H)$^+$, HPLC t$_R$ 0.85 min (method B). $^1$H NMR (400 MHz, CDCl$_3$) δ 7.39-7.31 (m, 2H), 7.23-7.15 (m, 1H), 4.34 (q, J=6.6 Hz, 1H), 4.01 (d, J=5.7 Hz, 1H), 3.78 (t, J=5.2 Hz, 2H), 3.25 (dd, J=16.0, 6.9 Hz, 1H), 3.03-2.86 (m, 2H), 2.80 (dd, J=15.8, 6.6 Hz, 1H), 0.92 (s, 9H), 0.09 (d, J=1.1 Hz, 6H).

Step C: 4-bromo-1-(2-((tert-butyldimethylsilyl)oxy)ethyl)-1,1a,6,6a-tetrahydroindeno[1,2-b]azirine

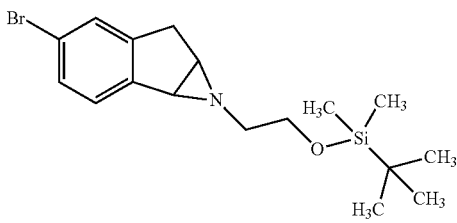 [SMILES: CC(C)(C)[Si](C)(C)OCCN1C2Cc3cc(Br)ccc3C21]

A solution of racemic (1RS,2RS)-5-bromo-1-((2-((tert-butyldimethylsilyl)oxy)ethyl)amino)-2,3-dihydro-1H-inden-2-ol (5.83 g, 15.09 mmol) in THF (100 mL) was treated with triphenylphosphine (5.94 g, 22.63 mmol). The resulting solution was cooled on an ice-water bath and treated dropwise over about 20 min with diethyl azodicarboxylate (3.58 mL, 22.63 mmol). The resulting thin brown suspension was stirred while the cooling bath was allowed to warm to rt. After 16 h, the mixture was concentrated and the residue was purified by column chromatography on silica gel (330 g), eluting with EtOAc-hexanes (gradient from 0-25%) to provide 4-bromo-1-(2-((tert-butyldimethylsilyl)oxy)ethyl)-1,1a,6,6a-tetrahydroindeno[1,2-b]azirine as a light brown-yellow syrup (4.693 g, 83% yield). LCMS m/z 368.0 (M+H)+, HPLC $t_R$ 0.91 min (method B). $^1$H NMR (400 MHz, CDCl$_3$) δ 7.31 (s, 1H), 7.27 (d, J=1.1 Hz, 2H), 3.84 (t, J=5.8 Hz, 2H), 3.16-3.06 (m, 1H), 3.04-2.93 (m, 2H), 2.69 (t, J=4.5 Hz, 1H), 2.63 (dt, J=11.8, 5.8 Hz, 1H), 2.47 (dt, J=12.0, 6.0 Hz, 1H), 0.95 (s, 9H), 0.10 (s, 6H).

Step D: (1RS,2RS)-5-bromo-N-(2-((tert-butyldimethylsilyl)oxy)ethyl)-1-((4-fluorophenyl)thio)-2,3-dihydro-1H-inden-2-amine (Racemic)

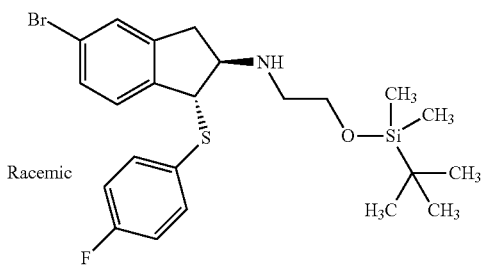 [SMILES: CC(C)(C)[Si](C)(C)OCCN[C@@H]1Cc2cc(Br)ccc2[C@H]1Sc1ccc(F)cc1]

A solution of 4-bromo-1-(2-((tert-butyldimethylsilyl)oxy)ethyl)-1,1a,6,6a-tetrahydroindeno[1,2-b]azirine (4.650 g, 12.62 mmol) in MeCN (60 mL) was treated rapidly dropwise with 4-fluorobenzenethiol (1.789 mL, 16.79 mmol) and the solution was stirred at rt. After 2 h, the mixture was concentrated to give a light greenish-brown oil. This was purified by column chromatography on silica gel (330 g), eluting with EtOAc-hexanes (gradient from 0-25%), to provide racemic (1RS,2RS)-5-bromo-N-(2-((tert-butyldimethylsilyl)oxy)ethyl)-1-((4-fluorophenyl)thio)-1H-inden-2-amine as a yellow-tan viscous oil (5.957 g, 95% yield). LCMS m/z 496.5 (M+H)+, HPLC $t_R$ 1.04 min (method B). $^1$H NMR (400 MHz, CDCl$_3$) δ 7.43-7.37 (m, 1H), 7.36-7.31 (m, 2H), 7.17 (d, J=8.6 Hz, 1H), 7.04-6.94 (m, 2H), 4.31 (d, J=4.4 Hz, 1H), 3.74-3.63 (m, 2H), 3.46 (dt, J=6.7, 4.6 Hz, 1H), 3.18 (dd, J=16.1, 6.8 Hz, 1H), 2.75-2.63 (m, 3H), 0.90 (s, 9H), 0.07 (s, 6H). $^{19}$F NMR (376 MHz, CDCl$_3$) δ −113.38 (tt, J=8.3, 5.4 Hz, 1F).

Step E: Tert-butyl (5-bromo-1-((4-fluorophenyl)thio)-2,3-dihydro-1H-inden-2-yl)(2-((tert-butyldimethylsilyl)oxy)ethyl)carbamate

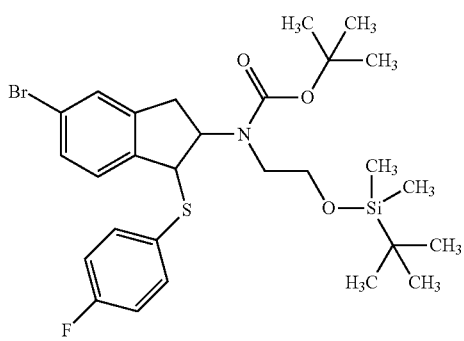 [SMILES: CC(C)(C)OC(=O)N(CCO[Si](C)(C)C(C)(C)C)C1Cc2cc(Br)ccc2C1Sc1ccc(F)cc1]

A solution of racemic (1RS,2RS)-5-bromo-N-(2-((tert-butyldimethylsilyl)oxy)ethyl)-1-((4-fluorophenyl)thio)-2,3-dihydro-1H-inden-2-amine (5.94 g, 11.96 mmol), Et$_3$N (2.168 mL, 15.55 mmol) and di-tert-butyl dicarbonate (3.61 mL, 15.55 mmol) in DCM (70 mL) was treated with 4-dimethylaminopyridine (0.073 g, 0.598 mmol) and stirred at rt. After 17 h, the solution was diluted with DCM, washed twice with water, then with saturated brine, dried over Na$_2$SO$_4$ and concentrated. The residue was purified by column chromatography on silica gel (330 g), eluting with EtOAc-hexanes (gradient from 0-10%). The product eluted in two peaks. Peak 1 provided one isomer of tert-butyl (5-bromo-1-((4-fluorophenyl)thio)-2,3-dihydro-1H-inden-2-yl)(2-((tert-butyldimethylsilyl)oxy)ethyl)carbamate as a colorless syrup (1.545 g, 22% yield). LCMS m/z 496.2 (M+H—COOC$_4$H$_9$)+, HPLC $t_R$ 1.09 min (method B). $^1$H NMR (400 MHz, CDCl$_3$) δ 7.43-7.25 (m, 5H), 6.97 (t, J=8.6 Hz, 2H), 5.01-4.68 (br. m, 1H), 4.43 (q, J=7.9 Hz, 1H), 3.78-2.91 (br. m, 6H), 1.48-1.25 (br. m, 9H), 0.89 (s, 9H), 0.06 (s, 3H), 0.05 (s, 3H). Peak 2 provided another isomer of tert-butyl (5-bromo-1-((4-fluorophenyl)thio)-2,3-dihydro-1H-inden-2-yl)(2-((tert-butyldimethylsilyl)oxy)ethyl)carbamate as a pale yellowish gum (4.814 g, 67% yield). LCMS m/z 496.2 (M+H—COOC$_4$H$_9$)+, HPLC $t_R$ 1.09 min (method B). $^1$H NMR (400 MHz, CDCl$_3$) δ 7.43-7.35 (m, 3H), 7.32-7.28 (m, 2H), 7.02-6.93 (m, 2H), 4.99 and 4.69 (2d, 1H), 4.61-4.34 (2q, 1H), 3.80-3.65 (2t, 2H), 3.49-3.01 (m, 4H), 1.60-1.48 (2s, 9H), 0.89 (s, 9H), 0.08-0.04 (2s, 6H). Both materials were combined and used in the subsequent reaction.

Step F: Tert-butyl (5-bromo-1-((4-fluorophenyl)sulfonyl)-2,3-dihydro-1H-inden-2-yl)(2-((tert-butyldimethylsilyl)oxy)ethyl)carbamate

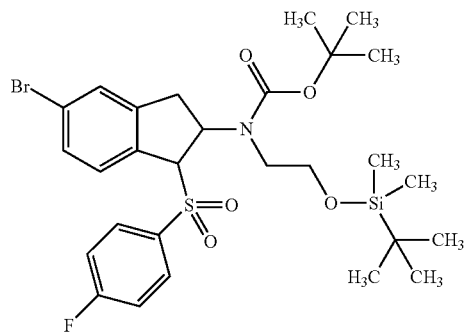 [SMILES: CC(C)(C)OC(=O)N(CCO[Si](C)(C)C(C)(C)C)C1Cc2cc(Br)ccc2C1S(=O)(=O)c1ccc(F)cc1]

A solution of tert-butyl (5-bromo-1-((4-fluorophenyl)thio)-2,3-dihydro-1H-inden-2-yl)(2-((tert-butyldimethylsilyl)oxy)ethyl)carbamate (6.34 g, 10.63 mmol) in DCM (85 mL) was stirred on an ice bath and treated with mCPBA (6.11 g, 26.6 mmol). After about 1 min the cooling bath was removed and the mixture was stirred at rt. After 4 h, the mixture was diluted with DCM, washed sequentially with 10% aqueous Na$_2$S$_2$O$_3$, 1.5 M aqueous K$_2$HPO$_4$ and brine, dried over Na$_2$SO$_4$ and concentrated. The residue was purified by column chromatography on silica gel (330 g), eluting with EtOAc-hexanes (gradient from 0-20%), to provide tert-butyl (5-bromo-1-((4-fluorophenyl)sulfonyl)-2,3-dihydro-1H-inden-2-yl)(2-((tert-butyldimethylsilyl)oxy)ethyl)carbamate as a white glassy solid (5.794 g, 87% yield). LCMS m/z 528.2 (M+H—COOC$_4$H$_9$)+, HPLC $t_R$ 1.35 min (method B). $^1$H NMR (400 MHz, CHLOROFORM-d) δ

7.72 (br. m., 2H), 7.51 (br. s, 1H), 7.41 (d, J=6.2 Hz, 1H), 7.30 (s, 1H), 7.16 (t, J=8.6 Hz, 2H), 5.34-4.89 (2 br. s., 1H), 4.75 (br. d., 1H), 3.86-3.62 (br. m., 2H), 3.62-3.26 (2 br. s., 1H), 3.16-3.04 (2d, 1H), 3.04-2.70 (br. m., 2H), 1.50-1.13 (2 br. s., 9H), 0.92 (s, 9H), 0.08 (s, 6H).

Step G: Tert-butyl (5-bromo-1-((4-fluorophenyl)sulfonyl)-2,3-dihydro-1H-inden-2-yl)(2-hydroxyethyl)carbamate

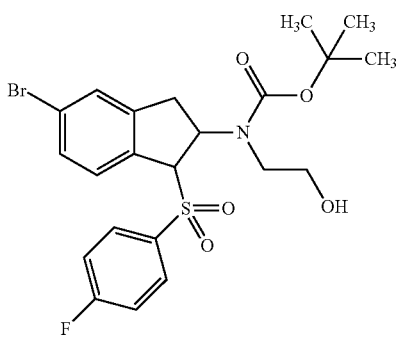 [SMILES: CC(C)(C)OC(=O)N(CCO)C1Cc2cc(Br)ccc2C1S(=O)(=O)c1ccc(F)cc1]

A solution of tert-butyl (5-bromo-1-((4-fluorophenyl)sulfonyl)-2,3-dihydro-1H-inden-2-yl)(2-((tert-butyldimethylsilyl)oxy)ethyl)carbamate (5.78 g, 9.19 mmol) in THF (100 mL) was stirred on an ice-water bath and treated dropwise with tetra-n-butylammonium fluoride, 1.0 M in THF (12 mL, 12.00 mmol) over about 7 min, forming a yellow-brown solution. After 80 min, the cold mixture was treated with saturated aqueous NH$_4$Cl (100 mL) and extracted with EtOAc. The aqueous phase was extracted again with EtOAc and the combined organic phases were washed with brine, dried over Na$_2$SO$_4$ and concentrated. The residue was purified by column chromatography on silica gel (330 g), eluting with EtOAc-hexanes (gradient from 0-60%), to provide tert-butyl (5-bromo-1-((4-fluorophenyl)sulfonyl)-2,3-dihydro-1H-inden-2-yl)(2-hydroxyethyl)carbamate as a white glassy solid. (3.796 g, 80% yield). LCMS m/z 458.1 (M+H—C$_4$H$_8$)$^+$, HPLC t$_R$ 1.04 min (method B). $^1$H NMR (400 MHz, CDCl$_3$) δ 7.75 (br. s., 2H), 7.43-7.38 (m, 1H), 7.34 (d, J=2.4 Hz, 1H), 7.31 (s, 1H), 7.19 (t, J=8.6 Hz, 2H), 5.10 (br. s., 1H), 4.78 (br. s., 1H), 3.80 (d, J=6.2 Hz, 1H), 3.74 (br. s., 1H), 3.43 (br. s., 1H), 3.25-3.17 (m, 1H), 3.17-3.07 (m, 1H), 3.02-2.88 (m, 1H), 2.70-2.32 (m, 1H), 1.32 (br. s., 9H).

Step H: Tert-butyl 6-bromo-3a-((4-fluorophenyl)sulfonyl)-3,3a,8,8a-tetrahydroindeno[2,1-b]pyrrole-1 (2H)-carboxylate

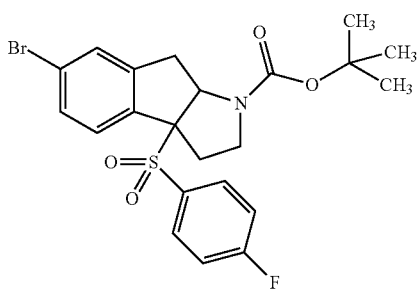 [SMILES: CC(C)(C)OC(=O)N1CCC2(S(=O)(=O)c3ccc(F)cc3)c3ccc(Br)cc3CC12]

A solution of tert-butyl (5-bromo-1-((4-fluorophenyl)sulfonyl)-2,3-dihydro-1H-inden-2-yl)(2-hydroxyethyl)carbamate (3.18 g, 6.18 mmol) in DCM (160 mL) was stirred on a water bath at rt and treated in one portion with MsCl (0.626 mL, 8.04 mmol). The solution was then treated dropwise over about 30 sec with Et$_3$N (1.12 mL, 8.04 mmol) and the resulting solution was stirred at rt. After 60 min, the mixture was treated with potassium tert-butoxide, 1.0 M in tetrahydrofuran (24.73 mL, 24.73 mmol) over about 3 min, gradually forming a slightly cloudy light brown solution, and stirring was continued. After 35 min, the mixture was treated with saturated aqueous NH$_4$Cl and diluted with DCM. The layers were mixed and separated and the aqueous phase was extracted again with DCM. The combined organic phases were dried over Na$_2$SO$_4$ and concentrated. The residue was purified by column chromatography on silica gel (330 g), eluting with EtOAc-hexanes (gradient from 0-30%), to provide tert-butyl 6-bromo-3a-((4-fluorophenyl)sulfonyl)-3,3a,8,8a-tetrahydroindeno[2,1-b]pyrrole-1 (2H)-carboxylate as a white glassy solid (2.812 g, 92% yield). LCMS m/z 481.1 (M+H+MeCN—C$_4$H$_8$)$^+$, HPLC t$_R$ 1.18 min (method B). $^1$H NMR (400 MHz, CDCl$_3$) δ 7.63-7.02 (br. m., 7H), 4.79 (d, J=5.9 Hz, 1H), 3.98-3.77 (2 br. s., 1H), 3.15-2.85 (br. m., 3H), 2.73-2.27 (2 br. m., 2H), 1.47 (2 br. s., 9H).

Step I: Tert-butyl 3a-((4-fluorophenyl)sulfonyl)-6-(perfluoropropan-2-yl)-3,3a,8,8a-tetrahydroindeno[2,1-b]pyrrole-1 (2H)-carboxylate

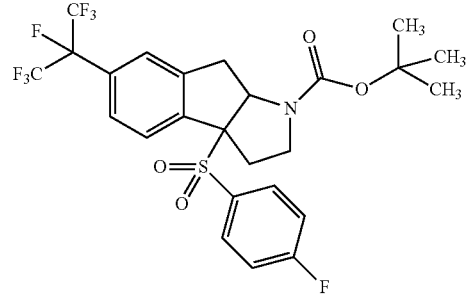 [SMILES: CC(C)(C)OC(=O)N1CCC2(S(=O)(=O)c3ccc(F)cc3)c3ccc(C(F)(C(F)(F)F)C(F)(F)F)cc3CC12]

A sealable reaction vessel was charged with activated copper powder (prepared as outlined in Step A of the preparation of Intermediate 2; 3.32 g, 52.2 mmol), tert-butyl 6-bromo-3a-((4-fluorophenyl)sulfonyl)-3,3a,8,8a-tetrahydroindeno[2,1-b]pyrrole-1(2H)-carboxylate (1.727 g, 3.48 mmol) and DMF (20 mL). The brick-red suspension was bubbled with argon, then treated with 1,1,1,2,3,3,3-heptafluoro-2-iodopropane (3.46 mL, 24.35 mmol), sealed under argon and heated with stirring on an oil bath at 120° C. After 4.5 h the mixture was cooled to rt, diluted with EtOAc and filtered through Celite. The solids were washed with EtOAc and the combined filtrates were washed with water. The organic phase was washed twice with 15% aqueous LiCl, then with brine, dried over Na$_2$SO$_4$ and concentrated. The residue was purified by column chromatography on silica gel (220 g), eluting with EtOAc-hexanes (gradient from 0-25%), to provide tert-butyl 3a-((4-fluorophenyl)sulfonyl)-6-(perfluoropropan-2-yl)-3,3a,8,8a-tetrahydroindeno[2,1-b]pyrrole-1(2H)-carboxylate as a light tan glassy solid (1.566 g, 74% yield). LCMS m/z 571.3 (M+H+MeCN—C$_4$H$_8$)$^+$, HPLC t$_R$ 1.18 min (method B). $^1$H NMR (400 MHz, CDCl$_3$) δ 7.80 (br. s., 1H), 7.66-7.35 (br. m, 4H), 7.00 (br. s, 2H), 4.83 (d, J=6.2 Hz, 1H), 3.91 (br. s., 1H), 3.22-2.90 (br. m, 3H), 2.72-2.27 (br. m, 2H), 1.49 (br. s., 9H). $^{19}$F NMR (376 MHz, CDCl$_3$) δ −75.40−−75.76 (m, 6F), −101.67 (br. s., 1F), −181.88 (m, 1F).

Step J: Tert-butyl 3a-((4-fluorophenyl)sulfonyl)-6-(perfluoropropan-2-yl)-3,3a,8,8a-tetrahydroindeno[2,1-b]pyrrole-1 (2H)-carboxylate (Two Homochiral Enantiomers)

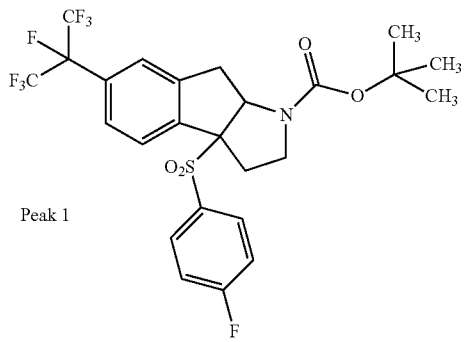

Peak 1

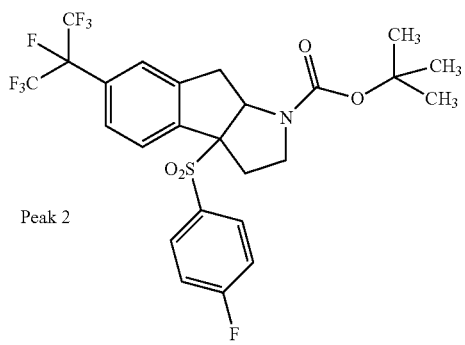

Peak 2

A sample of tert-butyl 3a-((4-fluorophenyl)sulfonyl)-6-(perfluoropropan-2-yl)-3,3a,8,8a-tetrahydroindeno[2,1-b]pyrrole-1(2H)-carboxylate (2.95 g, 5.04 mmol) was separated by chiral SFC using the following conditions: Column: Chiralpak® IC (30×250) mm, 5 m (Chiral Technologies Inc.); column temperature 35° C.; pressure 100 bars; mobile phase CO$_2$-MeOH (90:10); flow rate 180 mL/min; injection volume: 0.75 mL. Peak 1 (white glassy solid, 1.246 g, 80%) was eluted with $t_R$ 1.15 min. Peak 2 (white glassy solid, 1.273 g, 92%) was eluted with $t_R$ 1.6 min. LCMS and NMR of both products were the same as those of the racemic material obtained in Step I.

Step K: 3a-((4-fluorophenyl)sulfonyl)-6-(perfluoropropan-2-yl)-1,2,3,3a,8,8a-hexahydroindeno[2,1-b]pyrrole Hydrochloride (Two Homochiral Enantiomers)

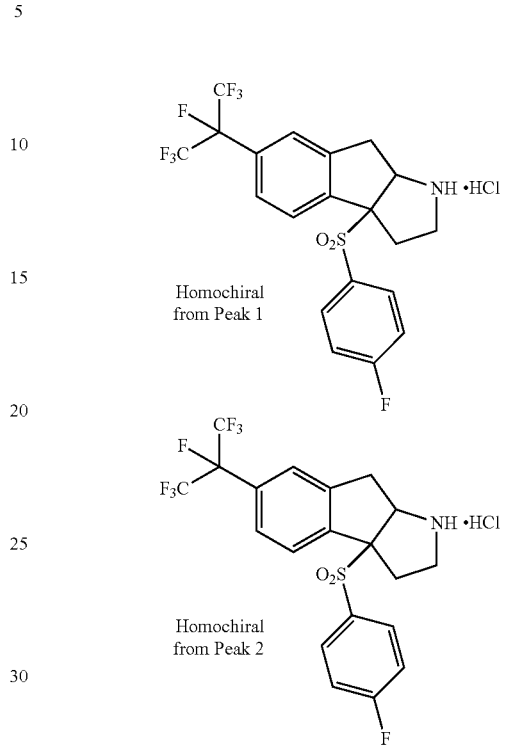

Homochiral from Peak 1

Homochiral from Peak 2

A solution of tert-butyl 3a-((4-fluorophenyl)sulfonyl)-6-(perfluoropropan-2-yl)-3,3a,8,8a-tetrahydroindeno[2,1-b]pyrrole-1(2H)-carboxylate (single enantiomer, Peak 1 from Step J; 1.225 g, 2.092 mmol) in DCM (20 mL) was treated with HCl, 4 M in 1,4-dioxane (16 mL, 64.0 mmol) and allowed to stand at rt. After 80 min, the solution was concentrated to provide one enantiomer of 3a-((4-fluorophenyl)sulfonyl)-6-(perfluoropropan-2-yl)-1,2,3,3a,8,8a-hexahydroindeno[2,1-b]pyrrole hydrochloride as an off-white glassy solid (1.12 g, 97% yield). LCMS m/z 486.2 (M+H)$^+$, HPLC $t_R$ 0.85 min (method B). $^1$H NMR (400 MHz, CDCl$_3$) δ 10.84-10.28 (br. m, 2H), 7.79 (d, J=8.4 Hz, 1H), 7.66 (d, J=8.4 Hz, 1H), 7.59 (dd, J=8.5, 4.7 Hz, 2H), 7.33 (s, 1H), 7.00 (t, J=8.3 Hz, 1H), 5.49 (d, J=7.0 Hz, 1H), 3.97 (d, J=7.5 Hz, 1H), 3.85-3.75 (m, 1H), 3.35 (td, J=12.3, 6.8 Hz, 1H), 3.08 (d, J=4.4 Hz, 1H), 2.92 (dd, J=19.0, 8.0 Hz, 1H), 2.70 (dd, J=13.1, 4.1 Hz, 1H). $^{19}$F NMR (376 MHz, CDCl$_3$) δ −75.53 (m, 6F), −100.46 (m, 1F), −181.90 (m, 1F).

Likewise, tert-butyl 3a-((4-fluorophenyl)sulfonyl)-6-(perfluoropropan-2-yl)-3,3a,8,8a-tetrahydroindeno[2,1-b]pyrrole-1(2H)-carboxylate (single enantiomer, Peak 2 from Step J; 1.256 g, 2.145 mmol) was converted into the other enantiomer of 3a-((4-fluorophenyl)sulfonyl)-6-(perfluoropropan-2-yl)-1,2,3,3a,8,8a-hexahydroindeno[2,1-b]pyrrole hydrochloride as an off-white glassy solid (1.15 g, 98% yield). LCMS and NMR same as that of the material obtained from Peak 1.

The Intermediates in Table 4 were prepared using the same or similar methods used in the preparation of Intermediates 94 and 95, by employing the appropriate thiol in Step D.

TABLE 4
| Intermediate number | Structure | LCMS m/z observed | HPLC $t_R$ (min) | HPLC method |
|---|---|---|---|---|
| 96 | 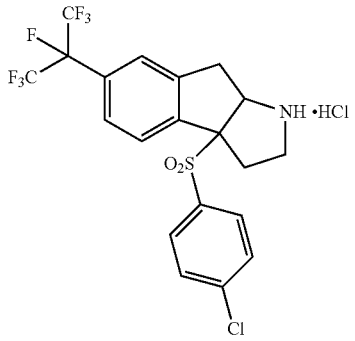 Homochiral from Peak 1 | 502.0 (M + H)+ | 0.88 | B |
| 97 | 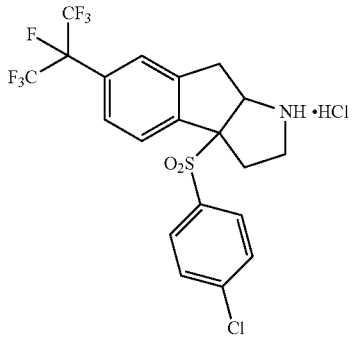 Homochiral from Peak 2 | 502.0 (M + H)+ | 0.88 | B |
Intermediates 98 and 99
8b-((4-fluorophenyl)sulfonyl)-6-(perfluoropropan-2-yl)-2,3,3a,8b-tetrahydro-1H-benzofuro[2,3-c]pyrrole Hydrochloride (Two Homochiral Enantiomers)
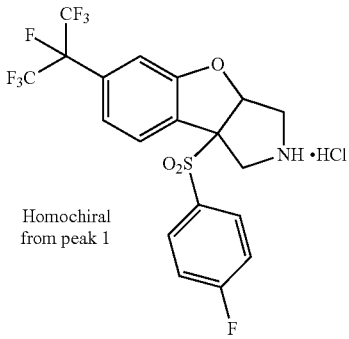
Homochiral from peak 1
-continued
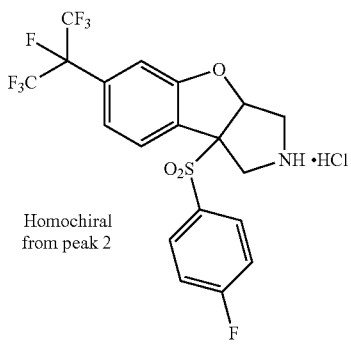
Homochiral from peak 2

Step A: 2-benzyl-6-bromo-8b-((4-fluorophenyl)sulfonyl)-2,3,3a,8b-tetrahydro-1H-benzofuro[2,3-c]pyrrole

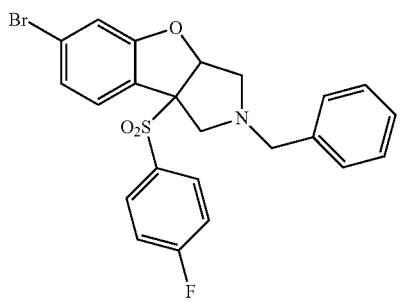 [SMILES: O=S(=O)(c1ccc(F)cc1)C12CN(Cc3ccccc3)CC1Oc1cc(Br)ccc12]

A solution of 6-bromo-3-((4-fluorophenyl)sulfonyl)benzofuran (Intermediate 9; 1.00 g, 2.82 mmol) in dry DCM (15 mL) was treated with N-benzyl-1-methoxy-N-((trimethylsilyl)methyl)methanamine (1.80 mL, 7.04 mmol) and stirred on an ice-water bath. This solution was treated dropwise with TFA (0.5 M in DCM, 2.82 mL, 1.408 mmol) over about 6 min. The resulting solution was stirred on ice. After 5 min the mixture was warmed to rt. After 2 h, the solution was diluted with DCM, washed with 1.5 M aqueous $K_2HPO_4$, dried over $Na_2SO_4$ and concentrated. The residue was purified by column chromatography on silica gel (120 g), eluting with EtOAc-hexanes (gradient from 0-30%), to provide 2-benzyl-6-bromo-8b-((4-fluorophenyl)sulfonyl)-2,3,3a,8b-tetrahydro-1H-benzofuro[2,3-c]pyrrole as a white glassy solid (1.27 g, 92% yield). LCMS m/z 488.1 $(M+H)^+$, HPLC $t_R$ 1.04 min (method B). $^1$H NMR (400 MHz, $CDCl_3$) δ 7.65 (dd, J=9.0, 5.1 Hz, 2H), 7.34-7.25 (m, 4H), 7.21-7.15 (m, 2H), 7.14-7.07 (m, 3H), 6.82 (d, J=1.5 Hz, 1H), 5.37 (dd, J=5.6, 1.9 Hz, 1H), 3.73-3.60 (m, 2H), 3.45 (d, J=9.7 Hz, 1H), 3.27 (d, J=9.7 Hz, 1H), 3.14-3.08 (m, 1H), 2.84 (dd, J=10.9, 5.6 Hz, 1H).

Step B: 2-benzyl-8b-((4-fluorophenyl)sulfonyl)-6-(perfluoropropan-2-yl)-2,3,3a,8b-tetrahydro-1H-benzofuro[2,3-c]pyrrole

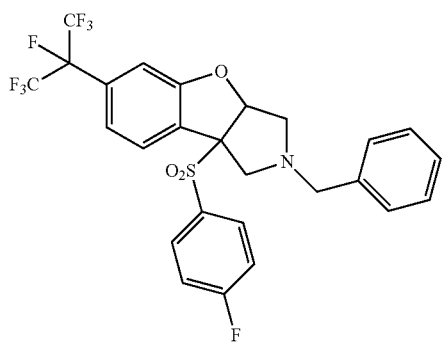 [SMILES: O=S(=O)(c1ccc(F)cc1)C12CN(Cc3ccccc3)CC1Oc1cc(C(F)(C(F)(F)F)C(F)(F)F)ccc12]

Following the procedure used in Step A of the preparation of Intermediate 2,2-benzyl-6-bromo-8b-((4-fluorophenyl)sulfonyl)-2,3,3a,8b-tetrahydro-1H-benzofuro[2,3-c]pyrrole (800 mg, 1.638 mmol) was converted into 2-benzyl-8b-((4-fluorophenyl)sulfonyl)-6-(perfluoropropan-2-yl)-2,3,3a,8b-tetrahydro-1H-benzofuro[2,3-c]pyrrole as a white glassy solid (646 mg, 68% yield). LCMS m/z 578.2 $(M+H)^+$, HPLC $t_R$ 1.16 min (method B). $^1$H NMR (400 MHz, $CDCl_3$) δ 7.64-7.55 (m, 3H), 7.35-7.26 (m, 3H), 7.24 (d, J=8.1 Hz, 1H), 7.21-7.15 (m, 2H), 7.03 (t, J=8.5 Hz, 2H), 6.86 (s, 1H), 5.42 (dd, J=5.8, 2.1 Hz, 1H), 3.76-3.63 (m, 2H), 3.50 (d, J=9.7 Hz, 1H), 3.35 (d, J=9.7 Hz, 1H), 3.13 (d, J=9.5 Hz, 1H), 2.90 (dd, J=10.8, 5.7 Hz, 1H). $^{19}$F NMR (376 MHz, $CDCl_3$) δ −75.63 (d, J=7.2 Hz, 6F), −101.83 (m, 1F), −181.37 (m, 1F).

Step C: 2-benzyl-8b-((4-fluorophenyl)sulfonyl)-6-(perfluoropropan-2-yl)-2,3,3a,8b-tetrahydro-1H-benzofuro[2,3-c]pyrrole (Two Single Enantiomers)

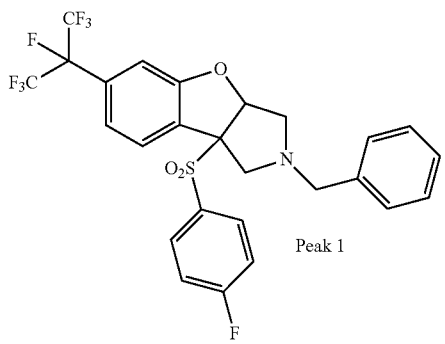

Peak 1

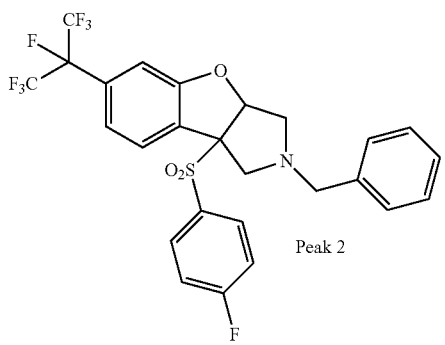

Peak 2

A sample of 2-benzyl-8b-((4-fluorophenyl)sulfonyl)-6-(perfluoropropan-2-yl)-2,3,3a,8b-tetrahydro-1H-benzofuro[2,3-c]pyrrole (640 mg, 1.109 mmol) was separated by chiral SFC using the following conditions: Column: Chiralcel® OD-H 50×250 mm, 5 m (Chiral Technologies Inc.); column temperature 35° C.; pressure 100 bars; mobile phase $CO_2$-MeOH (90:10); flow rate 250 mL/min; injection volume: 0.5 mL. Peak 1 (pale yellow glassy solid, 280 mg, 88%) was eluted with $t_R$ 5.7 min. Peak 2 (pale yellow glassy solid, 291 mg, 91%) was eluted with $t_R$ 6.2 min (100%). LCMS and NMR of both products were the same as those of the racemic material obtained in Step B.

Step D: 8b-((4-fluorophenyl)sulfonyl)-6-(perfluoropropan-2-yl)-2,3,3a,8b-tetrahydro-1H-benzofuro[2,3-c]pyrrole hydrochloride (Two Single Enantiomers)

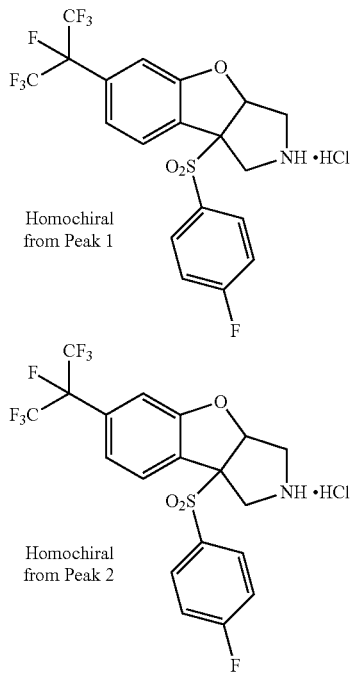

Homochiral from Peak 1

Homochiral from Peak 2

A solution of 2-benzyl-8b-((4-fluorophenyl)sulfonyl)-6-(perfluoropropan-2-yl)-2,3,3a,8b-tetrahydro-1H-benzofuro[2,3-c]pyrrole (single enantiomer, Peak 1 from Step C; 276 mg, 0.478 mmol) in MeOH (10 mL) was treated with 1.0 M aqueous HCl (0.574 mL, 0.574 mmol) and Pearlman's Catalyst (276 mg, 0.393 mmol). The flask was subjected to 5 evacuate-fill cycles with hydrogen, then was stirred under a hydrogen balloon at rt. After 16.5 h, the mixture was filtered through Celite, the solids were washed with MeOH and the combined filtrates were concentrated to provide one enantiomer of 8b-((4-fluorophenyl)sulfonyl)-6-(perfluoropropan-2-yl)-2,3,3a,8b-tetrahydro-1H-benzofuro[2,3-c]pyrrole hydrochloride as an off-white solid (250 In mg, quantitative yield). LCMS m/z 488.1 (M+H)$^+$, HPLC $t_R$ 0.87 min (method B). $^1$H NMR (400 MHz, DMSO-$d_6$) δ 10.23 (br. s., 2H), 7.83-7.75 (m, 2H), 7.72 (d, J=8.4 Hz, 1H), 7.43-7.32 (m, 3H), 7.03 (s, 1H), 6.01 (d, J=4.8 Hz, 1H), 4.26 (d, J=12.3 Hz, 1H), 4.00 (d, J=12.5 Hz, 1H), 3.69 (d, J=13.4 Hz, 1H), 3.65-3.55 (dd, J=13.6, 6.5 Hz, 1H).

Likewise, 2-benzyl-8b-((4-fluorophenyl)sulfonyl)-6-(perfluoropropan-2-yl)-2,3,3a,8b-tetrahydro-1H-benzofuro[2,3-c]pyrrole (single enantiomer, Peak 2 from Step C; 298 mg, 0.516 mmol) was converted into the other enantiomer of 8b-((4-fluorophenyl)sulfonyl)-6-(perfluoropropan-2-yl)-2,3,3a,8b-tetrahydro-1H-benzofuro[2,3-c]pyrrole hydrochloride as a pale yellow solid (246 mg, 91% yield). LCMS and NMR same as that of the material obtained from Peak 1.

The Intermediates in Table 5 were prepared using the same or similar methods used in the preparation of Intermediates 98 and 99, by employing the appropriate vinylic sulfone as the starting material.

TABLE 5

| Intermediate number | Structure | LCMS m/z observed | HPLC $t_R$ (min) | HPLC method |
|---|---|---|---|---|
| 100 | Homochiral from Peak 1 | 496.1 (M + H)$^+$ | 0.88 | B |
| 101 | Homochiral from Peak 2 | 496.1 (M + H)$^+$ | 0.88 | B |

TABLE 5-continued

| Intermediate number | Structure | LCMS m/z observed | HPLC t$_R$ (min) | HPLC method |
|---|---|---|---|---|
| 102 | 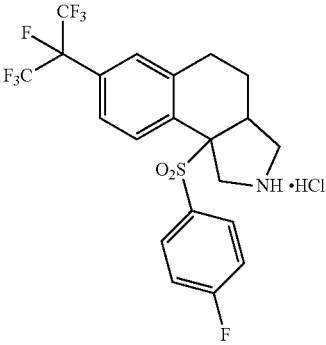 Homochiral from Peak 1 | 500.2 (M + H)$^+$ | 0.85 | B |
| 103 | 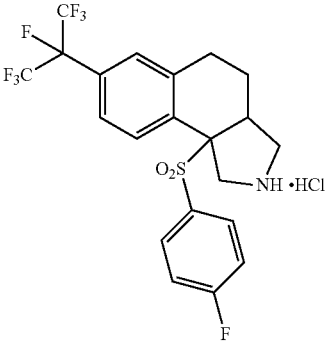 Homochiral from Peak 2 | 500.3 (M + H)$^+$ | 0.85 | B |

Intermediates 104 and 105

10b-((4-fluorophenyl)sulfonyl)-8-(perfluoropropan-2-yl)-1,3,4,4a,5,10b-hexahydro-2H-chromeno[3,4-c]pyridine Hydrochloride (Two Homochiral Enantiomers)

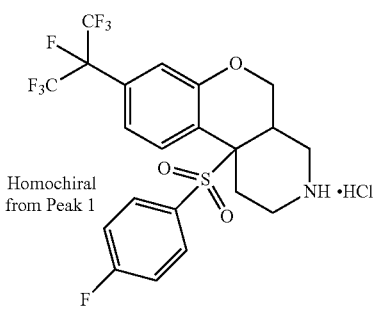
Homochiral from Peak 1

-continued

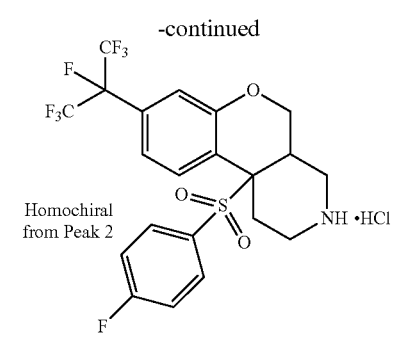
Homochiral from Peak 2

Step A: Dimethyl 2-(4-bromo-2-fluorobenzylidene)malonate

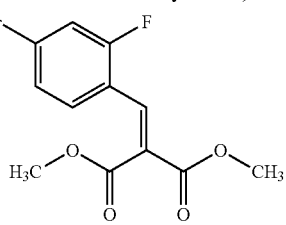

A solution of 4-bromo-2-fluorobenzaldehyde (20.07 g, 99 mmol), dimethyl malonate (14.73 mL, 129 mmol), benzoic acid (1.207 g, 9.89 mmol), and piperidine (1.953 mL, 19.77 mmol) in toluene (198 mL) was heated to reflux under a Dean-Stark water trap. After 4 h, the mixture was cooled to rt and concentrated The residue was dissolved in EtOAc, washed sequentially with saturated aqueous NH$_4$Cl, 1.5 M aqueous K$_2$HPO$_4$ and brine, dried over Na$_2$SO$_4$, filtered and concentrated to afford dimethyl 2-(4-bromo-2-fluorobenzylidene)malonate as an light brown oil in quantitative yield. $^1$H NMR (400 MHz, CDCl$_3$) δ 7.85 (s, 1H), 7.35-7.28 (m, 3H), 3.87 (s, 3H), 3.83 (s, 3H).

Step B: Dimethyl 2-((4-bromo-2-fluorophenyl)((4-fluorophenyl)thio)methyl)malonate

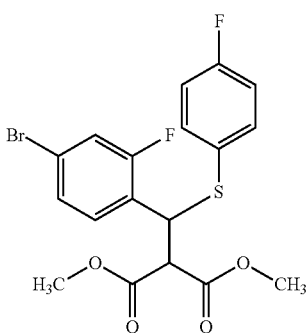 [SMILES: COC(=O)C(C(=O)OC)C(Sc1ccc(F)cc1)c1ccc(Br)cc1F]

A mixture of dimethyl 2-(4-bromo-2-fluorobenzylidene)malonate (19.29 g, 54.7 mmol), 4-fluorobenzenethiol (8.19 mL, 77 mmol), and K$_2$CO$_3$ (12.11 g, 88 mmol) in THF (238 mL) was heated at 60° C. for 4 h. The mixture was cooled to rt, filtered through Celite, and the solids were washed with EtOAc. The combined filtrates were concentrated and purified by column chromatography on silica gel (220 g), eluting with EtOAc-hexanes (5:95). A solid which formed in the effluent fractions was removed by filtration, and the combined filtrates were concentrated and re-purified by column chromatography on silica gel to provide dimethyl 2-((4-bromo-2-fluorophenyl)((4-fluorophenyl)thio)methyl)malonate as a yellow syrup (16.14 g, 66% yield). LCMS m/z 467.1 (M+Na)$^+$, HPLC t$_R$ 1.10 min (method B). $^1$H NMR (400 MHz, CDCl$_3$) δ 7.26-7.16 (m, 3H), 7.12 (dd, J=8.3, 1.2 Hz, 1H), 6.95 (t, J=8.7 Hz, 2H), 6.78 (t, J=8.0 Hz, 1H), 4.90 (d, J=11.7 Hz, 1H), 4.08 (dd, J=11.6, 0.6 Hz, 1H), 3.85 (s, 3H), 3.55 (s, 3H).

Step C: 2-((4-bromo-2-fluorophenyl)((4-fluorophenyl)thio)methyl)propane-1,3-diol

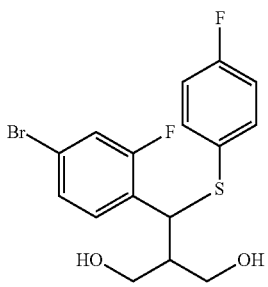 [SMILES: OCC(CO)C(Sc1ccc(F)cc1)c1ccc(Br)cc1F]

A solution of dimethyl 2-((4-bromo-2-fluorophenyl)((4-fluorophenyl)thio)methyl)malonate (16.14 g, 36.2 mmol) in THF (300 mL) was cooled in an ice-water bath and treated slowly with DIBAL-H (1 M in toluene; 149 mL, 149 mmol). The resulting mixture was stirred at rt overnight. After 17 h, the mixture was treated with ice and water, then with 1 M aqueous HCl (210 mL), and diluted with EtOAc. The organic phase was separated, washed sequentially with 1.5 M aqueous K$_2$HPO$_4$ and brine, dried over Na$_2$SO$_4$, filtered, and concentrated to afford 2-((4-bromo-2-fluorophenyl)((4-fluorophenyl)thio)methyl)propane-1,3-diol as a yellow syrup (13.65 g, 97% yield). $^1$H NMR (400 MHz, CDCl$_3$) δ 7.25-7.18 (m, 3H), 7.17-7.10 (m, 2H), 6.91 (t, J=8.7 Hz, 2H), 4.60 (d, J=10.3 Hz, 1H), 4.28-4.14 (m, 2H), 3.79 (dd, J=10.9, 3.2 Hz, 1H), 3.53 (dd, J=11.0, 5.7 Hz, 1H), 2.46-1.89 (m, 3H).

Step D: (7-bromo-4-((4-fluorophenyl)thio)chroman-3-yl)methanol

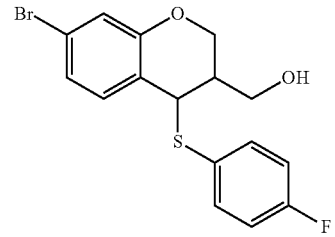 [SMILES: OCC1COc2cc(Br)ccc2C1Sc1ccc(F)cc1]

A solution of 2-((4-bromo-2-fluorophenyl)((4-fluorophenyl)thio)methyl)propane-1,3-diol (13.65 g, 35.1 mmol) in THF (501 mL) was treated portionwise at rt with NaH (60% in mineral oil; 5.51 g, 138 mmol). The resulting mixture was then heated at 60° C. After 4.5 h, the mixture was cooled to rt and treated with ice-water and 1 M aqueous HCl (100 mL). The layers were separated and the aqueous phase was extracted twice with EtOAc. The combined organic phases were washed with brine, dried over Na$_2$SO$_4$, filtered, and concentrated. The residue was purified by column chromatography on silica gel (220 g), eluting with EtOAc-hexanes (10-20%), to provide (7-bromo-4-((4-fluorophenyl)thio)chroman-3-yl)methanol as a dark yellow syrup (5.14 g, 40% yield). $^1$H NMR (400 MHz, CDCl$_3$) δ 7.43 (dd, J=8.8, 5.3 Hz, 2H), 7.14 (d, J=8.1 Hz, 1H), 7.07-6.98 (m, 4H), 4.51 (dd, J=11.2, 2.4 Hz, 1H), 4.30-4.20 (m, 2H), 3.70 (dd, J=10.8, 7.3 Hz, 1H), 3.54 (dd, J=10.8, 7.5 Hz, 1H), 2.19 (tq, J=7.3, 2.6 Hz, 1H).

Step E: (7-bromo-4-((4-fluorophenyl)sulfonyl)chroman-3-yl)methanol

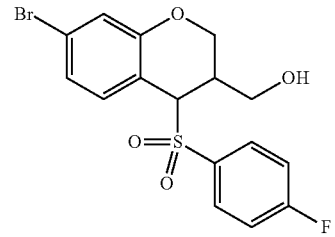 [SMILES: O=S(=O)(c1ccc(F)cc1)C1c2ccc(Br)cc2OCC1CO]

A solution of (7-bromo-4-((4-fluorophenyl)thio)chroman-3-yl)methanol (4.65 g, 12.59 mmol) in DCM (252 mL) was treated with mCPBA (6.77 g, 30.2 mmol) and stirred at rt. After 18 h, the mixture was diluted with DCM, washed sequentially with 10% aqueous Na$_2$S$_2$O$_3$, saturated aqueous NaHCO$_3$ and 1.5 M aqueous K$_2$HPO$_4$. The organic phase was dried over Na$_2$SO$_4$ and concentrated to afford (7-bromo-4-((4-fluorophenyl)sulfonyl)chroman-3-yl)methanol as a yellow glassy solid (3.94 g, 78% yield). LCMS m/z 422.9 (M+Na)$^+$, HPLC t$_R$ 0.91 min (method B). $^1$H NMR (400 MHz, CDCl$_3$) δ 7.80-7.74 (m, 2H), 7.24 (t, J=8.5 Hz, 2H), 7.05 (d, J=2.0 Hz, 1H), 6.98 (dd, J=8.4, 2.0 Hz, 1H), 6.84 (d, J=8.4 Hz, 1H), 4.43 (dd, J=11.7, 3.3 Hz, 1H), 4.31 (s, 1H), 4.19-4.11 (m, 1H), 3.70 (dd, J=10.7, 6.7 Hz, 1H), 3.50 (dd, J=10.7, 8.5 Hz, 1H), 2.80-2.69 (m, 1H).

Step F: 7-bromo-4-((4-fluorophenyl)sulfonyl)chromane-3-carbaldehyde

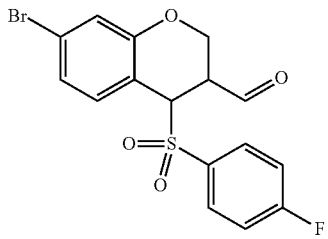 [SMILES: O=CC1COc2cc(Br)ccc2C1S(=O)(=O)c1ccc(F)cc1]

A solution of (7-bromo-4-((4-fluorophenyl)sulfonyl)chroman-3-yl)methanol (3.93 g, 9.79 mmol) in DCM (122 mL) was treated with 1,1,1-tris(acetyloxy)-1,1-dihydro-1,2-benziodoxol-3-(1H)-one (Dess-Martin periodinane; 4.15 g, 9.79 mmol) and stirred at rt. After 2 h, the mixture was concentrated, and the residue was dissolved in EtOAc, washed sequentially with 5% aqueous Na$_2$S$_2$O$_3$, saturated aqueous NaHCO$_3$ and brine, dried over Na$_2$SO$_4$ and concentrated to afford 7-bromo-4-((4-fluorophenyl)sulfonyl)chromane-3-carbaldehyde as a light yellow glassy solid (3.97 g, quantitative yield). $^1$H NMR (400 MHz, CDCl$_3$) 9.68 (s, 1H), 7.79 (dd, J=8.8, 5.1 Hz, 2H), 7.34-7.21 (m, 2H), 7.03 (d, J=2.0 Hz, 1H), 6.95 (dd, J=8.4, 2.0 Hz, 1H), 6.62 (d, J=8.4 Hz, 1H), 4.82-4.58 (m, 3H), 3.52 (dt, J=3.3, 1.9 Hz, 1H).

Step G: 2-(((7-bromo-4-((4-fluorophenyl)sulfonyl)chroman-3-yl)methyl)amino)ethanol

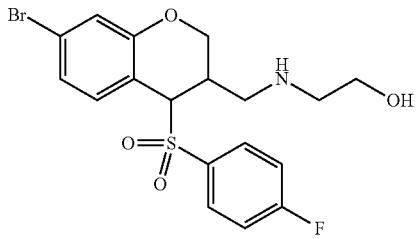 [SMILES: O=S(=O)(c1ccc(F)cc1)C1c2ccc(Br)cc2OCC1CNCCO]

A solution of 7-bromo-4-((4-fluorophenyl)sulfonyl)chroman-3-carbaldehyde (3.97 g, 9.94 mmol) in 1,2-dichloroethane (301 mL) was treated with 2-aminoethanol (1.020 mL, 16.90 mmol), then with sodium triacetoxyborohydride (5.56 g, 26.3 mmol). The resulting suspension was stirred at rt for 4.5 h, then was diluted with DCM, water and saturated aqueous NaHCO$_3$. The organic phase was separated and washed with brine, dried over Na$_2$SO$_4$ and concentrated to afford 2-(((7-bromo-4-((4-fluorophenyl)sulfonyl)chroman-3-yl)methyl)amino)ethanol as a yellow glassy solid (3.61 g, 82% yield). LCMS m/z 444.0 (M+H)$^+$, HPLC t$_R$ 0.71 min (method B).

Step H: Tert-butyl ((7-bromo-4-((4-fluorophenyl)sulfonyl)chroman-3-yl)methyl)(2-hydroxyethyl)carbamate

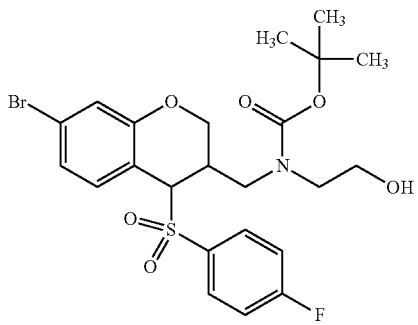 [SMILES: CC(C)(C)OC(=O)N(CCO)CC1COc2cc(Br)ccc2C1S(=O)(=O)c1ccc(F)cc1]

A solution of 2-(((7-bromo-4-((4-fluorophenyl)sulfonyl)chroman-3-yl)methyl)amino)ethanol (3.61 g, 8.12 mmol) in DCM (135 mL) was treated with di-tert-butyl dicarbonate (2.264 mL, 9.75 mmol), then with Et$_3$N (2.038 mL, 14.62 mmol). The mixture was stirred at rt for 5 h, then was diluted with DCM and washed with water. The organic phase was separated, washed with brine, dried over MgSO$_4$, filtered, and concentrated to afford tert-butyl ((7-bromo-4-((4-fluorophenyl)sulfonyl)chroman-3-yl)methyl)(2-hydroxyethyl)carbamate as a yellow sticky solid in quantitative yield. LCMS m/z 566.3 (M+Na)$^+$, HPLC t$_R$ 1.01 min (method B). $^1$H NMR (400 MHz, CDCl$_3$) δ 7.76 (dd, J=8.8, 5.1 Hz, 2H), 7.26-7.22 (m, 2H), 7.07 (d, J=2.0 Hz, 1H), 6.97 (d, J=7.9 Hz, 1H), 4.42 (d, J=11.7 Hz, 1H), 4.08-4.00 (m, 1H), 3.79-3.57 (m, 3H), 3.41-3.14 (m, 5H), 3.05-2.94 (m, 1H), 1.56 (s, 9H).

Step I: Tert-butyl 8-bromo-10b-((4-fluorophenyl)sulfonyl)-1,4a,5,10b-tetrahydro-2H-chromeno[3,4-c]pyridine-3(4H)-carboxylate

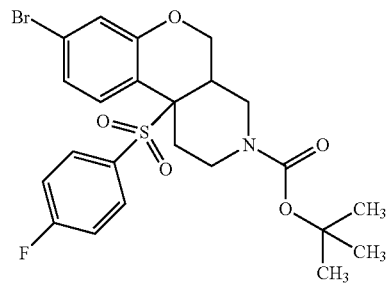 [SMILES: CC(C)(C)OC(=O)N1CCC2(S(=O)(=O)c3ccc(F)cc3)c3ccc(Br)cc3OCC2C1]

A solution of tert-butyl ((7-bromo-4-((4-fluorophenyl)sulfonyl)chroman-3-yl)methyl)(2-hydroxyethyl)carbamate (4.73 g, 8.08 mmol) in DCM (269 mL) at rt was treated with MsCl (0.630 mL, 8.08 mmol), then with Et$_3$N (1.464 mL, 10.50 mmol). The mixture was stirred at rt for 1 h, then potassium tert-butoxide (4.08 g, 36.4 mmol) was added and stirring was continued for 2 h more. The mixture was treated with half-saturated brine and diluted with additional DCM. The organic phase was separated, washed with brine, dried over Na$_2$SO$_4$, filtered, and concentrated. The residue was purified by column chromatography on silica gel (80 g), eluting with EtOAc-hexanes (10-20%) to provide tert-butyl 8-bromo-10b-((4-fluorophenyl)sulfonyl)-1,4a,5,10b-tetrahydro-2H-chromeno[3,4-c]pyridine-3(4H)-carboxylate as a white solid (1.78 g, 42% yield). LCMS m/z 548.2 (M+Na)$^+$, HPLC t$_R$ 1.12 (method B). $^1$H NMR (400 MHz, CDCl$_3$) δ 7.67-7.60 (m, 2H), 7.21 (t, J=8.6 Hz, 2H), 7.11 (d, J=2.0 Hz, 1H), 7.01 (dd, J=8.6, 2.0 Hz, 1H), 6.72 (br. s., 1H), 4.95 (br. s., 1H), 4.21-3.85 (m, 3H), 2.83-2.10 (m, 5H), 1.44 (s, 9H).

Step J: Tert-butyl 8-bromo-10b-((4-fluorophenyl) sulfonyl)-1,4a,5,10b-tetrahydro-2H-chromeno[3,4-c] pyridine-3(4H)-carboxylate (Two Homochiral Enantiomers)

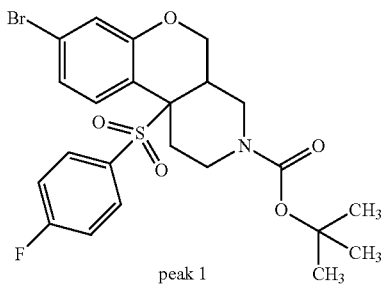

peak 1

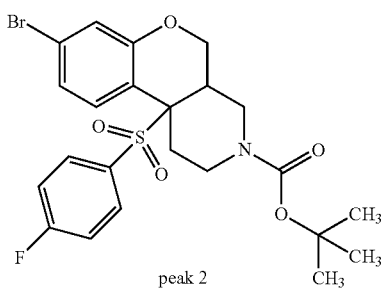

peak 2

A sample of racemic tert-butyl 8-bromo-10b-((4-fluorophenyl)sulfonyl)-1,4a,5,10b-tetrahydro-2H-chromeno[3,4-c]pyridine-3 (4H)-carboxylate (1.96 g) was separated by chiral SFC using the following conditions: Column: Lux® Cellulose-4 46×250 mm, 5 m (Phenomenex Inc.); column temperature 30° C.; pressure 100 bars; mobile phase CO$_2$-MeOH (84:16); flow rate 160 mL/min; injection volume 0.5 mL. Peak 1 (off-white solid, 0.81 g, 83%) was eluted with t$_R$ 5.2 min. Peak 2 (off-white solid, 0.867 g, 88%) was eluted with t$_R$ 5.9 min. LCMS and NMR of both products were the same as those of the racemic material obtained in Step I.

Step K: 10b-((4-fluorophenyl)sulfonyl)-8-(perfluoropropan-2-yl)-1,3,4,4a,5,10b-hexahydro-2H-chromeno[3,4-c]pyridine Hydrochloride (Two Homochiral Enantiomers)

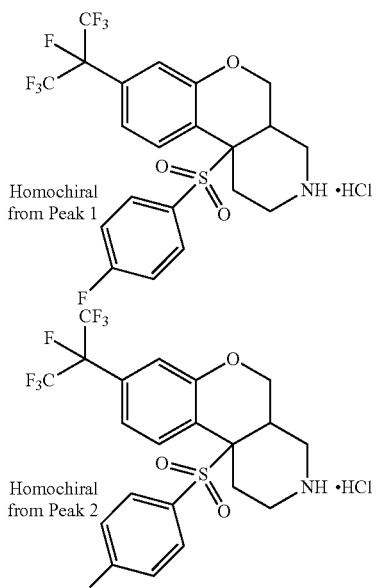

Homochiral from Peak 1

Homochiral from Peak 2

Following the procedures used in Steps I and K of the preparation of Intermediates 94 and 95, tert-butyl 8-bromo-10b-((4-fluorophenyl)sulfonyl)-1,4a,5,10b-tetrahydro-2H-chromeno[3,4-c]pyridine-3(4H)-carboxylate (homochiral, from Peak 1) was converted into one enantiomer of 10b-((4-fluorophenyl)sulfonyl)-8-(perfluoropropan-2-yl)-1,3,4,4a,5,10b-hexahydro-2H-chromeno[3,4-c]pyridine hydrochloride. LCMS m/z 516.1 (M+H)$^+$, HPLC t$_R$ 0.83 min (method B).

Likewise, tert-butyl 8-bromo-10b-((4-fluorophenyl)sulfonyl)-1,4a,5,10b-tetrahydro-2H-chromeno[3,4-c]pyridine-3 (4H)-carboxylate (homochiral, from Peak 2) was converted into the other enantiomer of 10b-((4-fluorophenyl)sulfonyl)-8-(perfluoropropan-2-yl)-1,3,4,4a,5,10b-hexahydro-2H-chromeno[3,4-c]pyridine hydrochloride. LCMS m/z 516.3 (M+H)$^+$, HPLC t$_R$ 0.83 min (method B).

Intermediate 106

9b-((4-chlorophenyl)sulfonyl)-7-(trifluoromethyl)-2,3,3a,4,5,9b-hexahydro-1H-benzo[e]indole Hydrochloride

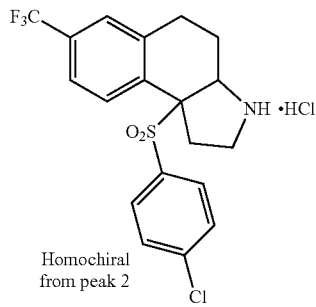 [SMILES: O=S(=O)(c1ccc(Cl)cc1)C12CCNC1CCc1cc(C(F)(F)F)ccc12 ; Cl]

Homochiral from peak 2

A mixture of tert-butyl 9b-((4-chlorophenyl)sulfonyl)-7-iodo-3a,4,5,9b-tetrahydro-1H-benzo[e]indole-3-carboxylate (homochiral, from peak 2, Intermediate 69; 100 mg, 0.17 mmol), CuI (33 mg, 0.17 mmol) and KF (30 mg, 0.52 mmol) was placed in a sealed vial which was evacuated and filled with nitrogen 3 times. DMF (2 mL) was added and the vessel was again evacuated and filled with nitrogen 3 times. Methyl 2,2-difluoro-2-(fluorosulfonyl)acetate (167 mg, 0.87 mmol) was added and the mixture was heated to 80° C. After 2 days, LCMS showed 70% conversion of the starting material. The mixture was cooled to rt, diluted with EtOAc, washed sequentially with 1.5 M aqueous $K_2HPO_4$, 10% aqueous LiCl and brine, dried over $Na_2SO_4$ and concentrated. The resulting oil was dissolved in DCM (2 mL) and treated with 4N HCl in 1,4-dioxane (2 mL). After 1 h the mixture was concentrated, affording 9b-((4-chlorophenyl)sulfonyl)-7-(trifluoromethyl)-2,3,3a,4,5,9b-hexahydro-1H-benzo[e]indole hydrochloride (single enantiomer, 83 mg, >100% yield). This material was used without further purification. LCMS m/z 416.0 (M+H)$^+$, HPLC $t_R$ 0.83 min (method B).

Intermediate 107

7-(pyridin-3-yl)-9b-tosyl-2,3,3a,4,5,9b-hexahydro-1H-benzo[e]indole Hydrochloride

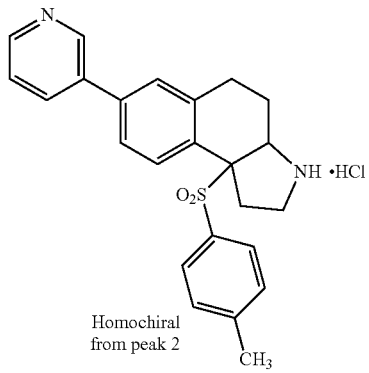 [SMILES: Cc1ccc(S(=O)(=O)C23CCNC2CCc2cc(-c4cccnc4)ccc23)cc1 ; Cl]

Homochiral from peak 2

A mixture of tert-butyl 7-iodo-9b-tosyl-3a,4,5,9b-tetrahydro-1H-benzo[e]indole-3-carboxylate (homochiral, from peak 2, Intermediate 70; 50 mg, 0.090 mmol), chloro(2-dicyclohexyl-phosphino-2',4',6'-triisopropyl-1,1'-biphenyl)[2-(2'-amino-1,1'-biphenyl)]palladium(II) (second generation Xphos precatalyst; 1.4 mg, 1.8 μmol), 2-(dicyclohexylphosphino)-2',4',6'-triisopropylbiphenyl (1.7 mg, 3.6 μmol), tetrahydroxydiboron (12 mg, 0.14 mmol), and potassium acetate (26.6 mg, 0.27 mmol) was placed in a pressure vial which was purged with nitrogen 4 times. Ethanol (bubbled with nitrogen to remove dissolved oxygen; 903 μL) and ethylene glycol (15 μL, 0.27 mmol) were added and the mixture was heated at 80° C. for 1.5 h. The mixture was cooled to rt and treated with 1 M aqueous $K_3PO_4$ (271 μL, 0.271 mmol) and 3-bromopyridine (13.4 mg, 0.085 mmol). The resulting mixture was warmed to 80° C. and stirred for 1 h. The mixture was cooled to rt and partitioned between EtOAc and brine. The organic layer was dried over $Na_2SO_4$ and concentrated. The residue was treated with 4 M HCl in 1,4-dioxane (0.5 mL) and allowed to stand at rt for 1 h. The mixture was concentrated affording crude 7-(pyridin-3-yl)-9b-tosyl-2,3,3a,4,5,9b-hexahydro-1H-benzo[e]indole hydrochloride (single enantiomer) which was used without further purification. LCMS m/z 405.2 (M+H)$^+$, HPLC $t_R$ 0.53 min (method B).

Intermediate 108

7-phenyl-9b-tosyl-2,3,3a,4,5,9b-hexahydro-1H-benzo[e]indole Hydrochloride

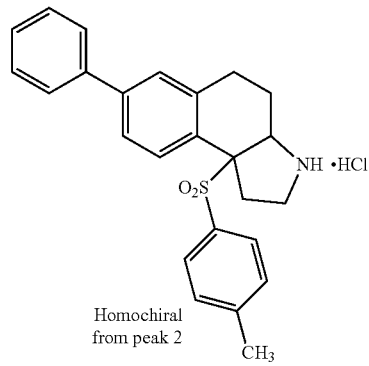 [SMILES: Cc1ccc(S(=O)(=O)C23CCNC2CCc2cc(-c4ccccc4)ccc23)cc1 ; Cl]

Homochiral from peak 2

A solution of tert-butyl 7-iodo-9b-tosyl-3a,4,5,9b-tetrahydro-1H-benzo[e]indole-3-carboxylate (homochiral, from peak 2, Intermediate 70; 20 mg, 0.036 mmol) in DMF (1 mL) was treated with 4,4,5,5-tetramethyl-2-phenyl-1,3,2-dioxaborolane (15 mg, 0.072 mmol), [1,1'-bis(di-tert-butylphosphino)ferrocene]dichloropalladium(II) (2.6 mg, 3.6 μmol), and 2 M aqueous $K_3PO_4$ (0.036 mL, 0.072 mmol), and the mixture was heated at 80° C. for 16 h. The mixture was cooled to rt and partitioned between EtOAc and brine. The organic phase was dried over $Na_2SO_4$ and concentrated. The residue was treated with 4 N HCl in 1,4-dioxane (0.5 mL) and allowed to stand at rt for 1 h. The mixture was concentrated to provide crude 7-phenyl-9b-tosyl-2,3,3a,4,5,9b-hexahydro-1H-benzo[e]indole hydrochloride which was used without further purification. LCMS m/z 404.2 (M+H)$^+$, HPLC $t_R$ 0.82 min (method B).

Intermediate 109

7-(tert-butyl)-9b-((3-fluorophenyl)sulfonyl)-2,3,3a,4,5,9b-hexahydro-1H-benzo[e]indole Trifluoroacetate

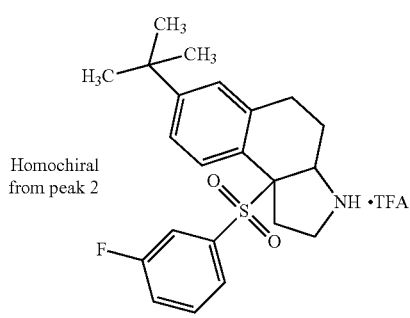 [SMILES: CC(C)(C)c1ccc2c(c1)CCC1NCCC21S(=O)(=O)c1cccc(F)c1 ; "·TFA"]

Homochiral from peak 2

A mixture of tert-butyl 7-bromo-9b-((3-fluorophenyl)sulfonyl)-3a,4,5,9b-tetrahydro-1H-benzo[e]indole-3-carboxylate (homochiral, from peak 2, Intermediate 73; 0.15 g, 0.294 mmol), THF (2.45 mL) and tert-butylzinc bromide (0.5 M in THF; 2.94 mL, 1.469 mmol) in a reaction vial was flushed with nitrogen. Tetrakis(triphenylphosphine)palladium (3.04 mg, 2.94 μmol) was added, and the vial was sealed and heated by microwave irradiation at 130° C. for 10 min. The cooled mixture was diluted with EtOAc (30 mL) and filtered. The filtrate was washed sequentially with water, saturated aqueous NaHCO$_3$ and brine, dried over Na$_2$SO$_4$ and concentrated. The residue was dissolved in DCM-TFA (2:1, 5 mL) and stirred at rt for 15 min. The mixture was concentrated to provide crude 7-(tert-butyl)-9b-((3-fluorophenyl)sulfonyl)-2,3,3a,4,5,9b-hexahydro-1H-benzo[e]indole trifluoroacetate (120 mg, about 75% purity, 79% yield) as a single enantiomer, used without further purification. LCMS m/z 388.0 (M+H)$^+$, HPLC t$_R$ 0.88 min (method B).

Intermediate 110

7-(tert-butyl)-9b-((3-fluorophenyl)sulfonyl)-2,3,3a,4,5,9b-hexahydro-1H-benzo[e]indole Trifluoroacetate

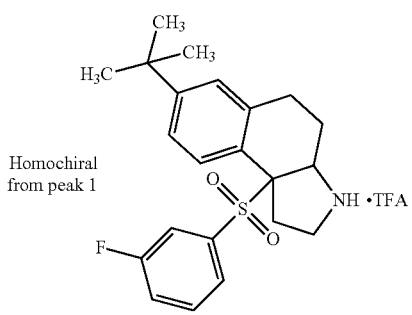 [SMILES: CC(C)(C)c1ccc2c(c1)CCC1NCCC21S(=O)(=O)c1cccc(F)c1 ; "·TFA"]

Following the procedure used to prepare Intermediate 109, tert-butyl 7-bromo-9b-((3-fluorophenyl)sulfonyl)-3a,4,5,9b-tetrahydro-1H-benzo[e]indole-3-carboxylate (homochiral, from peak 1, Intermediate 72) was converted into crude 7-(tert-butyl)-9b-((3-fluorophenyl)sulfonyl)-2,3,3a,4,5,9b-hexahydro-1H-benzo[e]indole trifluoroacetate as a single enantiomer, used without further purification. LCMS m/z 388.0 (M+H)$^+$, HPLC t$_R$ 0.87 min (method B).

Intermediate 111

7-chloro-9b-((3-fluorophenyl)sulfonyl)-2,3,3a,4,5,9b-hexahydro-1H-benzo[e]indole Hydrochloride

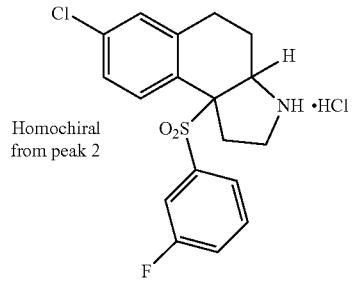 [SMILES: O=S(=O)(c1cccc(F)c1)C12CCNC1CCc1cc(Cl)ccc12 ; Cl]

Step A: Tert-butyl 7-chloro-9b-((3-fluorophenyl)sulfonyl)-1,2,3a,4,5,9b-hexahydro-3H-benzo[e]indole-3-carboxylate A mixture of copper(I) chloride (0.159 g, 1.607 mmol) and activated copper powder (prepared as outlined in Step A of the preparation of Intermediate 2; 0.102 g, 1.607 mmol) was placed in a sealable vial which was flushed with nitrogen. The mixture was treated with a solution of tert-butyl 7-bromo-9b-((3-fluorophenyl)sulfonyl)-3a,4,5,9b-tetrahydro-1H-benzo[e]indole-3-carboxylate (homochiral, from peak 2, Intermediate 73; 0.082 g, 0.161 mmol) in anhydrous pyridine (1.5 mL) and the vial was sealed and heated at 120° C. for 5.5 days. The mixture was cooled to rt and taken up in EtOAc (75 mL). The mixture was washed sequentially with 1 M aqueous HCl (2×50 mL) and brine (50 mL), dried over Na$_2$SO$_4$ and concentrated to give tert-butyl 7-chloro-9b-((3-fluorophenyl)sulfonyl)-1,2,3a,4,5,9b-hexahydro-3H-benzo[e]indole-3-carboxylate as an off-white foam (65 mg, 87% yield), used without further purification. LCMS m/z 451.0 (M+H+MeCN—C$_4$H$_8$)$^+$, HPLC t$_R$ 1.17 min (method B). $^1$H NMR (400 MHz, MeOH-d$_4$) δ 7.67 (d, J=8.4 Hz, 1H), 7.56-7.36 (m, 2H), 7.35-7.17 (m, 2H), 7.12-6.94 (m, 2H), 4.65-4.33 (m, 1H), 3.71-3.57 (m, 1H), 3.57-3.34 (m, 2H), 2.59-2.43 (m, 2H), 2.41-2.15 (m, 1H), 1.86 (t, J=13.6 Hz, 1H), 1.60-1.43 (m, 9H), 1.40-1.26 (m, 1H).

Step B: 7-chloro-9b-((3-fluorophenyl)sulfonyl)-2,3,3a,4,5,9b-hexahydro-1H-benzo[e]indole Hydrochloride A mixture of tert-butyl 7-chloro-9b-((3-fluorophenyl)sulfonyl)-3a,4,5,9b-tetrahydro-1H-benzo[e]indole-3-carboxylate (65 mg, 0.139 mmol) and HCl (4 M in 1,4-dioxane; 2.0 mL, 8.00 mmol) was stirred at rt for 1.5 h. The mixture was concentrated to give 7-chloro-9b-((3-fluorophenyl)sulfonyl)-2,3,3a,4,5,9b-hexahydro-1H-benzo[e]indole hydrochloride as a white solid which was used without further purification. LCMS m/z 366.0 (M+H)$^+$, HPLC $t_R$ 0.74 min (method B).

Intermediate 112

9b-((4-cyclopropylphenyl)sulfonyl)-7-(perfluoropropan-2-yl)-2,33a,4,5,9b-hexahydro-1H-benzo[e]indole Hydrochloride

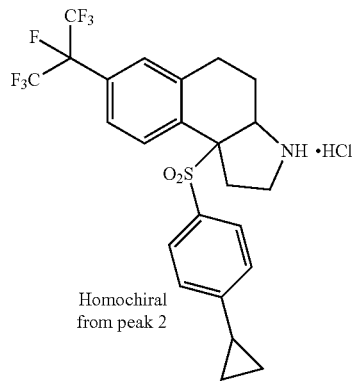 [SMILES: O=S(=O)(c1ccc(C2CC2)cc1)C12CCNC1CCc1cc(C(F)(C(F)(F)F)C(F)(F)F)ccc12 ; Cl]

Homochiral from peak 2

A solution of 9b-((4-bromophenyl)sulfonyl)-7-(perfluoropropan-2-yl)-2,3,3a,4,5,9b-hexahydro-1H-benzo[e]indole (homochiral, from peak 2, Intermediate 67; 100 mg, 0.15 mmol) and tetrakis(triphenylphosphine)palladium (8.8 mg, 7.6 μmol) in THF (1 mL) was placed in a sealed tube which was evacuated and filled with nitrogen three times. Cyclopropylzinc(II) bromide (0.6 mL, 0.3 mmol) was added and the mixture was heated at 70° C. for 2.5 h. The mixture was cooled to rt and partitioned between EtOAc and brine. The organic phase was dried over Na$_2$SO$_4$ and concentrated. The residue was treated with 4 M HCl in 1,4-dioxane (0.5 mL) and allowed to stand at rt for 1 h. The mixture was concentrated, affording crude 9b-((4-cyclopropylphenyl)sulfonyl)-7-(perfluoropropan-2-yl)-2,3,3a,4,5,9b-hexahydro-1H-benzo[e]indole hydrochloride (homochiral), which was used without further purification. LCMS m/z 522.1 (M+H)$^+$, HPLC $t_R$ 0.96 min (method B).

Intermediate 113

9b-((4-(methyl-d$_3$)phenyl)sulfonyl)-7-(perfluoropropan-2-yl)-2,3,3a,4,5,9b-hexahydro-1H-benzo[e]indole Hydrochloride

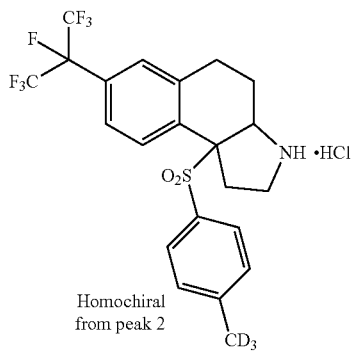 [SMILES: [2H]C([2H])([2H])c1ccc(S(=O)(=O)C23CCNC2CCc2cc(C(F)(C(F)(F)F)C(F)(F)F)ccc23)cc1 ; Cl]

Homochiral from peak 2

A solution of tert-butyl 9b-((4-bromophenyl)sulfonyl)-7-(perfluoropropan-2-yl)-3a,4,5,9b-tetrahydro-1H-benzo[e]indole-3-carboxylate (homochiral, from peak 2, Intermediate 67; 200 mg, 0.3 mmol) and iron(III) acetylacetonate (5.4 mg, 0.015 mmol) in THF (2 mL) was placed in a sealed tube which was evacuated and filled with nitrogen three times. The resulting dark red solution was treated dropwise with methyl-d$_3$-magnesium iodide (1.0 M in diethyl ether; 0.3 mL, 0.3 mmol) dropwise and the mixture was stirred at rt for 30 min. The mixture was partitioned between EtOAc and brine, and the organic phase was dried over Na$_2$SO$_4$ and concentrated. The residue was treated with 4 M HCl in 1,4-dioxane (0.5 mL) for 1 h. The mixture was concentrated, affording crude 9b-((4-(methyl-d$_3$)phenyl)sulfonyl)-7-(perfluoropropan-2-yl)-2,3,3a,4,5,9b-hexahydro-1H-benzo[e]indole hydrochloride (210 mg, >100%) which was used without further purification. LCMS m/z 499.1 (M+H)$^+$, HPLC $t_R$ 0.92 min (method B).

The Intermediates in Table 6 were prepared using the same methods or similar methods used to prepared Intermediate 113, by employing the appropriate bromine-substituted starting material.

TABLE 6

| Intermediate number | Structure | LCMS m/z observed | HPLC $t_R$ (min) | HPLC method |
|---|---|---|---|---|
| 114 | ![structure] Homochiral from peak 2 | 517.0 (M + H)$^+$ | 0.90 | B |

TABLE 6-continued

| Intermediate number | Structure | LCMS m/z observed | HPLC $t_R$ (min) | HPLC method |
|---|---|---|---|---|
| 115 | ![structure 115] Homochiral from peak 1 | 517.1 (M + H)+ | 0.91 | B |

Structure 115: benzo[e]indole core with CF₃ and F₃C substituents at position 7 (perfluoropropan-2-yl), NH·HCl, O₂S-linked to phenyl ring bearing CD₃ and F.

Intermediate 116

9b-((4-fluoro-3-isopropylphenyl)sulfonyl)-7-(perfluoropropan-2-yl)-2,3,3a,4,5,9b-hexahydro-1H-benzo[e]indole Hydrochloride

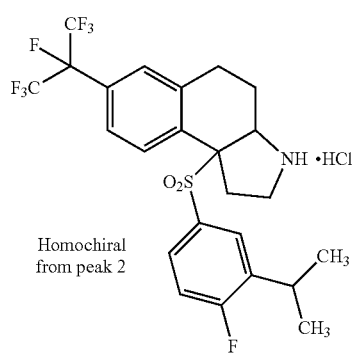 [SMILES: CC(C)c1cc(S(=O)(=O)C23CCNC2CCc2cc(C(F)(C(F)(F)F)C(F)(F)F)ccc23)ccc1F ; Cl]

Homochiral from peak 2

A mixture of tert-butyl 9b-((3-bromo-4-fluorophenyl)sulfonyl)-7-(perfluoropropan-2-yl)-3a,4,5,9b-tetrahydro-1H-benzo[e]indole-3-carboxylate (homochiral, from peak 2, Intermediate 84; 113 mg, 0.167 mmol), 4,4,5,5-tetramethyl-2-(prop-1-en-2-yl)-1,3,2-dioxaborolane (28.0 mg, 0.167 mmol) and 2 M aqueous $K_3PO_4$ (0.167 mL, 0.333 mmol) in THF (2 mL) was subjected to 3 evacuate-fill cycles with nitrogen. 1,1'-bis(di-tert-butylphosphino)ferrocene palladium dichloride (5.43 mg, 8.33 μmol) was added, and the mixture was again subjected to 3 evacuate-fill cycles with nitrogen. The mixture was stirred overnight, then was diluted with EtOAc, washed sequentially with 1.5 M aqueous $K_2HPO_4$ and water, dried and concentrated. The residue was dissolved in MeOH (5 mL), treated with Pd on charcoal (53.2 mg) and stirred at rt overnight under a hydrogen atmosphere (balloon pressure). The mixture was filtered and concentrated, and the residue was treated with HCl (4 M in 1,4-dioxane) followed by concentration to provide 9b-((4-fluoro-3-isopropylphenyl)sulfonyl)-7-(perfluoropropan-2-yl)-2,3,3a,4,5,9b-hexahydro-1H-benzo[e]indole hydrochloride. LCMS m/z 542.4 (M+H)+, HPLC $t_R$ 1.30 min (method B).

Intermediate 117

2-(4-((7-(perfluoropropan-2-yl)-1,2,3,3a,4,5-hexahydro-9bH-benzo[e]indol-9b-yl)sulfonyl)phenyl)propan-2-ol Hydrochloride

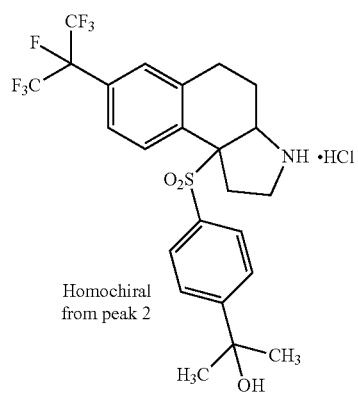 [SMILES: CC(C)(O)c1ccc(S(=O)(=O)C23CCNC2CCc2cc(C(F)(C(F)(F)F)C(F)(F)F)ccc23)cc1 ; Cl]

Homochiral from peak 2

A solution of tert-butyl 9b-((4-(methoxycarbonyl)phenyl)sulfonyl)-7-(perfluoropropan-2-yl)-3a,4,5,9b-tetrahydro-1H-benzo[e]indole-3-carboxylate (homochiral, from peak 2, Intermediate 68; 150 mg, 0.24 mmol) in THF (5 mL) was cooled in a dry ice-acetone bath and treated dropwise with methyllithium (3.1 M in 1,2-diethoxyethane; 0.23 mL, 0.7 mmol). The mixture was stirred at −78° C. for 30 min, then was treated with saturated aqueous $NH_4Cl$. The phases were separated and the aqueous phase was extracted twice with DCM. The combined organic phases were washed with brine, dried over $Na_2SO_4$ and concentrated. The residue was treated with 4 M HCl in 1,4-dioxane (0.5 mL) and allowed to stand at rt for 1 h. The mixture was concentrated, affording crude 2-(4-((7-(perfluoropropan-2-yl)-1,2,3,3a,4,5-hexahydro-9bH-benzo[e]indol-9b-yl)sulfonyl)phenyl)propan-2-ol which was used without further purification. LCMS m/z 540.3 (M+H)+, HPLC $t_R$ 0.80 min (method B).

Intermediate 118

(3aR,9bR)-9b-((4-fluorophenyl)sulfonyl)-7-(perfluoropropan-2-yl)-1,3,3a,4,5,9b-hexahydro-2H-benzo[e]indol-2-one

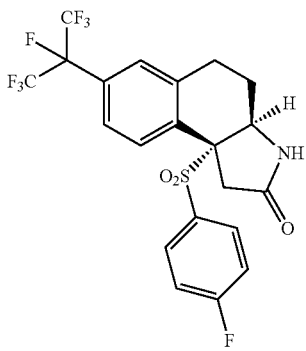 [SMILES: O=C1C[C@@]2(S(=O)(=O)c3ccc(F)cc3)c3ccc(C(F)(C(F)(F)F)C(F)(F)F)cc3CC[C@H]2N1]

Step A: Tert-butyl (3aR,9bR)-9b-((4-fluorophenyl)sulfonyl)-2-oxo-7-(perfluoropropan-2-yl)-1,2,3a,4,5,9b-hexahydro-3H-benzo[e]indole-3-carboxylate

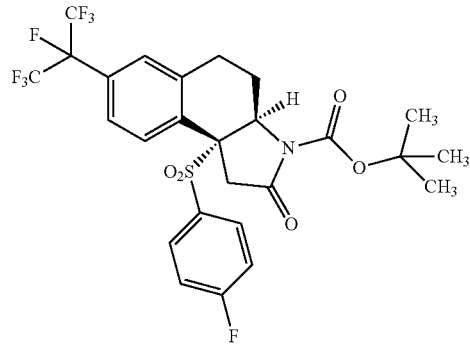 [SMILES: CC(C)(C)OC(=O)N1C(=O)C[C@@]2(S(=O)(=O)c3ccc(F)cc3)c3ccc(C(F)(C(F)(F)F)C(F)(F)F)cc3CC[C@@H]12]

A solution of (3aR,9bR)-tert-butyl 9b-((4-fluorophenyl)sulfonyl)-7-(perfluoropropan-2-yl)-3a,4,5,9b-tetrahydro-1H-benzo[e]indole-3-carboxylate (Intermediate 32 Step G; 0.70 g, 1.168 mmol) in EtOAc (6 mL) was added dropwise over 3 min to a mixture of ruthenium(III) chloride (0.242 g, 1.168 mmol) and sodium periodate (1.498 g, 7.01 mmol) in water (18.00 mL). The mixture was stirred at rt for 1 h, treated with additional ruthenium (III) chloride (24.2 mg, 0.117 mmol) and stirring was continued at rt for 1 h. The mixture was treated dropwise with 2-propanol (25 mL). The resulting mixture was filtered through Celite and the solids were washed with EtOAc. The combined filtrates were concentrated and the residue was partitioned between EtOAc (100 mL) and brine (100 mL). The organic phase was washed with brine, dried over $Na_2SO_4$ and concentrated. The residue was purified by column chromatography on silica gel (40 g), eluting with EtOAc-hexanes (gradient from 0-30%), to give (3aR,9bR)-tert-butyl 9b-((4-fluorophenyl)sulfonyl)-2-oxo-7-(perfluoropropan-2-yl)-3a,4,5,9b-tetrahydro-1H-benzo[e]indole-3-carboxylate as a white glassy solid (0.50 g, 70% yield). LCMS m/z 599.0 (M+H+MeCN—$C_4H_9$)$^+$, HPLC $t_R$ 1.16 min (method B).

Step B: (3aR,9bR)-9b-((4-fluorophenyl)sulfonyl)-7-(perfluoropropan-2-yl)-1,3,3a,4,5,9b-hexahydro-2H-benzo[e]indol-2-one

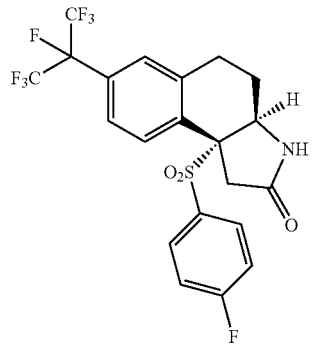 [SMILES: O=C1C[C@@]2(S(=O)(=O)c3ccc(F)cc3)c3ccc(C(F)(C(F)(F)F)C(F)(F)F)cc3CC[C@H]2N1]

A solution of (3aR,9bR)-tert-butyl 9b-((4-fluorophenyl)sulfonyl)-2-oxo-7-(perfluoropropan-2-yl)-3a,4,5,9b-tetrahydro-1H-benzo[e]indole-3-carboxylate (0.47 g, 0.766 mmol) in EtOAc (2 mL) was treated with HCl (2 M in diethyl ether; 1.915 mL, 3.83 mmol) and the mixture was stirred at rt for 15 h. The deprotection was incomplete so the mixture was concentrated, the residue was dissolved in DCM (5 mL), treated with TFA (1 mL) and stirred at rt for 10 min. The mixture was diluted with 1.5 M aqueous $K_2HPO_4$ (20 mL) and extracted with DCM (2×20 mL). The combined organic phases were dried over $Na_2SO_4$ and concentrated to give (3aR,9bR)-9b-((4-fluorophenyl)sulfonyl)-7-(perfluoropropan-2-yl)-1,3,3a,4,5,9b-hexahydro-2H-benzo[e]indol-2-one as a pale yellow solid (0.40 g, 92% yield). LCMS m/z 555.0 (M+H+MeCN)$^+$, HPLC $t_R$ 1.01 min (method B). $^1$H NMR (500 MHz, CDCl$_3$) δ 7.66 (d, J=8.4 Hz, 1H), 7.57 (d, J=8.7 Hz, 1H), 7.32 (dd, J=8.6, 5.0 Hz, 2H), 7.25 (s, 1H), 7.06-6.98 (m, 2H), 4.42 (ddd, J=11.4, 5.3, 0.8 Hz, 1H), 3.78 (d, J=18.3 Hz, 1H), 2.98 (d, J=18.3 Hz, 1H), 2.61 (dt, J=16.3, 3.7 Hz, 1H), 2.29-2.10 (m, 1H), 1.98-1.79 (m, 1H), 1.54-1.43 (m, 1H).

Intermediate 119

Mixture of (1s,4s)-4-(tert-butoxycarbonyl)-1-fluorocyclohexane-1-carboxylic Acid and (1s,4s)-4-(tert-butoxycarbonyl)-4-fluorocyclohexane-1-carboxylic Acid

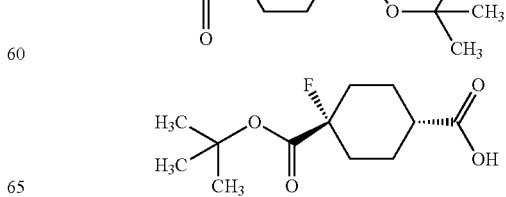

Step A: dimethyl (1s,4s)-1-fluorocyclohexane-1,4-dicarboxylate

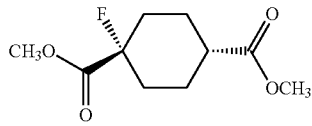

A solution of diisopropylamine (1.4 mL, 10.2 mmol) in THF (30 mL) was treated with n-butyllithium (2.5 M in hexanes, 4.1 mL, 10.2 mmol) at −78° C. and stirred at 0° C. for 30 min. The mixture was cooled to −78° C. and was treated with a solution of (1r,4r)-dimethyl cyclohexane-1,4-dicarboxylate (1.85 g, 9.24 mmol) in THF (15 mL) dropwise over 10 min. The resulting mixture was stirred at −78° C. for 30 min, then was treated with a solution of N-fluorobenzenesulfonimide (3.06 g, 9.70 mmol) in THF (15 mL). The mixture was warmed to rt and stirred for 2 h. After quenching with saturated aqueous NH$_4$Cl (20 mL), the mixture was diluted with EtOAc (300 mL), washed sequentially with water (30 mL) and brine (30 mL), dried (MgSO$_4$), filtered and concentrated. The residue was purified by column chromatography, eluting with EtOAc-hexanes (gradient from 0-10%), to give dimethyl (1s,4s)-1-fluorocyclohexane-1,4-dicarboxylate as the second peak from the column (330 mg, 16% yield, minor isomer). $^1$H NMR (400 MHz, CDCl$_3$) δ 3.76 (s, 3H), 3.66 (s, 3H), 2.44-2.29 (m, 1H), 2.26-1.73 (m, 8H).

Step B: (1s,4s)-1-fluorocyclohexane-1,4-dicarboxylic Acid

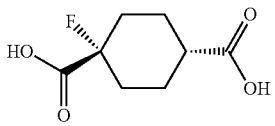 [SMILES: O=C(O)[C@H]1CC[C@](F)(C(=O)O)CC1]

A mixture of dimethyl (1s,4s)-1-fluorocyclohexane-1,4-dicarboxylate (180 mg, 0.83 mmol) in THF (6 mL) was treated with 1 M aqueous LiOH (4.95 mL, 4.95 mmol). After stirring at rt for 15 h, the mixture was acidified to pH 2-3 with 1 M aqueous HCl. After evaporation of organic solvents, the residue was treated with EtOAc (100 mL), washed sequentially with water (10 mL) and brine (10 mL), dried (MgSO$_4$), filtered and concentrated to give (1s,4s)-1-fluorocyclohexane-1,4-dicarboxylic acid (142 mg), used without further purification. $^1$H NMR (400 MHz, MeOH-d$_4$) δ 2.55-2.33 (m, 1H), 2.33-2.11 (m, 1H), 2.10-1.80 (m, 5H), 1.72 (qd, J=12.6, 3.6 Hz, 2H).

Step C: Mixture of (1s,4s)-4-(tert-butoxycarbonyl)-1-fluorocyclohexane-1-carboxylic Acid and (1s,4s)-4-(tert-butoxycarbonyl)-4-fluorocyclohexane-1-carboxylic Acid

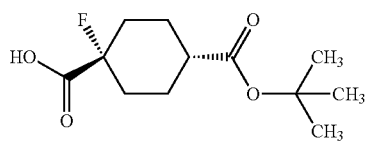

-continued

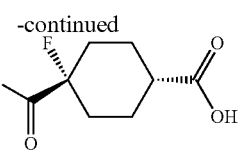

4-Dimethylaminopyridine (9.6 mg, 0.079 mmol) was added to a solution of (1s,4s)-1-fluorocyclohexane-1,4-dicarboxylic acid (50 mg, 0.263 mmol) and di-tert-butyl dicarbonate (73 μL, 0.316 mmol) in tert-butanol (2 mL). After stirring at rt for 15 h, the mixture was treated with EtOAc (60 mL), washed sequentially with 0.2 M aqueous HCl (5 mL), water (5 mL) and brine (5 mL), dried (MgSO$_4$), filtered and concentrated to give crude (1s,4s)-4-(tert-butoxycarbonyl)-1-fluorocyclohexane-1-carboxylic acid (55 mg), contaminated with (1s,4s)-4-(tert-butoxycarbonyl)-4-fluorocyclohexane-1-carboxylic acid, which was used without further purification. LCMS m/z 244.9 (M−H)$^-$, HPLC t$_R$ 0.94 min (method B).

Intermediate 120

(1s,4s)-4-(ethoxycarbonyl)-1-fluorocyclohexane-1-carboxylic Acid

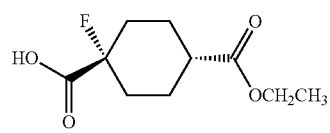 [SMILES: CCOC(=O)[C@H]1CC[C@](F)(C(=O)O)CC1]

Step A: Mixture of Ethyl (3r,6r)-1-oxaspiro[2.5]octane-6-carboxylate and Ethyl (3s,6s)-1-oxaspiro[2.5]octane-6-carboxylate

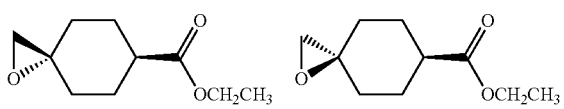

A suspension of potassium tert-butoxide (5.03 g, 44.8 mmol) in dry THF (100 mL) was treated with trimethylsulfoxonium iodide (10.21 g, 46.4 mmol) and the mixture was stirred at reflux under nitrogen for 2 h. The mixture was cooled to rt, treated dropwise over 2 min with a solution of ethyl 4-oxocyclohexanecarboxylate (5.3 g, 31.1 mmol) in THF (30 mL), then heated at reflux for 2.5 h. The mixture was cooled to rt, partitioned between EtOAc (250 mL) and water (150 mL) and the aqueous phase was extracted with EtOAc (2×50 mL). The combined organic phases were dried over Na$_2$SO$_4$ and concentrated. The residue was purified by column chromatography on silica gel (80 g), eluting with EtOAc-hexanes (gradient from 0-15%), to give a mixture of ethyl (3r,6r)-1-oxaspiro[2.5]octane-6-carboxylate and ethyl (3s,6s)-1-oxaspiro[2.5]octane-6-carboxylate (3.8 g, 66% yield). $^1$H NMR (400 MHz, CDCl$_3$) δ 4.13 (q, J=7.2 Hz, 2.2H), 2.63 (s, 2H), 2.60 (s, 0.2H), 2.47-2.29 (m, 1.2H), 2.13-2.04 (m, 0.2H), 2.02-1.94 (m, 1.2H), 1.93-1.89 (m, 0.2H), 1.89-1.81 (m, 9.6H), 1.81-1.78 (m, 1.6H), 1.77-1.70 (m, 0.4H), 1.56-1.45 (m, 0.2H), 1.42-1.33 (m, 2H), 1.25 (t, J=7.2 Hz, 3.2H).

Step B: Ethyl (1s,4s)-4-fluoro-4-(hydroxymethyl)cyclohexane-1-carboxylate

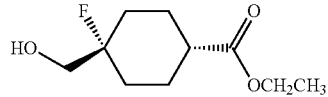

Hydrogen fluoride (70% in pyridine; 5 mL, 5.43 mmol) was cooled to −78° C. in a polypropylene vial and treated with a solution of the mixture of ethyl (3r,6r)-1-oxaspiro[2.5]octane-6-carboxylate and ethyl (3s,6s)-1-oxaspiro[2.5]octane-6-carboxylate from Step A (1.0 g, 5.43 mmol) in DCM (5 mL). The mixture was stirred at −78° C. for 4.5 h, then was poured into ice-cold 2 M aqueous NH$_4$OH (25 mL) and DCM (25 mL). The mixture was adjusted to pH 8 using concentrated aqueous NH$_4$OH and extracted with DCM (2×50 mL). The combined organic phases were washed sequentially with 1 M aqueous HCl (50 mL) and brine (50 mL), dried over Na$_2$SO$_4$ and concentrated. The residue was purified by column chromatography on silica gel (24 g), eluting with EtOAc-hexanes (gradient from 0-30%), to give (1s,4s)-ethyl 4-fluoro-4-(hydroxymethyl)cyclohexanecarboxylate as a solid (390 mg, 35% yield). $^1$H NMR (400 MHz, CDCl$_3$) δ 4.21-4.07 (m, 2H), 3.57 (dd, J=19.6, 5.7 Hz, 2H), 2.36-2.20 (m, 1H), 2.05 (dd, J=12.4, 9.4 Hz, 2H), 1.96-1.86 (m, 2H), 1.86-1.73 (m, 2H), 1.47-1.28 (m, 2H), 1.26 (t, J=7.2 Hz, 3H). (1r,4r)-ethyl 4-fluoro-4-(hydroxymethyl)cyclohexanecarboxylate was also isolated. $^1$H NMR (400 MHz, CDCl$_3$) δ 4.14 (q, J=7.1 Hz, 2H), 3.72-3.55 (m, 2H), 2.62-2.46 (m, 1H), 1.99-1.87 (m, 2H), 1.85-1.72 (m, 6H), 1.26 (t, J=7.2 Hz, 3H).

Step C: (1s,4s)-4-(ethoxycarbonyl)-1-fluorocyclohexane-1-carboxylic Acid

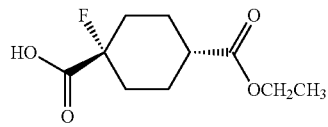 [SMILES: CCOC(=O)[C@H]1CC[C@](F)(C(=O)O)CC1]

A solution of (1s,4s)-ethyl 4-fluoro-4-(hydroxymethyl)cyclohexanecarboxylate (0.76 g, 3.72 mmol) in MeCN (8 mL) and tetrachloromethane (8.00 mL) was treated with a solution of periodic acid (3.48 g, 15.26 mmol) in water (12.00 mL), then with ruthenium(III) chloride hydrate (0.034 g, 0.149 mmol). The mixture was stirred at rt for 1.5 h, then was diluted with diethyl ether (60 mL) and stirred at rt for 10 min. The mixture was filtered and the phases were separated, and the aqueous phase was extracted with diethyl ether (2×20 mL). The combined organic phases were washed with brine (2×30 mL), dried over Na$_2$SO$_4$ and concentrated to give crude (1s,4s)-4-(ethoxycarbonyl)-1-fluorocyclohexanecarboxylic acid as a solid (0.74 g, 91% yield), used without further purification. $^1$H NMR (400 MHz, CDCl$_3$) δ 4.16 (q, J=7.3 Hz, 2H), 2.45-2.31 (m, 1H), 2.23-2.11 (m, 2H), 2.04-1.94 (m, 3H), 1.94-1.72 (m, 3H), 1.27 (t, J=7.2 Hz, 3H).

Intermediate 121

(1r,4r)-1-ethylcyclohexane-1,4-dicarboxylic Acid

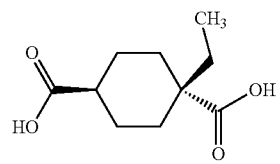

Step A: Dimethyl 4-vinylcyclohex-1-ene-1,4-dicarboxylate

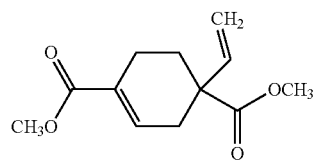

A stirred solution of methyl 3-hydroxy-2-methylenebutanoate (2.56 g, 21.13 mmol) in DCM (150 mL) at 0° C. under a nitrogen atmosphere was treated Et$_3$N (11.8 mL, 85 mmol) followed by MsCl (2.1 mL, 27.5 mmol). The reaction mixture was allowed to reach rt and stirring was continued for 12 h. The mixture was treated with water (50 mL) and extracted with DCM (3×50 mL). The combined organic layers were washed with 1.5 M aqueous HCl (2×50 mL) followed by 50 mL saturated brine, dried over Na$_2$SO$_4$, filtered and concentrated to provide a pale yellow liquid (3.7 g). The material was purified by column chromatography (24 g silica gel), eluting with EtOAc-petroleum ether (gradient from 5-7%), to yield dimethyl 4-vinylcyclohex-1-ene-1,4-dicarboxylate (1.9 g, 40% yield) as colorless liquid. $^1$H NMR (300 MHz, CDCl$_3$) δ 6.97 (m, 1H), 5.89 (dd, J=18, 9 Hz, 1H), 5.02-5.20 (m, 2H), 3.73 (s, 3H), 3.69 (s, 3H), 2.92-2.72 (m, 1H), 2.45-2.25 (m, 3H), 2.20-2.02 (m, 1H), 1.92-1.72 (m, 1H).

Step B: Dimethyl (1r,4r)-1-ethylcyclohexane-1,4-dicarboxylate

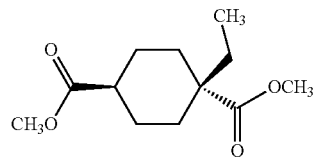

A solution of dimethyl 4-vinylcyclohex-1-ene-1,4-dicarboxylate (1 g, 4.46 mmol) in DCM (100 mL) was treated with iridium(I) hexafluorophosphate (1,5-cyclooctadiene)-(pyridine)-(tricyclohexylphosphine) (Crabtree's catalyst; 72 mg, 0.089 mmol). The solution was stirred under a hydrogen atmosphere (balloon pressure). The progress of the reaction was monitored by $^1$H NMR. After 24 h, another portion of Crabtree's catalyst (72 mg, 0.089 mmol) was added and stirring was continued for another 24 hours. The mixture was concentrated to yield a brownish gummy solid which was triturated with diethyl ether (30 mL) to produce a solid. The mixture was filtered and the solids were washed with diethyl ether (2×15 mL). The filtrate was concentrated under reduced pressure and purified by column chromatography (12 g silica gel), eluting with 5% EtOAc in petroleum ether, to yield dimethyl (1r,4r)-1-ethylcyclohexane-1,4-dicarboxylate (1 g, 98% yield) as colorless liquid. $^1$H NMR (300 MHz, CDCl$_3$) δ 3.69 (s, 6H), 2.52-2.28 (m, 1H), 1.90-1.50 (m, 10H), 0.82 (t, J=3.9 Hz, 3H).

Step C: ((1r,4r)-1-ethylcyclohexane-1,4-diyl)dimethanol

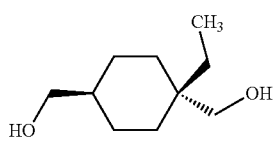

A solution of dimethyl (1r,4r)-1-ethylcyclohexane-1,4-dicarboxylate (200 mg, 0.876 mmol) in toluene (25 mL) was cooled to −78° C. under an argon atmosphere. The mixture was treated dropwise over 10 min with DIBAL-H (1.0 M in toluene, 4.4 mL, 4.38 mmol). The mixture was allowed to reach rt and stirred for 1 h, monitoring the reaction by TLC (silica gel, 10% EtOAc in hexanes). After complete conversion, the mixture was cooled to 0° C. and slowly treated with saturated aqueous NH$_4$Cl (about 5 mL). The mixture was further diluted with additional saturated aqueous NH$_4$Cl (30 mL) and extracted with EtOAc (3×30 mL). The combined organic layers were washed with brine (40 mL), dried over Na$_2$SO$_4$ and concentrated to yield ((1r,4r)-1-ethylcyclohexane-1,4-diyl)dimethanol as a colorless liquid (150 mg, 99% yield). $^1$H NMR (300 MHz, CDCl$_3$) δ 3.52-3.45 (m, 2H), 3.35-3.29 (m, 2H), 1.67-1.50 (m, 3H), 1.43 (q, J=7.6 Hz, 2H), 1.28-1.05 (m, 6H), 0.79 (t, J=7.6 Hz, 3H).

Step D: (1r,4r)-1-ethylcyclohexane-1,4-dicarboxylic Acid

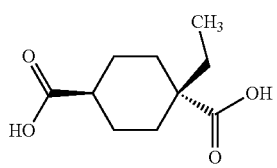

A solution of ((1r,4r)-1-ethylcyclohexane-1,4-diyl)dimethanol (150 mg, 0.871 mmol) in acetone (15 mL) at 0° C. was slowly treated with freshly prepared aqueous chromic acid [prepared by adding H$_2$SO$_4$ (0.278 mL, 5.22 mmol) to a cold solution of sodium dichromate dihydrate (1.04 g, 3.48 mmol) in water (5 mL) at 0° C. with stirring for 10 min]. The resulting mixture was stirred at rt for 3 h. After completion of the reaction (monitored by TLC), the mixture was partially concentrated and the aqueous residue was extracted with EtOAc (3×10 mL). The combined organic layers (light red in color) were repeatedly washed with brine (15 mL in each wash) until colorless, then was dried over Na$_2$SO$_4$ and concentrated to give (1r,4r)-1-ethylcyclohexane-1,4-dicarboxylic acid as a white solid (117 mg, 67% yield). $^1$H NMR (400 MHz, DMSO-d$_6$) δ 12.08 (br. s, 2H), 2.35-2.24 (m, 1H), 1.73-1.57 (m, 6H), 1.55-1.40 (m, 4H), 0.75 (t, J=8.0 Hz, 3H).

Intermediate 122

(2RS,4RS)-2-methyltetrahydro-2H-thiopyran-4-carboxylic Acid 1,1-dioxide

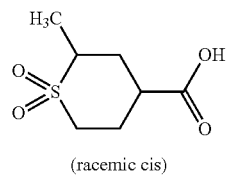

(racemic cis)

Step A: 4-((benzyloxy)methyl)tetrahydro-2H-thiopyran

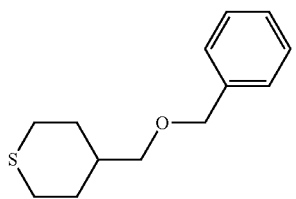 [SMILES: c1ccc(COCC2CCSCC2)cc1]

A suspension of NaH (60% in mineral oil; 1.234 g, 30.9 mmol) in DMF (50 mL) at 0° C. was treated portionwise with a solution of (tetrahydro-2H-thiopyran-4-yl)methanol (3.4 g, 25.7 mmol) in DMF (2 mL) and the mixture was stirred for 15 min. Benzyl bromide (3.36 mL, 28.3 mmol) was added dropwise over 2 min, and the mixture was left to warm to rt. After 1.5 h, the mixture was treated with saturated aqueous NH$_4$Cl (20 mL), diluted with water (50 mL) and extracted with EtOAc (75 mL). The organic phase was washed sequentially with 10% aqueous LiCl (3×30 mL) and brine (30 mL), dried over Na$_2$SO$_4$ and concentrated. The residue was purified by column chromatography on silica gel (120 g), eluting with EtOAc-hexanes (gradient from 0-10%), to give 4-((benzyloxy)methyl)tetrahydro-2H-thiopyran as a colorless oil (3.4 g, 60% yield). $^1$H NMR (400 MHz, CDCl$_3$) δ 7.43-7.27 (m, 5H), 4.50 (s, 2H), 3.31 (d, J=6.4 Hz, 2H), 2.75-2.66 (m, 2H), 2.66-2.57 (m, 2H), 2.16-2.07 (m, 2H), 1.79-1.62 (m, 1H), 1.51-1.34 (m, 2H).

Step B: 4-((benzyloxy)methyl)tetrahydro-2H-thiopyran 1,1-dioxide

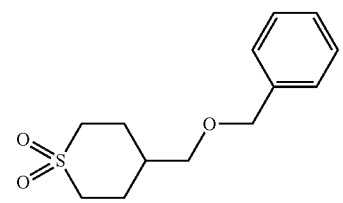 [SMILES: O=S1(=O)CCC(COCc2ccccc2)CC1]

A solution of 4-((benzyloxy)methyl)tetrahydro-2H-thiopyran (4.7 g, 21.14 mmol) in DCM (125 mL) at 0° C. was treated portionwise with mCPBA (77%; 9.95 g, 44.4 mmol) and the ice bath was removed to allow the mixture to warm to rt. After 2 h, the mixture was cooled to 0° C., filtered and the filtrate was stirred at rt for 10 min with 10% aqueous $Na_2S_2O_3$ (120 mL). The organic phase was separated and washed with 10% aqueous $K_2CO_3$ (2×150 mL), dried over $Na_2SO_4$ and concentrated. The residue was purified by column chromatography on silica gel (120 g), eluting with EtOAc-hexanes (gradient from 0-60%), to give 4-((benzyloxy)methyl)tetrahydro-2H-thiopyran 1,1-dioxide as a white solid (4.9 g, 91% yield). $^1$H NMR (400 MHz, $CDCl_3$) δ 7.42-7.28 (m, 5H), 4.51 (s, 2H), 3.43-3.30 (m, 2H), 3.14-2.87 (m, 4H), 2.20 (d, J=11.9 Hz, 2H), 2.00-1.76 (m, 3H).

Step C: (2RS,4RS)-4-((benzyloxy)methyl)-2-methyltetrahydro-2H-thiopyran 1,1-dioxide

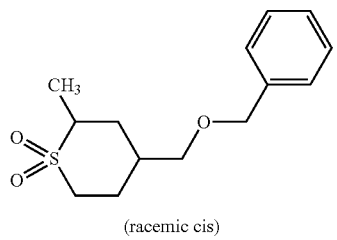 [SMILES: CC1CC(COCc2ccccc2)CCS1(=O)=O]

(racemic cis)

A solution of diisopropylamine (0.579 mL, 4.13 mmol) in THF (12 mL) under nitrogen was cooled to −78° C. and treated dropwise with n-butyllithium (2.4 M in hexanes; 1.556 mL, 3.74 mmol) and the mixture was stirred for 30 min, then at rt for 15 min. The mixture was cooled to −78° C., treated over 3 min with a solution of 4-((benzyloxy)methyl)tetrahydro-2H-thiopyran 1,1-dioxide (1.0 g, 3.93 mmol) in THF (5 mL) and stirred for 1 h. The mixture was then treated with a solution of iodomethane (0.257 mL, 4.13 mmol) in THF (0.5 mL). After 45 min, the cooling bath was removed and the mixture was allowed to warm to rt, then was stirred for 1 h. The mixture was treated with saturated aqueous $NH_4Cl$ (50 mL) and extracted with EtOAc (2×50 mL). The combined organic phases were washed with brine, dried over $Na_2SO_4$ and concentrated. The residue was purified by column chromatography on silica gel (80 g), eluting with EtOAc-hexanes (gradient from 0-35%) to give racemic cis-4-((benzyloxy)methyl)-2-methyltetrahydro-2H-thiopyran 1,1-dioxide as a white solid (450 mg, 43% yield). LCMS m/z 290.8 (M+Na)$^+$, HPLC $t_R$ 0.81 min (method B). $^1$H NMR (400 MHz, $CDCl_3$) δ 7.41-7.28 (m, 5H), 4.51 (s, 2H), 3.33 (d, J=6.2 Hz, 2H), 3.12 (dt, J=14.3, 3.4 Hz, 1H), 3.04-2.87 (m, 2H), 2.23-2.12 (m, 1H), 2.11-2.03 (m, 1H), 2.00-1.76 (m, 2H), 1.69-1.59 (m, 1H), 1.35 (d, J=6.8 Hz, 3H). The dimethylated side product (2R,4r,6S)-4-((benzyloxy)methyl)-2,6-dimethyltetrahydro-2H-thiopyran 1,1-dioxide was also isolated in 75% purity (250 mg, 23% yield). LCMS m/z 283.1 (M+H)$^+$, HPLC $t_R$ 0.88 min (method B).

Step D: (2RS,4RS)-4-(hydroxymethyl)-2-methyltetrahydro-2H-thiopyran 1,1-dioxide

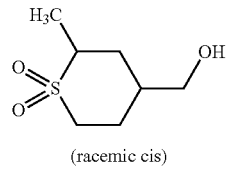

(racemic cis)

A solution of (2RS,4RS)-4-((benzyloxy)methyl)-2-methyltetrahydro-2H-thiopyran 1,1-dioxide (0.45 g, 1.677 mmol) in MeOH (2 mL) and ethanol (10 mL) was treated with palladium on carbon (160 mg, 0.075 mmol) and stirred under a hydrogen atmosphere (balloon pressure) for 1.5 h. The mixture was filtered to remove the catalyst and the filtrate was concentrated to give (2RS,4RS)-4-(hydroxymethyl)-2-methyltetrahydro-2H-thiopyran 1,1-dioxide as a white solid (280 mg, 94% yield). $^1$H NMR (400 MHz, $CDCl_3$) δ 3.53 (d, J=5.7 Hz, 1H), 3.20-3.09 (m, 1H), 3.06-2.85 (m, 2H), 2.24-2.12 (m, 1H), 2.10-2.00 (m, 2H), 1.92-1.73 (m, 2H), 1.67-1.52 (m, 1H), 1.36 (d, J=6.8 Hz, 3H).

Step E: (2RS,4RS)-2-methyltetrahydro-2H-thiopyran-4-carboxylic Acid 1,1-dioxide

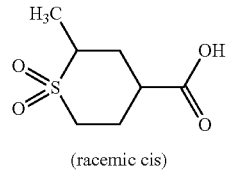

(racemic cis)

A solution of (2RS,4RS)-4-(hydroxymethyl)-2-methyltetrahydro-2H-thiopyran 1,1-dioxide (0.275 g, 1.543 mmol) in MeCN (0.9 mL) and $CCl_4$ (0.9 mL) was treated with a solution of sodium periodate (1.353 g, 6.33 mmol) in water (1.3 mL), then with ruthenium(III) chloride hydrate (0.014 g, 0.062 mmol), and the mixture was stirred at rt. After 30 min, the mixture was a yellow emulsion, and stirring was continued at rt for 30 min more with periodic sonication. An additional portion of ruthenium(III) chloride hydrate (0.014 g, 0.062 mmol) was added, and stirring was continued for 1 h with occasional sonication. The mixture was diluted with EtOAc (125 mL), the organic phase was separated and washed with water (25 mL), dried over $Na_2SO_4$ and concentrated. The residue was treated with EtOAc (125 mL) and MeOH (10 mL), filtered (Acrodisk syringe filter, 25 mm, 0.45 m) and concentrated to give (2RS,4RS)-2-methyltetrahydro-2H-thiopyran-4-carboxylic acid 1,1-dioxide as a gray solid (165 mg, 56% yield), used without further purification. $^1$H NMR (400 MHz, MeOH-$d_4$) δ 3.28-3.04 (m, 3H), 2.69 (tt, J=12.4, 3.3 Hz, 1H), 2.37 (d quin, J=14.1, 3.5 Hz, 1H), 2.28 (dq, J=14.2, 3.2 Hz, 1H), 2.18-2.03 (m, 1H), 1.86 (dt, J=14.3, 12.5 Hz, 1H), 1.29 (d, J=6.8 Hz, 3H).

Intermediate 123

(2R,4r,6S)-2,6-dimethyltetrahydro-2H-thiopyran-4-carboxylic Acid 1,1-dioxide

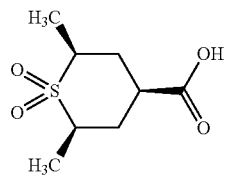

Following the procedures of Intermediate 122 Steps D and E, (2R,4r,6S)-4-((benzyloxy)methyl)-2,6-dimethyltetrahydro-2H-thiopyran 1,1-dioxide (isolated as a side product in Step C of the preparation of Intermediate 122) was converted into (2R,4r,6S)-2,6-dimethyltetrahydro-2H-thiopyran-4-carboxylic acid 1,1-dioxide. $^1$H NMR (400 MHz, CDCl$_3$) δ 3.12-2.97 (m, 2H), 2.70 (tt, J=12.5, 3.1 Hz, 1H), 2.32 (d, J=11.9 Hz, 2H), 2.17-2.04 (m, 2H), 1.43 (d, J=6.6 Hz, 6H).

Intermediate 124

(S)-1-(4-fluorobenzyl)-5-oxopyrrolidine-2-carboxylic Acid

A suspension of NaH (60% in mineral oil; 0.336 g, 8.40 mmol) in THF (11 mL) was treated with (S)-ethyl 5-oxopyrrolidine-2-carboxylate (0.88 g, 5.60 mmol). The mixture was stirred at rt for 15 min, then 1-(bromomethyl)-4-fluorobenzene (0.837 mL, 6.72 mmol) was added and the mixture was stirred at rt overnight. The mixture was concentrated to give crude methyl (S)-1-(4-fluorobenzyl)-5-oxopyrrolidine-2-carboxylate, used without purification. This was dissolved in THF-MeOH-water (3:1:1, 112 mL) and treated with LiOH monohydrate (0.267 g, 11.16 mmol). The mixture was stirred at rt for 20 h, then was partially concentrated. The aqueous residue was diluted with water and washed twice with EtOAc. The aqueous phase was acidified with 1 M aqueous HCl to about pH 2, and then was extracted with EtOAc. The organic phase was washed with brine, dried over Na$_2$SO$_4$ and concentrated to provide (S)-1-(4-fluorobenzyl)-5-oxopyrrolidine-2-carboxylic acid as a yellow syrup (0.54 g, 41% yield). LCMS m/z 238.3 (M+H)$^+$, HPLC t$_R$ 0.92 min (method B). $^1$H NMR (400 MHz, DMSO-d$_6$) δ 12.90 (br. s., 1H), 7.28-7.21 (m, 2H), 7.19-7.11 (m, 2H), 4.79 (d, J=15.0 Hz, 1H), 3.97-3.89 (m, 2H), 2.41-2.20 (m, 3H), 1.98-1.91 (m, 1H).

Intermediate 125

(S)-1-(2-(tert-butoxy)-2-oxoethyl)-5-oxopyrrolidine-2-carboxylic Acid

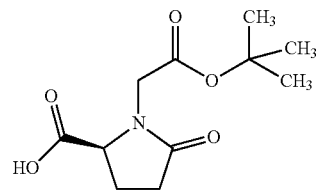 [SMILES: CC(C)(C)OC(=O)CN1C(=O)CC[C@H]1C(=O)O]

Step A: Methyl (S)-1-(2-(tert-butoxy)-2-oxoethyl)-5-oxopyrrolidine-2-carboxylate

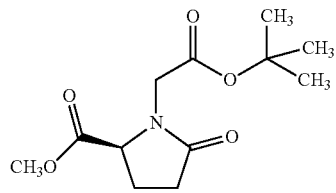

A solution of (S)-methyl 5-oxopyrrolidine-2-carboxylate (2.50 g, 17.47 mmol) in dry MeCN (45 mL) under nitrogen was stirred on an ice-water bath and treated portionwise over 30 min with NaH (60% in mineral oil; 0.768 g, 19.21 mmol) portionwise. The resulting suspension was stirred on ice for 90 min, then was treated dropwise over 15 min with a solution of tert-butyl 2-bromoacetate (2.84 mL, 19.21 mmol) in MeCN (4 mL). The resulting suspension was warmed to rt and stirred for 3 h, then was concentrated under vacuum. The residue was partitioned between EtOAc and water, and the aqueous phase was extracted again with EtOAc. The combined organic phases were washed with saturated brine, dried over Na$_2$SO$_4$ and concentrated. The residue was twice stirred vigorously with hexane, followed by decantation of the hexane layer. The residue was concentrated under vacuum to give a pale tan viscous oil. The combined hexane washes, on nearly complete concentration, formed two phases. The upper phase was decanted, and the lower phase was rinsed with a small amount of hexane by decantation and dried under vacuum to provide a colorless oil. The two oils were combined and concentrated further under vacuum to provide methyl (S)-1-(2-(tert-butoxy)-2-oxoethyl)-5-oxopyrrolidine-2-carboxylate (3.63 g, 78% yield). LCMS m/z 202 (M+H—C$_4$H$_8$)$^+$, 515 (2M+H)$^+$, HPLC t$_R$ 0.73 min (method B). $^1$H NMR (400 MHz, CDCl$_3$) δ 4.55 (d, J=17.8 Hz, 1H), 4.50-4.40 (m, 1H), 3.79 (s, 3H), 3.60 (d, J=18.0 Hz, 1H), 2.61-2.33 (m, 3H), 2.25-2.07 (m, 1H), 1.47 (s, 9H).

Step B: (S)-1-(2-(tert-butoxy)-2-oxoethyl)-5-oxopyrrolidine-2-carboxylic Acid

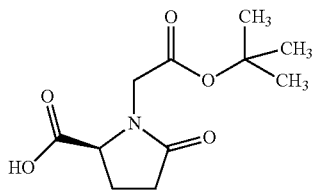 [SMILES: CC(C)(C)OC(=O)CN1C(=O)CC[C@H]1C(=O)O]

A solution of (S)-methyl 1-(2-(tert-butoxy)-2-oxoethyl)-5-oxopyrrolidine-2-carboxylate (0.25 g, 0.972 mmol) in THF (3 mL) was stirred on an ice-water bath and treated with a solution of LiOH hydrate (0.043 g, 1.020 mmol) in water (3 mL). The solution was stirred for 60 min, then was treated with 1 M aqueous HCl (1.03 mL) and concentrated. The residue was partitioned between EtOAc and a small amount of water and the aqueous phase was extracted again with EtOAc. The combined organic phases were dried over $Na_2SO_4$ and concentrated to provide (S)-1-(2-(tert-butoxy)-2-oxoethyl)-5-oxopyrrolidine-2-carboxylic acid as a light yellow-tan gum (220 mg, 89% yield). LCMS m/z 188 $(M+H-C_4H_8)^+$ and 509 $(2M+Na)^+$, HPLC $t_R$ 0.65 min (method B). $^1H$ NMR (400 MHz, $CDCl_3$) δ 4.53 (d, J=18.1 Hz, 1H), 4.52-4.42 (m, 1H), 3.70 (d, J=17.8 Hz, 1H), 2.67-2.41 (m, 3H), 2.33-2.17 (m, 1H), 1.48 (s, 9H).

The Intermediates in Table 7 were prepared using the same method or similar methods used to prepare Intermediates 124 and 125 by employing the appropriate starting materials.

TABLE 7

| Intermediate number | Structure | LCMS m/z observed | HPLC $t_R$ (min) | HPLC method |
|---|---|---|---|---|
| 126 | (S)-1-(4-cyanobenzyl)-5-oxopyrrolidine-2-carboxylic acid | 244.9 (M + H)⁺ | 0.57 | B |
| 127 | (S)-1-methyl-5-oxopyrrolidine-2-carboxylic acid | 165.9 (M + Na)⁺ | 0.40 | B |
| 128 | (S)-1-(methyl-d3)-5-oxopyrrolidine-2-carboxylic acid | 169.0 (M + Na)⁺ | 0.37 | B |
| 129 | (S)-1-acetyl-5-oxopyrrolidine-2-carboxylic acid | 171.9 (M + H)⁺ | 0.43 | B |
| 130 | (S)-1-(4-fluorobenzyl)-5-oxopyrrolidine-2-carboxylic acid | 237.9 (M + H)⁺ | 0.63 | B |
| 131 | (R)-1-(4-cyanobenzyl)-5-oxopyrrolidine-2-carboxylic acid | 244.9 (M + H)⁺ | 0.57 | B |

TABLE 7-continued

| Intermediate number | Structure | LCMS m/z observed | HPLC $t_R$ (min) | HPLC method |
|---|---|---|---|---|
| 132 | 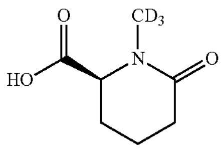 [SMILES: [2H]C([2H])([2H])N1C(=O)CCC[C@H]1C(=O)O] | 161.1 (M + H)+ | 0.40 | B |

Intermediate 133

(S)-1-(4-carbamoylbenzyl)-5-oxopyrrolidine-2-carboxylic Acid

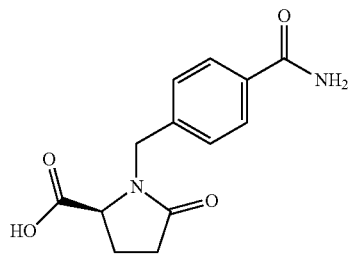 [SMILES: NC(=O)c1ccc(CN2C(=O)CC[C@H]2C(=O)O)cc1]

A suspension of (S)-1-(4-cyanobenzyl)-5-oxopyrrolidine-2-carboxylic acid (Intermediate 126, 0.120 g, 0.491 mmol) in 85% aqueous $H_2SO_4$ (1.637 mL, 24.57 mmol) was heated at 60° C. After 100 min, the mixture was cooled to rt and poured onto ice and water. The resulting mixture was extracted with EtOAc, and the organic phase was washed with brine, dried over $Na_2SO_4$, filtered, and concentrated to afford (S)-1-(4-carbamoylbenzyl)-5-oxopyrrolidine-2-carboxylic acid as a yellow solid (46 mg, 46% yield). LCMS m/z 263.0 (M+H)+, HPLC $t_R$ 0.43 min (method B). $^1$H NMR (400 MHz, DMSO-$d_6$): δ 13.01 (br. s., 1H), 7.93 (br. s., 1H), 7.83 (d, J=8.4 Hz, 2H), 7.31 (br. s., 1H), 7.27 (d, J=8.1 Hz, 2H), 4.87 (d, J=15.6 Hz, 1H), 4.01-3.92 (m, 2H), 2.33 (d, J=2.9 Hz, 3H), 1.98-1.93 (m, 1H).

Intermediate 134

(R)-1-(4-carbamoylbenzyl)-5-oxopyrrolidine-2-carboxylic Acid

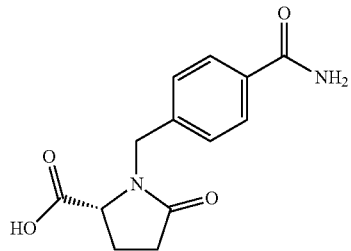 [SMILES: NC(=O)c1ccc(CN2C(=O)CC[C@@H]2C(=O)O)cc1]

Following the procedure used to prepare Intermediate 133, (R)-1-(4-cyanobenzyl)-5-oxopyrrolidine-2-carboxylic acid (Intermediate 131) was converted into (R)-1-(4-carbamoylbenzyl)-5-oxopyrrolidine-2-carboxylic acid in 68% yield. LCMS m/z 262.9 (M+H)+, HPLC $t_R$ 0.44 min (method B).

Intermediate 135

(S)-1-ethyl-5-oxopyrrolidine-2-carboxylic Acid

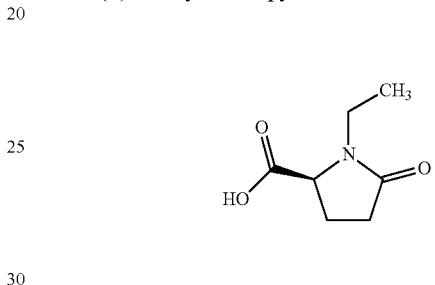

Step A: Diethyl Ethyl-L-glutamate

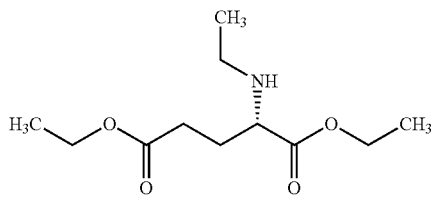 [SMILES: CCN[C@@H](CCC(=O)OCC)C(=O)OCC]

A mixture of (S)-diethyl 2-aminopentanedioate hydrochloride (1.5 g, 6.26 mmol) in THF (19 mL) and MeOH (10 mL) was treated with crushed KOH (0.410 g, 6.57 mmol) and stirred at rt for 10 min. The mixture was treated with a mixture of acetaldehyde (5 M in THF; 3.75 mL, 18.77 mmol) and acetic acid (0.394 mL, 6.88 mmol) in THF (2.4 mL). After 10 min, the reaction mixture was treated portionwise with sodium borohydride (0.474 g, 12.52 mmol). The mixture was stirred at rt for 18 h, then was concentrated. The residue was partitioned between EtOAc and 1.5 M aqueous $K_2HPO_4$. The organic phase was washed with brine, dried over $Na_2SO_4$, filtered and concentrated to afford crude diethyl ethyl-L-glutamate as a yellow oil (1.39 g, 96% yield). LCMS m/z 232.2 (M+H)+, HPLC $t_R$ 0.53 min (method B).

Step B: Ethyl (S)-1-ethyl-5-oxopyrrolidine-2-carboxylate

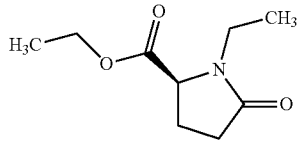

A solution of diethyl ethyl-L-glutamate (1.39 g, 6.01 mmol) in MeOH (12 mL) in a sealed vessel was heated at 140° C. for 15 min, then was heated via microwave irradiation for 15 min at 150° C. The mixture was cooled to rt, concentrated, and the residue was partitioned between EtOAc and 0.3 M aqueous HCl. The organic phase was washed sequentially with water and saturated aqueous NaHCO$_3$, dried over Na$_2$SO$_4$, filtered, and concentrated to afford crude ethyl (S)-1-ethyl-5-oxopyrrolidine-2-carboxylate as a brown oil (0.39 g, 35% yield). LCMS m/z 186.1 (M+H)$^+$, HPLC t$_R$ 0.61 min (method B). $^1$H NMR (400 MHz, CDCl$_3$) δ 4.28-4.18 (m, 3H), 3.76-3.64 (m, 1H), 3.11-2.99 (m, 1H), 2.58-2.46 (m, 1H), 2.42-2.26 (m, 2H), 2.14-2.03 (m, 1H), 1.30 (t, J=7.2 Hz, 3H), 1.14-1.10 (m, 3H).

Step C: (S)-1-ethyl-5-oxopyrrolidine-2-carboxylic Acid

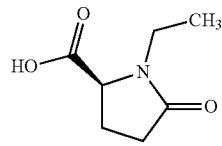

A mixture of ethyl (S)-1-ethyl-5-oxopyrrolidine-2-carboxylate (0.39 g, 2.106 mmol) and LiOH monohydrate (0.166 g, 6.95 mmol) in THF (6 mL), MeOH (2 mL) and water (2 mL) was stirred at rt. After 16 h the mixture was concentrated, and the residue was partitioned between 1 M aqueous HCl and chloroform-isopropanol (93:7). The organic phase was washed with brine, dried over Na$_2$SO$_4$, filtered and concentrated to afford (S)-1-ethyl-5-oxopyrrolidine-2-carboxylic acid as a brown syrup (0.357 g, quantitative yield), used without further purification. LCMS m/z 158.1 (M+H)$^+$, HPLC t$_R$ 0.19 min (method B). $^1$H NMR (400 MHz, CDCl$_3$): δ 4.93 (br. s, 1H), 4.27 (dd, J=9.0, 3.0 Hz, 1H), 3.85-3.65 (m, 1H), 3.09 (dq, J=14.1, 7.1 Hz, 1H), 2.67-2.50 (m, 1H), 2.49-2.29 (m, 2H), 2.25-2.12 (m, 1H), 1.14 (t, J=7.3 Hz, 3H).

Intermediate 136

(S)-1-isopropyl-5-oxopyrrolidine-2-carboxylic Acid

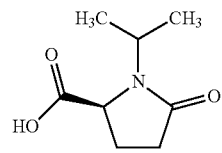

(S)-1-isopropyl-5-oxopyrrolidine-2-carboxylic acid was prepared by following the procedure used to prepare Intermediate 135, substituting acetone for acetaldehyde in Step A. LCMS m/z 172.1 (M+H)$^+$, HPLC t$_R$ 0.19 min (method B).

Intermediate 137

(2S,4S)-4-fluoro-1-(methyl-d$_3$)-5-oxopyrrolidine-2-carboxylic Acid

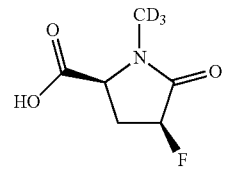 [SMILES: [2H]C([2H])([2H])N1C(=O)[C@@H](F)C[C@H]1C(=O)O]

Step A: 1-(tert-butyl) 2-methyl (2S,4S)-4-fluoropyrrolidine-1,2-dicarboxylate

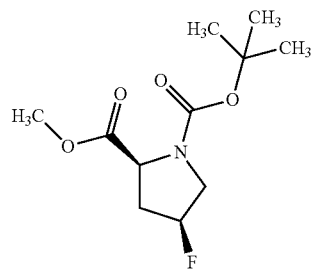 [SMILES: COC(=O)[C@@H]1C[C@H](F)CN1C(=O)OC(C)(C)C]

A solution of (2S,4S)-1-tert-butyl 2-methyl 4-hydroxypyrrolidine-1,2-dicarboxylate (10 g, 40.8 mmol) in DCM (204 mL) was cooled in an ice-water bath and treated slowly with DAST (6.46 mL, 48.9 mmol). The mixture was stirred at rt for 5.5 h, then was partitioned between water and additional DCM. The organic phase was washed with brine, dried over Na$_2$SO$_4$, filtered, and concentrated to afford 1-(tert-butyl) 2-methyl (2S,4S)-4-fluoropyrrolidine-1,2-dicarboxylate as a light yellow syrup (10.58 g, 94% yield, 90% estimated purity). LCMS m/z 270.2 (M+Na)$^+$, HPLC t$_R$ 0.80 min (method B).

Step B: 1-(tert-butyl) 2-methyl (2S,4S)-4-fluoro-5-oxopyrrolidine-1,2-dicarboxylate

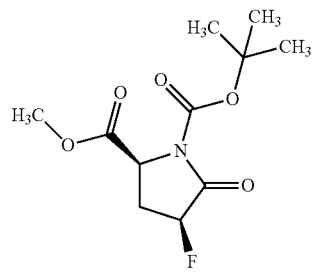 [SMILES: COC(=O)[C@@H]1C[C@H](F)C(=O)N1C(=O)OC(C)(C)C]

A solution of sodium periodate (44.6 g, 209 mmol) in water (435 ml) was treated with ruthenium(III) chloride hydrate (7.84 g, 34.8 mmol), forming a dark red solution. This was treated slowly with a solution of crude (2S,4S)-1-tert-butyl 2-methyl 4-fluoropyrrolidine-1,2-dicarboxylate (9.55 g, 34.8 mmol) in EtOAc (145 mL). The mixture was stirred at rt for 17 h, then was treated with isopropanol (80 mL) and stirred at rt for 3 h. The mixture was filtered through Celite and the solids were washed with water and EtOAc. The combined filtrates were diluted with additional EtOAc and water. The organic phase was separated, washed with brine, dried over $Na_2SO_4$, filtered, and concentrated. The residue was purified by column chromatography on silica gel (120 g), eluting with EtOAc-hexanes (10-50%), to provide 1-(tert-butyl) 2-methyl (2S,4S)-4-fluoro-5-oxopyrrolidine-1,2-dicarboxylate as a light yellow oil (67% yield). LCMS m/z 284.0 (M+Na)$^+$, HPLC $t_R$ 0.76 min (method B). $^1$H NMR (400 MHz, CDCl$_3$): δ 5.30-5.11 (m, 1H), 4.68 (dd, J=9.5, 2.0 Hz, 1H), 3.81 (s, 3H), 2.61-2.40 (m, 2H), 1.53 (s, 9H).

Step C: Methyl (2S,4S)-4-fluoro-5-oxopyrrolidine-2-carboxylate

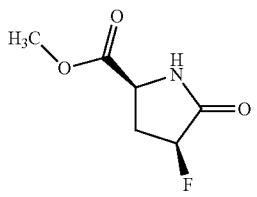

A solution of (2S,4S)-1-tert-butyl 2-methyl 4-fluoro-5-oxopyrrolidine-1,2-dicarboxylate (7.75 g, 25.8 mmol) in DCM (32 mL) was cooled in an ice-water bath and treated with TFA (12 mL). The mixture was stirred at rt for 2 h, then was concentrated and the residue partitioned between water and EtOAc. The organic phase was washed sequentially with 1.5 M aqueous $K_2HPO_3$ and brine, dried over $Na_2SO_4$, filtered, and concentrated. The aqueous phase was extracted with chloroform-isopropanol (3:1) to provide additional product. The two portions were combined to provide methyl (2S,4S)-4-fluoro-5-oxopyrrolidine-2-carboxylate as a dark yellow syrup (3.38 g, 81% yield). LCMS m/z 162.0 (M+H)$^+$, HPLC $t_R$ 0.41 min (method B). $^1$H NMR (400 MHz, CDCl$_3$) δ 6.86 (br. s., 1H), 5.23-5.03 (m, 1H), 4.47-4.34 (m, 1H), 3.82-3.78 (m, 3H), 2.69-2.58 (m, 2H).

Step D: Methyl (2S,4S)-4-fluoro-1-(methyl-d$_3$)-5-oxopyrrolidine-2-carboxylate

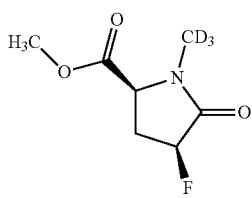

A mixture of (2S,4S)-methyl 4-fluoro-5-oxopyrrolidine-2-carboxylate (0.48 g, 2.98 mmol) and $Cs_2CO_3$ (2.426 g, 7.45 mmol) in MeCN (16.55 mL) was treated with iodomethane-d$_3$ (0.927 mL, 14.89 mmol) and heated at 45° C. overnight in a sealed vial. After 18 h, the mixture was cooled to rt, filtered and concentrated to afford methyl (2S,4S)-4-fluoro-1-(methyl-d$_3$)-5-oxopyrrolidine-2-carboxylate as a light yellow solid (0.53 g, quantitative yield). LCMS m/z 179.1 (M+H)$^+$, HPLC $t_R$ 0.46 min (method B).

Step E: (2S,4S)-4-fluoro-1-(methyl-d$_3$)-5-oxopyrrolidine-2-carboxylic Acid

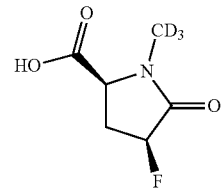 [SMILES: [2H]C([2H])([2H])N1C(=O)[C@@H](F)C[C@H]1C(=O)O]

A mixture of methyl (2S,4S)-4-fluoro-1-(methyl-d$_3$)-5-oxopyrrolidine-2-carboxylate (0.53 g, 2.97 mmol) and LiOH monohydrate (0.221 g, 9.22 mmol) in THF-MeOH-water (3:1:1) (29.7 mL) was stirred at rt for 18 h. The mixture was concentrated, the residue was treated with HCl (4 M in 1,4-dioxane, 2.380 mL, 9.52 mmol), and the mixture was concentrated again to dryness. The crude mixture containing (2S,4S)-4-fluoro-1-(methyl-d$_3$)-5-oxopyrrolidine-2-carboxylic acid was used without further purification. LCMS m/z 165.0 (M+H)$^+$, HPLC $t_R$ 0.35 min (method B).

Intermediate 138

(S)-4,4-difluoro-1-(methyl-d$_3$)-5-oxopyrrolidine-2-carboxylic Acid

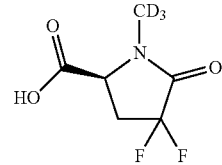

Step A: 1-(tert-butyl) 2-methyl (S)-4,4-difluoropyrrolidine-1,2-dicarboxylate

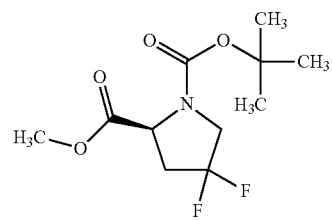 [SMILES: COC(=O)[C@@H]1CC(F)(F)CN1C(=O)OC(C)(C)C]

A solution of (S)-1-tert-butyl 2-methyl 4-oxopyrrolidine-1,2-dicarboxylate (5.02 g, 20.64 mmol) in DCM (83 mL) at −78° C. was treated dropwise with DAST (9.82 mL, 74.3 mmol). The mixture was stirred at this temperature for 15 min, then warmed to rt and stirred for 18 h. The mixture was cooled to 0° C., diluted with additional DCM and treated with ice and saturated aqueous NaHCO₃. The organic phase was separated, washed with brine, dried over Na₂SO₄, and concentrated. The residue was purified by column chromatography on silica gel (80 g), eluting with EtOAc-hexanes (10-20%), to provide 1-(tert-butyl) 2-methyl (S)-4,4-difluoropyrrolidine-1,2-dicarboxylate as a light yellow oil (4.48 g, 82% yield). LCMS m/z 288.1 (M+Na)⁺, HPLC $t_R$ 0.88 min (method B). ¹H NMR (400 MHz, CDCl₃) δ 4.64-4.40 (m, 1H), 3.93-3.73 (m, 5H), 2.83-2.60 (m, 1H), 2.47 (qd, J=13.6, 5.3 Hz, 1H), 1.46 (d, J=18.5 Hz, 9H).

Step B: (S)-4,4-difluoro-1-(methyl-d₃)-5-oxopyrrolidine-2-carboxylic Acid

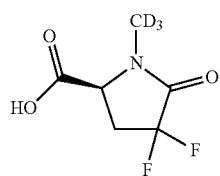 [SMILES: [2H]C([2H])([2H])N1C(=O)C(F)(F)C[C@H]1C(=O)O]

Following the procedures used in Steps B, C, D and E of the preparation of Intermediate 137, 1-(tert-butyl) 2-methyl (S)-4,4-difluoropyrrolidine-1,2-dicarboxylate was converted into (S)-4,4-difluoro-1-(methyl-d₃)-5-oxopyrrolidine-2-carboxylic acid. LCMS m/z 182.9 (M+H)⁺, HPLC $t_R$ 0.41 min (method B).

Intermediate 139

(2S,4S)-4-hydroxy-1-(methyl-d₃)-5-oxopyrrolidine-2-carboxylic Acid

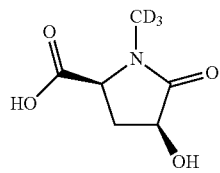 [SMILES: [2H]C([2H])([2H])N1C(=O)[C@@H](O)C[C@H]1C(=O)O]

Step A: 1-(tert-butyl) 2-methyl (2S,4S)-4-((tert-butyldimethylsilyl)oxy)pyrrolidine-1,2-dicarboxylate

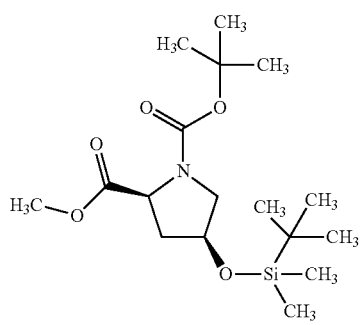 [SMILES: COC(=O)[C@@H]1C[C@H](O[Si](C)(C)C(C)(C)C)CN1C(=O)OC(C)(C)C]

A solution of (2S,4S)-1-tert-butyl 2-methyl 4-hydroxypyrrolidine-1,2-dicarboxylate (3.1 g, 12.64 mmol) in THF (56 mL), cooled in an ice-water bath, was treated slowly with a solution of tert-butylchlorodimethylsilane (2.286 g, 15.17 mmol) in THF (7.02 mL), then with Et₃N (2.82 mL, 20.22 mmol). The mixture was stirred at rt overnight. After 18 h, imidazole (1.721 g, 25.3 mmol) was added and the resulting thick suspension was stirred at rt overnight. Additional imidazole (0.42 g), tert-butylchlorodimethylsilane (1.1 g) and DMF (6 mL) were added and the mixture was heated at 45° C. for 6 h, then stirred at rt overnight. The mixture was concentrated and the residue was partitioned between EtOAc and water. The organic phase was washed with brine, dried over Na₂SO₄, filtered, and concentrated. The residue was purified by column chromatography on silica gel (80 g), eluting with EtOAc-hexanes (0-10%), to provide 1-(tert-butyl) 2-methyl (2S,4S)-4-((tert-butyldimethylsilyl)oxy)pyrrolidine-1,2-dicarboxylate as a colorless oil (4.76 g, quantitative yield). LCMS m/z 382.2 (M+Na)⁺, HPLC $t_R$ 1.16 min (method B). ¹H NMR (400 MHz, CDCl₃) δ 4.47-4.27 (m, 2H), 3.71 (s, 3H), 3.68-3.54 (m, 1H), 3.39-3.24 (m, 1H), 2.38-2.22 (m, 1H), 2.15-2.06 (m, 1H), 1.48 (s, 3H), 1.43 (s, 6H), 0.89-0.83 (m, 9H), 0.08-0.03 (m, 6H).).

Step B: 1-(tert-butyl) 2-methyl (2S,4S)-4-((tert-butyldimethylsilyl)oxy)-5-oxopyrrolidine-1,2-dicarboxylate

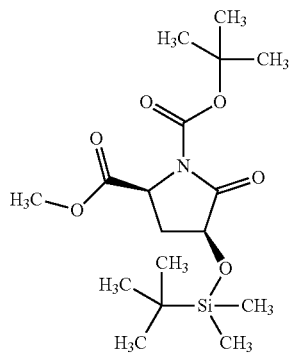 [SMILES: COC(=O)[C@@H]1C[C@H](O[Si](C)(C)C(C)(C)C)C(=O)N1C(=O)OC(C)(C)C]

A solution of sodium periodate (7.08 g, 33.1 mmol) in water (126 mL) was treated with ruthenium(IV) oxide hydrate (0.400 g, 2.65 mmol) and stirred at rt for 5 min. This mixture was then treated with a solution of (2S,4S)-1-tert-butyl 2-methyl 4-((tert-butyldimethylsilyl)oxy)pyrrolidine-1,2-dicarboxylate (4.76 g, 13.24 mmol) in EtOAc (63 mL) and stirred at rt. After 6 h, the mixture was diluted with EtOAc, filtered through Celite, and the solids were washed with water and EtOAc. The combined filtrates were partitioned between water and EtOAc. The organic phase was washed sequentially with saturated aqueous NaHCO₃, 10% aqueous Na₂S₂O₃ and brine, dried over Na₂SO₄, filtered and concentrated to afford 1-(tert-butyl) 2-methyl (2S,4S)-4-((tert-butyldimethylsilyl)oxy)-5-oxopyrrolidine-1,2-dicarboxylate as a colorless syrup (4.85 g, 98% yield). LCMS m/z 396.2 (M+Na)⁺, HPLC $t_R$ 1.08 min (method B). ¹H NMR (400 MHz, CDCl₃) δ 4.47 (dd, J=7.8, 6.9 Hz, 1H), 4.29 (t, J=7.3 Hz, 1H), 3.77 (s, 3H), 2.57 (dt, J=13.0, 7.7 Hz, 1H), 2.00 (dt, J=13.0, 7.0 Hz, 1H), 1.51 (s, 9H), 0.89 (s, 9H), 0.17 (s, 3H), 0.13 (s, 3H).

Step C: Methyl (2S,4S)-4-hydroxy-5-oxopyrrolidine-2-carboxylate

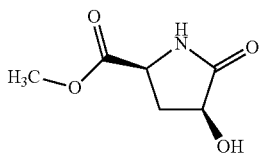

A solution of (2S,4S)-1-tert-butyl 2-methyl 4-((tert-butyldimethylsilyl)oxy)-5-oxopyrrolidine-1,2-dicarboxylate (4.85 g, 12.98 mmol) in DCM (16 mL) was cooled in an ice-water bath and treated with TFA (3 mL). The mixture was warmed to rt, stirred for 2 h, and concentrated to provide methyl (2S,4S)-4-hydroxy-5-oxopyrrolidine-2-carboxylate as a yellow syrup in quantitative yield. LCMS m/z 159.9 (M+H)$^+$, HPLC $t_R$ 0.38 min (method B). $^1$H NMR (400 MHz, CDCl$_3$) δ 7.25-6.70 (m, 1H), 4.47-4.36 (m, 2H), 4.26-4.16 (m, 1H), 3.81 (d, J=10.1 Hz, 3H), 2.96-2.70 (m, 1H), 2.21-2.08 (m, 1H).

Step D: (2S,4S)-4-hydroxy-1-(methyl-d$_3$)-5-oxopyrrolidine-2-carboxylic Acid

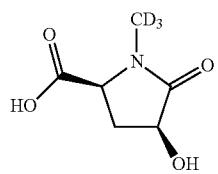 [SMILES: [2H]C([2H])([2H])N1C(=O)[C@@H](O)C[C@H]1C(=O)O]

Following the procedures used in Steps D and E of the preparation of Intermediate 137, methyl (2S,4S)-4-hydroxy-5-oxopyrrolidine-2-carboxylate was converted into (2S,4S)-4-hydroxy-1-(methyl-d$_3$)-5-oxopyrrolidine-2-carboxylic acid. LCMS m/z 163.0 (M+H)$^+$, HPLC $t_R$ 0.31 min (method B).

Intermediate 140

(2S,4S)-4-hydroxy-1-methyl-5-oxopyrrolidine-2-carboxylic Acid

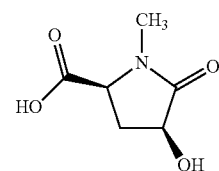

(2S,4S)-4-hydroxy-1-methyl-5-oxopyrrolidine-2-carboxylic acid was prepared using the procedures of Intermediate 139, substituting iodomethane for iodomethane-d$_3$. LCMS m/z 160.0 (M+H)$^+$, HPLC $t_R$ 0.26 min (method B).

The Intermediates in Table 8 were prepared using the same methods or similar methods used to prepare Intermediates 137 through 140.

TABLE 8

| Intermediate number | Structure | LCMS m/z observed | HPLC $t_R$ (min) | HPLC method |
|---|---|---|---|---|
| 141 | 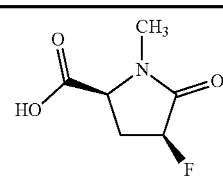 | 162.0 (M + H)$^+$ | 0.39 | B |
| 142 | 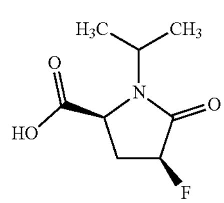 | 190.1 (M + H)$^+$ | 0.48 | B |
| 143 | 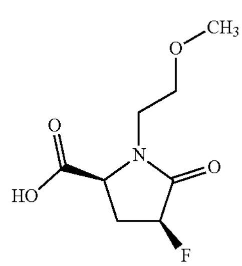 | 206.0 (M + H)$^+$ | 0.43 | B |

TABLE 8-continued

| Intermediate number | Structure | LCMS m/z observed | HPLC $t_R$ (min) | HPLC method |
|---|---|---|---|---|
| 144 | 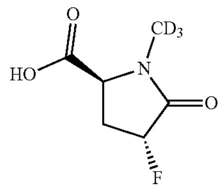 [SMILES: [2H]C([2H])([2H])N1C(=O)[C@H](F)C[C@H]1C(=O)O] | 164.9 (M + H)⁺ | 0.30 | B |
| 145 | 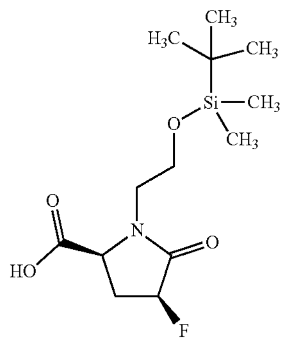 [SMILES: CC(C)(C)[Si](C)(C)OCCN1C(=O)[C@@H](F)C[C@H]1C(=O)O] | 306.0 (M + H)⁺ | 0.90 | B |
| 146 | 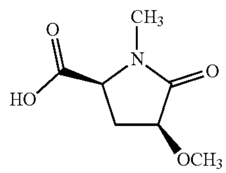 | 174.1 (M + H)⁺ | 0.38 | B |

Intermediates 147 and 148

Cis Methyl 3-methylpiperidine-4-carboxylate

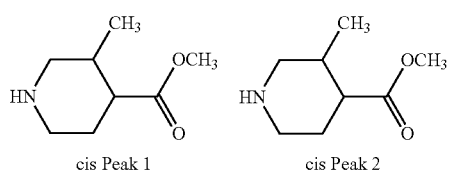

A solution of methyl 3-methylisonicotinate hydrochloride (2.63 g, 14 mmol) in acetic acid (25 mL) was treated with platinum(IV) oxide (0.20 g, 0.881 mmol) and stirred under a hydrogen atmosphere (50 psi) for 15 h. The catalyst was removed by filtration and the filtrate was concentrated. The residue was treated with 5% aqueous $K_2CO_3$ and extracted with DCM. The organic phase was dried and concentrated to give cis methyl 3-methylpiperidine-4-carboxylate, containing about 15% of the trans isomer, as an amber oil (1.4 g). The material was separated by chiral SFC using the following conditions: Column: Chiralpak® AD-H 50×250 mm, 5 m (Chiral Technologies Inc.); column temperature 35° C.; pressure 100 bars; mobile phase $CO_2$-MeOH (85:15) containing 0.1% $NH_4OH$; flow rate 250 mL/min; injection volume 1.5 mL. Peak 1 was eluted with $t_R$ 5.5 min. Peak 2 was eluted with $t_R$ 7.5 min. ¹H NMR (400 MHz, $CDCl_3$) δ 3.66 (s, 3H), 3.07 (dt, J=12.5, 4.3 Hz, 1H), 2.91-2.72 (m, 2H), 2.67-2.51 (m, 2H), 2.10 (ddd, J=10.9, 7.3, 3.7 Hz, 1H), 1.79 (dtd, J=13.9, 10.3, 4.1 Hz, 1H), 1.68-1.54 (m, 1H), 1.43 (br. s., 1H), 0.94 (d, J=7.0 Hz, 3H).

Intermediates 149 and 150

Trans Methyl 3-methylpiperidine-4-carboxylate

Anhydrous MeOH (25 mL) was treated portionwise with sodium (2.047 g, 89 mmol) and the mixture stirred until the metal was completely dissolved. This solution was treated with crude methyl 3-methylpiperidine-4-carboxylate (cis-trans mixture, about 85:15, prepared according to the procedure of Intermediates 147 and 148; 1.4 g, 8.91 mmol) and the solution was heated at reflux for 60 h. The solution was cooled to rt, neutralized with acetic acid and concentrated. The residue was treated with 2 M aqueous $K_2C_3$ (100 mL) and extracted with DCM (3×75 mL). The combined organic phases were dried over $Na_2SO_4$ and concentrated give methyl 3-methylpiperidine-4-carboxylate (cis-trans mixture, about 10:90) as a pale amber oil. LCMS m/z 157.9 (M+H)⁺, HPLC $t_R$ 0.44 min (method B). This material was separated by chiral SFC using the following conditions: Column: Lux® Cellulose-4 30×250 mm, 5 m (Phenomenex Inc.);

column temperature 35° C.; pressure 100 bars; mobile phase $CO_2$-MeOH (80:20); flow rate 180 mL/min; injection 85 mg in 1 mL. Two enantiomers of trans methyl 3-methylpiperidine-4-carboxylate were obtained, both contaminated with cis methyl 3-methylpiperidine-4-carboxylate (about 9%). Peak 1 (colorless oil, 250 mg): $^1$H NMR (400 MHz, MeOH-$d_4$) δ 3.69 (s, 3H), 3.05 (dt, J=12.7, 2.8 Hz, 1H), 2.98 (dd, J=12.8, 4.0 Hz, 1H), 2.56 (td, J=12.7, 2.9 Hz, 1H), 2.23 (dd, J=12.3, 11.4 Hz, 1H), 2.13 (ddd, J=12.1, 11.0, 3.7 Hz, 1H), 1.88-1.72 (m, 2H), 1.70-1.53 (m, 1H), 0.86 (d, J=6.6 Hz, 3H). Peak 2 (colorless oil, 350 mg): $^1$H NMR (400 MHz, $CDCl_3$) δ 3.66 (s, 3H), 3.07 (dt, J=12.5, 2.9 Hz, 1H), 3.00 (dd, J=12.5, 4.0 Hz, 1H), 2.55 (td, J=12.4, 2.9 Hz, 1H), 2.22 (dd, J=12.4, 11.1 Hz, 1H), 2.06 (ddd, J=11.9, 10.9, 3.7 Hz, 1H), 1.85-1.67 (m, 2H), 1.66-1.48 (m, 2H), 0.81 (d, J=6.4 Hz, 3H).

Example 1

(1R,4r)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylic Acid

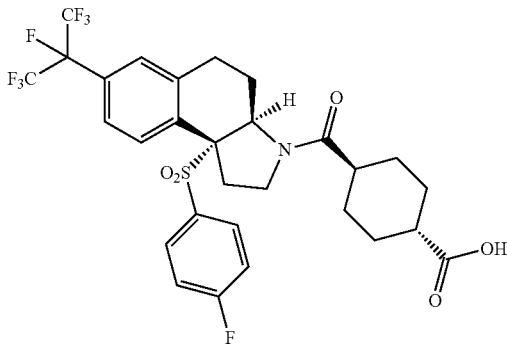 [SMILES: O=C(O)[C@H]1CC[C@H](C(=O)N2CC[C@@]3(S(=O)(=O)c4ccc(F)cc4)c4ccc(C(F)(C(F)(F)F)C(F)(F)F)cc4CC[C@@H]23)CC1]

Step A: methyl (1R,4r)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylate

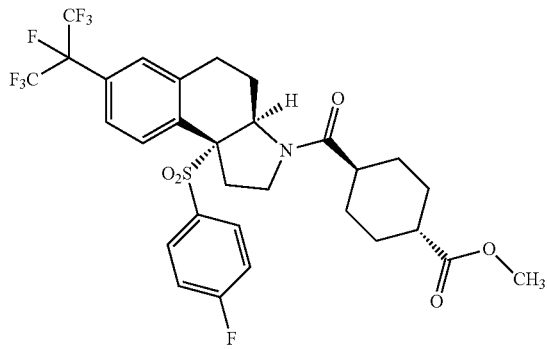 [SMILES: COC(=O)[C@H]1CC[C@H](C(=O)N2CC[C@@]3(S(=O)(=O)c4ccc(F)cc4)c4ccc(C(F)(C(F)(F)F)C(F)(F)F)cc4CC[C@@H]23)CC1]

A solution of ((3aR,9bR)-9b-((4-fluorophenyl)sulfonyl)-7-(perfluoropropan-2-yl)-2,3,3a,4,5,9b-hexahydro-1H-benzo[e]indole hydrochloride (Intermediate 32; 223 mg, 0.417 mmol), trans-4-(methoxycarbonyl)cyclohexanecarboxylic acid (0.140 g, 0.752 mmol) and DIPEA (0.358 mL, 2.052 mmol) in THF (4.2 mL) was treated with HATU (174 mg, 0.459 mmol). The mixture was stirred at rt for 2 h. Celite and EtOAc were added, and the mixture was concentrated to a dry powder, which was used to purify the material by column chromatography on silica gel, eluting with EtOAc-hexanes (gradient from 0-50%), to provide methyl (1R,4r)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylate (246 mg, 88% yield). LCMS m/z 668.1 (M+H)$^+$, HPLC $t_R$ 1.13 min (method B).

Step B: (1R,4r)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylic Acid

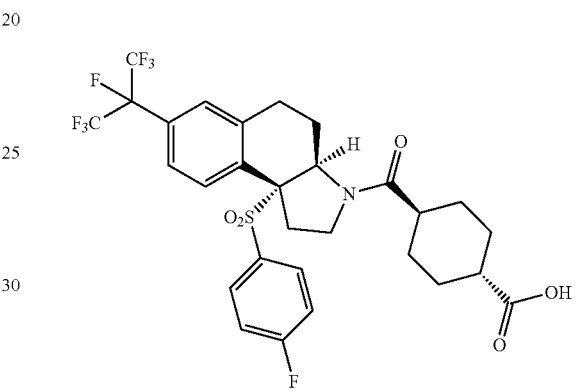

A solution of methyl (1R,4r)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylate (246 mg, 0.368 mmol) in THF (2.5 mL) was treated with a solution of LiOH hydrate (35 mg, 1.474 mmol) in water (1.3 mL). The mixture was stirred for 3 h at rt, when LCMS showed partial conversion of the starting material. Additional LiOH hydrate (13 mg, 0.553 mmol) was added and the mixture was stirred for 2 h more. The mixture was treated with 1 M aqueous HCl and washed with EtOAc (3×20 mL). The combined organic layers were dried over $Na_2SO_4$, filtered and concentrated to provide the crude product (250 mg). The material was further purified by chiral SFC (column: Lux® Cellulose-4 4.6×250 mm 5 m (Phenomenex Inc.); mobile phase: $CO_2$/MeOH (75:25); 35° C., 100 bar) to afford (1R,4r)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylic acid (140 mg, 58% yield). LCMS m/z 654.2 (M+H)$^+$, HPLC $t_R$ 1.06 min (method B). $^1$H NMR (400 MHz, DMSO-$d_6$) δ 12.13 (br. s., 1H), 7.95-7.78 (m, 1H), 7.69-7.57 (m, 1H), 7.42-7.32 (m, 2H), 7.32-7.22 (m, 2H), 7.22-7.03 (m, 1H), 4.66 (dd, J=11.8, 5.0 Hz, 1H), 3.79-3.64 (m, 2H), 3.38 (ddd, J=14.4, 7.4, 3.7 Hz, 1H), 2.77-2.59 (m, 2H), 2.37-2.24 (m, 3H), 2.14 (d, J=13.0 Hz, 1H), 2.02-1.81 (m, 3H), 1.69 (d, J=3.7 Hz, 2H), 1.46-1.24 (m, 4H). $^{19}$F NMR (376 MHz, DMSO-$d_6$) δ -104.9 (s, 1F), -77.3 (m, 1F), -77.0 (s, 6F).

Example 2

(1r,4r)-4-(10b-((4-fluorophenyl)sulfonyl)-8-(perfluoropropan-2-yl)-1,2,3,4,4a,5,6,10b-octahydrobenzo[f]quinoline-4-carbonyl)cyclohexane-1-carboxylic Acid (Homochiral)

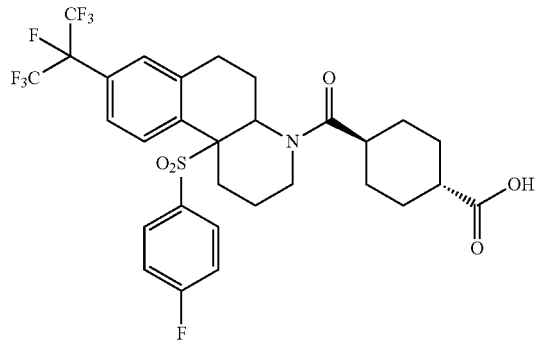

Homochiral from peak 2

A solution of trans-1,4-cyclohexanedicarboxylic acid monomethyl ester in DCM was treated with excess oxalyl chloride and catalytic DMF, and the mixture was stirred at rt for 1 h. The mixture was concentrated to provide (1r,4r)-methyl 4-(chlorocarbonyl)cyclohexanecarboxylate, which was used without further purification.

A solution of 10b-((4-fluorophenyl)sulfonyl)-8-(perfluoropropan-2-yl)-1,2,3,4,4a,5,6,10b-octahydrobenzo[f]quinoline (homochiral, from peak 2, Intermediate 61; 40 mg, 0.078 mmol), pyridine (0.5 mL) and DCM (1.5 mL) was cooled in an ice-water bath and treated with 4-dimethylaminopyridine (9.52 mg, 0.078 mmol), then was treated dropwise with a solution of crude (1r,4r)-methyl 4-(chlorocarbonyl)cyclohexanecarboxylate (47.8 mg, 0.234 mmol) in DCM (1 mL). The ice bath was removed and the mixture was stirred at rt overnight. The mixture was diluted with DCM (20 mL), washed sequentially with 1 M aqueous HCl, 1.5 M aqueous $K_2HPO_4$ and brine, dried over $Na_2SO_4$ and concentrated. The residue was dissolved in THF (2 mL) and MeOH (1 mL) and treated with a solution of lithium hydroxide monohydrate (65.4 mg, 1.558 mmol) in water (1 mL). The mixture was stirred at rt for 2.5 h, then was diluted with EtOAc (25 mL) and 1 M aqueous HCl (10 mL). The organic phase was separated, washed with brine, dried over $Na_2SO_4$ and concentrated. The residue was purified by preparative HPLC (method E, gradient 30-80% B, 25 min) to give homochiral (1r,4r)-4-(10b-((4-fluorophenyl)sulfonyl)-8-(perfluoropropan-2-yl)-1,2,3,4,4a,5,6,10b-octahydrobenzo[f]quinoline-4-carbonyl)cyclohexane-1-carboxylic acid (14 mg, 26% yield). LCMS m/z 668.1 (M+H)$^+$, HPLC $t_R$ 2.29 min (method C).

Examples 3 and 4

(1S,4s)-4-fluoro-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylic Acid and (1S,4s)-1-fluoro-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylic Acid

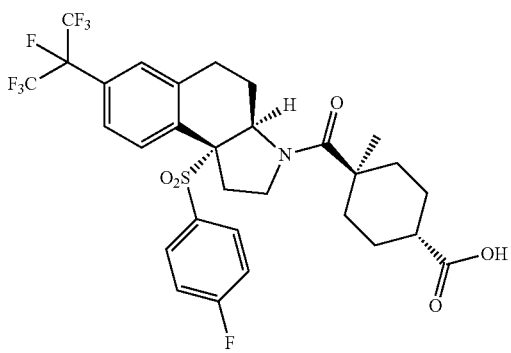 [SMILES: O=C(O)[C@H]1CC[C@H](C(=O)N2CC[C@@]3(S(=O)(=O)c4ccc(F)cc4)c4ccc(C(F)(C(F)(F)F)C(F)(F)F)cc4CC[C@@H]23)CC1]

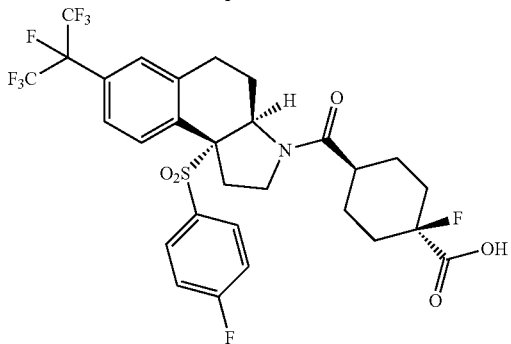

A solution of (3aR,9bR)-9b-((4-fluorophenyl)sulfonyl)-7-(perfluoropropan-2-yl)-2,3,3a,4,5,9b-hexahydro-1H-benzo[e]indole hydrochloride (Intermediate 32; 100 mg, 0.187 mmol) in DMF (2 mL) was treated with a mixture of (1s,4s)-4-(tert-butoxycarbonyl)-1-fluorocyclohexane-1-carboxylic acid and (1s,4s)-4-(tert-butoxycarbonyl)-4-fluorocyclohexane-1-carboxylic acid (Intermediate 119; 92 mg, 0.373 mmol). PyBOP (146 mg, 0.280 mmol) and $Et_3N$ (0.156 mL, 1.120 mmol) were added and the mixture was stirred at rt. When LCMS indicated that the reaction was complete, the mixture was concentrated and the residue was dissolved in DCM (1 mL) and treated with TFA (1 mL). After standing at rt for 1 h, the mixture was concentrated and the residue was purified by preparative HPLC (method E, gradient 20-75% B, 25 min). The major product isolated was (1S,4s)-4-fluoro-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylic acid (32.7 mg, 26% yield). LCMS m/z 672.2 (M+H)$^+$, HPLC $t_R$ 1.93 min (method C). $^1$H NMR (500 MHz, DMSO-$d_6$) δ 7.86 (d, J=8.3 Hz, 1H), 7.62 (d, J=8.3 Hz, 1H), 7.42-7.18 (m, 5H), 4.98-4.85 (m, 0.25H), 4.78 (dd, J=11.9, 4.8 Hz, 0.75H), 4.03-2.59 (m, 5H), 2.44-1.16 (m, 13H), suggesting a 3:1 mixture of amide bond rotamers.

A second product isolated was (1S,4s)-1-fluoro-4-((3aR,9bR)-9b-((4-fluorophenyl)sulfonyl)-7-(perfluoropropan-2- yl)-2,3,3a,4,5,9b-hexahydro-1H-benzo[e]indole-3-carbonyl)cyclohexane-1-carboxylic acid (6 mg, 5% yield). LCMS m/z 671.9 (M+H)+, HPLC t$_R$ 1.73 min (method C). $^1$H NMR (500 MHz, DMSO-d$_6$) δ 7.87 (d, J=8.4 Hz, 1H), 7.63 (d, J=8.3 Hz, 1H), 7.44-7.34 (m, 2H), 7.33 (s, 1H), 7.25 (t, J=8.4 Hz, 2H), 4.65 (dd, J=11.6, 4.7 Hz, 1H), 3.82-2.59 (m, 7H), 2.41-1.13 (m, 11H).

Example 5

(1R,4r)-1-ethyl-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylic Acid

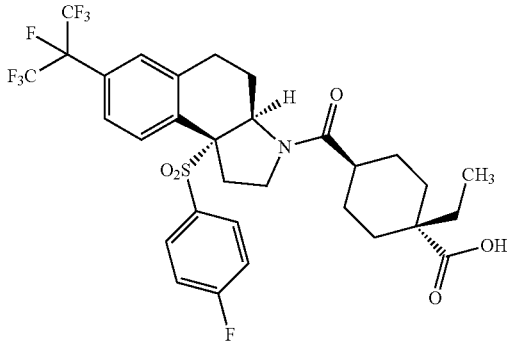 [SMILES: CC[C@]1(C(=O)O)CC[C@H](C(=O)N2CC[C@@]3(S(=O)(=O)c4ccc(F)cc4)c4ccc(C(F)(C(F)(F)F)C(F)(F)F)cc4CC[C@@H]23)CC1]

A solution of ((3aR,9bR)-9b-((4-fluorophenyl)sulfonyl)-7-(perfluoropropan-2-yl)-2,3,3a,4,5,9b-hexahydro-1H-benzo[e]indole (Intermediate 32; 30 mg, 0.060 mmol) in DMF (0.8 mL) was treated with (1r,4r)-1-ethylcyclohexane-1,4-dicarboxylic acid (Intermediate 121; 24.06 mg, 0.120 mmol), DIPEA (31.5 µL, 0.180 mmol) and HATU (34.3 mg, 0.090 mmol). The mixture was stirred at rt for 1 h, then was purified by preparative HPLC (method E, gradient 40-80% B) to provide (1R,4r)-1-ethyl-4-((3 aR,9bR)-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylic acid (10 mg, 24% yield). LCMS m/z 682.4 (M+H)+, HPLC t$_R$ 2.28 min (method C). $^1$H NMR (500 MHz, DMSO-d$_6$) δ 7.88 (d, J=8.4 Hz, 1H), 7.64 (d, J=8.2 Hz, 1H), 7.44-7.34 (m, 3H), 7.33-7.18 (m, 2H), 4.66 (dd, J=11.7, 4.7 Hz, 1H), 3.82-3.18 (m, 3H), 2.84-2.59 (m, 2H), 2.31 (br. s., 2H), 2.20-1.34 (m, 10H), 1.32-1.10 (m, 2H), 0.87-0.59 (m, 3H).

Example 6

((3aR,9bR)-9b-((4-fluorophenyl)sulfonyl)-7-(perfluoropropan-2-yl)-1,2,3a,4,5,9b-hexahydro-3H-benzo[e]indol-3-yl)(piperidin-4-yl)methanone

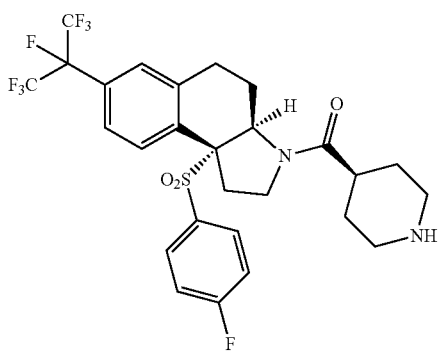

A mixture of (3aR,9bR)-9b-((4-fluorophenyl)sulfonyl)-7-(perfluoropropan-2-yl)-2,3,3a,4,5,9b-hexahydro-1H-benzo[e]indole (Intermediate 32; 120 mg, 0.240 mmol), 1-(tert-butoxycarbonyl)piperidine-4-carboxylic acid (66.1 mg, 0.288 mmol) and N-methylmorpholine (0.079 mL, 0.721 mmol) in DMF (2 mL) was treated with HATU (110 mg, 0.288 mmol). The mixture was stirred overnight at rt, then was diluted with EtOAc and washed sequentially with 10% aqueous LiCl (twice) and brine. The combined aqueous phases were extracted with EtOAc, and the combined organic phases were dried over MgSO$_4$ and concentrated. The residue was purified by column chromatography on silica gel (12 g), eluting with EtOAc-hexanes (gradient from 0-80%), to provide crude tert-butyl 4-((3 aR,9bR)-9b-((4-fluorophenyl)sulfonyl)-7-(perfluoropropan-2-yl)-2,3,3a,4,5,9b-hexahydro-1H-benzo[e]indole-3-carbonyl)piperidine-1-carboxylate. This material was dissolved in TFA (1 mL). After 1 h the mixture was concentrated, and the residue was dissolved in EtOAc and washed sequentially with 1.5 M aqueous K$_2$HPO$_4$ and brine. The combined aqueous phases were extracted with EtOAc, and the combined organic phases were dried over Na$_2$SO$_4$ and concentrated to provide a tan solid (138 mg, 94% yield). A portion of this material (16 mg) was further purified by preparative HPLC (method E, gradient 30-70% B, 20 min) to provide ((3aR,9bR)-9b-((4-fluorophenyl)sulfonyl)-7-(perfluoropropan-2-yl)-1,2,3a,4,5,9b-hexahydro-3H-benzo[e]indol-3-yl)(piperidin-4-yl)methanone (14.8 mg, 92% yield). LCMS m/z 611.1 (M+H)+, HPLC t$_R$ 1.82 min (method C).

Example 7

4-((3a-((4-fluorophenyl)sulfonyl)-6-(perfluoropropan-2-yl)-3,3a,8,8a-tetrahydroindeno[2,1-b]pyrrol-1(2H)-yl)sulfonyl)benzoic Acid

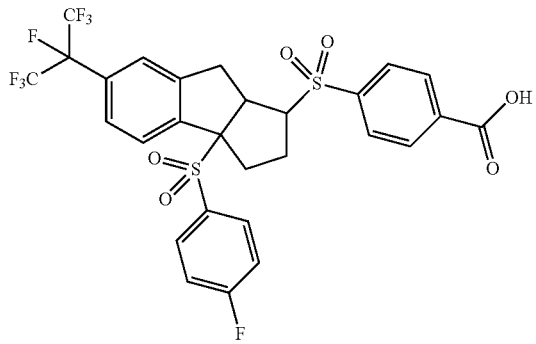

Homochiral from peak 1

A solution of 3a-((4-fluorophenyl)sulfonyl)-6-(perfluoropropan-2-yl)-1,2,3,3a,8,8a-hexahydroindeno[2,1-b]pyrrole hydrochloride (homochiral, from peak 1, Intermediate 94; 30 mg, 0.057 mmol) and methyl 4-(chlorosulfonyl)benzoate (20.23 mg, 0.086 mmol) in DMF (0.5 mL) was treated with Et$_3$N (0.024 mL, 0.172 mmol) and stirred at rt. After 18 h, the mixture was diluted with EtOAc, washed sequentially with water, 5% aqueous LiCl and brine, and concentrated. The residue was dissolved in THF (2.5 mL) and ethanol (1.25 mL), treated with a solution of LiOH monohydrate (72.4 mg, 1.725 mmol) in water (1.25 mL), and stirred vigorously at rt. After 16.25 h, the mixture was treated slowly with HCl (4 M in 1,4-dioxane, 0.75 mL) and concentrated. The residue was purified by preparative HPLC (method E, gradient 30-70% B, 23 min), followed by re-purification by HPLC (method F, gradient 45-90% B, 20 min) to provide homochiral 4-((3a-((4-fluorophenyl)sulfonyl)-6-(perfluoropropan-2-yl)-3,3a, 8,8a-tetrahydroindeno[2,1-b]pyrrol-1(2H)-yl)sulfonyl)benzoic acid (16.6 mg, 45% yield). LCMS m/z 670.2 (M+H)+, HPLC $t_R$ 1.85 min (method C). ¹H NMR (500 MHz, DMSO-$d_6$) δ 8.15 (d, J=8.1 Hz, 2H), 7.97 (d, J=8.2 Hz, 2H), 7.65 (q, J=8.2 Hz, 2H), 7.60 (s, 1H), 7.57 (dd, J=8.3, 5.0 Hz, 2H), 7.26 (t, J=8.5 Hz, 2H), 4.51 (d, J=6.1 Hz, 1H), 3.27 (d, J=18.2 Hz, 1H), 3.09-2.87 (m, 2H), 2.44 (d, J=12.8 Hz, 1H), 2.24-2.13 (m, 1H), one proton obscured by solvent peaks.

The Examples in Table 9 were prepared using procedures used to prepare Examples 1 through 7 or similar procedures, by reacting an appropriate amine intermediate with an appropriate acid, acid chloride, acid anhydride, sulfonyl chloride or sulfamyl chloride, followed by ester hydrolysis or other functional group deprotection as necessary.

TABLE 9

| Ex. # | Structure | LCMS m/z observed | HPLC $t_R$ (min) | HPLC method |
|---|---|---|---|---|
| 8 | 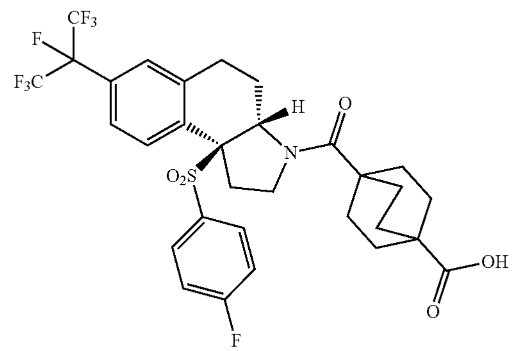 [SMILES: O=C(O)C12CCC(C(=O)N3CC[C@]4(S(=O)(=O)c5ccc(F)cc5)c5ccc(C(F)(C(F)(F)F)C(F)(F)F)cc5CC[C@H]34)(CC1)CC2] | 680.1 (M + H)+ | 1.08 | B |
| 9 | 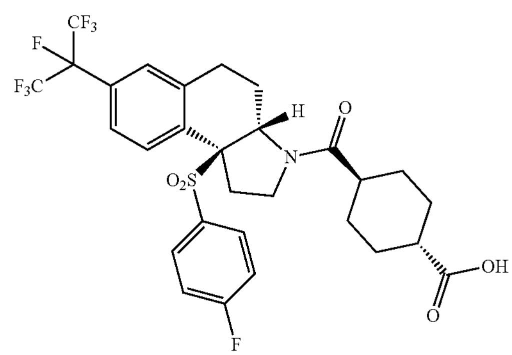 [SMILES: O=C(O)[C@H]1CC[C@H](C(=O)N2CC[C@]3(S(=O)(=O)c4ccc(F)cc4)c4ccc(C(F)(C(F)(F)F)C(F)(F)F)cc4CC[C@H]23)CC1] | 654.2 (M + H)+ | 1.06 | B |
| 10 | 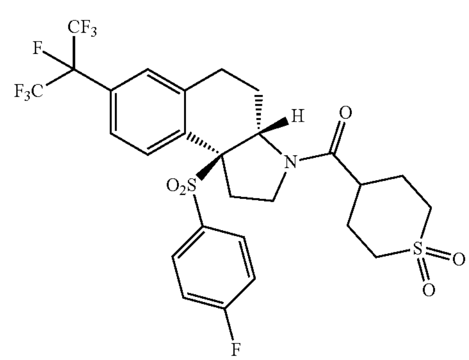 [SMILES: O=C(C1CCS(=O)(=O)CC1)N1CC[C@]2(S(=O)(=O)c3ccc(F)cc3)c3ccc(C(F)(C(F)(F)F)C(F)(F)F)cc3CC[C@H]12] | 660.0 (M + H)+ | 1.04 | B |

TABLE 9-continued

| Ex. # | Structure | LCMS m/z observed | HPLC $t_R$ (min) | HPLC method |
|---|---|---|---|---|
| 11 | 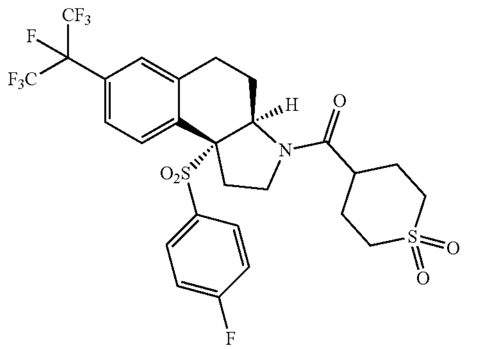 [SMILES: O=C(C1CCS(=O)(=O)CC1)N1CC[C@@]2(S(=O)(=O)c3ccc(F)cc3)c3ccc(C(F)(C(F)(F)F)C(F)(F)F)cc3CC[C@@H]12] | 660.0 (M + H)+ | 1.04 | B |
| 12 | 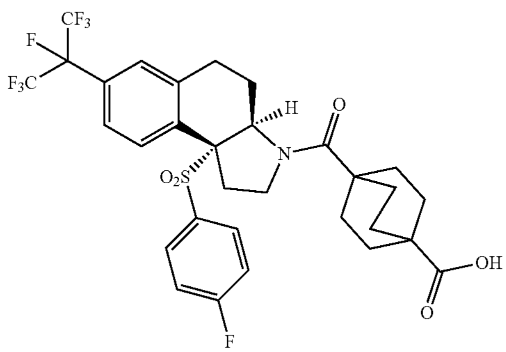 [SMILES: O=C(O)C12CCC(C(=O)N3CC[C@@]4(S(=O)(=O)c5ccc(F)cc5)c5ccc(C(F)(C(F)(F)F)C(F)(F)F)cc5CC[C@@H]34)(CC1)CC2] | 680.1 (M + H)+ | 1.08 | B |
| 13 | 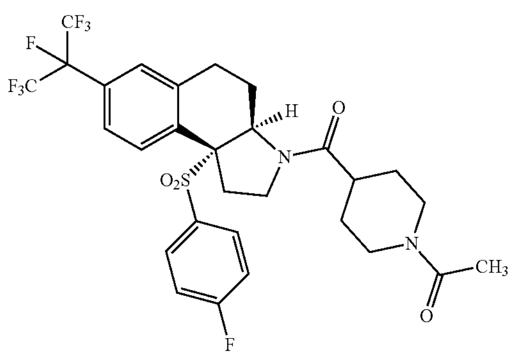 [SMILES: CC(=O)N1CCC(C(=O)N2CC[C@@]3(S(=O)(=O)c4ccc(F)cc4)c4ccc(C(F)(C(F)(F)F)C(F)(F)F)cc4CC[C@@H]23)CC1] | 653.1 (M + H)+ | 1.05 | B |
| 14 | Homochiral From Peak 2 | 670.0 (M + H)+ | 1.08 | B |

TABLE 9-continued
| Ex. # | Structure | LCMS m/z observed | HPLC $t_R$ (min) | HPLC method |
|---|---|---|---|---|
| 15 | 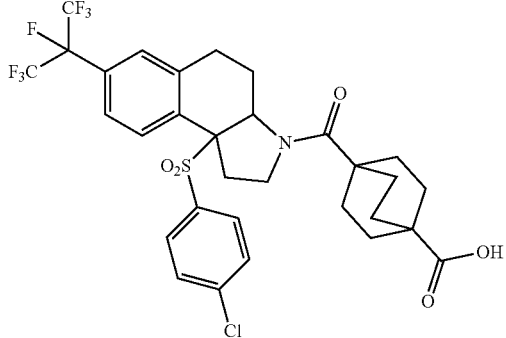 Homochiral from peak 2 | 696.0 (M + H)+ | 1.12 | B |
| 16 | 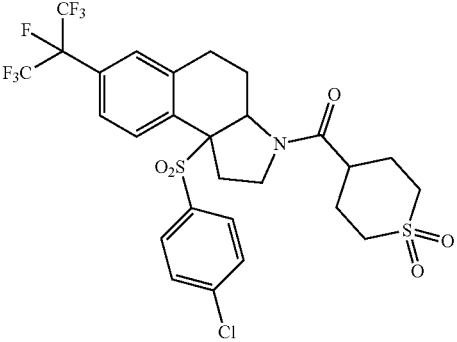 Homochiral from peak 2 | 676.0 (M + H)+ | 1.07 | B |
| 17 | 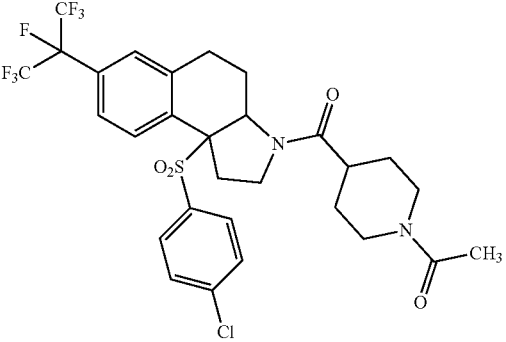 Homochiral from peak 2 | 669.1 (M + H)+ | 1.06 | B |

TABLE 9-continued
| Ex. # | Structure | LCMS m/z observed | HPLC $t_R$ (min) | HPLC method |
|---|---|---|---|---|
| 18 | 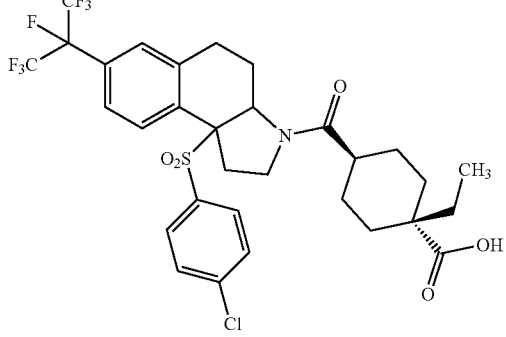<br>Homochiral from peak 2 | 698.1 (M + H)+ | 1.12 | B |
| 19 | 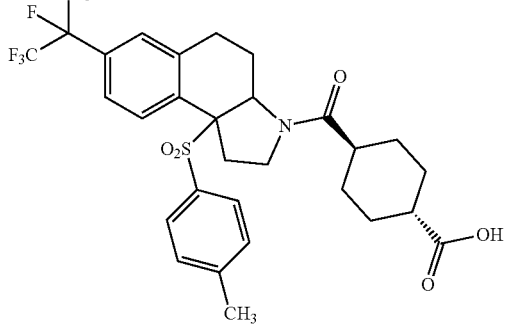<br>Homochiral from peak 2 | 650.1 (M + H)+ | 1.07 | B |
| 20 | 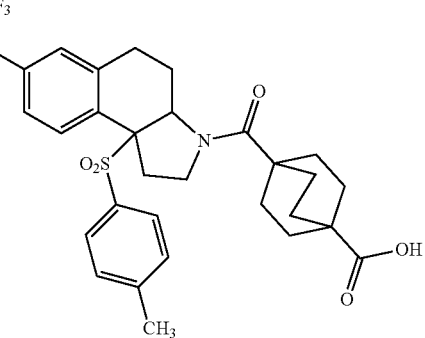<br>Homochiral from peak 2 | 676.1 (M + H)+ | 1.10 | B |

TABLE 9-continued
| Ex. # | Structure | LCMS m/z observed | HPLC $t_R$ (min) | HPLC method |
|---|---|---|---|---|
| 21 | 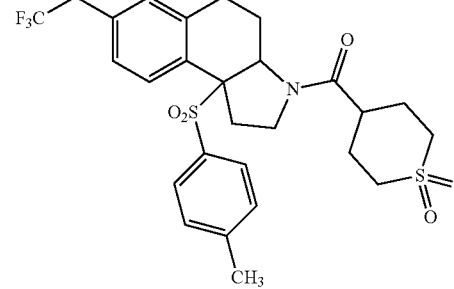<br>Homochiral from peak 2 | 656.1 (M + H)+ | 1.05 | B |
| 22 | <br>Homochiral from peak 2 | 649.2 (M + H)+ | 1.04 | B |
| 23 | <br>Homochiral from peak 2 | 682.2 (M + H)+ | 1.08 | B |

TABLE 9-continued
| Ex. # | Structure | LCMS m/z observed | HPLC $t_R$ (min) | HPLC method |
|---|---|---|---|---|
| 24 | 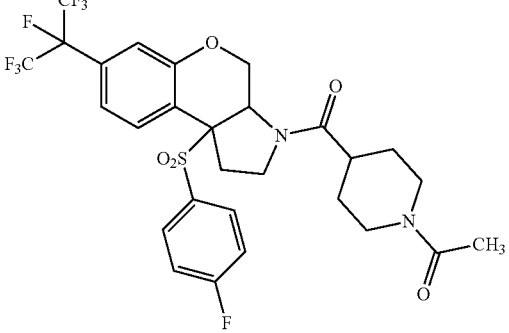 Homochiral from peak 2 | 655.3 (M + H)+ | 1.02 | B |
| 25 | 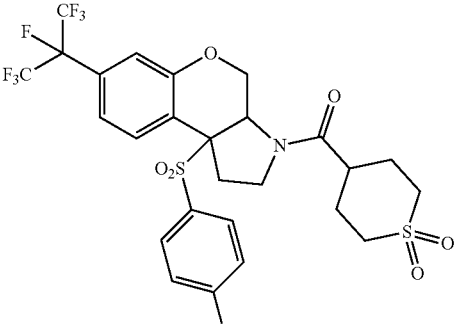 Homochiral from peak 2 | 662.3 (M + H)+ | 1.02 | B |
| 26 | 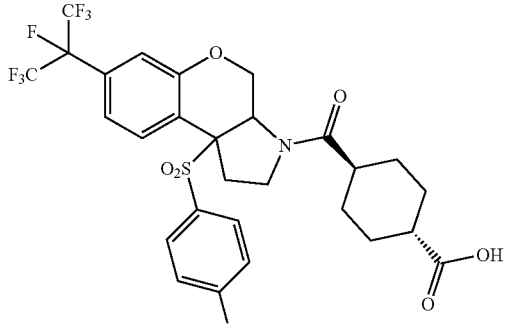 Homochiral from peak 2 | 656.3 (M + H)+ | 1.04 | B |
| 27 | 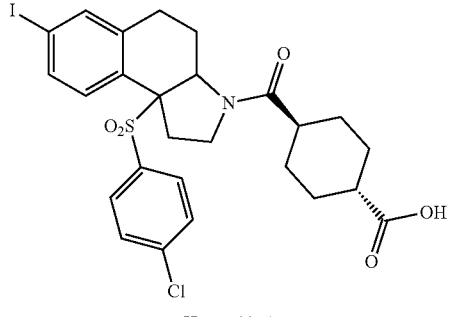 Homochiral from peak 2 | 628.0 (M + H)+ | 1.49 | C |

TABLE 9-continued
| Ex. # | Structure | LCMS m/z observed | HPLC $t_R$ (min) | HPLC method |
|---|---|---|---|---|
| 28 | 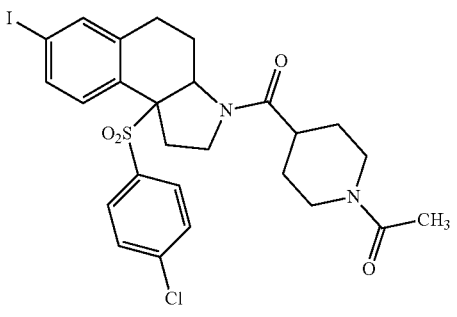<br>Homochiral from peak 2 | 627.0 (M + H)+ | 0.98 | B |
| 29 | 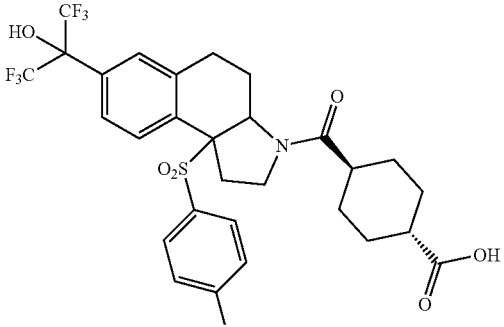<br>Homochiral from peak 2 | 668.3 (M + H)+ | 0.98 | B |
| 30 | 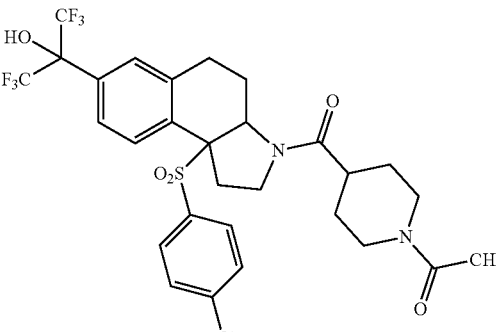<br>Homochiral from peak 2 | 667.3 (M + H)+ | 0.91 | B |

TABLE 9-continued
| Ex. # | Structure | LCMS m/z observed | HPLC $t_R$ (min) | HPLC method |
|---|---|---|---|---|
| 31 | 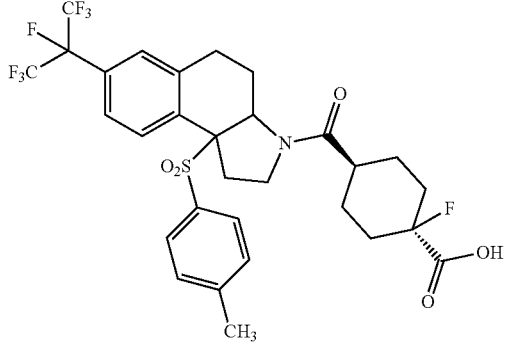<br>Homochiral from peak 2 | 668.2 (M + H)+ | 1.05 | B |
| 32 | 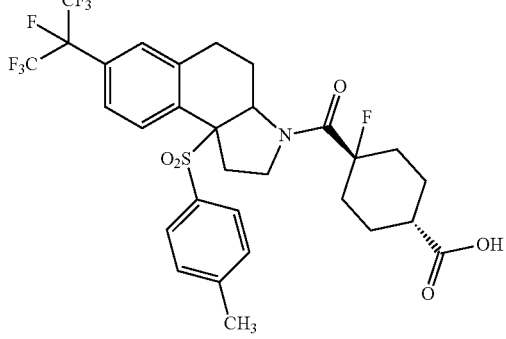<br>Homochiral from peak 2 | 668.2 (M + H)+ | 1.05 | B |
| 33 | 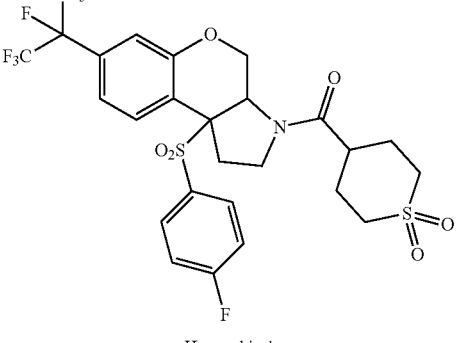<br>Homochiral from peak 2 | 660.0 (M + H)+ | 0.93 | B |
| 34 | 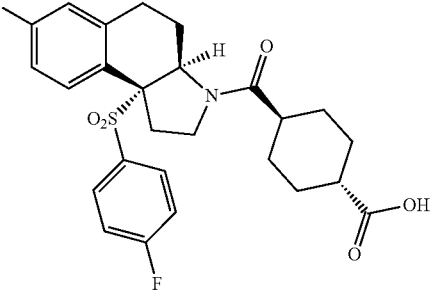 | 612.0 (M + H)+ | 1.00 | B |

TABLE 9-continued
| Ex. # | Structure | LCMS m/z observed | HPLC $t_R$ (min) | HPLC method |
|---|---|---|---|---|
| 35 | 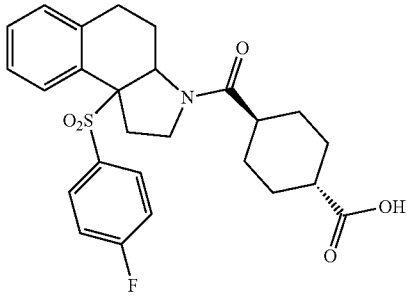 Homochiral from peak 2 | 486.1 (M + H)+ | 0.89 | B |
| 36 | 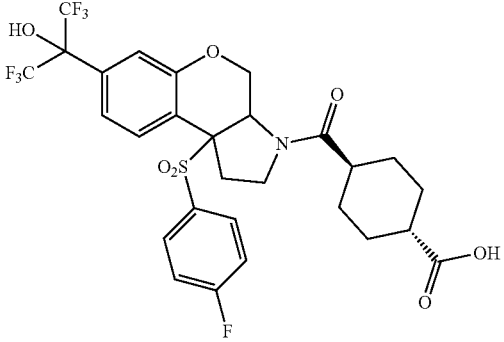 Homochiral from peak 2 | 654.1 (M + H)+ | 0.98 | B |
| 37 | 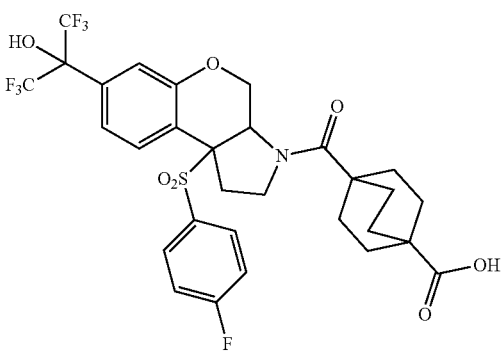 Homochiral from peak 2 | 680.1 (M + H)+ | 1.02 | B |
| 38 | 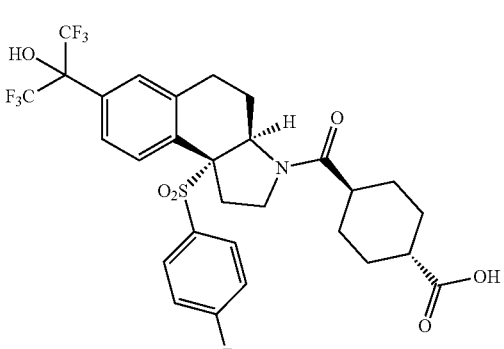 | 652.1 (M + H)+ | 1.06 | B |

TABLE 9-continued
| Ex. # | Structure | LCMS m/z observed | HPLC $t_R$ (min) | HPLC method |
|---|---|---|---|---|
| 39 | 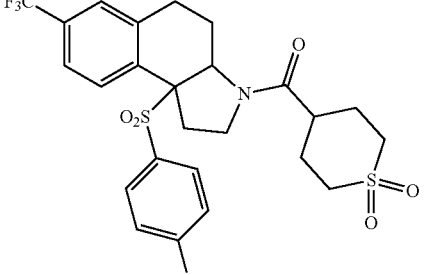 Homochiral from peak 2 | 576.3 (M + H)+ | 0.96 | B |
| 40 | 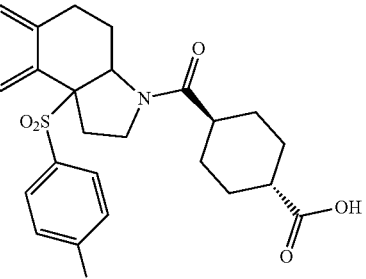 Homochiral from peak 2 | 570.0 (M + H)+ | 1.03 | B |
| 41 | 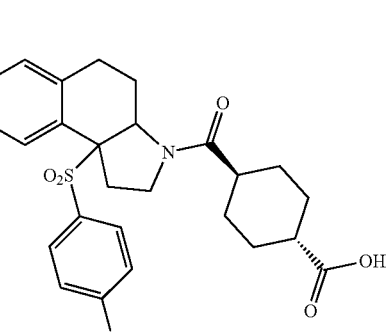 Homochiral from peak 2 | 559.3 (M + H)+ | 0.64 | B |
| 42 | 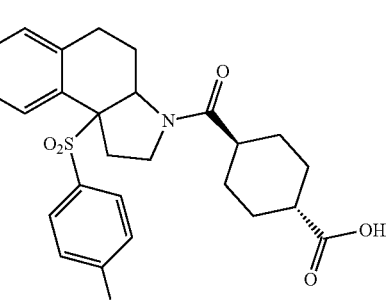 Homochiral from peak 2 | 558.4 (M + H)+ | 1.01 | B |

TABLE 9-continued
| Ex. # | Structure | LCMS m/z observed | HPLC $t_R$ (min) | HPLC method |
|---|---|---|---|---|
| 43 | 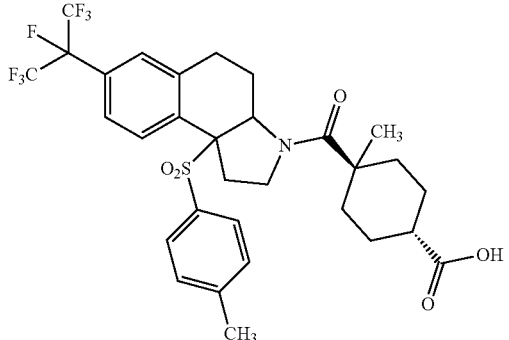 Homochiral from peak 2 | 664.3 (M + H)⁺ | 1.09 | B |
| 44 | 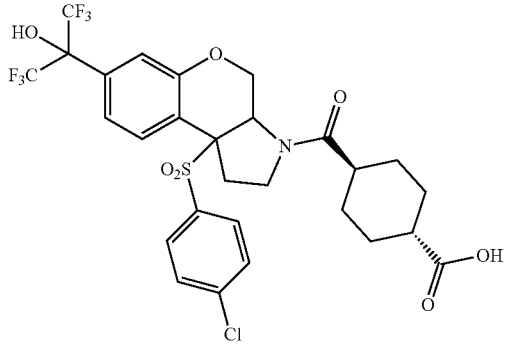 Homochiral from peak 2 | 670.1 (M + H)⁺ | 0.97 | B |
| 45 | 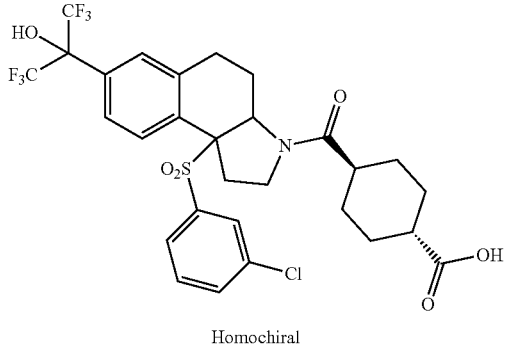 Homochiral from peak 2 | 668.1 (M + H)⁺ | 0.96 | B |

TABLE 9-continued
| Ex. # | Structure | LCMS m/z observed | HPLC $t_R$ (min) | HPLC method |
|---|---|---|---|---|
| 46 | 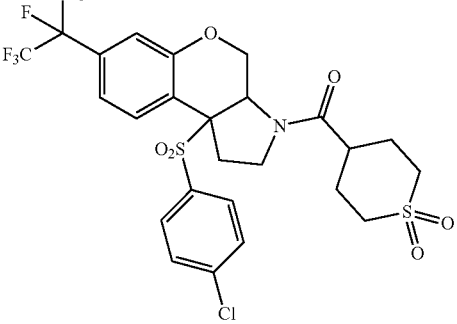<br>Homochiral from peak 2 | 678.0 (M + H)+ | 1.10 | B |
| 47 | 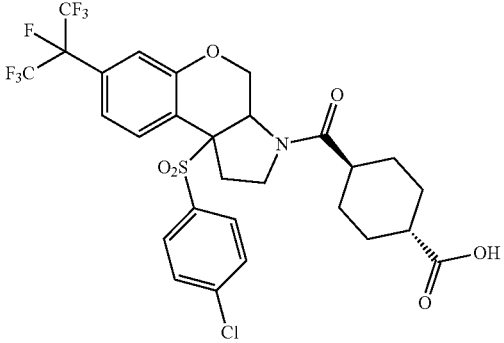<br>Homochiral from peak 2 | 672.1 (M + H)+ | 1.12 | B |
| 48 | 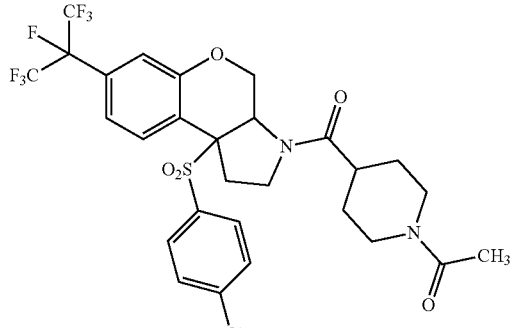<br>Homochiral from peak 2 | 671.2 (M + H)+ | 1.10 | B |
| 49 | 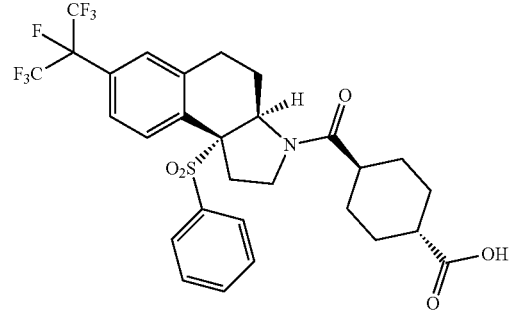 [SMILES: O=C(O)[C@H]1CC[C@H](C(=O)N2CC[C@@]3(S(=O)(=O)c4ccccc4)c4ccc(C(F)(C(F)(F)F)C(F)(F)F)cc4CC[C@@H]23)CC1] | 636.3 (M + H)+ | 1.03 | B |

TABLE 9-continued

| Ex. # | Structure | LCMS m/z observed | HPLC $t_R$ (min) | HPLC method |
|---|---|---|---|---|
| 50 | 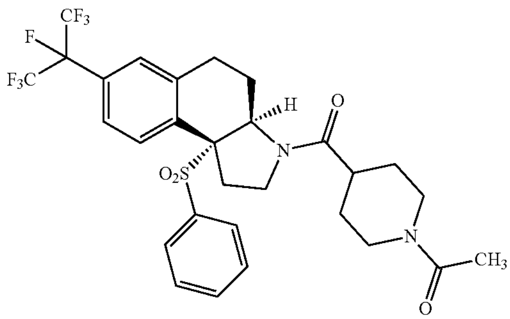 [SMILES: CC(=O)N1CCC(C(=O)N2CC[C@@]3(S(=O)(=O)c4ccccc4)c4ccc(C(F)(C(F)(F)F)C(F)(F)F)cc4CC[C@@H]23)CC1] | 635.3 (M + H)⁺ | 1.00 | B |
| 51 | Homochiral from peak 2 | 652.3 (M + H)⁺ | 1.05 | B |
| 52 | Homochiral from peak 2 | 651.3 (M + H)⁺ | 1.03 | B |
| 53 | Homochiral from peak 2 | 658.3 (M + H)⁺ | 1.04 | B |

TABLE 9-continued

| Ex. # | Structure | LCMS m/z observed | HPLC $t_R$ (min) | HPLC method |
|---|---|---|---|---|
| 54 | 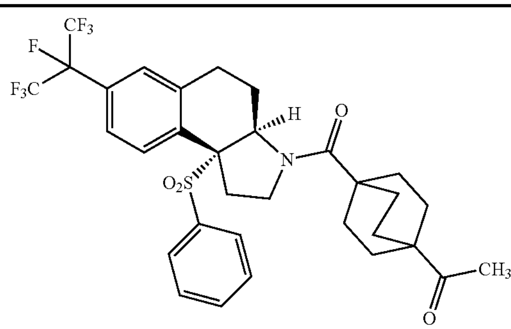 | 662.3 (M + H)+ | 1.06 | B |
| 55 | 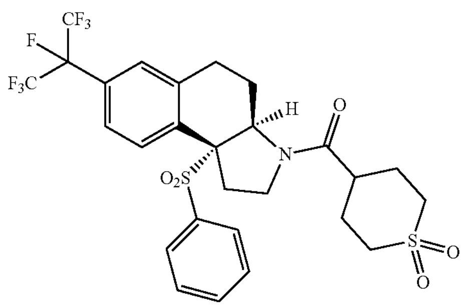 [SMILES: O=C(C1CCS(=O)(=O)CC1)N1CC[C@@]2(S(=O)(=O)c3ccccc3)c3ccc(C(F)(C(F)(F)F)C(F)(F)F)cc3CC[C@@H]12] | 642.3 (M + H)+ | 1.01 | B |
| 56 | 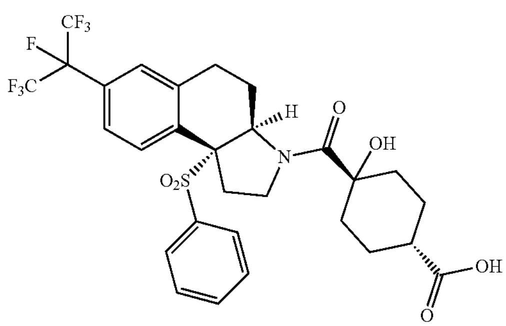 [SMILES: O=C(O)[C@H]1CC[C@](O)(C(=O)N2CC[C@@]3(S(=O)(=O)c4ccccc4)c4ccc(C(F)(C(F)(F)F)C(F)(F)F)cc4CC[C@@H]23)CC1] | 652.3 (M + H)+ | 1.00 | B |
| 57 | 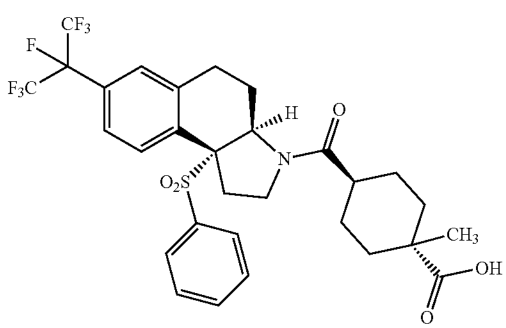 [SMILES: C[C@]1(C(=O)O)CC[C@H](C(=O)N2CC[C@@]3(S(=O)(=O)c4ccccc4)c4ccc(C(F)(C(F)(F)F)C(F)(F)F)cc4CC[C@@H]23)CC1] | 650.3 (M + H)+ | 1.09 | B |
| 58 | 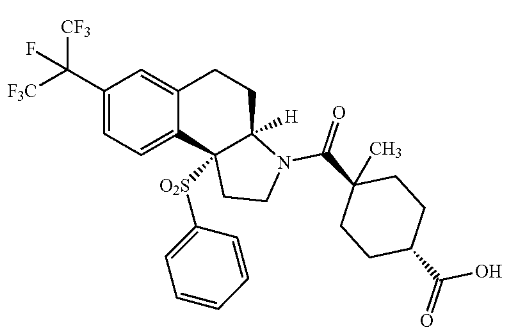 | 650.4 (M + H)+ | 1.06 | B |

TABLE 9-continued
| Ex. # | Structure | LCMS m/z observed | HPLC $t_R$ (min) | HPLC method |
|---|---|---|---|---|
| 59 | 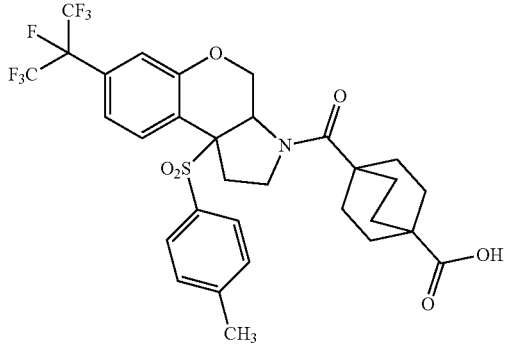<br>Homochiral from peak 2 | 678.3 (M + H)+ | 1.07 | B |
| 60 | 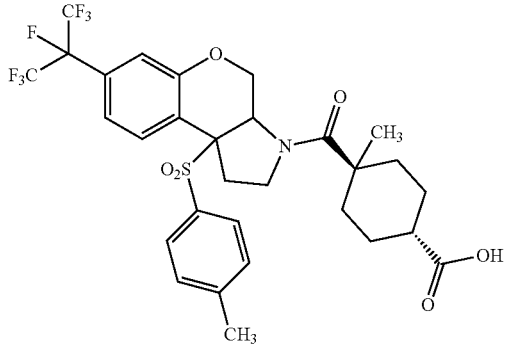<br>Homochiral from peak 2 | 666.1 (M + H)+ | 1.13 | B |
| 61 | 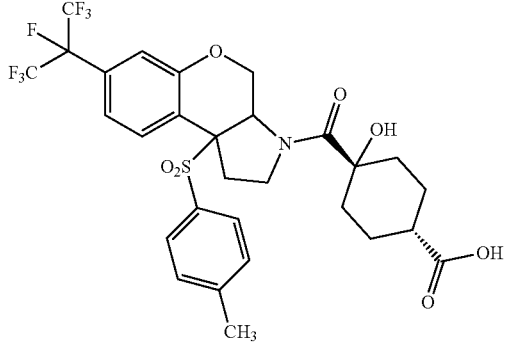<br>Homochiral from peak 2 | 668.3 (M + H)+ | 1.02 | B |

TABLE 9-continued
| Ex. # | Structure | LCMS m/z observed | HPLC $t_R$ (min) | HPLC method |
|---|---|---|---|---|
| 62 | 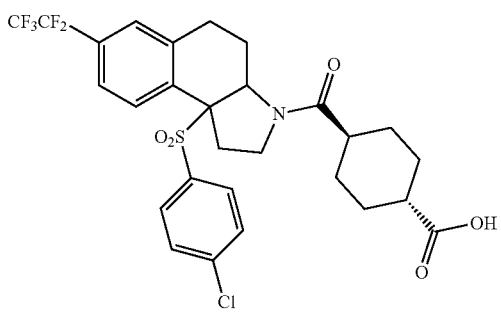 Homochiral from peak 2 | 620.1 (M + H)+ | 1.07 | B |
| 63 | 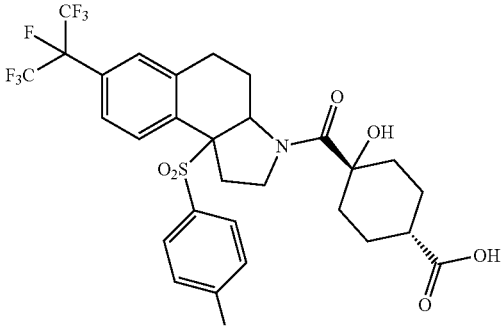 Homochiral from peak 2 | 686.2 (M + H)+ | 1.05 | B |
| 64 | 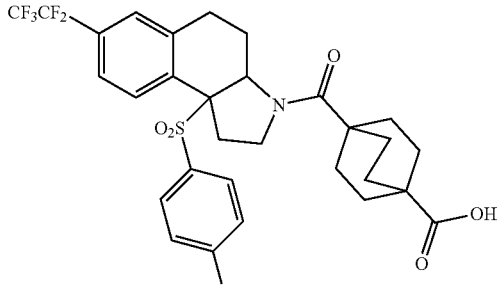 Homochiral from peak 2 | 647.2 (M + H)+ | 1.11 | B |
| 65 | 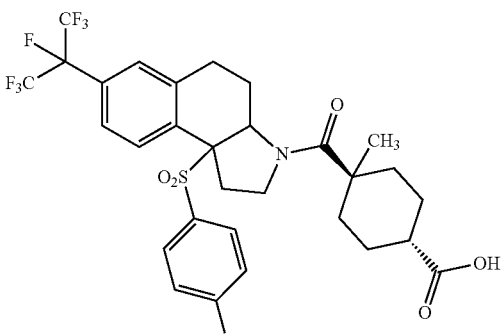 Homochiral from peak 2 | 684.2 (M + H)+ | 1.15 | B |

TABLE 9-continued

| Ex. # | Structure | LCMS m/z observed | HPLC $t_R$ (min) | HPLC method |
|---|---|---|---|---|
| 66 | 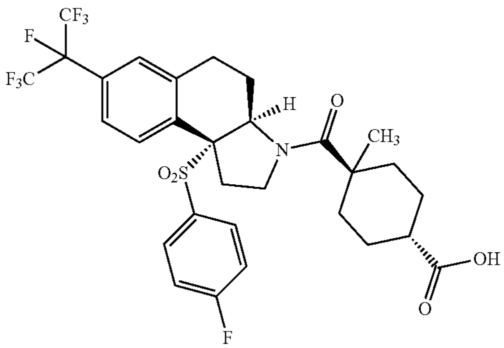 | 668.2 (M + H)+ | 1.10 | B |
| 67 | 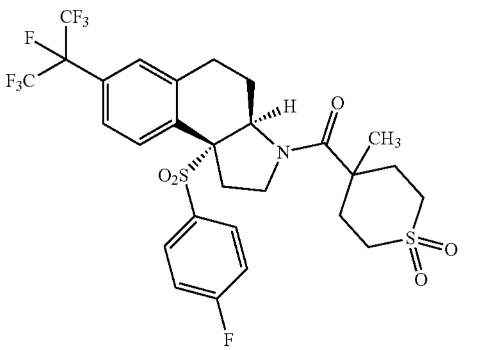 [SMILES: CC1(C(=O)N2CC[C@@]3(S(=O)(=O)c4ccc(F)cc4)c4ccc(C(F)(C(F)(F)F)C(F)(F)F)cc4CC[C@@H]23)CCS(=O)(=O)CC1] | 674.2 (M + H)+ | 1.10 | B |
| 68 | 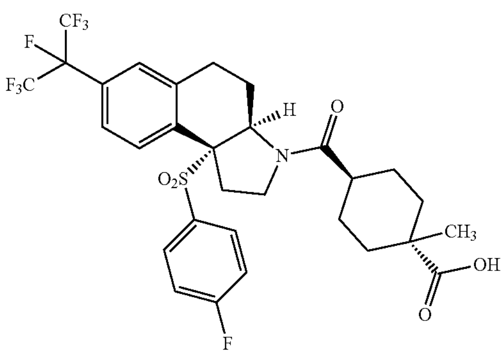 [SMILES: C[C@]1(C(=O)O)CC[C@H](C(=O)N2CC[C@@]3(S(=O)(=O)c4ccc(F)cc4)c4ccc(C(F)(C(F)(F)F)C(F)(F)F)cc4CC[C@@H]23)CC1] | 668.2 (M + H)+ | 1.10 | B |
| 69 | 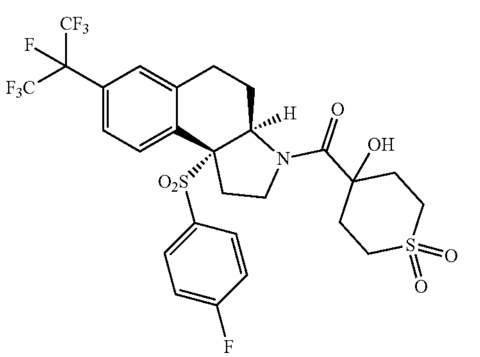 [SMILES: O=C(N1CC[C@@]2(S(=O)(=O)c3ccc(F)cc3)c3ccc(C(F)(C(F)(F)F)C(F)(F)F)cc3CC[C@@H]12)C1(O)CCS(=O)(=O)CC1] | 676.1 (M + H)+ | 1.05 | B |

TABLE 9-continued

| Ex. # | Structure | LCMS m/z observed | HPLC $t_R$ (min) | HPLC method |
|---|---|---|---|---|
| 70 | 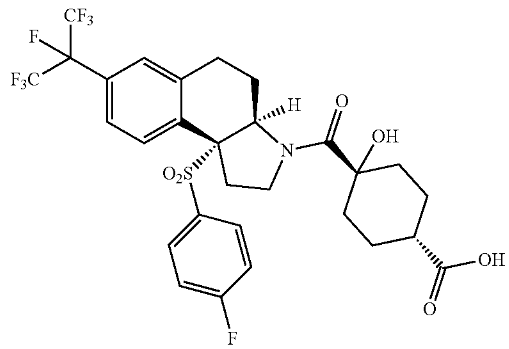 [SMILES: O=C(O)[C@H]1CC[C@](O)(C(=O)N2CC[C@@]3(S(=O)(=O)c4ccc(F)cc4)c4ccc(C(F)(C(F)(F)F)C(F)(F)F)cc4CC[C@@H]23)CC1] | 670.1 (M + H)⁺ | 1.06 | B |
| 71 | Homochiral from peak 2 | 586.1 (M + H)⁺ | 0.95 | B |
| 72 | Homochiral from peak 2 | 630.2 (M + H)⁺ | 1.07 | B |
| 73 | 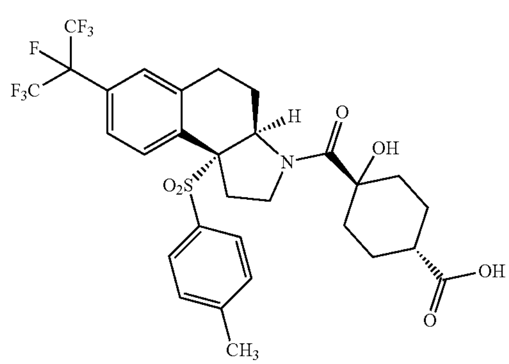 [SMILES: Cc1ccc(S(=O)(=O)[C@@]23CCN(C(=O)[C@]4(O)CC[C@@H](C(=O)O)CC4)[C@@H]2CCc2cc(C(F)(C(F)(F)F)C(F)(F)F)ccc23)cc1] | 666.2 (M + H)⁺ | 1.08 | B |

TABLE 9-continued
| Ex. # | Structure | LCMS m/z observed | HPLC $t_R$ (min) | HPLC method |
|---|---|---|---|---|
| 74 | 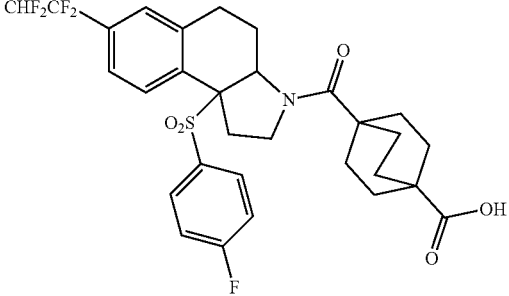 Homochiral from peak 2 | 612.3 (M + H)+ | 0.96 | B |
| 75 | 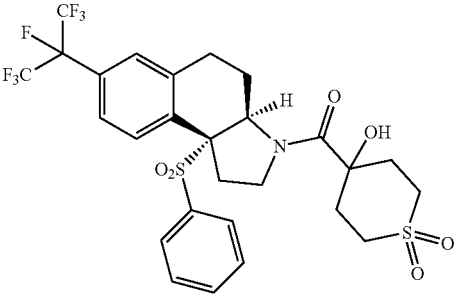 [SMILES: O=C(N1CC[C@@]2(S(=O)(=O)c3ccccc3)c3ccc(C(F)(C(F)(F)F)C(F)(F)F)cc3CC[C@@H]12)C1(O)CCS(=O)(=O)CC1] | 658.1 (M + H)+ | 1.03 | B |
| 76 | 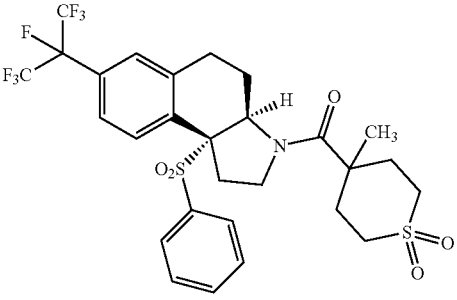 [SMILES: CC1(C(=O)N2CC[C@@]3(S(=O)(=O)c4ccccc4)c4ccc(C(F)(C(F)(F)F)C(F)(F)F)cc4CC[C@@H]23)CCS(=O)(=O)CC1] | 656.2 (M + H)+ | 1.09 | B |
| 77 | 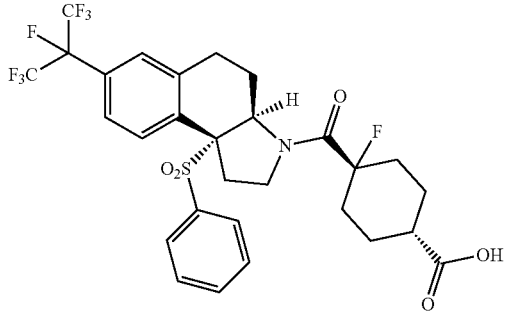 [SMILES: O=C(O)[C@H]1CC[C@](F)(C(=O)N2CC[C@@]3(S(=O)(=O)c4ccccc4)c4ccc(C(F)(C(F)(F)F)C(F)(F)F)cc4CC[C@@H]23)CC1] | 654.2 (M + H)+ | 1.10 | B |

TABLE 9-continued

| Ex. # | Structure | LCMS m/z observed | HPLC $t_R$ (min) | HPLC method |
|---|---|---|---|---|
| 78 | 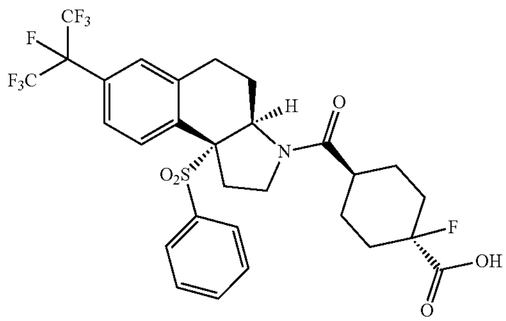 [SMILES: O=C([C@H]1CC[C@](F)(C(=O)O)CC1)N1CC[C@@]2(S(=O)(=O)c3ccccc3)c3ccc(C(F)(C(F)(F)F)C(F)(F)F)cc3CC[C@@H]12] | 654.2 (M + H)⁺ | 1.10 | B |
| 79 | 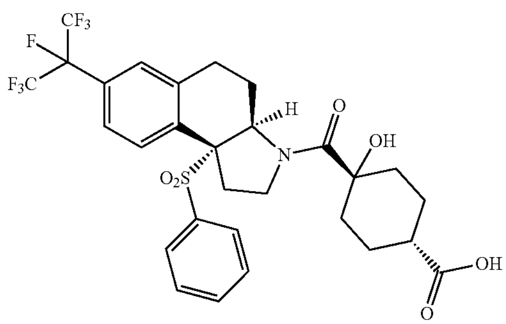 | 652.2 (M + H)⁺ | 1.04 | B |
| 80 | Homochiral from peak 2 | 604.2 (M + H)⁺ | 1.03 | B |
| 81 | Homochiral from peak 2 | 638.2 (M + H)⁺ | 1.06 | B |

TABLE 9-continued
| Ex. # | Structure | LCMS m/z observed | HPLC $t_R$ (min) | HPLC method |
|---|---|---|---|---|
| 82 | 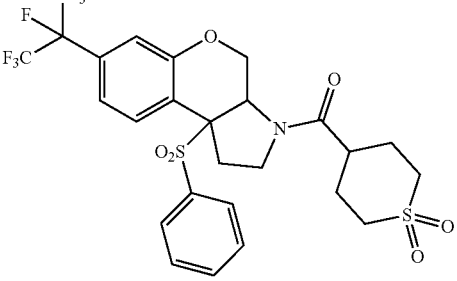 Homochiral from peak 2 | 644.2 (M + H)+ | 1.04 | B |
| 83 | 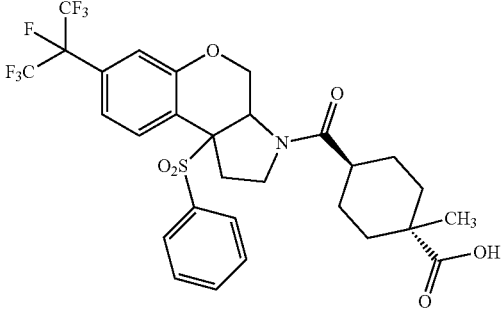 Homochiral from peak 2 | 652.2 (M + H)+ | 1.09 | B |
| 84 | 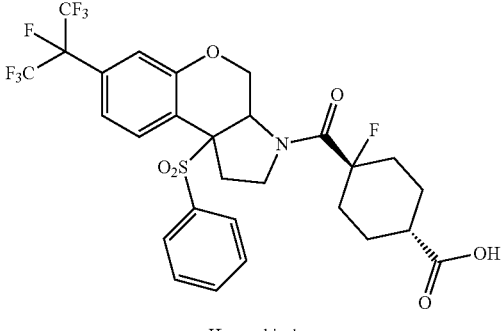 Homochiral from peak 2 | 656.2 (M + H)+ | 1.06 | B |
| 85 | 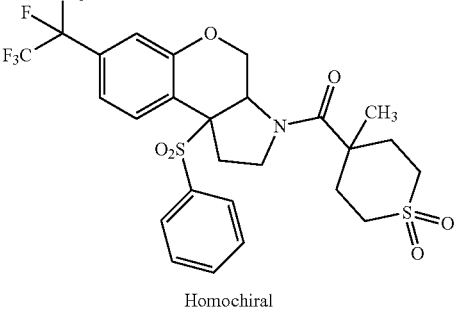 Homochiral from peak 2 | 658.1 (M + H)+ | 1.08 | B |

TABLE 9-continued
| Ex. # | Structure | LCMS m/z observed | HPLC $t_R$ (min) | HPLC method |
|---|---|---|---|---|
| 86 | 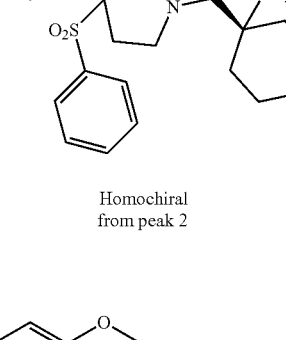<br>Homochiral from peak 2 | 652.2 (M + H)+ | 1.94 | C |
| 87 | 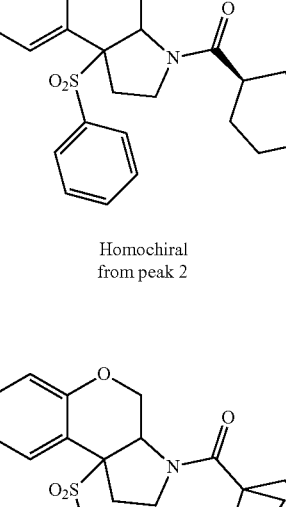<br>Homochiral from peak 2 | 656.2 (M + H)+ | 1.06 | B |
| 88 | 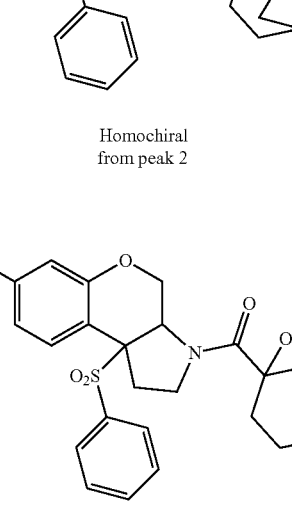<br>Homochiral from peak 2 | 664.2 (M + H)+ | 1.10 | B |
| 89 | 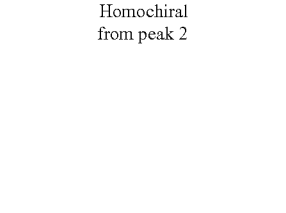<br>Homochiral from peak 2 | 660.1 (M + H)+ | 1.03 | B |

US 10,711,020 B2
TABLE 9-continued
| Ex. # | Structure | LCMS m/z observed | HPLC $t_R$ (min) | HPLC method |
|---|---|---|---|---|
| 90 | 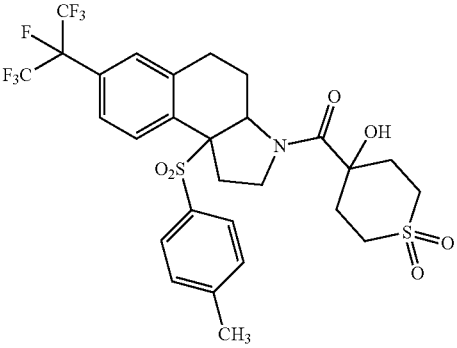<br>Homochiral from peak 2 | 672.2 (M + H)+ | 1.07 | B |
| 91 | 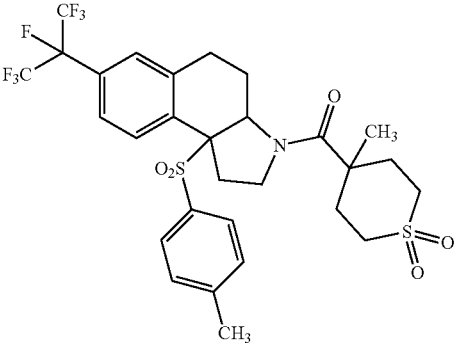<br>Homochiral from peak 2 | 670.2 (M + H)+ | 1.12 | B |
| 92 | 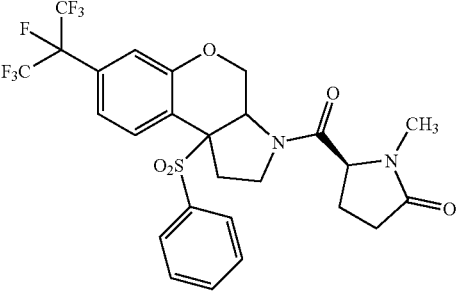<br>Homochiral from peak 2 | 609.1 (M + H)+ | 1.03 | B |
| 93 | 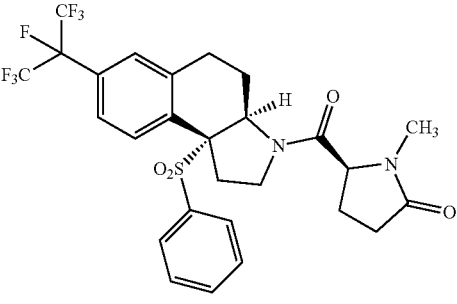 [SMILES: CN1C(=O)CC[C@H]1C(=O)N1CC[C@@]2(S(=O)(=O)c3ccccc3)c3ccc(C(F)(C(F)(F)F)C(F)(F)F)cc3CC[C@@H]12] | 607.1 (M + H)+ | 1.01 | B |

US 10,711,020 B2
233                                                                                                                                                                    234
TABLE 9-continued
| Ex. # | Structure | LCMS m/z observed | HPLC $t_R$ (min) | HPLC method |
|---|---|---|---|---|
| 94 | 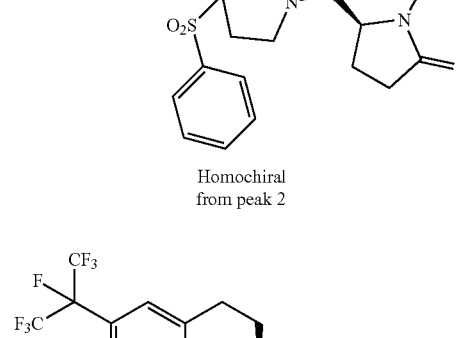<br>Homochiral from peak 2 | 612.1 (M + H)+ | 1.01 | B |
| 95 | 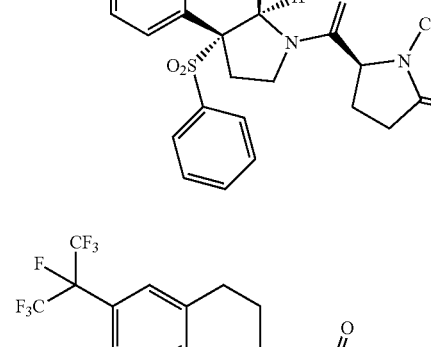 | 610.2 (M + H)+ | 1.01 | B |
| 96 | 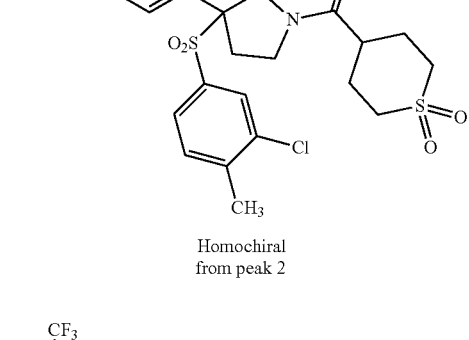<br>Homochiral from peak 2 | 690.1 (M + H)+ | 1.12 | B |
| 97 | 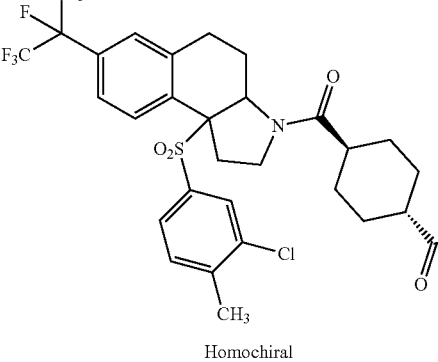<br>Homochiral from peak 2 | 684.1 (M + H)+ | 1.13 | B |

TABLE 9-continued
| Ex. # | Structure | LCMS m/z observed | HPLC t_R (min) | HPLC method |
|---|---|---|---|---|
| 98 | 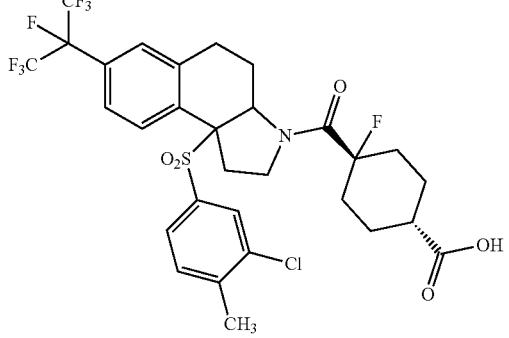 Homochiral from peak 2 | 702.2 (M + H)+ | 1.17 | B |
| 99 | 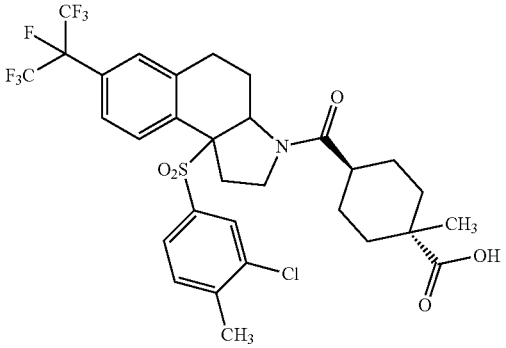 Homochiral from peak 2 | 698.2 (M + H)+ | 1.15 | B |
| 100 | 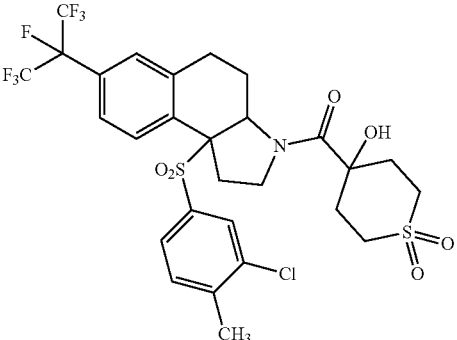 Homochiral from peak 2 | 706.1 (M + H)+ | 1.13 | B |

TABLE 9-continued
| Ex. # | Structure | LCMS m/z observed | HPLC $t_R$ (min) | HPLC method |
|---|---|---|---|---|
| 101 | 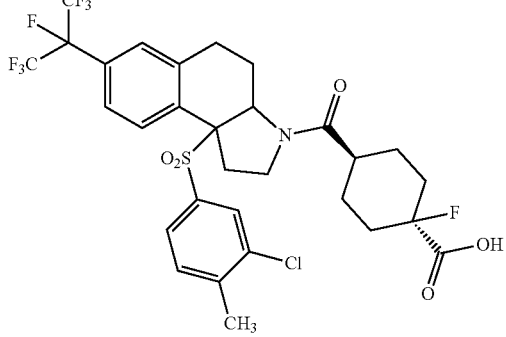 Homochiral from peak 2 | 702.2 (M + H)+ | 1.17 | B |
| 102 | 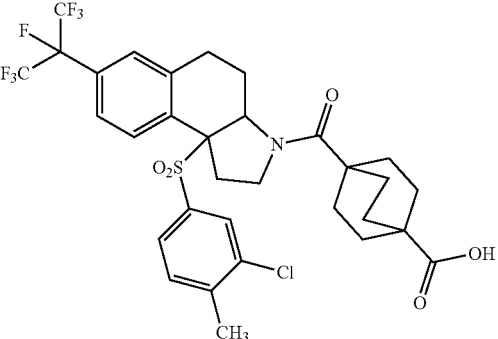 Homochiral from peak 2 | 702.2 (M + H)+ | 1.17 | B |
| 103 | 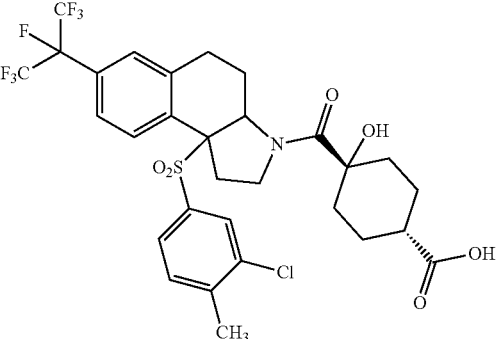 Homochiral from peak 2 | 700.1 (M + H)+ | 1.12 | B |

TABLE 9-continued
| Ex. # | Structure | LCMS m/z observed | HPLC $t_R$ (min) | HPLC method |
|---|---|---|---|---|
| 104 | 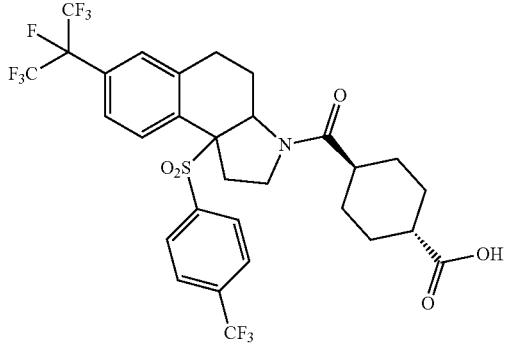 Homochiral from peak 2 | 704.2 (M + H)+ | 1.12 | B |
| 105 | 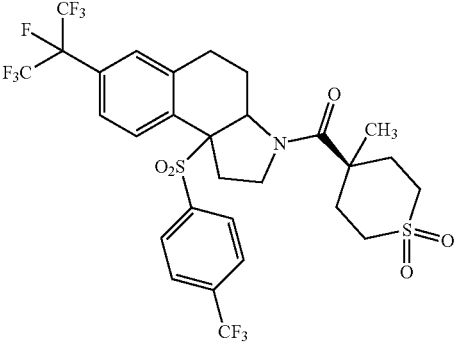 Homochiral from peak 2 | 724.1 (M + H)+ | 1.14 | B |
| 106 | 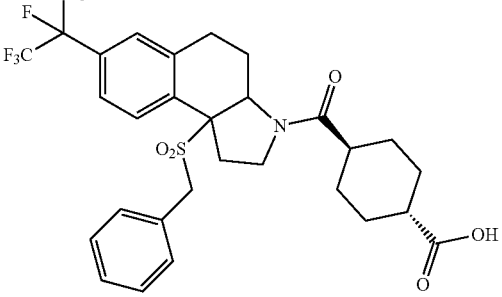 Homochiral from peak 2 | 650.2 (M + H)+ | 1.06 | B |
| 107 | 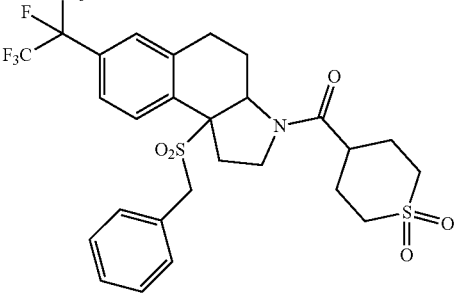 Homochiral from peak 2 | 656.2 (M + H)+ | 1.04 | B |

TABLE 9-continued

| Ex. # | Structure | LCMS m/z observed | HPLC $t_R$ (min) | HPLC method |
|---|---|---|---|---|
| 108 | Homochiral from peak 2 | 676.2 (M + H)+ | 1.10 | B |
| 109 | Homochiral from peak 2 | 730.4 (M + H)+ | 1.11 | B |
| 110 | Homochiral from peak 2 | 726.5 (M + H)+ | 1.15 | B |

TABLE 9-continued
| Ex. # | Structure | LCMS m/z observed | HPLC $t_R$ (min) | HPLC method |
|---|---|---|---|---|
| 111 | 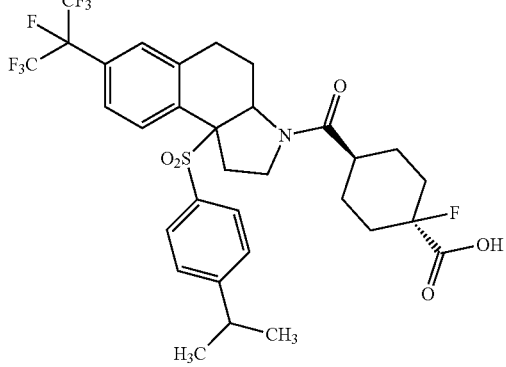 Homochiral from peak 2 | 696.4 $(M + H)^+$ | 1.15 | B |
| 112 | 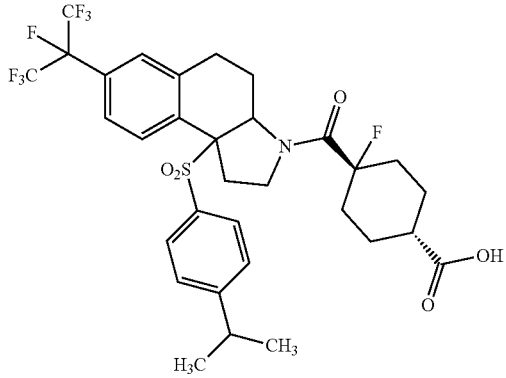 Homochiral from peak 2 | 696.4 $(M + H)^+$ | 1.15 | B |
| 113 | 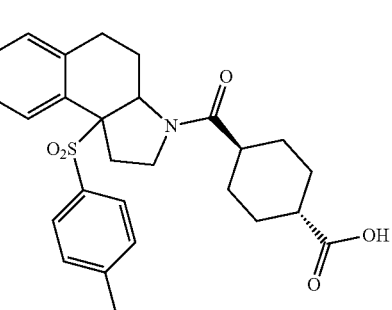 Homochiral from peak 2 | 678.5 $(M + H)^+$ | 1.12 | B |

TABLE 9-continued
| Ex. # | Structure | LCMS m/z observed | HPLC $t_R$ (min) | HPLC method |
|---|---|---|---|---|
| 114 | 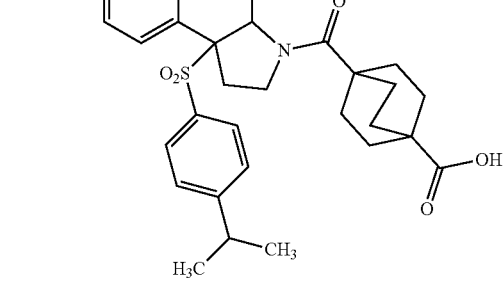 Homochiral from peak 2 | 704.5 (M + H)+ | 1.15 | B |
| 115 | 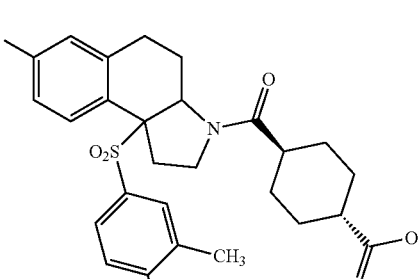 Homochiral from peak 2 | 642.1 (M + H)+ | 1.07 | B |
| 116 | 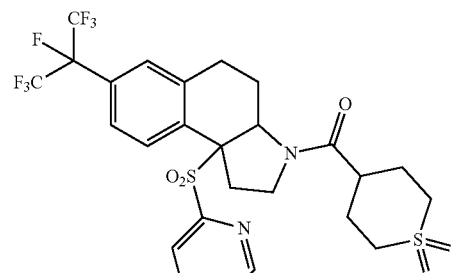 Homochiral from peak 2 | 643.3 (M + H)+ | 0.95 | B |
| 117 | 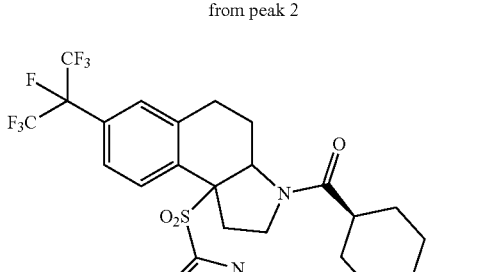 Homochiral from peak 2 | 637.6 (M + H)+ | 0.97 | B |

TABLE 9-continued
| Ex. # | Structure | LCMS m/z observed | HPLC $t_R$ (min) | HPLC method |
|---|---|---|---|---|
| 118 | 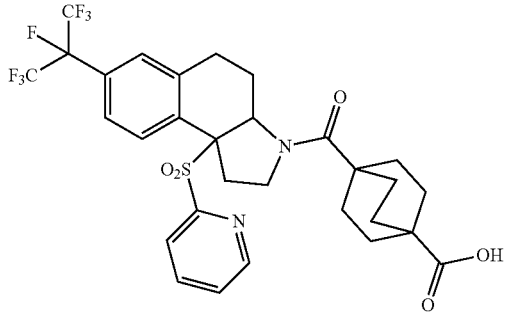 Homochiral from peak 2 | 663.4 (M + H)+ | 1.00 | B |
| 119 | Homochiral from peak 2 | 682.5 (M + H)+ | 1.13 | B |
| 120 | 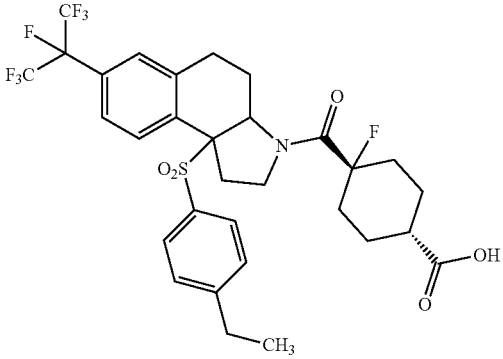 Homochiral from peak 2 | 682.5 (M + H)+ | 1.13 | B |

TABLE 9-continued
| Ex. # | Structure | LCMS m/z observed | HPLC $t_R$ (min) | HPLC method |
|---|---|---|---|---|
| 121 | 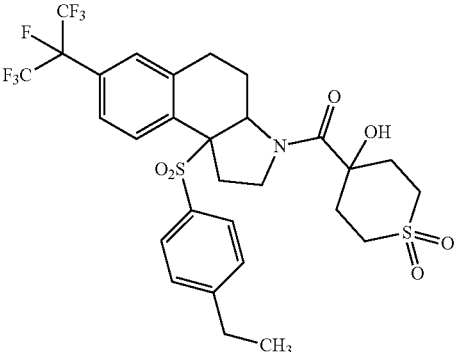<br>Homochiral from peak 2 | 686.4 $(M + H)^+$ | 1.07 | B |
| 122 | 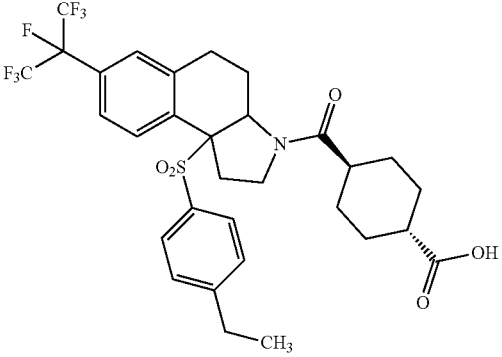<br>Homochiral from peak 2 | 664.5 $(M + H)^+$ | 1.09 | B |
| 123 | 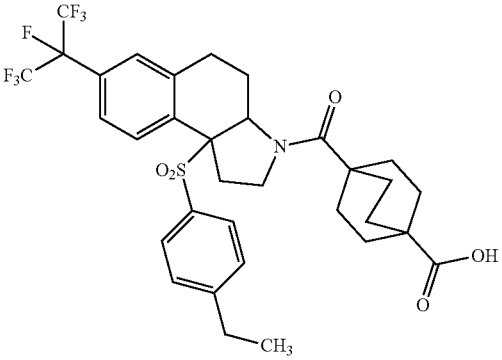<br>Homochiral from peak 2 | 690.5 $(M + H)^+$ | 1.12 | B |

TABLE 9-continued
| Ex. # | Structure | LCMS m/z observed | HPLC $t_R$ (min) | HPLC method |
|---|---|---|---|---|
| 124 | 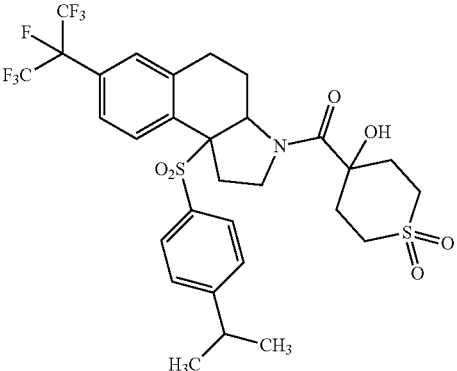 Homochiral from peak 2 | 700.4 (M + H)+ | 1.10 | B |
| 125 | 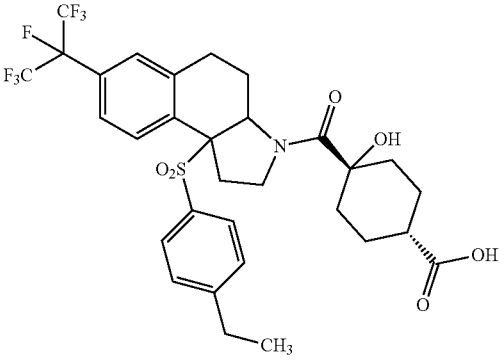 Homochiral from peak 2 | 680.4 (M + H)+ | 1.07 | B |
| 126 | 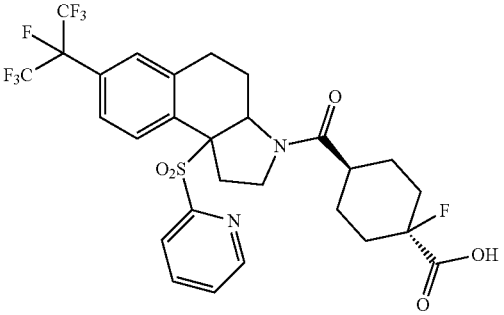 Homochiral from peak 2 | 655.3 (M + H)+ | 1.06 | B |

TABLE 9-continued

| Ex. # | Structure | LCMS m/z observed | HPLC $t_R$ (min) | HPLC method |
|---|---|---|---|---|
| 127 | Homochiral from peak 2 | 653.2 (M + H)+ | 0.98 | B |
| 128 | Homochiral from peak 2 | 655.3 (M + H)+ | 1.06 | B |
| 129 | Homochiral from peak 2 | 676.2 (M + H)+ | 1.10 | B |
| 130 | Homochiral from peak 2 | 674.2 (M + H)+ | 1.11 | B |

TABLE 9-continued

| Ex. # | Structure | LCMS m/z observed | HPLC $t_R$ (min) | HPLC method |
|---|---|---|---|---|
| 131 | Homochiral from peak 2 | 670.2 (M + H)+ | 1.10 | B |
| 132 | Homochiral from peak 2 | 674.2 (M + H)+ | 1.11 | B |
| 133 | Homochiral from peak 2 | 678.2 (M + H)+ | 1.05 | B |

TABLE 9-continued
| Ex. # | Structure | LCMS m/z observed | HPLC $t_R$ (min) | HPLC method |
|---|---|---|---|---|
| 134 | 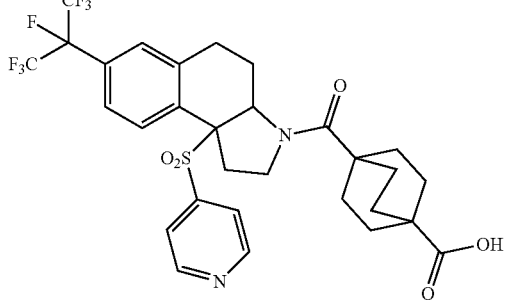 Homochiral from peak 2 | 663.5 (M + H)+ | 0.99 | B |
| 135 | 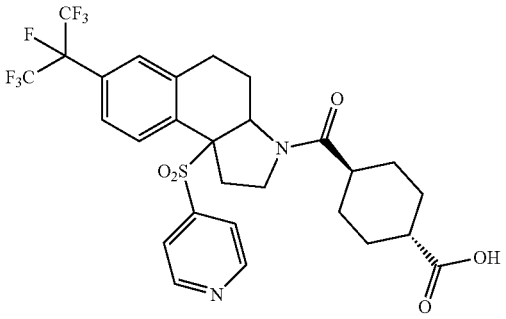 Homochiral from peak 2 | 637.5 (M + H)+ | 0.95 | B |
| 136 | 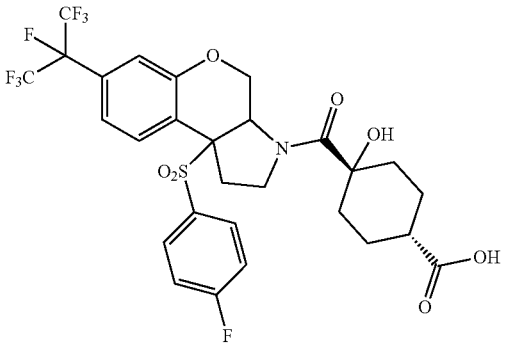 Homochiral from peak 2 | 672.2 (M + H)+ | 1.07 | B |

TABLE 9-continued
| Ex. # | Structure | LCMS m/z observed | HPLC $t_R$ (min) | HPLC method |
|---|---|---|---|---|
| 137 | 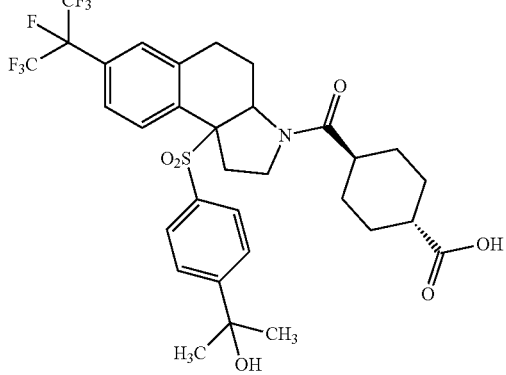 Homochiral from peak 2 | 694.5 (M + H)+ | 0.98 | B |
| 138 | 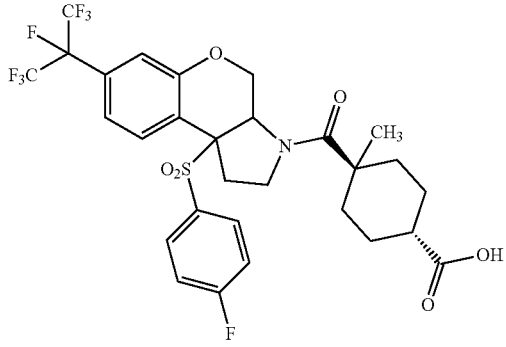 Homochiral from peak 2 | 670.5 (M + H)+ | 1.07 | B |
| 139 | 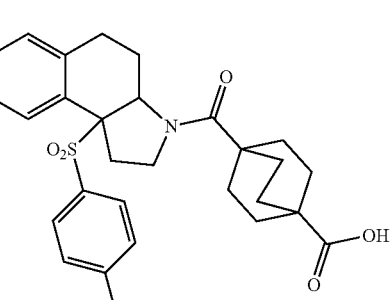 Homochiral from peak 2 | 720.5 (M + H)+ | 1.01 | B |

TABLE 9-continued
| Ex. # | Structure | LCMS m/z observed | HPLC $t_R$ (min) | HPLC method |
|---|---|---|---|---|
| 140 | 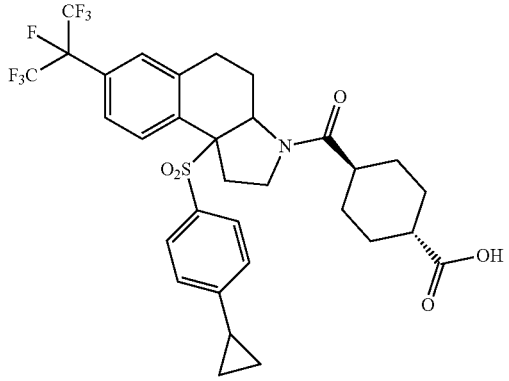<br>Homochiral from peak 2 | 676.1 (M + H)+ | 1.12 | B |
| 141 | 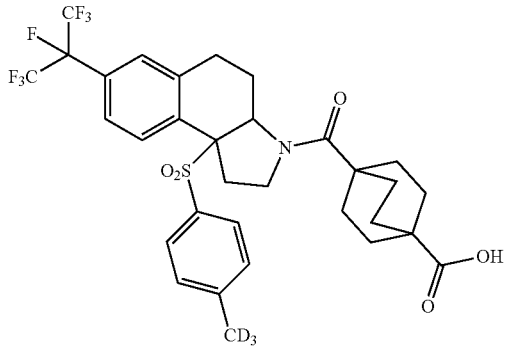<br>Homochiral from peak 2 | 679.5 (M + H)+ | 1.08 | B |
| 142 | 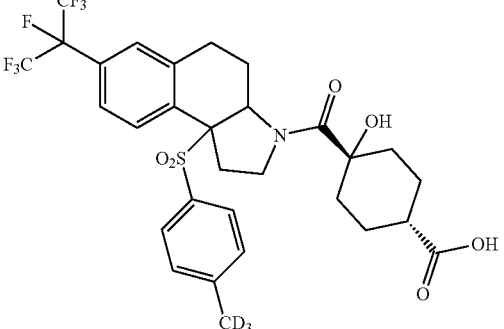<br>Homochiral from peak 2 | 669.1 (M + H)+ | 1.93 | C |

TABLE 9-continued
| Ex. # | Structure | LCMS m/z observed | HPLC $t_R$ (min) | HPLC method |
|---|---|---|---|---|
| 143 | 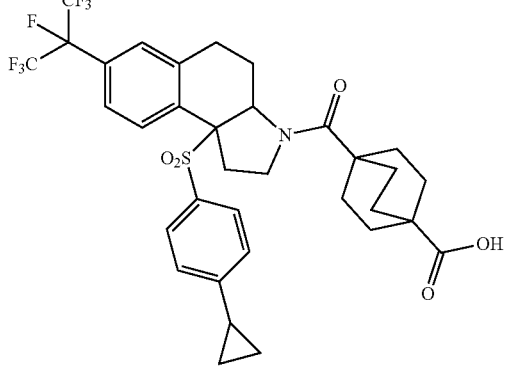<br>Homochiral from peak 2 | 702.5 (M + H)+ | 1.10 | B |
| 144 | 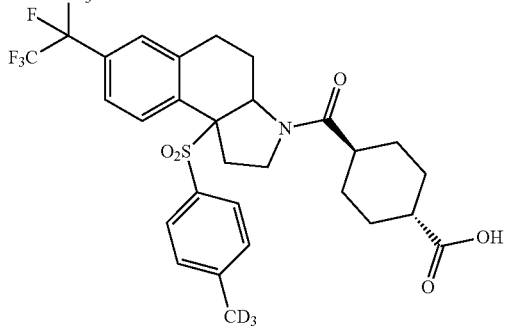<br>Homochiral from peak 2 | 653.4 (M + H)+ | 1.04 | B |
| 145 | 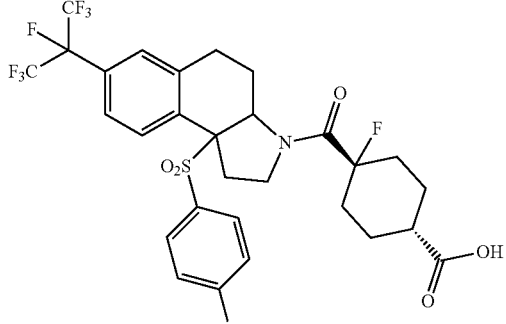<br>Homochiral from peak 2 | 671.5 (M + H)+ | 1.05 | B |

TABLE 9-continued
| Ex. # | Structure | LCMS m/z observed | HPLC $t_R$ (min) | HPLC method |
|---|---|---|---|---|
| 146 | 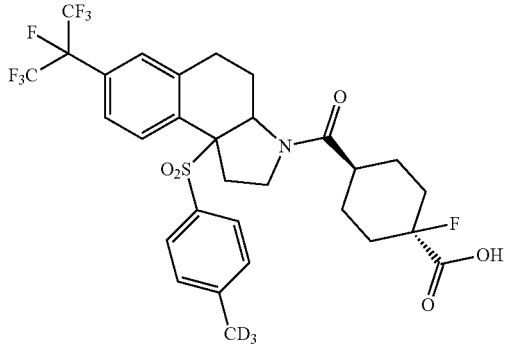<br>Homochiral from peak 2 | 671.5 (M + H)+ | 1.05 | B |
| 147 | 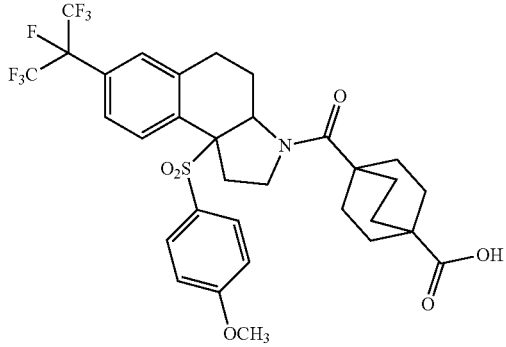<br>Homochiral from peak 2 | 692.5 (M + H)+ | 1.10 | B |
| 148 | 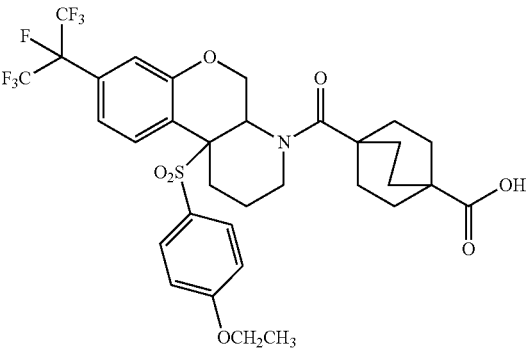<br>Homochiral from peak 2 | 722.2 (M + H)+ | 1.16 | B |

TABLE 9-continued
| Ex. # | Structure | LCMS m/z observed | HPLC $t_R$ (min) | HPLC method |
|---|---|---|---|---|
| 149 | 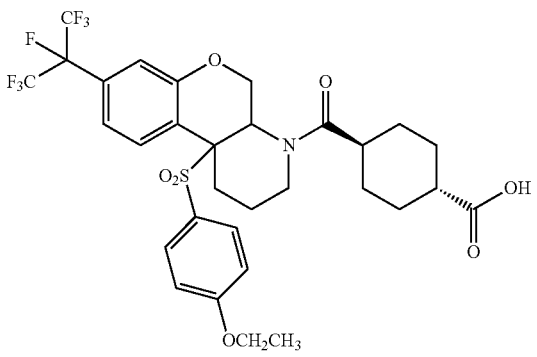<br>Homochiral from peak 2 | 696.2 $(M + H)^+$ | 1.13 | B |
| 150 | 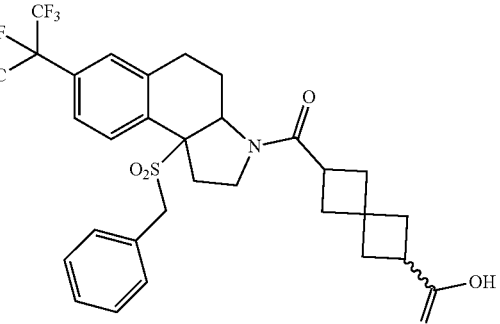<br>From peak 2 | 696.2 $(M + H)^+$ | 1.13 | B |
| 151 | 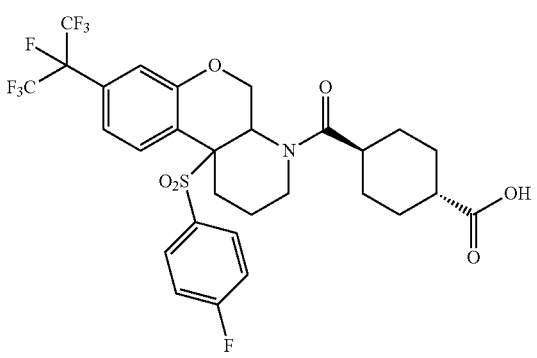<br>Homochiral from peak 2 | 670.2 $(M + H)^+$ | 1.10 | B |

TABLE 9-continued
| Ex. # | Structure | LCMS m/z observed | HPLC $t_R$ (min) | HPLC method |
|---|---|---|---|---|
| 152 | 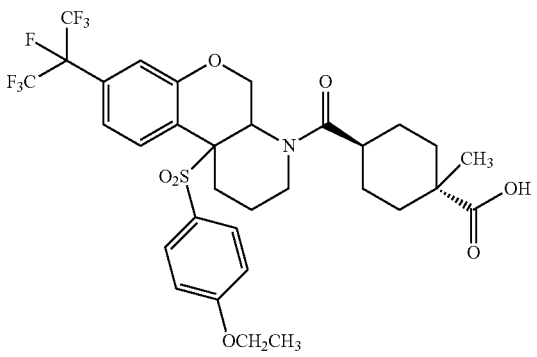<br>Homochiral from peak 2 | 710.2 (M + H)+ | 1.15 | B |
| 153 | 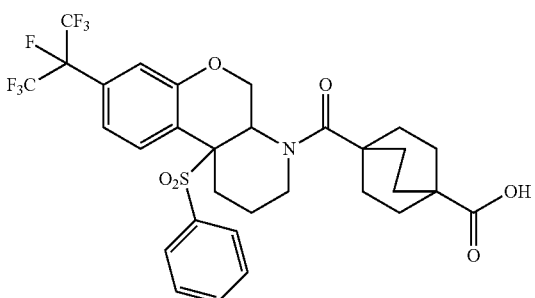<br>Homochiral from peak 2 | 696.2 (M + H)+ | 1.14 | B |
| 154 | 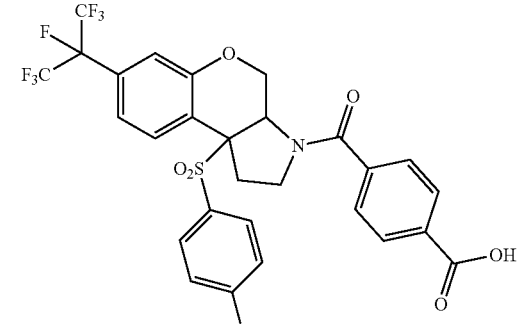<br>Homochiral from peak 2 | 650.1 (M + H)+ | 1.09 | B |

TABLE 9-continued

| Ex. # | Structure | LCMS m/z observed | HPLC $t_R$ (min) | HPLC method |
|---|---|---|---|---|
| 155 | From peak 2 | 668.1 (M + H)+ | 1.10 | B |
| 156 | Homochiral from peak 2 | 632.1 (M + H)+ | 1.08 | B |
| 157 | 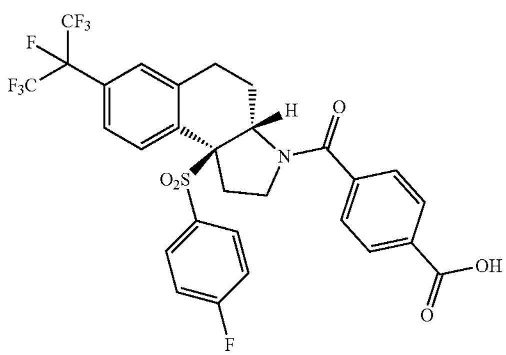 [SMILES: O=C(O)c1ccc(C(=O)N2CC[C@]3(S(=O)(=O)c4ccc(F)cc4)c4ccc(C(F)(C(F)(F)F)C(F)(F)F)cc4CC[C@H]23)cc1] | 648.1 (M + H)+ | 1.09 | B |
| 158 | 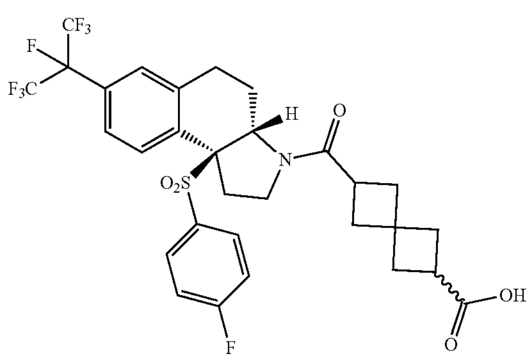 [SMILES: O=C(O)C1CC2(C1)CC(C(=O)N1CC[C@]3(S(=O)(=O)c4ccc(F)cc4)c4ccc(C(F)(C(F)(F)F)C(F)(F)F)cc4CC[C@H]13)C2] | 666.1 (M + H)+ | 1.10 | B |

TABLE 9-continued

| Ex. # | Structure | LCMS m/z observed | HPLC $t_R$ (min) | HPLC method |
|---|---|---|---|---|
| 159 | From peak 2 | 696.2 (M + H)+ | 1.16 | B |
| 160 | Homochiral from peak 2 | 650.1 (M + H)+ | 1.09 | B |
| 161 | From peak 2 | 682.1 (M + H)+ | 1.12 | B |
| 162 | From peak 2 | 708.2 (M + H)+ | 1.14 | B |

TABLE 9-continued

| Ex. # | Structure | LCMS m/z observed | HPLC $t_R$ (min) | HPLC method |
|---|---|---|---|---|
| 163 | Homochiral from peak 2 | 714.2 (M + H)+ | 1.17 | B |
| 164 | Homochiral from peak 2 | 688.2 (M + H)+ | 1.14 | B |
| 165 | From peak 2 | 650.2 (M + H)+ | 1.09 | B |
| 166 | From peak 2 | 662.3 (M + H)+ | 1.06 | B |

TABLE 9-continued

| Ex. # | Structure | LCMS m/z observed | HPLC $t_R$ (min) | HPLC method |
|---|---|---|---|---|
| 167 | Homochiral from peak 2 | 698.2 (M + H)+ | 1.08 | B |
| 168 | Homochiral from peak 2 | 658.4 (M + H)+ | 1.09 | B |
| 169 | [peak 1] Homochiral from peak 2 | 668.1 (M + H)+ | 1.10 | B |

TABLE 9-continued

| Ex. # | Structure | LCMS m/z observed | HPLC $t_R$ (min) | HPLC method |
|---|---|---|---|---|
| 170 | [Structure with CF3, F, F3C groups on chromene fused to pyrrolidine with O2S-phenyl-F substituent and acyl-spirocyclobutane-carboxylic acid; Homochiral from peak 2, [peak 2]] | 668.1 (M + H)+ | 1.10 | B |
| 171 | [Structure with CF3, F, F3C groups on tetrahydronaphthalene fused to pyrrolidine with O2S-phenyl-CH3 substituent and acyl-spirocyclobutane-carboxylic acid; Homochiral from peak 2, [peak 1]] | 662.1 (M + H)+ | 1.06 | B |
| 172 | [Structure with CF3, F, F3C groups on tetrahydronaphthalene fused to pyrrolidine with O2S-phenyl-CH3 substituent and acyl-spirocyclobutane-carboxylic acid; Homochiral from peak 2, [peak 2]] | 662.1 (M + H)+ | 1.06 | B |

TABLE 9-continued

| Ex. # | Structure | LCMS m/z observed | HPLC t$_R$ (min) | HPLC method |
|---|---|---|---|---|
| 173 | [Structure with CF$_3$, F, F$_3$C substituents on aromatic ring, sulfonyl-linked 4-CF$_3$-phenyl, spirocyclic carboxylic acid, peak 1] Homochiral from peak 2 | 716.2 (M + H)$^+$ | 1.07 | B |
| 174 | [Structure with CF$_3$, F, F$_3$C substituents on aromatic ring, sulfonyl-linked 4-CF$_3$-phenyl, spirocyclic carboxylic acid, peak 2] Homochiral from peak 2 | 716.2 (M + H)$^+$ | 1.07 | B |
| 175 | [Structure with CF$_3$, F, F$_3$C substituents on aromatic ring, sulfonyl-linked 2-pyridyl, spirocyclic carboxylic acid, peak 1] Homochiral from peak 2 | 649.2 (M + H)$^+$ | 0.96 | B |

TABLE 9-continued

| Ex. # | Structure | LCMS m/z observed | HPLC $t_R$ (min) | HPLC method |
|---|---|---|---|---|
| 176 | (structure shown) Homochiral from peak 2 | 649.2 (M + H)+ | 0.96 | B |
| 177 | (structure shown) Homochiral from peak 2 | 676.2 (M + H)+ | 1.08 | B |
| 178 | (structure shown) Homochiral from peak 2 | 676.2 (M + H)+ | 1.08 | B |

TABLE 9-continued
| Ex. # | Structure | LCMS m/z observed | HPLC $t_R$ (min) | HPLC method |
|---|---|---|---|---|
| 179 | 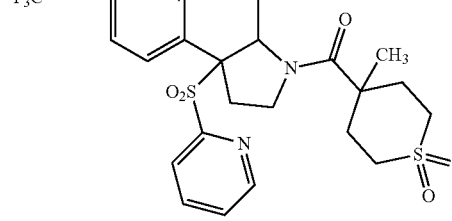  Homochiral from peak 2 | 657.1 (M + H)+ | 1.94 | C |
| 180 | 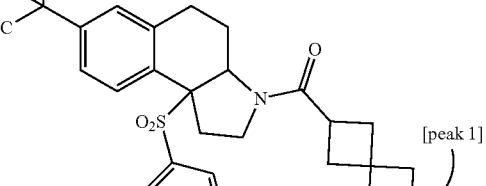  Homochiral from peak 2 | 682.3 (M + H)+ | 1.08 | B |
| 181 | 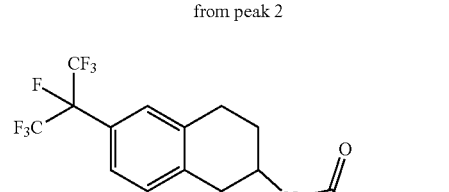  Homochiral from peak 2 | 643.1 (M + H)+ | 1.82 | C |
| 182 | 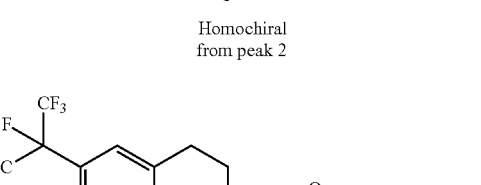  Homochiral from peak 2 | 682.3 (M + H)+ | 1.08 | B |

TABLE 9-continued

| Ex. # | Structure | LCMS m/z observed | HPLC t_R (min) | HPLC method |
|---|---|---|---|---|
| 183 | Homochiral from peak 2 | 659.1 (M + H)+ | 1.82 | C |
| 184 | From peak 2 | 642.2 (M + H)+ | 1.07 | B |
| 185 | From peak 2 | 696.2 (M + H)+ | 1.10 | B |
| 186 | From peak 2 | 656.2 (M + H)+ | 1.11 | B |

TABLE 9-continued
| Ex. # | Structure | LCMS m/z observed | HPLC $t_R$ (min) | HPLC method |
|---|---|---|---|---|
| 187 | <br>Homochiral from peak 2 | 710.2 (M + H)+ | 1.09 | B |
| 188 | 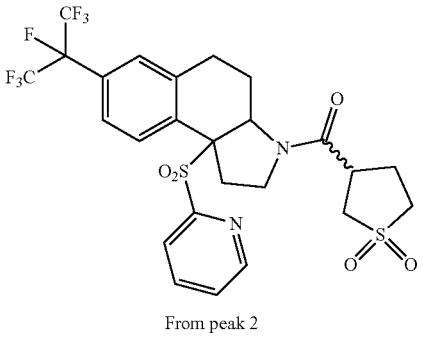 [SMILES: O=C(C1CCS(=O)(=O)C1)N1CCC2(S(=O)(=O)c3ccccn3)c3ccc(C(F)(C(F)(F)F)C(F)(F)F)cc3CCC12]<br>From peak 2 | 629.2 (M + H)+ | 0.98 | B |
| 189 | 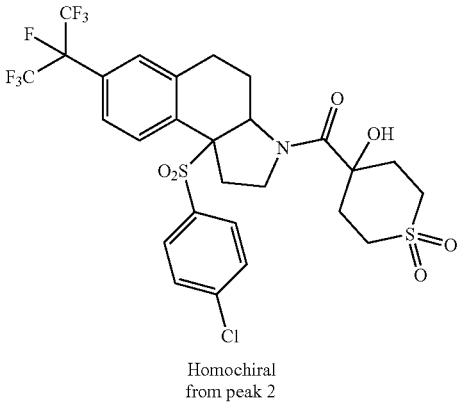<br>Homochiral from peak 2 | 692.2 (M + H)+ | 1.07 | B |
| 190 | 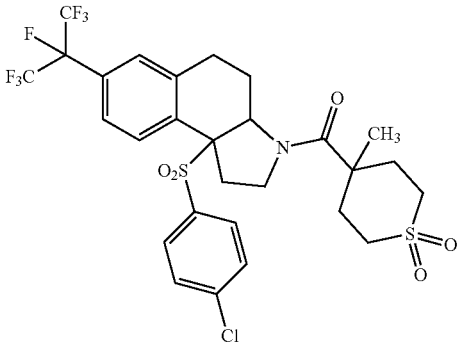<br>Homochiral from peak 2 | 690.2 (M + H)+ | 1.13 | B |

TABLE 9-continued
| Ex. # | Structure | LCMS m/z observed | HPLC $t_R$ (min) | HPLC method |
|---|---|---|---|---|
| 191 | 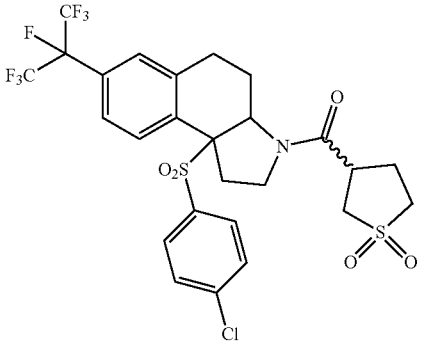<br>From peak 2 | 662.1 (M + H)+ | 1.09 | B |
| 192 | 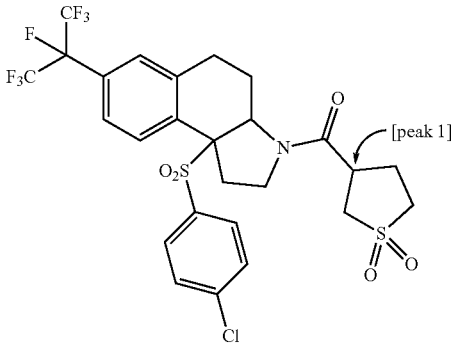<br>Homochiral from peak 2 | 662.1 (M + H)+ | 1.09 | B |
| 193 | 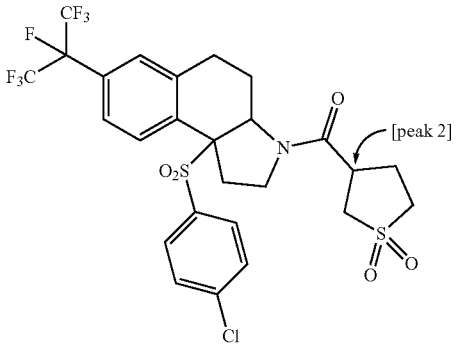<br>Homochiral from peak 2 | 662.1 (M + H)+ | 1.09 | B |

TABLE 9-continued
| Ex. # | Structure | LCMS m/z observed | HPLC $t_R$ (min) | HPLC method |
|---|---|---|---|---|
| 194 | 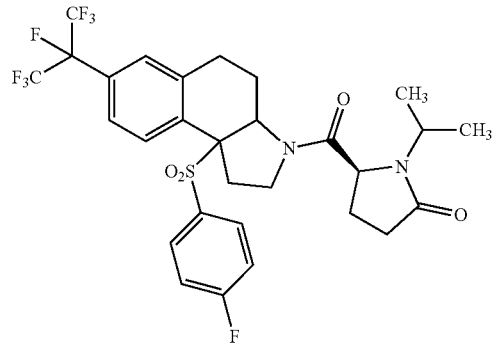<br>Homochiral<br>From peak 2 | 652.9 (M + H)+ | 2.16 | C |
| 195 | 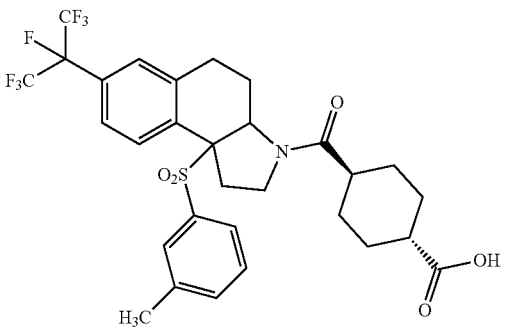<br>Homochiral<br>from peak 2 | 650.1 (M + H)+ | 2.20 | D |
| 196 | 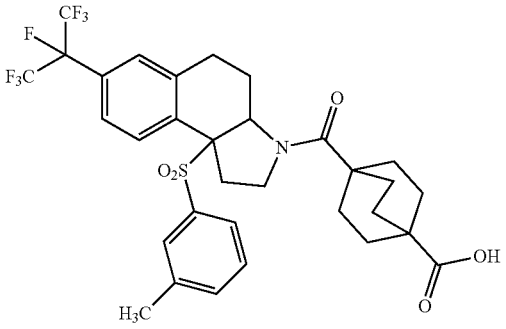<br>Homochiral<br>from peak 2 | 676.1 (M + H)+ | 2.30 | D |
| 197 | 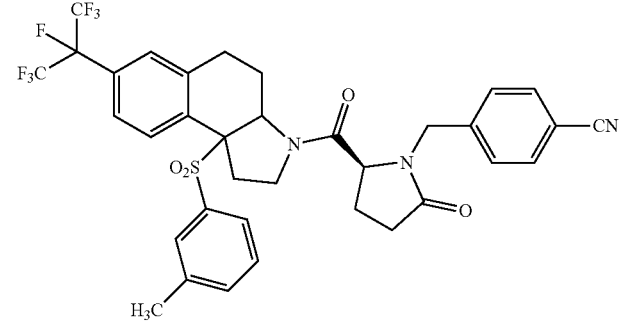<br>Homochiral<br>from peak 2 | 722.0 (M + H)+ | 2.31 | D |

TABLE 9-continued

| Ex. # | Structure | LCMS m/z observed | HPLC $t_R$ (min) | HPLC method |
|---|---|---|---|---|
| 198 | Homochiral from peak 2 | 624.3 (M + H)⁺ | 2.08 | D |
| 199 | Homochiral from peak 2 | 621.0 (M + H)⁺ | 2.09 | D |
| 200 | Homochiral from peak 2 | 656.4 (M + H)⁺ | 2.19 | D |
| 201 | Homochiral from peak 2 | 670.5 (M + H)⁺ | 2.32 | D |

TABLE 9-continued

| Ex. # | Structure | LCMS m/z observed | HPLC $t_R$ (min) | HPLC method |
|---|---|---|---|---|
| 202 | Homochiral from peak 2 | 666.1 (M + H)+ | 2.11 | D |
| 203 | Homochiral from peak 2 | 664.5 (M + H)+ | 2.35 | D |
| 204 | Homochiral from peak 2 | 596.2 (M + H)+ | 2.58 | D |
| 205 | Homochiral from peak 2 | 726.1 (M + H)+ | 2.24 | D |

TABLE 9-continued
| Ex. # | Structure | LCMS m/z observed | HPLC $t_R$ (min) | HPLC method |
|---|---|---|---|---|
| 206 | 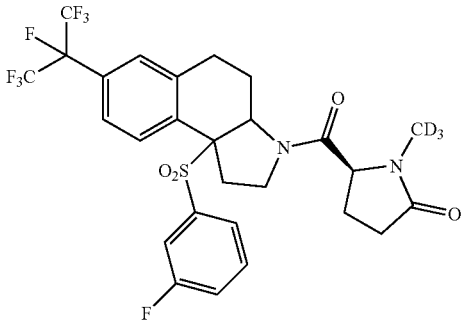<br>Homochiral from peak 2 | 628.1 (M + H)+ | 2.02 | D |
| 207 | 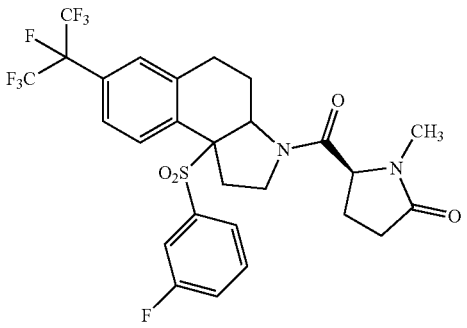<br>Homochiral from peak 2 | 625.2 (M + H)+ | 2.02 | D |
| 208 | 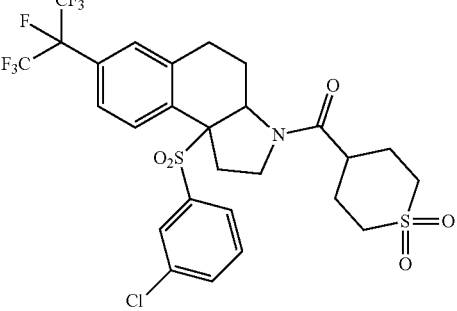<br>Homochiral from peak 2 | 676.3 (M + H)+ | 2.17 | D |
| 209 | 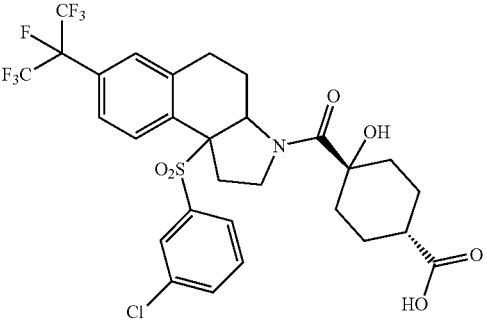<br>Homochiral from peak 2 | 685.9 (M + H)+ | 2.16 | D |

TABLE 9-continued
| Ex. # | Structure | LCMS m/z observed | HPLC $t_R$ (min) | HPLC method |
|---|---|---|---|---|
| 210 | 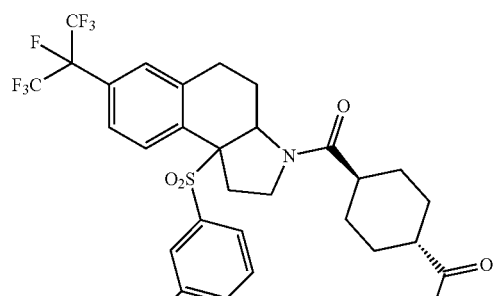<br>Homochiral from peak 2 | 670.5 (M + H)+ | 2.29 | D |
| 211 | 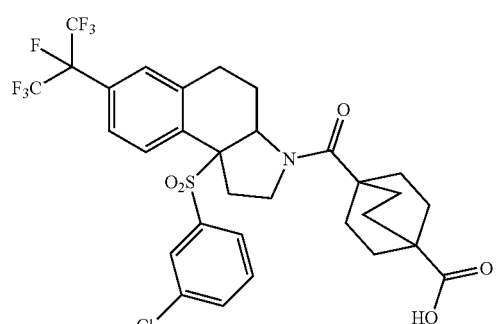<br>Homochiral from peak 2 | 696.5 (M + H)+ | 2.39 | D |
| 212 | 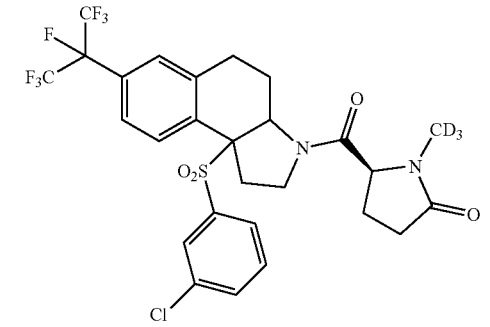<br>Homochiral from peak 2 | 644.2 (M + H)+ | 2.17 | D |
| 213 | 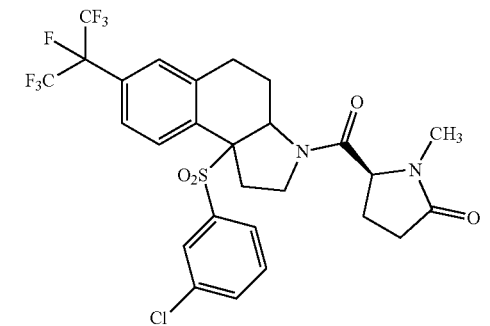<br>Homochiral from peak 2 | 641.4 (M + H)+ | 2.17 | D |

TABLE 9-continued
| Ex. # | Structure | LCMS m/z observed | HPLC $t_R$ (min) | HPLC method |
|---|---|---|---|---|
| 214 | 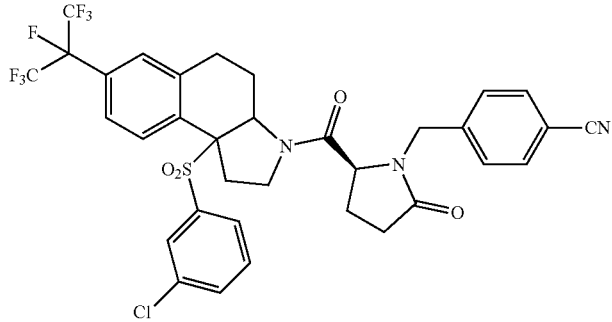 Homochiral from peak 2 | 742.5 (M + H)+ | 2.40 | D |
| 215 | 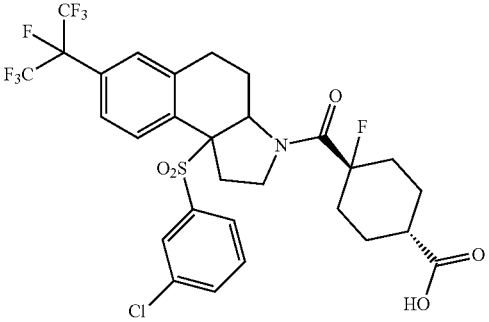 Homochiral from peak 2 | 688.1 (M + H)+ | 2.37 | D |
| 216 | 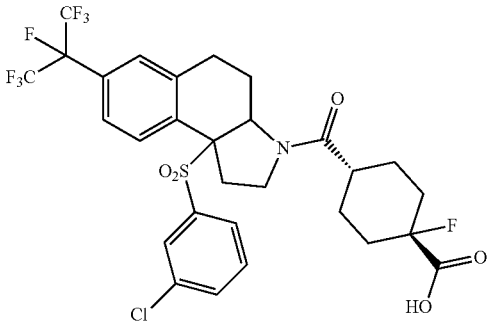 Homochiral from peak 2 | 688.0 (M + H)+ | 2.26 | D |
| 217 | 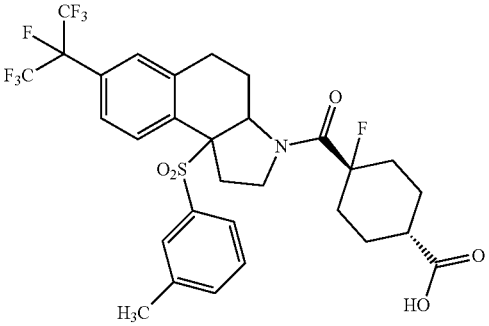 Homochiral from peak 2 | 668.0 (M + H)+ | 2.33 | D |

TABLE 9-continued
| Ex. # | Structure | LCMS m/z observed | HPLC $t_R$ (min) | HPLC method |
|---|---|---|---|---|
| 218 | 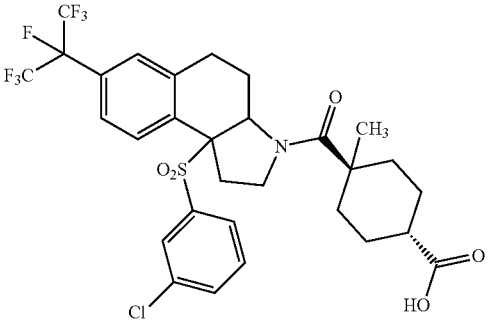 Homochiral from peak 2 | 684.5 (M + H)+ | 2.39 | D |
| 219 | 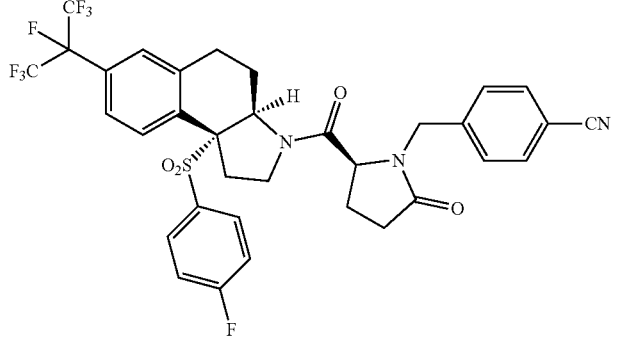 [SMILES: N#Cc1ccc(CN2C(=O)CC[C@H]2C(=O)N2CC[C@@]3(S(=O)(=O)c4ccc(F)cc4)c4ccc(C(F)(C(F)(F)F)C(F)(F)F)cc4CC[C@@H]23)cc1] | 726.5 (M + H)+ | 2.31 | D |
| 220 | 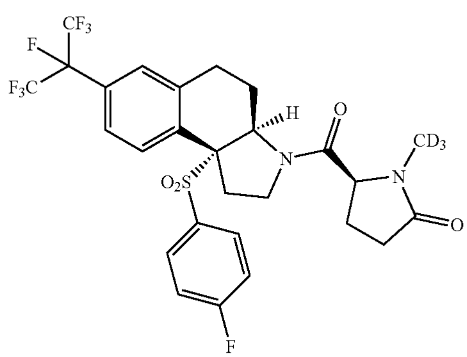 [SMILES: [2H]C([2H])([2H])N1C(=O)CC[C@H]1C(=O)N1CC[C@@]2(S(=O)(=O)c3ccc(F)cc3)c3ccc(C(F)(C(F)(F)F)C(F)(F)F)cc3CC[C@@H]12] | 628.1 (M + H)+ | 2.04 | D |
| 221 | 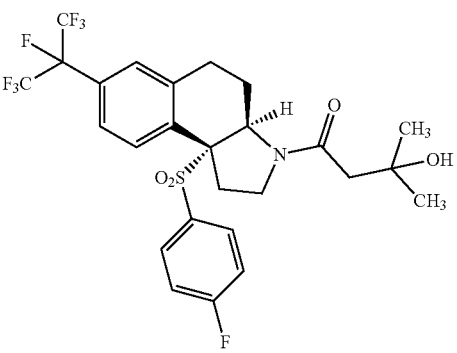 [SMILES: CC(C)(O)CC(=O)N1CC[C@@]2(S(=O)(=O)c3ccc(F)cc3)c3ccc(C(F)(C(F)(F)F)C(F)(F)F)cc3CC[C@@H]12] | 600.4 (M + H)+ | 2.26 | D |

TABLE 9-continued

| Ex. # | Structure | LCMS m/z observed | HPLC t$_R$ (min) | HPLC method |
|---|---|---|---|---|
| 222 | 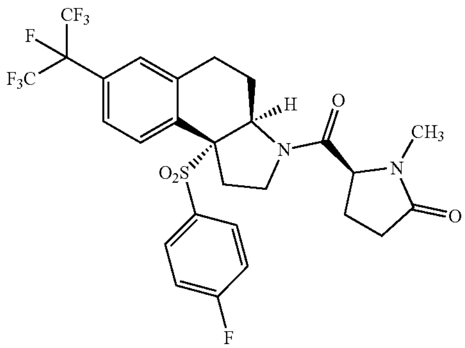 | 625.2 (M + H)+ | 2.04 | D |
| 223 | 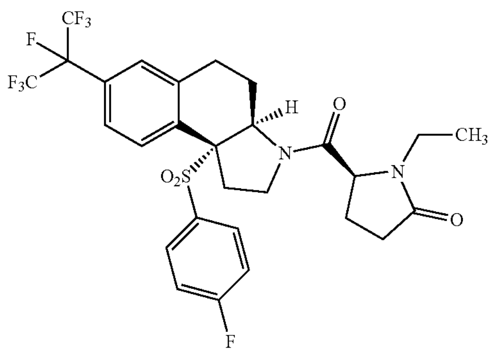 [SMILES: CCN1C(=O)CC[C@H]1C(=O)N1CC[C@@]2(S(=O)(=O)c3ccc(F)cc3)c3ccc(C(F)(C(F)(F)F)C(F)(F)F)cc3CC[C@@H]12] | 639.1 (M + H)+ | 2.11 | D |
| 224 | 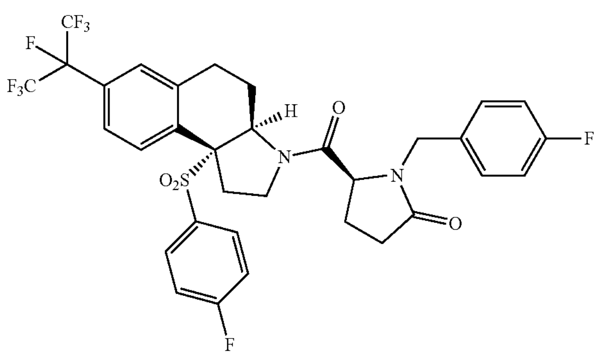 [SMILES: O=C1CC[C@@H](C(=O)N2CC[C@@]3(S(=O)(=O)c4ccc(F)cc4)c4ccc(C(F)(C(F)(F)F)C(F)(F)F)cc4CC[C@@H]23)N1Cc1ccc(F)cc1] | 719.4 (M + H)+ | 2.40 | D |
| 225 | 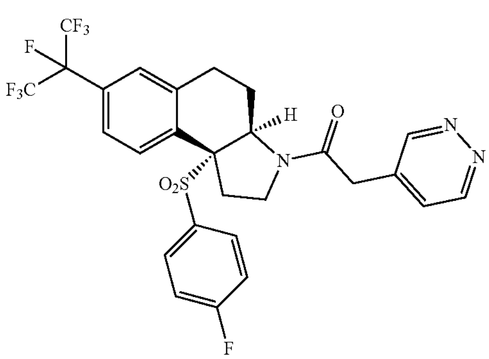 [SMILES: O=C(Cc1ccnnc1)N1CC[C@@]2(S(=O)(=O)c3ccc(F)cc3)c3ccc(C(F)(C(F)(F)F)C(F)(F)F)cc3CC[C@@H]12] | 620.0 (M + H)+ | 1.93 | D |

TABLE 9-continued
| Ex. # | Structure | LCMS m/z observed | HPLC $t_R$ (min) | HPLC method |
|---|---|---|---|---|
| 226 | 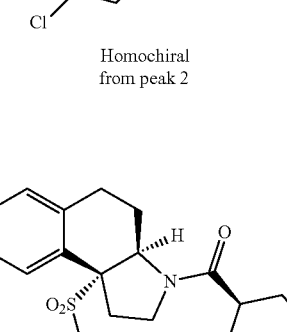 Homochiral from peak 2 | 636.2 (M + H)+ | 2.08 | D |
| 227 | 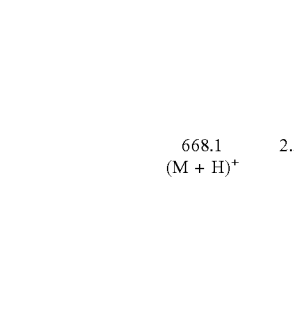 | 668.1 (M + H)+ | 2.31 | D |
| 228 | 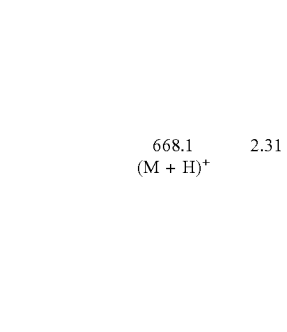 | 694.1 (M + H)+ | 2.43 | D |
| 229 | 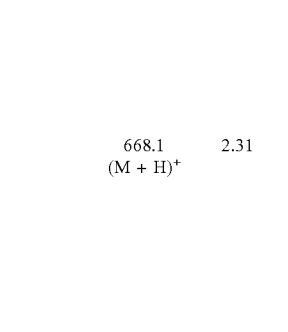 | 638.3 (M + H)+ | 2.16 | D |

TABLE 9-continued

| Ex. # | Structure | LCMS m/z observed | HPLC $t_R$ (min) | HPLC method |
|---|---|---|---|---|
| 230 | 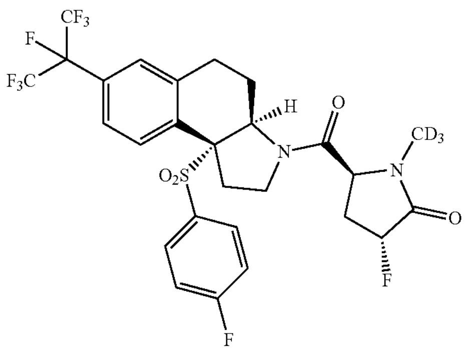 [SMILES: [2H]C([2H])([2H])N1C(=O)[C@H](F)C[C@H]1C(=O)N1CC[C@@]2(S(=O)(=O)c3ccc(F)cc3)c3ccc(C(F)(C(F)(F)F)C(F)(F)F)cc3CC[C@@H]12] | 645.9 (M + H)+ | 2.09 | D |
| 231 | 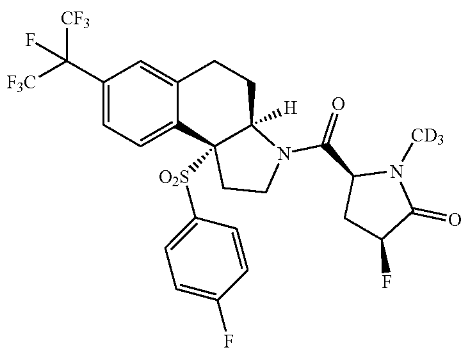 [SMILES: [2H]C([2H])([2H])N1C(=O)[C@@H](F)C[C@H]1C(=O)N1CC[C@@]2(S(=O)(=O)c3ccc(F)cc3)c3ccc(C(F)(C(F)(F)F)C(F)(F)F)cc3CC[C@@H]12] | 646.4 (M + H)+ | 2.17 | D |
| 232 | 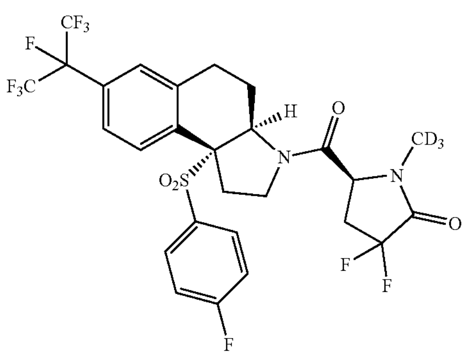 [SMILES: [2H]C([2H])([2H])N1C(=O)C(F)(F)C[C@H]1C(=O)N1CC[C@@]2(S(=O)(=O)c3ccc(F)cc3)c3ccc(C(F)(C(F)(F)F)C(F)(F)F)cc3CC[C@@H]12] | 664.4 (M + H)+ | 2.33 | D |
| 233 | Homochiral from peak 2 | 662.1 (M + H)+ | 2.20 | D |

TABLE 9-continued

| Ex. # | Structure | LCMS m/z observed | HPLC $t_R$ (min) | HPLC method |
|---|---|---|---|---|
| 234 | Homochiral from peak 2 | 680.2 (M + H)+ | 2.37 | D |
| 235 | Homochiral from peak 2 | 630.0 (M + H)+ | 2.17 | D |
| 236 | 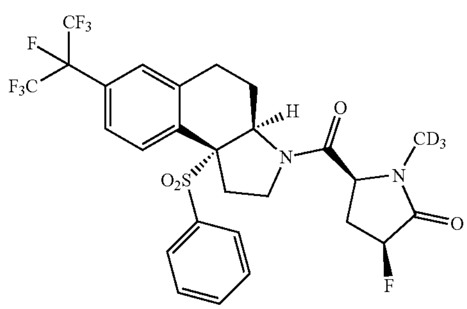 [SMILES: [2H]C([2H])([2H])N1C(=O)[C@@H](F)C[C@H]1C(=O)N1CC[C@@]2(S(=O)(=O)c3ccccc3)c3ccc(C(F)(C(F)(F)F)C(F)(F)F)cc3CC[C@@H]12] | 628.1 (M + H)+ | 2.07 | D |
| 237 | Homochiral from peak 2 | 648.0 (M + H)+ | 2.17 | D |

TABLE 9-continued
| Ex. # | Structure | LCMS m/z observed | HPLC $t_R$ (min) | HPLC method |
|---|---|---|---|---|
| 238 |  Homochiral from peak 2 | 664.2 (M + H)+ | 2.28 | D |
| 239 | 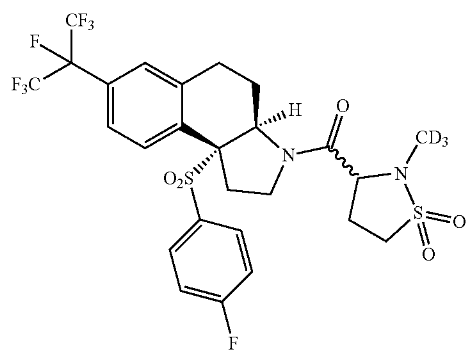 [SMILES: [2H]C([2H])([2H])N1C(C(=O)N2CC[C@@]3(S(=O)(=O)c4ccc(F)cc4)c4ccc(C(F)(C(F)(F)F)C(F)(F)F)cc4CC[C@@H]23)CCS1(=O)=O] | 664.2 (M + H)+ | 2.22 | D |
| 240 | 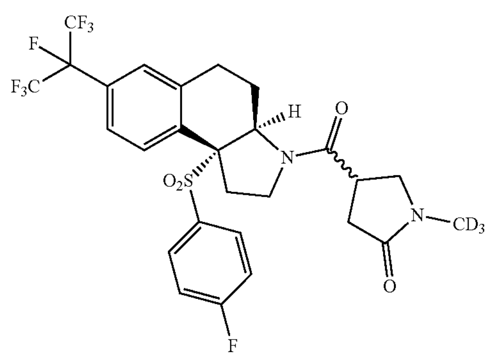 [SMILES: [2H]C([2H])([2H])N1CC(C(=O)N2CC[C@@]3(S(=O)(=O)c4ccc(F)cc4)c4ccc(C(F)(C(F)(F)F)C(F)(F)F)cc4CC[C@@H]23)CC1=O] | 628.0 (M + H)+ | 2.06 | D |
| 241 | 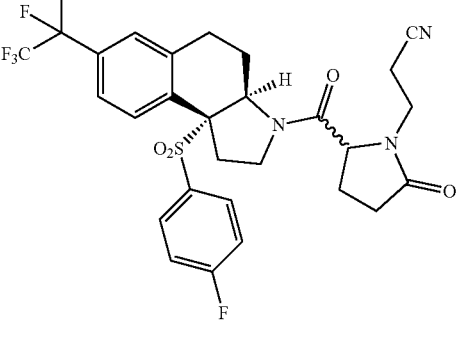 | 664.1 (M + H)+ | 2.11 | D |

TABLE 9-continued

| Ex. # | Structure | LCMS m/z observed | HPLC $t_R$ (min) | HPLC method |
|---|---|---|---|---|
| 242 | 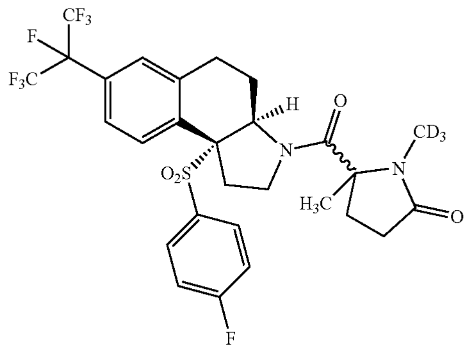 [SMILES: [2H]C([2H])([2H])N1C(=O)CCC1(C)C(=O)N1CC[C@@]2(S(=O)(=O)c3ccc(F)cc3)c3ccc(C(F)(C(F)(F)F)C(F)(F)F)cc3CC[C@@H]12] | 642.3 (M + H)+ | 2.20 | D |
| 243 | 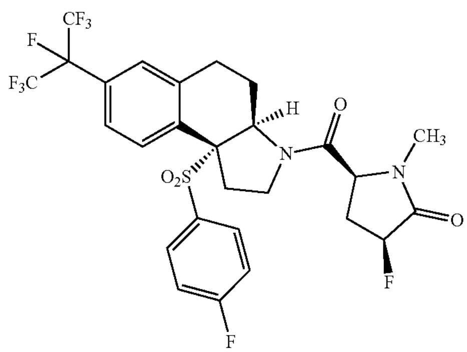 | 643.2 (M + H)+ | 2.16 | D |
| 244 | 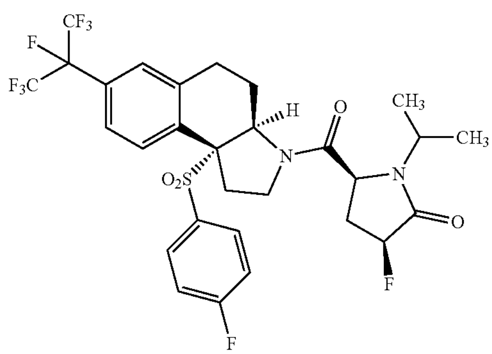 [SMILES: CC(C)N1C(=O)[C@@H](F)C[C@H]1C(=O)N1CC[C@@]2(S(=O)(=O)c3ccc(F)cc3)c3ccc(C(F)(C(F)(F)F)C(F)(F)F)cc3CC[C@@H]12] | 671.0 (M + H)+ | 2.29 | D |
| 245 | 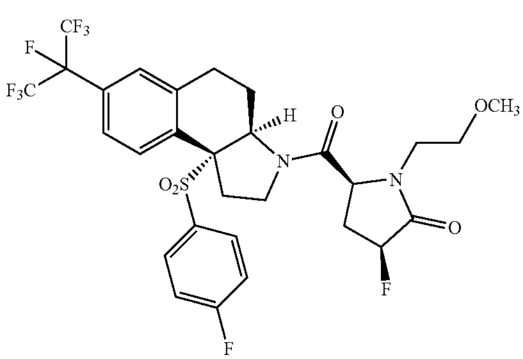 [SMILES: COCCN1C(=O)[C@@H](F)C[C@H]1C(=O)N1CC[C@@]2(S(=O)(=O)c3ccc(F)cc3)c3ccc(C(F)(C(F)(F)F)C(F)(F)F)cc3CC[C@@H]12] | 687.3 (M + H)+ | 2.24 | D |

TABLE 9-continued

| Ex. # | Structure | LCMS m/z observed | HPLC $t_R$ (min) | HPLC method |
|---|---|---|---|---|
| 246 | 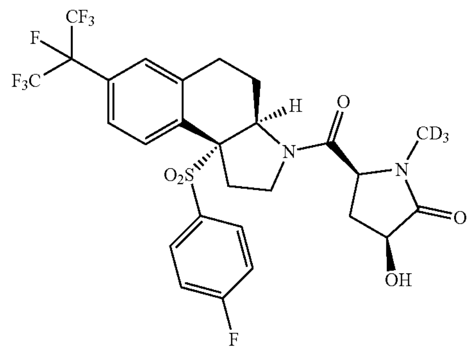 [SMILES: [2H]C([2H])([2H])N1C(=O)[C@@H](O)C[C@H]1C(=O)N1CC[C@@]2(S(=O)(=O)c3ccc(F)cc3)c3ccc(C(F)(C(F)(F)F)C(F)(F)F)cc3CC[C@@H]12] | 644.1 (M + H)+ | 1.99 | D |
| 247 | Homochiral from peak 2 | 669.2 (M + H)+ | 2.23 | D |
| 248 | Homochiral from peak 2 | 672.0 (M + H)+ | 2.32 | D |
| 249 | Homochiral from peak 2 | 668.2 (M + H)+ | 1.10 | B |

TABLE 9-continued

| Ex. # | Structure | LCMS m/z observed | HPLC $t_R$ (min) | HPLC method |
|---|---|---|---|---|
| 250 | Homochiral from peak 2 | 660.4 (M + H)+ | 2.21 | D |
| 251 | Homochiral from peak 2 | 670.4 (M + H)+ | 1.01 | B |
| 252 | Homochiral from peak 2 | 654.2 (M + H)+ | 1.09 | B |
| 253 | Homochiral from peak 2 | 660.0 (M + H)+ | 1.97 | D |

TABLE 9-continued

| Ex. # | Structure | LCMS m/z observed | HPLC $t_R$ (min) | HPLC method |
|---|---|---|---|---|
| 254 | 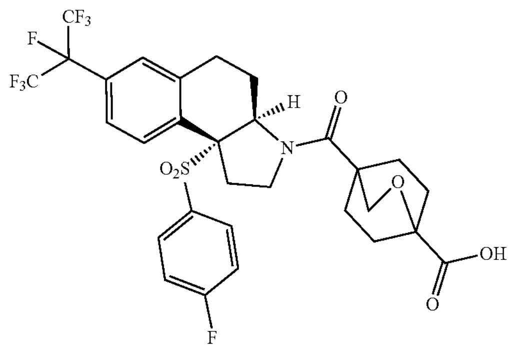 [SMILES: O=C(N1CC[C@@]2(S(=O)(=O)c3ccc(F)cc3)c3ccc(C(F)(C(F)(F)F)C(F)(F)F)cc3CC[C@@H]12)C12CCC(C(=O)O)(CC1)OC2] | 681.8 (M + H)+ | 2.09 | D |
| 255 | 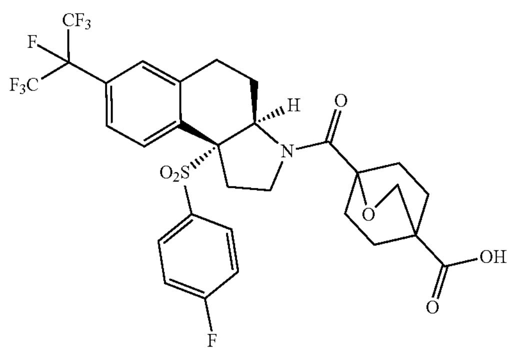 [SMILES: O=C(O)C12CCC(C(=O)N3CC[C@@]4(S(=O)(=O)c5ccc(F)cc5)c5ccc(C(F)(C(F)(F)F)C(F)(F)F)cc5CC[C@@H]34)(CC1)OC2] | 682.1 (M + H)+ | 1.12 | B |
| 256 | Homochiral from peak 2 | 698.1 (M + H)+ | 1.15 | B |
| 257 | From peak 2 | 682.2 (M + H)+ | 2.40 | D |

TABLE 9-continued
| Ex. # | Structure | LCMS m/z observed | HPLC $t_R$ (min) | HPLC method |
|---|---|---|---|---|
| 258 | 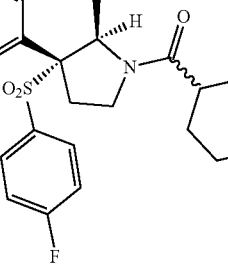 | 639.3 (M + H)+ | 2.09 | D |
| 259 | 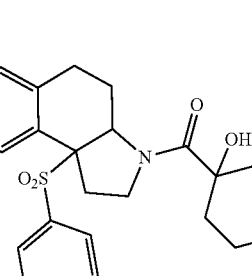 Homochiral from peak 2 | 676.2 (M + H)+ | 1.05 | B |
| 260 | 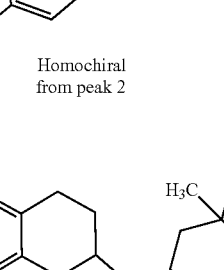 Homochiral from peak 2 | 628.2 (M + H)+ | 2.21 | D |
| 261 | 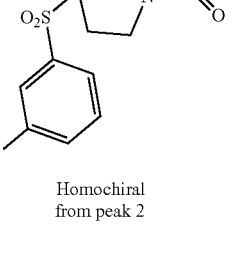 Homochiral from peak 2 | 670.3 (M + H)+ | 1.01 | B |

TABLE 9-continued

| Ex. # | Structure | LCMS m/z observed | HPLC $t_R$ (min) | HPLC method |
|---|---|---|---|---|
| 262 | Homochiral from peak 2 | 641.9 (M + H)+ | 2.00 | D |
| 263 | Homochiral from peak 2 | 586.0 (M + H)+ | 2.05 | D |
| 264 | Homochiral from peak 2 | 628.1 (M + H)+ | 2.18 | D |
| 265 | Homochiral from peak 2 | 654.2 (M + H)+ | 1.09 | B |

TABLE 9-continued
| Ex. # | Structure | LCMS m/z observed | HPLC $t_R$ (min) | HPLC method |
|---|---|---|---|---|
| 266 | 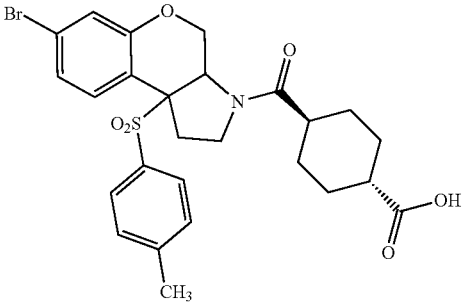<br>Homochiral from peak 2 | 561.9 (M + H)+ | 1.68 | C |
| 267 | 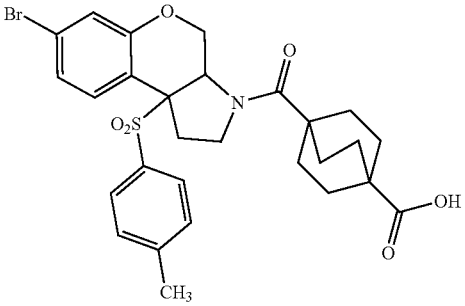<br>Homochiral from peak 2 | 588.1 (M + H)+ | 1.68 | C |
| 268 | 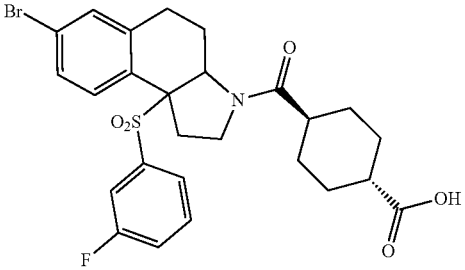<br>Homochiral from peak 2 | 564.1 (M + H)+ | 2.02 | D |
| 269 | 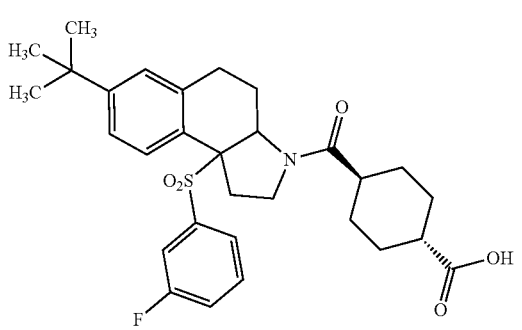<br>Homochiral from peak 2 | 542.1 (M + H)+ | 2.07 | D |

TABLE 9-continued
| Ex. # | Structure | LCMS m/z observed | HPLC $t_R$ (min) | HPLC method |
|---|---|---|---|---|
| 270 | 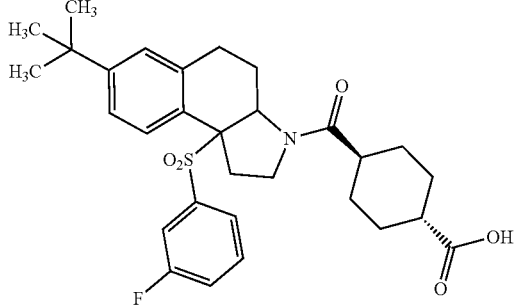<br>Homochiral from peak 1 | 542.2 (M + H)+ | 2.21 | D |
| 271 | 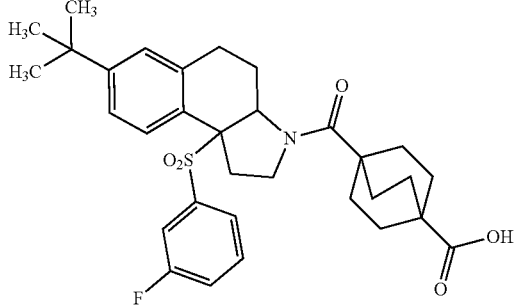<br>Homochiral from peak 2 | 568.5 (M + H)+ | 2.34 | D |
| 272 | 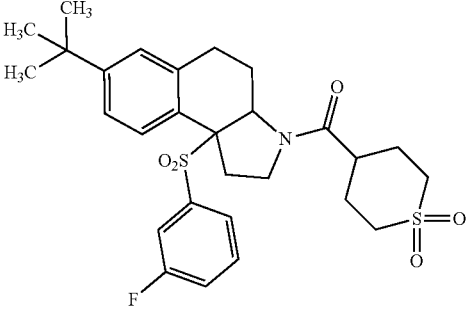<br>Homochiral from peak 2 | 548.1 (M + H)+ | 1.99 | D |
| 273 | 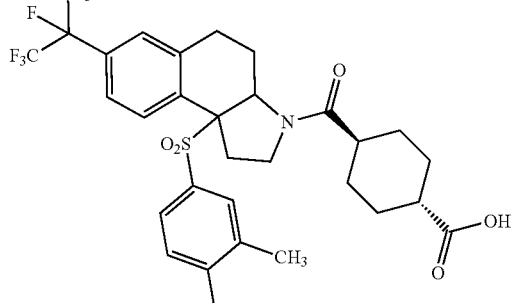<br>Homochiral from peak 2 | 664.1 (M + H)+ | 2.47 | D |

TABLE 9-continued
| Ex. # | Structure | LCMS m/z observed | HPLC $t_R$ (min) | HPLC method |
|---|---|---|---|---|
| 274 | 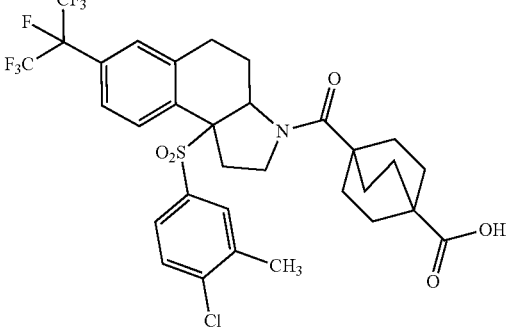<br>Homochiral from peak 2 | 710.2 (M + H)+ | 2.42 | D |
| 275 | 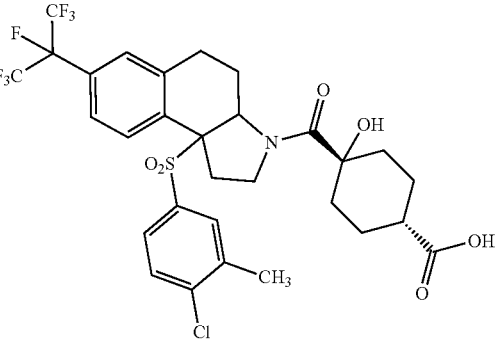<br>Homochiral from peak 2 | 700.1 (M + H)+ | 2.37 | D |
| 276 | 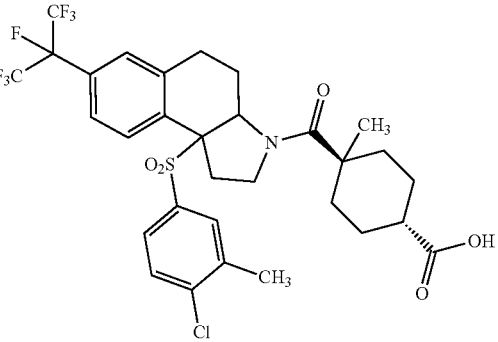<br>Homochiral from peak 2 | 698.1 (M + H)+ | 2.43 | D |

TABLE 9-continued
| Ex. # | Structure | LCMS m/z observed | HPLC $t_R$ (min) | HPLC method |
|---|---|---|---|---|
| 277 | 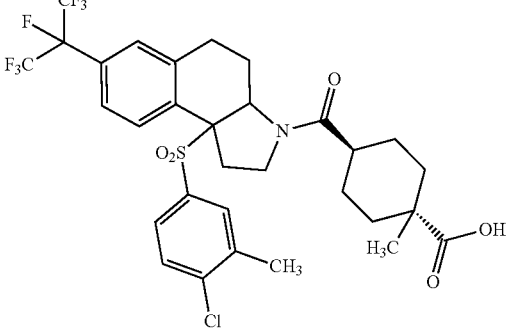 Homochiral from peak 2 | 698.4 (M + H)+ | 2.44 | D |
| 278 | 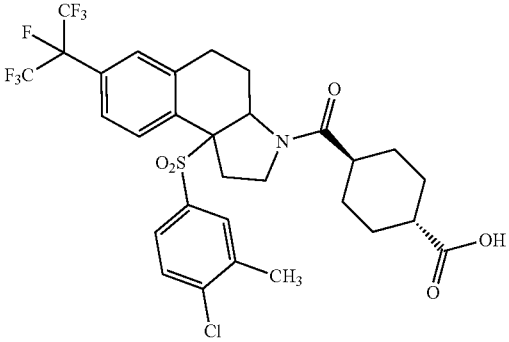 Homochiral from peak 2 | 684.2 (M + H)+ | 2.46 | D |
| 279 | 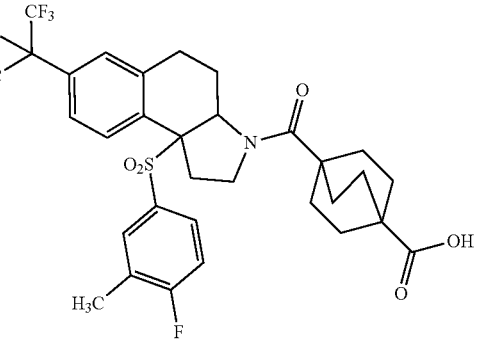 Homochiral from peak 2 | 694.2 (M + H)+ | 2.34 | D |

TABLE 9-continued
| Ex. # | Structure | LCMS m/z observed | HPLC $t_R$ (min) | HPLC method |
|---|---|---|---|---|
| 280 | 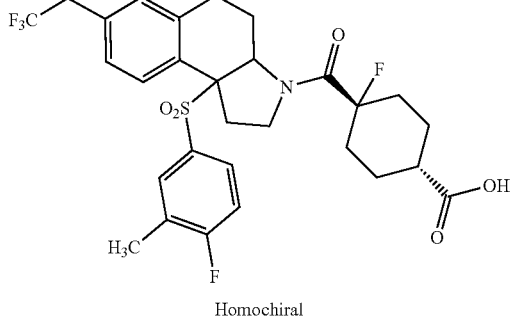<br>Homochiral from peak 2 | 686.1 $(M + H)^+$ | 2.42 | D |
| 281 | 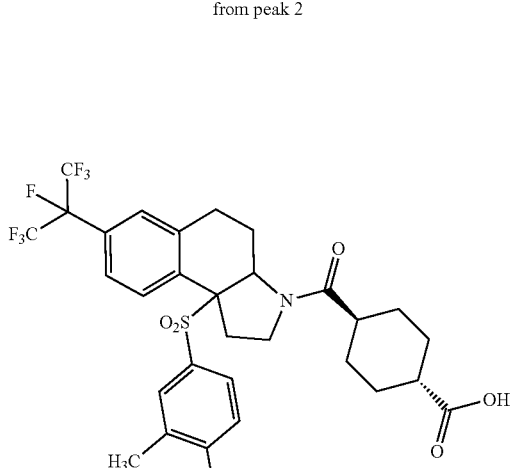<br>Homochiral from peak 2 | 668.2 $(M + H)^+$ | 2.25 | D |
| 282 | 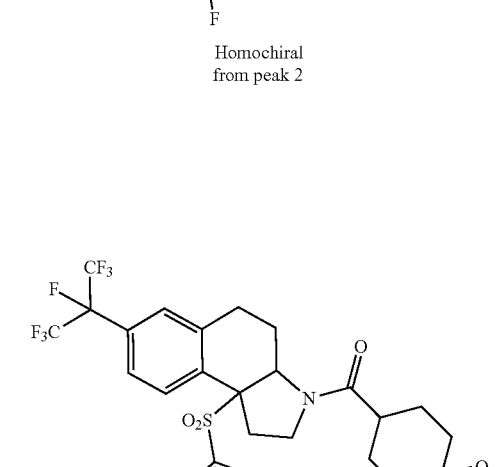<br>Homochiral from peak 2 | 674.1 $(M + H)^+$ | 2.22 | D |

TABLE 9-continued

| Ex. # | Structure | LCMS m/z observed | HPLC $t_R$ (min) | HPLC method |
|---|---|---|---|---|
| 283 | From peak 2 | 680.0 (M + H)+ | 2.28 | D |
| 284 | 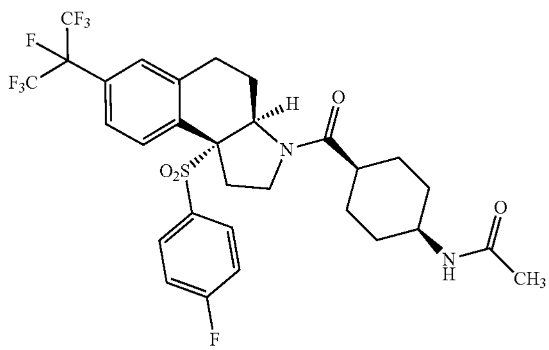 [SMILES: CC(=O)N[C@H]1CC[C@@H](C(=O)N2CC[C@@]3(S(=O)(=O)c4ccc(F)cc4)c4ccc(C(F)(C(F)(F)F)C(F)(F)F)cc4CC[C@@H]23)CC1] | 667.0 (M + H)+ | 2.15 | D |
| 285 | 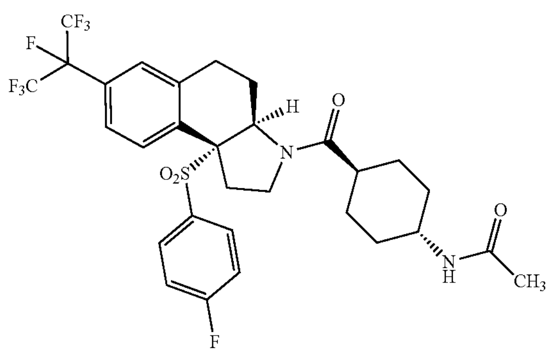 | 693.2 (M + H)+ | 2.23 | D |
| 286 | 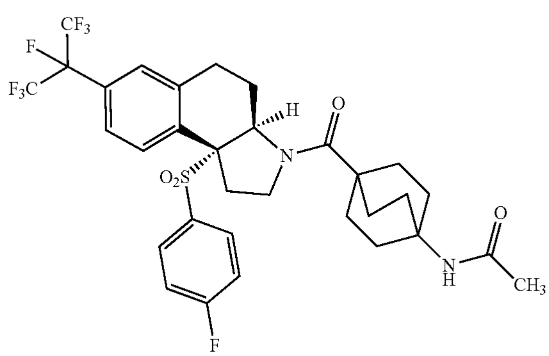 | 667.0 (M + H)+ | 2.14 | D |

TABLE 9-continued

| Ex. # | Structure | LCMS m/z observed | HPLC $t_R$ (min) | HPLC method |
|---|---|---|---|---|
| 287 | From peak 2 | 680.2 (M + H)⁺ | 2.27 | D |
| 288 | From peak 2 | 680.2 (M + H)⁺ | 2.27 | D |
| 289 | [cis, Peak 1] | 674.1 (M + H)⁺ | 1.05 | B |
| 290 | [cis, Peak 2] | 674.1 (M + H)⁺ | 1.05 | B |

TABLE 9-continued
| Ex. # | Structure | LCMS m/z observed | HPLC $t_R$ (min) | HPLC method |
|---|---|---|---|---|
| 291 | 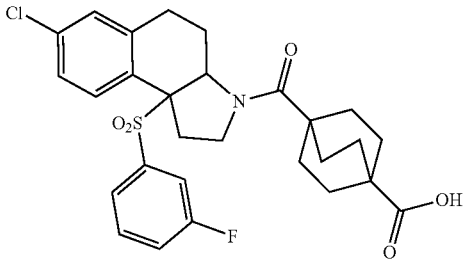 Homochiral from peak 2 | 546.2 (M + H)+ | 1.96 | D |
| 292 | 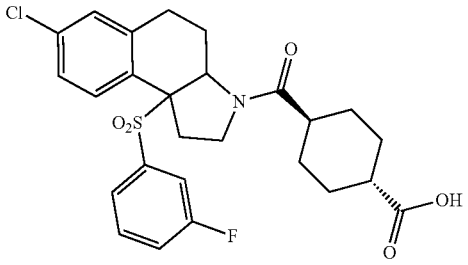 Homochiral from peak 2 | 520.1 (M + H)+ | 1.99 | D |
| 293 | 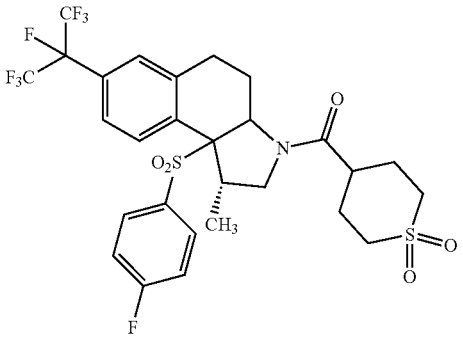 Homochiral from peak 1 | 674.3 (M + H)+ | 2.31 | C |
| 294 | 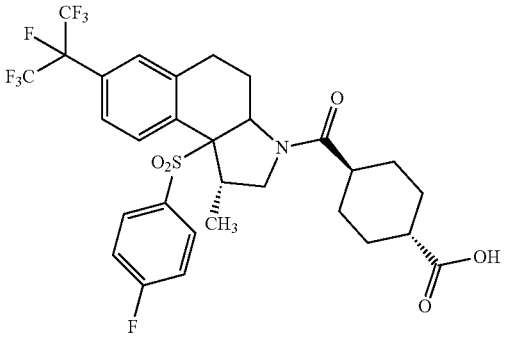 Homochiral from peak 1 | 668.3 (M + H)+ | 2.03 | C |

TABLE 9-continued
| Ex. # | Structure | LCMS m/z observed | HPLC $t_R$ (min) | HPLC method |
|---|---|---|---|---|
| 295 | 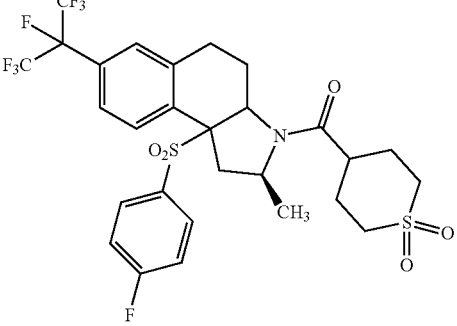<br>Homochiral from peak 1 | 674.1 (M + H)$^+$ | 2.19 | C |
| 296 | 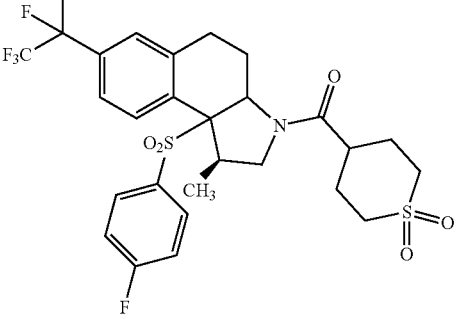<br>Homochiral from peak 1 | 674.0 (M + H)$^+$ | 2.20 | C |
| 297 | 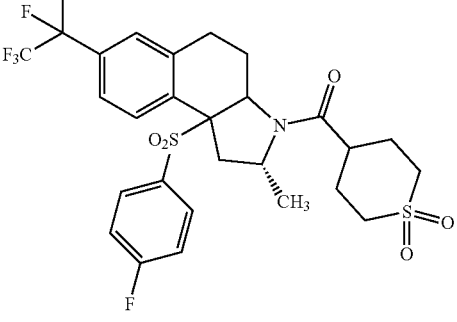<br>Homochiral from peak 2 | 674.2 (M + H)$^+$ | 2.26 | C |
| 298 | 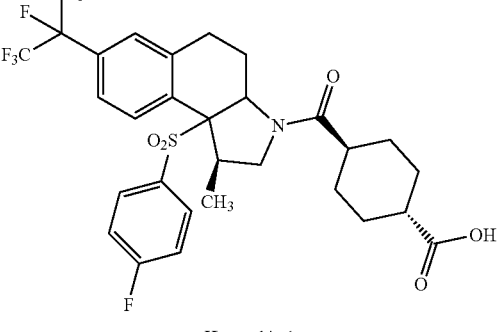<br>Homochiral from peak 1 | 668.1 (M + H)$^+$ | 1.98 | C |

TABLE 9-continued
| Ex. # | Structure | LCMS m/z observed | HPLC $t_R$ (min) | HPLC method |
|---|---|---|---|---|
| 299 | 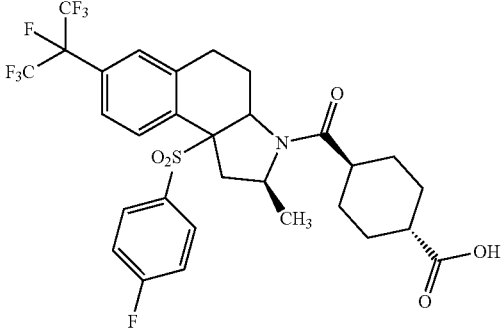<br>Homochiral from peak 1 | 667.9 (M + H)⁺ | 2.34 | C |
| 300 | 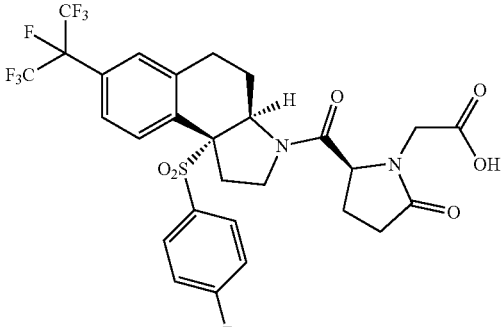 | 669.2 (M + H)⁺ | 1.65 | C |
| 301 | 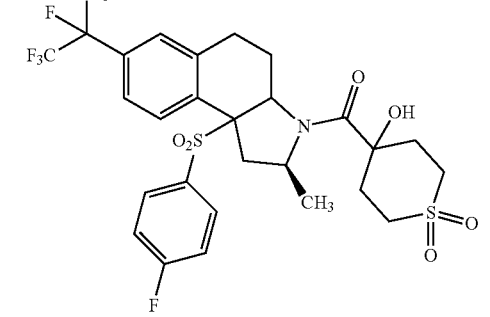<br>Homochiral from peak 1 | 690.1 (M + H)⁺ | 2.17 | C |
| 302 | 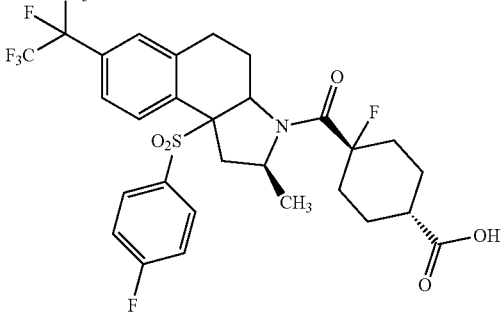<br>Homochiral from peak 1 | 686.2 (M + H)⁺ | 2.14 | C |

TABLE 9-continued
| Ex. # | Structure | LCMS m/z observed | HPLC $t_R$ (min) | HPLC method |
|---|---|---|---|---|
| 303 | 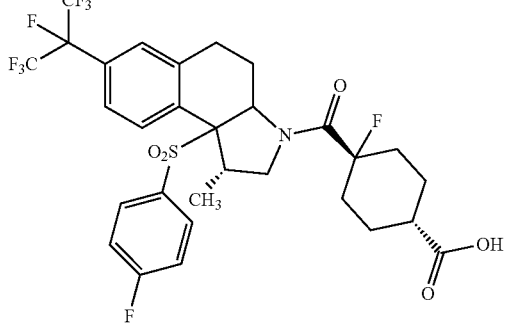 Homochiral from peak 1 | 686.3 (M + H)+ | 2.41 | C |
| 304 | 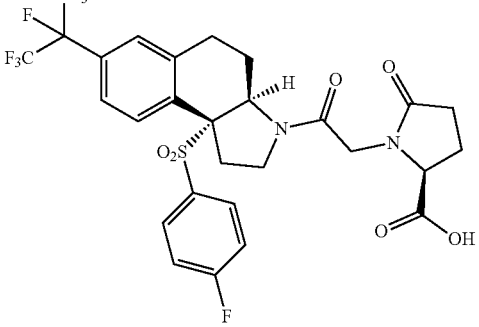 | 669.2 (M + H)+ | 1.61 | C |
| 305 | 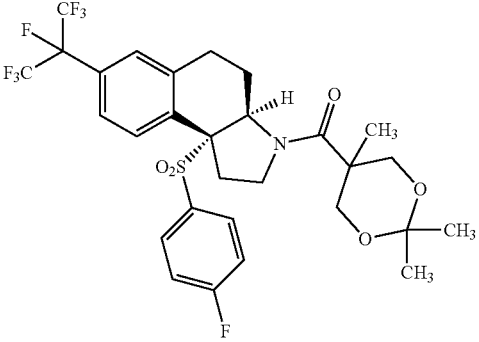 [SMILES: CC1(C)OCC(C)(C(=O)N2CC[C@@]3(S(=O)(=O)c4ccc(F)cc4)c4ccc(C(F)(C(F)(F)F)C(F)(F)F)cc4CC[C@@H]23)CO1] | 656.2 (M + H)+ | 2.55 | C |
| 306 | 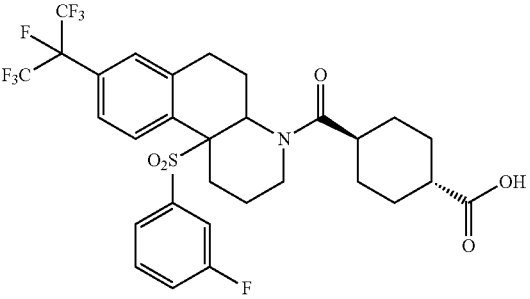 Homochiral from peak 2 | 668.2 (M + H)+ | 1.10 | B |

TABLE 9-continued
| Ex. # | Structure | LCMS m/z observed | HPLC $t_R$ (min) | HPLC method |
|---|---|---|---|---|
| 307 | 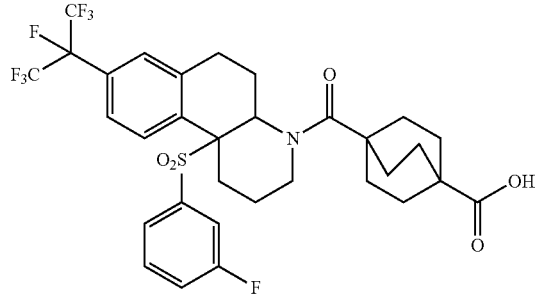 Homochiral from peak 2 | 694.5 (M + H)+ | 1.10 | B |
| 308 | 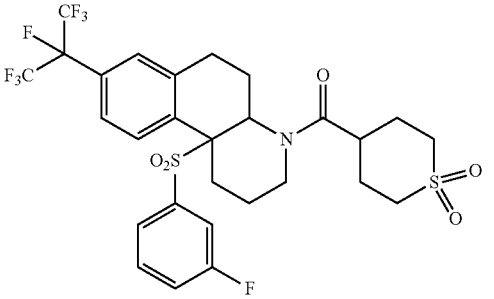 Homochiral from peak 2 | 674.4 (M + H)+ | 1.04 | B |
| 309 | 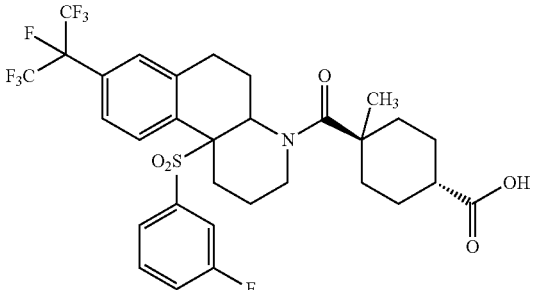 Homochiral from peak 2 | 682.2 (M + H)+ | 1.30 | B |
| 310 | 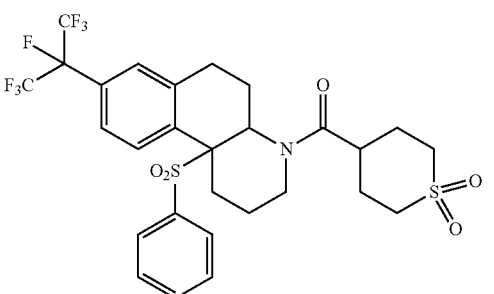 Homochiral from peak 2 | 674.1 (M + H)+ | 2.20 | C |

TABLE 9-continued
| Ex. # | Structure | LCMS m/z observed | HPLC $t_R$ (min) | HPLC method |
|---|---|---|---|---|
| 311 | 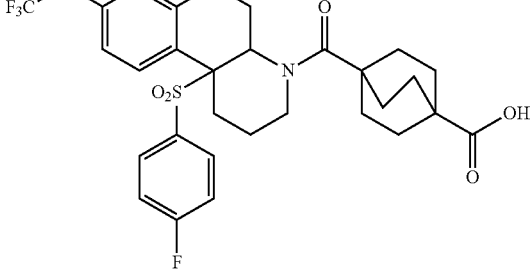 Homochiral from peak 2 | 694.1 (M + H)+ | 2.38 | C |
| 312 | 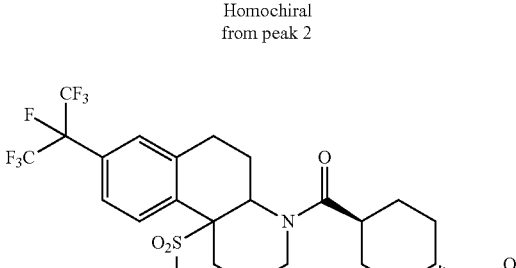 Homochiral from peak 2 | 650.3 (M + H)+ | 2.24 | C |
| 313 | 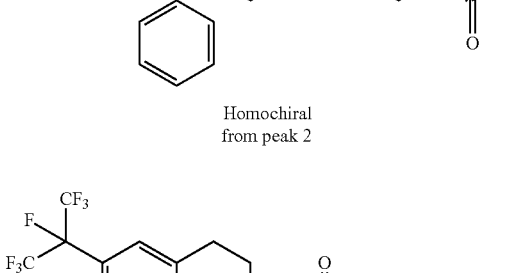 Homochiral from peak 2 | 676.4 (M + H)+ | 2.36 | C |
| 314 | 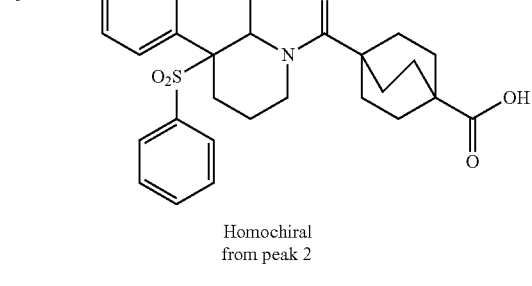 Homochiral from peak 2 | 664.0 (M + H)+ | 2.21 | C |

TABLE 9-continued
| Ex. # | Structure | LCMS m/z observed | HPLC $t_R$ (min) | HPLC method |
|---|---|---|---|---|
| 315 | 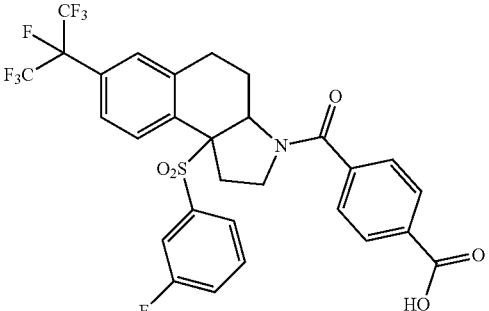<br>Homochiral from peak 2 | 648.1 (M + H)+ | 1.74 | C |
| 316 | 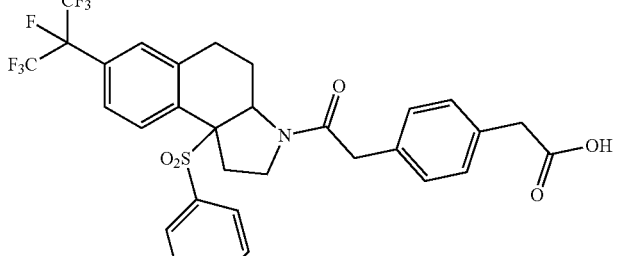<br>Homochiral from peak 2 | 676.2 (M + H)+ | 1.83 | C |
| 317 | 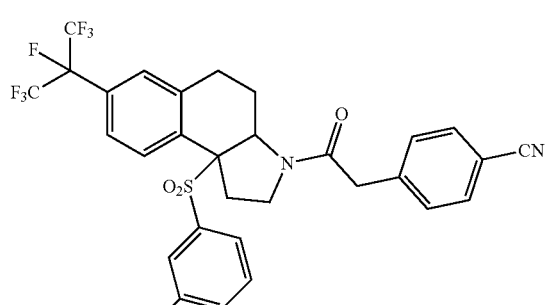<br>Homochiral from peak 2 | 643.2 (M + H)+ | 2.34 | C |
| 318 | 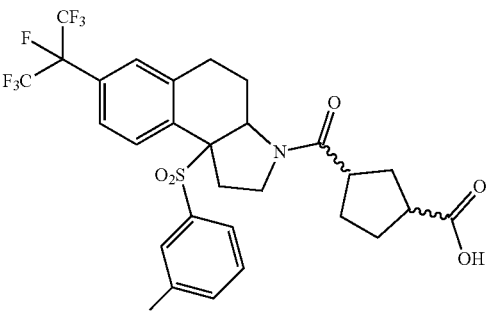<br>From peak 2 | 640.1 (M + H)+ | 1.98 | C |

TABLE 9-continued
| Ex. # | Structure | LCMS m/z observed | HPLC $t_R$ (min) | HPLC method |
|---|---|---|---|---|
| 319 | 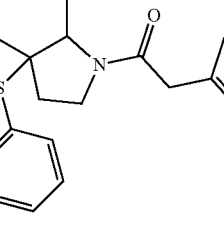<br>Homochiral<br>from peak 2 | 662.4 (M + H)+ | 1.81 | C |
| 320 | <br>Homochiral<br>from peak 2 | 663.4 (M + H)+ | 1.69 | C |
| 321 | <br>From peak 2 | 666.2 (M + H)+ | 2.04 | C |
| 322 | 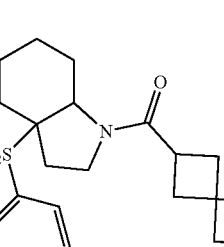 | 648.1 (M + H)+ | 2.19 | D |

TABLE 9-continued

| Ex. # | Structure | LCMS m/z observed | HPLC $t_R$ (min) | HPLC method |
|---|---|---|---|---|
| 323 | 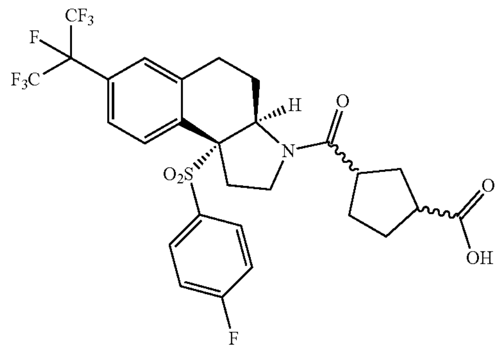 [SMILES: O=C(O)C1CCC(C(=O)N2CC[C@@]3(S(=O)(=O)c4ccc(F)cc4)c4ccc(C(F)(C(F)(F)F)C(F)(F)F)cc4CC[C@@H]23)C1] | 640.1 (M + H)+ | 1.84 | C |
| 324 | Homochiral from peak 2 | 650.1 (M + H)+ | 2.07 | D |
| 325 | Homochiral from peak 2 | 662.2 (M + H)+ | 1.81 | C |
| 326 | 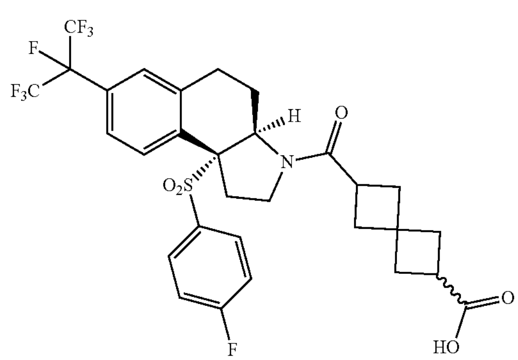 [SMILES: O=C(O)C1CC2(C1)CC(C(=O)N1CC[C@@]3(S(=O)(=O)c4ccc(F)cc4)c4ccc(C(F)(C(F)(F)F)C(F)(F)F)cc4CC[C@@H]13)C2] | 666.4 (M + H)+ | 1.89 | C |

TABLE 9-continued
| Ex. # | Structure | LCMS m/z observed | HPLC $t_R$ (min) | HPLC method |
|---|---|---|---|---|
| 327 | 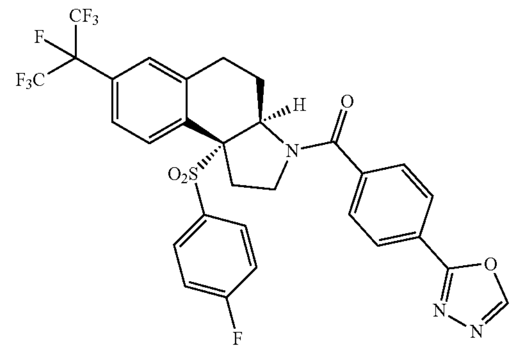 [SMILES: O=C(c1ccc(-c2nnco2)cc1)N1CC[C@@]2(S(=O)(=O)c3ccc(F)cc3)c3ccc(C(F)(C(F)(F)F)C(F)(F)F)cc3CC[C@@H]12] | 672.2 (M + H)⁺ | 2.30 | D |
| 328 | 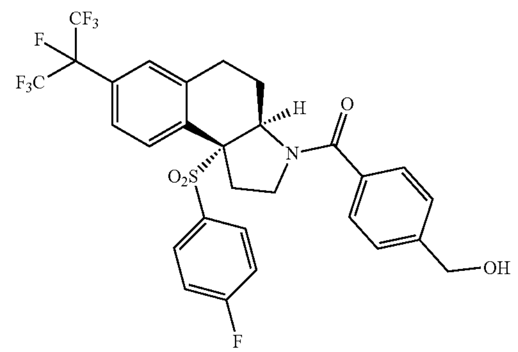 [SMILES: O=C(c1ccc(CO)cc1)N1CC[C@@]2(S(=O)(=O)c3ccc(F)cc3)c3ccc(C(F)(C(F)(F)F)C(F)(F)F)cc3CC[C@@H]12] | 634.0 (M + H)⁺ | 2.15 | D |
| 329 | 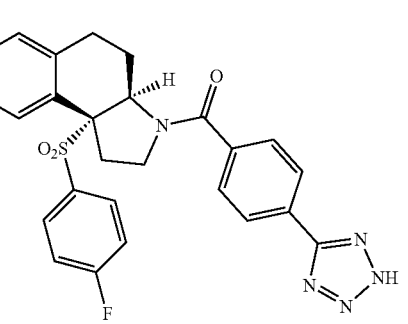 | 672.4 (M + H)⁺ | 1.81 | C |
| 330 | 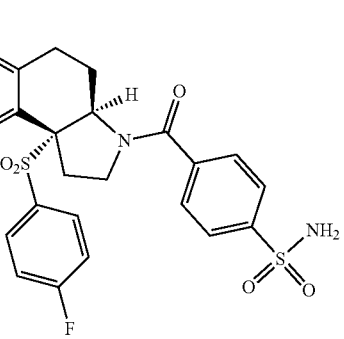 | 682.9 (M + H)⁺ | 2.13 | D |

TABLE 9-continued

| Ex. # | Structure | LCMS m/z observed | HPLC $t_R$ (min) | HPLC method |
|---|---|---|---|---|
| 331 | 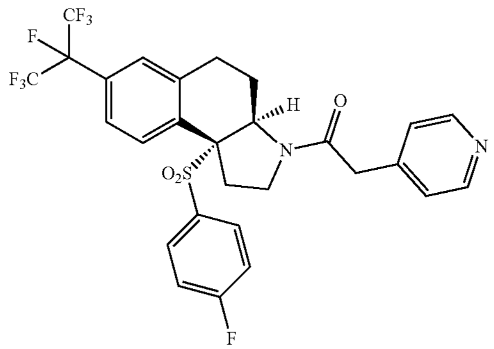 [SMILES: O=C(Cc1ccncc1)N1CC[C@@]2(S(=O)(=O)c3ccc(F)cc3)c3ccc(C(F)(C(F)(F)F)C(F)(F)F)cc3CC[C@@H]12] | 619.2 (M + H)+ | 1.85 | D |
| 332 | 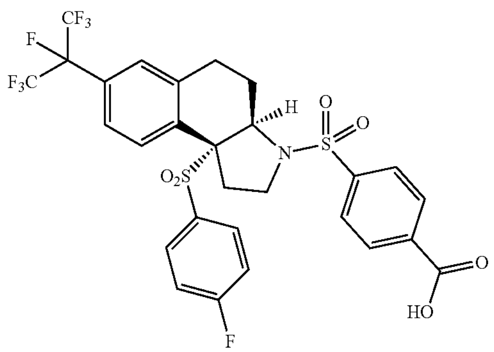 [SMILES: O=C(O)c1ccc(S(=O)(=O)N2CC[C@@]3(S(=O)(=O)c4ccc(F)cc4)c4ccc(C(F)(C(F)(F)F)C(F)(F)F)cc4CC[C@@H]23)cc1] | 684.1 (M + H)+ | 1.82 | C |
| 333 | 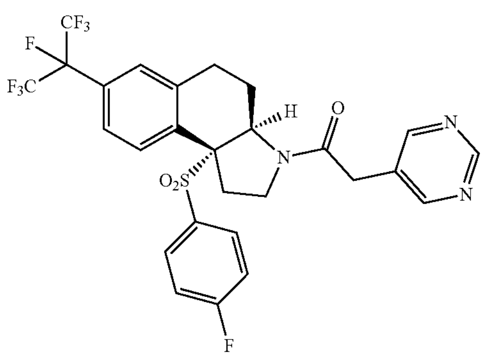 [SMILES: O=C(Cc1cncnc1)N1CC[C@@]2(S(=O)(=O)c3ccc(F)cc3)c3ccc(C(F)(C(F)(F)F)C(F)(F)F)cc3CC[C@@H]12] | 620.1 (M + H)+ | 2.07 | C |
| 334 | 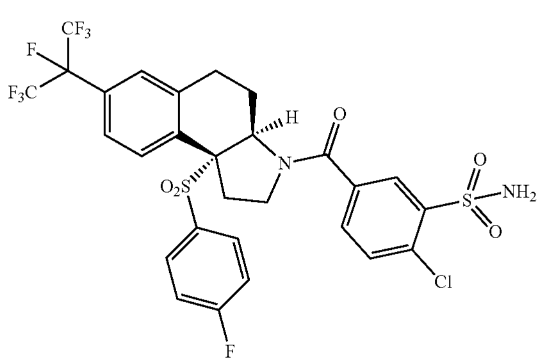 [SMILES: NS(=O)(=O)c1cc(C(=O)N2CC[C@@]3(S(=O)(=O)c4ccc(F)cc4)c4ccc(C(F)(C(F)(F)F)C(F)(F)F)cc4CC[C@@H]23)ccc1Cl] | 716.9 (M + H)+ | 2.24 | C |

TABLE 9-continued

| Ex. # | Structure | LCMS m/z observed | HPLC $t_R$ (min) | HPLC method |
|---|---|---|---|---|
| 335 | 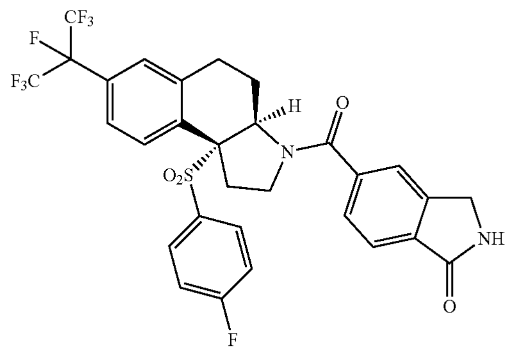 [SMILES: O=C1NCc2cc(C(=O)N3CC[C@@]4(S(=O)(=O)c5ccc(F)cc5)c5ccc(C(F)(C(F)(F)F)C(F)(F)F)cc5CC[C@@H]34)ccc21] | 659.1 (M + H)+ | 2.07 | C |
| 336 | 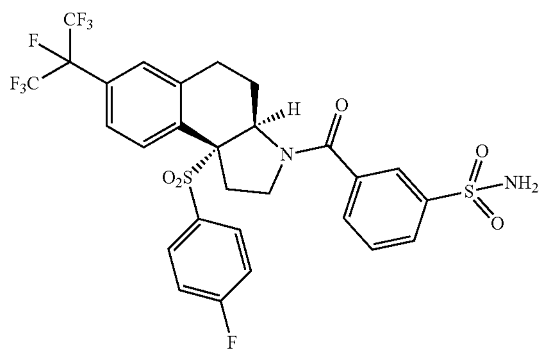 [SMILES: NS(=O)(=O)c1cccc(C(=O)N2CC[C@@]3(S(=O)(=O)c4ccc(F)cc4)c4ccc(C(F)(C(F)(F)F)C(F)(F)F)cc4CC[C@@H]23)c1] | 683.3 (M + H)+ | 2.17 | C |
| 337 | 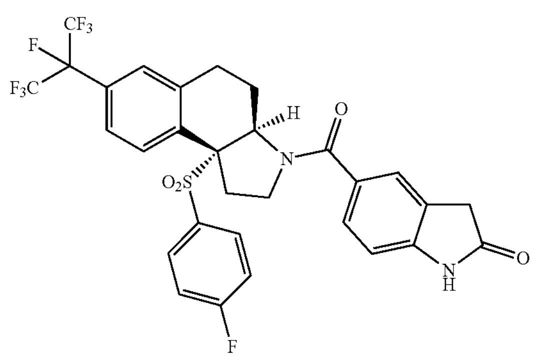 [SMILES: O=C1Cc2cc(C(=O)N3CC[C@@]4(S(=O)(=O)c5ccc(F)cc5)c5ccc(C(F)(C(F)(F)F)C(F)(F)F)cc5CC[C@@H]34)ccc2N1] | 659.0 (M + H)+ | 2.08 | D |
| 338 | 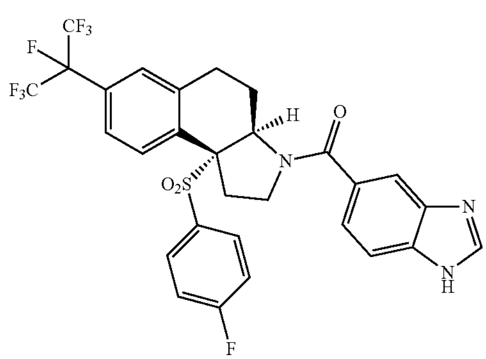 [SMILES: O=C(c1ccc2[nH]cnc2c1)N1CC[C@@]2(S(=O)(=O)c3ccc(F)cc3)c3ccc(C(F)(C(F)(F)F)C(F)(F)F)cc3CC[C@@H]12] | 644.1 (M + H)+ | 1.86 | D |

TABLE 9-continued
| Ex. # | Structure | LCMS m/z observed | HPLC $t_R$ (min) | HPLC method |
|---|---|---|---|---|
| 339 | 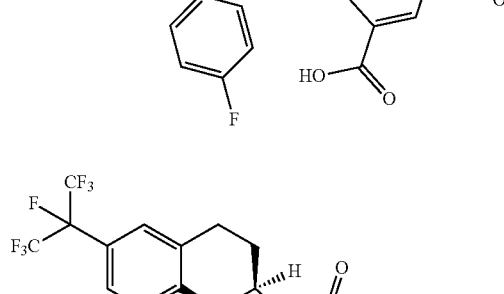 | 692.2 (M + H)+ | 1.44 | C |
| 340 | 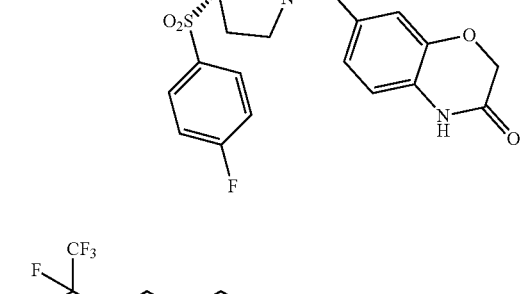 | 675.3 (M + H)+ | 2.19 | C |
| 341 | 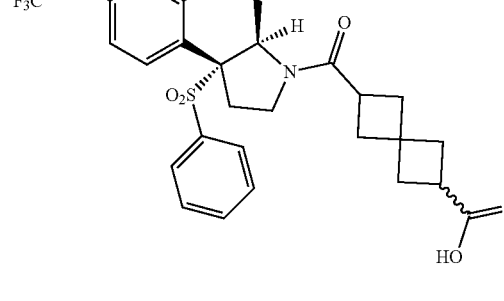 | 648.1 (M + H)+ | 1.81 | C |
| 342 | 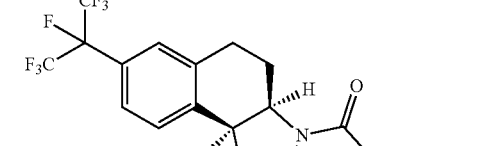 | 630.3 (M + H)+ | 1.72 | C |

TABLE 9-continued

| Ex. # | Structure | LCMS m/z observed | HPLC $t_R$ (min) | HPLC method |
|---|---|---|---|---|
| 343 | 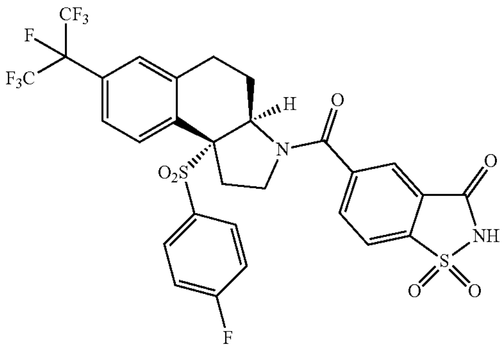 [SMILES: O=C1NS(=O)(=O)c2ccc(C(=O)N3CC[C@@]4(S(=O)(=O)c5ccc(F)cc5)c5ccc(C(F)(C(F)(F)F)C(F)(F)F)cc5CC[C@@H]34)cc21] | 709.3 (M + H)+ | 2.13 | D |
| 344 | 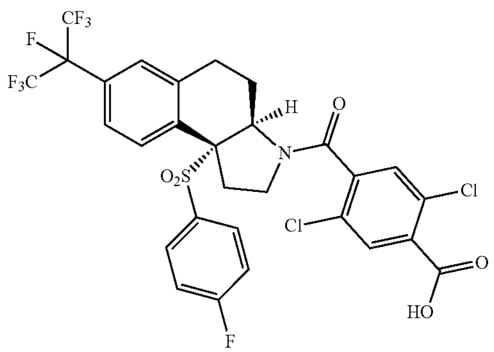 [SMILES: O=C(O)c1cc(Cl)c(C(=O)N2CC[C@@]3(S(=O)(=O)c4ccc(F)cc4)c4ccc(C(F)(C(F)(F)F)C(F)(F)F)cc4CC[C@@H]23)cc1Cl] | 716.3 (M + H)+ | 1.83 | C |
| 345 | 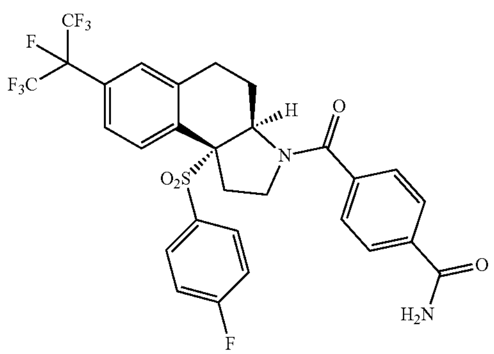 [SMILES: NC(=O)c1ccc(C(=O)N2CC[C@@]3(S(=O)(=O)c4ccc(F)cc4)c4ccc(C(F)(C(F)(F)F)C(F)(F)F)cc4CC[C@@H]23)cc1] | 647.1 (M + H)+ | 2.08 | C |
| 346 | 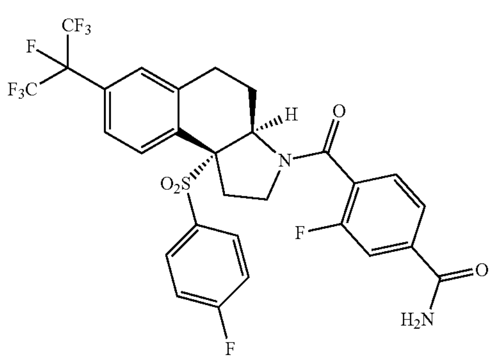 [SMILES: NC(=O)c1ccc(C(=O)N2CC[C@@]3(S(=O)(=O)c4ccc(F)cc4)c4ccc(C(F)(C(F)(F)F)C(F)(F)F)cc4CC[C@@H]23)c(F)c1] | 665.1 (M + H)+ | 2.14 | C |

TABLE 9-continued
| Ex. # | Structure | LCMS m/z observed | HPLC $t_R$ (min) | HPLC method |
|---|---|---|---|---|
| 347 | 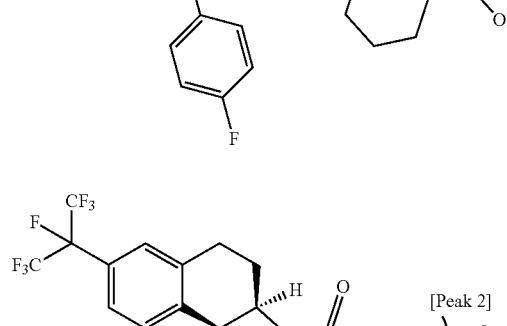 [Peak 1] | 654.1 (M + H)+ | 2.17 | D |
| 348 | 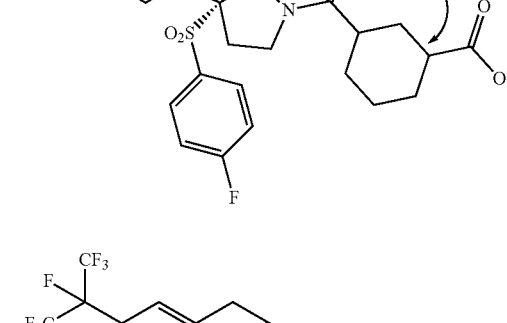 [Peak 2] | 654.4 (M + H)+ | 2.16 | D |
| 349 | 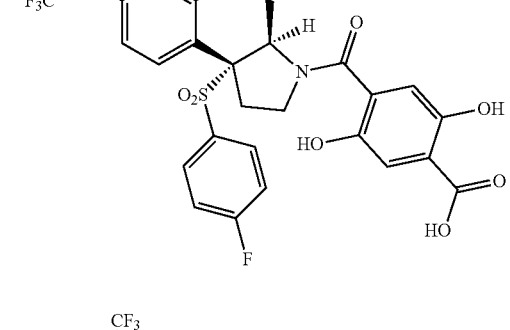 | 680.1 (M + H)+ | 1.79 | C |
| 350 | 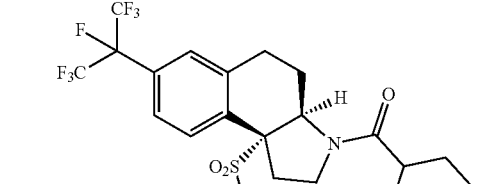 | 610.3 (M + H)+ | 2.59 | D |

TABLE 9-continued

| Ex. # | Structure | LCMS m/z observed | HPLC $t_R$ (min) | HPLC method |
|---|---|---|---|---|
| 351 | 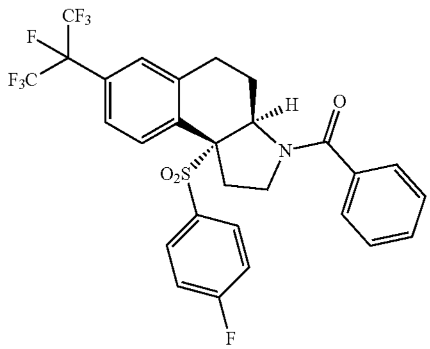 [SMILES: O=C(c1ccccc1)N1CC[C@@]2(S(=O)(=O)c3ccc(F)cc3)c3ccc(C(F)(C(F)(F)F)C(F)(F)F)cc3CC[C@@H]12] | 604.2 (M + H)+ | 2.39 | C |
| 352 | 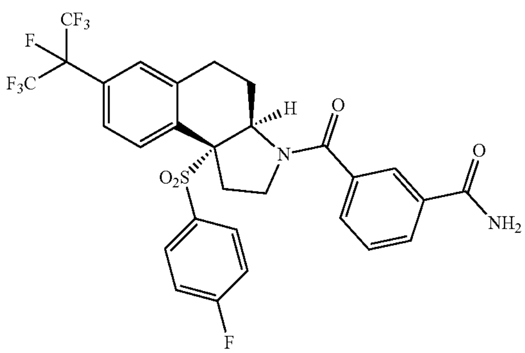 [SMILES: NC(=O)c1cccc(C(=O)N2CC[C@@]3(S(=O)(=O)c4ccc(F)cc4)c4ccc(C(F)(C(F)(F)F)C(F)(F)F)cc4CC[C@@H]23)c1] | 647.3 (M + H)+ | 2.03 | C |
| 353 | 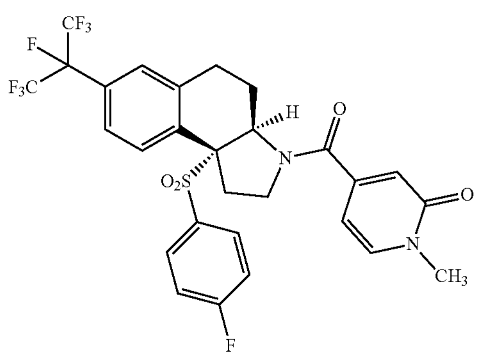 [SMILES: Cn1ccc(C(=O)N2CC[C@@]3(S(=O)(=O)c4ccc(F)cc4)c4ccc(C(F)(C(F)(F)F)C(F)(F)F)cc4CC[C@@H]23)cc1=O] | 635.2 (M + H)+ | 2.13 | D |
| 354 | 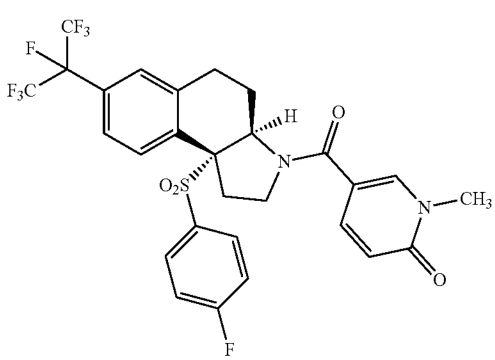 [SMILES: Cn1cc(C(=O)N2CC[C@@]3(S(=O)(=O)c4ccc(F)cc4)c4ccc(C(F)(C(F)(F)F)C(F)(F)F)cc4CC[C@@H]23)ccc1=O] | 635.1 (M + H)+ | 2.19 | D |

TABLE 9-continued

| Ex. # | Structure | LCMS m/z observed | HPLC $t_R$ (min) | HPLC method |
|---|---|---|---|---|
| 355 | 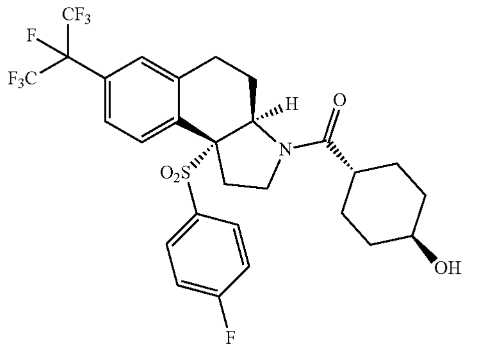 [SMILES: O=C([C@H]1CC[C@H](O)CC1)N1CC[C@@]2(S(=O)(=O)c3ccc(F)cc3)c3ccc(C(F)(C(F)(F)F)C(F)(F)F)cc3CC[C@@H]12] | 626.2 (M + H)+ | 2.24 | C |
| 356 | 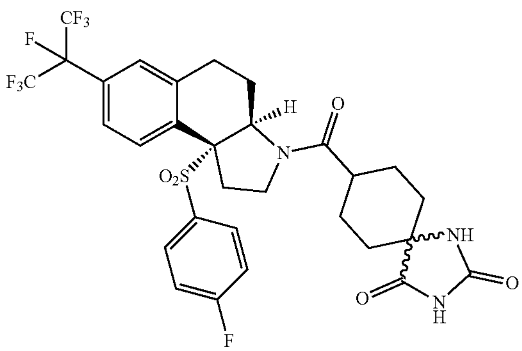 | 694.1 (M + H)+ | 2.12 | D |
| 357 | [Peak 1] | 666.2 (M + H)+ | 1.05 | B |
| 358 | [Peak 2] | 666.2 (M + H)+ | 1.05 | B |

TABLE 9-continued
| Ex. # | Structure | LCMS m/z observed | HPLC $t_R$ (min) | HPLC method |
|---|---|---|---|---|
| 359 | 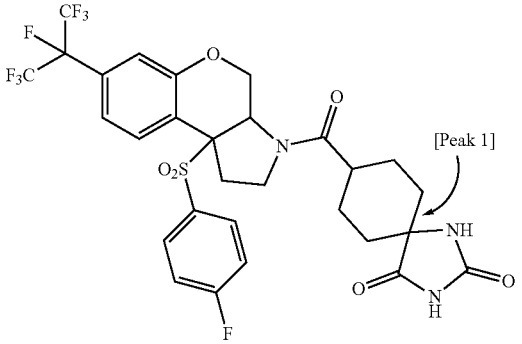 Homochiral from peak 2 | 696.0 (M + H)+ | 2.10 | C |
| 360 | 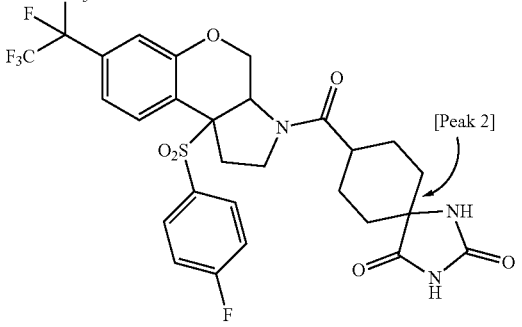 Homochiral from peak 2 | 696.3 (M + H)+ | 2.12 | C |
| 361 | 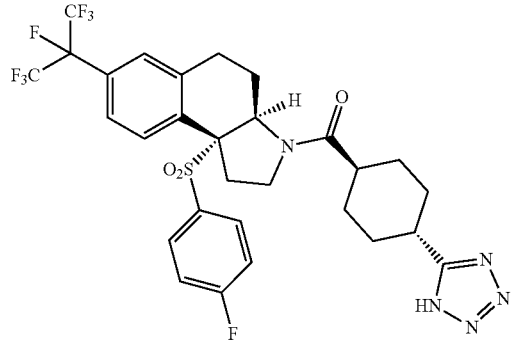 [SMILES: O=C([C@H]1CC[C@H](c2nnn[nH]2)CC1)N1CC[C@@]2(S(=O)(=O)c3ccc(F)cc3)c3ccc(C(F)(C(F)(F)F)C(F)(F)F)cc3CC[C@@H]12] | 678.3 (M + H)+ | 2.18 | D |
| 362 | 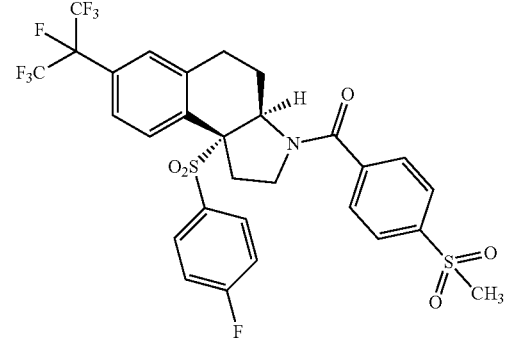 [SMILES: CS(=O)(=O)c1ccc(C(=O)N2CC[C@@]3(S(=O)(=O)c4ccc(F)cc4)c4ccc(C(F)(C(F)(F)F)C(F)(F)F)cc4CC[C@@H]23)cc1] | 682.2 (M + H)+ | 2.29 | C |

TABLE 9-continued
| Ex. # | Structure | LCMS m/z observed | HPLC $t_R$ (min) | HPLC method |
|---|---|---|---|---|
| 363 | 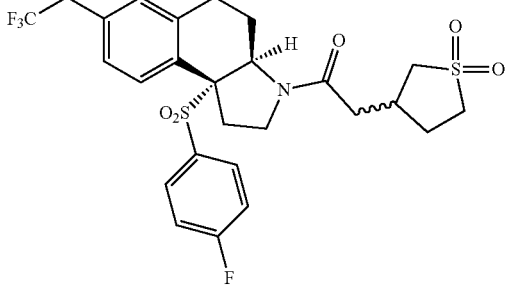 | 660.0 (M + H)+ | 2.19 | C |
| 364 | 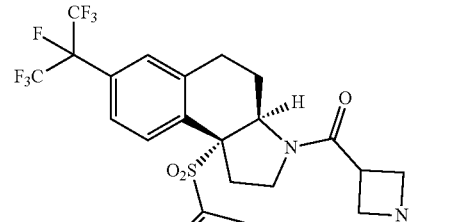 | 624.9 (M + H)+ | 2.07 | C |
| 365 | 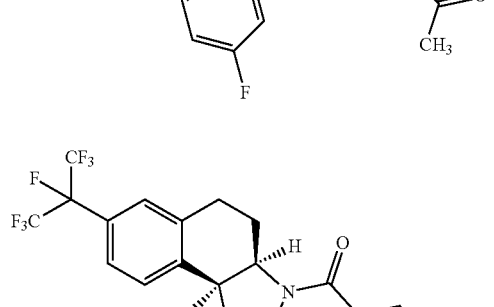 | 689.2 (M + H)+ | 2.18 | C |
| 366 | 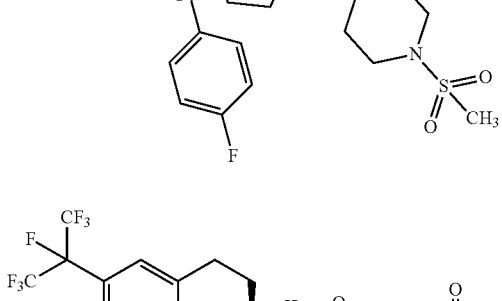 [Peak 1] | 660.2 (M + H)+ | 1.02 | B |

TABLE 9-continued

| Ex. # | Structure | LCMS m/z observed | HPLC $t_R$ (min) | HPLC method |
|---|---|---|---|---|
| 367 | [Peak 2] | 660.2 (M + H)+ | 1.02 | B |
| 368 | 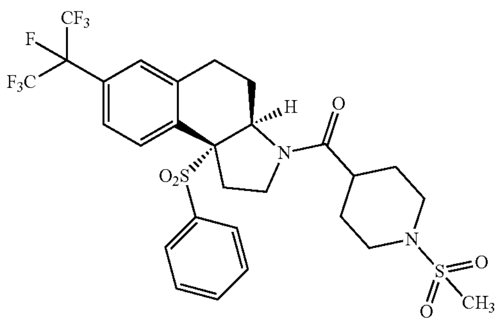 [SMILES: CS(=O)(=O)N1CCC(C(=O)N2CC[C@@]3(S(=O)(=O)c4ccccc4)c4ccc(C(F)(C(F)(F)F)C(F)(F)F)cc4CC[C@@H]23)CC1] | 671.2 (M + H)+ | 2.13 | C |
| 369 | Homochiral from Peak 2 | 703.2 (M + H)+ | 2.26 | D |
| 370 | Homochiral from Peak 2 | 689.2 (M + H)+ | 2.25 | C |

TABLE 9-continued

| Ex. # | Structure | LCMS m/z observed | HPLC $t_R$ (min) | HPLC method |
|---|---|---|---|---|
| 371 | 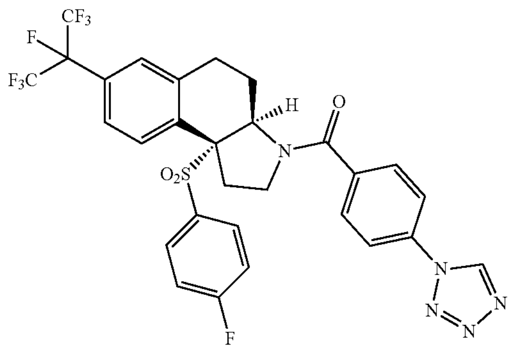 [SMILES: O=C(c1ccc(-n2cnnn2)cc1)N1CC[C@@]2(S(=O)(=O)c3ccc(F)cc3)c3ccc(C(F)(C(F)(F)F)C(F)(F)F)cc3CC[C@@H]12] | 672.0 (M + H)+ | 2.23 | D |
| 372 | 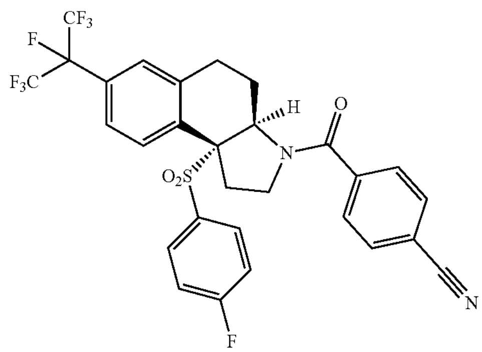 [SMILES: N#Cc1ccc(C(=O)N2CC[C@@]3(S(=O)(=O)c4ccc(F)cc4)c4ccc(C(F)(C(F)(F)F)C(F)(F)F)cc4CC[C@@H]23)cc1] | 629.2 (M + H)+ | 2.40 | C |
| 373 | 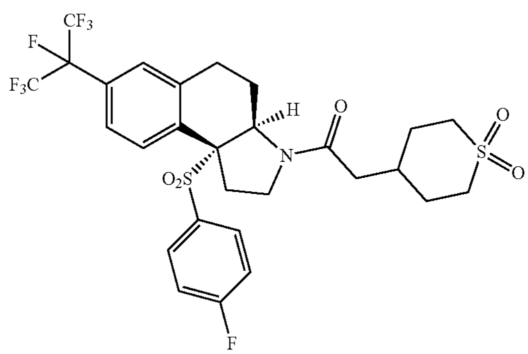 [SMILES: O=C(CC1CCS(=O)(=O)CC1)N1CC[C@@]2(S(=O)(=O)c3ccc(F)cc3)c3ccc(C(F)(C(F)(F)F)C(F)(F)F)cc3CC[C@@H]12] | 674.3 (M + H)+ | 2.19 | C |
| 374 | Homochiral from Peak 2 | 658.0 (M + H)+ | 2.14 | D |

TABLE 9-continued

| Ex. # | Structure | LCMS m/z observed | HPLC $t_R$ (min) | HPLC method |
|---|---|---|---|---|
| 375 | 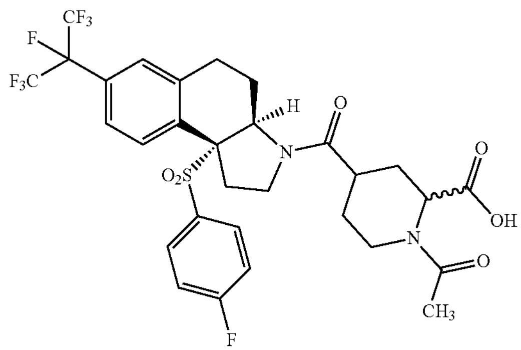 [SMILES: CC(=O)N1CCC(C(=O)N2CC[C@@]3(S(=O)(=O)c4ccc(F)cc4)c4ccc(C(F)(C(F)(F)F)C(F)(F)F)cc4CC[C@@H]23)CC1C(=O)O] | 697.2 (M + H)+ | 1.71 | C |
| 376 | 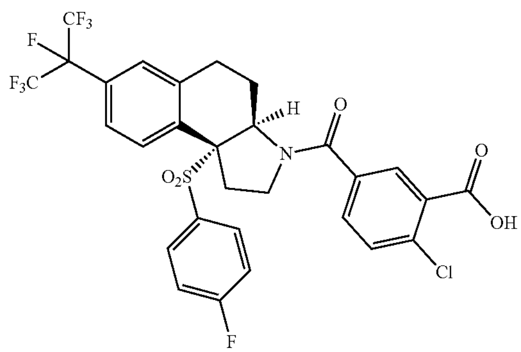 [SMILES: O=C(O)c1cc(C(=O)N2CC[C@@]3(S(=O)(=O)c4ccc(F)cc4)c4ccc(C(F)(C(F)(F)F)C(F)(F)F)cc4CC[C@@H]23)ccc1Cl] | 682.2 (M + H)+ | 2.34 | D |
| 377 | 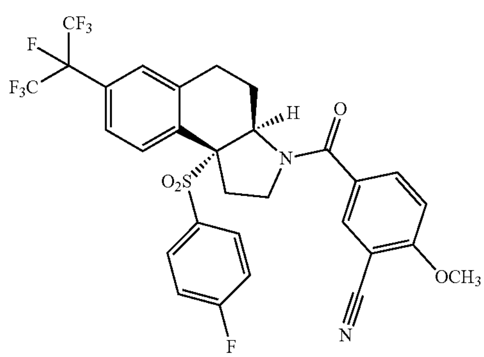 [SMILES: COc1ccc(C(=O)N2CC[C@@]3(S(=O)(=O)c4ccc(F)cc4)c4ccc(C(F)(C(F)(F)F)C(F)(F)F)cc4CC[C@@H]23)cc1C#N] | 659.2 (M + H)+ | 2.32 | C |
| 378 | 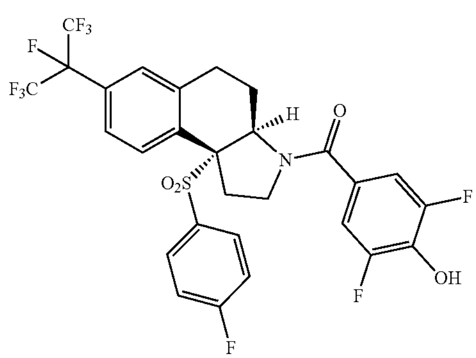 [SMILES: O=C(c1cc(F)c(O)c(F)c1)N1CC[C@@]2(S(=O)(=O)c3ccc(F)cc3)c3ccc(C(F)(C(F)(F)F)C(F)(F)F)cc3CC[C@@H]12] | 656.0 (M + H)+ | 2.20 | C |

TABLE 9-continued

| Ex. # | Structure | LCMS m/z observed | HPLC t$_R$ (min) | HPLC method |
|---|---|---|---|---|
| 379 | 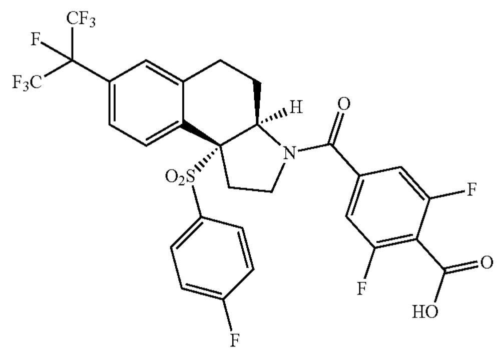 [SMILES: O=C(O)c1c(F)cc(C(=O)N2CC[C@@]3(S(=O)(=O)c4ccc(F)cc4)c4ccc(C(F)(C(F)(F)F)C(F)(F)F)cc4CC[C@@H]23)cc1F] | 684.2 (M + H)$^+$ | 2.24 | D |
| 380 | 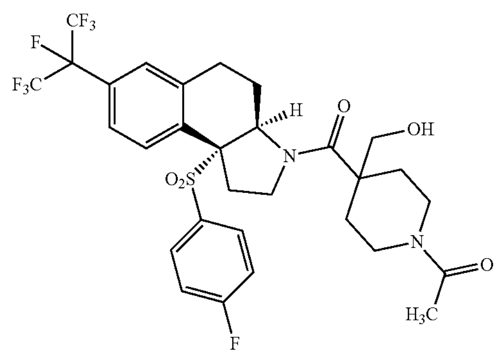 [SMILES: CC(=O)N1CCC(CO)(C(=O)N2CC[C@@]3(S(=O)(=O)c4ccc(F)cc4)c4ccc(C(F)(C(F)(F)F)C(F)(F)F)cc4CC[C@@H]23)CC1] | 683.1 (M + H)$^+$ | 2.00 | D |
| 381 | 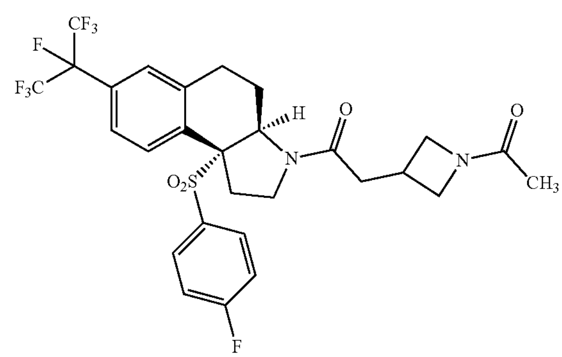 [SMILES: CC(=O)N1CC(CC(=O)N2CC[C@@]3(S(=O)(=O)c4ccc(F)cc4)c4ccc(C(F)(C(F)(F)F)C(F)(F)F)cc4CC[C@@H]23)C1] | 639.2 (M + H)$^+$ | 2.09 | C |
| 382 | 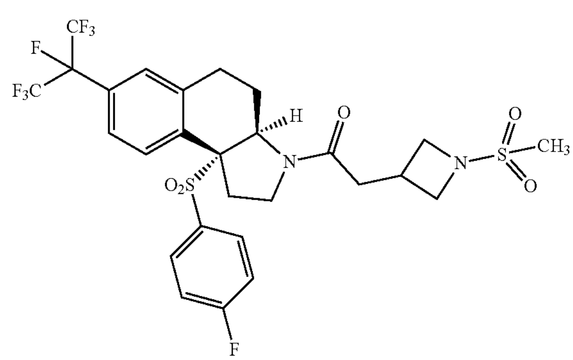 [SMILES: CS(=O)(=O)N1CC(CC(=O)N2CC[C@@]3(S(=O)(=O)c4ccc(F)cc4)c4ccc(C(F)(C(F)(F)F)C(F)(F)F)cc4CC[C@@H]23)C1] | 675.0 (M + H)$^+$ | 2.19 | D |

TABLE 9-continued

| Ex. # | Structure | LCMS m/z observed | HPLC $t_R$ (min) | HPLC method |
|---|---|---|---|---|
| 383 | 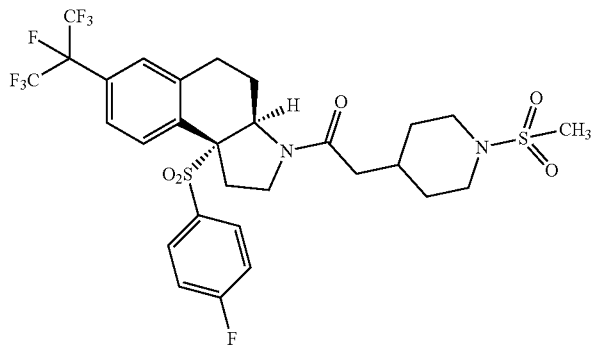 [SMILES: CS(=O)(=O)N1CCC(CC(=O)N2CC[C@@]3(S(=O)(=O)c4ccc(F)cc4)c4ccc(C(F)(C(F)(F)F)C(F)(F)F)cc4CC[C@@H]23)CC1] | 702.8 (M + H)+ | 2.28 | C |
| 384 | 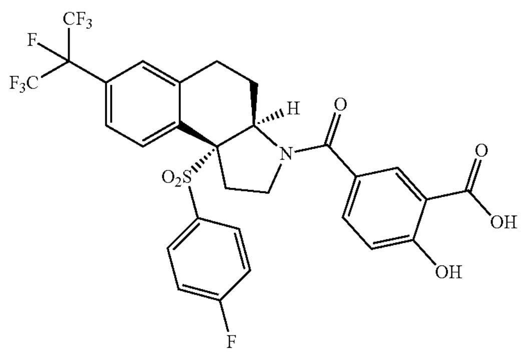 [SMILES: O=C(O)c1cc(C(=O)N2CC[C@@]3(S(=O)(=O)c4ccc(F)cc4)c4ccc(C(F)(C(F)(F)F)C(F)(F)F)cc4CC[C@@H]23)ccc1O] | 664.0 (M + H)+ | 1.80 | C |
| 385 | 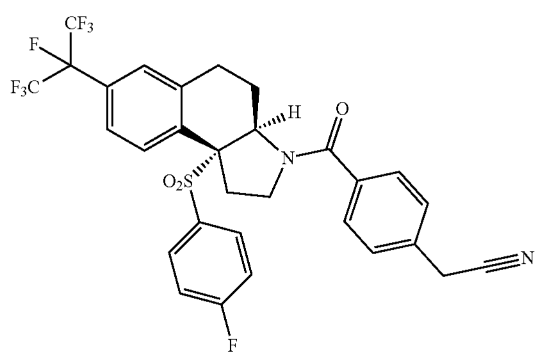 [SMILES: N#CCc1ccc(C(=O)N2CC[C@@]3(S(=O)(=O)c4ccc(F)cc4)c4ccc(C(F)(C(F)(F)F)C(F)(F)F)cc4CC[C@@H]23)cc1] | 643.2 (M + H)+ | 2.33 | D |
| 386 | 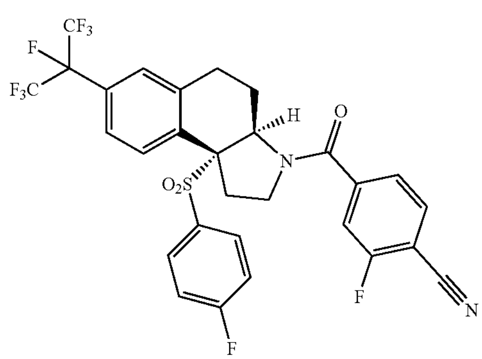 [SMILES: N#Cc1ccc(C(=O)N2CC[C@@]3(S(=O)(=O)c4ccc(F)cc4)c4ccc(C(F)(C(F)(F)F)C(F)(F)F)cc4CC[C@@H]23)cc1F] | 647.1 (M + H)+ | 1.15 | B |

TABLE 9-continued

| Ex. # | Structure | LCMS m/z observed | HPLC $t_R$ (min) | HPLC method |
|---|---|---|---|---|
| 387 | 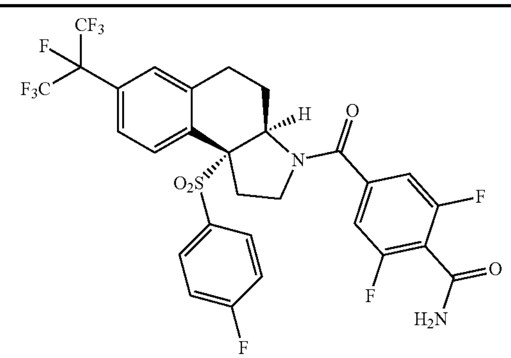 | 683.1 (M + H)+ | 2.14 | D |
| 388 | Homochiral from peak 2 | 676.0 (M + H)+ | 1.05 | B |
| 389 | Homochiral from peak 2 | 676.1 (M + H)+ | 1.04 | B |
| 390 | Homochiral from peak 2 | 690.0 (M + H)+ | 1.07 | B |

TABLE 9-continued

| Ex. # | Structure | LCMS m/z observed | HPLC $t_R$ (min) | HPLC method |
|---|---|---|---|---|
| 391 | [Structure with CF3, F, F3C substituents on bicyclic aromatic system, O2S linker to chlorophenyl, N-C(=O) linked to methyl-substituted thiane dioxide (peak 2); Homochiral from peak 2] | 690.0 (M + H)+ | 1.07 | B |
| 392 | [Structure with CF3, F, F3C substituents on bicyclic aromatic system, O2S linker to CD3/F-substituted phenyl, N-C(=O) linked to thiane dioxide; Homochiral from peak 2] | 677.1 (M + H)+ | 2.19 | C |
| 393 | [Structure with CF3, F, F3C substituents on bicyclic aromatic system, O2S linker to CD3/F-substituted phenyl, N-C(=O) linked to cyclohexanecarboxylic acid; Homochiral from peak 1] | 671.2 (M + H)+ | 2.01 | C |

TABLE 9-continued
| Ex. # | Structure | LCMS m/z observed | HPLC $t_R$ (min) | HPLC method |
|---|---|---|---|---|
| 394 | 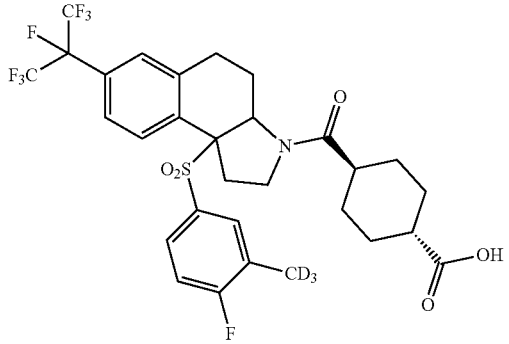 Homochiral from peak 2 | 671.2 (M + H)+ | 2.01 | C |
| 395 | 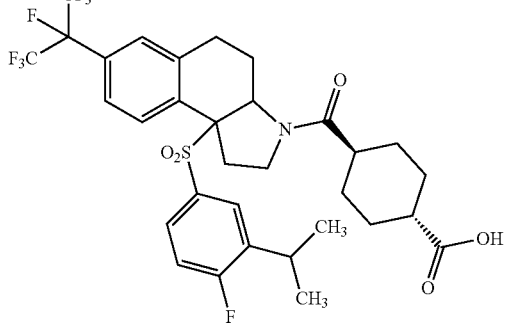 Homochiral from peak 2 | 696.1 (M + H)+ | 2.25 | C |
| 396 | 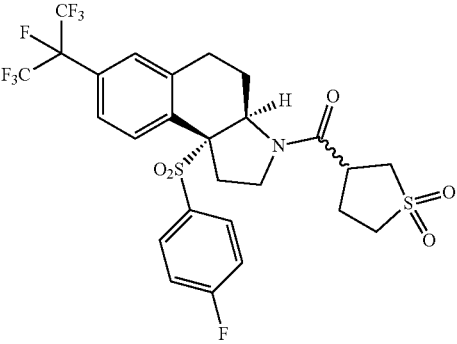 [SMILES: O=C(C1CCS(=O)(=O)C1)N1CC[C@@]2(S(=O)(=O)c3ccc(F)cc3)c3ccc(C(F)(C(F)(F)F)C(F)(F)F)cc3CC[C@@H]12] | 646.0 (M + H)+ | 2.18 | C |
| 397 | 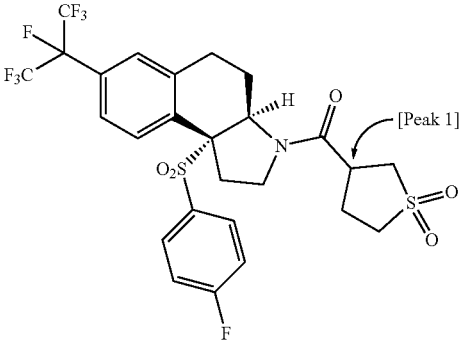 [SMILES: O=C(C1CCS(=O)(=O)C1)N1CC[C@@]2(S(=O)(=O)c3ccc(F)cc3)c3ccc(C(F)(C(F)(F)F)C(F)(F)F)cc3CC[C@@H]12] [Peak 1] | 646.0 (M + H)+ | 2.17 | C |

TABLE 9-continued

| Ex. # | Structure | LCMS m/z observed | HPLC $t_R$ (min) | HPLC method |
|---|---|---|---|---|
| 398 | 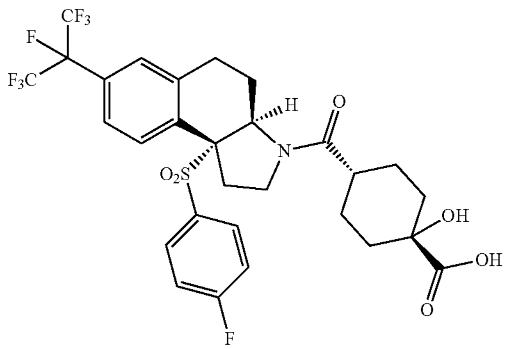 [SMILES: O=C([C@H]1CC[C@](O)(C(=O)O)CC1)N1CC[C@@]2(S(=O)(=O)c3ccc(F)cc3)c3ccc(C(F)(C(F)(F)F)C(F)(F)F)cc3CC[C@@H]12] | 669.9 (M + H)+ | 1.75 | C |
| 399 | Homochiral from peak 2 | 714.1 (M + H)+ | 2.25 | C |
| 400 | [Peak 2] | 646.3 (M + H)+ | 2.15 | C |
| 401 | Homochiral from peak 2 | 718.3 (M + H)+ | 2.35 | D |

TABLE 9-continued
| Ex. # | Structure | LCMS m/z observed | HPLC $t_R$ (min) | HPLC method |
|---|---|---|---|---|
| 402 | 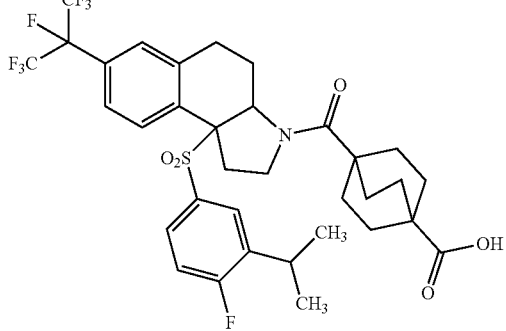<br>Homochiral from peak 2 | 722.1 (M + H)+ | 2.28 | C |
| 403 | 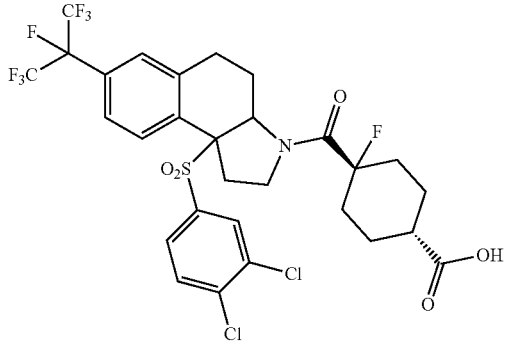<br>Homochiral from peak 2 | 722.2 (M + H)+ | 2.19 | C |
| 404 | 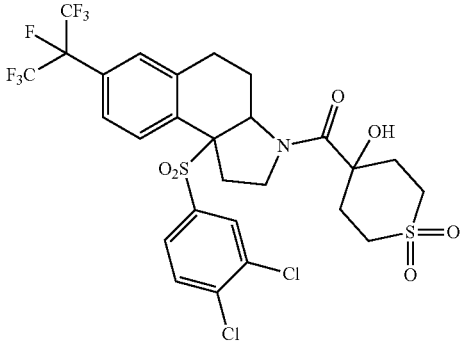<br>Homochiral from peak 2 | 725.4 (M − H)− | 2.34 | D |

TABLE 9-continued
| Ex. # | Structure | LCMS m/z observed | HPLC $t_R$ (min) | HPLC method |
|---|---|---|---|---|
| 405 | 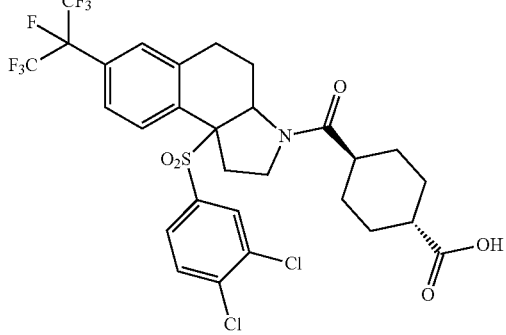<br>Homochiral from peak 2 | 704.0 (M + H)+ | 2.11 | C |
| 406 | 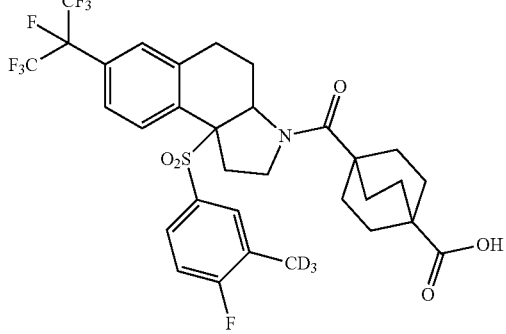<br>Homochiral from peak 2 | 697.1 (M + H)+ | 2.24 | C |
| 407 | 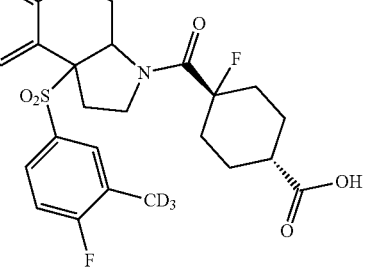<br>Homochiral from peak 2 | 688.8 (M + H)+ | 2.21 | C |
| 408 | 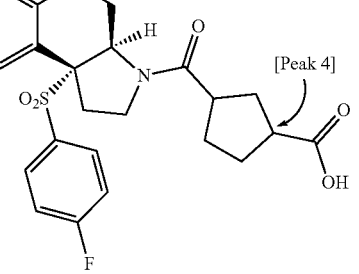 | 640.1 (M + H)+ | 1.04 | B |

TABLE 9-continued

| Ex. # | Structure | LCMS m/z observed | HPLC t$_R$ (min) | HPLC method |
|---|---|---|---|---|
| 409 | 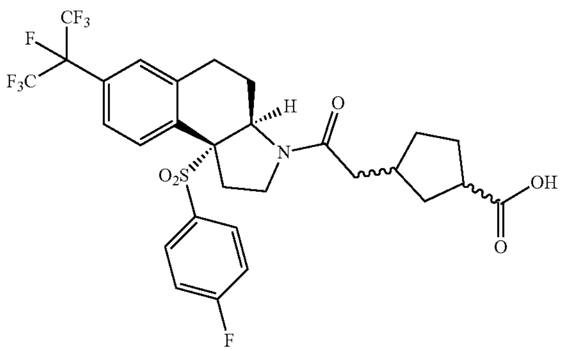 [SMILES: O=C(O)C1CCC(CC(=O)N2CC[C@@]3(S(=O)(=O)c4ccc(F)cc4)c4ccc(C(F)(C(F)(F)F)C(F)(F)F)cc4CC[C@@H]23)C1] | 654.3 (M + H)$^+$ | 1.93 | C |
| 410 | 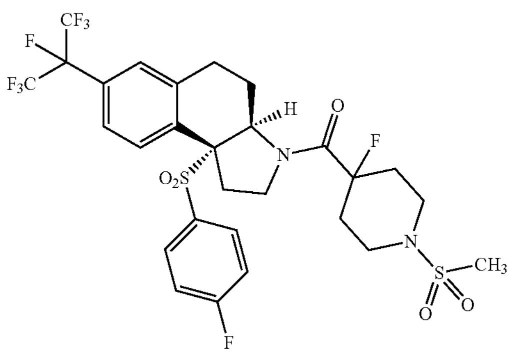 [SMILES: CS(=O)(=O)N1CCC(F)(C(=O)N2CC[C@@]3(S(=O)(=O)c4ccc(F)cc4)c4ccc(C(F)(C(F)(F)F)C(F)(F)F)cc4CC[C@@H]23)CC1] | 707.3 (M + H)$^+$ | 2.34 | C |
| 411 | 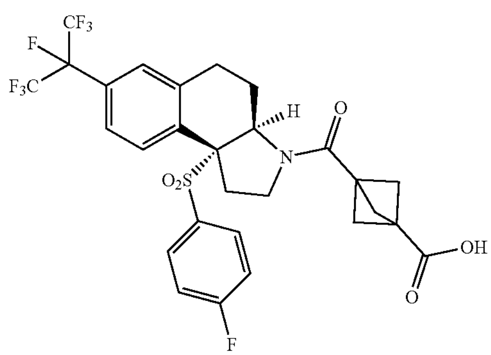 [SMILES: O=C(O)C12CC(C(=O)N3CC[C@@]4(S(=O)(=O)c5ccc(F)cc5)c5ccc(C(F)(C(F)(F)F)C(F)(F)F)cc5CC[C@@H]34)(C1)C2] | 637.9 (M + H)$^+$ | 1.84 | C |
| 412 | 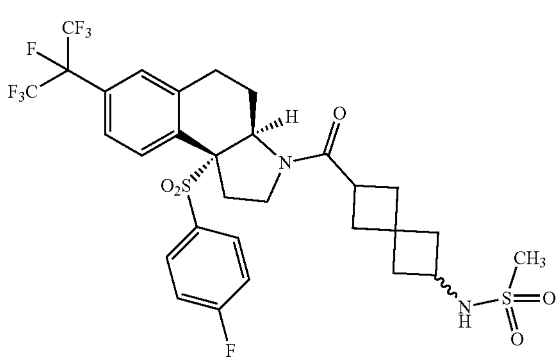 [SMILES: CS(=O)(=O)NC1CC2(C1)CC(C(=O)N1CC[C@@]3(S(=O)(=O)c4ccc(F)cc4)c4ccc(C(F)(C(F)(F)F)C(F)(F)F)cc4CC[C@@H]13)C2] | 715.3 (M + H)$^+$ | 2.24 | C |

TABLE 9-continued

| Ex. # | Structure | LCMS m/z observed | HPLC $t_R$ (min) | HPLC method |
|---|---|---|---|---|
| 413 | 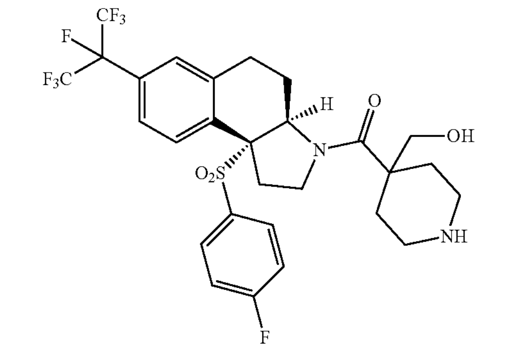 [SMILES: O=C(N1CC[C@@]2(S(=O)(=O)c3ccc(F)cc3)c3ccc(C(F)(C(F)(F)F)C(F)(F)F)cc3CC[C@@H]12)C1(CO)CCNCC1] | 641.2 (M + H)+ | 1.76 | C |
| 414 | 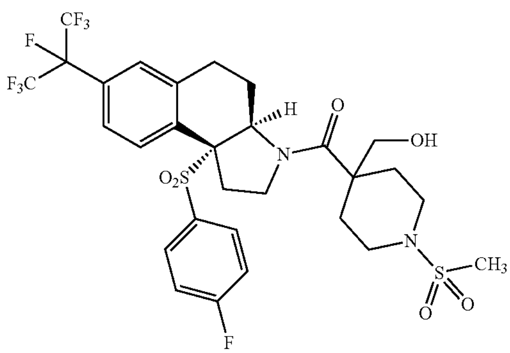 [SMILES: CS(=O)(=O)N1CCC(CO)(C(=O)N2CC[C@@]3(S(=O)(=O)c4ccc(F)cc4)c4ccc(C(F)(C(F)(F)F)C(F)(F)F)cc4CC[C@@H]23)CC1] | 719.1 (M + H)+ | 2.11 | C |
| 415 | 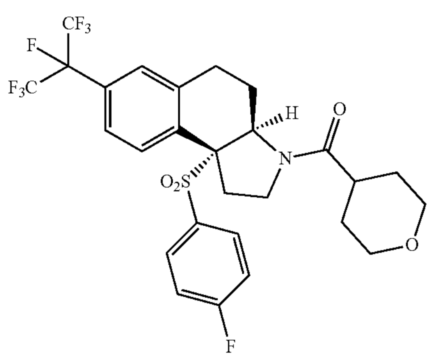 [SMILES: O=C(C1CCOCC1)N1CC[C@@]2(S(=O)(=O)c3ccc(F)cc3)c3ccc(C(F)(C(F)(F)F)C(F)(F)F)cc3CC[C@@H]12] | 611.9 (M + H)+ | 2.24 | C |
| 416 | 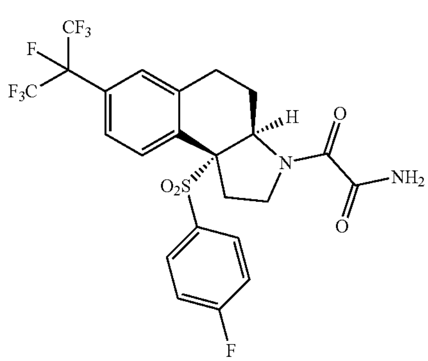 [SMILES: NC(=O)C(=O)N1CC[C@@]2(S(=O)(=O)c3ccc(F)cc3)c3ccc(C(F)(C(F)(F)F)C(F)(F)F)cc3CC[C@@H]12] | 571.2 (M + H)+ | 2.04 | C |

TABLE 9-continued

| Ex. # | Structure | LCMS m/z observed | HPLC $t_R$ (min) | HPLC method |
|---|---|---|---|---|
| 417 | 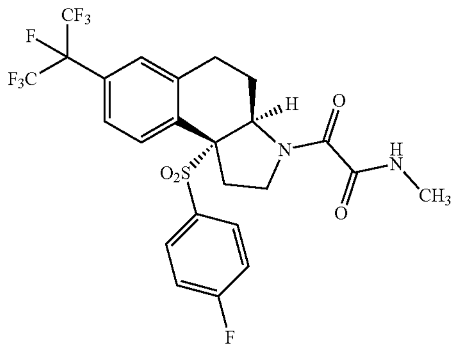 [SMILES: CNC(=O)C(=O)N1CC[C@@]2(S(=O)(=O)c3ccc(F)cc3)c3ccc(C(F)(C(F)(F)F)C(F)(F)F)cc3CC[C@@H]12] | 585.1 (M + H)+ | 2.19 | C |
| 418 | 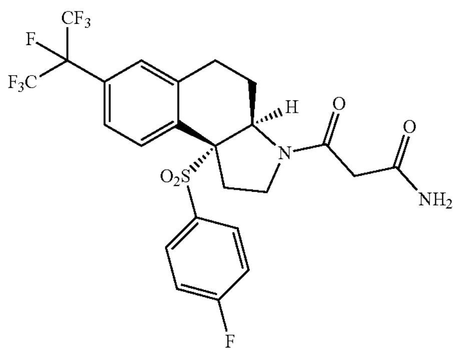 [SMILES: NC(=O)CC(=O)N1CC[C@@]2(S(=O)(=O)c3ccc(F)cc3)c3ccc(C(F)(C(F)(F)F)C(F)(F)F)cc3CC[C@@H]12] | 585.3 (M + H)+ | 2.04 | C |
| 419 | 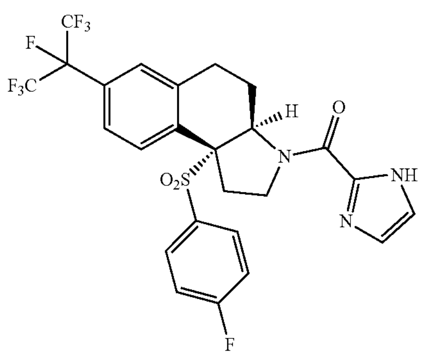 [SMILES: O=C(c1ncc[nH]1)N1CC[C@@]2(S(=O)(=O)c3ccc(F)cc3)c3ccc(C(F)(C(F)(F)F)C(F)(F)F)cc3CC[C@@H]12] | 594.0 (M + H)+ | 2.21 | C |
| 420 | 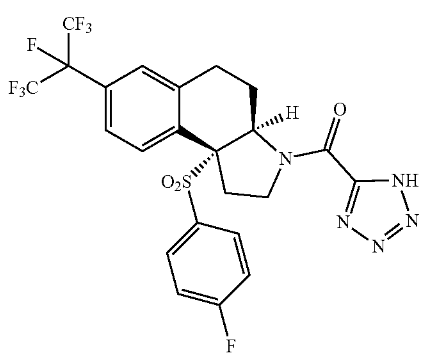 [SMILES: O=C(c1nnn[nH]1)N1CC[C@@]2(S(=O)(=O)c3ccc(F)cc3)c3ccc(C(F)(C(F)(F)F)C(F)(F)F)cc3CC[C@@H]12] | 596.3 (M + H)+ | 1.73 | C |

TABLE 9-continued

| Ex. # | Structure | LCMS m/z observed | HPLC $t_R$ (min) | HPLC method |
|---|---|---|---|---|
| 421 | 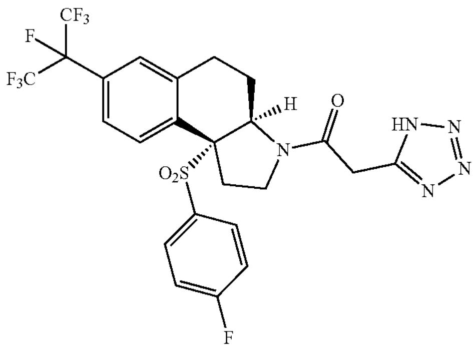 [SMILES: O=C(Cc1nnn[nH]1)N1CC[C@@]2(S(=O)(=O)c3ccc(F)cc3)c3ccc(C(F)(C(F)(F)F)C(F)(F)F)cc3CC[C@@H]12] | 608.1 (M + H)⁺ | 1.81 | C |
| 422 | 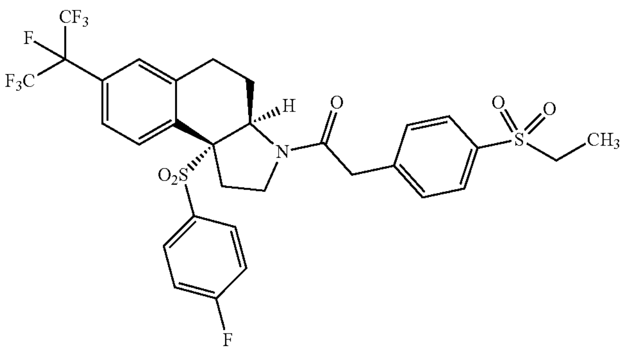 [SMILES: CCS(=O)(=O)c1ccc(CC(=O)N2CC[C@@]3(S(=O)(=O)c4ccc(F)cc4)c4ccc(C(F)(C(F)(F)F)C(F)(F)F)cc4CC[C@@H]23)cc1] | 711.0 (M + H)⁺ | 2.30 | C |
| 423 | 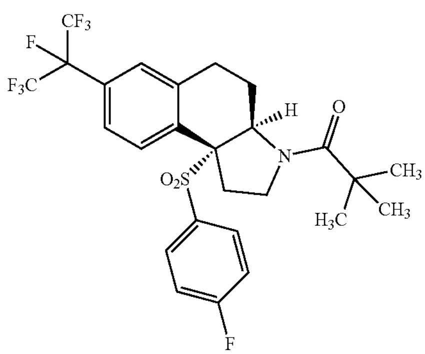 [SMILES: CC(C)(C)C(=O)N1CC[C@@]2(S(=O)(=O)c3ccc(F)cc3)c3ccc(C(F)(C(F)(F)F)C(F)(F)F)cc3CC[C@@H]12] | 584.3 (M + H)⁺ | 2.47 | C |
| 424 | 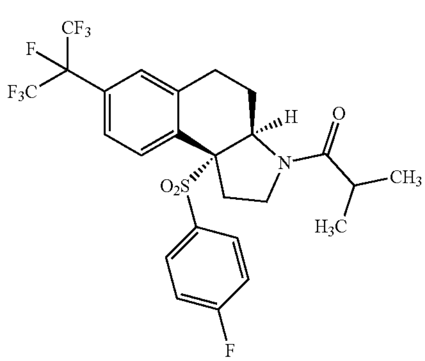 [SMILES: CC(C)C(=O)N1CC[C@@]2(S(=O)(=O)c3ccc(F)cc3)c3ccc(C(F)(C(F)(F)F)C(F)(F)F)cc3CC[C@@H]12] | 570.3 (M + H)⁺ | 2.32 | C |

TABLE 9-continued

| Ex. # | Structure | LCMS m/z observed | HPLC t$_R$ (min) | HPLC method |
|---|---|---|---|---|
| 425 | 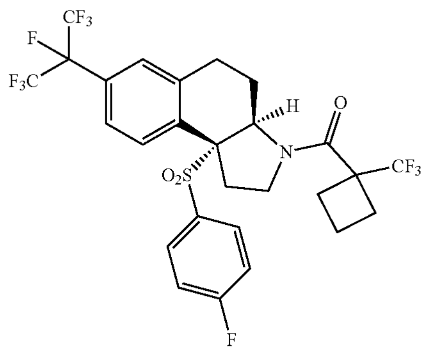 [SMILES: O=C(N1CC[C@@]2(S(=O)(=O)c3ccc(F)cc3)c3ccc(C(F)(C(F)(F)F)C(F)(F)F)cc3CC[C@@H]12)C1(C(F)(F)F)CCC1] | 649.8 (M + H)+ | 2.51 | C |
| 426 | 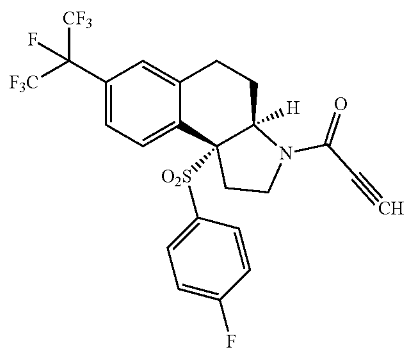 [SMILES: C#CC(=O)N1CC[C@@]2(S(=O)(=O)c3ccc(F)cc3)c3ccc(C(F)(C(F)(F)F)C(F)(F)F)cc3CC[C@@H]12] | 552.1 (M + H)+ | 2.30 | C |
| 427 | 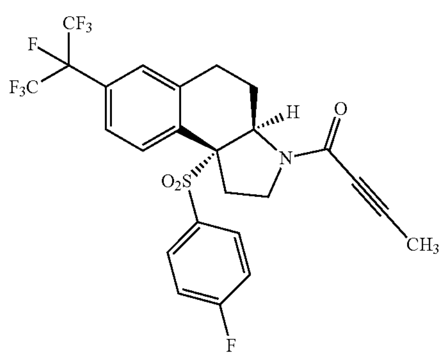 [SMILES: CC#CC(=O)N1CC[C@@]2(S(=O)(=O)c3ccc(F)cc3)c3ccc(C(F)(C(F)(F)F)C(F)(F)F)cc3CC[C@@H]12] | 566.3 (M + H)+ | 2.35 | C |
| 428 | 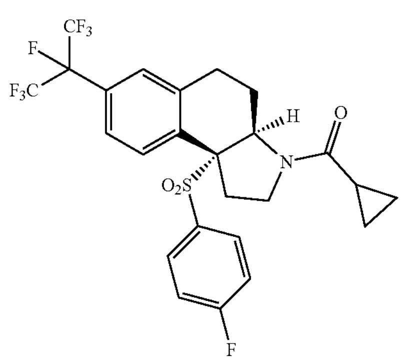 [SMILES: O=C(C1CC1)N1CC[C@@]2(S(=O)(=O)c3ccc(F)cc3)c3ccc(C(F)(C(F)(F)F)C(F)(F)F)cc3CC[C@@H]12] | 568.2 (M + H)+ | 2.33 | C |

TABLE 9-continued

| Ex. # | Structure | LCMS m/z observed | HPLC $t_R$ (min) | HPLC method |
|---|---|---|---|---|
| 429 | 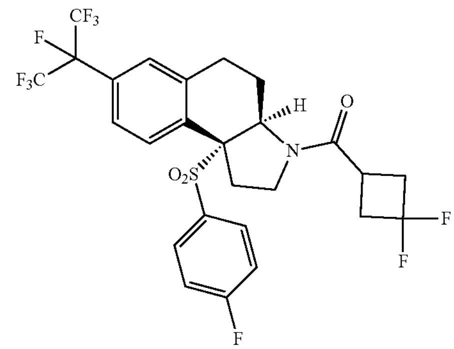 [SMILES: O=C(C1CC(F)(F)C1)N1CC[C@@]2(S(=O)(=O)c3ccc(F)cc3)c3ccc(C(F)(C(F)(F)F)C(F)(F)F)cc3CC[C@@H]12] | 618.2 (M + H)+ | 2.46 | C |
| 430 | 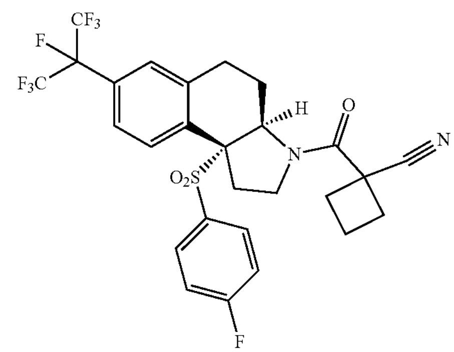 [SMILES: N#CC1(C(=O)N2CC[C@@]3(S(=O)(=O)c4ccc(F)cc4)c4ccc(C(F)(C(F)(F)F)C(F)(F)F)cc4CC[C@@H]23)CCC1] | 607.3 (M + H)+ | 2.48 | C |
| 431 | 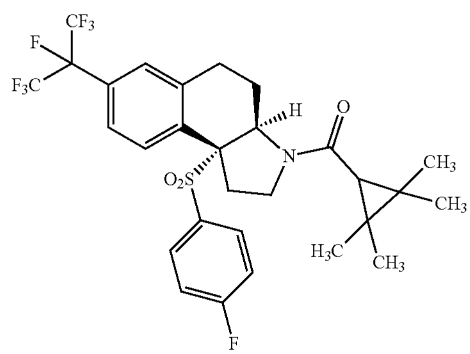 [SMILES: CC1(C)C(C(=O)N2CC[C@@]3(S(=O)(=O)c4ccc(F)cc4)c4ccc(C(F)(C(F)(F)F)C(F)(F)F)cc4CC[C@@H]23)C1(C)C] | 624.4 (M + H)+ | 2.77 | C |
| 432 | 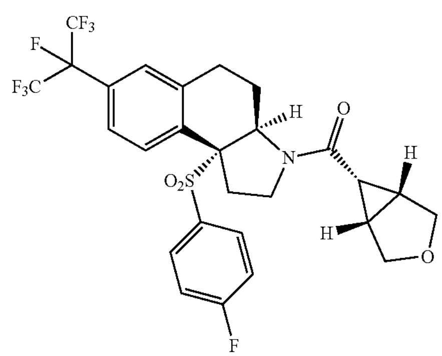 [SMILES: O=C([C@@H]1[C@@H]2COC[C@@H]21)N1CC[C@@]2(S(=O)(=O)c3ccc(F)cc3)c3ccc(C(F)(C(F)(F)F)C(F)(F)F)cc3CC[C@@H]12] | 610.2 (M + H)+ | 2.21 | C |

TABLE 9-continued

| Ex. # | Structure | LCMS m/z observed | HPLC $t_R$ (min) | HPLC method |
|---|---|---|---|---|
| 433 | 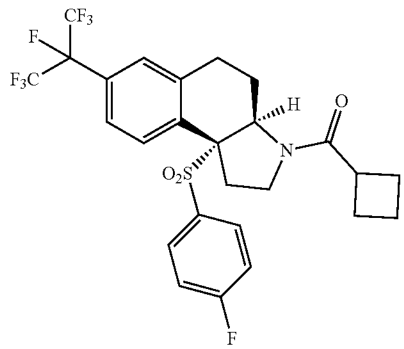 | 582.3 (M + H)+ | 2.46 | C |
| 434 | 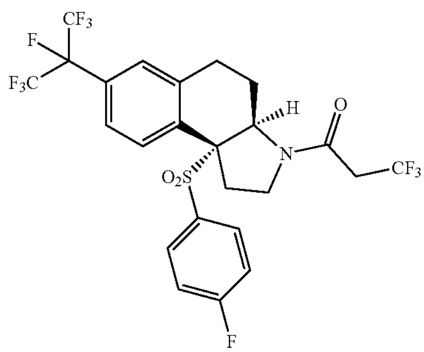 [SMILES: O=C(CC(F)(F)F)N1CC[C@@]2(S(=O)(=O)c3ccc(F)cc3)c3ccc(C(F)(C(F)(F)F)C(F)(F)F)cc3CC[C@@H]12] | 610.3 (M + H)+ | 2.43 | C |
| 435 | 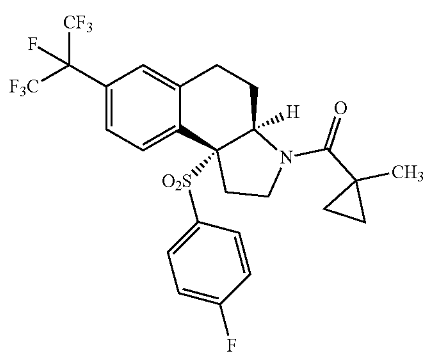 [SMILES: CC1(C(=O)N2CC[C@@]3(S(=O)(=O)c4ccc(F)cc4)c4ccc(C(F)(C(F)(F)F)C(F)(F)F)cc4CC[C@@H]23)CC1] | 582.1 (M + H)+ | 2.46 | C |
| 436 | [Peak 1] | 600.4 (M + H)+ | 2.30 | C |

TABLE 9-continued

| Ex. # | Structure | LCMS m/z observed | HPLC $t_R$ (min) | HPLC method |
|---|---|---|---|---|
| 437 | 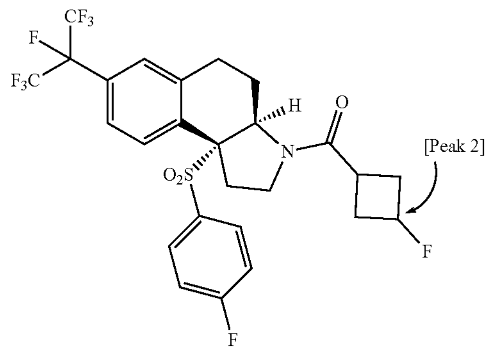 [SMILES: O=C(C1CC(F)C1)N1CC[C@@]2(S(=O)(=O)c3ccc(F)cc3)c3ccc(C(F)(C(F)(F)F)C(F)(F)F)cc3CC[C@@H]12] | 600.1 (M + H)⁺ | 2.34 | C |
| 438 | 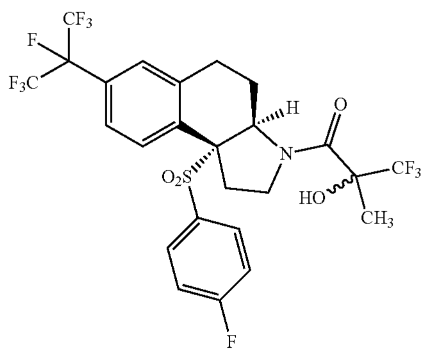 [SMILES: CC(O)(C(=O)N1CC[C@@]2(S(=O)(=O)c3ccc(F)cc3)c3ccc(C(F)(C(F)(F)F)C(F)(F)F)cc3CC[C@@H]12)C(F)(F)F] | 638.9 (M + H)⁺ | 2.45 | C |
| 439 | 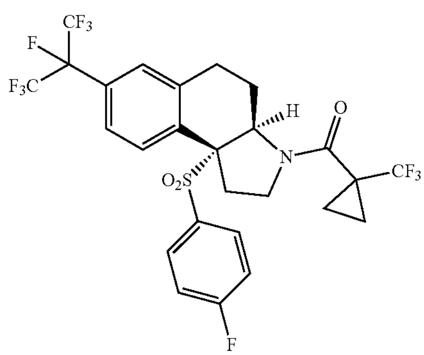 | 636.0 (M + H)⁺ | 2.56 | C |
| 440 | 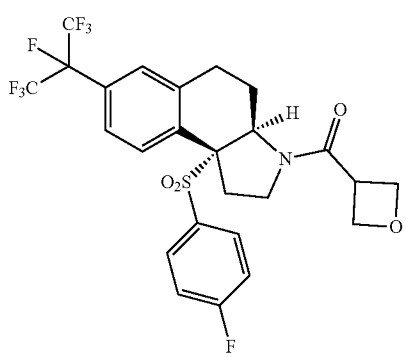 [SMILES: O=C(C1COC1)N1CC[C@@]2(S(=O)(=O)c3ccc(F)cc3)c3ccc(C(F)(C(F)(F)F)C(F)(F)F)cc3CC[C@@H]12] | 584.1 (M + H)⁺ | 2.24 | C |

TABLE 9-continued

| Ex. # | Structure | LCMS m/z observed | HPLC $t_R$ (min) | HPLC method |
|---|---|---|---|---|
| 441 | 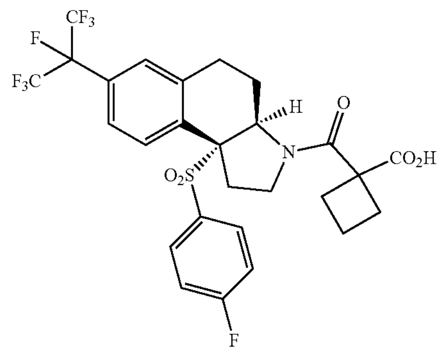 [SMILES: O=C(O)C1(C(=O)N2CC[C@@]3(S(=O)(=O)c4ccc(F)cc4)c4ccc(C(F)(C(F)(F)F)C(F)(F)F)cc4CC[C@@H]23)CCC1] | 626.3 (M + H)⁺ | 1.77 | C |
| 442 | 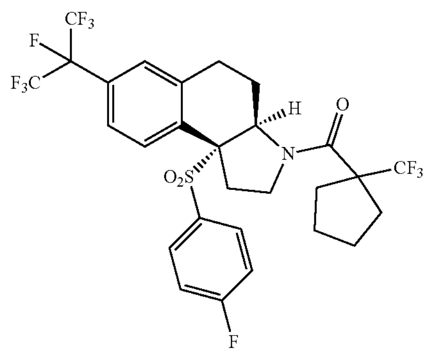 [SMILES: O=C(N1CC[C@@]2(S(=O)(=O)c3ccc(F)cc3)c3ccc(C(F)(C(F)(F)F)C(F)(F)F)cc3CC[C@@H]12)C1(C(F)(F)F)CCCC1] | 664.1 (M + H)⁺ | 2.74 | C |
| 443 | 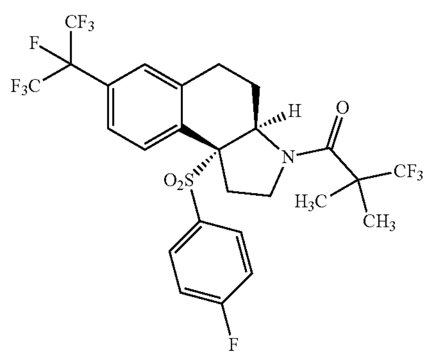 | 638.2 (M + H)⁺ | 2.62 | C |
| 444 | 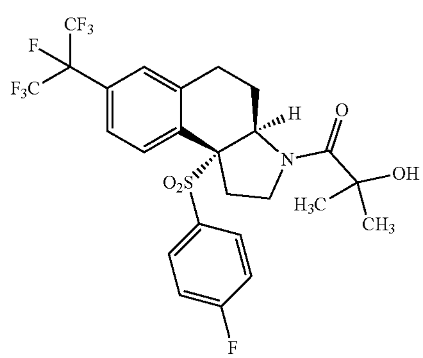 | 586.2 (M + H)⁺ | 2.25 | C |

TABLE 9-continued

| Ex. # | Structure | LCMS m/z observed | HPLC $t_R$ (min) | HPLC method |
|---|---|---|---|---|
| 445 | 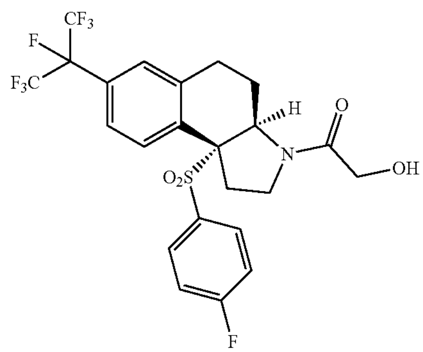 | 558.0 (M + H)+ | 2.11 | C |
| 446 | 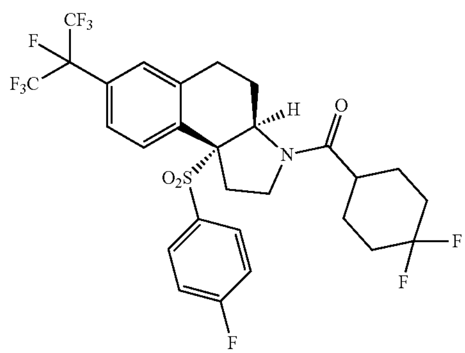 [SMILES: O=C(C1CCC(F)(F)CC1)N1CC[C@@]2(S(=O)(=O)c3ccc(F)cc3)c3ccc(C(F)(C(F)(F)F)C(F)(F)F)cc3CC[C@@H]12] | 646.3 (M + H)+ | 2.50 | C |
| 447 | 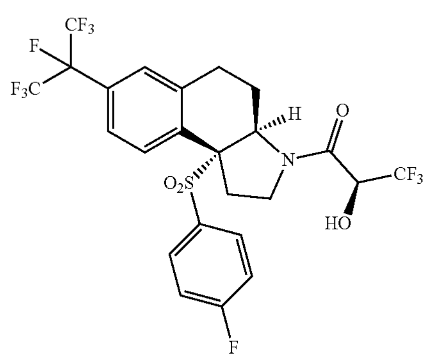 [SMILES: O=C([C@H](O)C(F)(F)F)N1CC[C@@]2(S(=O)(=O)c3ccc(F)cc3)c3ccc(C(F)(C(F)(F)F)C(F)(F)F)cc3CC[C@@H]12] | 626.1 (M + H)+ | 2.19 | C |
| 448 | 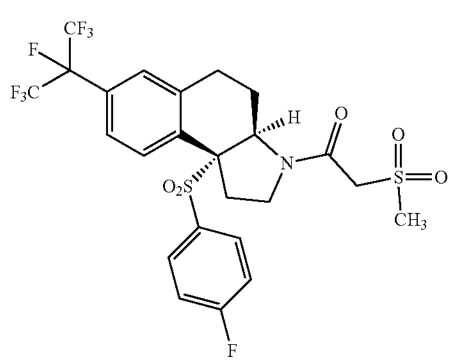 [SMILES: CS(=O)(=O)CC(=O)N1CC[C@@]2(S(=O)(=O)c3ccc(F)cc3)c3ccc(C(F)(C(F)(F)F)C(F)(F)F)cc3CC[C@@H]12] | 620.1 (M + H)+ | 2.12 | C |

TABLE 9-continued

| Ex. # | Structure | LCMS m/z observed | HPLC $t_R$ (min) | HPLC method |
|---|---|---|---|---|
| 449 | 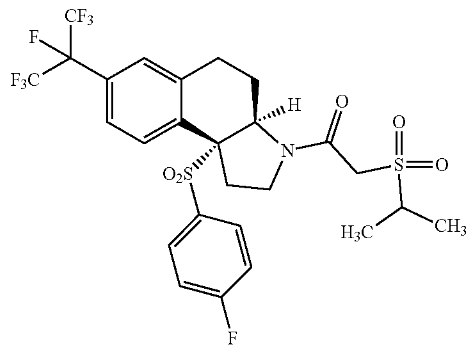 [SMILES: CC(C)S(=O)(=O)CC(=O)N1CC[C@@]2(S(=O)(=O)c3ccc(F)cc3)c3ccc(C(F)(C(F)(F)F)C(F)(F)F)cc3CC[C@@H]12] | 648.1 (M + H)+ | 2.24 | C |
| 450 | 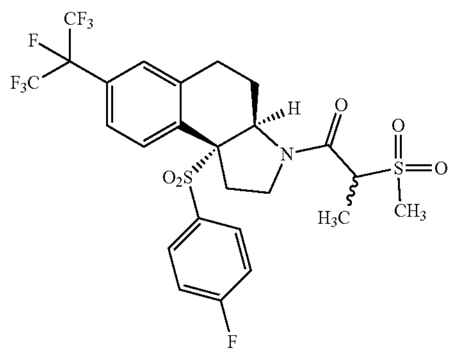 [SMILES: CC(C(=O)N1CC[C@@]2(S(=O)(=O)c3ccc(F)cc3)c3ccc(C(F)(C(F)(F)F)C(F)(F)F)cc3CC[C@@H]12)S(C)(=O)=O] | 634.2 (M + H)+ | 2.18 | C |
| 451 | 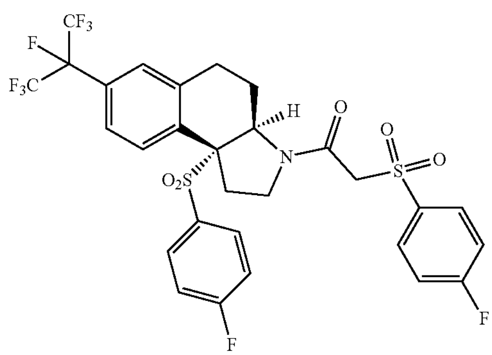 [SMILES: O=C(CS(=O)(=O)c1ccc(F)cc1)N1CC[C@@]2(S(=O)(=O)c3ccc(F)cc3)c3ccc(C(F)(C(F)(F)F)C(F)(F)F)cc3CC[C@@H]12] | 700.0 (M + H)+ | 2.38 | C |
| 452 | 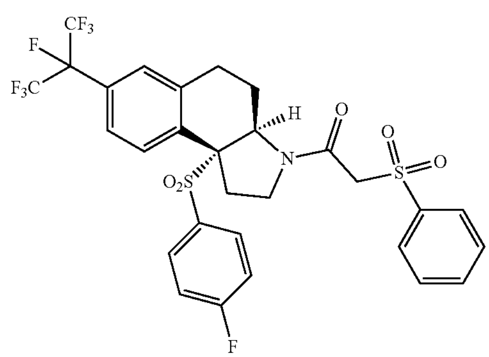 [SMILES: O=C(CS(=O)(=O)c1ccccc1)N1CC[C@@]2(S(=O)(=O)c3ccc(F)cc3)c3ccc(C(F)(C(F)(F)F)C(F)(F)F)cc3CC[C@@H]12] | 682.2 (M + H)+ | 2.42 | C |

TABLE 9-continued

| Ex. # | Structure | LCMS m/z observed | HPLC $t_R$ (min) | HPLC method |
|---|---|---|---|---|
| 453 | 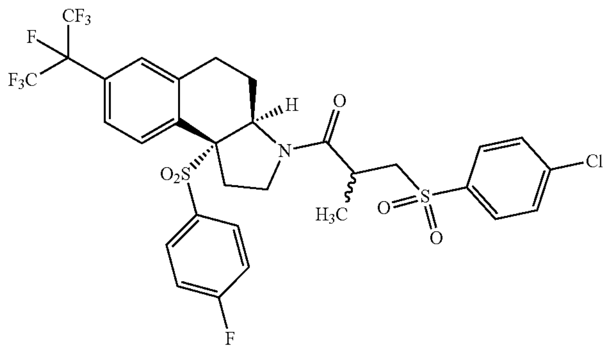 [SMILES: CC(CS(=O)(=O)c1ccc(Cl)cc1)C(=O)N1CC[C@@]2(S(=O)(=O)c3ccc(F)cc3)c3ccc(C(F)(C(F)(F)F)C(F)(F)F)cc3CC[C@@H]12] | 745.1 (M + H)+ | 2.55 | C |
| 454 | 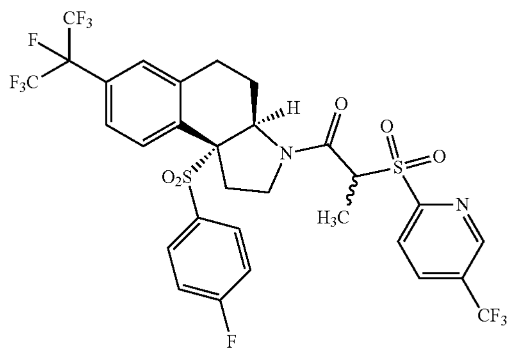 [SMILES: CC(C(=O)N1CC[C@@]2(S(=O)(=O)c3ccc(F)cc3)c3ccc(C(F)(C(F)(F)F)C(F)(F)F)cc3CC[C@@H]12)S(=O)(=O)c1ccc(C(F)(F)F)cn1] | 765.9 (M + H)+ | 2.51 | C |
| 455 | 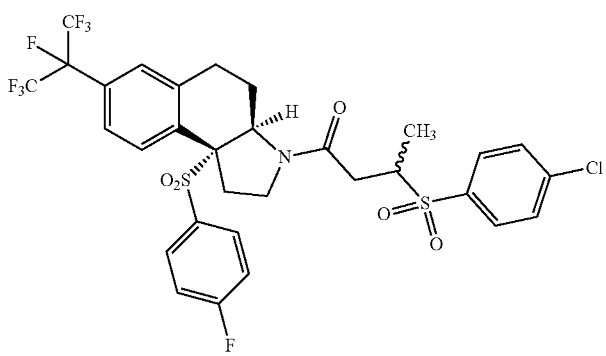 [SMILES: CC(CC(=O)N1CC[C@@]2(S(=O)(=O)c3ccc(F)cc3)c3ccc(C(F)(C(F)(F)F)C(F)(F)F)cc3CC[C@@H]12)S(=O)(=O)c1ccc(Cl)cc1] | 744.1 (M + H)+ | 2.57 | C |
| 456 | 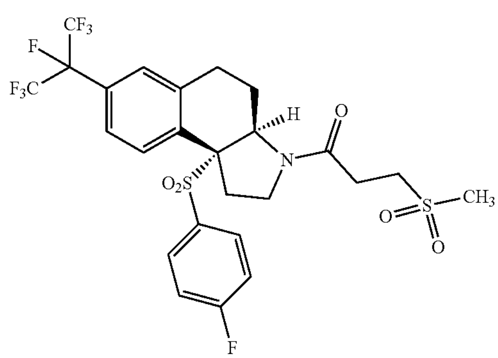 [SMILES: CS(=O)(=O)CCC(=O)N1CC[C@@]2(S(=O)(=O)c3ccc(F)cc3)c3ccc(C(F)(C(F)(F)F)C(F)(F)F)cc3CC[C@@H]12] | 633.8 (M + H)+ | 2.13 | C |

TABLE 9-continued

| Ex. # | Structure | LCMS m/z observed | HPLC t_R (min) | HPLC method |
|---|---|---|---|---|
| 457 | 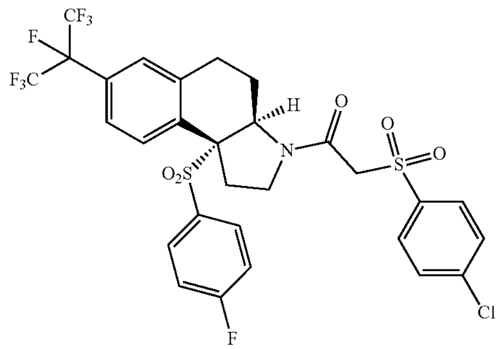 [SMILES: O=C(CS(=O)(=O)c1ccc(Cl)cc1)N1CC[C@@]2(S(=O)(=O)c3ccc(F)cc3)c3ccc(C(F)(C(F)(F)F)C(F)(F)F)cc3CC[C@@H]12] | 716.2 (M + H)+ | 2.51 | C |
| 458 | 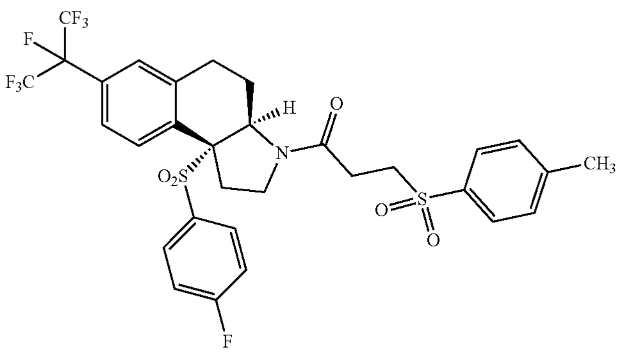 [SMILES: Cc1ccc(S(=O)(=O)CCC(=O)N2CC[C@@]3(S(=O)(=O)c4ccc(F)cc4)c4ccc(C(F)(C(F)(F)F)C(F)(F)F)cc4CC[C@@H]23)cc1] | 710.2 (M + H)+ | 2.49 | C |
| 459 | 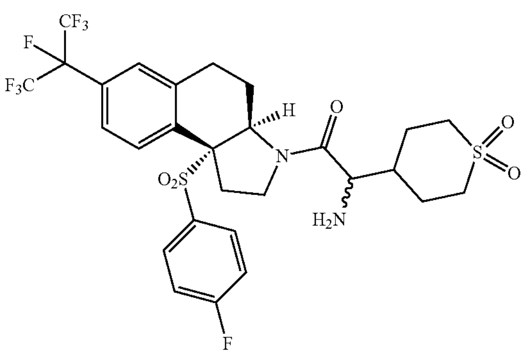 [SMILES: NC(C(=O)N1CC[C@@]2(S(=O)(=O)c3ccc(F)cc3)c3ccc(C(F)(C(F)(F)F)C(F)(F)F)cc3CC[C@@H]12)C1CCS(=O)(=O)CC1] | 689.1 (M + H)+ | 1.94 | C |
| 460 | 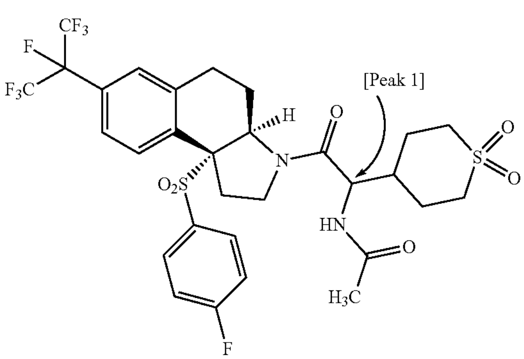 [SMILES: CC(=O)NC(C(=O)N1CC[C@@]2(S(=O)(=O)c3ccc(F)cc3)c3ccc(C(F)(C(F)(F)F)C(F)(F)F)cc3CC[C@@H]12)C1CCS(=O)(=O)CC1] | 731.0 (M + H)+ | 2.00 | C |

TABLE 9-continued

| Ex. # | Structure | LCMS m/z observed | HPLC $t_R$ (min) | HPLC method |
|---|---|---|---|---|
| 461 | 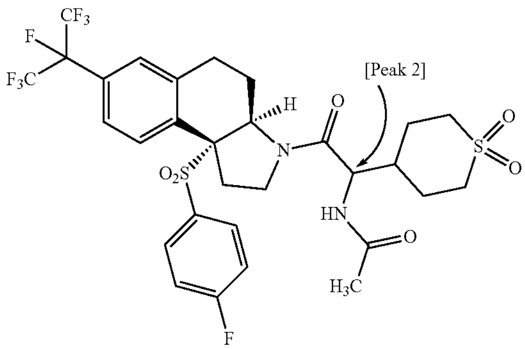 [SMILES: CC(=O)NC(C(=O)N1CC[C@@]2(S(=O)(=O)c3ccc(F)cc3)c3ccc(C(F)(C(F)(F)F)C(F)(F)F)cc3CC[C@@H]12)C1CCS(=O)(=O)CC1] | 731.2 (M + H)+ | 2.07 | C |
| 462 | 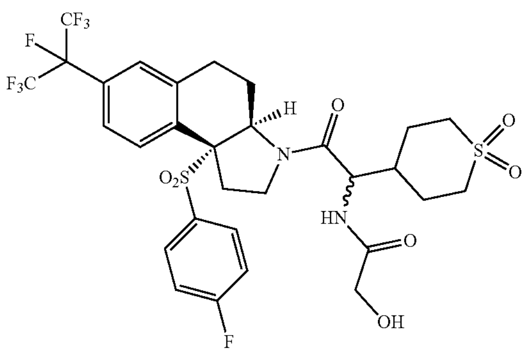 [SMILES: O=C(CO)NC(C(=O)N1CC[C@@]2(S(=O)(=O)c3ccc(F)cc3)c3ccc(C(F)(C(F)(F)F)C(F)(F)F)cc3CC[C@@H]12)C1CCS(=O)(=O)CC1] | 747.0 (M + H)+ | 1.91 | C |
| 463 | 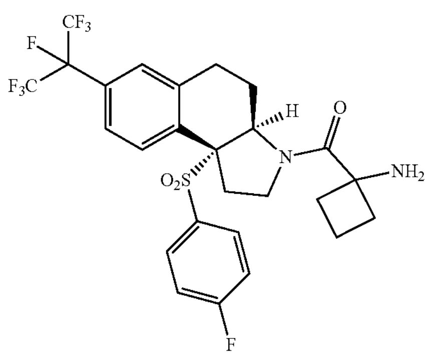 [SMILES: NC1(C(=O)N2CC[C@@]3(S(=O)(=O)c4ccc(F)cc4)c4ccc(C(F)(C(F)(F)F)C(F)(F)F)cc4CC[C@@H]23)CCC1] | 597.2 (M + H)+ | 2.15 | C |
| 464 | 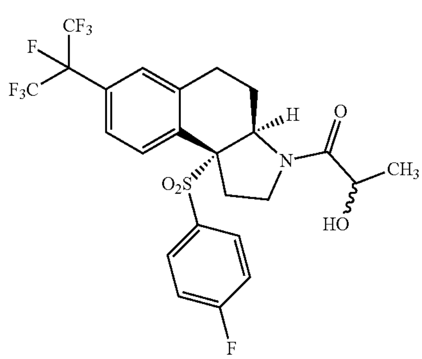 [SMILES: CC(O)C(=O)N1CC[C@@]2(S(=O)(=O)c3ccc(F)cc3)c3ccc(C(F)(C(F)(F)F)C(F)(F)F)cc3CC[C@@H]12] | 572.0 (M + H)+ | 2.16 | C |

TABLE 9-continued

| Ex. # | Structure | LCMS m/z observed | HPLC $t_R$ (min) | HPLC method |
|---|---|---|---|---|
| 465 | 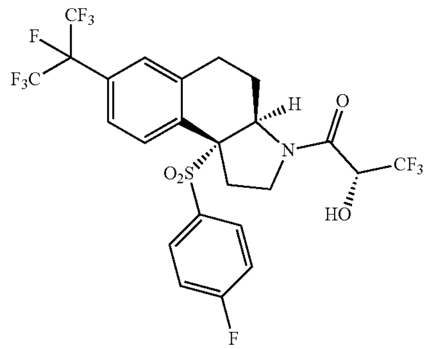 [SMILES: O=C([C@@H](O)C(F)(F)F)N1CC[C@@]2(S(=O)(=O)c3ccc(F)cc3)c3ccc(C(F)(C(F)(F)F)C(F)(F)F)cc3CC[C@@H]12] | 626.1 (M + H)+ | 2.38 | C |
| 466 | 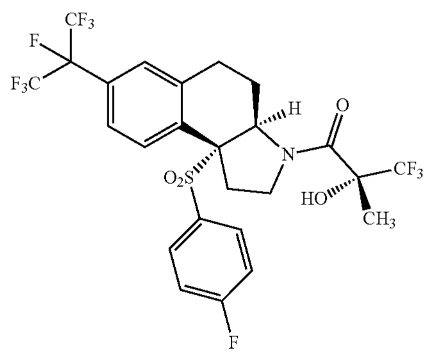 [SMILES: C[C@@](O)(C(=O)N1CC[C@@]2(S(=O)(=O)c3ccc(F)cc3)c3ccc(C(F)(C(F)(F)F)C(F)(F)F)cc3CC[C@@H]12)C(F)(F)F] | 640.0 (M + H)+ | 2.40 | C |
| 467 | 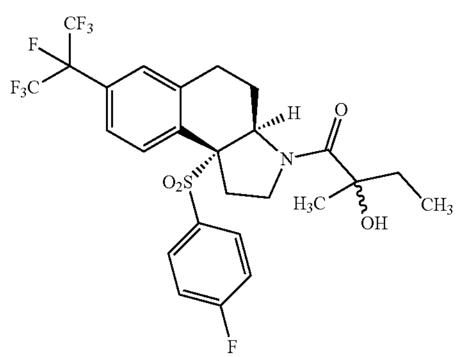 [SMILES: CCC(C)(O)C(=O)N1CC[C@@]2(S(=O)(=O)c3ccc(F)cc3)c3ccc(C(F)(C(F)(F)F)C(F)(F)F)cc3CC[C@@H]12] | 600.2 (M + H)+ | 2.30 | C |
| 468 | 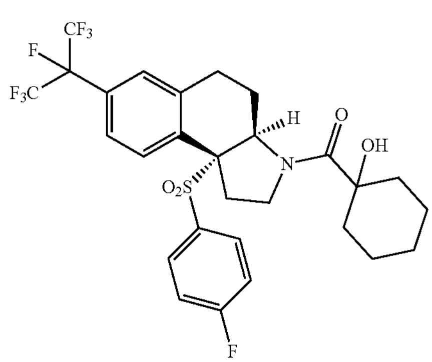 [SMILES: O=C(N1CC[C@@]2(S(=O)(=O)c3ccc(F)cc3)c3ccc(C(F)(C(F)(F)F)C(F)(F)F)cc3CC[C@@H]12)C1(O)CCCCC1] | 625.9 (M + H)+ | 2.47 | C |

TABLE 9-continued

| Ex. # | Structure | LCMS m/z observed | HPLC $t_R$ (min) | HPLC method |
|---|---|---|---|---|
| 469 | 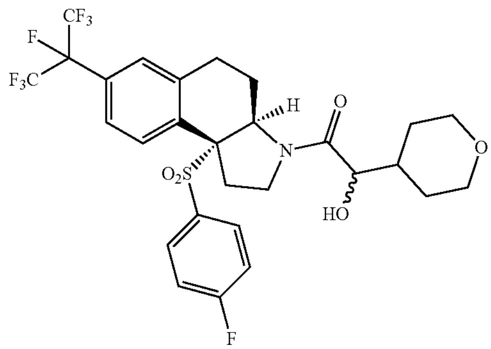 [SMILES: O=C(C(O)C1CCOCC1)N1CC[C@@]2(S(=O)(=O)c3ccc(F)cc3)c3ccc(C(F)(C(F)(F)F)C(F)(F)F)cc3CC[C@@H]12] | 642.2 (M + H)+ | 2.18 | C |
| 470 | 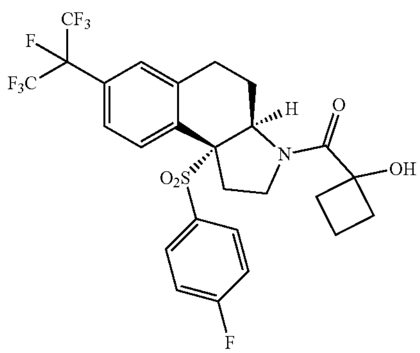 | 598.0 (M + H)+ | 2.28 | C |
| 471 | 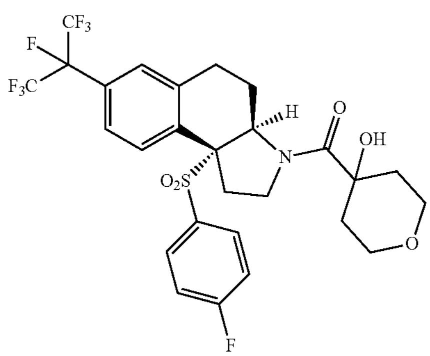 [SMILES: O=C(N1CC[C@@]2(S(=O)(=O)c3ccc(F)cc3)c3ccc(C(F)(C(F)(F)F)C(F)(F)F)cc3CC[C@@H]12)C1(O)CCOCC1] | 628.2 (M + H)+ | 2.17 | C |
| 472 | 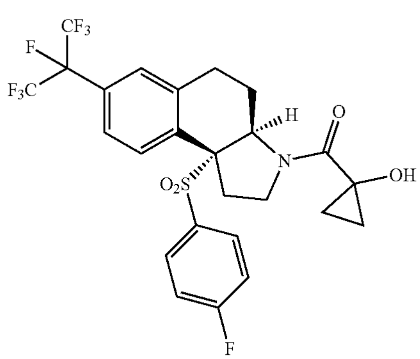 | 584.1 (M + H)+ | 2.20 | C |

TABLE 9-continued

| Ex. # | Structure | LCMS m/z observed | HPLC $t_R$ (min) | HPLC method |
|---|---|---|---|---|
| 473 | 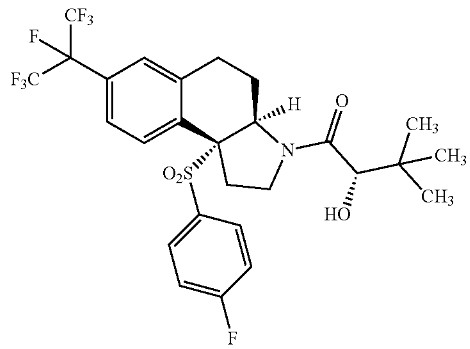 [SMILES: CC(C)(C)[C@H](O)C(=O)N1CC[C@@]2(S(=O)(=O)c3ccc(F)cc3)c3ccc(C(F)(C(F)(F)F)C(F)(F)F)cc3CC[C@@H]12] | 613.9 (M + H)⁺ | 2.50 | C |
| 474 | 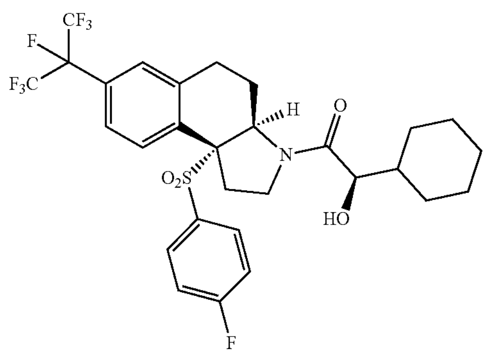 [SMILES: O=C([C@H](O)C1CCCCC1)N1CC[C@@]2(S(=O)(=O)c3ccc(F)cc3)c3ccc(C(F)(C(F)(F)F)C(F)(F)F)cc3CC[C@@H]12] | 640.0 (M + H)⁺ | 2.53 | C |
| 475 | 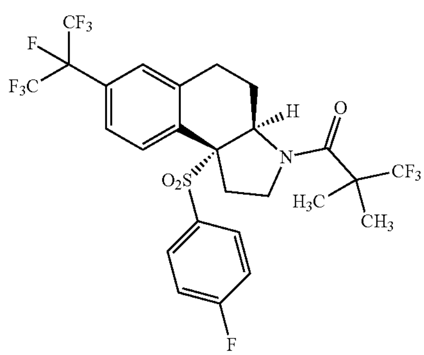 [SMILES: CC(C)(C(=O)N1CC[C@@]2(S(=O)(=O)c3ccc(F)cc3)c3ccc(C(F)(C(F)(F)F)C(F)(F)F)cc3CC[C@@H]12)C(F)(F)F] | 638.1 (M + H)⁺ | 2.55 | C |
| 476 | 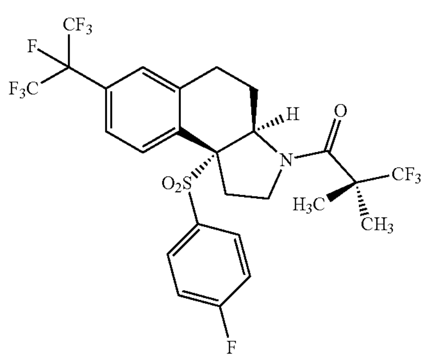 | 640.2 (M + H)⁺ | 2.36 | C |

TABLE 9-continued

| Ex. # | Structure | LCMS m/z observed | HPLC $t_R$ (min) | HPLC method |
|---|---|---|---|---|
| 477 | 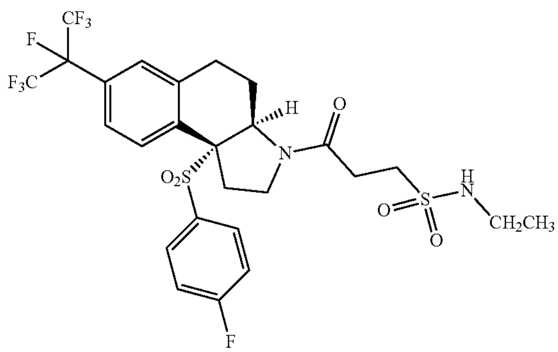 [SMILES: CCNS(=O)(=O)CCC(=O)N1CC[C@@]2(S(=O)(=O)c3ccc(F)cc3)c3ccc(C(F)(C(F)(F)F)C(F)(F)F)cc3CC[C@@H]12] | 663.0 (M + H)+ | 2.19 | C |
| 478 | 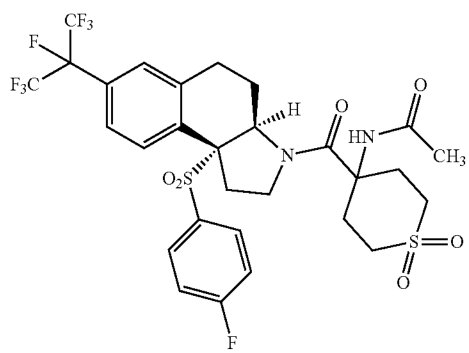 [SMILES: CC(=O)NC1(C(=O)N2CC[C@@]3(S(=O)(=O)c4ccc(F)cc4)c4ccc(C(F)(C(F)(F)F)C(F)(F)F)cc4CC[C@@H]23)CCS(=O)(=O)CC1] | 717.0 (M + H)+ | 2.00 | C |
| 479 | 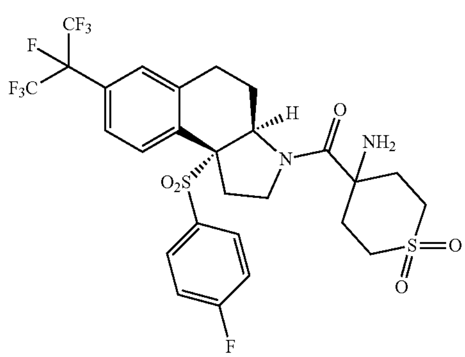 [SMILES: NC1(C(=O)N2CC[C@@]3(S(=O)(=O)c4ccc(F)cc4)c4ccc(C(F)(C(F)(F)F)C(F)(F)F)cc4CC[C@@H]23)CCS(=O)(=O)CC1] | 675.2 (M + H)+ | 2.09 | C |
| 480 | 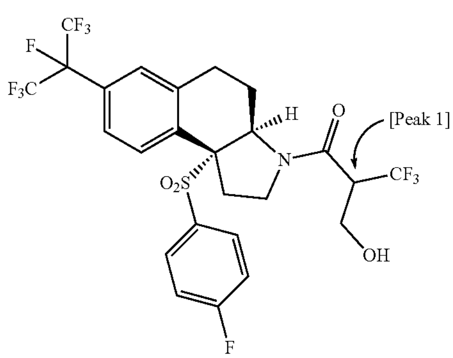 [SMILES: O=C(C(CO)C(F)(F)F)N1CC[C@@]2(S(=O)(=O)c3ccc(F)cc3)c3ccc(C(F)(C(F)(F)F)C(F)(F)F)cc3CC[C@@H]12] | 640.1 (M + H)+ | 1.84 | C |

TABLE 9-continued

| Ex. # | Structure | LCMS m/z observed | HPLC $t_R$ (min) | HPLC method |
|---|---|---|---|---|
| 481 | 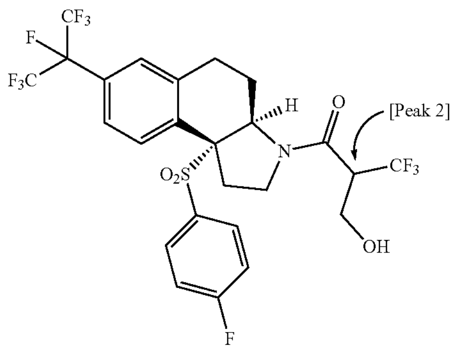 [SMILES: O=C(C(CO)C(F)(F)F)N1CC[C@@]2(S(=O)(=O)c3ccc(F)cc3)c3ccc(C(F)(C(F)(F)F)C(F)(F)F)cc3CC[C@@H]12] | 640.0 (M + H)+ | 1.89 | C |
| 482 | 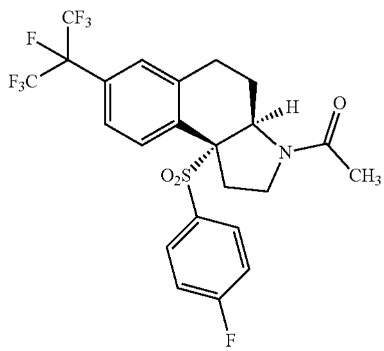 [SMILES: CC(=O)N1CC[C@@]2(S(=O)(=O)c3ccc(F)cc3)c3ccc(C(F)(C(F)(F)F)C(F)(F)F)cc3CC[C@@H]12] | 541.9 (M + H)+ | 2.11 | C |
| 483 | 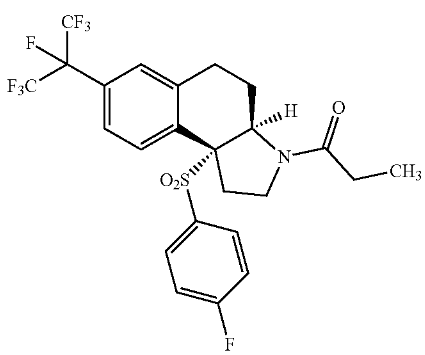 [SMILES: CCC(=O)N1CC[C@@]2(S(=O)(=O)c3ccc(F)cc3)c3ccc(C(F)(C(F)(F)F)C(F)(F)F)cc3CC[C@@H]12] | 556.3 (M + H)+ | 2.23 | C |
| 484 | 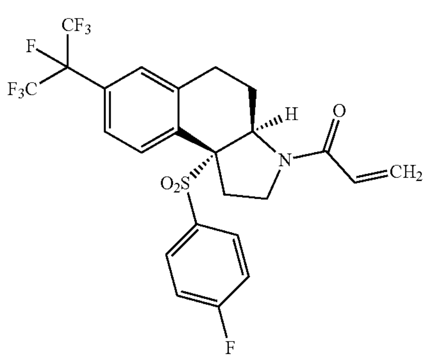 [SMILES: C=CC(=O)N1CC[C@@]2(S(=O)(=O)c3ccc(F)cc3)c3ccc(C(F)(C(F)(F)F)C(F)(F)F)cc3CC[C@@H]12] | 554.1 (M + H)+ | 2.20 | C |

TABLE 9-continued

| Ex. # | Structure | LCMS m/z observed | HPLC $t_R$ (min) | HPLC method |
|---|---|---|---|---|
| 485 | [Peak 1] | 600.1 (M + H)+ | 2.37 | C |
| 486 | [Peak 2] | 600.1 (M + H)+ | 2.35 | C |
| 487 | 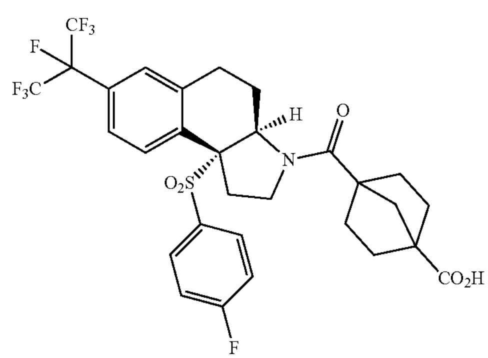 [SMILES: O=C(O)C12CCC(C(=O)N3CC[C@@]4(S(=O)(=O)c5ccc(F)cc5)c5ccc(C(F)(C(F)(F)F)C(F)(F)F)cc5CC[C@@H]34)(CC1)C2] | 666.1 (M + H)+ | 1.85 | C |
| 488 | 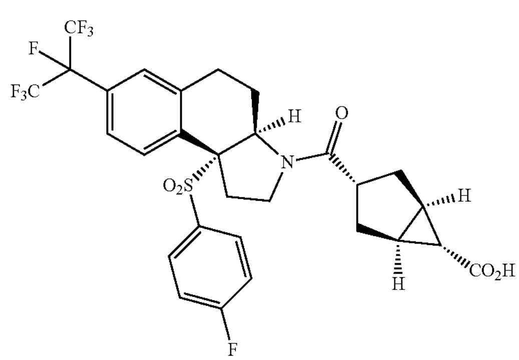 [SMILES: O=C(O)[C@H]1[C@@H]2C[C@@H](C(=O)N3CC[C@@]4(S(=O)(=O)c5ccc(F)cc5)c5ccc(C(F)(C(F)(F)F)C(F)(F)F)cc5CC[C@@H]34)C[C@@H]21] | 652.2 (M + H)+ | 1.88 | C |

TABLE 9-continued

| Ex. # | Structure | LCMS m/z observed | HPLC $t_R$ (min) | HPLC method |
|---|---|---|---|---|
| 489 | 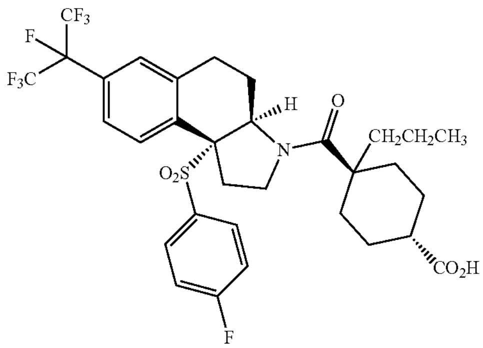 | 696.0 (M + H)+ | 2.14 | C |
| 490 | 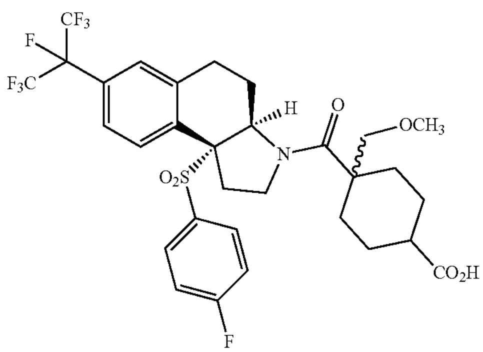 [SMILES: COCC1(C(=O)N2CC[C@@]3(S(=O)(=O)c4ccc(F)cc4)c4ccc(C(F)(C(F)(F)F)C(F)(F)F)cc4CC[C@@H]23)CCC(C(=O)O)CC1] | 698.0 (M + H)+ | 2.22 | D |
| 491 | 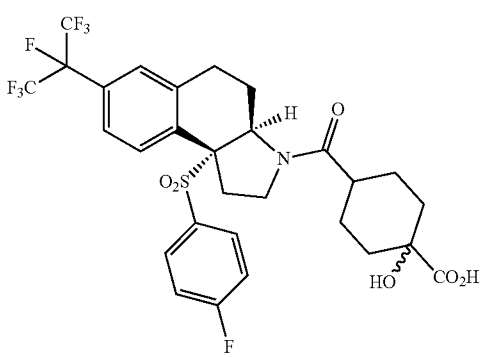 [SMILES: O=C(C1CCC(O)(C(=O)O)CC1)N1CC[C@@]2(S(=O)(=O)c3ccc(F)cc3)c3ccc(C(F)(C(F)(F)F)C(F)(F)F)cc3CC[C@@H]12] | 670.2 (M + H)+ | 2.04, 2.07 | D |
| 492 | 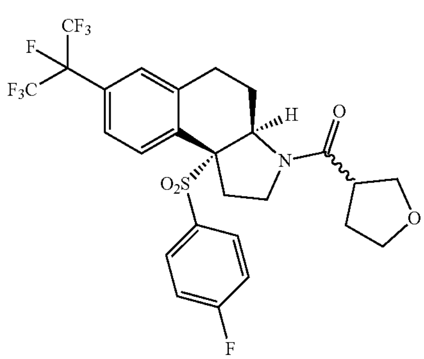 [SMILES: O=C(C1CCOC1)N1CC[C@@]2(S(=O)(=O)c3ccc(F)cc3)c3ccc(C(F)(C(F)(F)F)C(F)(F)F)cc3CC[C@@H]12] | 598.1 (M + H)+ | 2.20 | C |

TABLE 9-continued

| Ex. # | Structure | LCMS m/z observed | HPLC $t_R$ (min) | HPLC method |
|---|---|---|---|---|
| 493 | 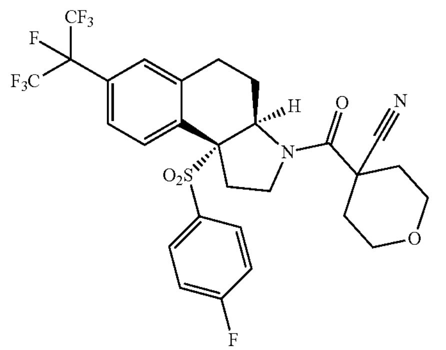 [SMILES: N#CC1(C(=O)N2CC[C@@]3(S(=O)(=O)c4ccc(F)cc4)c4ccc(C(F)(C(F)(F)F)C(F)(F)F)cc4CC[C@@H]23)CCOCC1] | 637.2 (M + H)+ | 2.36 | C |
| 494 | 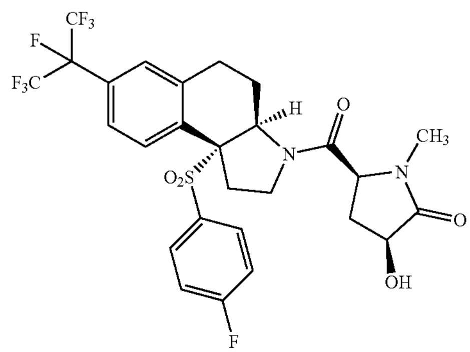 [SMILES: CN1C(=O)[C@@H](O)C[C@H]1C(=O)N1CC[C@@]2(S(=O)(=O)c3ccc(F)cc3)c3ccc(C(F)(C(F)(F)F)C(F)(F)F)cc3CC[C@@H]12] | 641.3 (M + H)+ | 2.02 | C |
| 495 | 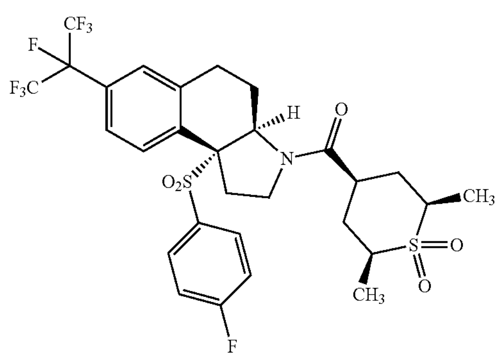 [SMILES: C[C@@H]1C[C@H](C(=O)N2CC[C@@]3(S(=O)(=O)c4ccc(F)cc4)c4ccc(C(F)(C(F)(F)F)C(F)(F)F)cc4CC[C@@H]23)C[C@H](C)S1(=O)=O] | 688.2 (M + H)+ | 2.25 | C |
| 496 | 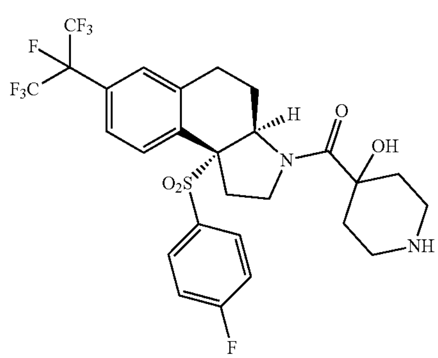 [SMILES: O=C(N1CC[C@@]2(S(=O)(=O)c3ccc(F)cc3)c3ccc(C(F)(C(F)(F)F)C(F)(F)F)cc3CC[C@@H]12)C1(O)CCNCC1] | 627.2 (M + H)+ | 1.80 | C |

TABLE 9-continued
| Ex. # | Structure | LCMS m/z observed | HPLC $t_R$ (min) | HPLC method |
|---|---|---|---|---|
| 497 | 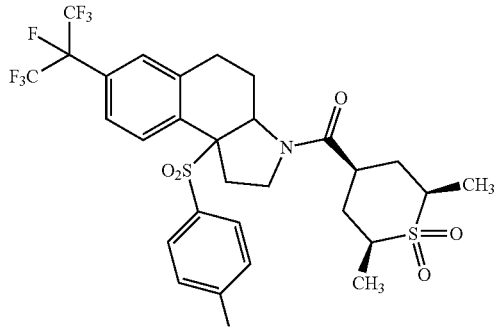 Homochiral from peak 2 | 704.1 (M + H)+ | 2.32 | C |
| 498 | 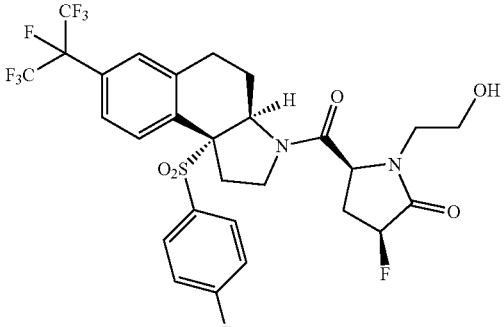 | 673.2 (M + H)+ | 2.09 | C |
| 499 | 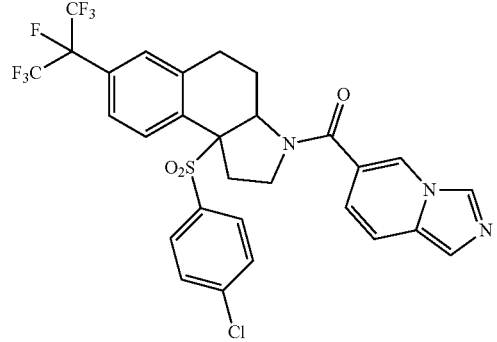 Homochiral from peak 2 | 660.2 (M + H)+ | 2.31 | C |
| 500 | 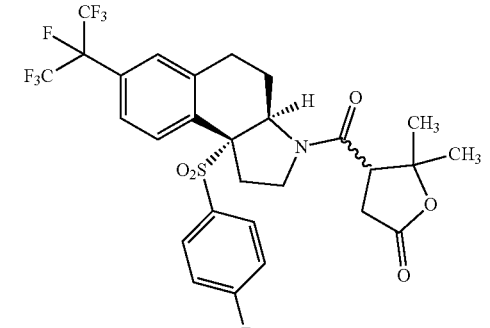 | 640.2 (M + H)+ | 2.26 2.29 | C |

TABLE 9-continued

| Ex. # | Structure | LCMS m/z observed | HPLC t$_R$ (min) | HPLC method |
|---|---|---|---|---|
| 501 | 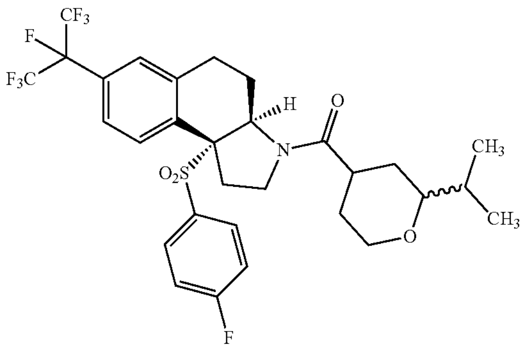 [SMILES: CC(C)C1CC(C(=O)N2CC[C@@]3(S(=O)(=O)c4ccc(F)cc4)c4ccc(C(F)(C(F)(F)F)C(F)(F)F)cc4CC[C@@H]23)CCO1] | 654.3 (M + H)⁺ | 2.54 2.56 | C |
| 502 | 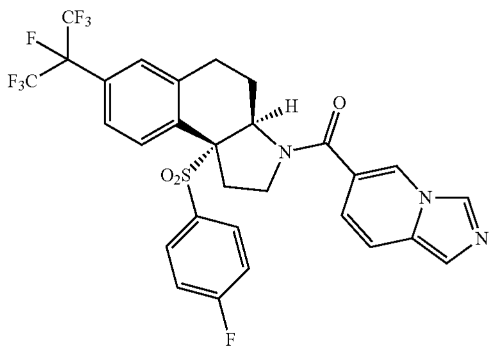 [SMILES: O=C(c1ccc2cncn2c1)N1CC[C@@]2(S(=O)(=O)c3ccc(F)cc3)c3ccc(C(F)(C(F)(F)F)C(F)(F)F)cc3CC[C@@H]12] | 644.2 (M + H)⁺ | 2.21 | C |
| 503 | 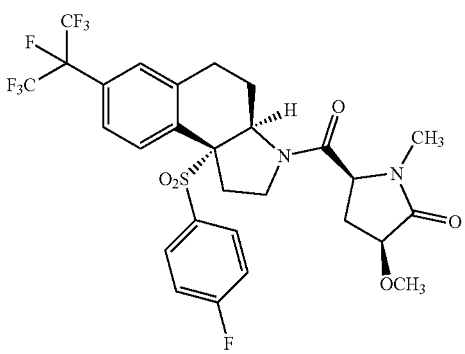 [SMILES: CO[C@H]1C[C@@H](C(=O)N2CC[C@@]3(S(=O)(=O)c4ccc(F)cc4)c4ccc(C(F)(C(F)(F)F)C(F)(F)F)cc4CC[C@@H]23)N(C)C1=O] | 654.9 (M + H)⁺ | 2.16 | C |
| 504 | From peak 2 | 686.2 (M + H)⁺ | 2.03 | C |

TABLE 9-continued

| Ex. # | Structure | LCMS m/z observed | HPLC $t_R$ (min) | HPLC method |
|---|---|---|---|---|
| 505 | 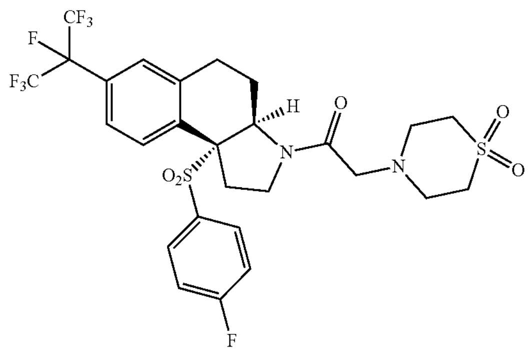 | 675.1 (M + H)+ | 2.18 | C |
| 506 | Homochiral from peak 2 | 684.2 (M + H)+ | 1.90 | C |
| 507 | From peak 2 | 686.3 (M + H)+ | 2.01 | C |
| 508 | Homochiral from peak 2 | 655.2 (M + H)+ | 1.04 | B |

TABLE 9-continued
| Ex. # | Structure | LCMS m/z observed | HPLC $t_R$ (min) | HPLC method |
|---|---|---|---|---|
| 509 | 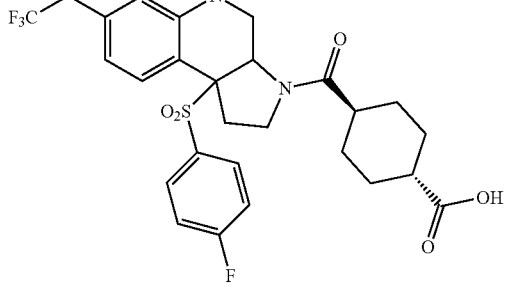<br>Homochiral from peak 1 | 655.2 (M + H)+ | 1.04 | B |
| 510 | 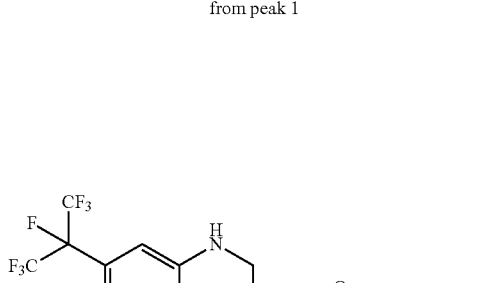<br>Homochiral from peak 2 | 681.1 (M + H)+ | 1.93 | C |
| 511 | 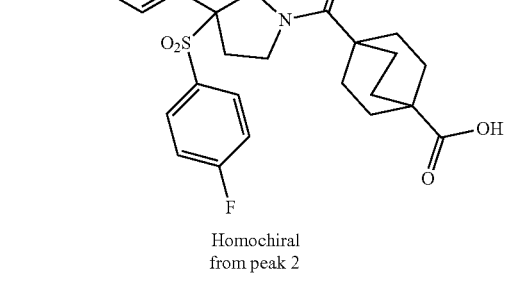<br>Homochiral from peak 2 | 673.2 (M + H)+ | 1.09 | B |

TABLE 9-continued
| Ex. # | Structure | LCMS m/z observed | HPLC $t_R$ (min) | HPLC method |
|---|---|---|---|---|
| 512 | 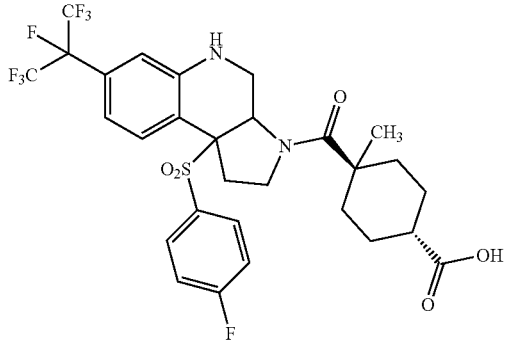 Homochiral from peak 2 | 669.2 (M + H)+ | 1.98 | C |
| 513 | 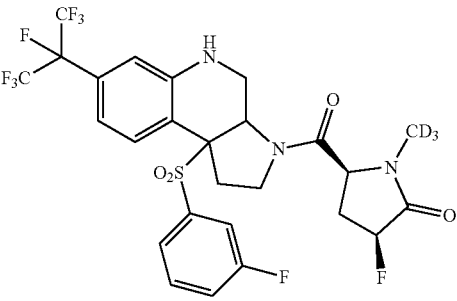 Homochiral from peak 2 | 647.1 (M + H)+ | 1.05 | B |
| 514 | 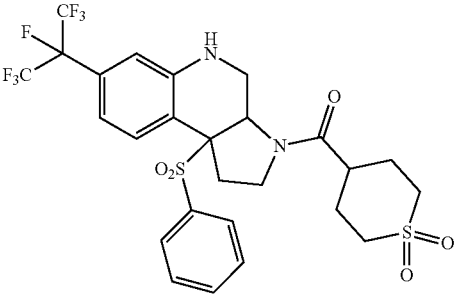 Homochiral from peak 2 | 643.1 (M + H)+ | 0.99 | B |
| 515 | 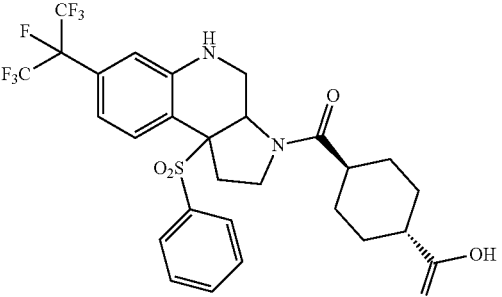 Homochiral from peak 2 | 637.1 (M + H)+ | 1.02 | B |

TABLE 9-continued
| Ex. # | Structure | LCMS m/z observed | HPLC $t_R$ (min) | HPLC method |
|---|---|---|---|---|
| 516 | 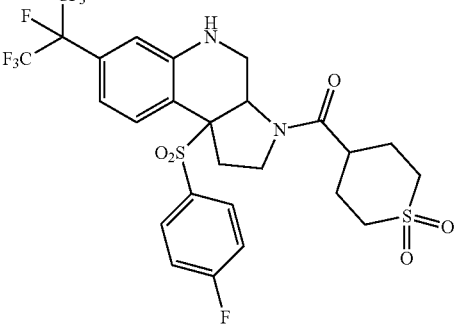<br>Homochiral from peak 2 | 661.1 (M + H)+ | 1.01 | B |
| 517 | 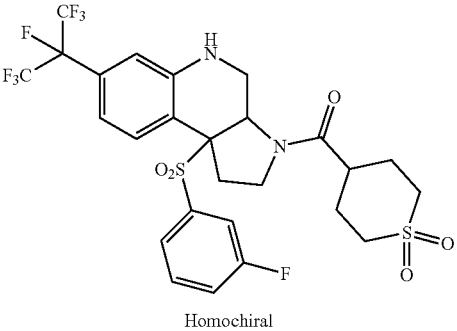<br>Homochiral from peak 1 | 661.1 (M + H)+ | 1.01 | B |
| 518 | 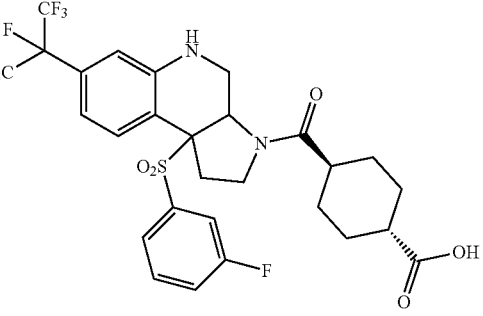<br>Homochiral from peak 1 | 655.3 (M + H)+ | 1.00 | B |
| 519 | 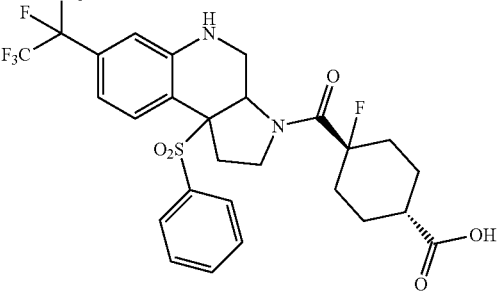<br>Homochiral from peak 2 | 655.3 (M + H)+ | 0.99 | B |

TABLE 9-continued
| Ex. # | Structure | LCMS m/z observed | HPLC $t_R$ (min) | HPLC method |
|---|---|---|---|---|
| 520 | 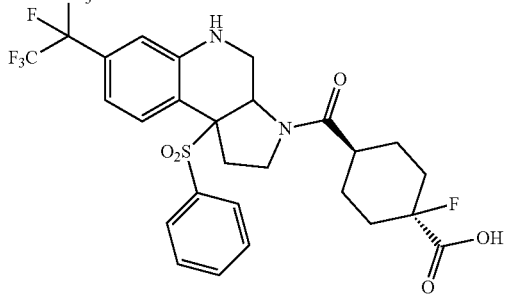<br>Homochiral from peak 2 | 655.3 (M + H)+ | 0.99 | B |
| 521 | 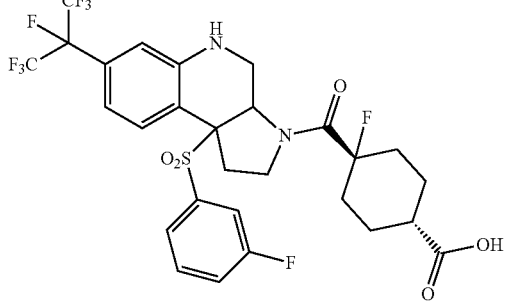<br>Homochiral from peak 1 | 673.2 (M + H)+ | 1.03 | B |
| 522 | 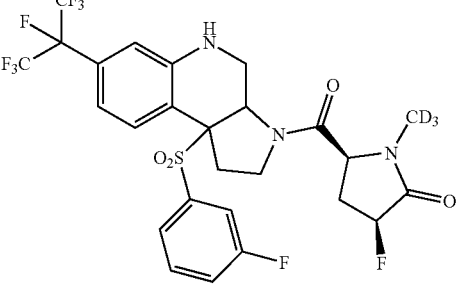<br>Homochiral from peak 1 | 647.1 (M + H)+ | 1.01 | B |
| 523 | 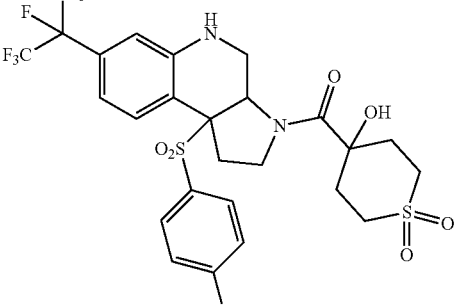<br>Homochiral from peak 2 | 677.2 (M + H)+ | 2.02 | D |

TABLE 9-continued
| Ex. # | Structure | LCMS m/z observed | HPLC $t_R$ (min) | HPLC method |
|---|---|---|---|---|
| 524 | 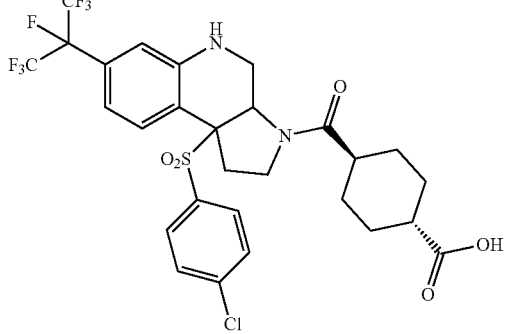<br>Homochiral from peak 2 | 671.2 (M + H)+ | 1.92 | C |
| 525 | 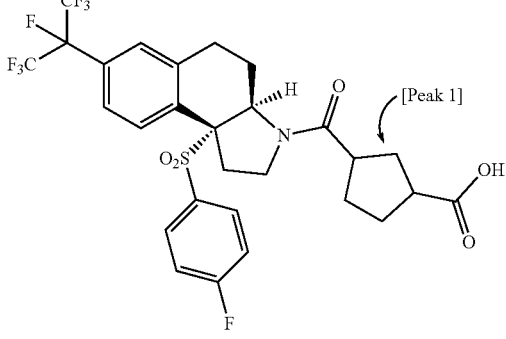 | 654.2 (M + H)+ | 1.05 | B |
| 526 | 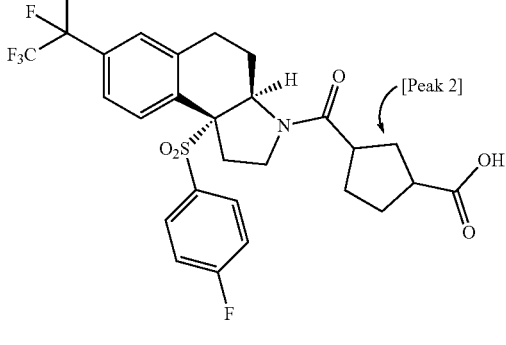 | 654.2 (M + H)+ | 1.04 | B |
| 527 | 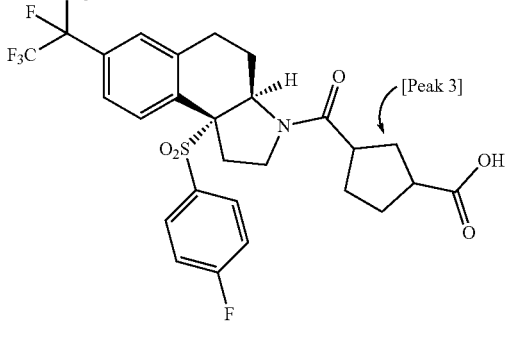 | 654.2 (M + H)+ | 1.04 | B |

TABLE 9-continued

| Ex. # | Structure | LCMS m/z observed | HPLC $t_R$ (min) | HPLC method |
|---|---|---|---|---|
| 528 | [Peak 4] | 654.2 (M + H)+ | 1.04 | B |
| 529 | 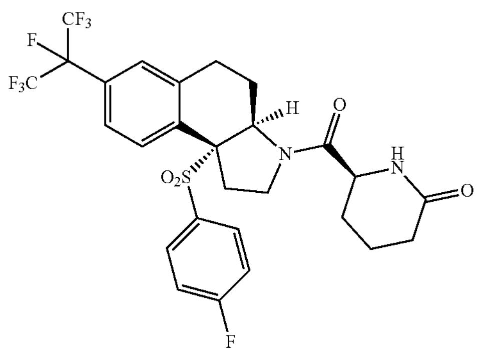 [SMILES: O=C1CCC[C@@H](C(=O)N2CC[C@@]3(S(=O)(=O)c4ccc(F)cc4)c4ccc(C(F)(C(F)(F)F)C(F)(F)F)cc4CC[C@@H]23)N1] | 625.1 (M + H)+ | 2.03 | C |
| 530 | From peak 2 | 661.9 (M + H)+ | 2.20 | C |
| 531 | Homochiral from peak 2 | 693.2 (M + H)+ | 2.26 | C |

TABLE 9-continued

| Ex. # | Structure | LCMS m/z observed | HPLC $t_R$ (min) | HPLC method |
|---|---|---|---|---|
| 532 | Homochiral from peak 2 | 660.0 (M + H)+ | 2.28 | C |
| 533 | 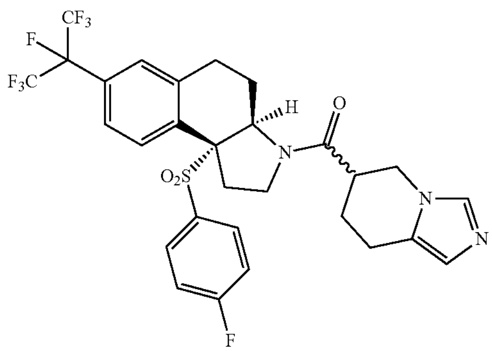 [SMILES: O=C(C1CCc2cncn2C1)N1CC[C@@]2(S(=O)(=O)c3ccc(F)cc3)c3ccc(C(F)(C(F)(F)F)C(F)(F)F)cc3CC[C@@H]12] | 648.2 (M + H)+ | 2.09 | C |
| 534 | From peak 2 | 664.1 (M + H)+ | 2.20 | C |
| 535 | Homochiral from peak 2 | 677.1 (M + H)+ | 2.18 | C |

TABLE 9-continued
| Ex. # | Structure | LCMS m/z observed | HPLC $t_R$ (min) | HPLC method |
|---|---|---|---|---|
| 536 | 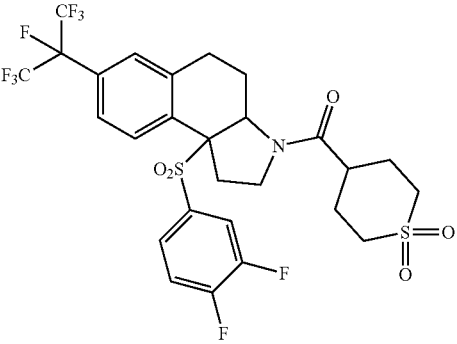<br>Homochiral from peak 2 | 677.9 (M + H)+ | 2.20 | C |
| 537 | 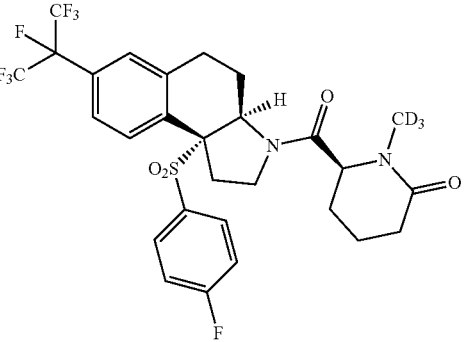 | 642.1 (M + H)+ | 2.10 | C |
| 538 | 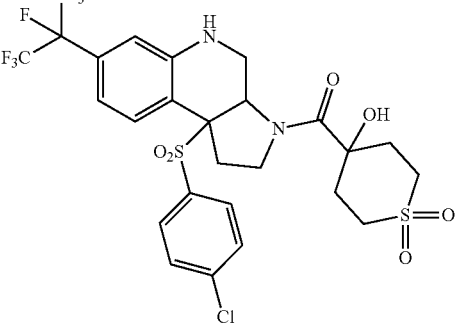<br>Homochiral from peak 2 | 693.3 (M + H)+ | 2.16 | C |
| 539 | 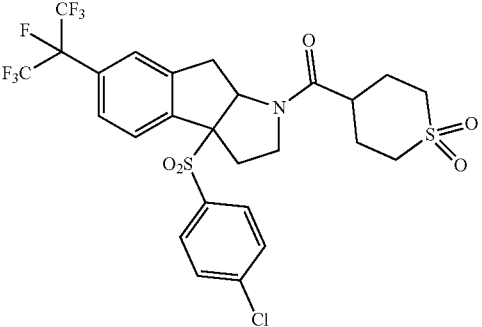<br>Homochiral from peak 1 | 662.1 (M + H)+ | 1.06 | B |

TABLE 9-continued
| Ex. # | Structure | LCMS m/z observed | HPLC $t_R$ (min) | HPLC method |
|---|---|---|---|---|
| 540 | 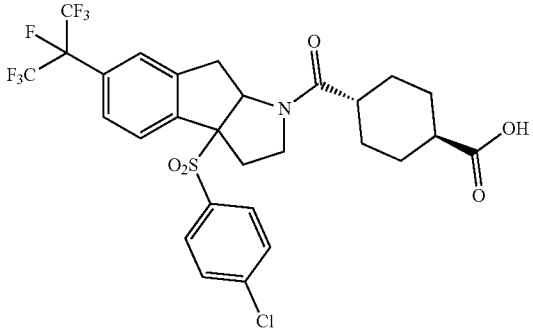<br>Homochiral from peak 1 | 656.1 (M + H)+ | 1.08 | B |
| 541 | 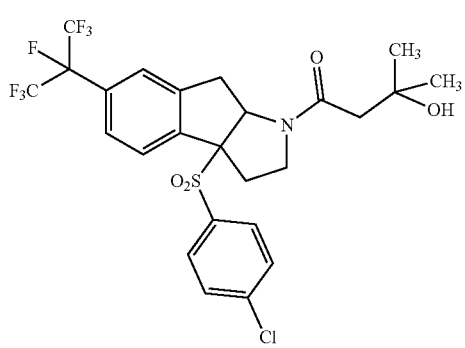<br>Homochiral from peak 1 | 602.2 (M + H)+ | 1.11 | B |
| 542 | 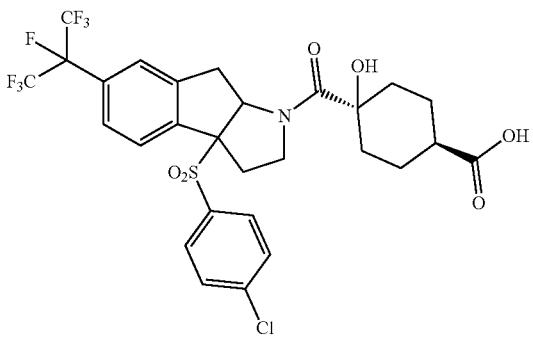<br>Homochiral from peak 1 | 672.1 (M + H)+ | 1.06 | B |
| 543 | 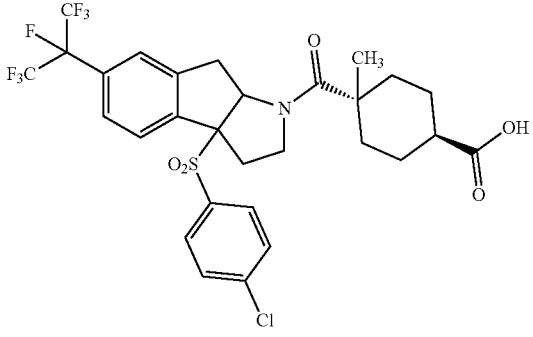<br>Homochiral from peak 1 | 670.1 (M + H)+ | 1.12 | B |

TABLE 9-continued
| Ex. # | Structure | LCMS m/z observed | HPLC $t_R$ (min) | HPLC method |
|---|---|---|---|---|
| 544 | 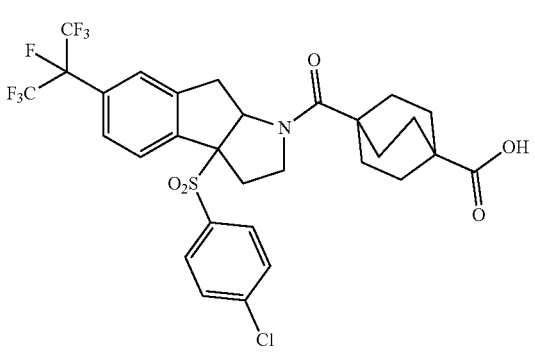 Homochiral from peak 1 | 682.2 (M + H)$^+$ | 2.02 | C |
| 545 | 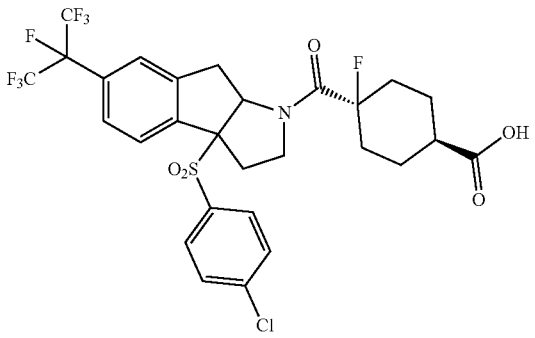 Homochiral from peak 1 | 673.9 (M + H)$^+$ | 1.95 | C |
| 546 | 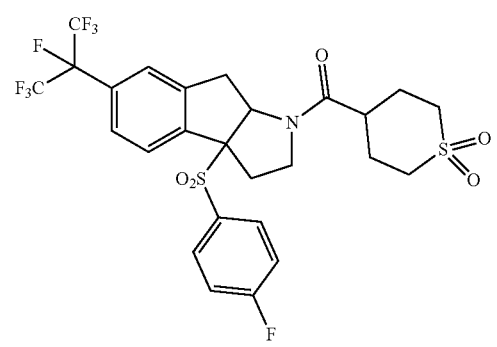 Homochiral from peak 1 | 646.3 (M + H)$^+$ | 2.03 | C |

TABLE 9-continued
| Ex. # | Structure | LCMS m/z observed | HPLC $t_R$ (min) | HPLC method |
|---|---|---|---|---|
| 547 | 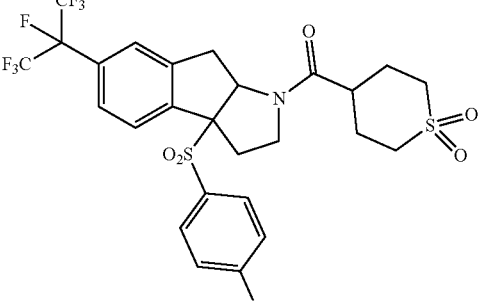<br>Homochiral from peak 2 | 646.4 (M + H)+ | 2.04 | C |
| 548 | 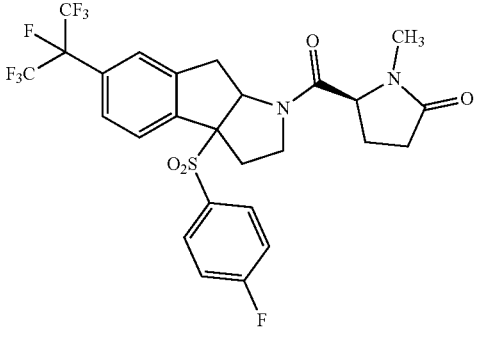<br>Homochiral from peak 1 | 610.8 (M + H)+ | 1.93 | C |
| 549 | 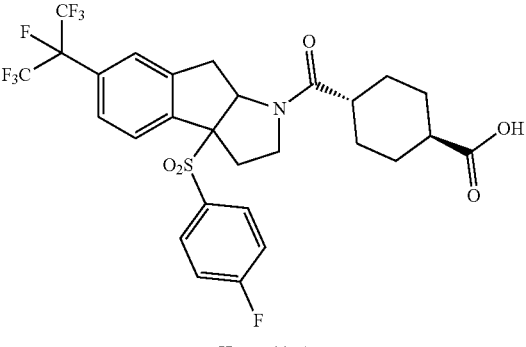<br>Homochiral from peak 2 | 640.4 (M + H)+ | 1.81 | C |
| 550 | 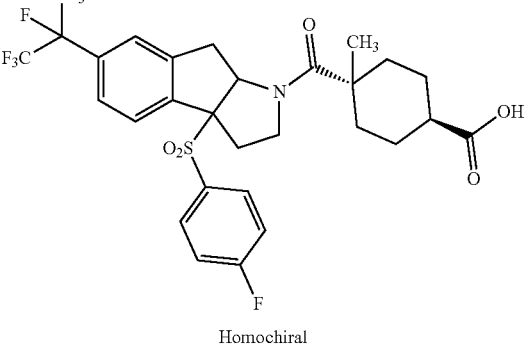<br>Homochiral from peak 1 | 653.9 (M + H)+ | 2.08 | C |

TABLE 9-continued
| Ex. # | Structure | LCMS m/z observed | HPLC $t_R$ (min) | HPLC method |
|---|---|---|---|---|
| 551 | 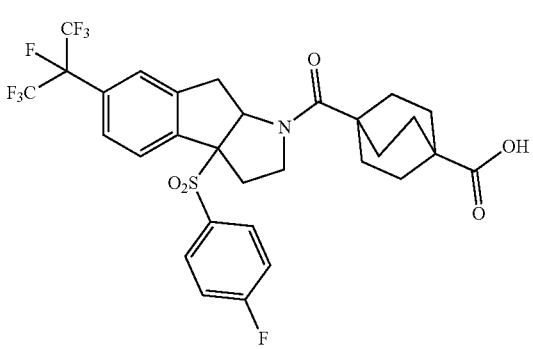<br>Homochiral from peak 1 | 666.4 (M + H)+ | 1.93 | C |
| 552 | 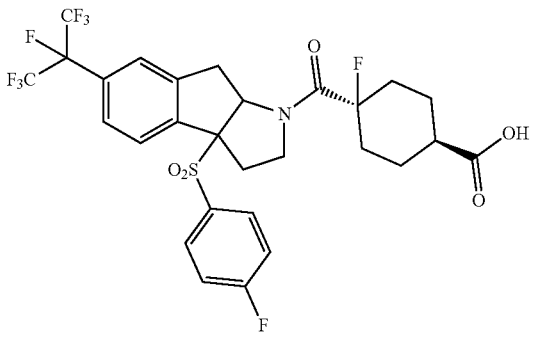<br>Homochiral from peak 1 | 658.2 (M + H)+ | 1.84 | C |
| 553 | 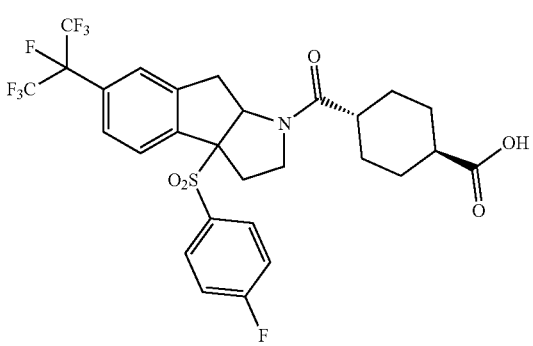<br>Homochiral from peak 1 | 640.0 (M + H)+ | 1.79 | C |

TABLE 9-continued
| Ex. # | Structure | LCMS m/z observed | HPLC $t_R$ (min) | HPLC method |
|---|---|---|---|---|
| 554 | 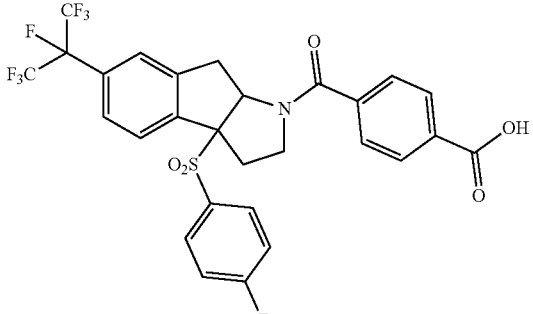<br>Homochiral from peak 1 | 634.4 (M + H)+ | 1.70 | C |
| 555 | 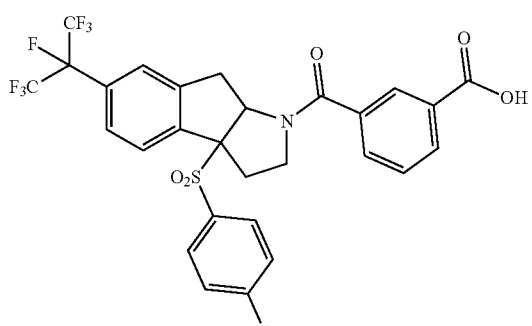<br>Homochiral from peak 1 | 634.3 (M + H)+ | 1.71 | C |
| 556 | 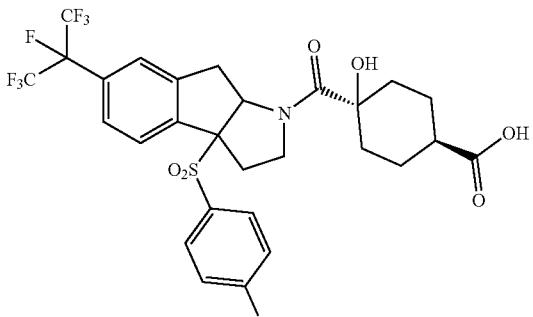<br>Homochiral from peak 1 | 655.8 (M + H)+ | 1.71 | C |
| 557 | 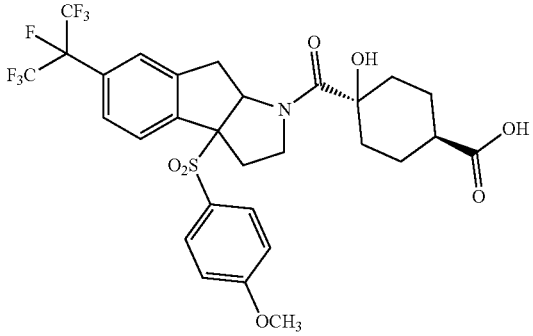<br>Homochiral from peak 1 | 668.0 (M + H)+ | 1.68 | C |

TABLE 9-continued

| Ex. # | Structure | LCMS m/z observed | HPLC t$_R$ (min) | HPLC method |
|---|---|---|---|---|
| 558 | From peak 1 | 640.2 (M + H)$^+$ | 1.08 | B |
| 559 | Homochiral from peak 1 | 652.1 (M + H)$^+$ | 1.07 | B |
| 560 | Homochiral from peak 1 | 652.1 (M + H)$^+$ | 1.08 | B |
| 561 | Homochiral from peak 1 | 686.4 (M + H)$^+$ | 1.93 | C |

TABLE 9-continued
| Ex. # | Structure | LCMS m/z observed | HPLC $t_R$ (min) | HPLC method |
|---|---|---|---|---|
| 562 | 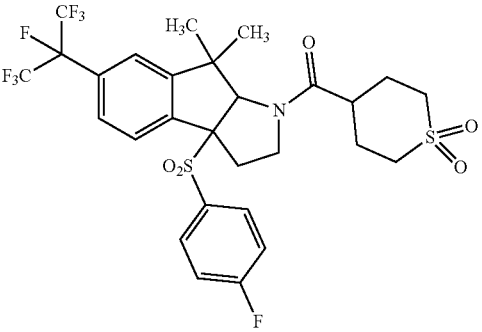 Homochiral from peak 1 | 674.3 (M + H)+ | 2.16 | C |
| 563 | 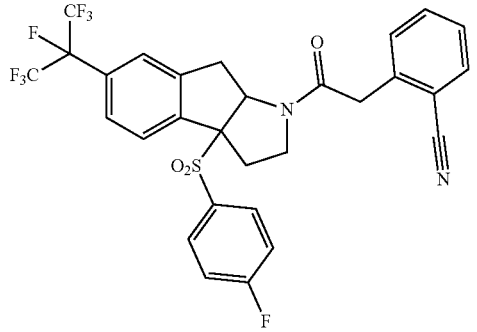 Homochiral from peak 1 | 629.0 (M + H)+ | 2.34 | C |
| 564 | 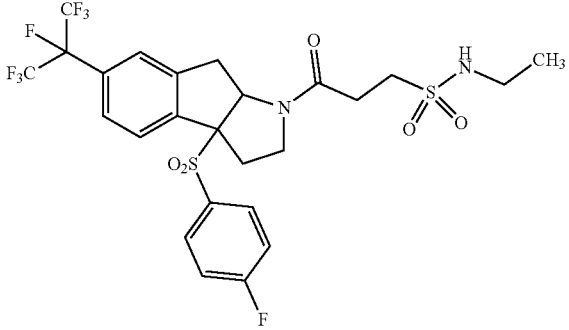 Homochiral from peak 1 | 649.2 (M + H)+ | 2.10 | C |

TABLE 9-continued
| Ex. # | Structure | LCMS m/z observed | HPLC $t_R$ (min) | HPLC method |
|---|---|---|---|---|
| 565 | 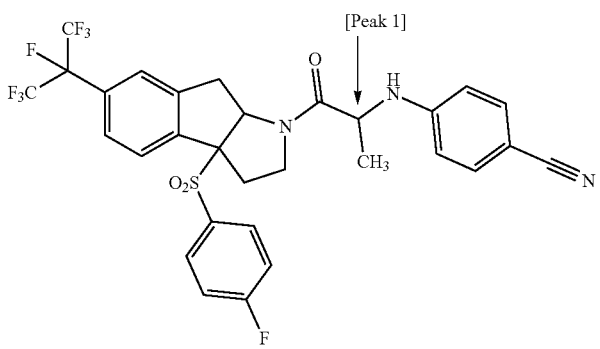<br>Homochiral from peak 1 | 658.2 (M + H)+ | 2.26 | C |
| 566 | 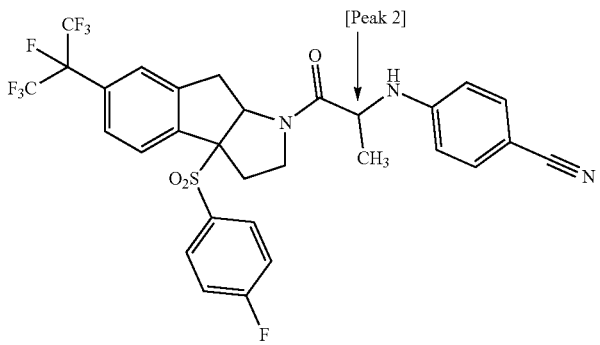<br>Homochiral from peak 1 | 658.0 (M + H)+ | 2.30 | C |
| 567 | 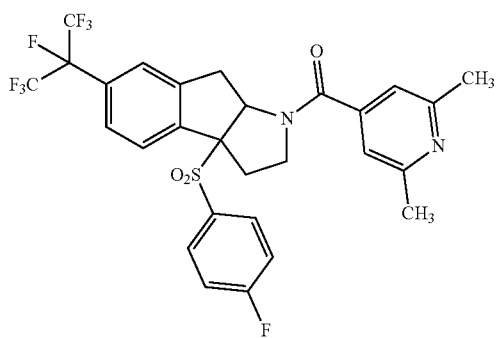<br>Homochiral from peak 1 | 621.1 (M + H)+ | 2.05 | C |

TABLE 9-continued
| Ex. # | Structure | LCMS m/z observed | HPLC $t_R$ (min) | HPLC method |
|---|---|---|---|---|
| 568 | 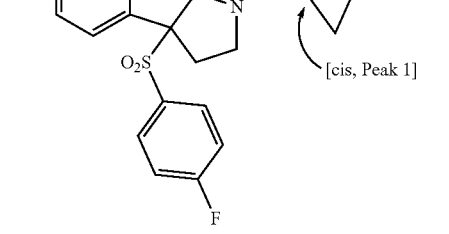 Homochiral from peak 1 | 630.1 (M + H)+ | 2.51 | C |
| 569 |  Homochiral from peak 1 | 630.2 (M + H)+ | 2.60 | C |
| 570 |  Homochiral from peak 1 | 647.4 (M + H)+ | 2.22 | C |
| 571 | 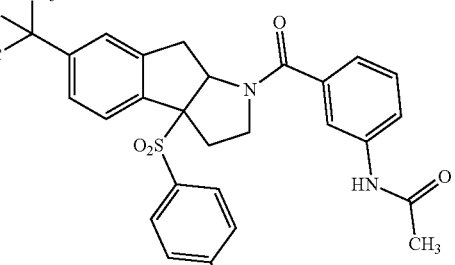 Homochiral from peak 1 | 659.1 (M + H)+ | 2.21 | C |

TABLE 9-continued
| Ex. # | Structure | LCMS m/z observed | HPLC $t_R$ (min) | HPLC method |
|---|---|---|---|---|
| 572 | 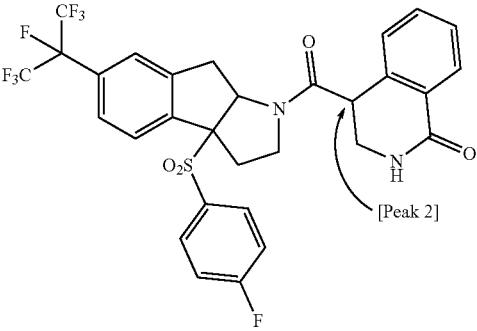<br>Homochiral from peak 1 | 659.4 (M + H)+ | 2.27 | C |
| 573 | 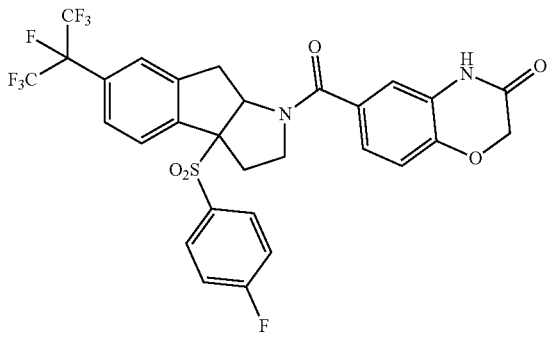<br>Homochiral from peak 1 | 661.1 (M + H)+ | 2.26 | C |
| 574 | 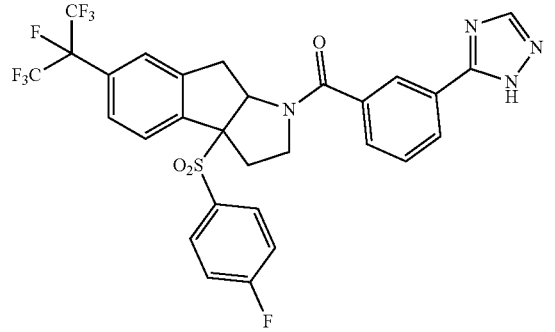<br>Homochiral from peak 1 | 657.1 (M + H)+ | 2.14 | C |

TABLE 9-continued
| Ex. # | Structure | LCMS m/z observed | HPLC $t_R$ (min) | HPLC method |
|---|---|---|---|---|
| 575 | 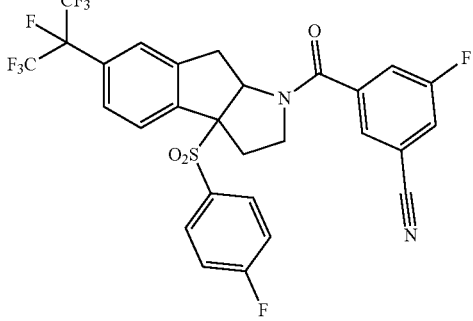<br>Homochiral from peak 1 | 632.9 (M + H)+ | 2.26 | C |
| 576 | 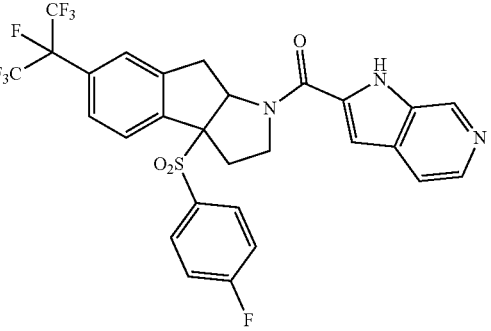<br>Homochiral from peak 1 | 630.0 (M + H)+ | 2.13 | C |
| 577 | 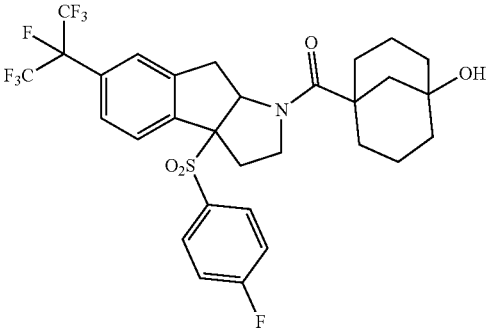<br>Homochiral from peak 1 | 651.9 (M + H)+ | 2.37 | C |
| 578 | 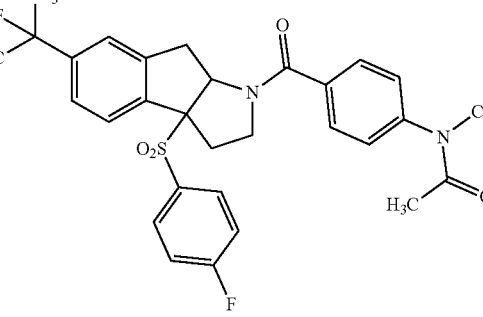<br>Homochiral from peak 1 | 661.1 (M + H)+ | 2.22 | C |

TABLE 9-continued
| Ex. # | Structure | LCMS m/z observed | HPLC $t_R$ (min) | HPLC method |
|---|---|---|---|---|
| 579 | 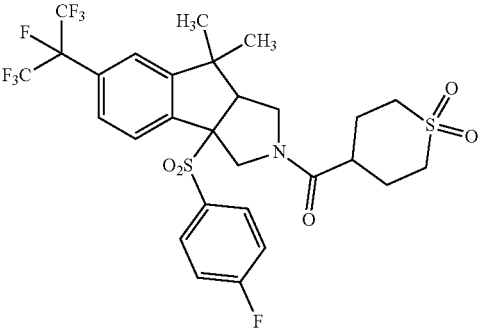<br>Homochiral from peak 1 | 656.1 (M + H)+ | 2.07 | C |
| 580 | 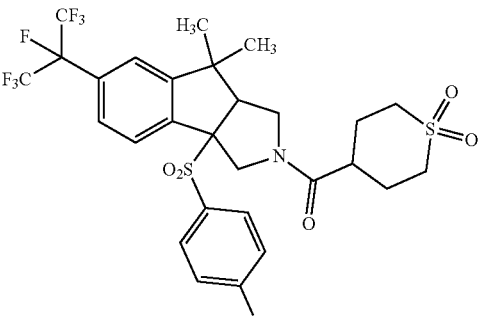<br>Homochiral from peak 2 | 656.1 (M + H)+ | 2.07 | C |
| 581 | 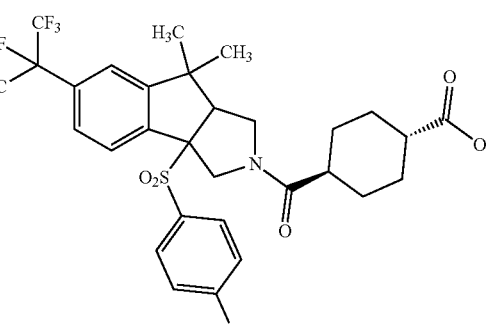<br>Homochiral from peak 1 | 650.1 (M + H)+ | 1.80 | C |
| 582 | 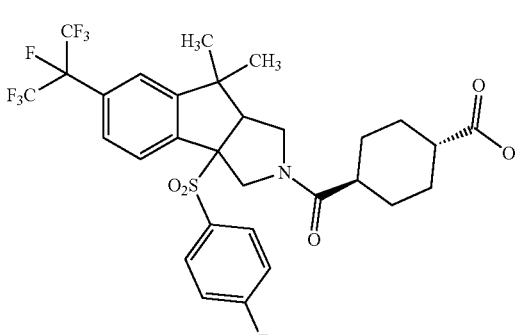<br>Homochiral from peak 2 | 650.1 (M + H)+ | 1.81 | C |

TABLE 9-continued
| Ex. # | Structure | LCMS m/z observed | HPLC $t_R$ (min) | HPLC method |
|---|---|---|---|---|
| 583 | 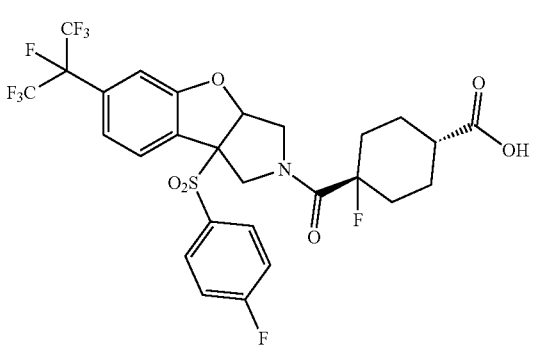<br>Homochiral from peak 2 | 660.1 $(M + H)^+$ | 1.89 | C |
| 584 | 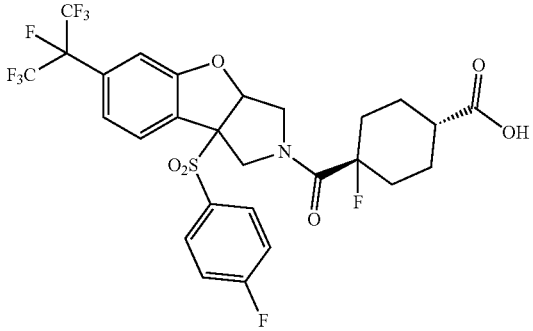<br>Homochiral from peak 1 | 660.1 $(M + H)^+$ | 1.84 | C |
| 585 | 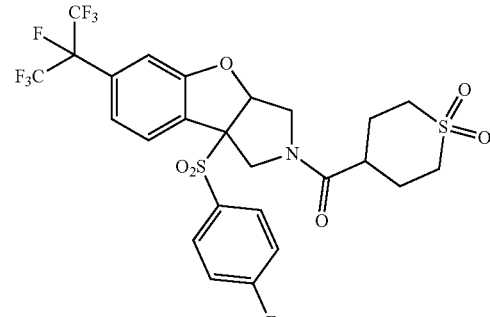<br>Homochiral from peak 2 | 648.0 $(M + H)^+$ | 1.99 | C |

TABLE 9-continued
| Ex. # | Structure | LCMS m/z observed | HPLC $t_R$ (min) | HPLC method |
|---|---|---|---|---|
| 586 | 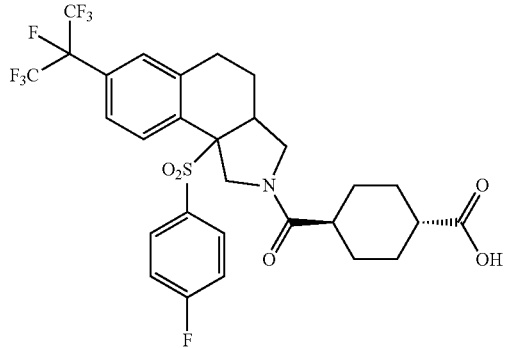<br>Homochiral from peak 1 | 654.5 (M + H)⁺ | 1.02 | B |
| 587 | 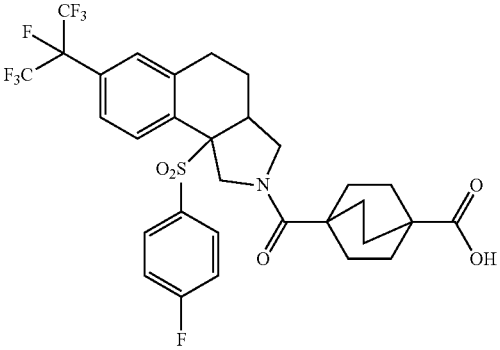<br>Homochiral from peak 1 | 680.4 (M + H)⁺ | 1.04 | B |
| 588 | 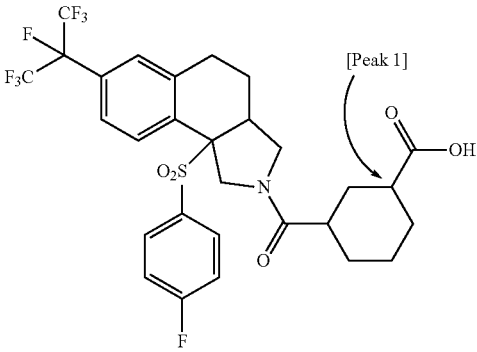<br>Homochiral from peak 1 | 654.1 (M + H)⁺ | 2.181 | D |

TABLE 9-continued
| Ex. # | Structure | LCMS m/z observed | HPLC $t_R$ (min) | HPLC method |
|---|---|---|---|---|
| 589 | 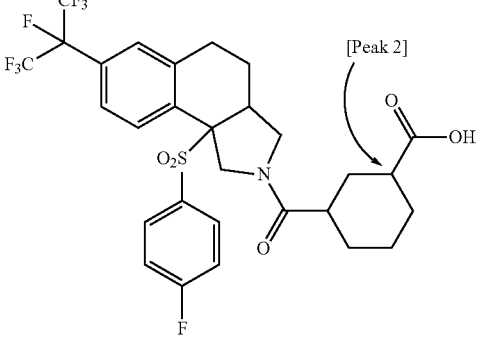<br>Homochiral from peak 1 | 654.2 (M + H)+ | 2.158 | D |
| 590 | 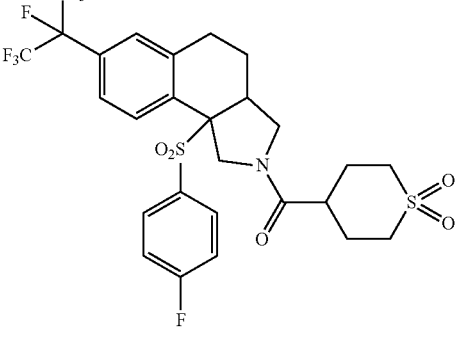<br>Homochiral from peak 1 | 660.0 (M + H)+ | 2.094 | D |
| 591 | 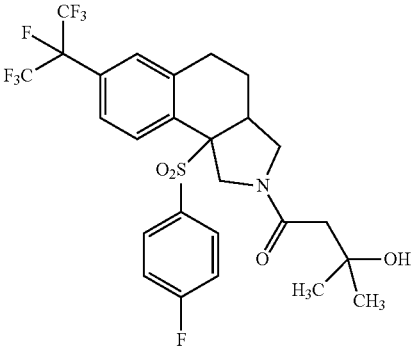<br>Homochiral from peak 1 | 599.8 (M + H)+ | 2.205 | D |

TABLE 9-continued
| Ex. # | Structure | LCMS m/z observed | HPLC $t_R$ (min) | HPLC method |
|---|---|---|---|---|
| 592 | 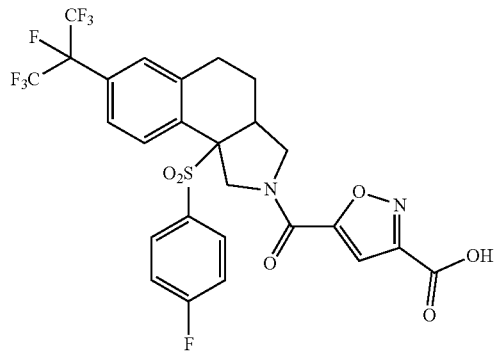 Homochiral from peak 1 | 638.9 (M + H)+ | 2.163 | D |
| 593 | 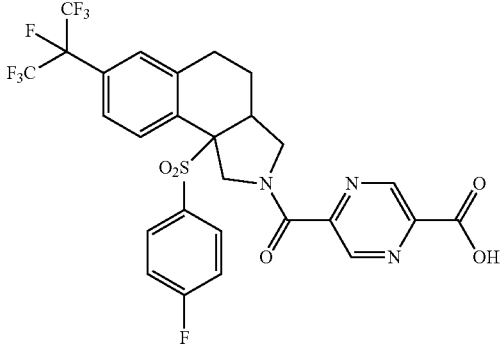 Homochiral from peak 1 | 650.2 (M + H)+ | 2.239 | D |
| 594 | 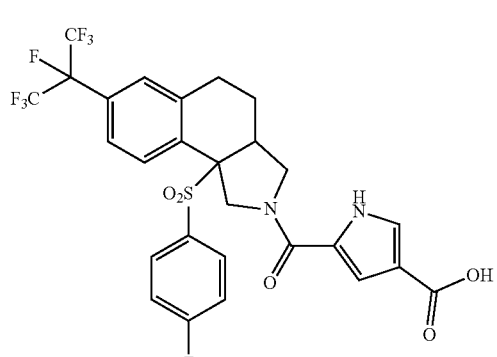 Homochiral from peak 1 | 637.2 (M + H)+ | 1.983 | D |

TABLE 9-continued
| Ex. # | Structure | LCMS m/z observed | HPLC $t_R$ (min) | HPLC method |
|---|---|---|---|---|
| 595 | 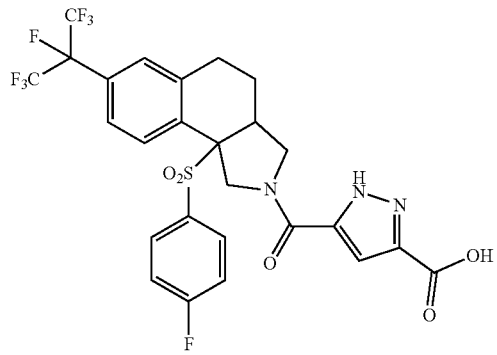 Homochiral from peak 1 | 637.8 (M + H)+ | 2.003 | D |
| 596 | 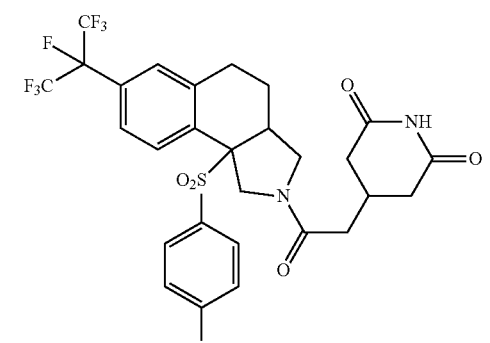 Homochiral from peak 1 | 653.4 (M + H)+ | 2.03 | C |
| 597 | 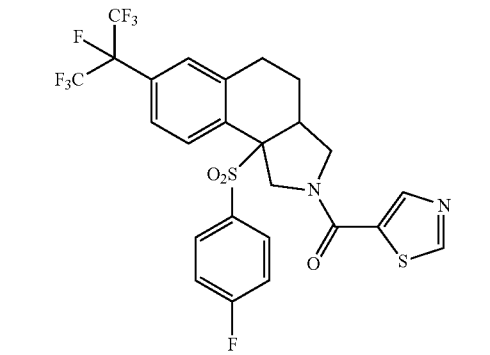 Homochiral from peak 1 | 611.3 (M + H)+ | 2.19 | C |

TABLE 9-continued
| Ex. # | Structure | LCMS m/z observed | HPLC $t_R$ (min) | HPLC method |
|---|---|---|---|---|
| 598 | 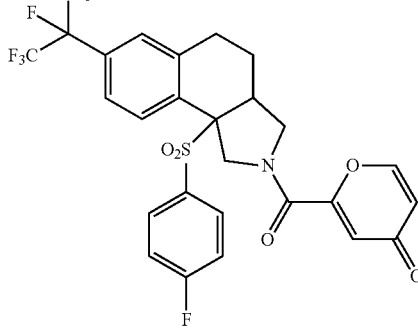<br>Homochiral from peak 1 | 622.3 (M + H)+ | 2.11 | C |
| 599 | 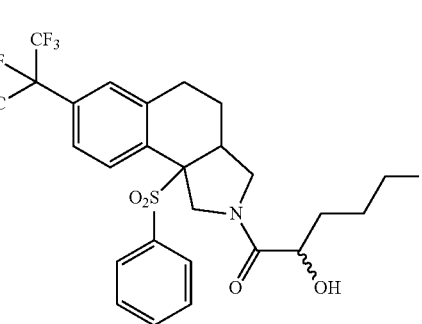<br>From peak 1 | 614.4 (M + H)+ | 2.38 | C |
| 600 | 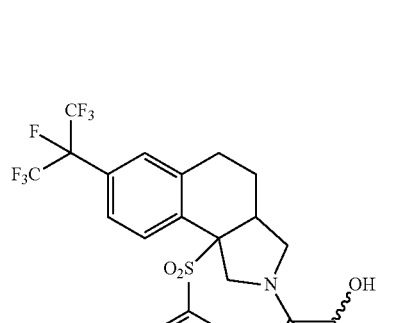<br>From peak 1 | 640.4 (M + H)+ | 2.5 | C |

TABLE 9-continued
| Ex. # | Structure | LCMS m/z observed | HPLC $t_R$ (min) | HPLC method |
|---|---|---|---|---|
| 601 | 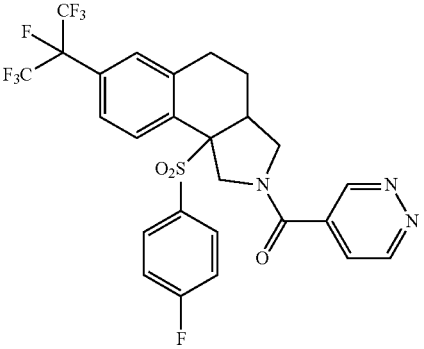 Homochiral from peak 1 | 606.3 (M + H)+ | 2.05 | D |
| 602 | 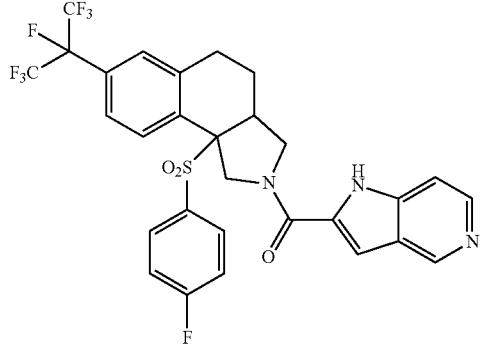 Homochiral from peak 1 | 644.4 (M + H)+ | 2.11 | C |
| 603 | 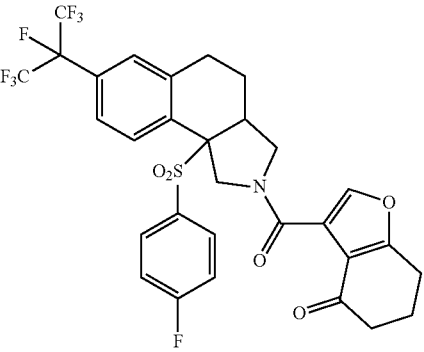 Homochiral from peak 1 | 662.4 (M + H)+ | 2.26 | C |

TABLE 9-continued
| Ex. # | Structure | LCMS m/z observed | HPLC $t_R$ (min) | HPLC method |
|---|---|---|---|---|
| 604 | 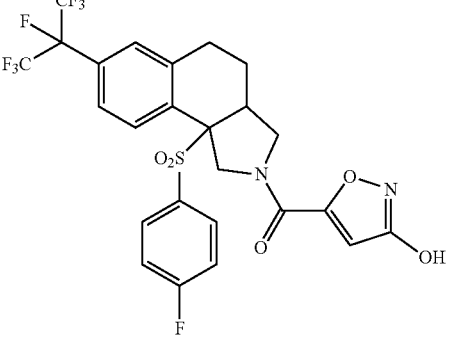  Homochiral from peak 1 | 611.3 (M + H)⁺ | 1.81 | C |
| 605 | 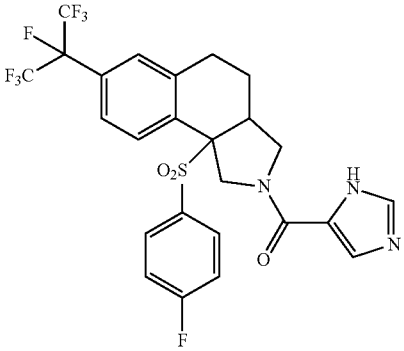  Homochiral from peak 1 | 594 (M + H)⁺ | 1.95 | C |
| 606 | 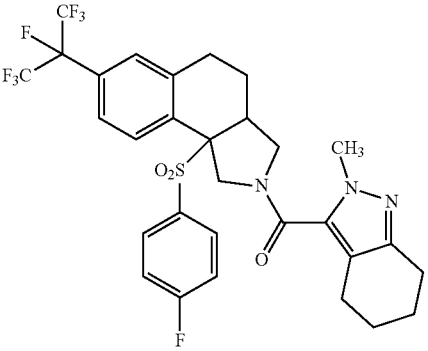  Homochiral from peak 1 | 662.4 (M + H)⁺ | 2.43 | C |

TABLE 9-continued
| Ex. # | Structure | LCMS m/z observed | HPLC $t_R$ (min) | HPLC method |
|---|---|---|---|---|
| 607 | 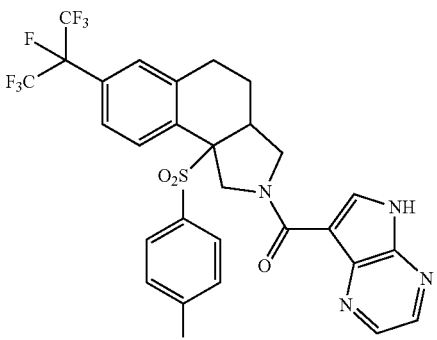<br>Homochiral from peak 1 | 645.4 (M + H)+ | 2.08 | C |
| 608 | 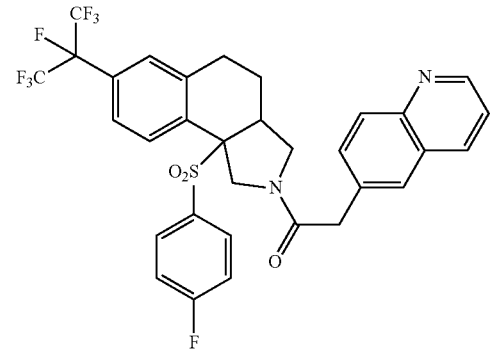<br>Homochiral from peak 1 | 669.1 (M + H)+ | 2.2 | C |
| 609 | 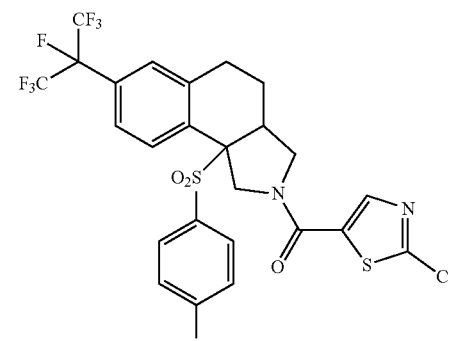<br>Homochiral from peak 1 | 645.3 (M + H)+ | 2.42 | C |

TABLE 9-continued
| Ex. # | Structure | LCMS m/z observed | HPLC $t_R$ (min) | HPLC method |
|---|---|---|---|---|
| 610 | 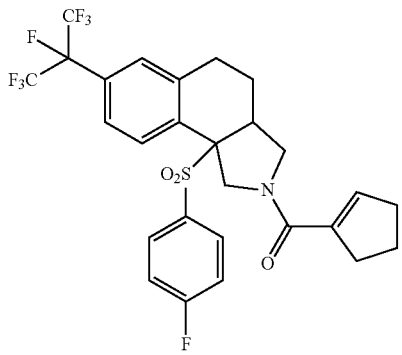<br>Homochiral from peak 1 | 593.8 (M + H)$^+$ | 2.33 | D |
| 611 | 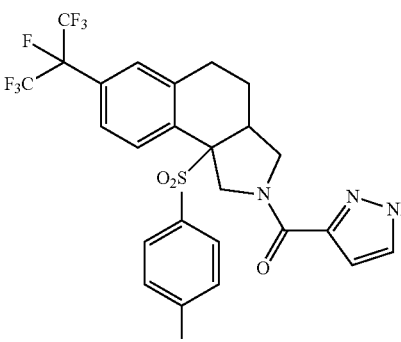<br>Homochiral from peak 1 | 594.0 | 2.05 | D |
| 612 | 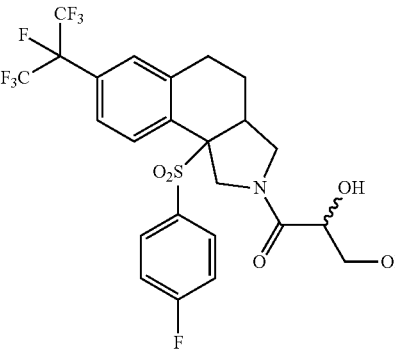<br>From peak 1 | 587.8 (M + H)$^+$ | 1.88 | C |

TABLE 9-continued
| Ex. # | Structure | LCMS m/z observed | HPLC $t_R$ (min) | HPLC method |
|---|---|---|---|---|
| 613 | 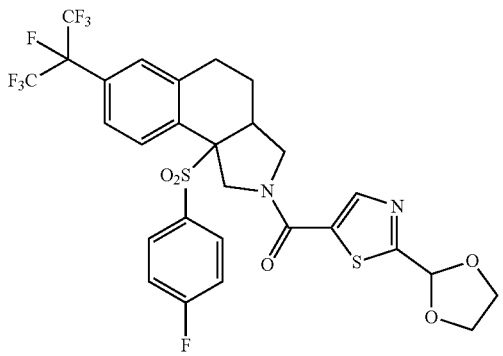 Homochiral from peak 1 | 682.8 (M + H)+ | 2.22 | C |
| 614 | 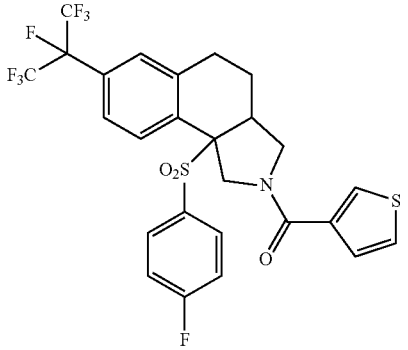 Homochiral from peak 1 | 609.9 (M + H)+ | 2.27 | D |
| 615 | 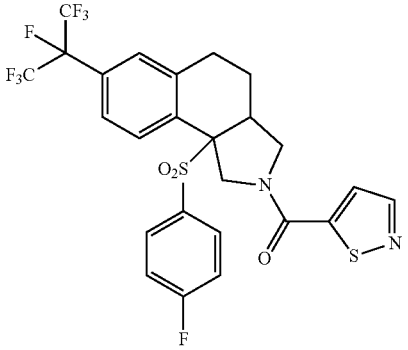 Homochiral from peak 1 | 610.9 (M + H)+ | 2.24 | C |

US 10,711,020 B2
TABLE 9-continued
| Ex. # | Structure | LCMS m/z observed | HPLC $t_R$ (min) | HPLC method |
|---|---|---|---|---|
| 616 | 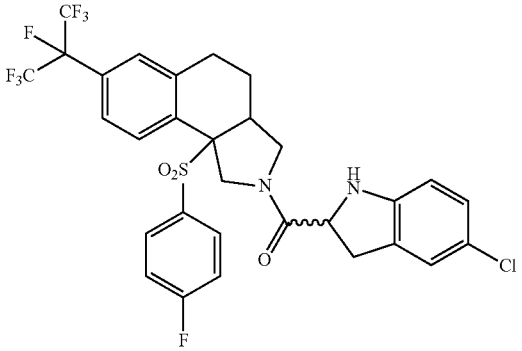<br>From peak 1 | 679.1 (M + H)+ | 2.45 | C |
| 617 | 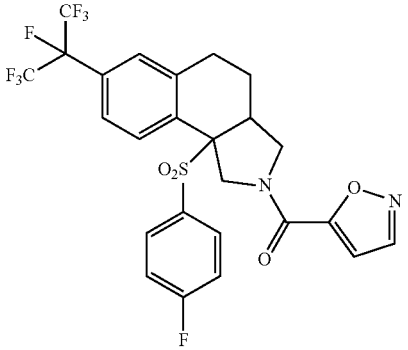<br>Homochiral from peak 1 | 594.9 (M + H)+ | 2.2 | C |
| 618 | 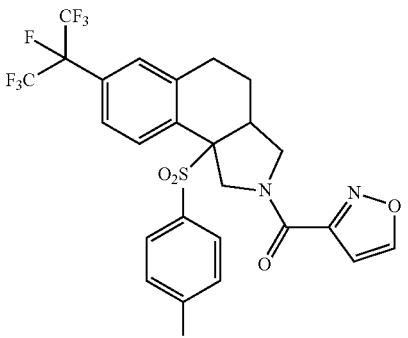<br>Homochiral from peak 1 | 595.1 (M + H)+ | 2.24 | D |

TABLE 9-continued
| Ex. # | Structure | LCMS m/z observed | HPLC $t_R$ (min) | HPLC method |
|---|---|---|---|---|
| 619 | 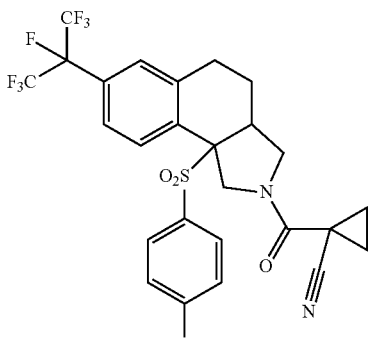<br>Homochiral from peak 1 | 593.0 (M + H)⁺ | 2.26 | C |
| 620 | 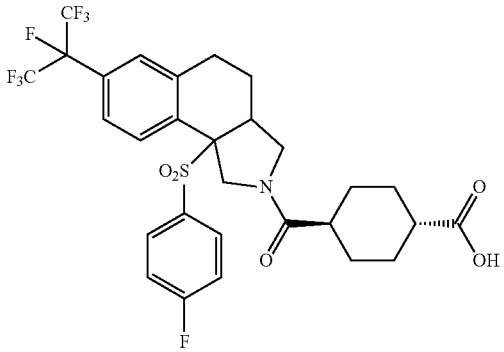<br>Homochiral from peak 2 | 654.4 (M + H)⁺ | 2.170 | D |
| 621 | 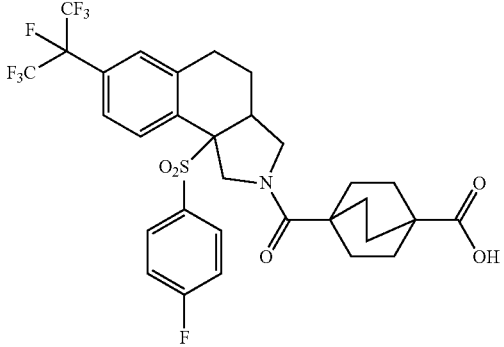<br>Homochiral from peak 2 | 680.4 (M + H)⁺ | 2.26 | D |

TABLE 9-continued
| Ex. # | Structure | LCMS m/z observed | HPLC $t_R$ (min) | HPLC method |
|---|---|---|---|---|
| 622 | 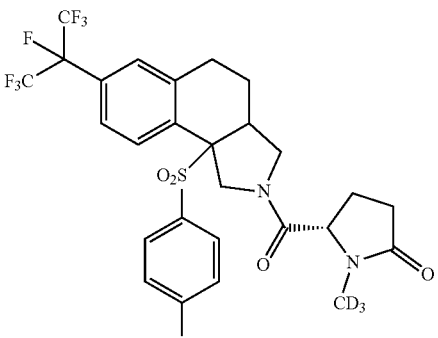<br>Homochiral from peak 2 | 628.1 (M + H)+ | 2.053 | D |
| 623 | 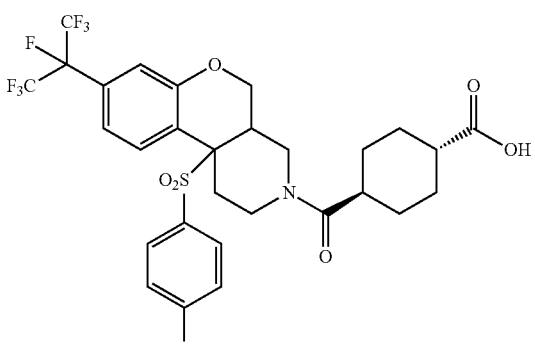<br>Homochiral from peak 1 | 670.3 (M + H)+ | 1.01 | B |
| 624 | 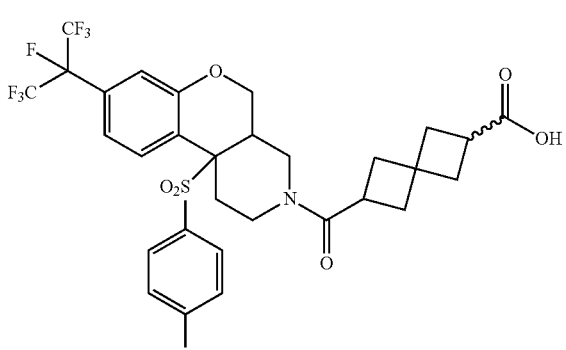<br>From peak 1 | 682.3 (M + H)+ | 1.02 | B |

TABLE 9-continued
| Ex. # | Structure | LCMS m/z observed | HPLC $t_R$ (min) | HPLC method |
|---|---|---|---|---|
| 625 | 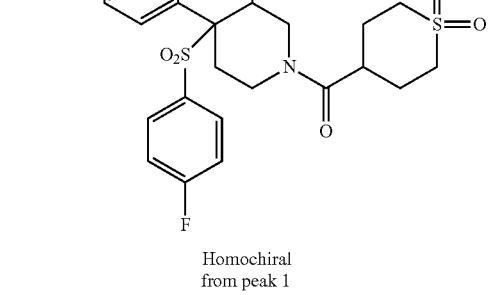<br>Homochiral from peak 1 | 676.2 (M + H)+ | 0.99 | B |
| 626 | 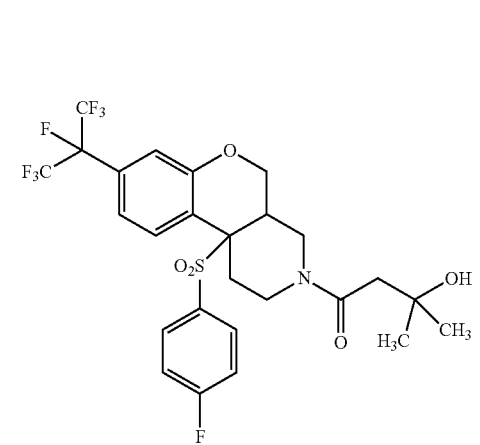<br>Homochiral from peak 1 | 616.2 (M + H)+ | 1.03 | B |
| 627 | 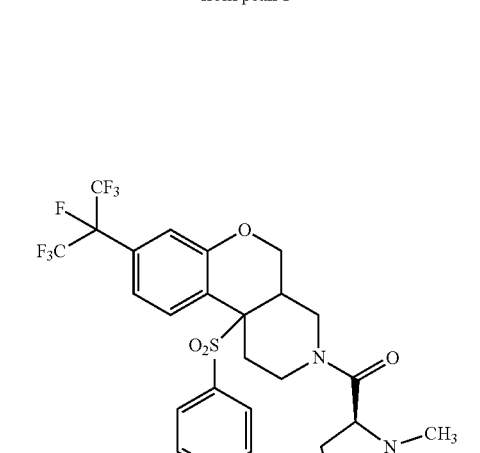<br>Homochiral from peak 1 | 641.2 (M + H)+ | 0.97 | B |

TABLE 9-continued
| Ex. # | Structure | LCMS m/z observed | HPLC $t_R$ (min) | HPLC method |
|---|---|---|---|---|
| 628 | 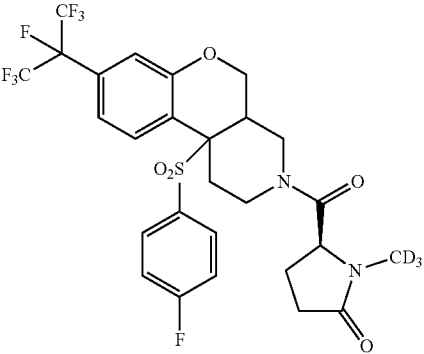 Homochiral from peak 1 | 644.2 (M + H)+ | 0.98 | B |
| 629 | 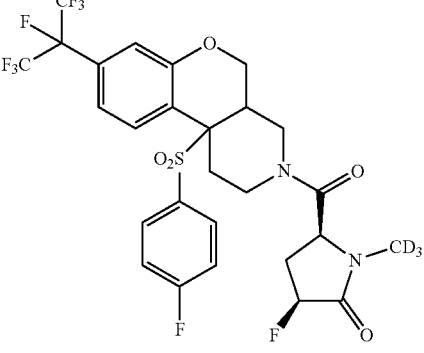 Homochiral from peak 1 | 662.2 (M + H)+ | 1.00 | B |
| 630 | 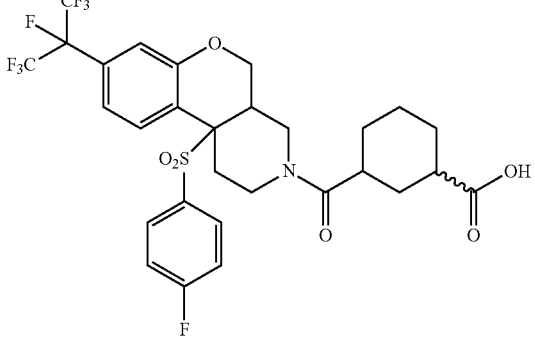 From peak 1 | 670.3 (M + H)+ | 1.03 | B |

TABLE 9-continued
| Ex. # | Structure | LCMS m/z observed | HPLC $t_R$ (min) | HPLC method |
|---|---|---|---|---|
| 631 | 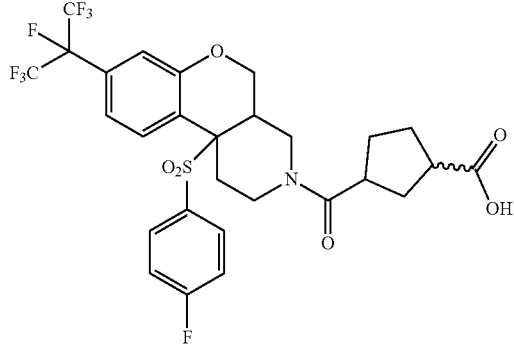<br>From peak 1 | 656.3 (M + H)+ | 1.01 | B |
| 632 | 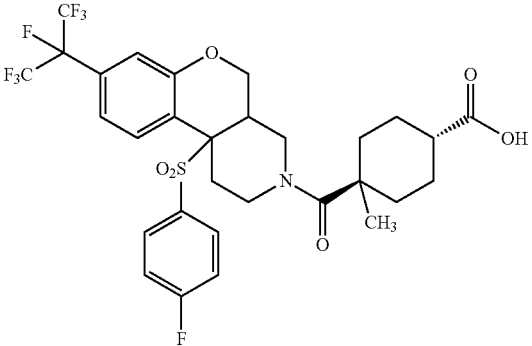<br>Homochiral from peak 1 | 683.9 (M + H)+ | 1.04 | B |
| 633 | 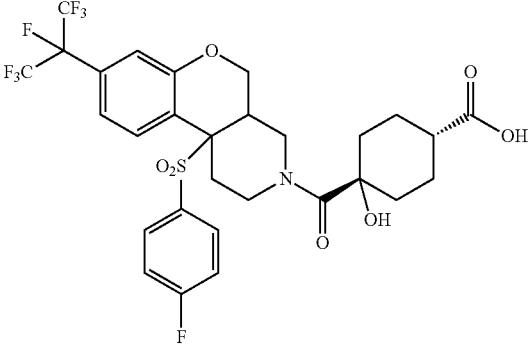<br>Homochiral from peak 1 | 686.2 (M + H)+ | 1.00 | B |

TABLE 9-continued

| Ex. # | Structure | LCMS m/z observed | HPLC $t_R$ (min) | HPLC method |
|---|---|---|---|---|
| 634 | ![structure] Homochiral from peak 2 | 670.3 (M + H)+ | 1.01 | B |
| 635 | ![structure] Homochiral from peak 2 | 676.3 (M + H)+ | 1.00 | B |

Example 636

(3 aR,9bR)—N-ethyl-9b-((4-fluorophenyl)sulfonyl)-7-(perfluoropropan-2-yl)-1,2,3a,4,5,9b-hexahydro-3H-benzo[e]indole-3-carboxamide

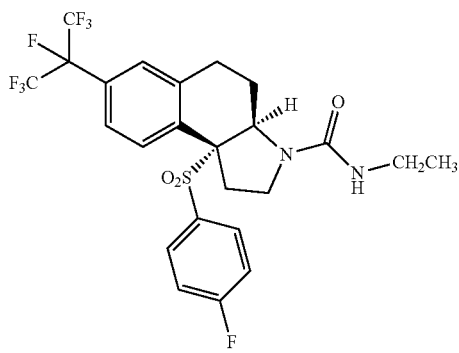 [SMILES: CCNC(=O)N1CC[C@@]2(S(=O)(=O)c3ccc(F)cc3)c3ccc(C(F)(C(F)(F)F)C(F)(F)F)cc3CC[C@@H]12]

A solution of (3aR,9bR)-9b-((4-fluorophenyl)sulfonyl)-7-(perfluoropropan-2-yl)-2,3,3a,4,5,9b-hexahydro-1H-benzo[e]indole hydrochloride (Intermediate 32; 15 mg, 0.028 mmol) in DMF (1 mL) was treated with DIPEA (0.020 mL, 0.112 mmol) and ethyl isocyanate (4.43 µL, 0.056 mmol). The mixture was stirred at rt for 2 h, then was treated with water (0.1 mL, 5.55 mmol) and purified by preparative HPLC (method E, gradient 40-80% B, 20 min) to afford (3aR,9bR)—N-ethyl-9b-((4-fluorophenyl)sulfonyl)-7-(perfluoropropan-2-yl)-1,2,3a,4,5,9b-hexahydro-3H-benzo[e]indole-3-carboxamide (11.2 mg, 67% yield). LCMS m/z 571.3 (M+H)+, HPLC $t_R$ 2.26 min (method C). $^1$H NMR (500 MHz, DMSO-$d_6$) δ 7.82 (d, J=8.4 Hz, 1H), 7.60 (d, J=8.4 Hz, 1H), 7.46-7.37 (m, 2H), 7.32 (br. s., 1H), 7.23 (t, J=8.5 Hz, 2H), 6.28 (br. s., 1H), 4.55 (dd, J=11.7, 4.7 Hz, 1H), 3.42-3.35 (m, 1H), 3.33-3.27 (m, 1H), 3.27-3.20 (m, 1H), 3.09-2.98 (m, 2H), 2.67-2.56 (m, 1H), 2.29 (d, J=9.0 Hz, 1H), 1.96 (t, J=14.5 Hz, 1H), 1.26-1.14 (m, 2H), 1.00 (t, J=7.1 Hz, 3H).

Example 637

1-((3aR,9bR)-9b-((4-fluorophenyl)sulfonyl)-7-(per-fluoropropan-2-yl)-2,3,3a,4,5,9b-hexahydro-1H-benzo[e]indole-3-carbonyl)-3-methylpiperidine-4-carboxylic Acid

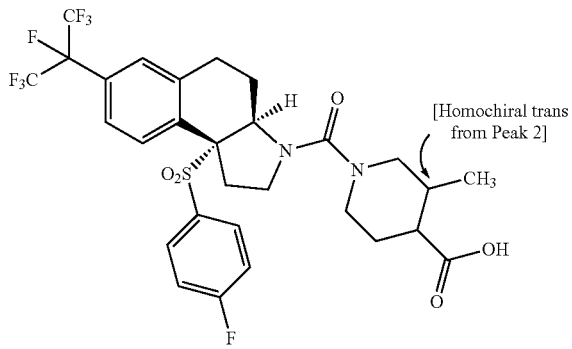 [SMILES: CC1CN(C(=O)N2CC[C@@]3(S(=O)(=O)c4ccc(F)cc4)c4ccc(C(F)(C(F)(F)F)C(F)(F)F)cc4CC[C@@H]23)CCC1C(=O)O]

[Homochiral trans from Peak 2]

Step B: 1-((3aR,9bR)-9b-((4-fluorophenyl)sulfo-nyl)-7-(perfluoropropan-2-yl)-2,3,3a,4,5,9b-hexa-hydro-1H-benzo[e]indole-3-carbonyl)-3-methylpip-eridine-4-carboxylic Acid

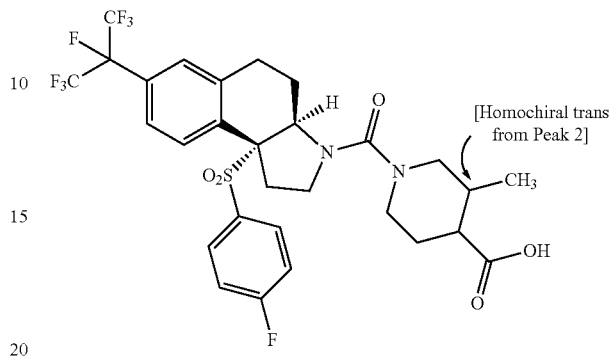

[Homochiral trans from Peak 2]

Step A: (3aR,9bR)-9b-((4-fluorophenyl)sulfonyl)-7-(perfluoropropan-2-yl)-1,2,3a,4,5,9b-hexahydro-3H-benzo[e]indole-3-carbonyl Chloride

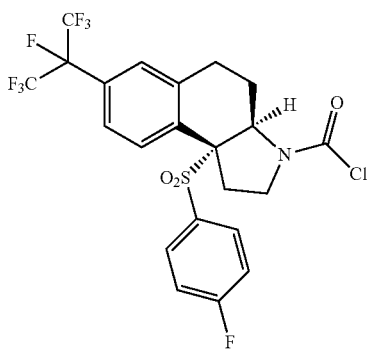 [SMILES: O=C(Cl)N1CC[C@@]2(S(=O)(=O)c3ccc(F)cc3)c3ccc(C(F)(C(F)(F)F)C(F)(F)F)cc3CC[C@@H]12]

A solution of triphosgene (143 mg, 0.481 mmol) in DCM (5 mL) was placed under nitrogen and cooled to −78° C. The mixture was treated with pyridine (0.162 mL, 2.002 mmol), stirred for 5 min, and then warmed to rt. After 10 min, a solution of (3aR,9bR)-9b-((4-fluorophenyl)sulfonyl)-7-(perfluoropropan-2-yl)-2,3,3a,4,5,9b-hexahydro-1H-benzo[e]indole hydrochloride (Intermediate 32; 200 mg, 0.400 mmol) and pyridine (0.081 mL, 1.001 mmol) in DCM (2 mL) was added dropwise to the mixture, which then then stirred at rt overnight. The mixture was partitioned between DCM (25 mL) and 1 M aqueous HCl (15 mL). The organic phase was washed with brine, dried over $Na_2SO_4$ and concentrated to give (3aR,9bR)-9b-((4-fluorophenyl)sulfo-nyl)-7-(perfluoropropan-2-yl)-1,2,3a,4,5,9b-hexahydro-3H-benzo[e]indole-3-carbonyl chloride as an orange solid (180 mg, 80% yield) which was used without further purification.

A solution of crude (3aR,9bR)-9b-((4-fluorophenyl)sul-fonyl)-7-(perfluoropropan-2-yl)-1,2,3a,4,5,9b-hexahydro-3H-benzo[e]indole-3-carbonyl chloride (40 mg, 0.071 mmol) and DIPEA (0.037 mL, 0.214 mmol) in DMF (1.2 mL) was treated with trans methyl 3-methylpiperidine-4-carboxylate (homochiral, from peak 2, Intermediate 150; 22.38 mg, 0.142 mmol) and the mixture was stirred at rt. After 2 h, the mixture was diluted with EtOAc (10 mL), washed sequentially with 1 M aqueous HCl, 10% aqueous LiCl and brine, dried over $Na_2SO_4$ and concentrated to give crude methyl 1-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-3-methylpiperidine-4-carboxy-late. LCMS m/z 683.2 (M+H)$^+$, HPLC $t_R$ 1.16 min (method B). This material was dissolved in THF (2 mL) and treated with a solution of LiOH monohydrate (59.7 mg, 1.424 mmol) in water (1 mL). The mixture was heated at 55° C. for 5 h, cooled to rt and partitioned between EtOAc (10 mL) and 1 M aqueous HCl (5 mL). The organic phase was washed with brine, dried and concentrated. The residue was purified by HPLC (method E, gradient 35-65%) to provide 1-((3aR, 9bR)-9b-((4-fluorophenyl)sulfonyl)-7-(perfluoropropan-2-yl)-2,3,3a,4,5,9b-hexahydro-1H-benzo[e]indole-3-carbo-nyl)-3-methylpiperidine-4-carboxylic acid (10 mg, 21% yield). LCMS m/z 669.2 (M+H)$^+$, HPLC $t_R$ 2.23 min (method C). $^1$H NMR (500 MHz, DMSO-$d_6$) δ 7.87 (d, J=8.5 Hz, 1H), 7.62 (d, J=8.2 Hz, 1H), 7.46-7.36 (m, 3H), 7.35-7.26 (m, 2H), 4.76 (dd, J=8.9, 4.5 Hz, 1H), 3.72-3.28 (m, 2H), 3.13-3.00 (m, 1H), 2.70-2.47 (m, 5H), 2.40 (t, J=12.3 Hz, 1H), 2.16-1.95 (m, 2H), 1.93-1.70 (m, 2H), 1.64-1.37 (m, 3H), 0.83 (d, J=6.3 Hz, 3H).

The Examples in Table 10 were prepared using proce-dures used to prepare Example 637 or similar procedures by using appropriate amine starting materials, followed by ester hydrolysis or other protecting group removal if appropriate.

TABLE 10

| Ex. # | Structure | LCMS m/z observed | HPLC $t_R$ (min) | HPLC method |
|---|---|---|---|---|
| 638 | [Structure with CF3, F3C substituents on bicyclic system, O2S-phenyl-F group, N-piperidine with CH3 and COOH; Homochiral cis from Peak 2] | 668.9 (M + H)+ | 2.22 | D |
| 639 | [Structure with CF3, F3C substituents on bicyclic system, O2S-phenyl-F group, N-piperidine with CH3 and COOH; Homochiral trans from Peak 1] | 669.5 (M + H)+ | 2.22 | D |
| 640 | [Structure with CF3, F3C substituents on bicyclic system, O2S-phenyl-F group, N-piperidine with CH3 and COOH; Homochiral cis from Peak 1] | 669.2 (M + H)+ | 2.23 | D |
| 641 | [Structure with CF3, F3C, O (chromene), O2S-phenyl-F group, N-piperidine with CH3 and COOH; Homochiral from Peak 2; Homochiral cis from Peak 1] | 671.0 (M + H)+ | 1.80 | C |

TABLE 10-continued
| Ex. # | Structure | LCMS m/z observed | HPLC $t_R$ (min) | HPLC method |
|---|---|---|---|---|
| 642 | 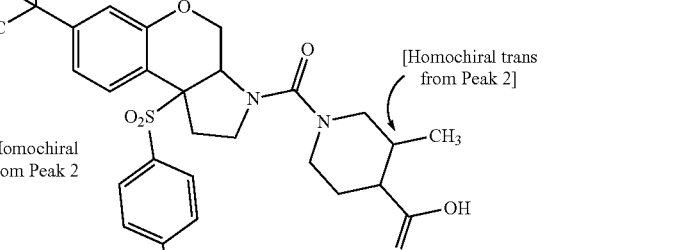 | 671.4 (M + H)⁺ | 1.79 | C |
| 643 | 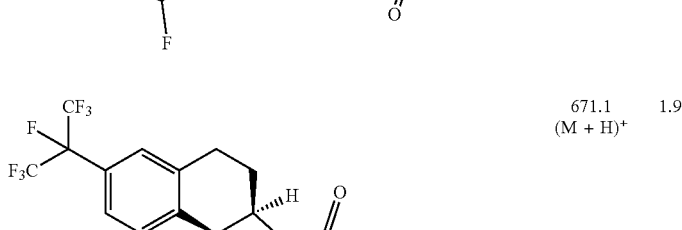 | 671.1 (M + H)⁺ | 1.99 | D |
| 644 | 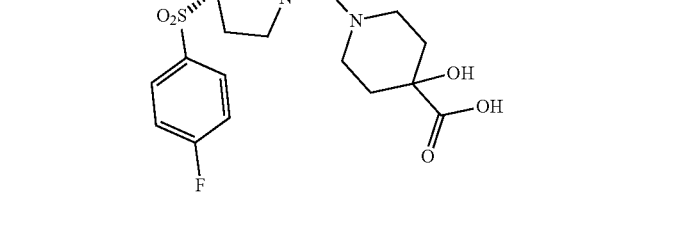 | 654.4 (M + H)⁺ | 2.12 | D |
| 645 | 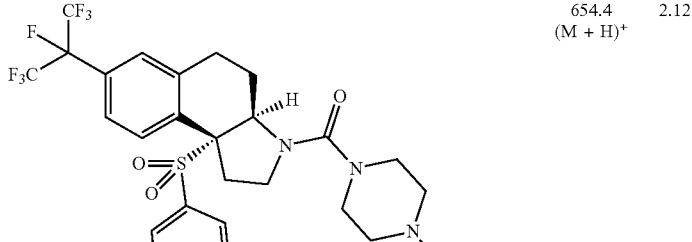 | 627.4 (M + H)⁺ | 2.17 | D |

TABLE 10-continued

| Ex. # | Structure | LCMS m/z observed | HPLC t_R (min) | HPLC method |
|---|---|---|---|---|
| 646 | 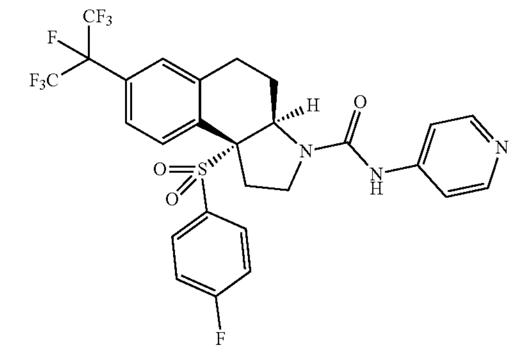 [SMILES: O=C(Nc1ccncc1)N1CC[C@@]2(S(=O)(=O)c3ccc(F)cc3)c3ccc(C(F)(C(F)(F)F)C(F)(F)F)cc3CC[C@@H]12] | 620.3 (M + H)+ | 1.97 | D |
| 647 | 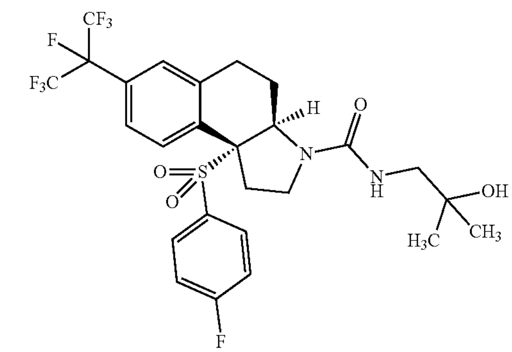 [SMILES: CC(C)(O)CNC(=O)N1CC[C@@]2(S(=O)(=O)c3ccc(F)cc3)c3ccc(C(F)(C(F)(F)F)C(F)(F)F)cc3CC[C@@H]12] | 615.4 (M + H)+ | 2.12 | D |
| 648 | 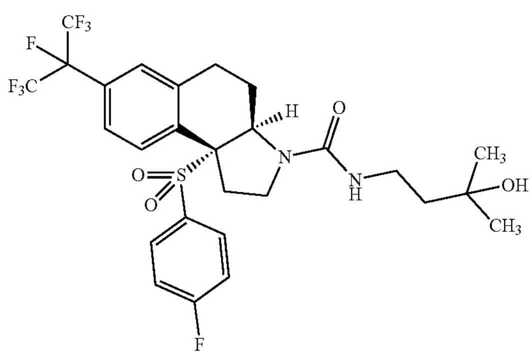 [SMILES: CC(C)(O)CCNC(=O)N1CC[C@@]2(S(=O)(=O)c3ccc(F)cc3)c3ccc(C(F)(C(F)(F)F)C(F)(F)F)cc3CC[C@@H]12] | 629.4 (M + H)+ | 2.15 | D |
| 649 | 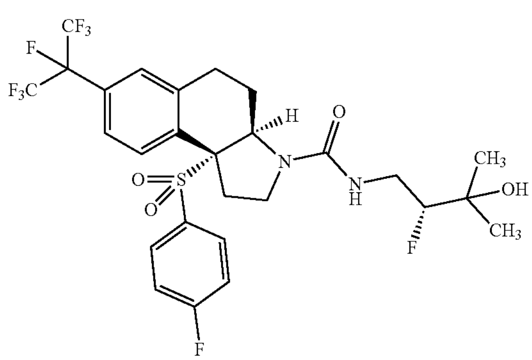 [SMILES: CC(C)(O)[C@H](F)CNC(=O)N1CC[C@@]2(S(=O)(=O)c3ccc(F)cc3)c3ccc(C(F)(C(F)(F)F)C(F)(F)F)cc3CC[C@@H]12] | 647.4 (M + H)+ | 2.17 | D |

TABLE 10-continued

| Ex. # | Structure | LCMS m/z observed | HPLC $t_R$ (min) | HPLC method |
|---|---|---|---|---|
| 650 | 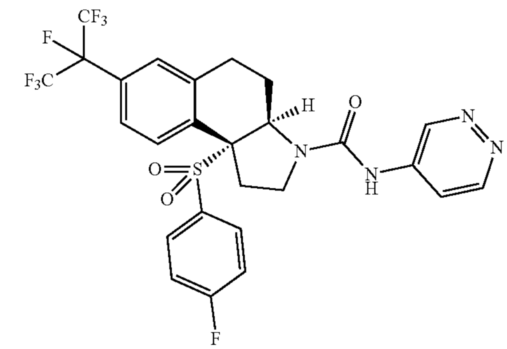 [SMILES: O=C(Nc1ccnnc1)N1CC[C@@]2(S(=O)(=O)c3ccc(F)cc3)c3ccc(C(F)(C(F)(F)F)C(F)(F)F)cc3CC[C@@H]12] | 621.2 (M + H)+ | 2.03 | D |
| 651 | 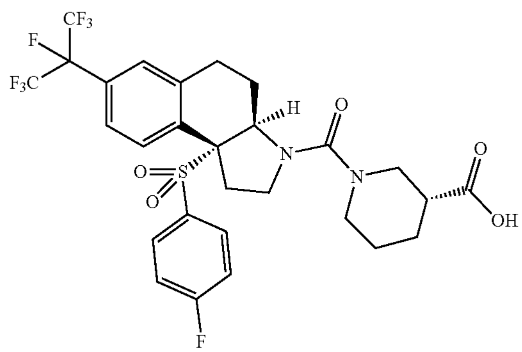 [SMILES: O=C(O)[C@@H]1CCCN(C(=O)N2CC[C@@]3(S(=O)(=O)c4ccc(F)cc4)c4ccc(C(F)(C(F)(F)F)C(F)(F)F)cc4CC[C@@H]23)C1] | 656.2 (M + H)+ | 2.21 | D |
| 652 | 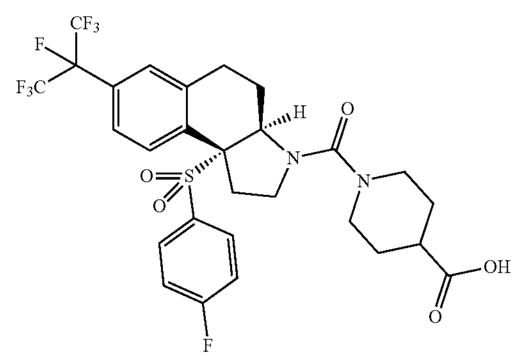 [SMILES: O=C(O)C1CCN(C(=O)N2CC[C@@]3(S(=O)(=O)c4ccc(F)cc4)c4ccc(C(F)(C(F)(F)F)C(F)(F)F)cc4CC[C@@H]23)CC1] | 655.0 (M + H)+ | 2.13 | D |
| 653 | 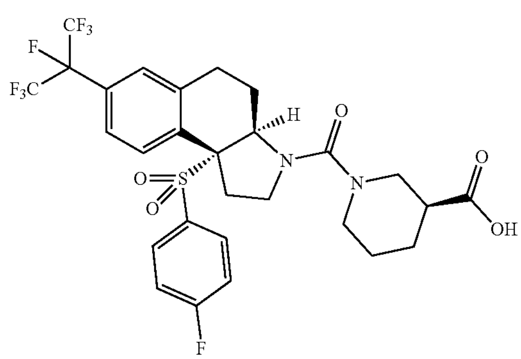 [SMILES: O=C(O)[C@H]1CCCN(C(=O)N2CC[C@@]3(S(=O)(=O)c4ccc(F)cc4)c4ccc(C(F)(C(F)(F)F)C(F)(F)F)cc4CC[C@@H]23)C1] | 655.4 (M + H)+ | 2.22 | D |

TABLE 10-continued
| Ex. # | Structure | LCMS m/z observed | HPLC $t_R$ (min) | HPLC method |
|---|---|---|---|---|
| 654 | 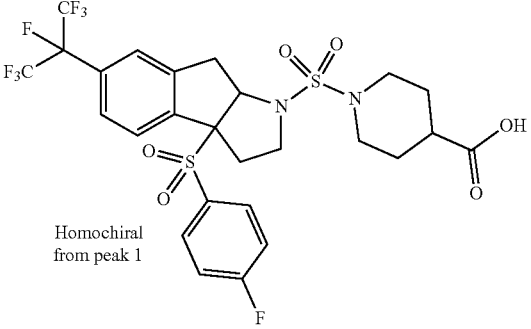 [SMILES: O=C(O)C1CCN(S(=O)(=O)N2CCC3(S(=O)(=O)c4ccc(F)cc4)c4ccc(C(F)(C(F)(F)F)C(F)(F)F)cc4CC23)CC1] Homochiral from peak 1 | 677.3 (M + H)+ | 1.82 | C |
| 655 | 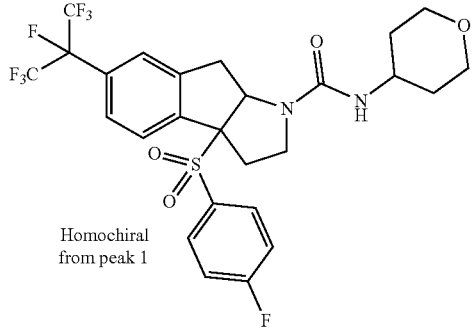 [SMILES: O=C(NC1CCOCC1)N1CCC2(S(=O)(=O)c3ccc(F)cc3)c3ccc(C(F)(C(F)(F)F)C(F)(F)F)cc3CC12] Homochiral from peak 1 | 613.2 (M + H)+ | 2.12 | C |
| 656 | 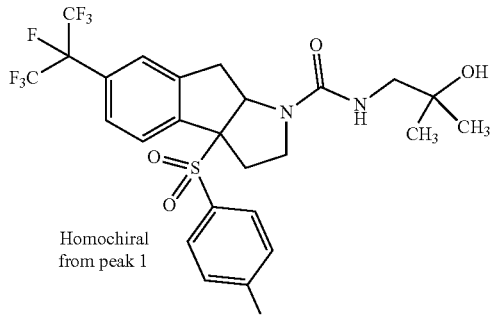 Homochiral from peak 1 | 601.2 (M + H)+ | 2.06 | C |
| 657 | 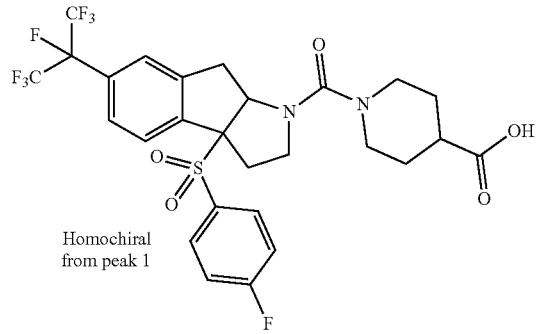 [SMILES: O=C(O)C1CCN(C(=O)N2CCC3(S(=O)(=O)c4ccc(F)cc4)c4ccc(C(F)(C(F)(F)F)C(F)(F)F)cc4CC23)CC1] Homochiral from peak 1 | 641.1 (M + H)+ | 1.76 | C |

TABLE 10-continued
| Ex. # | Structure | LCMS m/z observed | HPLC $t_R$ (min) | HPLC method |
|---|---|---|---|---|
| 658 | 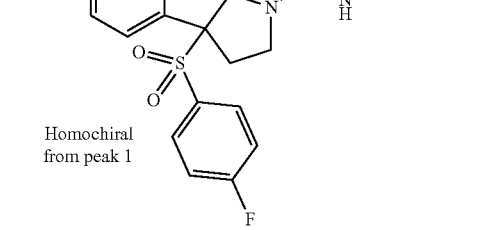 | 615.2 (M + H)⁺ | 2.09 | C |
| 659 | 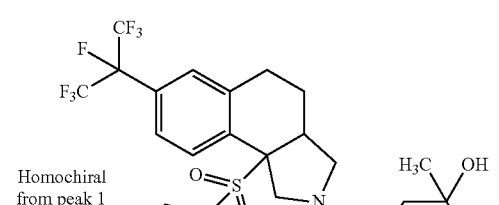 | 615.4 (M + H)⁺ | 2.14 | D |
| 660 | 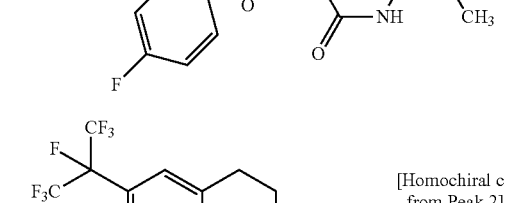 | 669.4 (M + H)⁺ | 2.23 | D |
| 661 | 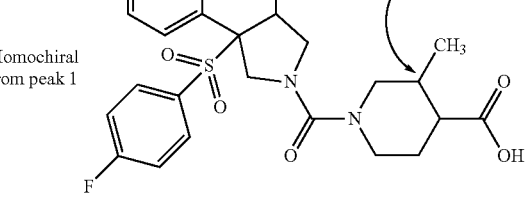 | 683.4 (M + H)⁺ | 2.48 | D |
| 662 | 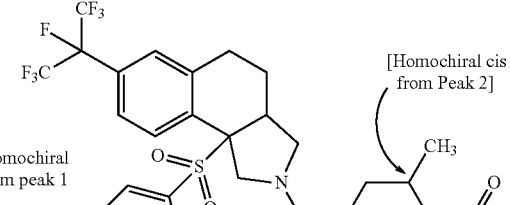 | 669.4 (M + H)⁺ | 2.25 | D |

TABLE 10-continued
| Ex. # | Structure | LCMS m/z observed | HPLC $t_R$ (min) | HPLC method |
|---|---|---|---|---|
| 663 | 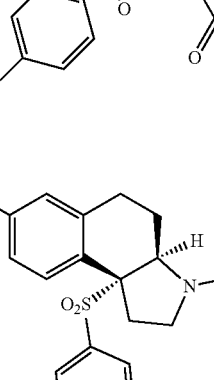 | 683.3 (M + H)+ | 2.50 | D |
| 664 | 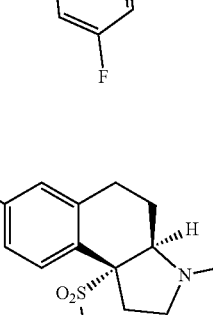 | 675.2 (M + H)+ | 2.06 | C |
| 665 | 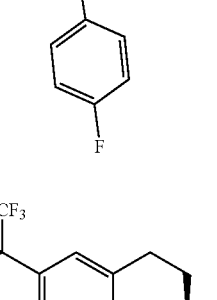 | 689.1 (M + H)+ | 2.04 | C |
| 666 | 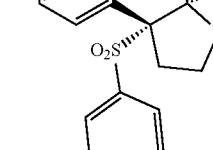 | 661.1 (M + H)+ | 2.13 | C |

TABLE 10-continued

| Ex. # | Structure | LCMS m/z observed | HPLC t$_R$ (min) | HPLC method |
|---|---|---|---|---|
| 667 | 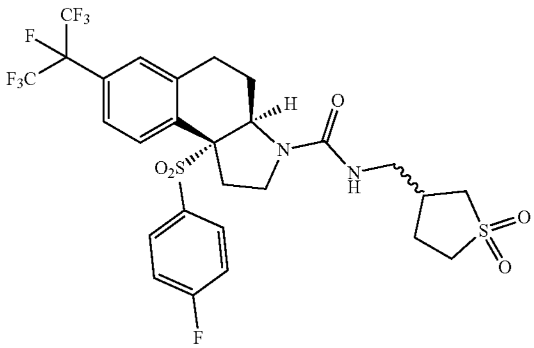 [SMILES: O=C(NCC1CCS(=O)(=O)C1)N1CC[C@@]2(S(=O)(=O)c3ccc(F)cc3)c3ccc(C(F)(C(F)(F)F)C(F)(F)F)cc3CC[C@@H]12] | 675.0 (M + H)$^+$ | 2.06 | C |
| 668 | 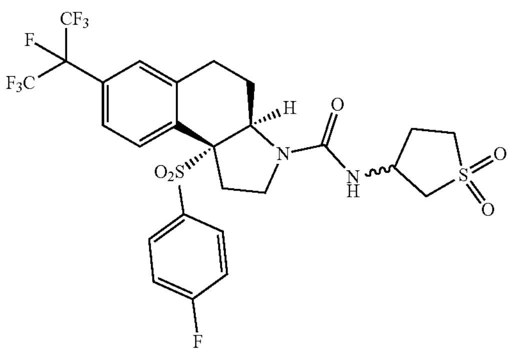 [SMILES: O=C(NC1CCS(=O)(=O)C1)N1CC[C@@]2(S(=O)(=O)c3ccc(F)cc3)c3ccc(C(F)(C(F)(F)F)C(F)(F)F)cc3CC[C@@H]12] | 661.2 (M + H)$^+$ | 2.09 | C |
| 669 | 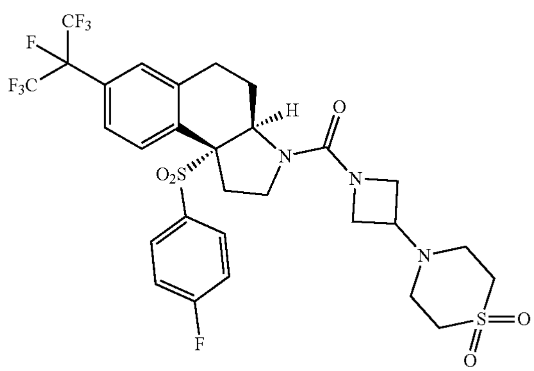 [SMILES: O=C(N1CC(N2CCS(=O)(=O)CC2)C1)N1CC[C@@]2(S(=O)(=O)c3ccc(F)cc3)c3ccc(C(F)(C(F)(F)F)C(F)(F)F)cc3CC[C@@H]12] | 716.0 (M + H)$^+$ | 2.06 | C |
| 670 | 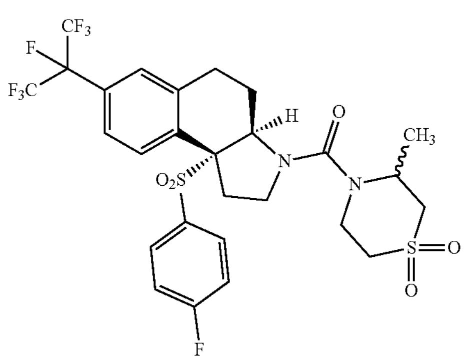 [SMILES: CC1CS(=O)(=O)CCN1C(=O)N1CC[C@@]2(S(=O)(=O)c3ccc(F)cc3)c3ccc(C(F)(C(F)(F)F)C(F)(F)F)cc3CC[C@@H]12] | 675.1 (M + H)$^+$ | 2.25 | C |

TABLE 10-continued

| Ex. # | Structure | LCMS m/z observed | HPLC t$_R$ (min) | HPLC method |
|---|---|---|---|---|
| 671 | 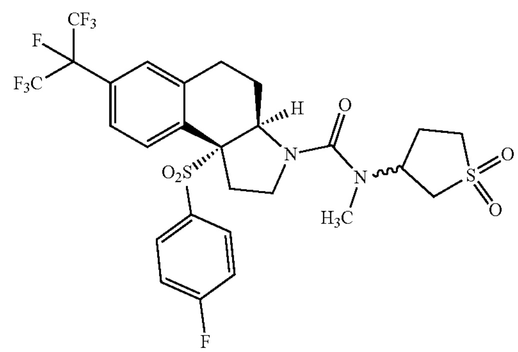 [SMILES: CN(C(=O)N1CC[C@@]2(S(=O)(=O)c3ccc(F)cc3)c3ccc(C(F)(C(F)(F)F)C(F)(F)F)cc3CC[C@@H]12)C1CCS(=O)(=O)C1] | 675.2 (M + H)$^+$ | 2.23 | C |
| 672 | 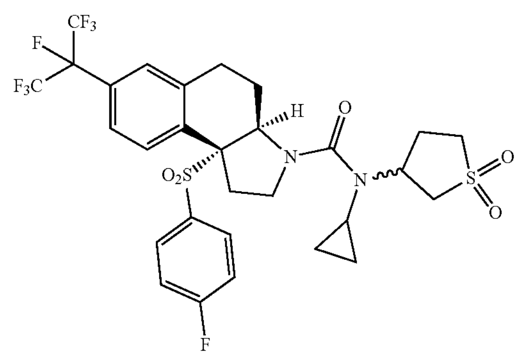 [SMILES: O=C(N(C1CC1)C1CCS(=O)(=O)C1)N1CC[C@@]2(S(=O)(=O)c3ccc(F)cc3)c3ccc(C(F)(C(F)(F)F)C(F)(F)F)cc3CC[C@@H]12] | 701.0 (M + H)$^+$ | 2.35 | C |
| 673 | 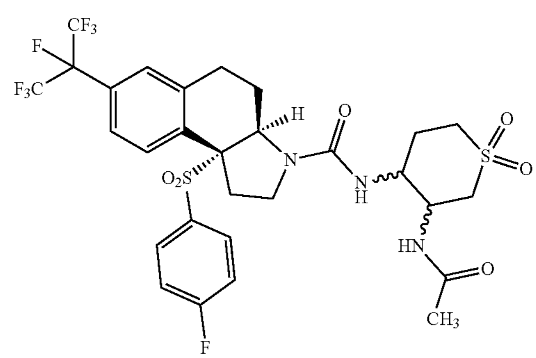 [SMILES: CC(=O)NC1CS(=O)(=O)CCC1NC(=O)N1CC[C@@]2(S(=O)(=O)c3ccc(F)cc3)c3ccc(C(F)(C(F)(F)F)C(F)(F)F)cc3CC[C@@H]12] | 732.3 (M + H)$^+$ | 2.07 | C |
| 674 | 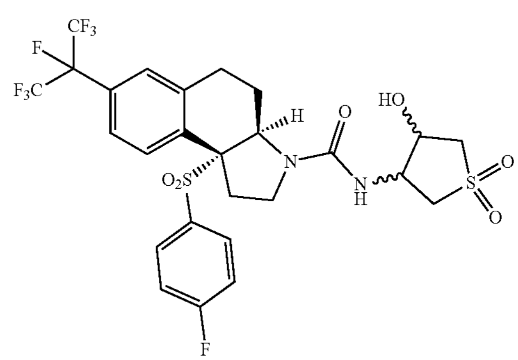 [SMILES: O=C(NC1CS(=O)(=O)CC1O)N1CC[C@@]2(S(=O)(=O)c3ccc(F)cc3)c3ccc(C(F)(C(F)(F)F)C(F)(F)F)cc3CC[C@@H]12] | 677.3 (M + H)$^+$ | 1.99 2.01 | C |

TABLE 10-continued

| Ex. # | Structure | LCMS m/z observed | HPLC t$_R$ (min) | HPLC method |
|---|---|---|---|---|
| 675 | [Peak 1] | 661.1 (M + H)$^+$ | 2.11 | C |
| 676 | [Peak 2] | 660.8 (M + H)$^+$ | 2.11 | C |
| 677 | 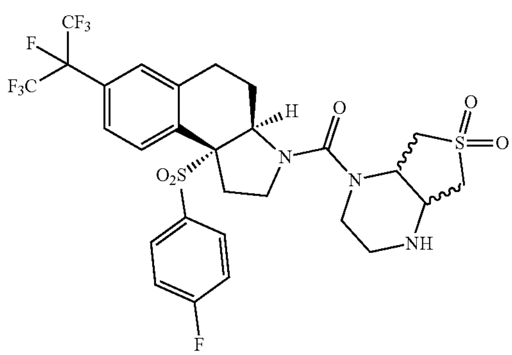 [SMILES: O=C(N1CCNC2CS(=O)(=O)CC21)N1CC[C@@]2(S(=O)(=O)c3ccc(F)cc3)c3ccc(C(F)(C(F)(F)F)C(F)(F)F)cc3CC[C@@H]12] | 702.0 (M + H)$^+$ | 1.81 | D |
| 678 | [Peak 1] | 675.1 (M + H)$^+$ | 2.11 | C |

TABLE 10-continued

| Ex. # | Structure | LCMS m/z observed | HPLC $t_R$ (min) | HPLC method |
|---|---|---|---|---|
| 679 | 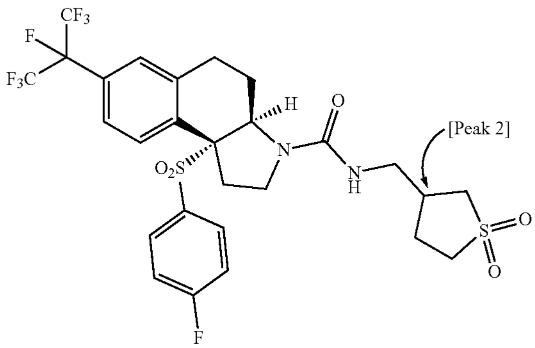 [SMILES: O=C(NCC1CCS(=O)(=O)C1)N1CC[C@@]2(S(=O)(=O)c3ccc(F)cc3)c3ccc(C(F)(C(F)(F)F)C(F)(F)F)cc3CC[C@@H]12] | 675.1 (M + H)+ | 2.11 | C |
| 680 | 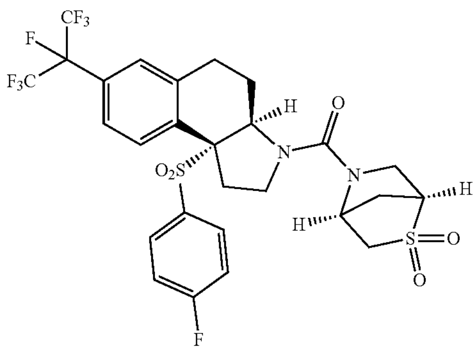 [SMILES: O=C(N1C[C@@H]2C[C@H]1CS2(=O)=O)N1CC[C@@]2(S(=O)(=O)c3ccc(F)cc3)c3ccc(C(F)(C(F)(F)F)C(F)(F)F)cc3CC[C@@H]12] | 672.9 (M + H)+ | 2.15 | C |
| 681 | 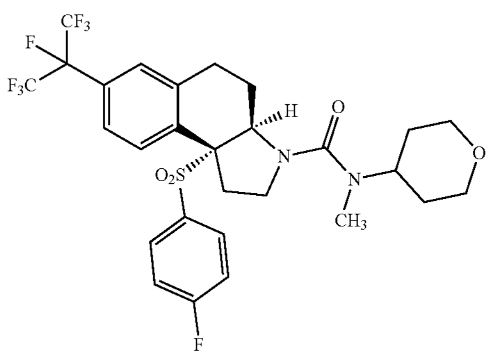 [SMILES: CN(C(=O)N1CC[C@@]2(S(=O)(=O)c3ccc(F)cc3)c3ccc(C(F)(C(F)(F)F)C(F)(F)F)cc3CC[C@@H]12)C1CCOCC1] | 641.2 (M + H)+ | 2.31 | C |
| 682 | 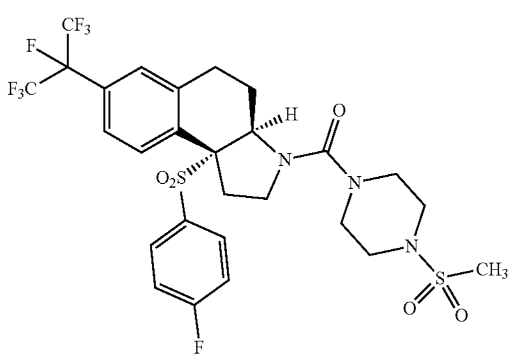 [SMILES: CS(=O)(=O)N1CCN(C(=O)N2CC[C@@]3(S(=O)(=O)c4ccc(F)cc4)c4ccc(C(F)(C(F)(F)F)C(F)(F)F)cc4CC[C@@H]23)CC1] | 690.2 (M + H)+ | 2.21 | C |

TABLE 10-continued

| Ex. # | Structure | LCMS m/z observed | HPLC $t_R$ (min) | HPLC method |
|---|---|---|---|---|
| 683 | 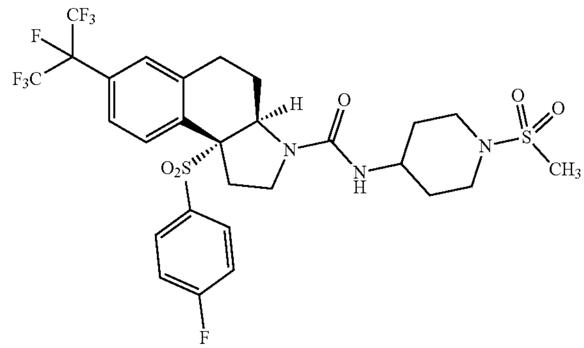 [SMILES: CS(=O)(=O)N1CCC(NC(=O)N2CC[C@@]3(S(=O)(=O)c4ccc(F)cc4)c4ccc(C(F)(C(F)(F)F)C(F)(F)F)cc4CC[C@@H]23)CC1] | 703.9 (M + H)+ | 2.18 | C |
| 684 | 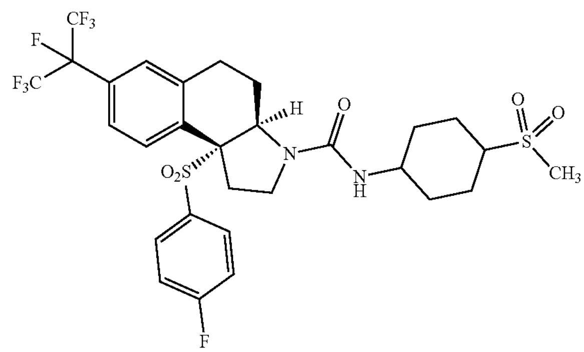 | 689.1 (M + H)+ | 2.14 | C |

Example 685

(1r,4r)-4-(9b-((4-fluorophenyl)sulfonyl)-5-methyl-7-(perfluoropropan-2-yl)-2,3,3a,4,5,9b-hexahydro-1H-pyrrolo[2,3-c]quinoline-3-carbonyl)cyclohexane-1-carboxylic Acid

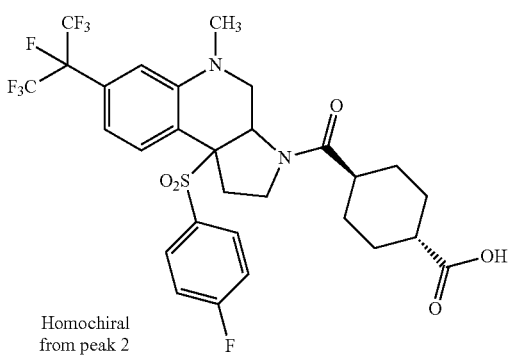 [SMILES: CN1CC2N(C(=O)[C@H]3CC[C@H](C(=O)O)CC3)CCC2(S(=O)(=O)c2ccc(F)cc2)c2ccc(C(F)(C(F)(F)F)C(F)(F)F)cc21]

Homochiral from peak 2

A solution of homochiral (1r,4r)-4-(9b-((4-fluorophenyl)sulfonyl)-7-(perfluoropropan-2-yl)-2,3,3a,4,5,9b-hexahydro-1H-pyrrolo[2,3-c]quinoline-3-carbonyl)cyclohexanecarboxylic acid (Example 509; 50 mg, 0.076 mmol) in MeOH (764 µL) was treated with 37% aqueous formaldehyde (62 mg, 0.76 mmol), acetic acid (87 µL, 1.5 mmol) and sodium cyanoborohydride (48 mg, 0.76 mmol), and stirred at rt for 1 h. The mixture was diluted with EtOAc and washed with 1 M aqueous HCl. The organic phase was dried over $Na_2SO_4$ and concentrated. The residue was purified by chiral SFC using the following conditions: Column: Lux® Cellulose-4 46×250 mm, 5 µm (Phenomenex Inc.); column temperature 35° C.; pressure 100 bars; mobile phase $CO_2$-MeOH (75:25). This provided (1r,4r)-4-(9b-((4-fluorophenyl)sulfonyl)-7-(perfluoropropan-2-yl)-2,3,3a,4,5,9b-hexahydro-1H-pyrrolo[2,3-c]quinoline-3-carbonyl) cyclohexanecarboxylic acid (32 mg, 62% yield). LCMS m/z 669.2 (M+H)+, HPLC $t_R$ 1.09 min (method B). $^1$H NMR (400 MHz, MeOH-$d_4$) δ 7.86 (d, J=8.4 Hz, 1H), 7.43-7.35 (m, 2H), 7.13-6.96 (m, 3H), 6.77 (s, 1H), 4.76 (dd, J=10.3, 5.5 Hz, 1H), 4.01-3.88 (m, 1H), 3.86-3.75 (m, 1H), 3.68-3.48 (m, 2H), 3.15 (s, 3H), 2.83-2.70 (m, 1H), 2.66-2.50 (m, 2H), 2.42-2.26 (m, 1H), 2.18-1.94 (m, 3H), 1.94-1.83 (m, 1H), 1.64-1.44 (m, 4H). $^{19}$F NMR (376 MHz, MeOH-$d_4$) δ −104.9 (s, 1F), −77.3 (m, 1F), −77.0 (s, 6F).

The Examples in Table 11 were prepared using procedures used to prepare Example 685 or similar procedures, by using an appropriate amine starting material with an appropriate carbonyl compound.

TABLE 11
| Ex. # | Structure | LCMS m/z observed | HPLC $t_R$ (min) | HPLC method |
|---|---|---|---|---|
| 686 | 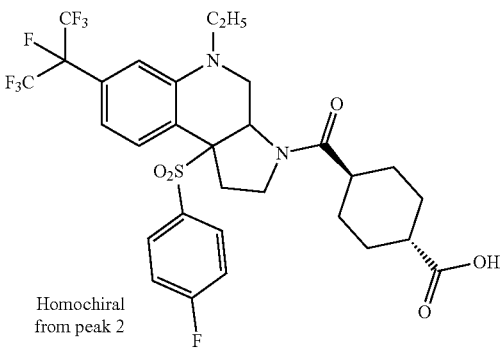 [SMILES: CCN1CC2N(C(=O)[C@H]3CC[C@H](C(=O)O)CC3)CCC2(S(=O)(=O)c2ccc(F)cc2)c2ccc(C(F)(C(F)(F)F)C(F)(F)F)cc21] Homochiral from peak 2 | 683.2 (M + H)$^+$ | 1.13 | B |
| 687 | 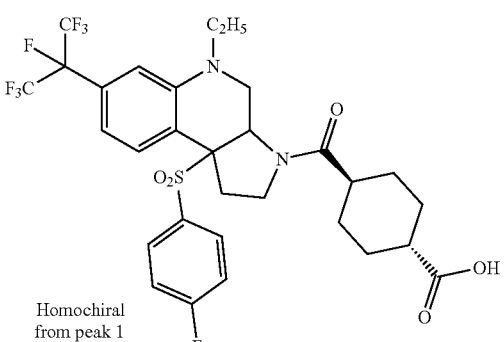 Homochiral from peak 1 | 683.2 (M + H)$^+$ | 1.13 | B |
| 688 | 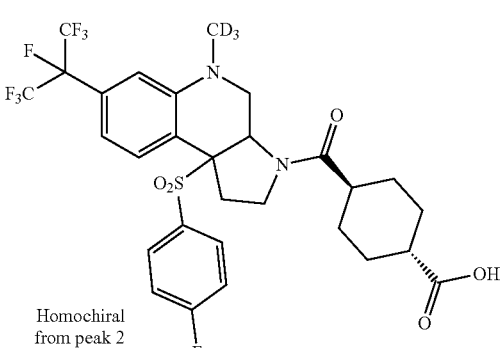 Homochiral from peak 2 | 672.2 (M + H)$^+$ | 1.10 | B |
| 689 | 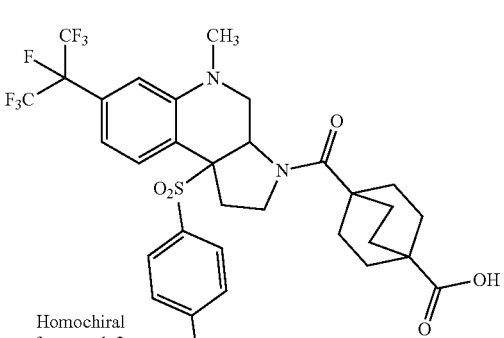 Homochiral from peak 2 | 695.5 (M + H)$^+$ | 1.14 | B |

TABLE 11-continued
| Ex. # | Structure | LCMS m/z observed | HPLC $t_R$ (min) | HPLC method |
|---|---|---|---|---|
| 690 | 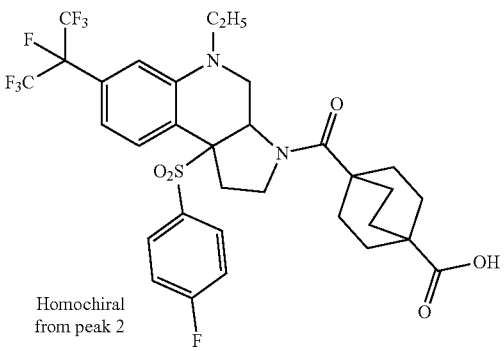 [SMILES: CCN1CC2N(C(=O)C34CCC(C(=O)O)(CC3)CC4)CCC2(S(=O)(=O)c2ccc(F)cc2)c2ccc(C(F)(C(F)(F)F)C(F)(F)F)cc21] Homochiral from peak 2 | 709.5 (M + H)+ | 1.17 | B |
| 691 | 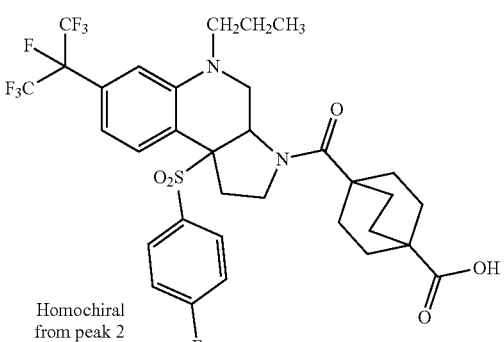 Homochiral from peak 2 | 723.2 (M + H)+ | 2.29 | C |
| 692 | 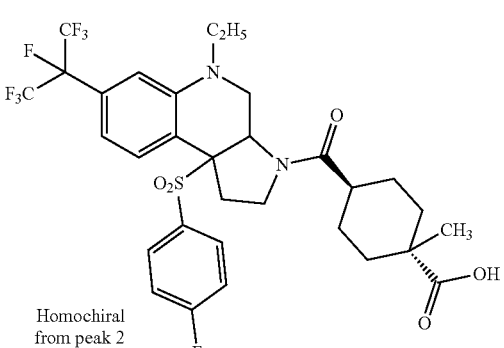 Homochiral from peak 2 | 697.3 (M + H)+ | 1.16 | B |
| 693 | 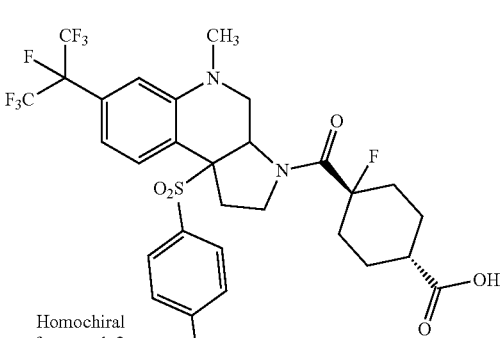 Homochiral from peak 2 | 687.1 (M + H)+ | 1.14 | B |

TABLE 11-continued
| Ex. # | Structure | LCMS m/z observed | HPLC $t_R$ (min) | HPLC method |
|---|---|---|---|---|
| 694 | 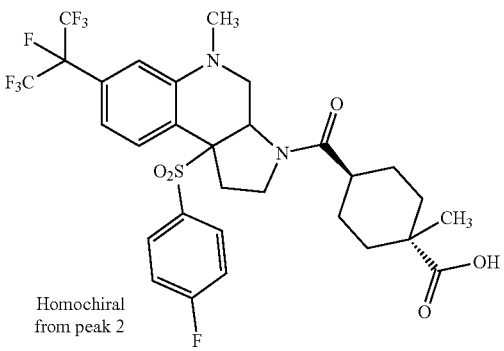 [SMILES: CN1CC2N(C(=O)[C@H]3CC[C@](C)(C(=O)O)CC3)CCC2(S(=O)(=O)c2ccc(F)cc2)c2ccc(C(F)(C(F)(F)F)C(F)(F)F)cc21] Homochiral from peak 2 | 683.2 (M + H)+ | 1.12 | B |
| 695 | 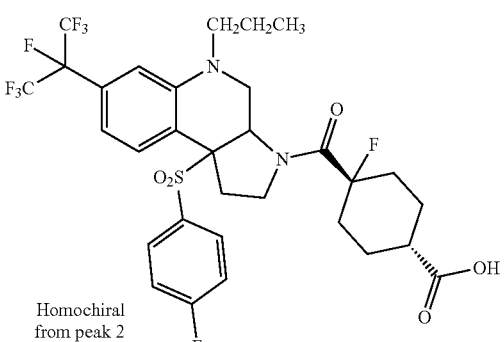 Homochiral from peak 2 | 715.2 (M + H)+ | 1.19 | B |
| 696 | 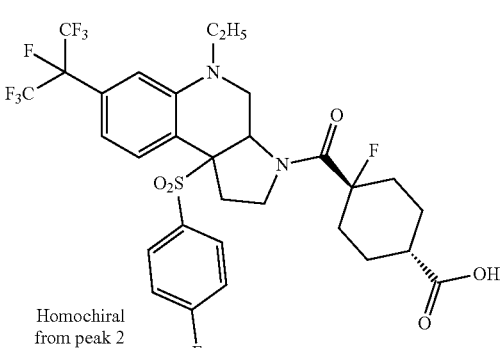 Homochiral from peak 2 | | 1.17 | B |
| 697 | 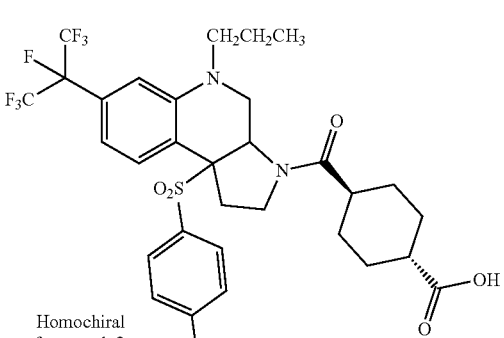 Homochiral from peak 2 | 697.1 (M + H)+ | 1.17 | B |

TABLE 11-continued
| Ex. # | Structure | LCMS m/z observed | HPLC $t_R$ (min) | HPLC method |
|---|---|---|---|---|
| 698 | 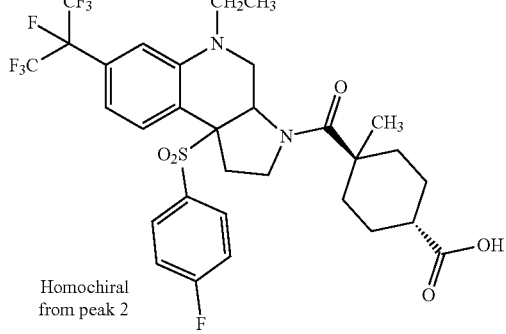 Homochiral from peak 2 | 697.2 (M + H)+ | 1.17 | B |
| 699 | 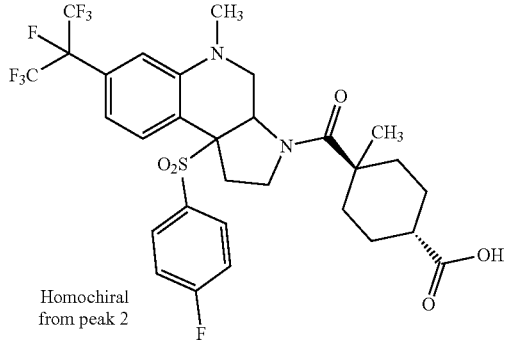 [SMILES: CN1CC2N(C(=O)[C@]3(C)CC[C@@H](C(=O)O)CC3)CCC2(S(=O)(=O)c2ccc(F)cc2)c2ccc(C(F)(C(F)(F)F)C(F)(F)F)cc21] Homochiral from peak 2 | 683.1 (M + H)+ | 1.14 | B |
| 700 | 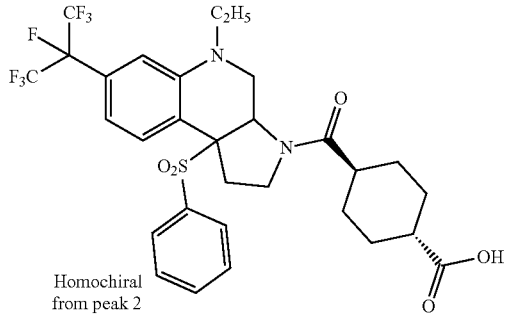 [SMILES: CCN1CC2N(C(=O)[C@H]3CC[C@H](C(=O)O)CC3)CCC2(S(=O)(=O)c2ccccc2)c2ccc(C(F)(C(F)(F)F)C(F)(F)F)cc21] Homochiral from peak 2 | 665.2 (M + H)+ | 1.07 | B |
| 701 | 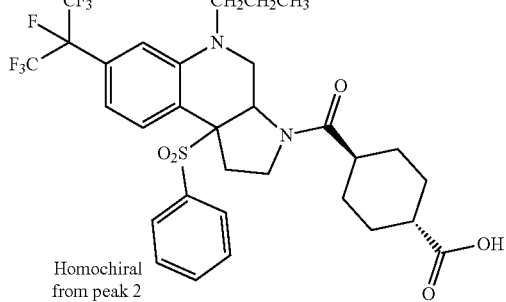 Homochiral from peak 2 | 679.5 (M + H)+ | 1.10 | B |

TABLE 11-continued
| Ex. # | Structure | LCMS m/z observed | HPLC $t_R$ (min) | HPLC method |
|---|---|---|---|---|
| 702 | 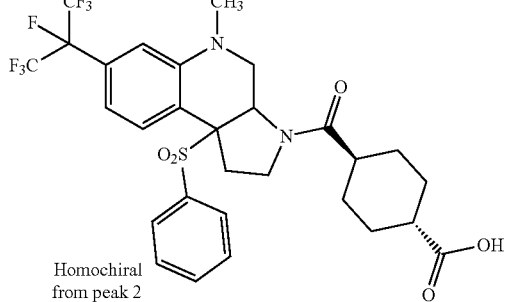 Homochiral from peak 2 | 651.1 (M + H)+ | 1.04 | B |
| 703 | 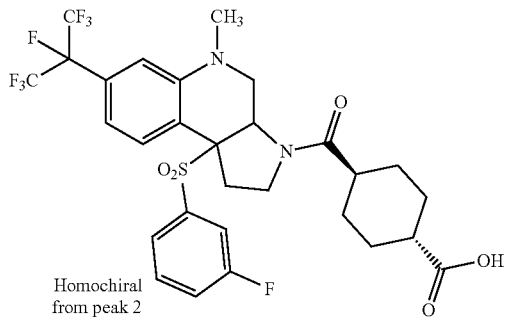 [SMILES: CN1CC2N(C(=O)[C@H]3CC[C@H](C(=O)O)CC3)CCC2(S(=O)(=O)c2cccc(F)c2)c2ccc(C(F)(C(F)(F)F)C(F)(F)F)cc21] Homochiral from peak 2 | 669.2 (M + H)+ | 1.08 | B |
| 704 | 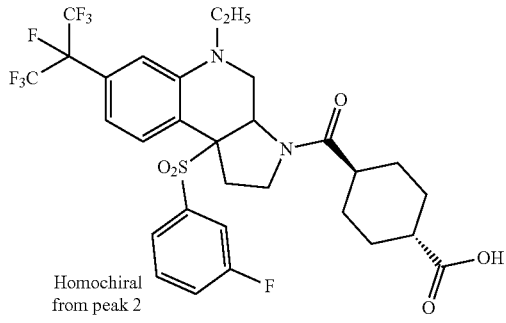 [SMILES: CCN1CC2N(C(=O)[C@H]3CC[C@H](C(=O)O)CC3)CCC2(S(=O)(=O)c2cccc(F)c2)c2ccc(C(F)(C(F)(F)F)C(F)(F)F)cc21] Homochiral from peak 2 | 683.2 (M + H)+ | 1.11 | B |
| 705 | 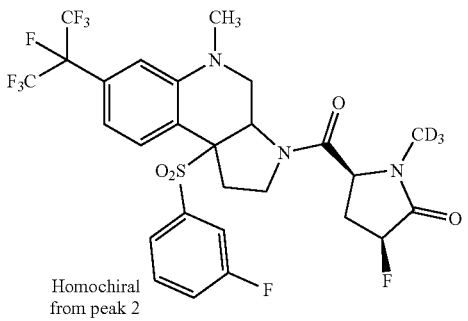 [SMILES: [2H]C([2H])([2H])N1C(=O)[C@@H](F)C[C@H]1C(=O)N1CCC2(S(=O)(=O)c3cccc(F)c3)c3ccc(C(F)(C(F)(F)F)C(F)(F)F)cc3N(C)CC12] Homochiral from peak 2 | 661.2 (M + H)+ | 1.08 | B |

TABLE 11-continued
| Ex. # | Structure | LCMS m/z observed | HPLC $t_R$ (min) | HPLC method |
|---|---|---|---|---|
| 706 | 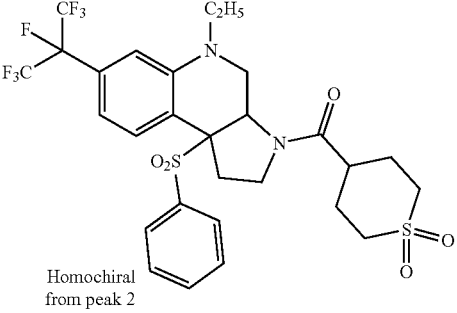 [SMILES: CCN1CC2N(C(=O)C3CCS(=O)(=O)CC3)CCC2(S(=O)(=O)c2ccccc2)c2ccc(C(F)(C(F)(F)F)C(F)(F)F)cc21] Homochiral from peak 2 | 671.1 (M + H)+ | 1.08 | B |
| 707 | 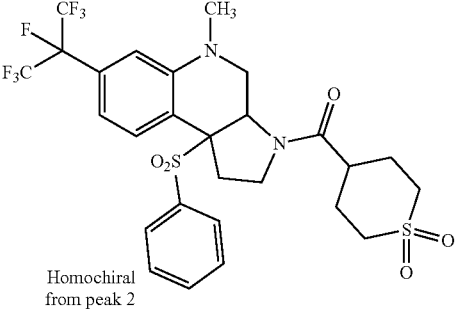 [SMILES: CN1CC2N(C(=O)C3CCS(=O)(=O)CC3)CCC2(S(=O)(=O)c2ccccc2)c2ccc(C(F)(C(F)(F)F)C(F)(F)F)cc21] Homochiral from peak 2 | 657.1 (M + H)+ | 1.05 | B |
| 708 | 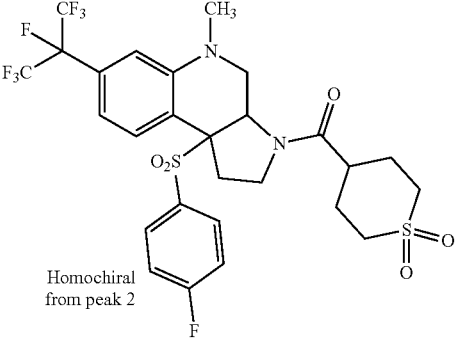 [SMILES: CN1CC2N(C(=O)C3CCS(=O)(=O)CC3)CCC2(S(=O)(=O)c2ccc(F)cc2)c2ccc(C(F)(C(F)(F)F)C(F)(F)F)cc21] Homochiral from peak 2 | 675.1 (M + H)+ | 1.06 | B |
| 709 | 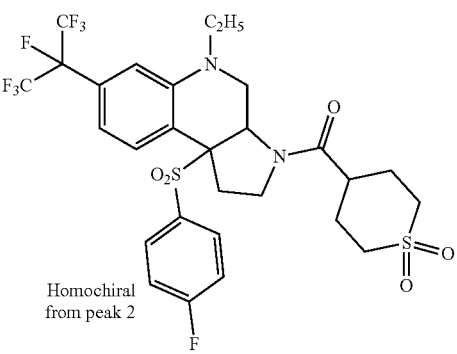 [SMILES: CCN1CC2N(C(=O)C3CCS(=O)(=O)CC3)CCC2(S(=O)(=O)c2ccc(F)cc2)c2ccc(C(F)(C(F)(F)F)C(F)(F)F)cc21] Homochiral from peak 2 | 689.1 (M + H)+ | 1.09 | B |

TABLE 11-continued

| Ex. # | Structure | LCMS m/z observed | HPLC $t_R$ (min) | HPLC method |
|---|---|---|---|---|
| 710 | (structure: CF3, F, F3C-substituted quinoline with N-CH3; O2S linked to 3-fluorophenyl; pyrrolidine N-acyl tetrahydrothiopyran 1,1-dioxide; Homochiral from peak 1) | 675.1 (M + H)+ | 1.95 | C |
| 711 | (structure: CF3, F, F3C-substituted quinoline with N-C2H5; O2S-phenyl; pyrrolidine N-acyl 1-fluorocyclohexane-4-carboxylic acid; Homochiral from peak 2) | 683.2 (M + H)+ | 2.21 | C |
| 712 | (structure: CF3, F, F3C-substituted quinoline with N-CH3; O2S-phenyl; pyrrolidine N-acyl 1-fluorocyclohexane-4-carboxylic acid; Homochiral from peak 2) | 669.2 (M + H)+ | 2.29 | C |
| 713 | (structure: CF3, F, F3C-substituted quinoline with N-C2H5; O2S linked to 3-fluorophenyl; pyrrolidine N-acyl cyclohexane-4-carboxylic acid; Homochiral from peak 1) | 683.5 (M + H)+ | 1.10 | B |

TABLE 11-continued
| Ex. # | Structure | LCMS m/z observed | HPLC $t_R$ (min) | HPLC method |
|---|---|---|---|---|
| 714 | 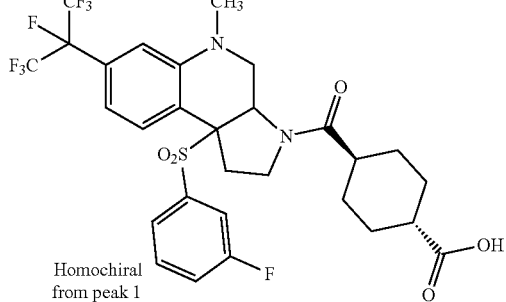 Homochiral from peak 1 | 669.4 (M + H)+ | 1.10 | B |
| 715 | 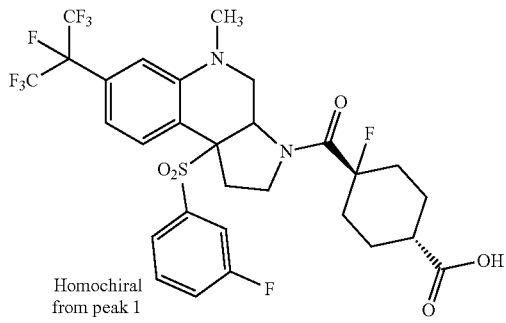 [SMILES: CN1CC2N(C(=O)[C@]3(F)CC[C@@H](C(=O)O)CC3)CCC2(S(=O)(=O)c2cccc(F)c2)c2ccc(C(F)(C(F)(F)F)C(F)(F)F)cc21] Homochiral from peak 1 | 687.1 (M + H)+ | 1.07 | B |
| 716 | 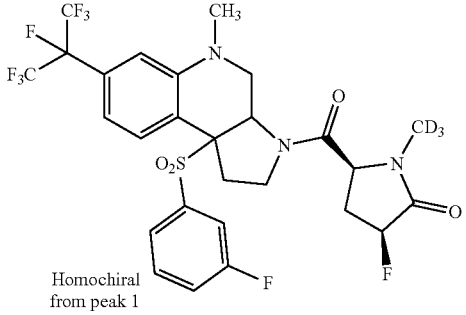 [SMILES: [2H]C([2H])([2H])N1C(=O)[C@@H](F)C[C@H]1C(=O)N1CCC2(S(=O)(=O)c3cccc(F)c3)c3ccc(C(F)(C(F)(F)F)C(F)(F)F)cc3N(C)CC12] Homochiral from peak 1 | 661.1 (M + H)+ | 1.05 | B |
| 717 | 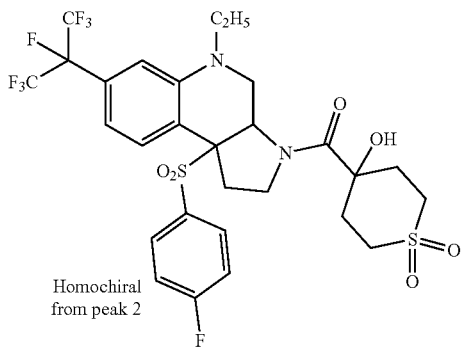 [SMILES: CCN1CC2N(C(=O)C3(O)CCS(=O)(=O)CC3)CCC2(S(=O)(=O)c2ccc(F)cc2)c2ccc(C(F)(C(F)(F)F)C(F)(F)F)cc21] Homochiral from peak 2 | 691.2 (M + H)+ | 2.15 | C |

TABLE 11-continued
| Ex. # | Structure | LCMS m/z observed | HPLC $t_R$ (min) | HPLC method |
|---|---|---|---|---|
| 718 | 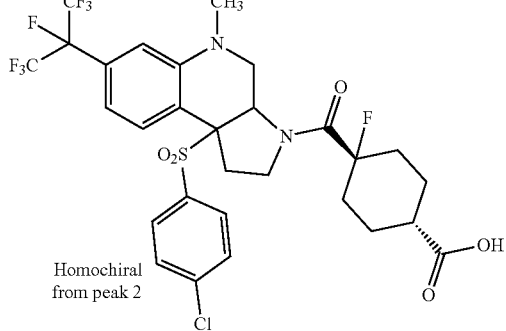 | 685.2 (M + H)+ | 2.03 | C |
| 719 | 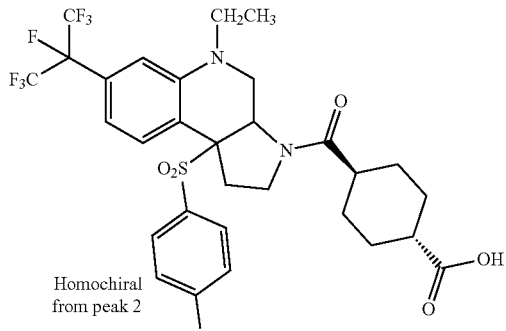 | 699.1 (M + H)+ | 2.15 | C |
| 720 | 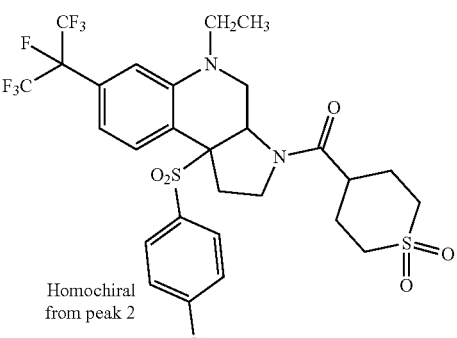 | 705.0 (M + H)+ | 2.39 | C |

Example 721

2-((3aR,9bR)-9b-((4-fluorophenyl)sulfonyl)-7-(perfluoropropan-2-yl)-1,2,3a,4,5,9b-hexahydro-3H-benzo[e]indol-3-yl)acetamide

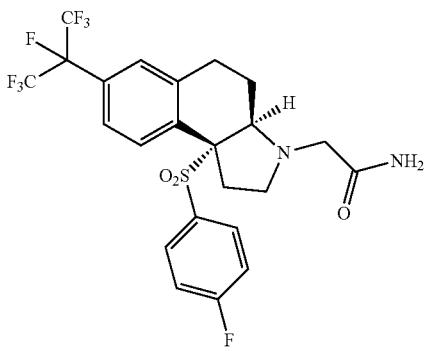 [SMILES: NC(=O)CN1CC[C@@]2(S(=O)(=O)c3ccc(F)cc3)c3ccc(C(F)(C(F)(F)F)C(F)(F)F)cc3CC[C@@H]12]

A solution of (3aR,9bR)-9b-((4-fluorophenyl)sulfonyl)-7-(perfluoropropan-2-yl)-2,3,3a,4,5,9b-hexahydro-1H-benzo[e]indole hydrochloride (Intermediate 32; 15 mg, 0.028 mmol) in DCM (2 mL) was treated with 2-bromoacetamide (15.5 mg, 0.112 mmol). DIPEA (0.049 mL, 0.28 mmol) was added and the mixture was stirred at rt for 24 h. The mixture was concentrated and the residue was purified by preparative HPLC (method E, gradient 35-100% B, 15 min) to afford 2-((3aR,9bR)-9b-((4-fluorophenyl)sulfonyl)-7-(perfluoropropan-2-yl)-1,2,3a,4,5,9b-hexahydro-3H-benzo[e]indol-3-yl)acetamide (10.8 mg, 69% yield). LCMS m/z 557.0 (M+H)$^+$, HPLC $t_R$ 2.06 min (method C). $^1$H NMR (500 MHz, DMSO-d$_6$) δ 7.51 (s, 2H), 7.37-7.27 (m, 4H), 7.26-7.19 (m, 2H), 7.11 (br. s., 1H), 3.70-3.62 (m, 0.5H), 3.60-3.50 (m, 1H), 3.41 (d, J=16.1 Hz, 0.5H), 3.13-3.02 (m, 2H), 2.96 (d, J=16.2 Hz, 1H), 2.71-2.64 (m, 1H), 2.60 (d, J=16.2 Hz, 1H), 2.42-2.32 (m, 1H), 2.10 (d, J=7.3 Hz, 1H), 1.90 (t, J=13.2 Hz, 1H), 1.34-1.23 (m, 1H).

Example 722

(RS)-2-((3aR,9bR)-9b-((4-fluorophenyl)sulfonyl)-7-(perfluoropropan-2-yl)-1,2,3a,4,5,9b-hexahydro-3H-benzo[e]indol-3-yl)propanamide

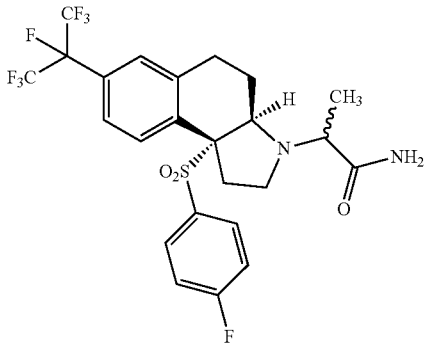 [SMILES: CC(C(N)=O)N1CC[C@@]2(S(=O)(=O)c3ccc(F)cc3)c3ccc(C(F)(C(F)(F)F)C(F)(F)F)cc3CC[C@@H]12]

A solution of (3aR,9bR)-9b-((4-fluorophenyl)sulfonyl)-7-(perfluoropropan-2-yl)-2,3,3a,4,5,9b-hexahydro-1H-benzo[e]indole hydrochloride (Intermediate 32; 15 mg, 0.028 mmol) in DMF (1.5 mL) was treated with racemic 2-bromopropanamide (17 mg, 0.112 mmol). DIPEA (0.049 mL, 0.28 mmol) was added and the mixture was heated at 60° C. for 16 h. The mixture was cooled to rt and purified by preparative HPLC (method E, gradient 45-90% B, 22 min) to afford (RS)-2-((3aR,9bR)-9b-((4-fluorophenyl)sulfonyl)-7-(perfluoropropan-2-yl)-1,2,3a,4,5,9b-hexahydro-3H-benzo[e]indol-3-yl)propanamide (9.5 mg, 58% yield). LCMS m/z 570.8 (M+H)$^+$, HPLC $t_R$ 2.13 and 2.15 min (method C). $^1$H NMR (500 MHz, DMSO-d$_6$) δ 7.59-7.37 (m, 3H), 7.37-7.13 (m, 4H), 7.06 (br. s., 1H), 6.95 (br. s., 1H), 3.51-3.42 (m, 0.5H), 3.38-3.29 (m, 0.5H), 3.18-3.00 (m, 1.5H), 2.99-2.86 (m, 2.5H), 2.76 (s, 0.5H), 2.58 (br. s., 0.5H), 2.41-2.33 (m, 0.5H), 2.31-2.23 (m, 0.5H), 2.22-2.15 (m, 0.5H), 2.12-2.03 (m, 0.5H), 1.92-1.73 (m, 1.5H), 1.30-1.22 (m, 0.5H), 1.20 (d, J=6.9 Hz, 1.5H), 1.14 (d, J=6.8 Hz, 1.5H).

Example 723

2-((3aR,9bR)-9b-((4-fluorophenyl)sulfonyl)-7-(perfluoropropan-2-yl)-1,2,3a,4,5,9b-hexahydro-3H-benzo[e]indol-3-yl)-N-(methyl-d$_3$)acetamide

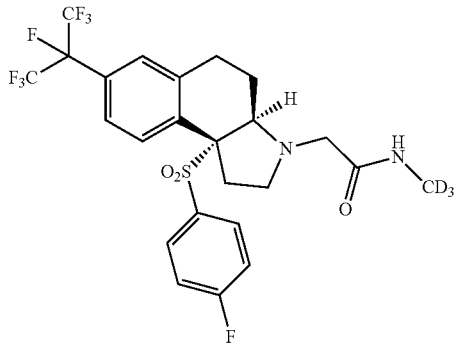 [SMILES: [2H]C([2H])([2H])NC(=O)CN1CC[C@@]2(S(=O)(=O)c3ccc(F)cc3)c3ccc(C(F)(C(F)(F)F)C(F)(F)F)cc3CC[C@@H]12]

A solution of (3aR,9bR)-9b-((4-fluorophenyl)sulfonyl)-7-(perfluoropropan-2-yl)-2,3,3a,4,5,9b-hexahydro-1H-benzo[e]indole hydrochloride (Intermediate 32; 21.1 mg, 0.037 mmol) in DMF (1 mL) was treated with methyl 2-bromoacetate (0.012 mL, 0.123 mmol). DIPEA (0.049 mL, 0.28 mmol) was added and the mixture was stirred at rt for 2 h. The mixture was treated with brine (1 mL) and extracted with EtOAc (10 mL). The organic extract was washed with brine, dried over Na$_2$SO$_4$ and concentrated. The residue was dissolved in THF (2 mL) and treated with a solution of LiOH monohydrate (13.29 mg, 0.555 mmol) in water (0.5 mL). MeOH (0.3 mL) was added to afford a clear solution and the mixture was stirred at rt for 2 h. The mixture was concentrated and diluted with EtOAc (5 mL) and 1 M aqueous HCl (5 mL). The organic layer was separated, washed with brine, dried over Na$_2$SO$_4$ and concentrated. The residue was dissolved in DMF (2 mL) and treated with HATU (56.3 mg, 0.148 mmol), DIPEA and methan-d$_3$-amine hydrochloride (10.44 mg, 0.148 mmol). The mixture was stirred at rt for 16 h. The mixture was purified by preparative HPLC (method F, gradient 45-90% B, 20 min) to afford 2-((3aR,9bR)-9b-((4-fluorophenyl)sulfonyl)-7-(perfluoropropan-2-yl)-1,2,3a,4,5,9b-hexahydro-3H-benzo[e]indol-3-yl)-N-(methyl-d$_3$)acetamide (8.1 mg, 37% yield). LCMS m/z 574.3 (M+H)$^+$, HPLC $t_R$ 2.19 min (method C). $^1$H NMR (500 MHz, DMSO-d$_6$) δ 7.72 (s, 1H), 7.56-7.44 (m, 2H), 7.39-7.29 (m, 3H), 7.28-7.16 (m, 2H), 3.68 (dd, J=9.4, 6.1 Hz, 1H), 3.41 (br. s., 1H), 3.10 (dd, J=13.5, 5.3 Hz, 1H), 3.06-2.99 (m, 1H), 2.97 (s, 1H), 2.71-2.57 (m, 2H), 2.44-2.32 (m, 1H), 2.08 (dd, J=12.5, 5.2 Hz, 1H), 1.91 (t, J=13.5 Hz, 1H), 1.38-1.24 (m, 1H).

The Examples in Table 12 were prepared using the procedures used to prepare Examples 721 through 723, or similar procedures, by using the appropriate alkyl bromide or alkyl chloride, followed by ester hydrolysis or other protecting group removal if required.

TABLE 12

| Ex. # | Structure | MS observed | HPLC ret. time (min.) | HPLC method |
|---|---|---|---|---|
| 724 | 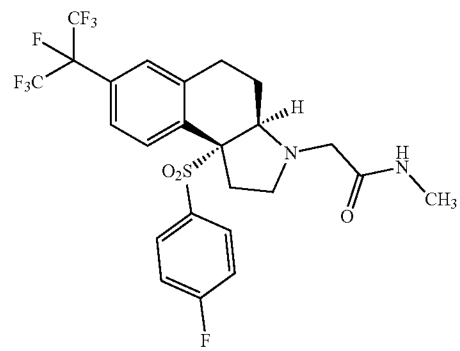 [SMILES: CNC(=O)CN1CC[C@@]2(S(=O)(=O)c3ccc(F)cc3)c3ccc(C(F)(C(F)(F)F)C(F)(F)F)cc3CC[C@@H]12] | 570.8 (M + H)+ | 2.14 | C |
| 725 | 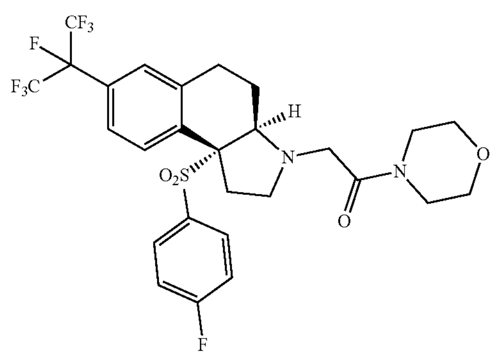 [SMILES: O=C(CN1CC[C@@]2(S(=O)(=O)c3ccc(F)cc3)c3ccc(C(F)(C(F)(F)F)C(F)(F)F)cc3CC[C@@H]12)N1CCOCC1] | 627.0 (M + H)+ | 2.19 | C |
| 726 | 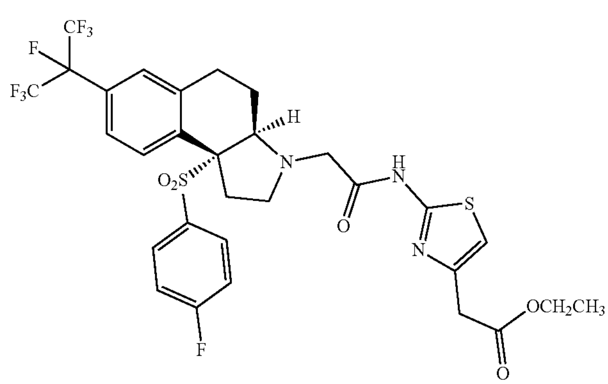 [SMILES: CCOC(=O)Cc1csc(NC(=O)CN2CC[C@@]3(S(=O)(=O)c4ccc(F)cc4)c4ccc(C(F)(C(F)(F)F)C(F)(F)F)cc4CC[C@@H]23)n1] | 726.0 (M + H)+ | 2.46 | C |

TABLE 12-continued

| Ex. # | Structure | MS observed | HPLC ret. time (min.) | HPLC method |
|---|---|---|---|---|
| 727 | 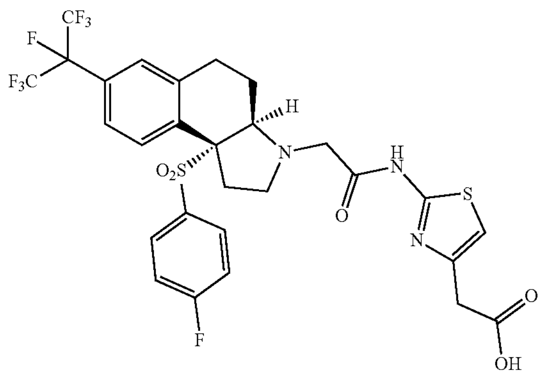 [SMILES: O=C(O)Cc1csc(NC(=O)CN2CC[C@@]3(S(=O)(=O)c4ccc(F)cc4)c4ccc(C(F)(C(F)(F)F)C(F)(F)F)cc4CC[C@@H]23)n1] | 698.4 (M + H)+ | 1.83 | C |
| 728 | 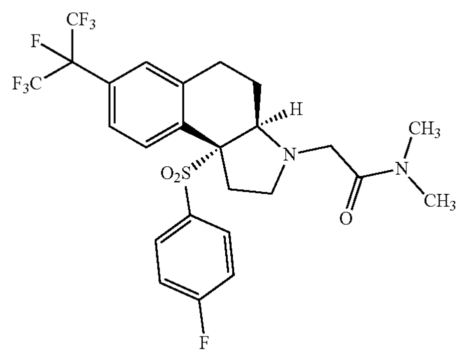 | 548.8 (M + H)+ | 2.22 | C |
| 729 | 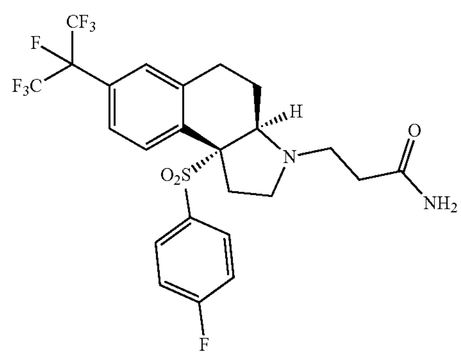 [SMILES: NC(=O)CCN1CC[C@@]2(S(=O)(=O)c3ccc(F)cc3)c3ccc(C(F)(C(F)(F)F)C(F)(F)F)cc3CC[C@@H]12] | 571.0 (M + H)+ | 2.01 | C |
| 730 | 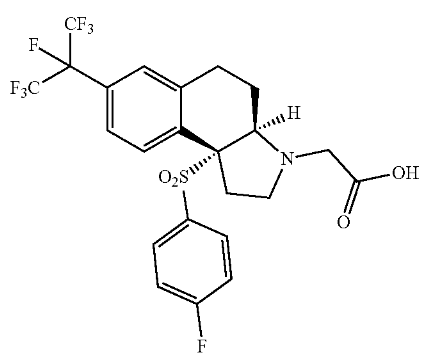 [SMILES: O=C(O)CN1CC[C@@]2(S(=O)(=O)c3ccc(F)cc3)c3ccc(C(F)(C(F)(F)F)C(F)(F)F)cc3CC[C@@H]12] | 558.2 (M + H)+ | 1.72 | C |

TABLE 12-continued

| Ex. # | Structure | MS observed | HPLC ret. time (min.) | HPLC method |
|---|---|---|---|---|
| 731 | 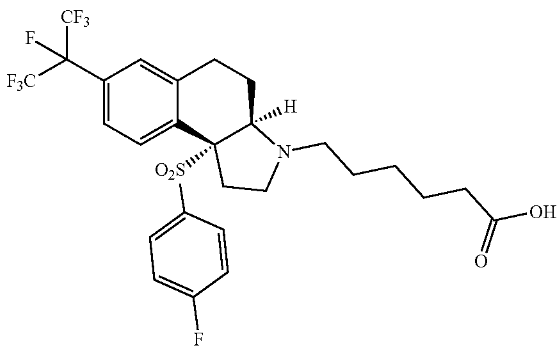 [SMILES: O=C(O)CCCCCN1CC[C@@]2(S(=O)(=O)c3ccc(F)cc3)c3ccc(C(F)(C(F)(F)F)C(F)(F)F)cc3CC[C@@H]12] | 614.1 (M + H)+ | 2.14 | C |
| 732 | 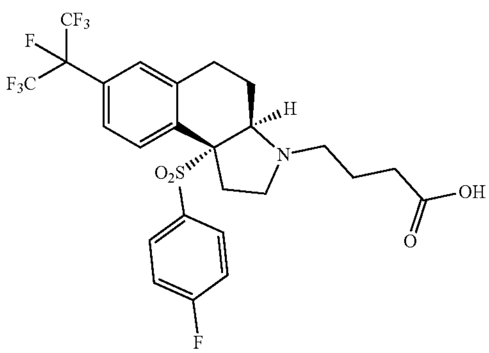 [SMILES: O=C(O)CCCN1CC[C@@]2(S(=O)(=O)c3ccc(F)cc3)c3ccc(C(F)(C(F)(F)F)C(F)(F)F)cc3CC[C@@H]12] | 586.3 (M + H)+ | 1.86 | C |
| 733 | 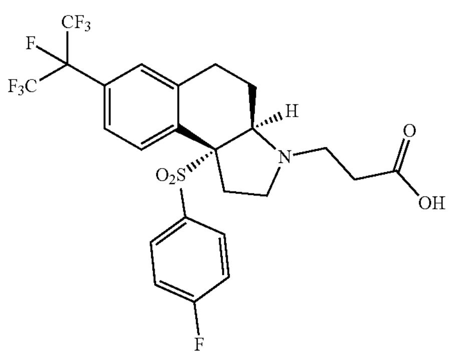 [SMILES: O=C(O)CCN1CC[C@@]2(S(=O)(=O)c3ccc(F)cc3)c3ccc(C(F)(C(F)(F)F)C(F)(F)F)cc3CC[C@@H]12] | 572.0 (M + H)+ | 1.81 | C |
| 734 | 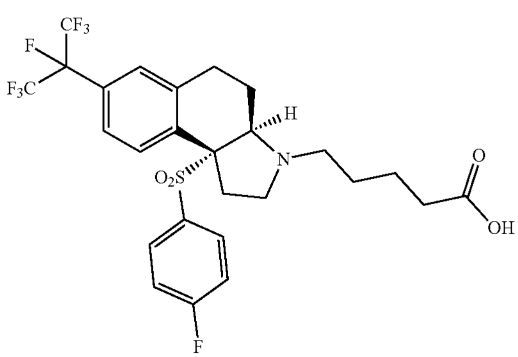 [SMILES: O=C(O)CCCCN1CC[C@@]2(S(=O)(=O)c3ccc(F)cc3)c3ccc(C(F)(C(F)(F)F)C(F)(F)F)cc3CC[C@@H]12] | 599.9 (M + H)+ | 1.96 | C |

TABLE 12-continued

| Ex. # | Structure | MS observed | HPLC ret. time (min.) | HPLC method |
|---|---|---|---|---|
| 735 | 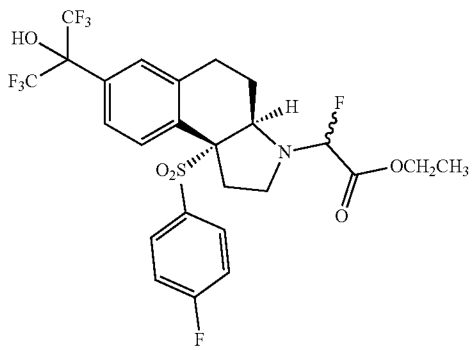 [SMILES: CCOC(=O)C(F)N1CC[C@@]2(S(=O)(=O)c3ccc(F)cc3)c3ccc(C(O)(C(F)(F)F)C(F)(F)F)cc3CC[C@@H]12] | 600.4 (M + H)+ | 2.37 | C |
| 736 | 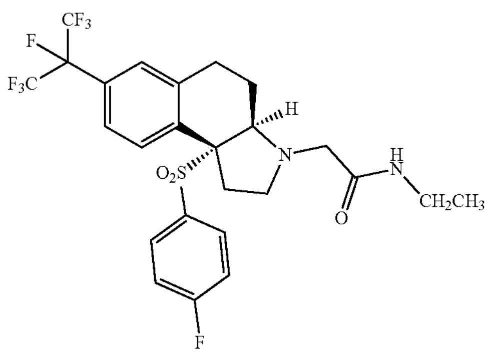 [SMILES: CCNC(=O)CN1CC[C@@]2(S(=O)(=O)c3ccc(F)cc3)c3ccc(C(F)(C(F)(F)F)C(F)(F)F)cc3CC[C@@H]12] | 585.3 (M + H)+ | 2.29 | C |
| 737 | 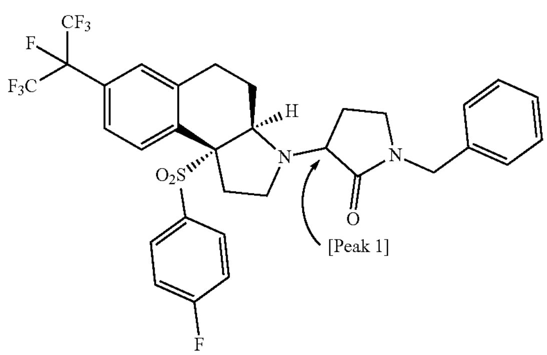 [SMILES: O=C1C(N2CC[C@@]3(S(=O)(=O)c4ccc(F)cc4)c4ccc(C(F)(C(F)(F)F)C(F)(F)F)cc4CC[C@@H]23)CCN1Cc1ccccc1] | 673.5 (M + H)+ | 2.57 | C |
| 738 | 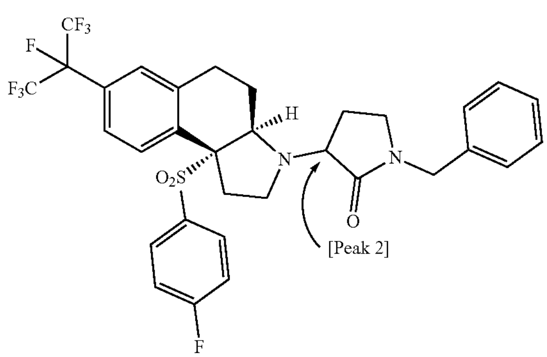 [SMILES: O=C1C(N2CC[C@@]3(S(=O)(=O)c4ccc(F)cc4)c4ccc(C(F)(C(F)(F)F)C(F)(F)F)cc4CC[C@@H]23)CCN1Cc1ccccc1] | 673.4 (M + H)+ | 2.51 | C |

TABLE 12-continued

| Ex. # | Structure | MS observed | HPLC ret. time (min.) | HPLC method |
|---|---|---|---|---|
| 739 | 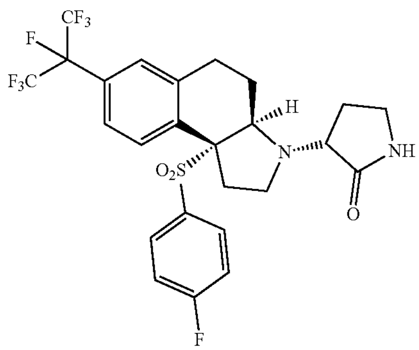 | 583.0 (M + H)+ | 2.06 | C |
| 740 | [Peak 1] | 660.3 (M + H)+ | 2.24 | C |
| 741 | [Peak 2] | 660.0 (M + H)+ | 2.21 | C |
| 742 | Homochiral from peak 2 | 572.8 (M + H)+ | 2.07 | C |

TABLE 12-continued
| Ex. # | Structure | MS observed | HPLC ret. time (min.) | HPLC method |
|---|---|---|---|---|
| 743 | 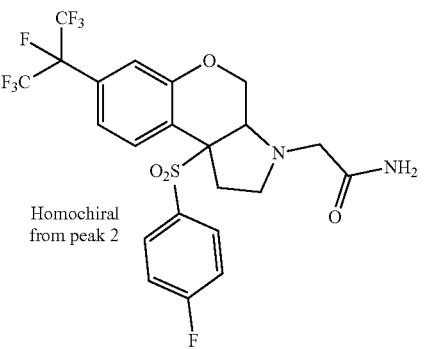 [SMILES: NC(=O)CN1CCC2(S(=O)(=O)c3ccc(F)cc3)c3ccc(C(F)(C(F)(F)F)C(F)(F)F)cc3OCC12] Homochiral from peak 2 | 558.9 (M + H)+ | 1.99 | C |
| 744 | 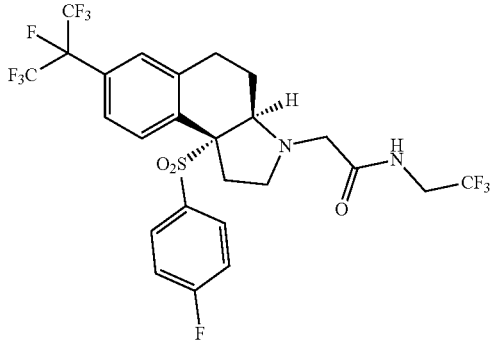 [SMILES: O=C(CN1CC[C@@]2(S(=O)(=O)c3ccc(F)cc3)c3ccc(C(F)(C(F)(F)F)C(F)(F)F)cc3CC[C@@H]12)NCC(F)(F)F] | 639.4 (M + H)+ | 2.40 | C |
| 745 | 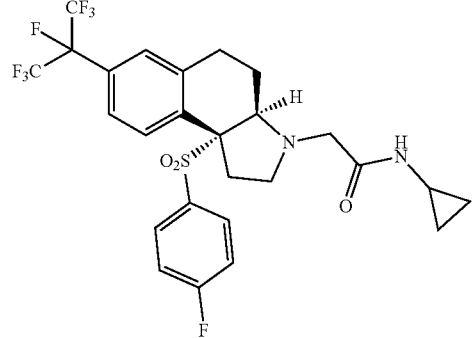 [SMILES: O=C(CN1CC[C@@]2(S(=O)(=O)c3ccc(F)cc3)c3ccc(C(F)(C(F)(F)F)C(F)(F)F)cc3CC[C@@H]12)NC1CC1] | 597.3 (M + H)+ | 2.31 | C |
| 746 | 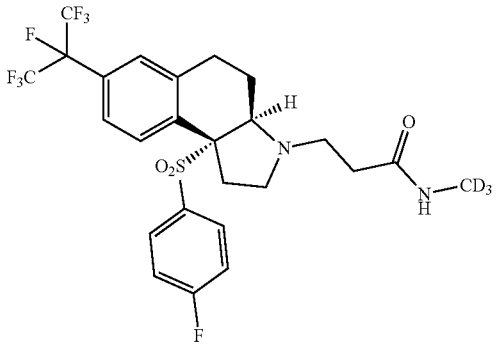 [SMILES: [2H]C([2H])([2H])NC(=O)CCN1CC[C@@]2(S(=O)(=O)c3ccc(F)cc3)c3ccc(C(F)(C(F)(F)F)C(F)(F)F)cc3CC[C@@H]12] | 588.4 (M + H)+ | 2.12 | C |

TABLE 12-continued

| Ex. # | Structure | MS observed | HPLC ret. time (min.) | HPLC method |
|---|---|---|---|---|
| 747 | [Peak 1] | 650.4 (M + H)+ | 2.38 | C |
| 748 | [Peak 2] | 650.4 (M + H)+ | 2.44 | C |
| 749 | [Peak 1] | 587.9 (M + H)+ | 2.22 | C |
| 750 | [Peak 2] | 588.2 (M + H)+ | 2.24 | C |

TABLE 12-continued

| Ex. # | Structure | MS observed | HPLC ret. time (min.) | HPLC method |
|---|---|---|---|---|
| 751 | 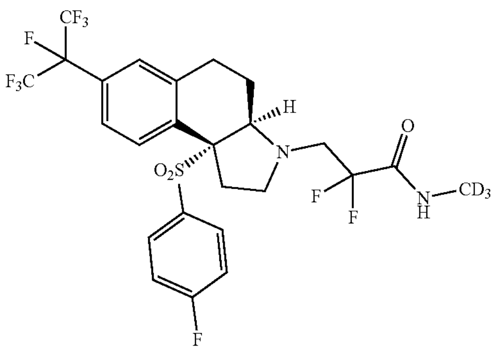 [SMILES: [2H]C([2H])([2H])NC(=O)C(F)(F)CN1CC[C@@]2(S(=O)(=O)c3ccc(F)cc3)c3ccc(C(F)(C(F)(F)F)C(F)(F)F)cc3CC[C@@H]12] | 623.8 (M + H)+ | 2.31 | C |
| 752 | 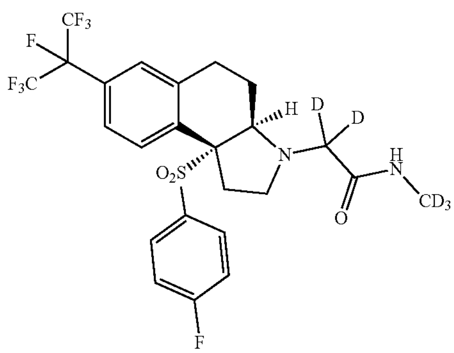 [SMILES: [2H]C([2H])([2H])NC(=O)C([2H])([2H])N1CC[C@@]2(S(=O)(=O)c3ccc(F)cc3)c3ccc(C(F)(C(F)(F)F)C(F)(F)F)cc3CC[C@@H]12] | 576.3 (M + H)+ | 2.19 | C |
| 753 | [Peak 1] | 602.1 (M + H)+ | 2.26 | C |
| 754 | [Peak 2] | 602.0 (M + H)+ | 2.32 | C |

TABLE 12-continued

| Ex. # | Structure | MS observed | HPLC ret. time (min.) | HPLC method |
|---|---|---|---|---|
| 755 | 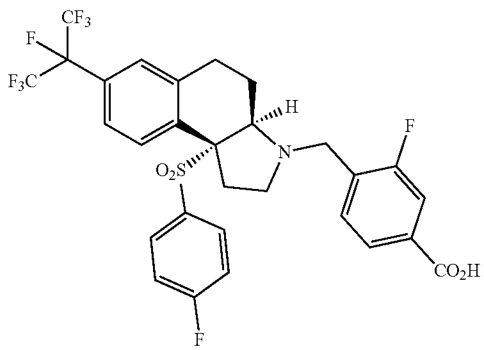 [SMILES: O=C(O)c1ccc(CN2CC[C@@]3(S(=O)(=O)c4ccc(F)cc4)c4ccc(C(F)(C(F)(F)F)C(F)(F)F)cc4CC[C@@H]23)c(F)c1] | 652.3 (M + H)+ | 2.02 | C |
| 756 | 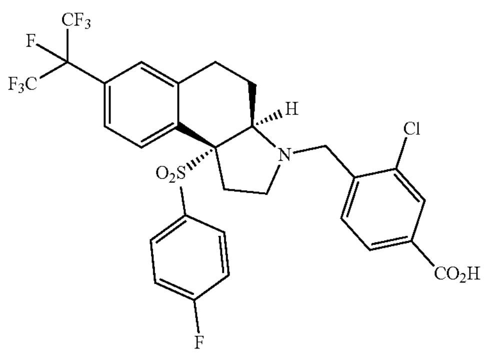 [SMILES: O=C(O)c1ccc(CN2CC[C@@]3(S(=O)(=O)c4ccc(F)cc4)c4ccc(C(F)(C(F)(F)F)C(F)(F)F)cc4CC[C@@H]23)c(Cl)c1] | 668.3 (M + H)+ | 2.10 | C |
| 757 | 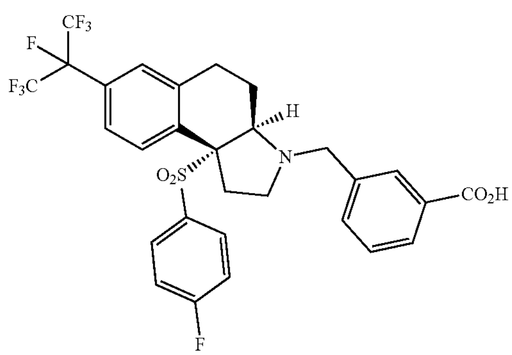 [SMILES: O=C(O)c1cccc(CN2CC[C@@]3(S(=O)(=O)c4ccc(F)cc4)c4ccc(C(F)(C(F)(F)F)C(F)(F)F)cc4CC[C@@H]23)c1] | 634.1 (M + H)+ | 2.09 | C |
| 758 | 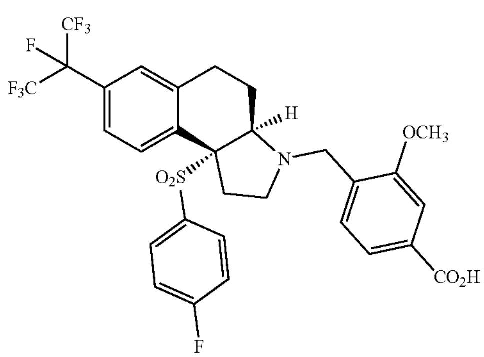 [SMILES: COc1cc(C(=O)O)ccc1CN1CC[C@@]2(S(=O)(=O)c3ccc(F)cc3)c3ccc(C(F)(C(F)(F)F)C(F)(F)F)cc3CC[C@@H]12] | 664.2 (M + H)+ | 2.07 | C |

TABLE 12-continued

| Ex. # | Structure | MS observed | HPLC ret. time (min.) | HPLC method |
|---|---|---|---|---|
| 759 | 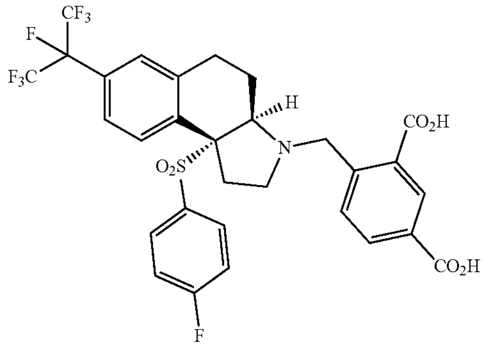 [SMILES: O=C(O)c1ccc(CN2CC[C@@]3(S(=O)(=O)c4ccc(F)cc4)c4ccc(C(F)(C(F)(F)F)C(F)(F)F)cc4CC[C@@H]23)c(C(=O)O)c1] | 678.0 (M + H)+ | 1.67 | C |

Example 760

1-(4-(((3aR,9bR)-9b-((4-fluorophenyl)sulfonyl)-7-(perfluoropropan-2-yl)-1,2,3a,4,5,9b-hexahydro-3H-benzo[e]indol-3-yl)methyl)piperidin-1-yl)ethan-1-one

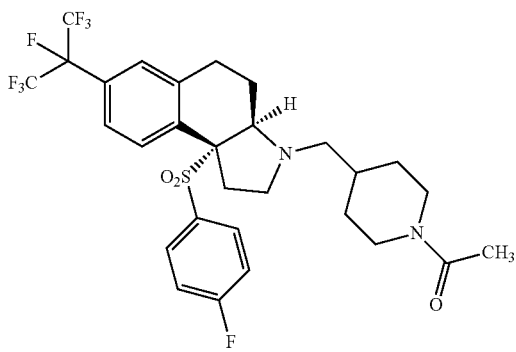 [SMILES: CC(=O)N1CCC(CN2CC[C@@]3(S(=O)(=O)c4ccc(F)cc4)c4ccc(C(F)(C(F)(F)F)C(F)(F)F)cc4CC[C@@H]23)CC1]

A solution of (3aR,9bR)-9b-((4-fluorophenyl)sulfonyl)-7-(perfluoropropan-2-yl)-2,3,3a,4,5,9b-hexahydro-1H-benzo[e]indole hydrochloride (Intermediate 32; 20 mg, 0.037 mmol) in 1,2-dichloroethane (2 mL) was treated with tert-butyl 4-formylpiperidine-1-carboxylate (19.9 mg, 0.093 mmol). DIPEA (0.02 mL, 0.112 mmol) was added and the mixture was stirred at rt for 30 min. The mixture was then treated with sodium triacetoxyborohydride (27.7 mg, 0.131 mmole). After 16 h, the mixture was concentrated. The residue was taken up in EtOAc (10 mL) and washed with 1 M aqueous NaOH (5 mL). The organic phase was dried over $Na_2SO_4$, filtered and concentrated. The residue was dissolved in DCM (3 mL) and TFA (0.5 mL) and the mixture was stirred at rt for 20 min. The mixture was concentrated, and the residue was dissolved in DCM (2 mL) and treated with $Et_3N$ (0.049 mL, 0.35 mmol) followed by a solution of acetyl chloride (7.11 µL, 0.100 mmol) in DCM (0.5 mL). The mixture was stirred at rt for 1.5 h, then was treated with MeOH (0.5 mL). The mixture was stirred at rt for 5 min and concentrated. The residue was purified by preparative HPLC (method F, gradient 30-70% B, 20 min) to afford 1-(4-(((3aR,9bR)-9b-((4-fluorophenyl)sulfonyl)-7-(perfluoropropan-2-yl)-1,2,3a,4,5,9b-hexahydro-3H-benzo[e]indol-3-yl)methyl)piperidin-1-yl)ethan-1-one (13.8 mg, 86% yield). LCMS m/z 639.1 (M+H)+, HPLC $t_R$ 2.37 min (method C). 1H NMR (500 MHz, DMSO-$d_6$) δ 7.52 (d, J=8.3 Hz, 1H), 7.46-7.31 (m, 4H), 7.31-7.21 (m, 3H), 7.16 (s, 1H), 7.06 (s, 1H), 4.35 (t, J=12.6 Hz, 1H), 3.81 (br. s., 1H), 3.54-3.36 (m, 1H), 3.33-3.21 (m, 1H), 3.13-2.95 (m, 2H), 2.77 (d, J=15.7 Hz, 1H), 2.60-2.53 (m, 3H), 2.06 (br. s., 1H), 1.98 (d, J=2.2 Hz, 3H), 1.95-1.67 (m, 3H), 1.56 (d, J=11.5 Hz, 1H), 1.25-0.92 (m, 2H).

Example 761

(3aR,9bR)-9b-((4-fluorophenyl)sulfonyl)-3-((1-methyl-1H-1,24-triazol-5-yl)methyl)-7-(perfluoropropan-2-yl)-2,3,3a,4,5,9b-hexahydro-1H-benzo[e]indole

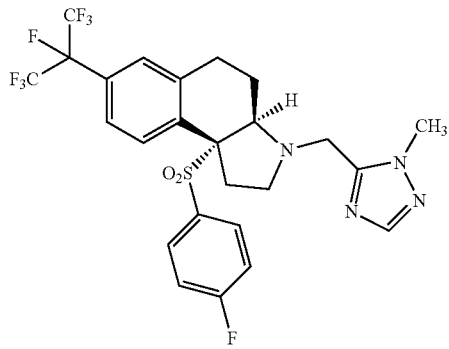 [SMILES: Cn1ncnc1CN1CC[C@@]2(S(=O)(=O)c3ccc(F)cc3)c3ccc(C(F)(C(F)(F)F)C(F)(F)F)cc3CC[C@@H]12]

A solution of (3aR,9bR)-9b-((4-fluorophenyl)sulfonyl)-7-(perfluoropropan-2-yl)-2,3,3a,4,5,9b-hexahydro-1H-benzo[e]indole hydrochloride (Intermediate 32; 15 mg, 0.030 mmol) in DMF (1 mL) was treated with 1-methyl-1H-1,2,4-triazole-5-carbaldehyde (16.68 mg, 0.150 mmol) and $Et_3N$ (6.1 µL, 0.044 mmol). Sodium triacetoxyborohydride (63.7 mg, 0.300 mmole) was added and the mixture was stirred at rt for 3 h. The mixture was treated with water (0.1 mL, 5.55 mmol) and purified by preparative HPLC (method E, gradient 45-90% B, 22 min) to afford (3aR,9bR)-9b-((4-fluorophenyl)sulfonyl)-3-((1-methyl-1H-1,2,4-triazol-5-yl)methyl)-7-(perfluoropropan-2-yl)-2,3,3a,4,5,9b-hexahydro-1H-benzo[e]indole (12.0 mg, 67% yield). LCMS m/z 594.9 (M+H)+, HPLC $t_R$ 2.17 min (method C). 1H NMR (500 MHz, DMSO-$d_6$) δ 7.85 (s, 1H), 7.54-7.43 (m, 2H), 7.35-7.27 (m, 3H), 7.27-7.18 (m, 2H), 4.15 (d, J=14.1 Hz, 1H), 3.85 (d, J=14.1 Hz, 1H), 3.79 (s, 2H), 3.10 (dd, J=14.0, 5.3 Hz, 1H), 2.88 (t, J=7.7 Hz, 1H), 2.77-2.69 (m, 1H), 2.59-2.53 (m, 1H), 2.36-2.23 (m, 1H), 2.10-1.97 (m, 1H), 1.87 (t, J=13.2 Hz, 1H), 1.28-1.13 (m, 3H).

The Examples in Table 13 were prepared using the procedures used to prepare Examples 760 and 761 using the appropriate carbonyl compound, followed by ester hydrolysis or other protecting group removal if required.

TABLE 13

| Ex. # | Structure | MS observed | HPLC ret. time (min.) | HPLC method |
|---|---|---|---|---|
| 762 | 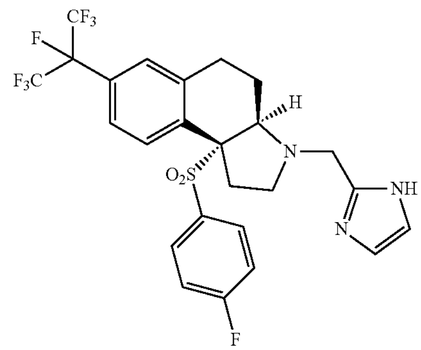 | 579.8 (M + H)+ | 2.03 | C |
| 763 | 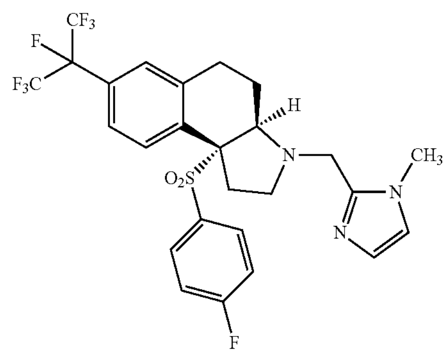 [SMILES: Cn1ccnc1CN1CC[C@@]2(S(=O)(=O)c3ccc(F)cc3)c3ccc(C(F)(C(F)(F)F)C(F)(F)F)cc3CC[C@@H]12] | 593.9 (M + H)+ | 2.24 | C |
| 764 | 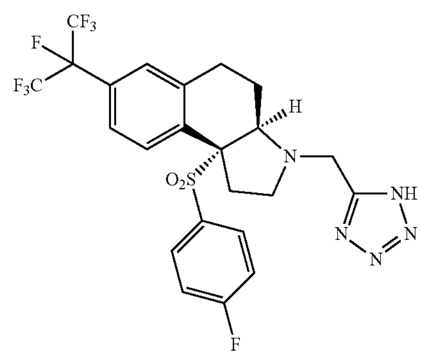 [SMILES: O=S(=O)(c1ccc(F)cc1)[C@@]12CCN(Cc3nnn[nH]3)[C@@H]1CCc1cc(C(F)(C(F)(F)F)C(F)(F)F)ccc12] | 582.3 (M + H)+ | 1.68 | C |
| 765 | 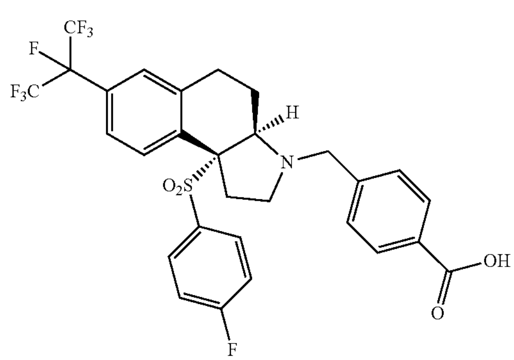 [SMILES: O=C(O)c1ccc(CN2CC[C@@]3(S(=O)(=O)c4ccc(F)cc4)c4ccc(C(F)(C(F)(F)F)C(F)(F)F)cc4CC[C@@H]23)cc1] | 634.2 (M + H)+ | 1.94 | C |

TABLE 13-continued

| Ex. # | Structure | MS observed | HPLC ret. time (min.) | HPLC method |
|---|---|---|---|---|
| 766 | 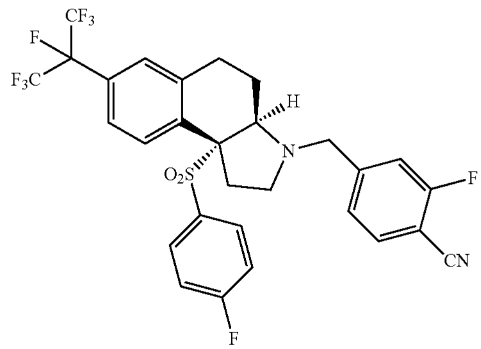 [SMILES: N#Cc1ccc(CN2CC[C@@]3(S(=O)(=O)c4ccc(F)cc4)c4ccc(C(F)(C(F)(F)F)C(F)(F)F)cc4CC[C@@H]23)cc1F] | 633.0 (M + H)+ | 2.68 | C |
| 767 | 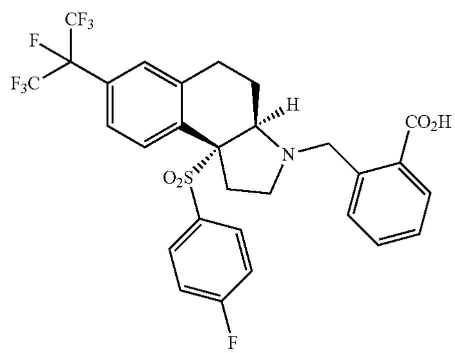 [SMILES: O=C(O)c1ccccc1CN1CC[C@@]2(S(=O)(=O)c3ccc(F)cc3)c3ccc(C(F)(C(F)(F)F)C(F)(F)F)cc3CC[C@@H]12] | 634.2 (M + H)+ | 2.06 | C |
| 768 | 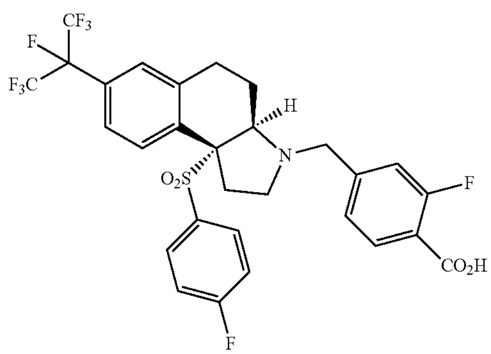 | 652.0 (M + H)+ | 2.02 | C |
| 769 | 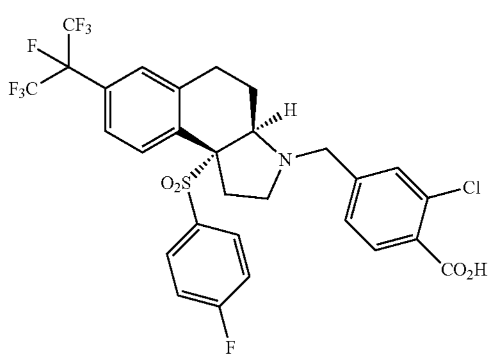 [SMILES: O=C(O)c1ccc(CN2CC[C@@]3(S(=O)(=O)c4ccc(F)cc4)c4ccc(C(F)(C(F)(F)F)C(F)(F)F)cc4CC[C@@H]23)cc1Cl] | 668.1 (M + H)+ | 1.94 | C |

Example 770

9b-((4-fluorophenyl)sulfonyl)-7-iodo-2-oxo-1,2,3a,4,5,9b-hexahydro-3H-benzo[e]indol-3-yl)acetic Acid

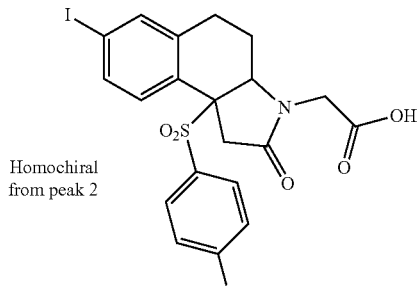

Homochiral from peak 2

Step A: 9b-((4-fluorophenyl)sulfonyl)-7-iodo-1,3,3a,4,5,9b-hexahydro-2H-benzo[e]indol-2-one

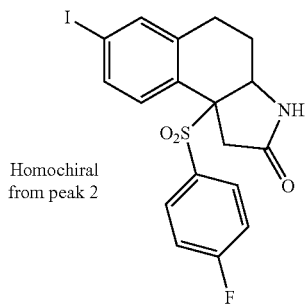 [SMILES: O=C1CC2(S(=O)(=O)c3ccc(F)cc3)c3ccc(I)cc3CCC2N1]

Homochiral from peak 2

Following the procedures used to prepare Intermediate 118, homochiral tert-butyl 9b-((4-fluorophenyl)sulfonyl)-7-iodo-1,2,3a,4,5,9b-hexahydro-3H-benzo[e]indole-3-carboxylate (Intermediate 71) was converted into homochiral 9b-((4-fluorophenyl)sulfonyl)-7-iodo-1,3,3a,4,5,9b-hexahydro-2H-benzo[e]indol-2-one in 59% yield. LCMS m/z 513.0 (M+H+MeCN)$^+$, HPLC $t_R$ 0.91 min (method B). $^1$H NMR (400 MHz, CDCl$_3$) δ 7.67-7.62 (m, 1H), 7.50-7.42 (m, 2H), 7.41 (s, 1H), 7.18 (d, J=8.4 Hz, 1H), 7.12 (dd, J=8.9, 8.3 Hz, 2H), 4.44-4.32 (m, 1H), 3.69 (d, J=18.5 Hz, 1H), 2.89 (d, J=18.3 Hz, 1H), 2.49 (dt, J=16.2, 3.8 Hz, 1H), 2.21-2.07 (m, 1H), 1.95-1.80 (m, 1H), 1.50-1.33 (m, 1H).

Step B: Tert-butyl 2-(9b-((4-fluorophenyl)sulfonyl)-7-iodo-2-oxo-1,2,3a,4,5,9b-hexahydro-3H-benzo[e]indol-3-yl)acetate

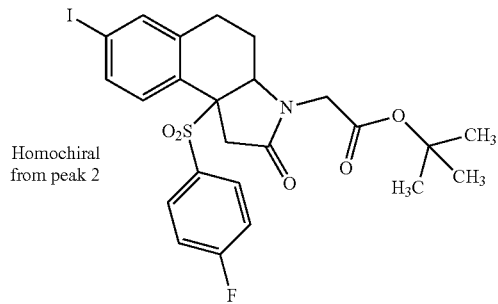 [SMILES: CC(C)(C)OC(=O)CN1C(=O)CC2(S(=O)(=O)c3ccc(F)cc3)c3ccc(I)cc3CCC12]

Homochiral from peak 2

A solution of homochiral 9b-((4-fluorophenyl)sulfonyl)-7-iodo-3,3a,4,5-tetrahydro-1H-benzo[e]indol-2-one (0.07 g, 0.149 mmol) in THF (1 mL) was cooled to −78° C. and treated with potassium bis(trimethylsilyl)amide (1 M; 0.149 mL, 0.149 mmol), stirred for 20 min, then treated with tert-butyl bromoacetate (0.066 mL, 0.446 mmol). After 30 min, the mixture was allowed to warm to rt over 1 h and treated with saturated aqueous NH$_4$Cl. The mixture was extracted with EtOAc, and the organic phase was dried and concentrated. The residue was purified by column chromatography on silica gel to give crude homochiral tert-butyl 2-(9b-((4-fluorophenyl)sulfonyl)-7-iodo-2-oxo-1,2,3a,4,5,9b-hexahydro-3H-benzo[e]indol-3-yl)acetate (0.11 g) which was used in the next step without further purification. LCMS m/z 530.0 (M+H—C$_4$H$_8$)$^+$, HPLC $t_R$ 1.09 min (method B).

Step C: 2-(9b-((4-fluorophenyl)sulfonyl)-7-iodo-2-oxo-1,2,3a,4,5,9b-hexahydro-3H-benzo[e]indol-3-yl)acetic Acid

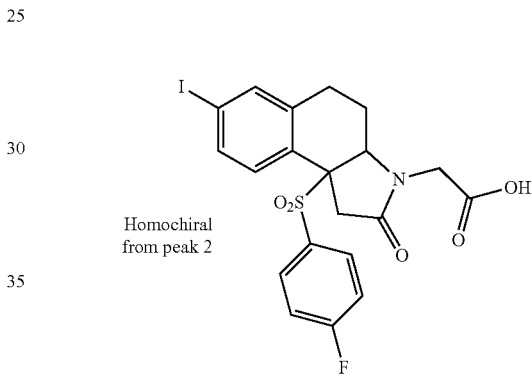

Homochiral from peak 2

A solution of crude homochiral tert-butyl 2-(9b-((4-fluorophenyl)sulfonyl)-7-iodo-2-oxo-1,2,3a,4,5,9b-hexahydro-3H-benzo[e]indol-3-yl)acetate (0.11 g, 0.188 mmol) in DCM (0.1 mL) was treated with 85% phosphoric acid (0.103 mL, 1.503 mmol) and stirred at rt for 48 h. The mixture was diluted with water (10 mL) and extracted with EtOAc (20 mL). The organic phase was washed sequentially with water (3×15 mL) and brine (15 mL), dried over Na$_2$SO$_4$ and concentrated. The residue was purified by preparative HPLC (method E, gradient 10-50% B) to give homochiral 2-(9b-((4-fluorophenyl)sulfonyl)-7-iodo-2-oxo-1,2,3a,4,5,9b-hexahydro-3H-benzo[e]indol-3-yl)acetic acid (51 mg, 51% yield). LCMS m/z 528.1 (M−H)$^-$, HPLC $t_R$ 1.34 min (method C). $^1$H NMR (500 MHz, DMSO-d$_6$) δ 7.67 (d, J=8.2 Hz, 1H), 7.60 (dd, J=8.4, 5.0 Hz, 2H), 7.52 (s, 1H), 7.41 (t, J=8.5 Hz, 2H), 7.18 (d, J=8.2 Hz, 1H), 4.39 (dd, J=11.3, 5.2 Hz, 1H), 3.98-3.68 (m, 2H), 3.05 (d, J=18.6 Hz, 1H), 2.50 (br. s., 2H), 2.17 (dd, J=8.5, 4.0 Hz, 1H), 1.87 (t, J=13.7 Hz, 1H), 1.43-1.15 (m, 1H).

Example 771

9b-((4-fluorophenyl)sulfonyl)-3,5-dimethyl-7-(perfluoropropan-2-yl)-2,3,3a,4,5,9b-hexahydro-1H-pyrrolo[2,3-c]quinolone

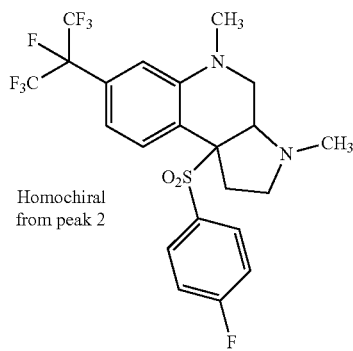 [SMILES: CN1CC2N(C)CCC2(S(=O)(=O)c2ccc(F)cc2)c2ccc(C(F)(C(F)(F)F)C(F)(F)F)cc21]

Homochiral from peak 2

A solution of 9b-((4-fluorophenyl)sulfonyl)-7-(perfluoropropan-2-yl)-2,3,3a,4,5,9b-hexahydro-1H-pyrrolo[2,3-c]quinoline dihydrochloride (homochiral, from peak 2, Intermediate 88; 20 mg, 0.040 mmol) in MeOH (200 μL) was treated with acetic acid (114 μL, 1.998 mmol), 37% aqueous formaldehyde (29.8 μL, 0.400 mmol) and sodium cyanoborohydride (25.1 mg, 0.400 mmol). The mixture was stirred at rt for 1 h, then was diluted with EtOAc, washed with 1 M aqueous NaOH, dried over $Na_2SO_4$ and concentrated. The residue was purified by preparative HPLC (method E, gradient 50-100% B, 25 min) to provide 9b-((4-fluorophenyl)sulfonyl)-3,5-dimethyl-7-(perfluoropropan-2-yl)-2,3,3a,4,5,9b-hexahydro-1H-pyrrolo[2,3-c]quinoline (5.6 mg, 27% yield). LCMS m/z 528.8 (M+H)$^+$, HPLC $t_R$ 2.3 min (method C). $^1$H NMR (500 MHz, DMSO-d$_6$) δ 7.47 (d, J=8.2 Hz, 1H), 7.38-7.30 (m, 2H), 7.20 (t, J=8.7 Hz, 2H), 6.97 (d, J=8.2 Hz, 1H), 6.49 (s, 1H), 3.52 (br. s., 1H), 3.28 (dd, J=12.2, 5.4 Hz, 1H), 3.07 (dd, J=13.8, 6.9 Hz, 1H), 3.00 (t, J=7.8 Hz, 1H), 2.76 (dd, J=12.1, 7.0 Hz, 1H), 2.60-2.52 (s+m, 4H), 2.43-2.19 (s+m, 4H).

Example 772

(3aR,9bR)-9b-((4-fluorophenyl)sulfonyl)-7-(perfluoropropan-2-yl)-3-phenyl-2,3,3a,4,5,9b-hexahydro-1H-benzo[e]indole

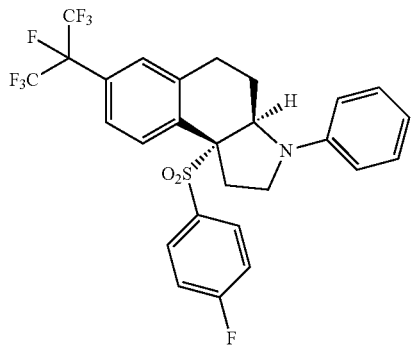 [SMILES: O=S(=O)(c1ccc(F)cc1)[C@@]12CCN(c3ccccc3)[C@@H]1CCc1cc(C(F)(C(F)(F)F)C(F)(F)F)ccc12]

A solution of (3aR,9bR)-9b-((4-fluorophenyl)sulfonyl)-7-(perfluoropropan-2-yl)-2,3,3a,4,5,9b-hexahydro-1H-benzo[e]indole hydrochloride (Intermediate 32; 15 mg, 0.028 mmol) and bromobenzene (8.79 mg, 0.056 mmol) in 1,4-dioxane (1 mL) was bubbled with nitrogen for 2 min. Palladium(II) acetate (1.26 mg, 5.60 μmol), BINAP (5.23 mg, 8.40 μmol) and $Cs_2CO_3$ (54.7 mg, 0.168 mmol) were added, and the mixture was heated at 90° C. under a nitrogen atmosphere for 16 h. The mixture was cooled to rt, diluted with EtOAc (5 mL) and washed with brine (5 mL). The organic phase was dried over $Na_2SO_4$, filtered and concentrated. The residue was purified by preparative HPLC (method F, gradient 45-100% B, 25 min) to afford (3aR,9bR)-9b-((4-fluorophenyl)sulfonyl)-7-(perfluoropropan-2-yl)-3-phenyl-2,3,3a,4,5,9b-hexahydro-1H-benzo[e]indole (3.6 mg, 22% yield). LCMS m/z 575.9 (M+H)$^+$, HPLC $t_R$ 2.69 min (method C). $^1$H NMR (500 MHz, DMSO-d$_6$) δ 7.88 (d, J=8.3 Hz, 1H), 7.62 (d, J=8.4 Hz, 1H), 7.46 (dd, J=8.2, 5.1 Hz, 2H), 7.36 (s, 1H), 7.19 (t, J=7.7 Hz, 2H), 7.12 (t, J=8.6 Hz, 2H), 6.75-6.61 (m, 2H), 4.45 (dd, J=11.7, 4.7 Hz, 1H), 3.52 (s, 1H), 3.39 (br. s., 1H), 3.27-3.13 (m, 1H), 2.76-2.65 (m, 3H), 2.40 (d, J=8.8 Hz, 1H), 2.23 (t, J=14.3 Hz, 1H), 1.23 (d, J=12.0 Hz, 1H).

Example 773

4-((3aR,9bR)-9b-((4-fluorophenyl)sulfonyl)-7-(perfluoropropan-2-yl)-1,2,3a,4,5,9b-hexahydro-3H-benzo[e]indol-3-yl)benzoic Acid

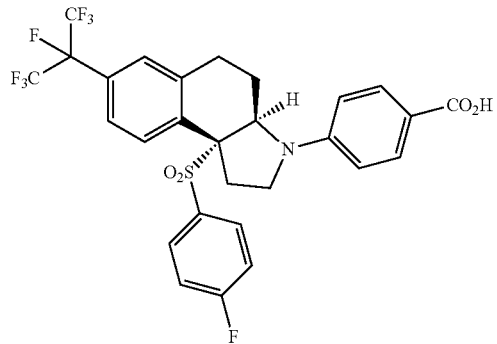 [SMILES: O=C(O)c1ccc(N2CC[C@@]3(S(=O)(=O)c4ccc(F)cc4)c4ccc(C(F)(C(F)(F)F)C(F)(F)F)cc4CC[C@@H]23)cc1]

A solution of (3aR,9bR)-9b-((4-fluorophenyl)sulfonyl)-7-(perfluoropropan-2-yl)-2,3,3a,4,5,9b-hexahydro-1H-benzo[e]indole hydrochloride (Intermediate 32; 20 mg, 0.037 mmol) and tert-butyl 4-bromobenzoate (19.19 mg, 0.075 mmol) in 1,4-dioxane (2 mL) was bubbled with nitrogen for 2 min. Palladium(II) acetate (1.676 mg, 7.46 μmol), BINAP (6.97 mg, 8.40 μmol) and $Cs_2CO_3$ (73.0 mg, 0.224 mmol) were added, and the mixture was heated at 90° C. under a nitrogen atmosphere for 16 h. The mixture was cooled to rt, diluted with EtOAc (10 mL) and washed with brine (10 mL). The organic phase was dried over $Na_2SO_4$, filtered and concentrated. The residue was dissolved in DCM (2 mL) and treated with TFA (1 mL). The mixture was stirred at rt for 4 h, concentrated, and the residue was purified by preparative HPLC (method E, gradient 45-90% B, 19 min) to afford 4-((3aR,9bR)-9b-((4-fluorophenyl)sulfonyl)-7-(perfluoropropan-2-yl)-1,2,3a,4,5,9b-hexahydro-3H-benzo[e]indol-3-yl)benzoic acid (17.4 mg, 70% yield). LCMS m/z 618.0 (M−H)$^-$, HPLC $t_R$ 2.14 min (method C). $^1$H NMR (500 MHz, DMSO-d$_6$) δ 7.90 (d, J=8.4 Hz, 1H), 7.77 (d, J=8.4

Hz, 2H), 7.63 (d, J=8.3 Hz, 1H), 7.57-7.47 (m, 2H), 7.39 (s, 1H), 7.13 (t, J=8.5 Hz, 2H), 6.71 (d, J=8.4 Hz, 2H), 4.55 (dd, J=11.7, 4.4 Hz, 1H), 3.16 (s, 3H), 2.81-2.67 (m, 3H), 2.43-2.26 (m, 2H), 1.29 (d, J=11.8 Hz, 1H).

Example 774

(3aR,9bR)-9b-((4-fluorophenyl)sulfonyl)-7-(perfluoropropan-2-yl)-3-(pyridin-2-yl)-2,3,3a,4,5,9b-hexahydro-1H-benzo[e]indole

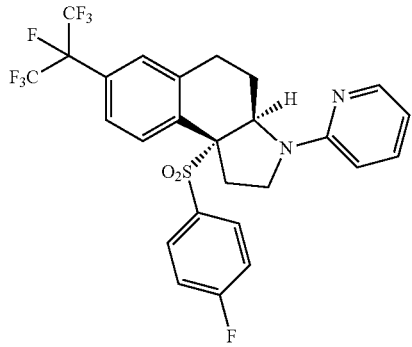 [SMILES: O=S(=O)(c1ccc(F)cc1)[C@@]12CCN(c3ccccn3)[C@@H]1CCc1cc(C(F)(C(F)(F)F)C(F)(F)F)ccc12]

A solution of (3aR,9bR)-9b-((4-fluorophenyl)sulfonyl)-7-(perfluoropropan-2-yl)-2,3,3a,4,5,9b-hexahydro-1H-benzo[e]indole hydrochloride (Intermediate 32; 15 mg, 0.028 mmol) and bromopyridine (13.27 mg, 0.084 mmol) in 1,4-dioxane (2 mL) was bubbled with nitrogen for 2 min. Palladium(II) acetate (1.26 mg, 5.60 μmol), Xantphos (4.05 mg, 7.00 μmol) and sodium tert-butoxide (16.14 mg, 0.168 mmol) were added, and the mixture was heated at 90° C. under nitrogen for 16 h. The mixture was cooled to rt, diluted with EtOAc (5 mL) and washed with brine (5 mL). The organic phase was dried over $Na_2SO_4$, filtered and concentrated. The residue was purified by preparative HPLC (method E, gradient 30-70% B, 20 min) to afford (3aR,9bR)-9b-((4-fluorophenyl)sulfonyl)-7-(perfluoropropan-2-yl)-3-(pyridin-2-yl)-2,3,3a,4,5,9b-hexahydro-1H-benzo[e]indole (11.2 mg, 65% yield). LCMS m/z 577.3 $(M+H)^+$, HPLC $t_R$ 2.64 min (method C). $^1H$ NMR (500 MHz, DMSO-$d_6$) δ 8.13 (d, J=4.8 Hz, 1H), 7.90 (d, J=8.4 Hz, 1H), 7.74 (br. s., 1H), 7.65 (d, J=8.5 Hz, 1H), 7.50-7.41 (m, 2H), 7.38 (s, 1H), 7.21-7.11 (m, 2H), 6.83 (d, J=5.9 Hz, 2H), 4.83 (dd, J=11.7, 4.6 Hz, 1H), 3.74-3.64 (m, 1H), 2.86-2.70 (m, 3H), 2.54 (s, 2H), 2.19 (t, J=15.2 Hz, 1H), 1.34 (d, J=12.6 Hz, 1H).

The Examples in Table 14 were prepared using the procedures used to prepare Examples 772 through 774 or similar procedures, using an appropriate aryl bromide or iodide followed by ester hydrolysis or other protecting group removal if required.

TABLE 14

| Ex. #r | Structure | LCMS m/z observed | HPLC $t_R$ (min.) | HPLC method |
|---|---|---|---|---|
| 775 | 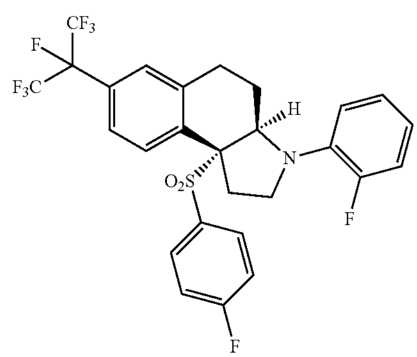 [SMILES: O=S(=O)(c1ccc(F)cc1)[C@@]12CCN(c3ccccc3F)[C@@H]1CCc1cc(C(F)(C(F)(F)F)C(F)(F)F)ccc12] | 594.0 $(M + H)^+$ | 2.85 | C |
| 776 | 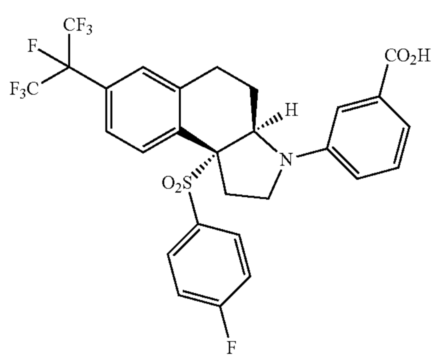 [SMILES: O=C(O)c1cccc(N2CC[C@@]3(S(=O)(=O)c4ccc(F)cc4)c4ccc(C(F)(C(F)(F)F)C(F)(F)F)cc4CC[C@@H]23)c1] | 620.3 $(M + H)^+$ | 1.97 | C |

TABLE 14-continued

| Ex. #r | Structure | LCMS m/z observed | HPLC t$_R$ (min.) | HPLC method |
|---|---|---|---|---|
| 777 | 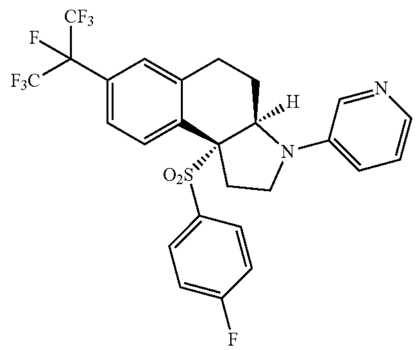 | 577.2 (M + H)$^+$ | 2.35 | C |
| 778 | 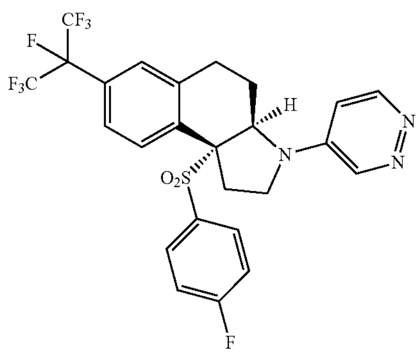 [SMILES: O=S(=O)(c1ccc(F)cc1)[C@@]12CCN(c3ccnnc3)[C@@H]1CCc1cc(C(F)(C(F)(F)F)C(F)(F)F)ccc12] | 578.2 (M + H)$^+$ | 2.10 | C |
| 779 | 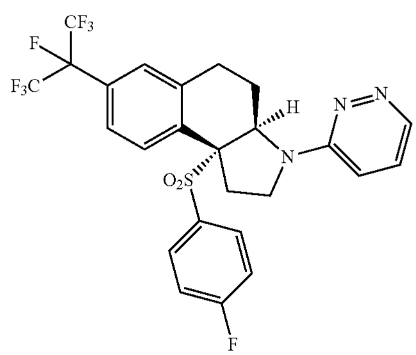 | 578.0 (M + H)$^+$ | 2.22 | C |
| 780 | 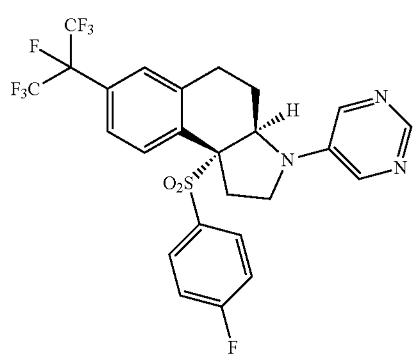 [SMILES: O=S(=O)(c1ccc(F)cc1)[C@@]12CCN(c3cncnc3)[C@@H]1CCc1cc(C(F)(C(F)(F)F)C(F)(F)F)ccc12] | 578.1 (M + H)$^+$ | 2.22 | C |

TABLE 14-continued

| Ex. #r | Structure | LCMS m/z observed | HPLC $t_R$ (min.) | HPLC method |
|---|---|---|---|---|
| 781 | 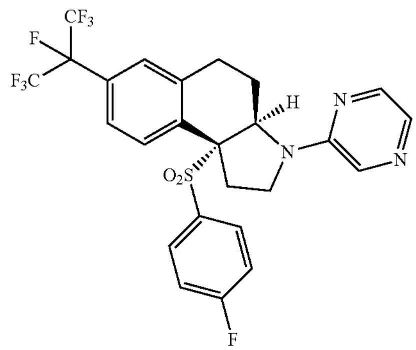 | 578.0 (M + H)⁺ | 2.40 | C |
| 782 | 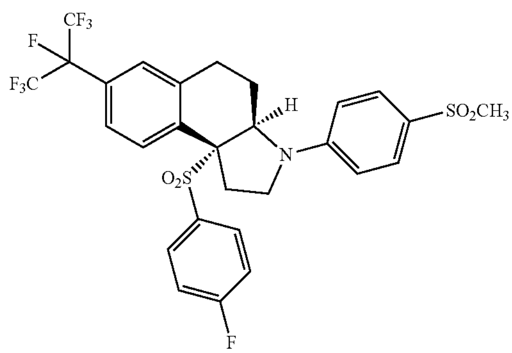 [SMILES: CS(=O)(=O)c1ccc(N2CC[C@@]3(S(=O)(=O)c4ccc(F)cc4)c4ccc(C(F)(C(F)(F)F)C(F)(F)F)cc4CC[C@@H]23)cc1] | 654.1 (M + H)⁺ | 2.39 | C |
| 783 | 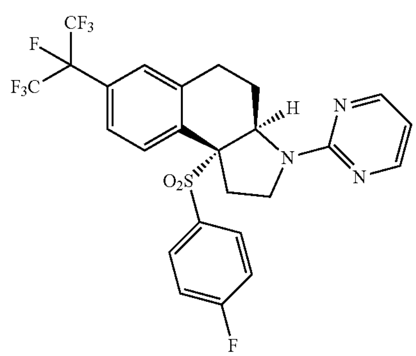 | 577.9 (M + H)⁺ | 2.44 | C |
| 784 | 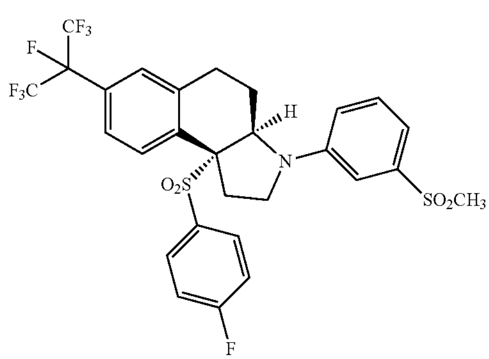 [SMILES: CS(=O)(=O)c1cccc(N2CC[C@@]3(S(=O)(=O)c4ccc(F)cc4)c4ccc(C(F)(C(F)(F)F)C(F)(F)F)cc4CC[C@@H]23)c1] | 654.3 (M + H)⁺ | 2.41 | C |

TABLE 14-continued

| Ex. #r | Structure | LCMS m/z observed | HPLC t_R (min.) | HPLC method |
|---|---|---|---|---|
| 785 | 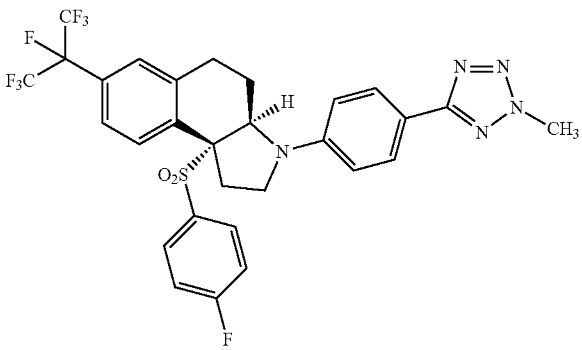 [SMILES: Cn1nnc(-c2ccc(N3CC[C@@]4(S(=O)(=O)c5ccc(F)cc5)c5ccc(C(F)(C(F)(F)F)C(F)(F)F)cc5CC[C@@H]34)cc2)n1] | 658.0 (M + H)+ | 2.57 | C |
| 786 | 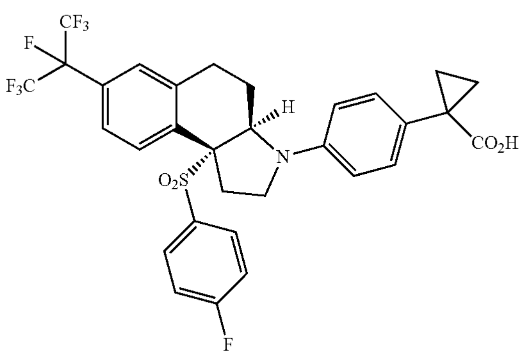 [SMILES: O=C(O)C1(c2ccc(N3CC[C@@]4(S(=O)(=O)c5ccc(F)cc5)c5ccc(C(F)(C(F)(F)F)C(F)(F)F)cc5CC[C@@H]34)cc2)CC1] | 660.4 (M + H)+ | 2.28 | C |
| 787 | 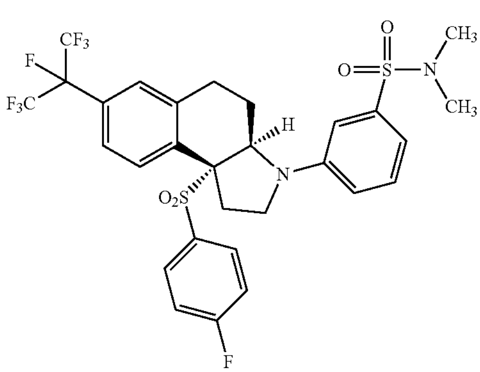 [SMILES: CN(C)S(=O)(=O)c1cccc(N2CC[C@@]3(S(=O)(=O)c4ccc(F)cc4)c4ccc(C(F)(C(F)(F)F)C(F)(F)F)cc4CC[C@@H]23)c1] | 683.3 (M + H)+ | 2.51 | C |

Example 788

(3aR,9bR)-9b-((4-fluorophenyl)sulfonyl)-7-(perfluoropropan-2-yl)-1,2,3a,4,5,9b-hexahydro-3H-benzo[e]indole-3-carbonitrile

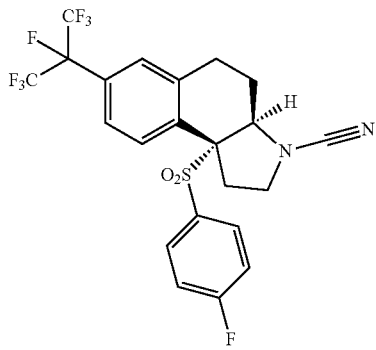 [SMILES: N#CN1CC[C@@]2(S(=O)(=O)c3ccc(F)cc3)c3ccc(C(F)(C(F)(F)F)C(F)(F)F)cc3CC[C@@H]12]

A solution of (3aR,9bR)-9b-((4-fluorophenyl)sulfonyl)-7-(perfluoropropan-2-yl)-2,3,3a,4,5,9b-hexahydro-1H-benzo[e]indole hydrochloride (Intermediate 32; 15 mg, 0.028 mmol) in DMF (1 mL) was treated with $Cs_2CO_3$ (48.9 mg, 0.150 mmol) and cyanogen bromide (9.54 mg, 0.09 mmol). The mixture was stirred at rt for 2 h, treated with water (0.1 mL, 5.55 mmol) and purified by preparative HPLC (method E, gradient 40-80% B, 20 min) to afford (3aR,9bR)-9b-((4-fluorophenyl)sulfonyl)-7-(perfluoropropan-2-yl)-1,2,3a,4,5,9b-hexahydro-3H-benzo[e]indole-3-carbonitrile (10.6 mg, 67% yield). LCMS m/z 525.3 (M+H)$^+$, HPLC $t_R$ 2.35 min (method C). $^1$H NMR (500 MHz, DMSO-$d_6$) δ 7.75 (d, J=8.5 Hz, 1H), 7.61 (d, J=8.2 Hz, 1H), 7.47-7.38 (m, 2H), 7.32 (s, 1H), 7.22 (t, J=8.7 Hz, 2H), 4.55 (dd, J=10.8, 5.3 Hz, 1H), 3.65-3.55 (m, 2H), 3.38 (d, J=9.2 Hz, 1H), 3.28 (dt, J=14.0, 5.0 Hz, 1H), 2.71-2.56 (m, 1H), 2.24-2.15 (m, 1H), 1.89 (t, J=13.1 Hz, 1H), 1.54-1.38 (m, 1H).

Example 789

(1r,4r)-4-(5-(tert-butoxycarbonyl)-9b-((4-fluorophenyl)sulfonyl)-7-(perfluoropropan-2-yl)-2,3,3a,4,5,9b-hexahydro-1H-pyrrolo[2,3-c]quinoline-3-carbonyl)cyclohexane-1-carboxylic Acid

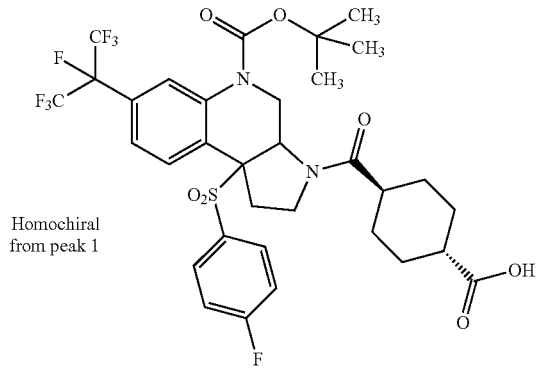 [SMILES: CC(C)(C)OC(=O)N1CC2N(C(=O)[C@H]3CC[C@H](C(=O)O)CC3)CCC2(S(=O)(=O)c2ccc(F)cc2)c2ccc(C(F)(C(F)(F)F)C(F)(F)F)cc21]

Homochiral from peak 1

Step A: Tert-butyl 7-bromo-9b-((4-fluorophenyl)sulfonyl)-3-((1r,4r)-4-(2-methoxy-2-oxoacetyl)cyclohexane-1-carbonyl)-1,2,3,3a,4,9b-hexahydro-5H-pyrrolo[2,3-c]quinoline-5-carboxylate

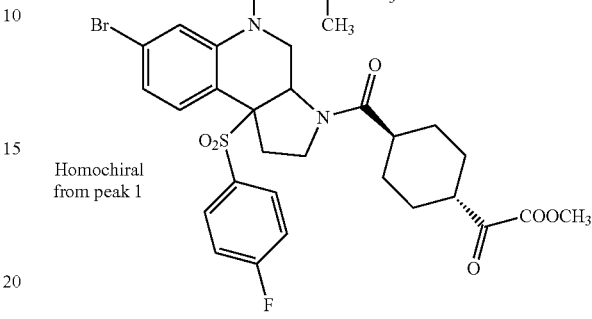

Homochiral from peak 1

A solution of tert-butyl 7-bromo-9b-((4-fluorophenyl)sulfonyl)-2,3,3a,4-tetrahydro-1H-pyrrolo[2,3-c]quinoline-5(9bH)-carboxylate (the product from Intermediate 88 Step C; 4.09 g, 8 mmol) in DCM (80 mL) was treated with (1r,4r)-4-(methoxycarbonyl)cyclohexanecarboxylic acid (2.234 g, 12.00 mmol), DIPEA (4.19 ml, 24.00 mmol) and HATU (4.56 g, 12.00 mmol). The mixture was stirred at rt for 1 h. The mixture was concentrated and purified by column chromatography on silica gel, eluting with EtOAc-hexanes, to provide tert-butyl 7-bromo-9b-((4-fluorophenyl)sulfonyl)-3-((1 r,4r)-4-(methoxycarbonyl)cyclohexanecarbonyl)-2,3,3a,4-tetrahydro-1H-pyrrolo[2,3-c]quinoline-5(9bH)-carboxylate. LCMS m/z 623.4 (M+H—$C_4H_8$)$^+$, HPLC $t_R$ 1.15 min (method B).

This material was separated by chiral SFC using the following conditions: Column: Lux® Cellulose-4 50×250 mm, 5 µm (Phenomenex Inc.); column temperature 35° C.; pressure 100 bars; mobile phase $CO_2$-MeOH (80:20); flow rate 300 mL/min. Peak 1 was eluted with $t_R$ 6.6 min. Peak 2 was eluted with $t_R$ 8.2 min.

Step B: Tert-butyl 9b-((4-fluorophenyl)sulfonyl)-3-((1r,4r)-4-(2-methoxy-2-oxoacetyl)cyclohexane-1-carbonyl)-7-(perfluoropropan-2-yl)-1,2,3,3a,4,9b-hexahydro-5H-pyrrolo[2,3-c]quinoline-5-carboxylate

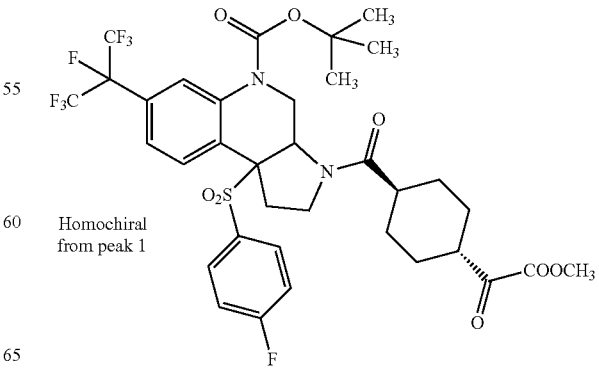

Homochiral from peak 1

Following the procedure of Intermediate 2 Step A, tert-butyl 7-bromo-9b-((4-fluorophenyl)sulfonyl)-3-((1r,4r)-4-(methoxycarbonyl)cyclohexanecarbonyl)-2,3,3a,4-tetrahydro-1H-pyrrolo[2,3-c]quinoline-5(9bH)-carboxylate (1 g, 1.471 mmol) was converted into tert-butyl 9b-((4-fluorophenyl)sulfonyl)-3-((1r,4r)-4-(methoxycarbonyl)cyclohexanecarbonyl)-7-(perfluoropropan-2-yl)-2,3,3a,4-tetrahydro-1H-pyrrolo[2,3-c]quinoline-5(9bH)-carboxylate (0.35 g, 31% yield). LCMS m/z 713.5 (M+H—$C_4H_8$)$^+$, HPLC $t_R$ 1.18 min (method B).

Step C: (1r,4r)-4-(5-(tert-butoxycarbonyl)-9b-((4-fluorophenyl)sulfonyl)-7-(perfluoropropan-2-yl)-2,3,3a,4,5,9b-hexahydro-1H-pyrrolo[2,3-c]quinoline-3-carbonyl)cyclohexane-1-carboxylic Acid

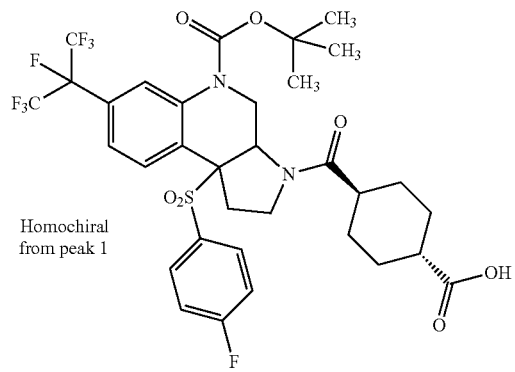 [SMILES: CC(C)(C)OC(=O)N1CC2N(C(=O)[C@H]3CC[C@H](C(=O)O)CC3)CCC2(S(=O)(=O)c2ccc(F)cc2)c2ccc(C(F)(C(F)(F)F)C(F)(F)F)cc21]

Homochiral from peak 1

A solution of tert-butyl 9b-((4-fluorophenyl)sulfonyl)-3-((1r,4r)-4-(methoxycarbonyl)cyclohexanecarbonyl)-7-(perfluoropropan-2-yl)-2,3,3a,4-tetrahydro-1H-pyrrolo[2,3-c]quinoline-5(9bH)-carboxylate (25 mg, 0.033 mmol) in 1,4-dioxane (325 μL) was treated with a solution of LiOH hydrate (7.79 mg, 0.325 mmol) in water (58.6 μL, 3.25 mmol). After 2 h at rt, the mixture was diluted with DMF and purified by preparative HPLC (method E, gradient 40-100% B, 20 min) to provide (1r,4r)-4-(5-(tert-butoxycarbonyl)-9b-((4-fluorophenyl)sulfonyl)-7-(perfluoropropan-2-yl)-2,3,3a,4,5,9b-hexahydro-1H-pyrrolo[2,3-c]quinoline-3-carbonyl)cyclohexane-1-carboxylic acid (7.6 mg, 31% yield). LCMS m/z 755.3 (M+H)$^+$, HPLC $t_R$ 1.15 min (method B). $^1$H NMR (500 MHz, DMSO-$d_6$) δ 7.93 (d, J=8.2 Hz, 1H), 7.55 (d, J=8.8 Hz, 2H), 7.20 (d, J=8.9 Hz, 4H), 4.66 (dd, J=12.3, 5.3 Hz, 1H), 4.55 (dd, J=11.0, 5.5 Hz, 1H), 3.81-3.67 (m, 1H), 2.82-2.70 (m, 1H), 2.63 (t, J=11.8 Hz, 1H), 2.41 (br. s., 1H), 2.20 (br. s., 1H), 1.92 (d, J=14.0 Hz, 2H), 1.83-1.64 (m, 2H), 1.51-1.35 (m, 6H), 1.32 (s, 9H).

Example 790

(1r,4r)-4-(9b-((4-chlorophenyl)sulfonyl)-7-(perfluoropropyl)-2,3,3a,4,5,9b-hexahydro-1H-benzo[e]indole-3-carbonyl)cyclohexane-1-carboxylic Acid

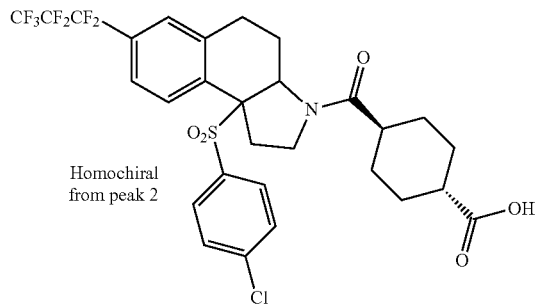

Homochiral from peak 2

Step A: Methyl (1r,4r)-4-(9b-((4-chlorophenyl)sulfonyl)-7-iodo-2,3,3a4,5,9b-hexahydro-1H-benzo[e]indole-3-carbonyl)cyclohexane-1-carboxylate

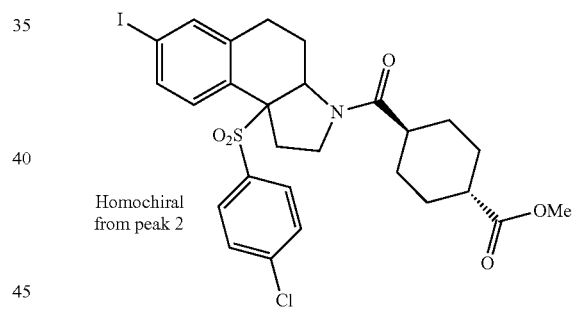

Homochiral from peak 2

A solution of crude 9b-((4-chlorophenyl)sulfonyl)-7-iodo-2,3,3a,4,5,9b-hexahydro-1H-benzo[e]indole hydrochloride (Intermediate 63, prepared from 0.25 g of homochiral tert-butyl 9b-((4-chlorophenyl)sulfonyl)-7-iodo-3a,4,5,9b-tetrahydro-1H-benzo[e]indole-3-carboxylate) in THF (1 mL) was treated with (1r,4r)-4-(methoxycarbonyl)cyclohexanecarboxylic acid (0.097 g, 0.523 mmol), PyBOP (0.272 g, 0.523 mmol) and Et$_3$N (0.304 mL, 2.178 mmol). The mixture was stirred at rt for 1 h, then was diluted with EtOAc, washed sequentially with 1.5 M aqueous K$_2$HPO$_4$, water and brine and concentrated to provide crude methyl (1r,4r)-4-(9b-((4-chlorophenyl)sulfonyl)-7-iodo-2,3,3a,4,5,9b-hexahydro-1H-benzo[e]indole-3-carbonyl)cyclohexane-1-carboxylate as a light yellow solid (430 mg, >100% yield) which was used without further purification. LCMS m/z 642.0 (M+H)$^+$, HPLC $t_R$ 1.14 min (method B).

Step B: (1r,4r)-4-(9b-((4-chlorophenyl)sulfonyl)-7-(perfluoropropyl)-2,3,3a,4,5,9b-hexahydro-1H-benzo[e]indole-3-carbonyl)cyclohexane-1-carboxylic Acid

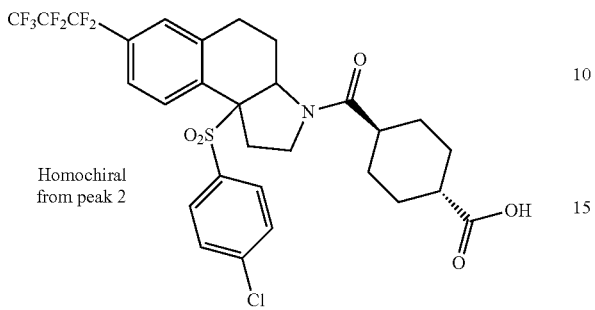

Homochiral from peak 2

A sample of wet activated copper (prepared according to the procedure in Step A of Intermediate 2; 150 mg) was washed by decantation twice with MeOH, then twice with dry DMF. This was combined with (1r,4r)-methyl 4-(-9b-((4-chlorophenyl)sulfonyl)-7-iodo-2,3,3a,4,5,9b-hexahydro-1H-benzo[e]indole-3-carbonyl)cyclohexanecarboxylate (30 mg, 0.047 mmol) and DMF (1 mL). The mixture was sonicated for 1 min, treated with 1,1,1,2,2,3,3-heptafluoro-3-iodopropane (69.1 mg, 0.237 mmol), and heated at 120° C. After 7 h, the mixture was cooled to rt, filtered and concentrated. The residue was dissolved in THF (1 mL) and treated with a solution of LiOH hydrate (22.38 mg, 0.935 mmol) in water (0.2 mL) and the mixture was heated at 60° C. After 1 h, the mixture was cooled to rt, acidified with 1 M aqueous HCl, concentrated, diluted with DMF and purified by preparative HPLC (method E, gradient 30-80% B, 20 min) to provide (1r,4r)-4-(9b-((4-chlorophenyl)sulfonyl)-7-(perfluoropropyl)-2,3,3a,4,5,9b-hexahydro-1H-benzo[e]indole-3-carbonyl)cyclohexane-1-carboxylic acid (14.4 mg, 46% yield). LCMS m/z 670.3 (M+H)$^+$, HPLC t$_R$ 1.07 min (method B).

Example 791

(1r,4r)-4-(9b-((4-chlorophenyl)sulfonyl)-7-(1,1,2,2-tetrafluoroethyl)-2,3,3a,4,5,9b-hexahydro-1H-benzo[e]indole-3-carbonyl)cyclohexane-1-carboxylic Acid

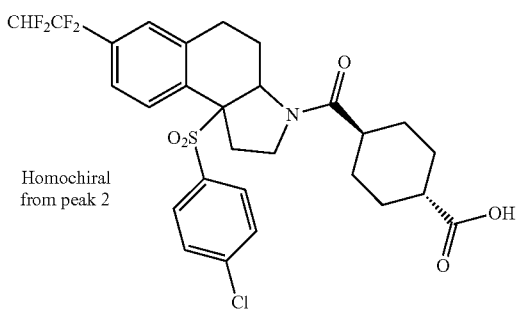

Homochiral from peak 2

Following the procedure used to prepare Example 790 but substituting 1,1,2,2-tetrafluoro-1-iodoethane for 1,1,1,2,2,3,3-heptafluoro-3-iodopropane in Step B, (1r,4r)-methyl 4-(-9b-((4-chlorophenyl)sulfonyl)-7-iodo-2,3,3a,4,5,9b-hexahydro-1H-benzo[e]indole-3-carbonyl)cyclohexanecarboxylate (30 mg, 0.047 mmol) was converted to (1r,4r)-4-(9b-((4-chlorophenyl)sulfonyl)-7-(1,1,2,2-tetrafluoroethyl)-2,3,3a,4,5,9b-hexahydro-1H-benzo[e]indole-3-carbonyl)cyclohexane-1-carboxylic acid (8.8 mg, 31% yield). LCMS m/z 602.1 (M+H)$^+$, HPLC t$_R$ 0.99 min (method B).

Example 792

4-(9b-((4-cyanophenyl)sulfonyl)-7-(perfluoropropan-2-yl)-2,3,3a,4,5,9b-hexahydro-1H-benzo[e]indole-3-carbonyl)bicyclo[2.2.2]octane-1-carboxylic Acid

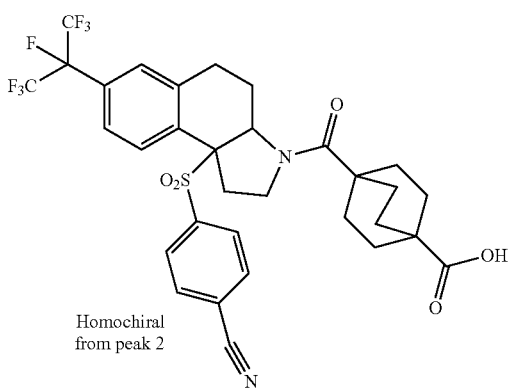 [SMILES: N#Cc1ccc(S(=O)(=O)C23CCN(C(=O)C45CCC(C(=O)O)(CC4)CC5)C2CCc2cc(C(F)(C(F)(F)F)C(F)(F)F)ccc23)cc1]

Homochiral from peak 2

Step A: Methyl 4-(9b-((4-bromophenyl)sulfonyl)-7-(perfluoropropan-2-yl)-2,3,3a,4,5,9b-hexahydro-1H-benzo[e]indole-3-carbonyl)bicyclo[2.2.2]octane-1-carboxylate

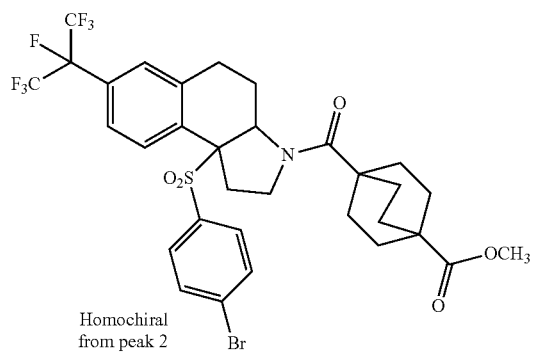 [SMILES: COC(=O)C12CCC(C(=O)N3CCC4(S(=O)(=O)c5ccc(Br)cc5)c5ccc(C(F)(C(F)(F)F)C(F)(F)F)cc5CCC34)(CC1)CC2]

Homochiral from peak 2

A solution of crude 9b-((4-bromophenyl)sulfonyl)-7-(perfluoropropan-2-yl)-2,3,3a,4,5,9b-hexahydro-1H-benzo[e]indole hydrochloride (homochiral, from peak 2, Intermediate 67, prepared from 120 mg of tert-butyl 9b-((4-bromophenyl)sulfonyl)-7-(perfluoropropan-2-yl)-3a,4,5,9b-tetrahydro-1H-benzo[e]indole-3-carboxylate) in THF (2 mL) was treated with 4-(methoxycarbonyl)bicyclo[2.2.2]octane-1-carboxylic acid (77 mg, 0.363 mmol), PyBOP (113 mg, 0.218 mmol) and DIPEA (0.063 mL, 0.363 mmol). The mixture was heated at 80° C. for 3 h, then was cooled to rt, diluted with EtOAc, washed sequentially with 1.5 M aqueous K$_2$HPO$_4$, water and brine, dried and concentrated. The residue was purified by column chromatography on silica gel, eluting with EtOAc-hexanes (gradient from 0-60%), to provide methyl 4-(9b-((4-bromophenyl)sulfonyl)-7-(perfluoropropan-2-yl)-2,3,3a,4,5,9b-hexahydro-1H-benzo[e]indole-3-carbonyl)bicyclo[2.2.2]octane-1-carboxylate (120 mg, 88%). LCMS m/z 754.5 (M+H)$^+$, HPLC $t_R$ 1.18 min (method B).

Step B: methyl 4-(9b-((4-cyanophenyl)sulfonyl)-7-(perfluoropropan-2-yl)-2,3,3a,4,5,9b-hexahydro-1H-benzo[e]indole-3-carbonyl)bicyclo[2.2.2]octane-1-carboxylate

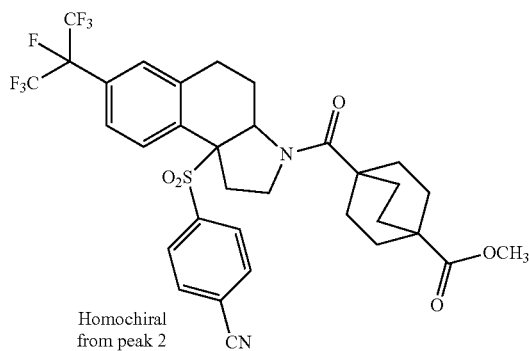 [SMILES: COC(=O)C12CCC(C(=O)N3CCC4(S(=O)(=O)c5ccc(C#N)cc5)c5ccc(C(F)(C(F)(F)F)C(F)(F)F)cc5CCC34)(CC1)CC2]

A mixture of methyl 4-(9b-((4-bromophenyl)sulfonyl)-7-(perfluoropropan-2-yl)-2,3,3a,4,5,9b-hexahydro-1H-benzo[e]indole-3-carbonyl)bicyclo[2.2.2]octane-1-carboxylate (20 mg, 0.027 mmol), zinc cyanide (3 mg, 0.027 mmol) and tetrakis(triphenylphosphine)palladium (3 mg, 2.7 µmol) in DMF (1 mL) was subjected to three evacuate-fill cycles with nitrogen. The mixture was heated at 120° C. for 30 min, then was cooled to rt. The mixture was partitioned between EtOAc and brine, and the organic phase was dried over Na$_2$SO$_4$ and concentrated to provide crude methyl 4-(9b-((4-cyanophenyl)sulfonyl)-7-(perfluoropropan-2-yl)-2,3,3a,4,5,9b-hexahydro-1H-benzo[e]indole-3-carbonyl)bicyclo[2.2.2]octane-1-carboxylate which was used without further purification. LCMS m/z 701.2 (M+H)$^+$, HPLC $t_R$ 1.17 min (method B).

Step C: 4-(9b-((4-cyanophenyl)sulfonyl)-7-(perfluoropropan-2-yl)-2,3,3a,4,5,9b-hexahydro-1H-benzo[e]indole-3-carbonyl)bicyclo[2.2.2]octane-1-carboxylic Acid

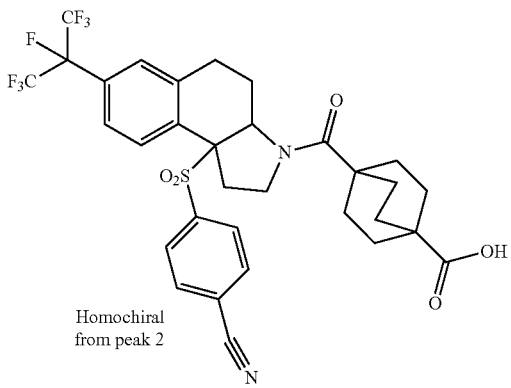 [SMILES: N#Cc1ccc(S(=O)(=O)C23CCN(C(=O)C45CCC(C(=O)O)(CC4)CC5)C2CCc2cc(C(F)(C(F)(F)F)C(F)(F)F)ccc23)cc1]

A solution of the crude methyl 4-(9b-((4-cyanophenyl)sulfonyl)-7-(perfluoropropan-2-yl)-2,3,3a,4,5,9b-hexahydro-1H-benzo[e]indole-3-carbonyl)bicyclo[2.2.2]octane-1-carboxylate (from Step B) in THF (1 mL) and water (0.1 mL) was treated with LiOH hydrate (6.35 mg, 0.265 mmol) and heated at 50° C. overnight. The mixture was cooled to rt, acidified with 1 M aqueous HCl, and extracted with EtOAc. The organic phase was washed with water, dried over Na$_2$SO$_4$ and concentrated. The residue was purified by preparative HPLC (method E, gradient 30-70% B, 20 min) to provide 4-(9b-((4-cyanophenyl)sulfonyl)-7-(perfluoropropan-2-yl)-2,3,3a,4,5,9b-hexahydro-1H-benzo[e]indole-3-carbonyl)bicyclo[2.2.2]octane-1-carboxylic acid (3.1 mg, 17% yield). LCMS m/z 687.2 (M+H)$^+$, HPLC $t_R$ 1.98 min (method C). $^1$H NMR (500 MHz, DMSO-d$_6$) δ 7.91 (d, J=8.2 Hz, 2H), 7.87 (d, J=8.5 Hz, 1H), 7.63 (d, J=8.3 Hz, 1H), 7.49 (d, J=8.2 Hz, 2H), 7.35 (s, 1H), 4.85 (dd, J=11.5, 4.8 Hz, 1H), 4.00-3.86 (m, 1H), 3.71 (br. s., 1H), 3.35 (br. s., 1H), 2.76-2.59 (m, 2H), 2.21 (d, J=8.8 Hz, 1H), 1.95 (t, J=14.6 Hz, 1H), 1.79-1.51 (m, 12H), 1.30-1.12 (m, 1H).

Example 793

4-(9b-((4-(dimethylamino)phenyl)sulfonyl)-7-(perfluoropropan-2-yl)-2,3,3a,4,5,9b-hexahydro-1H-benzo[e]indole-3-carbonyl)bicyclo[2.2.2]octane-1-carboxylic Acid

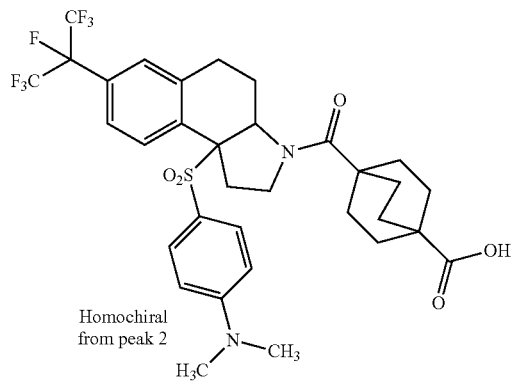 [SMILES: CN(C)c1ccc(S(=O)(=O)C23CCN(C(=O)C45CCC(C(=O)O)(CC4)CC5)C2CCc2cc(C(F)(C(F)(F)F)C(F)(F)F)ccc23)cc1]

A mixture of homochiral methyl 4-(9b-((4-bromophenyl)sulfonyl)-7-(perfluoropropan-2-yl)-2,3,3a,4,5,9b-hexahydro-1H-benzo[e]indole-3-carbonyl)bicyclo[2.2.2]octane-1-carboxylate (Example 792 Step A; 20 mg, 0.027 mmol), BINAP (8 mg, 0.013 mmol), sodium tert-butoxide (5 mg, 0.053 mmol) and tris(dibenzylideneacetone)dipalladium (4.9 mg, 5.3 µmol) in toluene (1 mL) was subjected to three evacuate-fill cycles with nitrogen. Dimethylamine (0.066 mL, 0.13 mmol) was added and the mixture was heated in a sealed vessel at 100° C. for 2 h. The mixture was cooled to rt and partitioned between EtOAc and brine. The organic phase was dried over Na$_2$SO$_4$ and concentrated, and the residue was purified by preparative HPLC (method E, gradient 30-80% B, 20 min) to provide 4-(9b-((4-(dimethylamino)phenyl)sulfonyl)-7-(perfluoropropan-2-yl)-2,3,3a,4,5,9b-hexahydro-1H-benzo[e]indole-3-carbonyl)bicyclo[2.2.2]octane-1-carboxylic acid (1.9 mg, 10% yield). LCMS m/z 705.2 (M+H)$^+$, HPLC $t_R$ 2.31 min (method C). $^1$H NMR (500 MHz, DMSO-d$_6$) δ 7.88 (d, J=8.5 Hz, 1H), 7.61 (d, J=8.3 Hz, 1H), 7.32 (br. s., 1H), 6.98 (d, J=8.0 Hz, 2H), 6.52 (d, J=8.7 Hz, 2H), 4.78 (dd, J=11.1, 4.8 Hz, 1H), 3.98-3.80

(m, 1H), 3.64 (br. s., 1H), 3.21 (br. s., 1H), 2.96 (s, 6H), 2.66-2.56 (m, 2H), 2.22 (m, 1H), 1.86 (t, J=13.7 Hz, 1H), 1.79-1.49 (m, 12H), 1.14 (m, 1H).

Example 794

(1r,4r)-4-(9b-((4-(isoxazol-4-yl)phenyl)sulfonyl)-7-(perfluoropropan-2-yl)-2,3a,4,5,9b-hexahydro-1H-benzo[e]indole-3-carbonyl)cyclohexane-1-carboxylic Acid

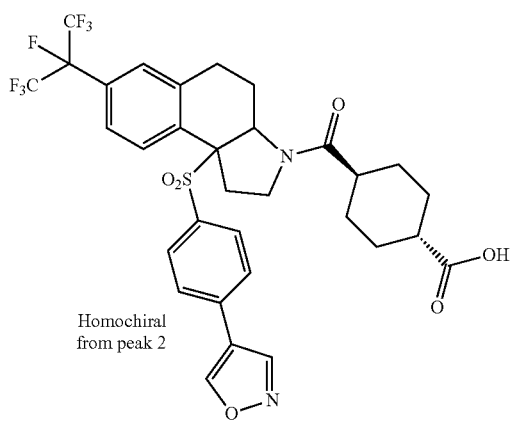 [SMILES: O=C(O)[C@H]1CC[C@H](C(=O)N2CCC3(S(=O)(=O)c4ccc(-c5cnoc5)cc4)c4ccc(C(F)(C(F)(F)F)C(F)(F)F)cc4CCC23)CC1]

Homochiral from peak 2

Step A: Methyl (1r,4r)-4-(9b-((4-chlorophenyl)sulfonyl)-7-(perfluoropropan-2-yl)-2,3,3a,4,5,9b-hexahydro-1H-benzo[e]indole-3-carbonyl)cyclohexanecarboxylate

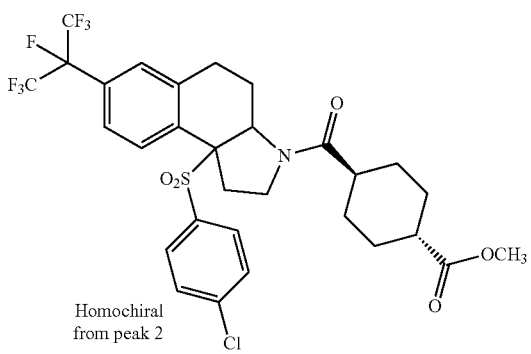 [SMILES: COC(=O)[C@H]1CC[C@H](C(=O)N2CCC3(S(=O)(=O)c4ccc(Cl)cc4)c4ccc(C(F)(C(F)(F)F)C(F)(F)F)cc4CCC23)CC1]

Homochiral from peak 2

Following the procedure of Example 790 Step A, 9b-((4-chlorophenyl)sulfonyl)-7-(perfluoropropan-2-yl)-2,3,3a,4,5,9b-hexahydro-1H-benzo[e]indole hydrochloride (homochiral, from peak 2, Intermediate 35) was converted into methyl (1r,4r)-4-(9b-((4-chlorophenyl)sulfonyl)-7-(perfluoropropan-2-yl)-2,3,3a,4,5,9b-hexahydro-1H-benzo[e]indole-3-carbonyl)cyclohexanecarboxylate, which was used without further purification. LCMS m/z 684.3 (M+H)$^+$, HPLC $t_R$ 1.13 (method B).

Step B: Methyl (1r,4r)-4-(9b-((4-(isoxazol-4-yl)phenyl)sulfonyl)-7-(perfluoropropan-2-yl)-2,3,3a,4,5,9b-hexahydro-1H-benzo[e]indole-3-carbonyl)cyclohexane-1-carboxylate

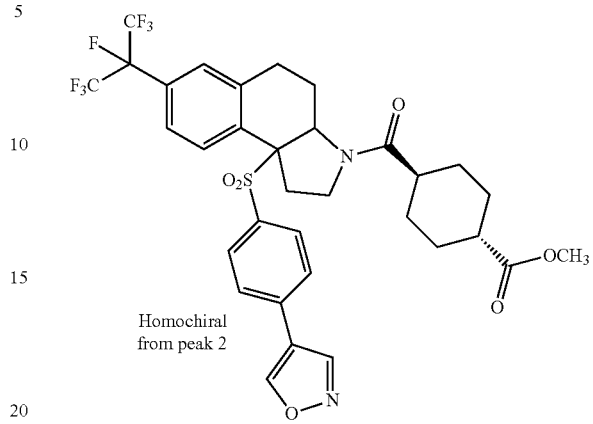

Homochiral from peak 2

A mixture of (1r,4r)-methyl 4-(9b-((4-chlorophenyl)sulfonyl)-7-(perfluoropropan-2-yl)-2,3,3a,4,5,9b-hexahydro-1H-benzo[e]indole-3-carbonyl)cyclohexanecarboxylate (40 mg, 0.058 mmol), 4-(4,4,5,5-tetramethyl-1,3,2-dioxaborolan-2-yl)isoxazole (23 mg, 0.12 mmol) and K$_3$PO$_4$ (0.088 mL, 0.18 mmol) in DMF (1 mL) was subjected to three evacuate-fill cycles with nitrogen. Chloro(2-dicyclohexylphosphino-2',4',6'-triisopropyl-1,1'-biphenyl)[2-(2'-amino-1,1'-biphenyl)]palladium(II) (second generation Xphos precatalyst; 2.3 mg, 2.9 µmol) was added and the mixture was again subjected to three evacuate-fill cycles with nitrogen. The mixture was heated at 110° C. for 3 h, then was cooled to rt and diluted with EtOAc. The solution was washed sequentially with 10% aqueous LiCl, water and brine, dried over Na$_2$SO$_4$ and to provide crude methyl (1r,4r)-4-(9b-((4-(isoxazol-4-yl)phenyl)sulfonyl)-7-(perfluoropropan-2-yl)-2,3,3a,4,5,9b-hexahydro-1H-benzo[e]indole-3-carbonyl)cyclohexane-1-carboxylate which was used without further purification. LCMS m/z 717.4 (M+H)$^+$, HPLC $t_R$ 1.02 min (method B).

Step C: (1r,4r)-4-(9b-((4-(isoxazol-4-yl)phenyl)sulfonyl)-7-(perfluoropropan-2-yl)-2,3,3a,4,5,9b-hexahydro-1H-benzo[e]indole-3-carbonyl)cyclohexane-1-carboxylic Acid

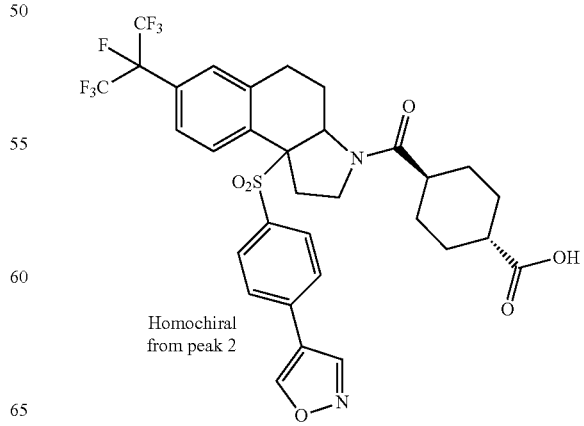

Homochiral from peak 2

A solution of crude methyl (1r,4r)-4-(9b-((4-(isoxazol-4-yl)phenyl)sulfonyl)-7-(perfluoropropan-2-yl)-2,3,3a,4,5,9b-hexahydro-1H-benzo[e]indole-3-carbonyl)cyclohexane-1-carboxylate (from Step B) in THF (1 mL) and water (0.2 mL) was treated with LiOH (14.0 mg, 0.585 mmol) and stirred at rt overnight. The mixture was acidified with 1 M aqueous HCl, and extracted twice with EtOAc. The combined organic phases were dried over Na$_2$SO$_4$ and concentrated. The residue was purified by preparative HPLC (method E, gradient 15-55% B, 20 min), then purified again by preparative HPLC (method E, gradient 20-45% B, 25 min) to provide (1r,4r)-4-(9b-((4-(isoxazol-4-yl)phenyl)sulfonyl)-7-(perfluoropropan-2-yl)-2,3,3a,4,5,9b-hexahydro-1H-benzo[e]indole-3-carbonyl)cyclohexane-1-carboxylic acid (2 mg, 4.6% yield). LCMS m/z 703.3 (M+H)$^+$, HPLC t$_R$ 0.95 min (method B).

Example 795

(1r,4r)-4-(9b-((4-(1H-pyrazol-4-yl)phenyl)sulfonyl)-7-(perfluoropropan-2-yl)-2,3,3a,4,5,9b-hexahydro-1H-benzo[e]indole-3-carbonyl)cyclohexane-1-carboxylic Acid

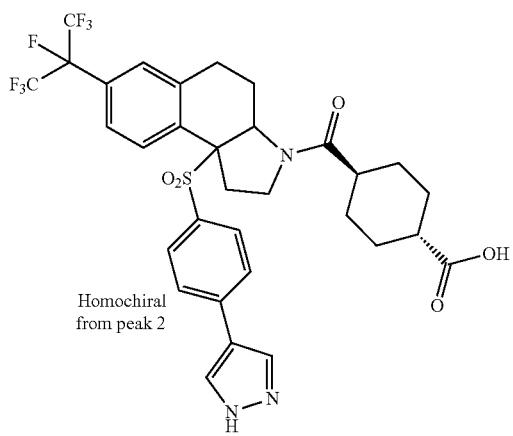 [SMILES: O=C(O)[C@H]1CC[C@H](C(=O)N2CCC3(S(=O)(=O)c4ccc(-c5cn[nH]c5)cc4)c4ccc(C(F)(C(F)(F)F)C(F)(F)F)cc4CCC23)CC1]

Following the procedures used to prepare Example 794, but substituting tert-butyl 4-(4,4,5,5-tetramethyl-1,3,2-dioxaborolan-2-yl)-1H-pyrazole-1-carboxylate in place of 4-(4,4,5,5-tetramethyl-1,3,2-dioxaborolan-2-yl)isoxazole in Step B, 9b-((4-chlorophenyl)sulfonyl)-7-(perfluoropropan-2-yl)-2,3,3a,4,5,9b-hexahydro-1H-benzo[e]indole hydrochloride (homochiral, from peak 2, Intermediate 35) was converted into (1r,4r)-4-(9b-((4-(1H-pyrazol-4-yl)phenyl)sulfonyl)-7-(perfluoropropan-2-yl)-2,3,3a,4,5,9b-hexahydro-1H-benzo[e]indole-3-carbonyl)cyclohexane-1-carboxylic acid after deprotection with TFA. LCMS m/z 702.4 (M+H)$^+$, HPLC t$_R$ 1.55 min (analytical HPLC condition C).

Example 796

(1r,4r)-4-(9b-((3-cyclopropylphenyl)sulfonyl)-7-(perfluoropropan-2-yl)-2,3,3a,4,5,9b-hexahydro-1H-benzo[e]indole-3-carbonyl)cyclohexane-1-carboxylic Acid

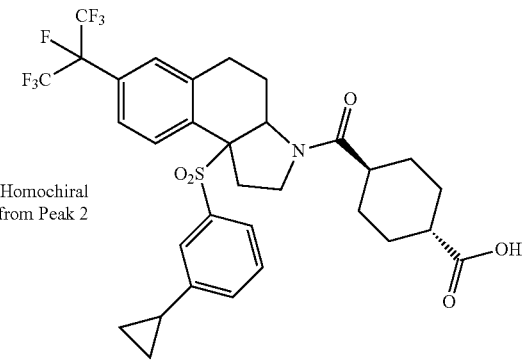 [SMILES: O=C(O)[C@H]1CC[C@H](C(=O)N2CCC3(S(=O)(=O)c4cccc(C5CC5)c4)c4ccc(C(F)(C(F)(F)F)C(F)(F)F)cc4CCC23)CC1]

Step A: Methyl (1r,4r)-4-(9b-((3-bromophenyl)sulfonyl)-7-(perfluoropropan-2-yl)-2,3,3a,4,5,9b-hexahydro-1H-benzo[e]indole-3-carbonyl)cyclohexane-1-carboxylate

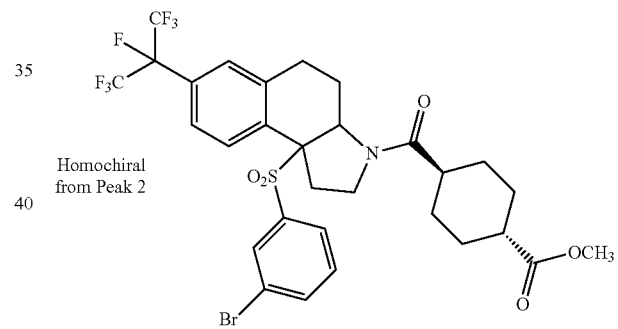

A solution of tert-butyl 9b-((3-bromophenyl)sulfonyl)-7-(perfluoropropan-2-yl)-3a,4,5,9b-tetrahydro-1H-benzo[e]indole-3-carboxylate (homochiral, from peak 2, Intermediate 75; 0.35 g, 0.530 mmol) in DCM (10 mL) was treated with TFA (6 mL, 78 mmol) and the mixture was stirred at rt for 1 h, then was concentrated. The residue was dissolved in DCM (50 mL) and the solution was washed with 1.5 M aqueous K$_2$HPO$_4$ (50 mL), dried over Na$_2$SO$_4$ and concentrated. The residue was dissolved in DCM (10 mL) and treated with DIPEA (0.294 mL, 1.681 mmol) and a solution of trans-methyl 4-(chlorocarbonyl)cyclohexane-1-carboxylate in DCM (2 mL), prepared from treatment of trans-1,4-cyclohexanedicarboxylic acid monomethyl ester (0.099 g, 0.530 mmol) with excess oxalyl chloride and a catalytic amount of DMF in DCM. The mixture was stirred at rt for 1.5 h, diluted with DCM (50 mL), washed with 1 M aqueous HCl and 1.5 M aqueous K$_2$HPO$_4$, dried over Na$_2$SO$_4$ and concentrated. The residue was purified by column chromatography on silica gel to give methyl (1r,4r)-4-(9b-((3-bromophenyl)sulfonyl)-7-(perfluoropropan-2-yl)-2,3,3a,4,5,9b-hexahydro-1H-benzo[e]indole-3-carbonyl)

cyclohexane-1-carboxylate as a yellow solid (365 mg, 95% yield). LCMS m/z 728.1 (M+H)+, HPLC $t_R$ 1.18 min (method B).

Step B: (1r,4r)-4-(9b-((3-cyclopropylphenyl)sulfonyl)-7-(perfluoropropan-2-yl)-2,3,3a,4,5,9b-hexahydro-1H-benzo[e]indole-3-carbonyl)cyclohexane-1-carboxylic Acid

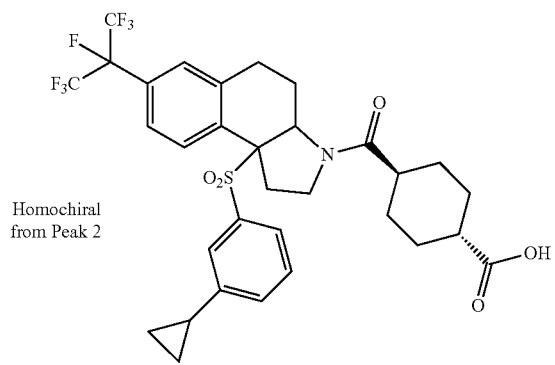 [SMILES: O=C(O)[C@H]1CC[C@H](C(=O)N2CCC3(S(=O)(=O)c4cccc(C5CC5)c4)c4ccc(C(F)(C(F)(F)F)C(F)(F)F)cc4CCC23)CC1]

Homochiral from Peak 2

A mixture of methyl (1r,4r)-4-(9b-((3-bromophenyl)sulfonyl)-7-(perfluoropropan-2-yl)-2,3,3a,4,5,9b-hexahydro-1H-benzo[e]indole-3-carbonyl)cyclohexane-1-carboxylate (0.05 g, 0.069 mmol) and cyclopropylzinc bromide (0.5 M in THF; 0.138 mL, 0.069 mmol) in THF (0.572 ml) in a sealable vial was flushed with nitrogen and treated with tetrakis(triphenylphosphine)palladium (0.793 mg, 0.686 μmol). The vial was sealed and heated by microwave irradiation at 130° C. for 15 min. The cooled mixture was diluted with EtOAc (15 mL) and washed sequentially with 1 M aqueous HCl and brine. The organic phase was dried and concentrated, and the residue was treated with THF (3 mL), MeOH (1 mL) and a solution of LiOH monohydrate (0.058 g, 1.373 mmol) in water (1 mL) for 3 h. The mixture was diluted with EtOAc (8 mL), washed sequentially with 1 M aqueous HCl (6 mL) and brine (6 mL), dried over $Na_2SO_4$ and concentrated. The residue was purified by preparative HPLC (method E, gradient 30-90% B, 20 min, followed by method F, gradient 45-90% F, 20 min) to provide (1r,4r)-4-(9b-((3-cyclopropylphenyl)sulfonyl)-7-(perfluoropropan-2-yl)-2,3,3a,4,5,9b-hexahydro-1H-benzo[e]indole-3-carbonyl)cyclohexane-1-carboxylic acid (13 mg, 26% yield). LCMS m/z 676.1 (M+H)+, HPLC $t_R$ 2.01 min (method C). $^1$H NMR (500 MHz, DMSO-$d_6$) δ 7.91-7.81 (m, 1H), 7.63 (d, J=8.0 Hz, 1H), 7.43-7.25 (m, 3H), 7.16 (d, J=7.3 Hz, 1H), 6.83 (s, 1H), 4.65 (dd, J=11.7, 4.8 Hz, 1H), 3.80-3.08 (m, 2H), 2.63 (d, J=12.3 Hz, 3H), 2.40-1.09 (m, 14H), 0.93 (d, J=6.6 Hz, 2H), 0.67-0.38 (m, 2H).

The Examples in Table 15 were prepared using procedures used to prepare Example 796, using the appropriate organozinc reagent in place of cyclopropylzinc bromide.

TABLE 15

| Ex. # | Structure | LCMS m/z observed | HPLC $t_R$ (min) | HPLC method |
|---|---|---|---|---|
| 797 | Homochiral from Peak 2 | 678.5 (M + H)+ | 2.42 | D |
| 798 | Homochiral from Peak 2 | 692.3 (M + H)+ | 2.43 | D |

Example 799

(1R,4r)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-4-methylcyclohexanecarboxamide

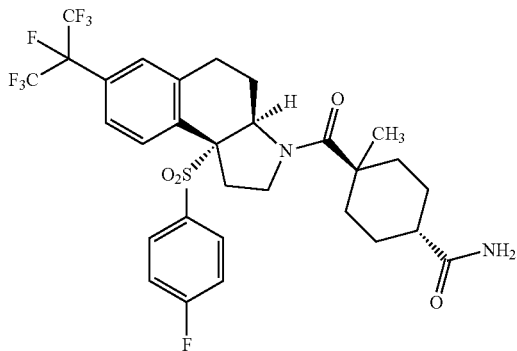 [SMILES: C[C@]1(C(=O)N2CC[C@@]3(S(=O)(=O)c4ccc(F)cc4)c4ccc(C(F)(C(F)(F)F)C(F)(F)F)cc4CC[C@@H]23)CC[C@H](C(N)=O)CC1]

A solution of (1R,4r)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-4-methylcyclohexanecarboxylic acid (Example 66; 33 mg, 0.049 mmol) in DMF (1 mL) was treated with BOP (32.8 mg, 0.074 mmol) and stirred at rt for 10 min. The mixture was then treated with aqueous NH$_4$OH (0.5 mL, 12.84 mmol). After 30 min, the mixture was diluted with EtOAc and washed sequentially with 10% aqueous LiCl (twice) and brine. The combined aqueous layers were extracted with EtOAc, and the combined organic layers were dried over Na$_2$SO$_4$ and concentrated. The residue was purified by preparative HPLC (method F, gradient 40-80% B, 19 min) to afford (1R,4r)-4-((3 aR,9bR)-9b-((4-fluorophenyl)sulfonyl)-7-(perfluoropropan-2-yl)-2,3,3a,4,5,9b-hexahydro-1H-benzo[e]indole-3-carbonyl)-4-methylcyclohexanecarboxamide (10.3 mg, 31% yield). LCMS m/z 667.2 (M+H)$^+$, $t_R$ 2.22 min (method D). $^1$H NMR (500 MHz, DMSO-d$_6$) δ 7.88 (d, J=8.5 Hz, 1H), 7.63 (d, J=8.5 Hz, 1H), 7.35-7.30 (m, 3H), 7.28-7.23 (m, 2H), 7.19 (d, J=11.3 Hz, 1H), 6.67 (br. s., 1H), 4.88 (dd, J=11.6, 4.9 Hz, 1H), 4.00-3.92 (m, 1H), 3.74-3.67 (m, 1H), 2.72-2.62 (m, 2H), 2.23 (dt, J=7.8, 3.7 Hz, 1H), 2.08-2.00 (m, 1H), 1.90-1.81 (m, 1H), 1.71-1.51 (m, 9H), 1.28-1.19 (m, 1H), 1.13 (s, 3H).

The Examples in Table 16 were prepared using procedures used to prepare Example 799, using the appropriate acid as starting material.

TABLE 16

| Ex. # | Structure | LCMS m/z observed | HPLC $t_R$ (min) | HPLC method |
|---|---|---|---|---|
| 800 | 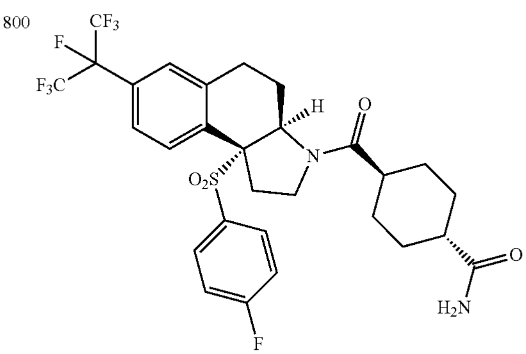 | 653.4 (M + H)$^+$ | 1.99 | C |
| 801 | 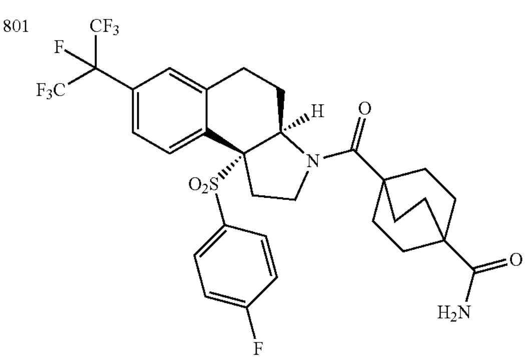 | 679.2 (M + H)$^+$ | 2.08 | C |

Example 802

(2-((3aR,9bR)-9b-((4-fluorophenyl)sulfonyl)-7-(per-fluoropropan-2-yl)-1,2,3a,4,5,9b-hexahydro-3H-benzo[e]indol-3-yl)acetyl)glycine

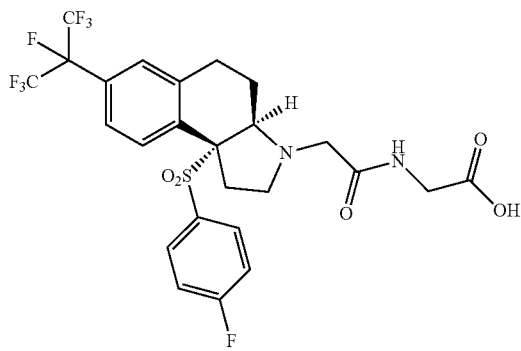 [SMILES: O=C(O)CNC(=O)CN1CC[C@@]2(S(=O)(=O)c3ccc(F)cc3)c3ccc(C(F)(C(F)(F)F)C(F)(F)F)cc3CC[C@@H]12]

A solution of 2-((3aR,9bR)-9b-((4-fluorophenyl)sulfonyl)-7-(perfluoropropan-2-yl)-4,5-dihydro-1H-benzo[e]indol-3-yl)acetic acid (Example 730, as the TFA salt; 75 mg, 0.112 mmol) in DMF (1 mL) was treated with 1-hydroxybenzotriazole (25.7 mg, 0.168 mmol), N-(3-dimethylaminopropyl)-N-ethylcarbodiimide (32.1 mg, 0.168 mmol), and tert-butyl 2-aminoacetate hydrochloride (28.1 mg, 0.168 mmol). The mixture was stirred overnight, then was diluted with EtOAc and brine. The organic layer was separated and washed sequentially with brine (3×) and saturated aqueous NaHCO$_3$, dried over MgSO$_4$, filtered, and concentrated to give crude tert-butyl (2-((3aR,9bR)-9b-((4-fluorophenyl)sulfonyl)-7-(perfluoropropan-2-yl)-1,2,3a,4,5,9b-hexahydro-3H-benzo[e]indol-3-yl)acetyl)glycinate (110 mg, >100% yield), used without purification. LCMS m/z 671.3 (M+H)$^+$, HPLC t$_R$ 0.98 min (method B). A portion of this material (40 mg) was dissolved in DCM (1 mL), treated with TFA (2 mL) and stirred at rt. After 4 h, the solution was concentrated and the residue was purified by preparative HPLC (method E, gradient 17-57% B, 25 min) to provide (2-((3aR,9bR)-9b-((4-fluorophenyl)sulfonyl)-7-(perfluoropropan-2-yl)-1,2,3a,4,5,9b-hexahydro-3H-benzo[e]indol-3-yl)acetyl)glycine (2.9 mg, 7% yield). LCMS m/z 615.1 (M+H)$^+$, t$_R$ 1.72 min (method C). $^1$H NMR (500 MHz, DMSO-d$_6$) δ 8.06 (br. s., 1H), 7.52 (s, 2H), 7.40-7.30 (m, 3H), 7.30-7.20 (m, 2H), 3.83-3.62 (m, 2H), 3.23-3.09 (m, 2H), 3.03 (d, J=16.2 Hz, 1H), 2.75-2.58 (m, 2H), 2.45-2.30 (m, 1H), 2.12 (br. s., 1H), 2.00-1.85 (m, 1H), 1.41-1.25 (m, 1H), 2 protons obscured by solvent peak.

Example 803

1-((1R,3s,5S)-3-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-8-azabicyclo[3.2.1]octan-8-yl)ethan-1-one

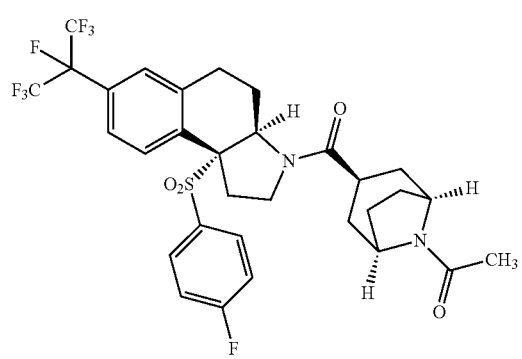 [SMILES: CC(=O)N1[C@@H]2CC[C@H]1C[C@H](C(=O)N1CC[C@@]3(S(=O)(=O)c4ccc(F)cc4)c4ccc(C(F)(C(F)(F)F)C(F)(F)F)cc4CC[C@@H]13)C2]

Step A: ((1R,3s,5S)-8-azabicyclo[3.2.1]octan-3-yl)((3aR,9bR)-9b-((4-fluorophenyl)sulfonyl)-7-(perfluoropropan-2-yl)-1,2,3a,4,5,9b-hexahydro-3H-benzo[e]indol-3-yl)methanone

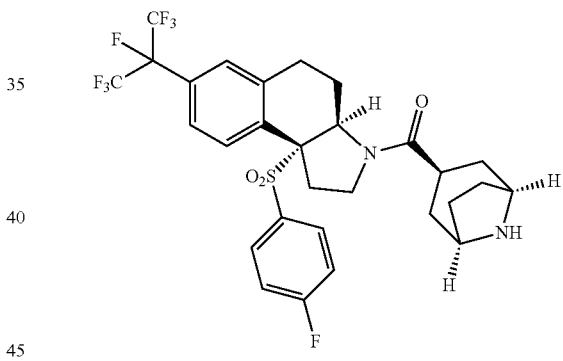

A mixture of (3aR,9bR)-9b-((4-fluorophenyl)sulfonyl)-7-(perfluoropropan-2-yl)-2,3,3a,4,5,9b-hexahydro-1H-benzo[e]indole (Intermediate 32; 80 mg, 0.160 mmol), (1R,3s,5S)-8-(tert-butoxycarbonyl)-8-azabicyclo[3.2.1]octane-3-carboxylic acid (40.9 mg, 0.160 mmol), DIPEA (0.084 mL, 0.481 mmol) and DMF (2 mL) was treated with 2,4,6-tripropyl-1,3,5,2,4,6-trioxatriphosphorinane-2,4,6-trioxide (50% in DMF; 0.150 mL, 0.240 mmol) and stirred at rt for 30 min. The mixture was diluted with EtOAc (20 mL), washed sequentially with 1 M aqueous HCl and brine, dried over Na$_2$SO$_4$ and concentrated. The residue was dissolved in DCM (2 mL), treated with TFA (1 mL) and the mixture was stirred at rt for 1 h. The mixture was concentrated and the residue was dissolved in DCM (20 mL), washed with 1.5 M aqueous K$_2$HPO$_4$ (2×10 mL), dried over Na$_2$SO$_4$ and concentrated to give crude ((1R,3s,5S)-8-azabicyclo[3.2.1]octan-3-yl)((3aR,9bR)-9b-((4-fluorophenyl)sulfonyl)-7-(perfluoropropan-2-yl)-1,2,3a,4,5,9b-hexahydro-3H-benzo[e]indol-3-yl)methanone, used without further purification. LCMS m/z 637.2 (M+H)$^+$, HPLC t$_R$ 0.96 min (method B).

Step B: 1-((1R,3s,5S)-3-((3aR,9bR)-9b-((4-fluorophenyl)sulfonyl)-7-(perfluoropropan-2-yl)-2,3,3a,4,5,9b-hexahydro-H-benzo[e]indole-3-carbonyl)-8-azabicyclo[3.2.1]octan-8-yl)ethan-1-one Step A: ((3aR,9bR)-9b-((4-fluorophenyl)sulfonyl)-7-(perfluoropropan-2-yl)-1,2,3a,4,5,9b-hexahydro-3H-benzo[e]indol-3-yl)(4-methylpiperidin-4-yl)methanone Hydrochloride

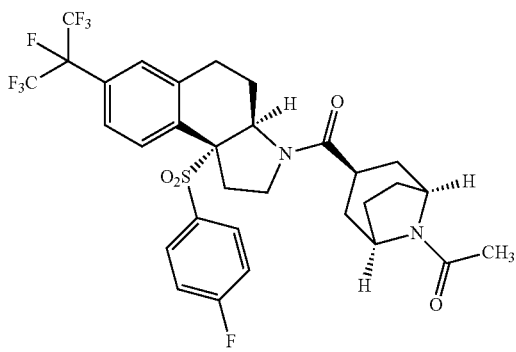 [SMILES: CC(=O)N1[C@@H]2CC[C@H]1C[C@H](C(=O)N1CC[C@@]3(S(=O)(=O)c4ccc(F)cc4)c4ccc(C(F)(C(F)(F)F)C(F)(F)F)cc4CC[C@@H]13)C2]

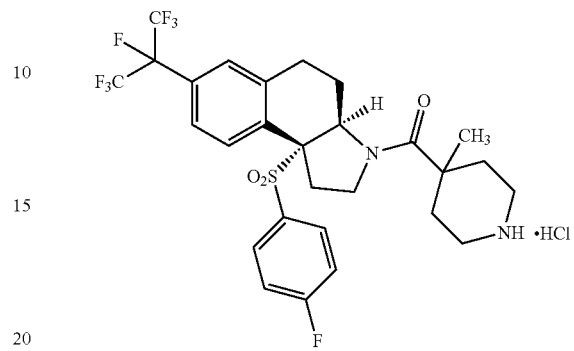

A solution of crude ((1R,3s,5S)-8-azabicyclo[3.2.1]octan-3-yl)((3aR,9bR)-9b-((4-fluorophenyl)sulfonyl)-7-(perfluoropropan-2-yl)-1,2,3a,4,5,9b-hexahydro-3H-benzo[e]indol-3-yl)methanone (50 mg, 0.079 mmol) in DCM (1 mL) and pyridine (0.5 mL) was treated dropwise with acetyl chloride (1 M in DCM; 0.314 mL, 0.314 mmol) and the mixture was stirred at rt for 30 min. The mixture was diluted with DCM (15 mL), washed sequentially with 1 M aqueous HCl (2×10 mL) and brine (10 mL), dried and concentrated. The residue was purified by preparative HPLC (method E, gradient 40-80% B, 25 min, then method F, gradient 47-72% B, 25 min) to provide 1-((1R,3s,5S)-3-((3 aR,9bR)-9b-((4-fluorophenyl)sulfonyl)-7-(perfluoropropan-2-yl)-2,3,3a,4,5,9b-hexahydro-1H-benzo[e]indole-3-carbonyl)-8-azabicyclo[3.2.1]octan-8-yl)ethan-1-one (17 mg, 32% yield). LCMS m/z 679.2 (M+H)$^+$, HPLC $t_R$ 2.11 (method D).

A mixture of (3aR,9bR)-9b-((4-fluorophenyl)sulfonyl)-7-(perfluoropropan-2-yl)-2,3,3a,4,5,9b-hexahydro-1H-benzo[e]indole hydrochloride (Intermediate 32; 25 mg, 0.047 mmol), 1-(tert-butoxycarbonyl)-4-methylpiperidine-4-carboxylic acid (13.62 mg, 0.056 mmol) and DIPEA (0.024 mL, 0.140 mmol) in DMF (1 mL) was treated with HATU (21.29 mg, 0.056 mmol) and stirred at rt for 5 h. The mixture was diluted with EtOAc and washed sequentially with 10% aqueous LiCl (twice) and brine. The combined aqueous phases were extracted with EtOAc, and the combined organic phases were dried over MgSO$_4$ and concentrated. The residue was dissolved in HCl (4 M in 1,4-dioxane; 1 mL, 4.00 mmol) and stirred at rt overnight. The solution was concentrated to provide crude ((3aR,9bR)-9b-((4-fluorophenyl)sulfonyl)-7-(perfluoropropan-2-yl)-1,2,3a,4,5,9b-hexahydro-3H-benzo[e]indol-3-yl)(4-methylpiperidin-4-yl)methanone hydrochloride (31.1 mg), used without further purification. LCMS m/z 625.1 (M+H)$^+$, HPLC $t_R$ 0.91 min (method B).

Example 804

((3aR,9bR)-9b-((4-fluorophenyl)sulfonyl)-7-(perfluoropropan-2-yl)-1,2,3a,4,5,9b-hexahydro-3H-benzo[e]indol-3-yl)(4-methyl-1-(methylsulfonyl)piperidin-4-yl)methanone Step B: ((3aR,9bR)-9b-((4-fluorophenyl)sulfonyl)-7-(perfluoropropan-2-yl)-1,2,3a,4,5,9b-hexahydro-3H-benzo[e]indol-3-yl)(4-methyl-1-(methylsulfonyl)piperidin-4-yl)methanone

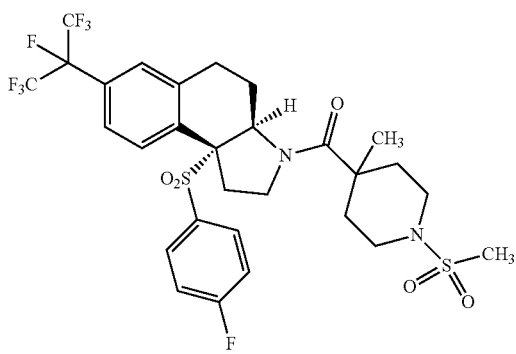 [SMILES: CC1(C(=O)N2CC[C@@]3(S(=O)(=O)c4ccc(F)cc4)c4ccc(C(F)(C(F)(F)F)C(F)(F)F)cc4CC[C@@H]23)CCN(S(C)(=O)=O)CC1]

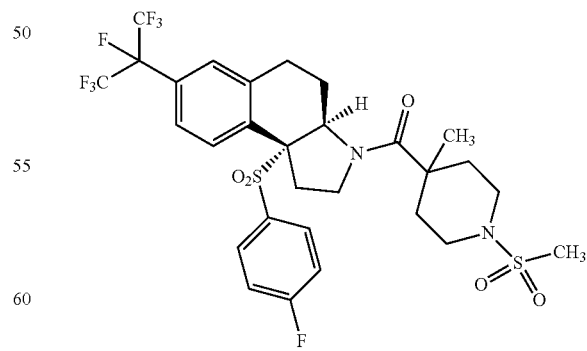

A solution of crude ((3aR,9bR)-9b-((4-fluorophenyl)sulfonyl)-7-(perfluoropropan-2-yl)-4,5-dihydro-1H-benzo[e]indol-3-yl)(4-methylpiperidin-4-yl)methanone hydrochloride (31.1 mg, 0.047 mmol) and Et$_3$N (0.033 mL, 0.235 mmol) in DCM (1 mL) was treated at rt with MsCl (7.33 μL, 0.094 mmol) and stirred overnight at rt. The mixture was concentrated and the residue was purified by preparative HPLC (method E, gradient 45-100%, 19 min) to provide ((3aR,9bR)-9b-((4-fluorophenyl)sulfonyl)-7-(perfluoropropan-2-yl)-4,5-dihydro-1H-benzo[e]indol-3-yl)(4-methyl-1-(methylsulfonyl)piperidin-4-yl)methanone (10.1 mg, 31% yield). LCMS m/z 703.0 (M+H)+, HPLC $t_R$ 2.33 min (method C). $^1$H NMR (500 MHz, DMSO-$d_6$) δ 7.87 (d, J=8.4 Hz, 1H), 7.63 (d, J=8.6 Hz, 1H), 7.33-7.28 (m, 3H), 7.26-7.21 (m, 2H), 4.90 (dd, J=11.5, 5.0 Hz, 1H), 3.98-3.90 (m, 1H), 3.38-3.31 (m, 1H), 3.30-3.24 (m, 2H), 3.02-2.93 (m, 1H), 2.88-2.81 (m, 1H), 2.80 (s, 3H), 2.73-2.64 (m, 2H), 2.62 (br. s., 1H), 2.25 (dd, J=8.2, 4.3 Hz, 1H), 2.18-2.11 (m, 2H), 1.87-1.78 (m, 1H), 1.55-1.44 (m, 2H), 1.30-1.20 (m, 1H), 1.15 (s, 3H).

The Examples in Table 17 were prepared using procedures used to prepare Examples 803 and 804 or similar procedures, using the appropriate amine and acid starting materials and appropriate acyl chloride, sulfonyl chloride or other reagent as appropriate.

TABLE 17

| Ex. # | Structure | LCMS m/z observed | HPLC $t_R$ (min) | HPLC method |
|---|---|---|---|---|
| 805 | 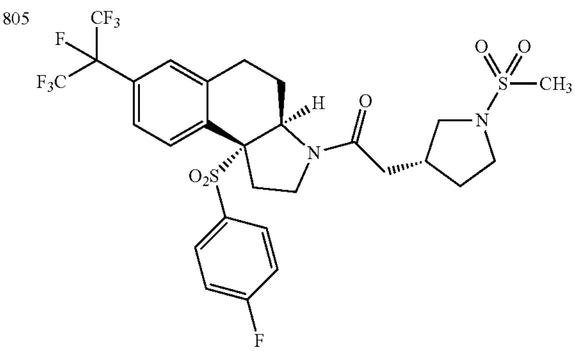 | 688.9 (M + H)+ | 2.22 | C |
| 806 | 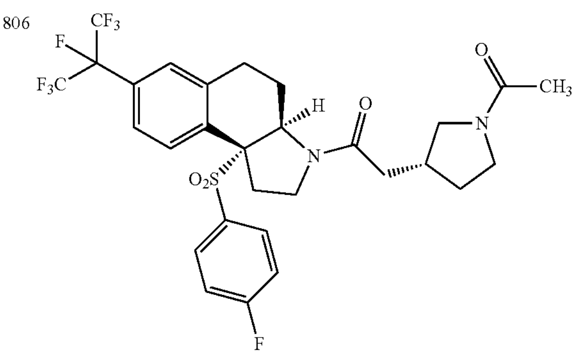 | 653.0 (M + H)+ | 2.05 | C |
| 807 | 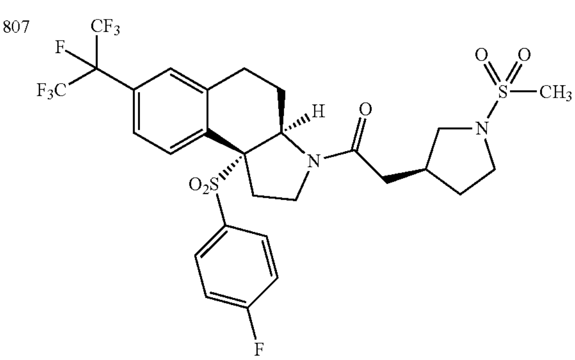 | 689.3 (M + H)+ | 2.18 | C |

TABLE 17-continued

| Ex. # | Structure | LCMS m/z observed | HPLC t$_R$ (min) | HPLC method |
|---|---|---|---|---|
| 808 | 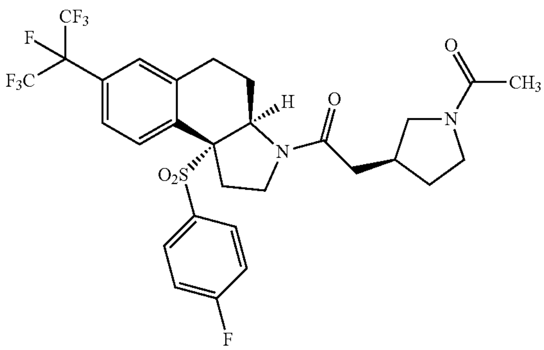 [SMILES: CC(=O)N1CC[C@@H](CC(=O)N2CC[C@@]3(S(=O)(=O)c4ccc(F)cc4)c4ccc(C(F)(C(F)(F)F)C(F)(F)F)cc4CC[C@@H]23)C1] | 652.9 (M + H)$^+$ | 2.09 | C |
| 809 | 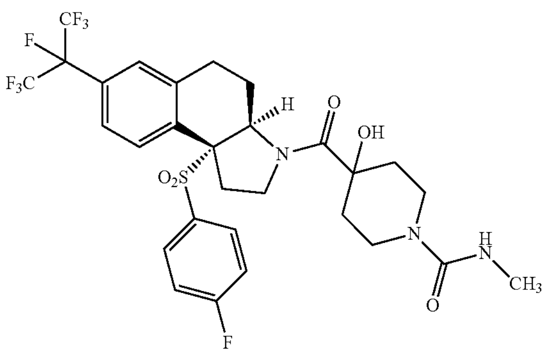 [SMILES: CNC(=O)N1CCC(O)(C(=O)N2CC[C@@]3(S(=O)(=O)c4ccc(F)cc4)c4ccc(C(F)(C(F)(F)F)C(F)(F)F)cc4CC[C@@H]23)CC1] | 684.2 (M + H)$^+$ | 2.03 | C |
| 810 | 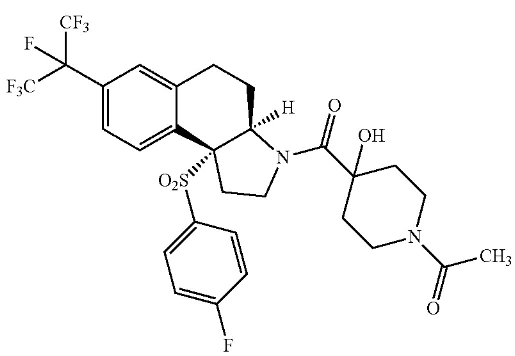 [SMILES: CC(=O)N1CCC(O)(C(=O)N2CC[C@@]3(S(=O)(=O)c4ccc(F)cc4)c4ccc(C(F)(C(F)(F)F)C(F)(F)F)cc4CC[C@@H]23)CC1] | 669.0 (M + H)$^+$ | 2.03 | C |
| 811 | 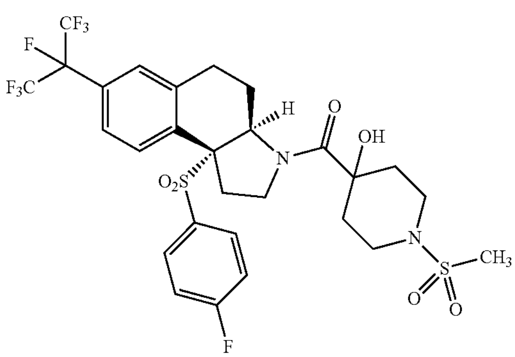 [SMILES: CS(=O)(=O)N1CCC(O)(C(=O)N2CC[C@@]3(S(=O)(=O)c4ccc(F)cc4)c4ccc(C(F)(C(F)(F)F)C(F)(F)F)cc4CC[C@@H]23)CC1] | 705.0 (M + H)$^+$ | 2.15 | C |

TABLE 17-continued

| Ex. # | Structure | LCMS m/z observed | HPLC $t_R$ (min) | HPLC method |
|---|---|---|---|---|
| 812 | 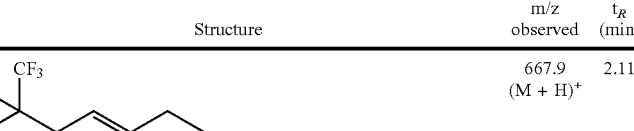 | 667.9 (M + H)+ | 2.11 | C |

Example 813

4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)piperidine-1-carbonitrile

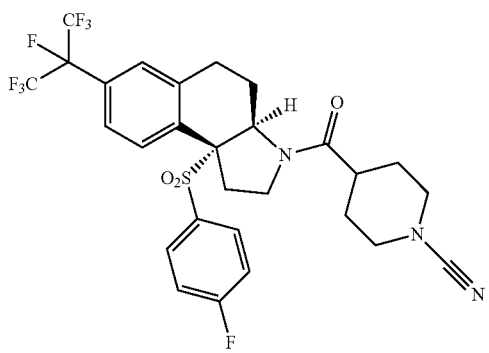 [SMILES: N#CN1CCC(C(=O)N2CC[C@@]3(S(=O)(=O)c4ccc(F)cc4)c4ccc(C(F)(C(F)(F)F)C(F)(F)F)cc4CC[C@@H]23)CC1]

Step A: ((3aR,9bR)-9b-((4-fluorophenyl)sulfonyl)-7-(perfluoropropan-2-yl)-1,2,3a,4,5,9b-hexahydro-3H-benzo[e]indol-3-yl)(piperidin-4-yl)methanone

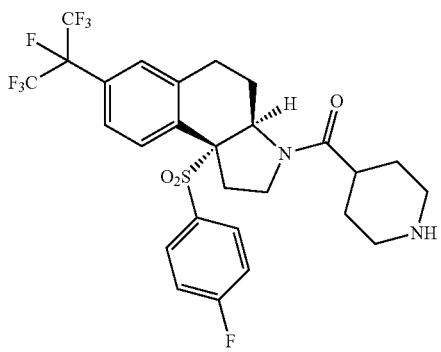 [SMILES: O=C(C1CCNCC1)N1CC[C@@]2(S(=O)(=O)c3ccc(F)cc3)c3ccc(C(F)(C(F)(F)F)C(F)(F)F)cc3CC[C@@H]12]

A solution of ((3aR,9bR)-9b-((4-fluorophenyl)sulfonyl)-7-(perfluoropropan-2-yl)-2,3,3a,4,5,9b-hexahydro-1H-benzo[e]indole hydrochloride (Intermediate 32; 30 mg, 0.060 mmol) in DCM (0.6 mL) was treated with 1-(tert-butoxycarbonyl)piperidine-4-carboxylic acid (27.5 mg, 0.120 mmol), DIPEA (31.5 µL, 0.180 mmol) and HATU (34.3 mg, 0.090 mmol). The mixture was stirred at rt for 1 h. The mixture was then treated with TFA (1 mL) and the mixture was stirred for 1 h more, then was concentrated. The residue was dissolved in EtOAc, washed twice with 1 M aqueous NaOH, dried over $Na_2SO_4$ and concentrated. to provide crude ((3aR,9bR)-9b-((4-fluorophenyl)sulfonyl)-7-(perfluoropropan-2-yl)-1,2,3a,4,5,9b-hexahydro-3H-benzo[e]indol-3-yl)(piperidin-4-yl)methanone trifluoroacetate, used without purification. LCMS m/z 611.1 (M+H)+, HPLC $t_R$ 0.91 min (method B).

Step B: 4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)piperidine-1-carbonitrile The crude ((3aR,9bR)-9b-((4-fluorophenyl)sulfonyl)-7-(perfluoropropan-2-yl)-1,2,3a,4,5,9b-hexahydro-3H-benzo[e]indol-3-yl)(piperidin-4-yl)methanone from step A was dissolved in DCM (2 mL) and treated with $Et_3N$ (0.033 mL, 0.240 mmol) and cyanogen bromide (12.73 mg, 0.120 mmol). After 1 h at rt, the mixture was concentrated and the residue was purified by preparative HPLC (method E, gradient 40-85% B, 25 min) to give 4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)piperidine-1-carbonitrile (9.6 mg, 25% yield). LCMS m/z 636.0 (M+H)+, HPLC $t_R$ 1.06 min (method B).

Example 814

((3aR,9bR)-9b-((4-fluorophenyl)sulfonyl)-7-(perfluoropropan-2-yl)-1,2,3a,4,5,9b-hexahydro-3H-benzo[e]indol-3-yl)(1-(oxetan-3-yl)piperidin-4-yl)methanone

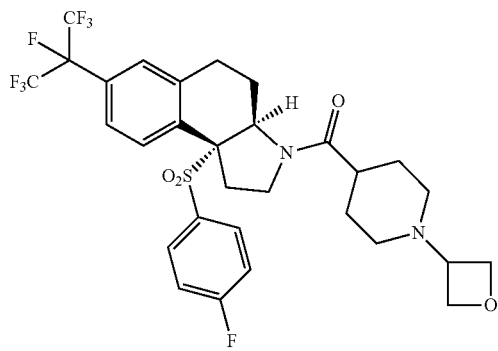 [SMILES: O=C(C1CCN(C2COC2)CC1)N1CC[C@@]2(S(=O)(=O)c3ccc(F)cc3)c3ccc(C(F)(C(F)(F)F)C(F)(F)F)cc3CC[C@@H]12]

Crude ((3 aR,9bR)-9b-((4-fluorophenyl)sulfonyl)-7-(perfluoropropan-2-yl)-1,2,3a,4,5,9b-hexahydro-3H-benzo[e]indol-3-yl)(piperidin-4-yl)methanone (Example 813 Step A; prepared from 40 mg of Intermediate 32) was dissolved in anhydrous MeOH (2 mL), treated with 3-oxetanone (28.9 mg, 0.400 mmol) and stirred at rt for 1 h. The mixture was then treated with sodium cyanoborohydride (20.13 mg, 0.320 mmol) and stirred at rt for 1 h. The mixture was treated with 1 M aqueous HCl (5 mL) and concentrated. The residue was partitioned between EtOAc (20 mL) and 1.5 M aqueous $K_2HPO_4$ (15 mL) and the organic phase was washed with brine and concentrated. The residue was purified by preparative HPLC (method E, gradient 40-80% B, 20 min) to give ((3aR,9bR)-9b-((4-fluorophenyl)sulfonyl)-7-(perfluoropropan-2-yl)-1,2,3a,4,5,9b-hexahydro-3H-benzo[e]indol-3-yl)(1-(oxetan-3-yl)piperidin-4-yl)methanone (7.5 mg, 13% yield). LCMS m/z 666.9 (M+H)$^+$, HPLC $t_R$ 1.82 min (method D).

The Examples in Table 18 were prepared using procedures used to prepare Example 814 or similar procedures.

TABLE 18

| Ex. # | Structure | LCMS m/z observed | HPLC $t_R$ (min) | HPLC method |
|---|---|---|---|---|
| 815 | 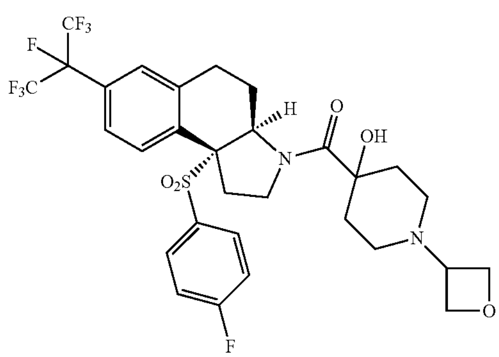 [SMILES: O=C(N1CC[C@@]2(S(=O)(=O)c3ccc(F)cc3)c3ccc(C(F)(C(F)(F)F)C(F)(F)F)cc3CC[C@@H]12)C1(O)CCN(C2COC2)CC1] | 683.3 (M + H)$^+$ | 1.77 | D |
| 816 Homochiral from peak 2 | | 683.3 (M + H)$^+$ | 2.06 | D |

TABLE 18-continued

| Ex. # | Structure | LCMS m/z observed | HPLC $t_R$ (min) | HPLC method |
|---|---|---|---|---|
| 817 | 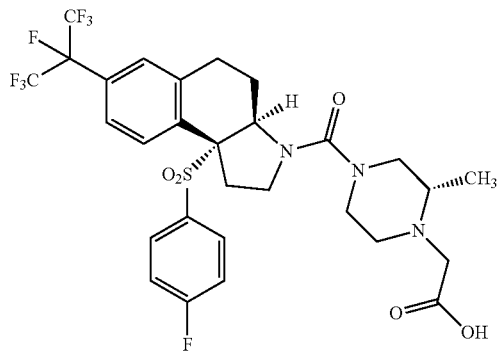 | 693.4 (M + H)⁺ | 1.90 | D |

Example 818

2-((S)-4-((3 aR,9bR)-9b-((4-fluorophenyl)sulfonyl)-7-(perfluoropropan-2-yl)-2,3,3a,4,5,9b-hexahydro-1H-benzo[e]indole-3-carbonyl)-2-methylpiperazin-1-yl)acetic Acid

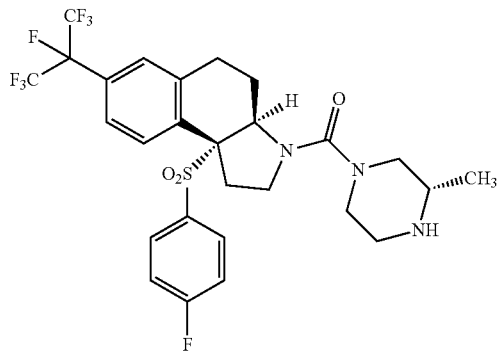 [SMILES: C[C@H]1CN(C(=O)N2CC[C@@]3(S(=O)(=O)c4ccc(F)cc4)c4ccc(C(F)(C(F)(F)F)C(F)(F)F)cc4CC[C@@H]23)CCN1]

Step A: ((3aR,9bR)-9b-((4-fluorophenyl)sulfonyl)-7-(perfluoropropan-2-yl)-1,2,3a,4,5,9b-hexahydro-3H-benzo[e]indol-3-yl)((S)-3-methylpiperazin-1-yl)methanone A solution of (3aR,9bR)-9b-((3-fluorophenyl)sulfonyl)-7-(perfluoropropan-2-yl)-2,3,3a,4,5,9b-hexahydro-1H-benzo[e]indole hydrochloride (Intermediate 32; 0.05 g, 0.100 mmol) and triphosgene (0.012 g, 0.039 mmol) in DCM (1 mL) was treated at rt with DIPEA (0.087 mL, 0.501 mmol). After stirring for 30 min, the mixture was treated with tert-butyl (S)-2-methylpiperazine-1-carboxylate (0.020 g, 0.100 mmol) and stirred overnight at rt. The mixture was diluted with DCM and washed sequentially with saturated aqueous NaHCO₃ and brine. The combined aqueous layers were extracted with DCM, and the combined organic layers were dried over MgSO₄ and concentrated. The residue was dissolved in DCM (1 mL) and treated with TFA (0.5 mL, 6.49 mmol). After stirring for 2 h, the mixture was concentrated. The residue was dissolved in EtOAc and washed sequentially with 1.5 M aqueous K₂HPO₄ and brine, dried over MgSO₄ and concentrated to provide crude ((3aR,9bR)-9b-((4-fluorophenyl)sulfonyl)-7-(perfluoropropan-2-yl)-1,2,3a,4,5,9b-hexahydro-3H-benzo[e]indol-3-yl)((S)-3-methylpiperazin-1-yl)methanone (0.06 g), used without further purification. LCMS m/z 626.2 (M+H)⁺, $t_R$ 0.92 min (method B).

Step B: 2-((S)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-2-methylpiperazin-1-yl)acetic Acid

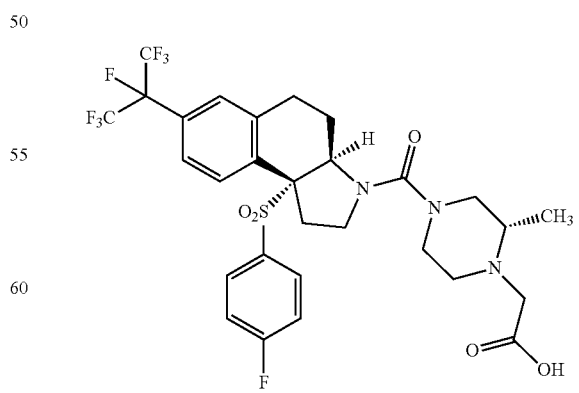

A mixture of crude ((3aR,9bR)-9b-((4-fluorophenyl)sulfonyl)-7-(perfluoropropan-2-yl)-1,2,3a,4,5,9b-hexahydro- 3H-benzo[e]indol-3-yl)((S)-3-methylpiperazin-1-yl)methanone (0.06 g, 0.096 mmol), $Cs_2CO_3$ (0.078 g, 0.240 mmol) and tert-butyl bromoacetate (0.022 mL, 0.144 mmol) in DMF (0.75 mL) was heated at 60° C. After 6 h, the mixture was cooled to rt, diluted with EtOAc and washed sequentially with 10% aqueous LiCl (2×) and brine. The combined aqueous layers were extracted with EtOAc, and the combined organic layers were dried over $Na_2SO_4$ and concentrated. The residue was dissolved in DCM (1.5 mL), treated with TFA (0.75 mL, 9.73 mmol) and stirred at rt. After 4 h, the mixture was concentrated, and the residue was purified by preparative HPLC (method E, gradient 30-70% B, 20 min) to provide 2-((S)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-2-methylpiperazin-1-yl)acetic acid (23.6 mg, 36% yield). LCMS m/z 684.1 (M+H)$^+$, $t_R$ 1.84 min (method C). $^1$H NMR (500 MHz, DMSO-$d_6$) δ 7.87 (d, J=8.4 Hz, 1H), 7.63-7.53 (m, 3H), 7.34 (br. s., 1H), 7.30 (d, J=6.8 Hz, 1H), 6.72 (d, J=7.3 Hz, 1H), 4.80 (dd, J=8.8, 4.5 Hz, 1H), 4.08-3.99 (m, 1H), 3.87-3.79 (m, 1H), 3.58 (d, J=14.7 Hz, 1H), 3.14-3.06 (m, 2H), 3.03-2.93 (m, 2H), 2.66-2.53 (m, 4H), 1.96-1.86 (m, 2H), 1.76-1.68 (m, 2H), 1.50-1.41 (m, 2H), 1.14 (d, J=5.9 Hz, 3H).

Example 819

1-((3aR,9bR)-9b-((4-fluorophenyl)sulfonyl)-7-(perfluoropropan-2-yl)-1,2,3a,4,5,9b-hexahydro-3H-benzo[e]indol-3-yl)-3-hydroxy-2-(hydroxymethyl)-2-methylpropan-1-one

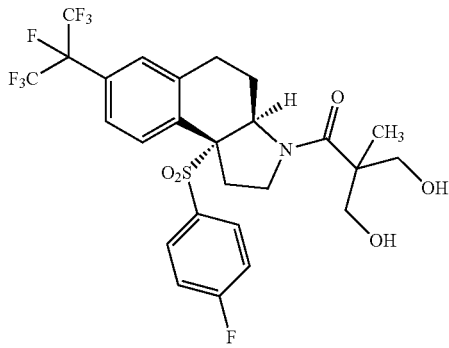 [SMILES: CC(CO)(CO)C(=O)N1CC[C@@]2(S(=O)(=O)c3ccc(F)cc3)c3ccc(C(F)(C(F)(F)F)C(F)(F)F)cc3CC[C@@H]12]

A solution of ((3aR,9bR)-9b-((4-fluorophenyl)sulfonyl)-7-(perfluoropropan-2-yl)-4,5-dihydro-1H-benzo[e]indol-3-yl)(2,2,5-trimethyl-1,3-dioxan-5-yl)methanone (Example 305; 76 mg, 0.087 mmol) in MeOH (5 mL) was treated with p-toluenesulfonic acid hydrate (1.654 mg, 8.69 μmol) and stirred at rt. After 60 min, the mixture was concentrated and the residue was dissolved in EtOAc, washed with saturated aqueous $NaHCO_3$ and brine, dried over $Na_2SO_4$ and concentrated to provide a tan glassy solid (64 mg, >100% yield, about 80% purity). A sample of this material (12 mg) was purified by preparative HPLC (method E, gradient 40-80% B, 20 min) to provide 1-((3aR,9bR)-9b-((4-fluorophenyl)sulfonyl)-7-(perfluoropropan-2-yl)-1,2,3a,4,5,9b-hexahydro-3H-benzo[e]indol-3-yl)-3-hydroxy-2-(hydroxymethyl)-2-methylpropan-1-one (6.2 mg, 11% yield). LCMS m/z 616.1 (M+H)$^+$, HPLC $t_R$ 2.00 min (method C). $^1$H NMR (500 MHz, DMSO-$d_6$) δ 7.88 (d, J=8.5 Hz, 1H), 7.63 (d, J=8.4 Hz, 1H), 7.39-7.30 (m, 3H), 7.29-7.19 (m, 2H), 4.82 (dd, J=11.1, 4.8 Hz, 1H), 4.65 (t, J=5.3 Hz, 1H), 4.55 (br. s., 1H), 4.10-3.95 (m, 1H), 3.58-3.23 (m, 2H), 2.76-2.59 (m, 2H), 2.51 (br. s., 4H), 2.30-2.15 (m, 1H), 1.88 (t, J=14.2 Hz, 1H), 1.34-1.17 (m, 1H), 1.01 (s, 3H).

Example 820

((3aR,9bR)-9b-((4-fluorophenyl)sulfonyl)-7-(perfluoropropan-2-yl)-1,2,3a,4,5,9b-hexahydro-3H-benzo[e]indol-3-yl)(2-hydroxy-5-methyl-2-oxido-1,3,2-dioxaphosphinan-5-yl)methanone

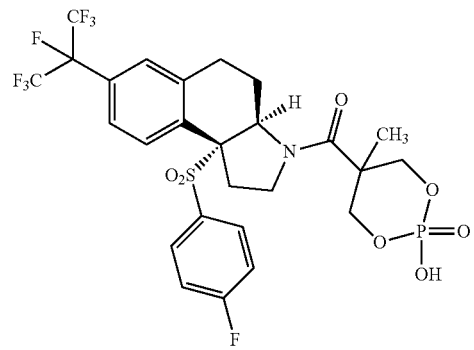 [SMILES: CC1(C(=O)N2CC[C@@]3(S(=O)(=O)c4ccc(F)cc4)c4ccc(C(F)(C(F)(F)F)C(F)(F)F)cc4CC[C@@H]23)COP(=O)(O)OC1]

A solution of phosphorus oxychloride (7.33 μL, 0.079 mmol) in pyridine (0.5 mL) was stirred on an ice-water bath and treated in portions over 50 min with a solution of crude 1-((3aR,9bR)-9b-((4-fluorophenyl)sulfonyl)-7-(perfluoropropan-2-yl)-4,5-dihydro-1H-benzo[e]indol-3-yl)-3-hydroxy-2-(hydroxymethyl)-2-methylpropan-1-one (Example 819; 55 mg, 0.071 mmol) in pyridine (0.5 mL). The mixture was warmed to rt and stirred for 35 min. The solution was then added dropwise to a stirred solution of $NaHCO_3$ (26.4 mg, 0.315 mmol) in water (1 mL), causing gas evolution. After stirring for 60 min, the mixture was concentrated and the residue was purified by preparative HPLC (method E, gradient 20-60% B, 20 min) to provide ((3aR,9bR)-9b-((4-fluorophenyl)sulfonyl)-7-(perfluoropropan-2-yl)-1,2,3a,4,5,9b-hexahydro-3H-benzo[e]indol-3-yl)(2-hydroxy-5-methyl-2-oxido-1,3,2-dioxaphosphinan-5-yl)methanone (28.4 mg, 59% yield). LCMS m/z 677.9 (M+H)$^+$, 676.3 (M−H)$^-$, HPLC $t_R$ 1.73 min (method C). $^1$H NMR (600 MHz, DMSO-$d_6$) δ 7.87 (d, J=8.5 Hz, 1H), 7.62 (d, J=8.3 Hz, 1H), 7.34-7.27 (m, 3H), 7.27-7.19 (m, 2H), 4.83 (dd, J=11.5, 5.0 Hz, 1H), 4.38-4.24 (m, 2H), 4.03-3.27 (m, 4H), 2.77-2.59 (m, 2H), 2.26-2.15 (m, 1H), 1.83 (t, J=13.9 Hz, 1H), 1.33-1.23 (m, 1H), 1.21 (s, 3H); one proton presumably hidden by solvent peak.

Example 821

(2-amino-5-methyl-2-oxido-1,3,2-dioxaphosphinan-5-yl)((3aR,9bR)-9b-((4-fluorophenyl)sulfonyl)-7-(perfluoropropan-2-yl)-1,2,3a,4,5,9b-hexahydro-3H-benzo[e]indol-3-yl)methanone

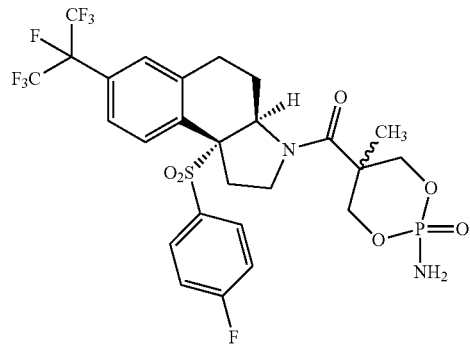 [SMILES: CC1(C(=O)N2CC[C@@]3(S(=O)(=O)c4ccc(F)cc4)c4ccc(C(F)(C(F)(F)F)C(F)(F)F)cc4CC[C@@H]23)COP(N)(=O)OC1]

Following the procedure of Example 820 but quenching the reaction mixture into aqueous ammonia instead of aqueous NaHCO$_3$, 1-((3aR,9bR)-9b-((4-fluorophenyl)sulfonyl)-7-(perfluoropropan-2-yl)-4,5-dihydro-1H-benzo[e]indol-3-yl)-3-hydroxy-2-(hydroxymethyl)-2-methylpropan-1-one (Example 819) was converted into (2-amino-5-methyl-2-oxido-1,3,2-dioxaphosphinan-5-yl)((3aR,9bR)-9b-((4-fluorophenyl)sulfonyl)-7-(perfluoropropan-2-yl)-1,2,3a,4,5,9b-hexahydro-3H-benzo[e]indol-3-yl)methanone as a mixture of isomers in 13% yield. LCMS m/z 677.4 (M+H)+, HPLC t$_R$ 2.02 min (method C). $^1$H NMR (500 MHz, DMSO-d$_6$) δ 7.89 (d, J=8.0 Hz, 1H), 7.64 (d, J=8.1 Hz, 1H), 7.34 (br. s., 1H), 7.32-7.18 (m, 4H), 5.07-4.77 (m, 2H), 4.62-4.40 (m, 2H), 4.25-4.02 (m, 2H), 4.03-3.86 (m, 1H), 3.76 (br. s., 1H), 3.38 (br. s., 1H), 2.82-2.60 (m, 2H), 2.22 (m, 1H), 1.92-1.67 (m, 1H), 1.43-1.18 (m, 3H).

Examples 822 and 823

(2,5-dimethyl-2-oxido-1,3,2-dioxaphosphinan-5-yl)((3aR,9bR)-9b-((4-fluorophenyl)sulfonyl)-7-(perfluoropropan-2-yl)-1,2,3a,4,5,9b-hexahydro-3H-benzo[e]indol-3-yl)methanone (Two Homochiral Isomers)

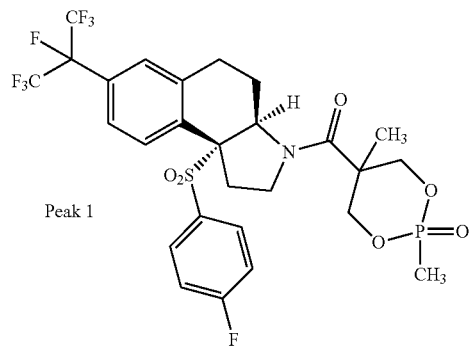

Peak 1

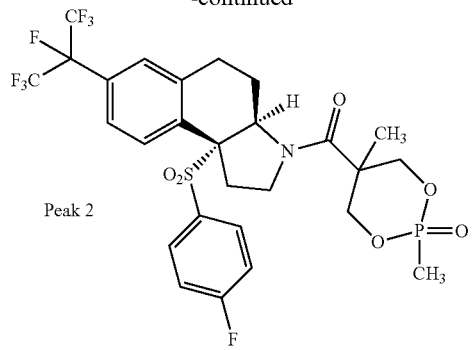

Peak 2

Following the procedure of Example 820 but using methylphosphonic dichloride in place of phosphorus oxychloride, 1-((3aR,9bR)-9b-((4-fluorophenyl)sulfonyl)-7-(perfluoropropan-2-yl)-4,5-dihydro-1H-benzo[e]indol-3-yl)-3-hydroxy-2-(hydroxymethyl)-2-methylpropan-1-one (Example 819) was converted into two isomers of (2,5-dimethyl-2-oxido-1,3,2-dioxaphosphinan-5-yl)((3aR,9bR)-9b-((4-fluorophenyl)sulfonyl)-7-(perfluoropropan-2-yl)-1,2,3a,4,5,9b-hexahydro-3H-benzo[e]indol-3-yl)methanone, which were separated by preparative HPLC (method E, gradient 40-80%, 19 min).

Peak 1 (11% yield): LCMS m/z 676.0 (M+H)$^+$, HPLC t$_R$ 2.12 min (method C). $^1$H NMR (500 MHz, DMSO-d$_6$) δ 7.90 (d, J=8.5 Hz, 1H), 7.65 (d, J=8.0 Hz, 1H), 7.34 (br. s., 1H), 7.31-7.21 (m, 4H), 4.85 (dd, J=11.5, 4.8 Hz, 1H), 4.58 (t, J=10.1 Hz, 1H), 4.51 (t, J=10.0 Hz, 1H), 4.36-4.18 (m, 2H), 4.04-3.93 (m, 1H), 3.77 (br. s., 1H), 3.42-3.11 (m, 1H), 2.82-2.70 (m, 1H), 2.67 (d, J=16.6 Hz, 1H), 2.21 (d, J=8.1 Hz, 1H), 1.83 (t, J=13.7 Hz, 1H), 1.54 (d, J=17.1 Hz, 3H), 1.32 (s+m, 4H).

Peak 2 (18% yield): LCMS m/z 676.1 (M+H)$^+$, HPLC t$_R$ 2.23 min (method C). $^1$H NMR (500 MHz, DMSO-d$_6$) δ 7.96-7.85 (m, 1H), 7.65 (d, J=7.6 Hz, 1H), 7.39-7.21 (m, 5H), 5.00-4.77 (m, 1H), 4.73-4.51 (m, 2H), 4.24 (dd, J=12.2, 7.3 Hz, 1H), 4.10 (dd, J=10.8, 6.4 Hz, 1H), 3.97 (q, J=8.2 Hz, 1H), 3.85-3.44 (m, 2H), 2.86-2.72 (m, 1H), 2.72-2.61 (m, 2H), 2.18 (d, J=8.1 Hz, 1H), 1.97-1.76 (m, 1H), 1.60 (d, J=16.9 Hz, 3H), 1.45-1.20 (m, 1H), 1.13 (s, 3H).

Examples 824 and 825

2-fluoro-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)benzamide and 2-fluoro-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)benzoic acid

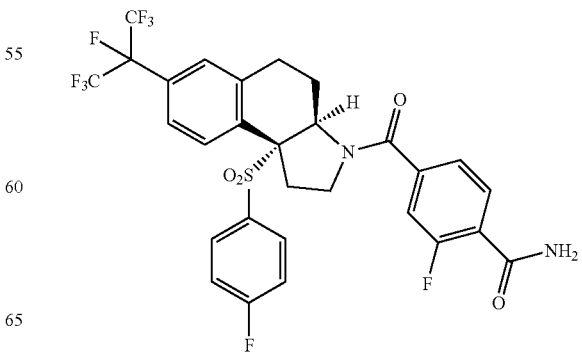

-continued

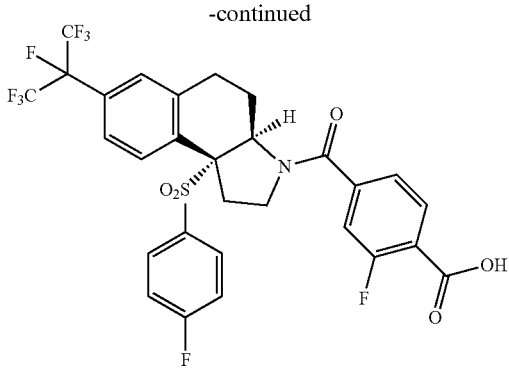

A solution of crude 2-fluoro-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)benzonitrile (Example 386, prepared from 70 mg of Intermediate 32) in acetic acid (3.2 mL, 55.9 mmol) was treated with concentrated aqueous HCl (0.8 mL, 26.3 mmol) and heated at 70° C. for 7 h. The mixture was cooled to rt and concentrated, and the residue was purified by preparative HPLC to provide 2-fluoro-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)benzamide (Example 824; 8 mg, 9% yield). LCMS m/z 665.1 (M+H)$^+$, $t_R$ 1.06 min (method B). $^1$H NMR (400 MHz, MeOH-d$_4$) δ 7.98 (d, J=8.8 Hz, 1H), 7.91 (d, J=7.9 Hz, 1H), 7.63 (d, J=8.4 Hz, 1H), 7.47-7.40 (m, 3H), 7.38 (s, 1H), 7.33 (s, 1H), 7.14 (d, J=8.8 Hz, 2H), 5.10 (dd, J=11.7, 5.1 Hz, 1H), 3.84-3.75 (m, 1H), 3.72-3.64 (m, 1H), 3.53-3.44 (m, 1H), 2.75-2.66 (m, 2H), 2.52-2.45 (m, 1H), 2.11-2.02 (m, 1H), 1.63-1.50 (m, 1H).

Also isolated was 2-fluoro-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)benzoic acid (Example 825; 11.1 mg, 12% yield). LCMS m/z 666.3 (M+H)$^+$, $t_R$ 1.05 min (method B). $^1$H NMR (400 MHz, MeOH-d$_4$) δ 8.05 (dd, J=7.9, 3.1 Hz, 1H), 7.98 (d, J=8.4 Hz, 1H), 7.65-7.61 (m, 1H), 7.47-7.32 (m, 5H), 7.16-7.11 (m, 2H), 5.10 (dd, J=11.9, 5.3 Hz, 1H), 3.82-3.75 (m, 1H), 3.72-3.64 (m, 1H), 3.52-3.44 (m, 1H), 2.75-2.66 (m, 2H), 2.52-2.45 (m, 1H), 2.10-2.04 (m, 1H), 1.62-1.53 (m, 1H).

Also isolated was recovered starting material (Example 386; 9.5 mg, 11% yield).

Example 826

(RS)-2-(2-chloro-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)phenyl)-2-hydroxyacetic Acid

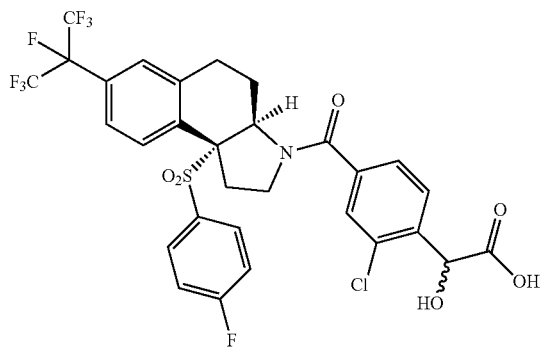 [SMILES: O=C(O)C(O)c1ccc(C(=O)N2CC[C@@]3(S(=O)(=O)c4ccc(F)cc4)c4ccc(C(F)(C(F)(F)F)C(F)(F)F)cc4CC[C@@H]23)cc1Cl]

A solution of 2-chloro-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)benzaldehyde (prepared by the procedure of Example 1 Step A, from Intermediate 32 and 3-chloro-4-formylbenzoic acid; 53.3 mg, 0.08 mmol) and cyanotrimethylsilane (0.054 mL, 0.400 mmol) in DCM (1.5 mL) was stirred on an ice-water bath and treated with titanium(IV) isopropoxide (0.234 mL, 0.800 mmol). The mixture was stirred for 5 h, then was treated with cyanotrimethylsilane (0.054 mL, 0.400 mmol) and titanium(IV) isopropoxide (0.234 mL, 0.800 mmol). After stirring overnight at rt, the mixture was treated with 1 N aqueous HCl and diluted with DCM and filtered, dried over MgSO$_4$ and concentrated. The residue was treated with acetic acid (1.6 mL, 27.9 mmol) and concentrated aqueous HCl (0.4 mL, 13.16 mmol) and stirred at 70° C. for 2.5 h. The mixture was cooled to rt, diluted with EtOAc and washed sequentially with water and brine. The combined aqueous layers were extracted with additional EtOAc, and the combined organic layers were dried over MgSO$_4$, filtered and concentrated. The residue was purified by preparative HPLC (method E, gradient 45-90% B, 20 min) to afford (RS)-2-(2-chloro-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)phenyl)-2-hydroxyacetic acid (15.4 mg, 25% yield). LCMS m/z 712.1 (M+H)$^+$, $t_R$ 1.80 min (Method C). $^1$H NMR (500 MHz, DMSO-d$_6$) δ 7.85 (d, J=8.5 Hz, 1H), 7.63 (d, J=8.0 Hz, 1H), 7.51 (d, J=7.3 Hz, 1H), 7.46 (br. s., 2H), 7.40-7.37 (m, 3H), 7.30 (t, J=8.2 Hz, 2H), 5.22 (br. s., 1H), 4.95 (dd, J=11.2, 4.8 Hz, 1H), 3.63-3.57 (m, 1H), 3.40-3.35 (m, 1H), 3.33-3.26 (m, 1H), 2.79-2.71 (m, 1H), 2.69-2.61 (m, 1H), 2.31-2.25 (m, 1H), 2.11-2.02 (m, 1H), 1.55-1.45 (m, 1H).

Example 827

(RS)-2-(4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)phenyl)-2-hydroxyacetic Acid

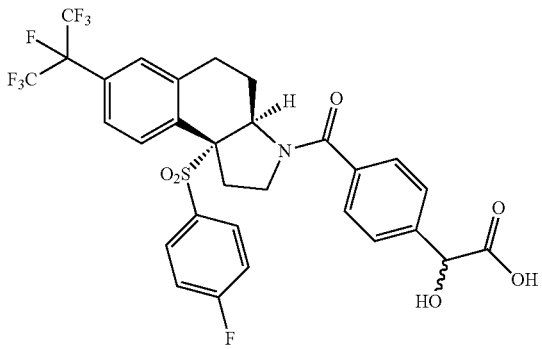 [SMILES: O=C(O)C(O)c1ccc(C(=O)N2CC[C@@]3(S(=O)(=O)c4ccc(F)cc4)c4ccc(C(F)(C(F)(F)F)C(F)(F)F)cc4CC[C@@H]23)cc1]

(RS)-2-(4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)phenyl)-2-hydroxyacetic acid was prepared by the procedure of Example 826 but substituting 4-formylbenzoic acid for 3-chloro-4-formylbenzoic acid in the preparation of the starting material. LCMS m/z 678.1 (M+H)$^+$, $t_R$ 1.74 min (Method C).

Example 828

(4-fluoro-1,1-dioxidotetrahydro-2H-thiopyran-4-yl)((3aR,9bR)-9b-((4-fluorophenyl)sulfonyl)-7-(perfluoropropan-2-yl)-1,2,3a4,5,9b-hexahydro-3H-benzo[e]indol-3-yl)methanone

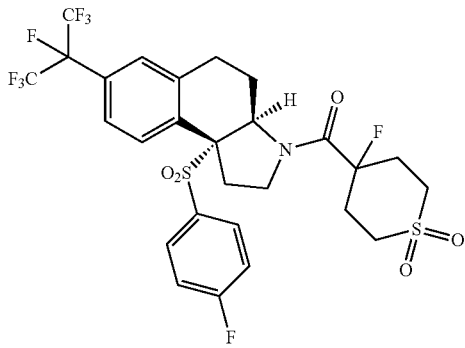 [SMILES: O=C(N1CC[C@@]2(S(=O)(=O)c3ccc(F)cc3)c3ccc(C(F)(C(F)(F)F)C(F)(F)F)cc3CC[C@@H]12)C1(F)CCS(=O)(=O)CC1]

A solution of ((3aR,9bR)-9b-((4-fluorophenyl)sulfonyl)-7-(perfluoropropan-2-yl)-4,5-dihydro-1H-benzo[e]indol-3-yl)(4-hydroxy-1,1-dioxidotetrahydro-2H-thiopyran-4-yl)methanone (Example 69; 20 mg, 0.030 mmol) in DCM (1 mL) was treated with DAST (0.020 mL, 0.148 mmol) and stirred at rt. After 75 min the mixture was treated with saturated aqueous NaHCO$_3$ (1.5 mL) and the layers were separated. The aqueous phase was extracted twice with EtOAc, and the combined organic phases were dried over Na$_2$SO$_4$ and concentrated. The residue was purified by preparative HPLC (method E, gradient 40-90% B, 20 min) to provide (4-fluoro-1,1-dioxidotetrahydro-2H-thiopyran-4-yl)((3aR,9bR)-9b-((4-fluorophenyl)sulfonyl)-7-(perfluoropropan-2-yl)-1,2,3a,4,5,9b-hexahydro-3H-benzo[e]indol-3-yl)methanone (8.8 mg, 44% yield). LCMS m/z 678.1 (M+H)$^+$, HPLC t$_R$ 2.31 (method C). $^1$H NMR (500 MHz, DMSO-d$_6$) δ 7.93-7.85 (m, 1H), 7.65 (d, J=8.2 Hz, 1H), 7.40-7.30 (m, 3H), 7.27 (t, J=8.5 Hz, 2H), 4.81 (dd, J=11.7, 4.7 Hz, 1H), 3.96 (d, J=4.6 Hz, 1H), 3.92-3.77 (m, 1H), 3.61-3.11 (m, 4H), 2.87-2.31 (m, 7H), 2.29-2.13 (m, 1H), 1.92 (t, J=13.9 Hz, 1H), 1.47-1.30 (m, 1H).

Example 829

((3aR,9bR)-9b-((4-fluorophenyl)sulfonyl)-7-(perfluoropropan-2-yl)-1,2,3a,4,5,9b-hexahydro-3H-benzo[e]indol-3-yl)(4-fluorotetrahydro-2H-pyran-4-yl)methanone

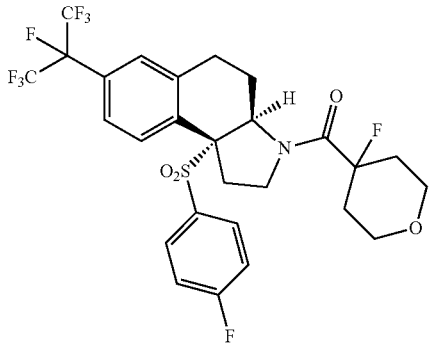 [SMILES: O=C(N1CC[C@@]2(S(=O)(=O)c3ccc(F)cc3)c3ccc(C(F)(C(F)(F)F)C(F)(F)F)cc3CC[C@@H]12)C1(F)CCOCC1]

Following the procedure of Example 828, ((3aR,9bR)-9b-((4-fluorophenyl)sulfonyl)-7-(perfluoropropan-2-yl)-1,2,3a,4,5,9b-hexahydro-3H-benzo[e]indol-3-yl)(4-hydroxytetrahydro-2H-pyran-4-yl)methanone (Example 471; 12.5 mg, 0.020 mmol) was converted into ((3aR,9bR)-9b-((4-fluorophenyl)sulfonyl)-7-(perfluoropropan-2-yl)-1,2,3a,4,5,9b-hexahydro-3H-benzo[e]indol-3-yl)(4-fluorotetrahydro-2H-pyran-4-yl)methanone (6.9 mg, 55% yield). LCMS m/z 630.2 (M+H)$^+$, HPLC t$_R$ 2.43 min (method C). $^1$H NMR (500 MHz, DMSO-d$_6$) δ 7.93-7.82 (m, 1H), 7.65 (d, J=8.0 Hz, 1H), 7.42-7.17 (m, 5H), 5.53-4.51 (m, 2H), 4.09-3.06 (m, 5H), 2.86-2.57 (m, 4H), 2.35-1.20 (m, 6H).

Example 830

(3S,4R)-4-(9b-((3-fluorophenyl)sulfonyl)-7-(perfluoropropan-2-yl)-2,3,3a,4,5,9b-hexahydro-1H-benzo[e]indole-3-carbonyl)-3-methylcyclohexane-1-carboxylic Acid

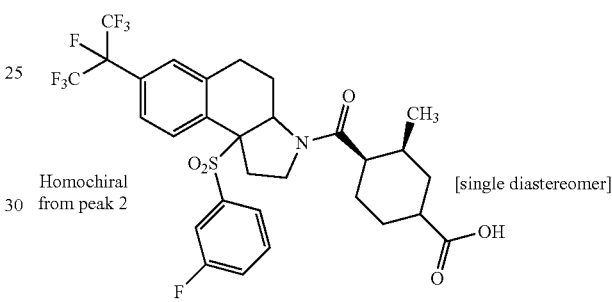

Step A: (3S,4R)-4-(9b-((3-fluorophenyl)sulfonyl)-7-(perfluoropropan-2-yl)-2,3,3a,4,5,9b-hexahydro-1H-benzo[e]indole-3-carbonyl)-3-methylcyclohexan-1-one

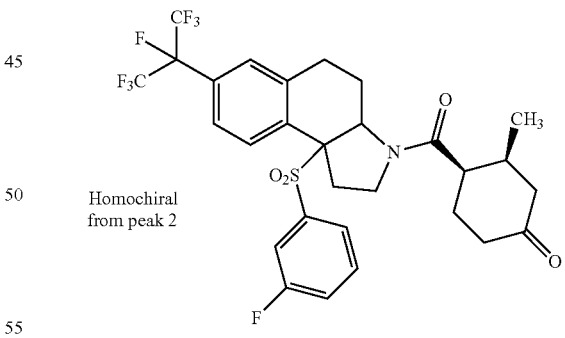

A solution of 9b-((3-fluorophenyl)sulfonyl)-7-(perfluoropropan-2-yl)-2,3,3a,4,5,9b-hexahydro-1H-benzo[e]indole hydrochloride (homochiral, from peak 2, Intermediate 43; 100 mg, 0.2 mmol) in DMF (1.5 mL) was treated with (1R,2S)-2-methyl-4-oxocyclohexanecarboxylic acid (Tetrahedron 1994, 50, 11743; 40.7 mg, 0.26 mmol), HATU (99 mg, 0.26 mmol), and 4-methylmorpholine (0.066 mL, 0.601 mmol). The mixture was stirred at rt overnight, then was diluted with EtOAc and saturated brine. The organic phase was separated and washed sequentially with brine (3×), 1 M aqueous HCl and saturated aqueous NaHCO$_3$, dried over MgSO₄, filtered and concentrated to give crude (3S,4R)-4-(9b-((3-fluorophenyl)sulfonyl)-7-(perfluoropropan-2-yl)-2,3,3a,4,5,9b-hexahydro-1H-benzo[e]indole-3-carbonyl)-3-methylcyclohexan-1-one (105 mg, 82% yield). LCMS m/z 638.3 (M+H)⁺, HPLC t_R 1.08 min (method B).

Step B: (4R,5S)-4-(9b-((3-fluorophenyl)sulfonyl)-7-(perfluoropropan-2-yl)-2,3,3a,4,5,9b-hexahydro-1H-benzo[e]indole-3-carbonyl)-5-methylcyclohex-1-en-1-yl Trifluoromethanesulfonate

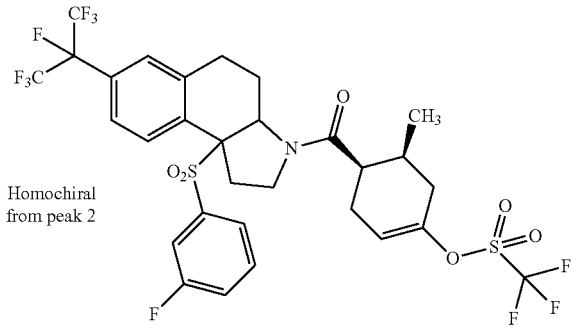 [SMILES: C[C@H]1CC(OS(=O)(=O)C(F)(F)F)=CC[C@H]1C(=O)N1CCC2(S(=O)(=O)c3cccc(F)c3)c3ccc(C(F)(C(F)(F)F)C(F)(F)F)cc3CCC12]

Homochiral from peak 2

A solution of (3S,4R)-4-(9b-((3-fluorophenyl)sulfonyl)-7-(perfluoropropan-2-yl)-2,3,3a,4,5,9b-hexahydro-1H-benzo[e]indole-3-carbonyl)-3-methylcyclohexanone (100 mg, 0.157 mmol) in THF (2 mL) at −78° C. was treated with 1,1,1-trifluoro-N-phenyl-N-((trifluoromethyl)sulfonyl)methanesulfonamide (61.6 mg, 0.173 mmol). Potassium bis(trimethylsilyl)amide (1 M in THF; 0.2 mL, 0.2 mmol) was then added dropwise at −78° C. After stirring for 30 min, the mixture was warmed to rt, stirred for 1.5 h, then was treated with water. The mixture was extracted with EtOAc, and the organic phase was washed with brine, dried over MgSO₄ and concentrated to provide crude (4R,5S)-4-(9b-((3-fluorophenyl)sulfonyl)-7-(perfluoropropan-2-yl)-2,3,3a,4,5,9b-hexahydro-1H-benzo[e]indole-3-carbonyl)-5-methylcyclohex-1-en-1-yl trifluoromethanesulfonate (82 mg, 68% yield). LCMS m/z 770.4 (M+H)⁺, HPLC t_R 1.21 min (method B).

Step C: Methyl (4R,5S)-4-(9b-((3-fluorophenyl)sulfonyl)-7-(perfluoropropan-2-yl)-2,3,3a,4,5,9b-hexahydro-1H-benzo[e]indole-3-carbonyl)-5-methylcyclohex-1-ene-1-carboxylate

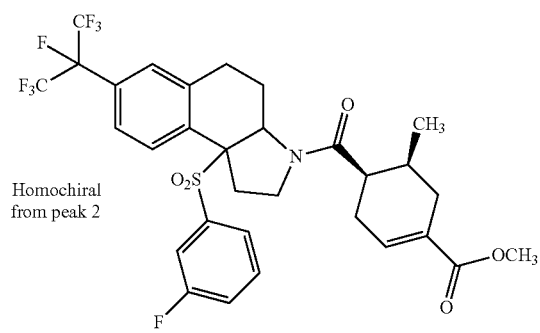 [SMILES: COC(=O)C1=CC[C@@H](C(=O)N2CCC3(S(=O)(=O)c4cccc(F)c4)c4ccc(C(F)(C(F)(F)F)C(F)(F)F)cc4CCC23)[C@@H](C)C1]

Homochiral from peak 2

A solution of (4R,5S)-4-(9b-((3-fluorophenyl)sulfonyl)-7-(perfluoropropan-2-yl)-2,3,3a,4,5,9b-hexahydro-H-benzo[e]indole-3-carbonyl)-5-methylcyclohex-1-en-1-yl trifluoromethanesulfonate (80 mg, 0.104 mmol) in DMF (1 mL) and MeOH (1 mL) was treated with palladium(II) acetate (2.3 mg, 10.39 μmol), 1,1′-bis(diphenylphosphino)ferrocene (5.76 mg, 10.39 μmol), and tri-n-butylamine (0.075 mL, 0.312 mmol). Carbon monoxide was bubbled through the mixture for 10 min. The mixture was then heated at 80° C. under a carbon monoxide atmosphere (balloon pressure) for 2 h. After cooling to rt, the mixture was diluted with EtOAc and water. The organic phase was separated, washed with brine (3×), dried over MgSO₄, filtered and concentrated. The residue was purified by preparative HPLC (method G, gradient 20-100% B, 10 min) to give methyl (4R,5S)-4-(9b-((3-fluorophenyl)sulfonyl)-7-(perfluoropropan-2-yl)-2,3,3a,4,5,9b-hexahydro-1H-benzo[e]indole-3-carbonyl)-5-methylcyclohex-1-ene-1-carboxylate (70.2 mg, 99% yield). LCMS m/z 680.2 (M+H)⁺, HPLC t_R 1.14 min (method B).

Step D: Methyl (3S,4R)-4-(9b-((3-fluorophenyl)sulfonyl)-7-(perfluoropropan-2-yl)-2,3,3a,4,5,9b-hexahydro-1H-benzo[e]indole-3-carbonyl)-3-methylcyclohexane-1-carboxylate

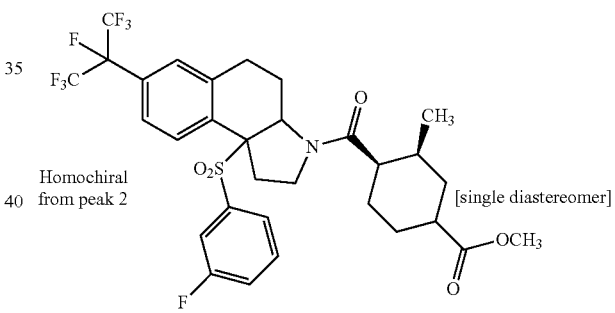

Homochiral from peak 2                     [single diastereomer]

A solution of (4R,5S)-methyl 4-((3aR,9bR)-9b-((3-fluorophenyl)sulfonyl)-7-(perfluoropropan-2-yl)-2,3,3a,4,5,9b-hexahydro-1H-benzo[e]indole-3-carbonyl)-5-methylcyclohex-1-enecarboxylate (35 mg, 0.051 mmol) in DCM (1.5 mL) was treated with iridium(I) hexafluorophosphate (1,5-cyclooctadiene)-(pyridine)-(tricyclohexylphosphine) (Crabtree's catalyst; 12.4 mg, 0.015 mmol) and the mixture was stirred at rt overnight under a hydrogen atmosphere (balloon pressure). The mixture was filtered and the filtrate was concentrated to give a single diastereomer of crude methyl (3S,4R)-4-(9b-((3-fluorophenyl)sulfonyl)-7-(perfluoropropan-2-yl)-2,3,3a,4,5,9b-hexahydro-1H-benzo[e]indole-3-carbonyl)-3-methylcyclohexane-1-carboxylate (36.9 mg, quantitative yield). LCMS m/z 682.5 (M+H)⁺, HPLC t_R 1.14 min (method B).

Step E: (3S,4R)-4-(9b-((3-fluorophenyl)sulfonyl)-7-(perfluoropropan-2-yl)-2,3,3a,4,5,9b-hexahydro-1H-benzo[e]indole-3-carbonyl)-3-methylcyclohexane-1-carboxylic Acid

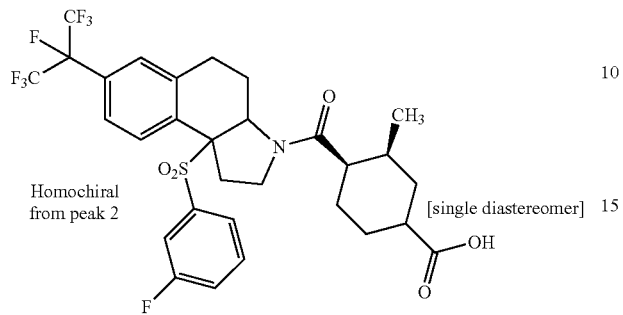

Homochiral from peak 2                [single diastereomer]

A solution of methyl (3S,4R)-4-(9b-((3-fluorophenyl)sulfonyl)-7-(perfluoropropan-2-yl)-2,3,3a,4,5,9b-hexahydro-1H-benzo[e]indole-3-carbonyl)-3-methylcyclohexane-1-carboxylate (36 mg, 0.053 mmol) in THF (1.5 mL) and MeOH (0.2 mL) was treated with 1 M aqueous LiOH (0.211 mL, 0.211 mmol). The mixture was stirred overnight at rt, then was purified by preparative HPLC (method G, gradient 20-100% B, 10 min) to give a single diastereomer of (3S,4R)-4-(9b-((3-fluorophenyl)sulfonyl)-7-(perfluoropropan-2-yl)-2,3,3a,4,5,9b-hexahydro-1H-benzo[e]indole-3-carbonyl)-3-methylcyclohexane-1-carboxylic acid (9 mg, 26% yield). LCMS m/z 668.4 (M+H)+, HPLC $t_R$ 1.06 min (method B). $^1$H NMR (400 MHz, MeOH-$d_4$) δ 8.00 (d, J=8.4 Hz, 1H), 7.63 (d, J=8.8 Hz, 1H), 7.50-7.34 (m, 2H), 7.30-7.18 (m, 2H), 6.81 (dd, J=8.1, 2.0 Hz, 1H), 4.87 (s, 1H), 4.12-3.98 (m, 1H), 3.89 (td, J=9.9, 3.1 Hz, 1H), 3.56 (ddd, J=14.7, 8.1, 2.5 Hz, 1H), 3.40-3.34 (m, 1H), 2.79-2.65 (m, 2H), 2.63-2.52 (m, 2H), 2.50-2.42 (m, 2H), 2.03 (d, J=9.0 Hz, 1H), 1.99-1.85 (m, 3H), 1.84-1.72 (m, 1H), 1.65-1.43 (m, 2H), 1.39-1.22 (m, 1H), 1.10 (d, J=7.0 Hz, 3H).

Example 831

(3S,4R)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-3-methylcyclohexane-1-carboxylic Acid

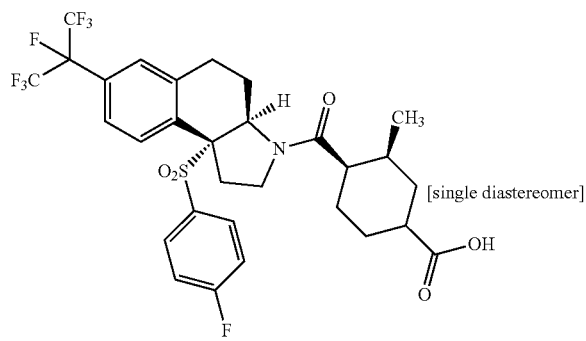 [SMILES: C[C@H]1CC(C(=O)O)CC[C@H]1C(=O)N1CC[C@@]2(S(=O)(=O)c3ccc(F)cc3)c3ccc(C(F)(C(F)(F)F)C(F)(F)F)cc3CC[C@@H]12]

[single diastereomer]

Following the procedures of Example 830, (3aR,9bR)-9b-((4-fluorophenyl)sulfonyl)-7-(perfluoropropan-2-yl)-2,3,3a,4,5,9b-hexahydro-1H-benzo[e]indole hydrochloride (Intermediate 32) was converted into a single diastereomer of (3S,4R)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-3-methylcyclohexane-1-carboxylic acid. LCMS m/z 668.2 (M+H)+, HPLC $t_R$ 2.01 min (method C).

Example 832

(3R,4R)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-3-methylcyclohexane-1-carboxylic Acid

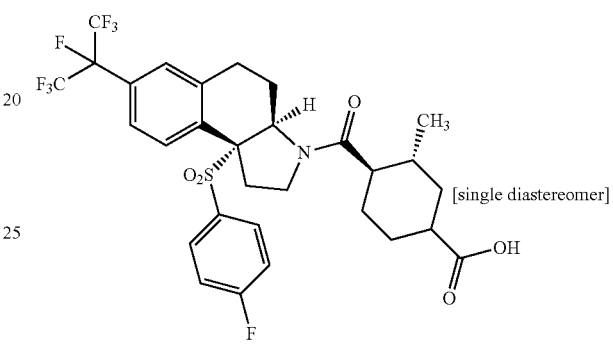

[single diastereomer]

Step A. (R)-4-benzyl-3-((1R,2R)-2-methyl-4-oxocyclohexane-1-carbonyl)oxazolidin-2-one

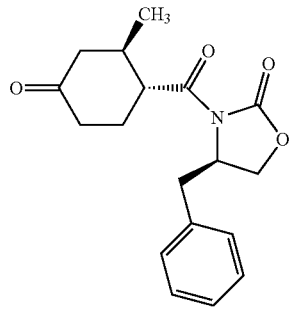 [SMILES: C[C@@H]1CC(=O)CC[C@H]1C(=O)N1C(=O)OC[C@H]1Cc1ccccc1]

A solution of (R,E)-4-benzyl-3-(but-2-enoyl)oxazolidin-2-one (8.0 g, 32.6 mmol) in DCM (40 mL) at −78° C. was treated with diethylaluminum chloride (1 M in hexane, 48.9 mL, 48.9 mmol). After 10 min, (buta-1,3-dien-2-yloxy)trimethylsilane (20.1 mL, 114 mmol) in DCM (5 mL) was added dropwise at −78° C. The solution was warmed to rt and stirred overnight. A mixture of THF (4 mL) and 6 M aqueous HCl (4 mL) was added, and the mixture was stirred for 30 min. Celite and EtOAc was added, and the mixture was filtered. The filtrate was washed with brine, dried over MgSO$_4$, filtered, and concentrated. The residue was purified by column chromatography on silica gel, eluting with EtOAc-hexanes, to give (R)-4-benzyl-3-((1R,2R)-2-methyl-4-oxocyclohexane-1-carbonyl)oxazolidin-2-one (1.2 g, 12% yield). LCMS m/z 316.2 (M+H)+, HPLC $t_R$ 0.87 min (method B). $^1$H NMR (400 MHz, CDCl$_3$) δ 7.38-7.28 (m, 3H), 7.24-7.19 (m, 2H), 4.74 (ddt, J=9.3, 7.4, 3.2 Hz, 1H), 4.32-4.20 (m, 2H), 3.79 (td, J=10.7, 3.4 Hz, 1H), 3.26 (dd, J=13.4, 3.3 Hz, 1H), 2.82 (dd, J=13.4, 9.5 Hz, 1H), 2.54-2.44 (m, 3H), 2.42-2.27 (m, 2H), 2.16 (dd, J=14.0, 12.7 Hz, 1H), 1.90-1.76 (m, 1H), 1.02 (d, J=6.4 Hz, 3H).

Step B. (R)-4-benzyl-3-((7R,8R)-7-methyl-1,4-dioxaspiro[4.5]decane-8-carbonyl)oxazolidin-2-one

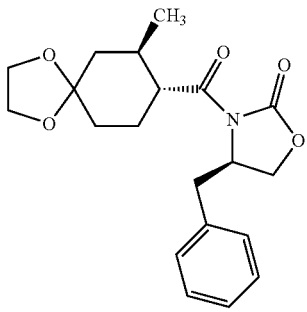 [SMILES: C[C@@H]1CC2(CC[C@H]1C(=O)N1C(=O)OC[C@H]1Cc1ccccc1)OCCO2]

A solution of (R)-4-benzyl-3-((1R,2R)-2-methyl-4-oxocyclohexanecarbonyl)oxazolidin-2-one (1.0 g, 3.17 mmol) was dissolved in DCM (10 mL) and cooled to 0° C. The mixture was treated with 2,2,7,7-tetramethyl-3,6-dioxa-2,7-disilaoctane (0.974 mL, 3.96 mmol), stirred for 5 min, then treated with trimethylsilyl trifluoromethanesulfonate (0.059 mL, 0.317 mmol). The mixture was warmed to rt and stirred overnight. Et$_3$N (0.075 mL, 0.539 mmol) was added, followed by saturated aqueous NaHCO$_3$. The mixture was extracted with DCM, and the organic phase was dried over MgSO$_4$, filtered, and concentrated. The residue was purified by column chromatography on silica gel, eluting with EtOAc-hexanes, to give (R)-4-benzyl-3-((7R,8R)-7-methyl-1,4-dioxaspiro[4.5]decane-8-carbonyl)oxazolidin-2-one (750 mg, 66% yield). LCMS m/z 360.3 (M+H)$^+$, HPLC t$_R$ 0.94 min (method B).

Step C. (7R,8R)-7-methyl-1,4-dioxaspiro[4.5]decane-8-carboxylic Acid

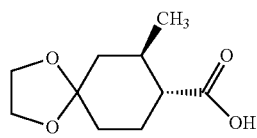

A solution of (R)-4-benzyl-3-((7R,8R)-7-methyl-1,4-dioxaspiro[4.5]decane-8-carbonyl)oxazolidin-2-one (750 mg, 2.087 mmol) in THF (15 mL) was cooled to 0° C. and treated with 33% aqueous hydrogen peroxide (0.853 mL, 8.35 mmol). After 5 min, 1 M aqueous LiOH (4.17 mL, 4.17 mmol) was added and the mixture was stirred for 2 h. Saturated aqueous Na$_2$SO$_3$ and saturated aqueous NaHCO$_3$ were added, followed by water. The mixture was partially concentrated, and the aqueous residue was extracted with DCM (3×). The aqueous phase was acidified with 6 M aqueous HCl and extracted with EtOAc. This organic phase was dried over MgSO$_4$, filtered and concentrated to give crude (7R,8R)-7-methyl-1,4-dioxaspiro[4.5]decane-8-carboxylic acid (290 mg, 69% yield), used without further purification. LCMS m/z 201.1 (M+H)+, HPLC t$_R$ 0.60 min (method B).

Step D. (3R,4R)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-3-methylcyclohexan-1-one

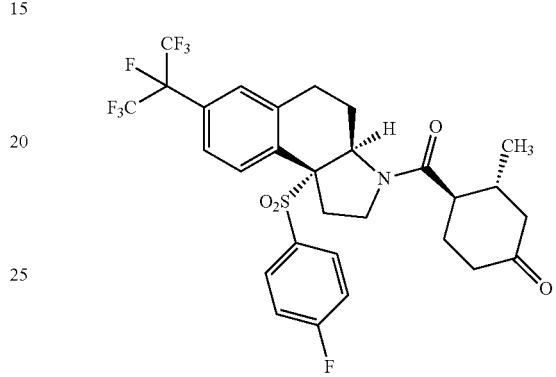

A solution of (3aR,9bR)-9b-((4-fluorophenyl)sulfonyl)-7-(perfluoropropan-2-yl)-2,3,3a,4,5,9b-hexahydro-1H-benzo[e]indole (Intermediate 32; 100 mg, 0.200 mmol) in DMF (1.5 mL) was treated with (7R,8R)-7-methyl-1,4-dioxaspiro[4.5]decane-8-carboxylic acid (40 mg, 0.200 mmol), HATU (76 mg, 0.200 mmol), and 4-methylmorpholine (0.066 mL, 0.599 mmol). The mixture was stirred overnight, then diluted with EtOAc and saturated brine. The organic phase was removed, and washed sequentially with brine (3×), 1 M aqueous HCl and saturated aqueous NaHCO$_3$, dried over MgSO$_4$, filtered, and concentrated to give a mixture of ((3aR,9bR)-9b-((4-fluorophenyl)sulfonyl)-7-(perfluoropropan-2-yl)-1,2,3a,4,5,9b-hexahydro-3H-benzo[e]indol-3-yl)((7R,8R)-7-methyl-1,4-dioxaspiro[4.5]decan-8-yl)methanone (LCMS m/z 682.3 (M+H)$^+$, HPLC t$_R$ 1.11 min) and (3R,4R)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-3-methylcyclohexan-1-one (LCMS m/z 638.3 (M+H)$^+$, HPLC t$_R$ 1.07 min, method B). The material was dissolved in THF (2 mL), treated with 6 M aqueous HCl (1 mL) and stirred at rt overnight. The mixture was extracted with EtOAc, and the organic phase was washed sequentially with brine (3×), 1 M aqueous HCl and saturated aqueous NaHCO$_3$, dried over MgSO$_4$, filtered and concentrated. The residue was purified by column chromatography on silica gel, eluting with EtOAc-hexanes, to give (3R,4R)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-3-methylcyclohexanone (48 mg, 38% yield). LCMS m/z 638.3 (M+H)$^+$, t$_R$ 1.06 min (method B).

Step E: (3R,4R)-4-((3aR,9bR)-9b-((4-fluorophenyl) sulfonyl)-7-(perfluoropropan-2-yl)-2,3,3a,4,5,9b-hexahydro-1H-benzo[e]indole-3-carbonyl)-3-methylcyclohexane-1-carboxylic Acid

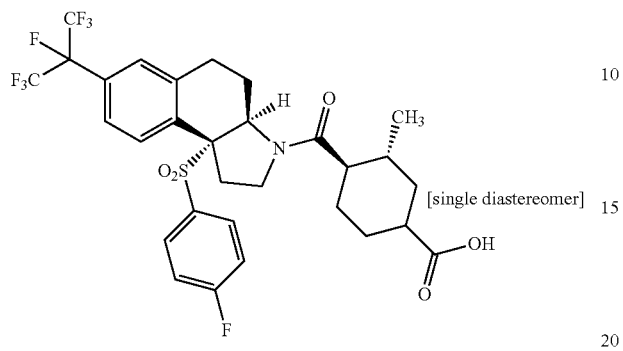

[single diastereomer]

Following the procedures of Example 830 Steps B-E, (3R,4R)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-3-methylcyclohexanone was converted into a single diastereomer of (3R,4R)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-3-methylcyclohexane-1-carboxylic acid. LCMS m/z 668.3 (M+H)$^+$, HPLC $t_R$ 1.05 min (method B).

Example 833

(9b-((3-fluorophenyl)sulfonyl)-7-(perfluoropropan-2-yl)-1,2,3a,4,5,9b-hexahydro-3H-benzo[e]indol-3-yl)((1R,2S)-4-hydroxy-2-methylcyclohexyl)methanone

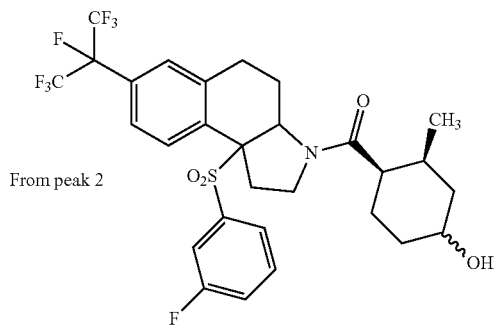 [SMILES: C[C@H]1CC(O)CC[C@H]1C(=O)N1CCC2(S(=O)(=O)c3cccc(F)c3)c3ccc(C(F)(C(F)(F)F)C(F)(F)F)cc3CCC12]

From peak 2

A solution of homochiral (3S,4R)-4-(9b-((3-fluorophenyl)sulfonyl)-7-(perfluoropropan-2-yl)-2,3,3a,4,5,9b-hexahydro-1H-benzo[e]indole-3-carbonyl)-3-methylcyclohexan-1-one (Example 830 Step A; 30 mg, 0.047 mmol) in MeOH (1.5 mL) was treated with NaBH$_4$ (1.78 mg, 0.047 mmol). The mixture was stirred overnight at rt, then was filtered and purified by preparative HPLC (method G, gradient 20-100% B, 10 min) to give (9b-((3-fluorophenyl) sulfonyl)-7-(perfluoropropan-2-yl)-1,2,3a,4,5,9b-hexahydro-3H-benzo[e]indol-3-yl)((1R,2S)-4-hydroxy-2-methylcyclohexyl)methanone as a mixture of diastereomers (9.1 mg, 29% yield). LCMS m/z 640.4 (M+H)$^+$, HPLC $t_R$ 1.07 min (method B). $^1$H NMR (400 MHz, MeOH-d$_4$) δ 7.98 (d, J=8.4 Hz, 1H), 7.61 (d, J=8.1 Hz, 1H), 7.39-7.33 (m, 2H), 7.25 (s, 1H), 7.07 (t, J=8.7 Hz, 2H), 4.04-3.95 (m, 1H), 3.80 (td, J=9.7, 2.5 Hz, 1H), 3.65-3.50 (m, 2H), 2.82-2.76 (m, 1H), 2.69 (dt, J=14.7, 9.6 Hz, 1H), 2.61-2.54 (m, 1H), 2.51-2.44 (m, 1H), 2.16-2.04 (m, 1H), 1.92-1.79 (m, 3H), 1.73-1.64 (m, 4H), 1.26 (dd, J=13.1, 2.8 Hz, 1H), 1.13 (d, J=7.0 Hz, 3H), 1.02 (dd, J=10.6, 6.8 Hz, 1H).

Examples 834 and 835

(9b-((3-fluorophenyl)sulfonyl)-7-(perfluoropropan-2-yl)-1,2,3a,4,5,9b-hexahydro-3H-benzo[e]indol-3-yl)((1R,2S)-4-hydroxy-2,4-dimethylcyclohexyl) methanone (2 Single Diastereomers)

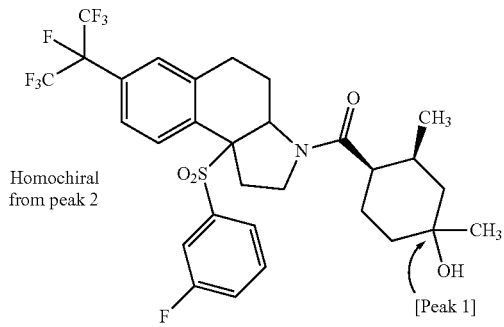

Homochiral from peak 2

[Peak 1]

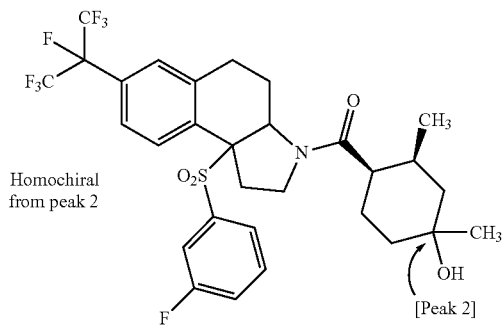

Homochiral from peak 2

[Peak 2]

A solution of homochiral (3S,4R)-4-(9b-((3-fluorophenyl)sulfonyl)-7-(perfluoropropan-2-yl)-2,3,3a,4,5,9b-hexahydro-1H-benzo[e]indole-3-carbonyl)-3-methylcyclohexan-1-one (Example 830 Step A; 30 mg, 0.047 mmol) in THF (1mL) was cooled to 0° C. and treated with methylmagnesium bromide (3 M in diethyl ether; 0.024 mL, 0.071 mmol). The mixture was warmed to rt over 1 h, then was treated with saturated aqueous NaHCO$_3$ and extracted with EtOAc. The organic phase was washed with brine (3×), dried over MgSO$_4$, filtered and concentrated. The residue was purified by preparative HPLC (method E, gradient 40-100% B, 20 min, then method E, gradient 55-80% B, 25 min) to provide two separated diastereomers of (9b-((3-fluorophenyl)sulfonyl)-7-(perfluoropropan-2-yl)-1,2,3a,4,5,9b-hexahydro-3H-benzo[e]indol-3-yl)((1R,2S)-4-hydroxy-2,4-dimethylcyclohexyl)methanone. Peak 1 (Example 834, 3.3 mg, 11% yield) LCMS m/z 654.5 (M+H)$^+$, HPLC $t_R$ 2.36 min (method D). Peak 2 (Example 835, 2.0 mg, 6% yield) LCMS m/z 654.4 (M+H)$^+$, HPLC $t_R$ 2.37 min (method D).

Examples 836 and 837

(1R,2S)-4-(9b-((3-fluorophenyl)sulfonyl)-7-(perfluoropropan-2-yl)-2,3,3a,4,5,9b-hexahydro-1H-benzo[e]indole-3-carbonyl)-2-methylcyclohexane-1-carboxylic Acid (2 Single Diastereomers)

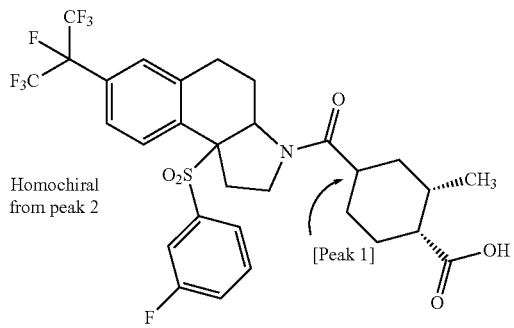

Homochiral from peak 2

[Peak 1]

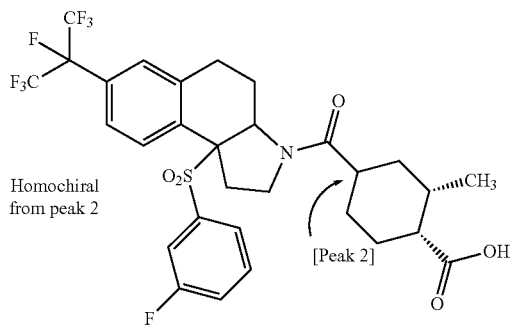

Homochiral from peak 2

[Peak 2]

Step A: Tert-butyl (1R,2S)-2-methyl-4-oxocyclohexane-1-carboxylate

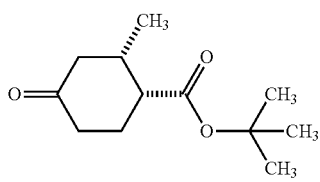

A solution of (1R,2S)-2-methyl-4-oxocyclohexanecarboxylic acid (Tetrahedron 1994, 50, 11743; 150 mg, 0.96 mmol) in tert-butanol (2.5 mL) and THF (2.5 mL) was treated with (E)-tert-butyl N,N'-diisopropylcarbamimidate (385 mg, 1.921 mmol). The mixture was stirred overnight at rt, filtered and concentrated. The residue was taken up in diethyl ether, filtered, and the filtrate was concentrated. The residue was purified by column chromatography on silica gel, eluting with EtOAc-hexanes (gradient from 0-10%), to give tert-butyl (1R,2S)-2-methyl-4-oxocyclohexane-1-carboxylate (62 mg, 30% yield). LCMS m/z 157.1 (M+H—$C_4H_8$)$^+$, HPLC $t_R$ 0.9 min (Method B).

Step B: Tert-butyl (1R,6S)-6-methyl-4-(((trifluoromethyl)sulfonyl)oxy)cyclohex-3-ene-1-carboxylate Following the procedure of Example 830 Step B, tert-butyl (1R,2S)-2-methyl-4-oxocyclohexane-1-carboxylate was converted into tert-butyl (1R,6S)-6-methyl-4-(((trifluoromethyl)sulfonyl)oxy)cyclohex-3-ene-1-carboxylate in 99% yield. LCMS m/z 367.1 (M+Na)$^+$, HPLC $t_R$ 1.15 min (method B).

Step C: Tert-butyl (1R,6S)-4-(9b-((3-fluorophenyl)sulfonyl)-7-(perfluoropropan-2-yl)-2,3,3a,4,5,9b-hexahydro-1H-benzo[e]indole-3-carbonyl)-6-methylcyclohex-3-ene-1-carboxylate

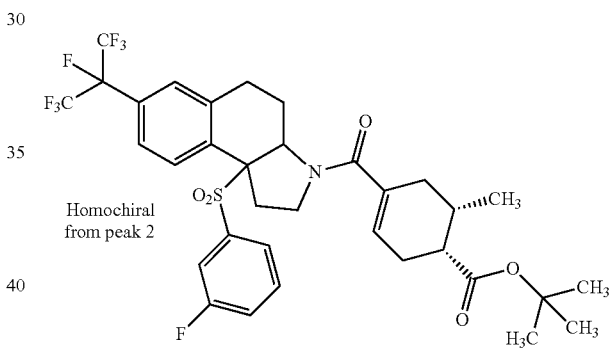

Homochiral from peak 2

A solution of (1R,6S)-tert-butyl 6-methyl-4-(((trifluoromethyl)sulfonyl)oxy) cyclohex-3-enecarboxylate (80 mg, 0.232 mmol) in DMF (1.5 mL) was treated with 9b-((3-fluorophenyl)sulfonyl)-7-(perfluoropropan-2-yl)-2,3,3a,4,5,9b-hexahydro-1H-benzo[e]indole hydrochloride (homochiral, from peak 2, Intermediate 43; 116 mg, 0.232 mmol) and tri-n-butylamine (0.17 mL, 0.697 mmol). Carbon monoxide was bubbled through this solution for 5 min. Bis(triphenylphosphine)palladium(II) chloride (8.15 mg, 0.012 mmol) was added and the mixture was again bubbled with carbon monoxide for 5 min. The mixture was heated at 98° C. under an atmosphere of carbon monoxide (balloon pressure) for 2 h. After cooling to rt, the mixture was diluted with water and extracted with EtOAc. The organic phase was washed with brine (3×), dried over $MgSO_4$, filtered and concentrated. The residue was purified by column chromatography on silica gel, eluting with EtOAc-hexanes, to give homochiral tert-butyl (1R,6S)-4-(9b-((3-fluorophenyl)sulfonyl)-7-(perfluoropropan-2-yl)-2,3,3a,4,5,9b-hexahydro-1H-benzo[e]indole-3-carbonyl)-6-methylcyclohex-3-ene-1-carboxylate (63 mg, 38% yield). LCMS m/z 722.5 (M+H)$^+$, HPLC $t_R$ 1.21 min (method B).

Step D: Tert-butyl (1R,2S)-4-(9b-((3-fluorophenyl)
sulfonyl)-7-(perfluoropropan-2-yl)-233a,4,5,9b-
hexahydro-1H-benzo[e]indole-3-carbonyl)-2-meth-
ylcyclohexane-1-carboxylate (Mixture of
Diastereomers)

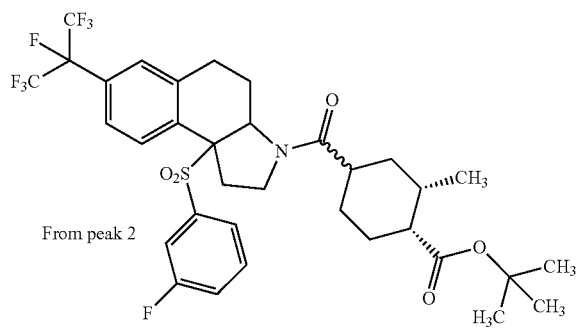 [SMILES: C[C@H]1CC(C(=O)N2CCC3(S(=O)(=O)c4cccc(F)c4)c4ccc(C(F)(C(F)(F)F)C(F)(F)F)cc4CCC23)CC[C@H]1C(=O)OC(C)(C)C]

From peak 2

A solution of tert-butyl (1R,6S)-4-(9b-((3-fluorophenyl)
sulfonyl)-7-(perfluoropropan-2-yl)-2,3,3a,4,5,9b-hexa-
hydro-1H-benzo[e]indole-3-carbonyl)-6-methylcyclohex-3-
ene-1-carboxylate (30 mg, 0.042 mmol) in DCM (1.5 mL)
was treated with iridium(I) hexafluorophosphate (1,5-cy-
clooctadiene)-(pyridine)-(tricyclohexylphosphine) (Crab-
tree's catalyst; 8 mg, 9.94 μmol) and stirred at rt overnight
under a hydrogen atmosphere (balloon pressure). The mix-
ture was filtered and concentrated to provide tert-butyl
(1R,2S)-4-(9b-((3-fluorophenyl)sulfonyl)-7-(perfluoropro-
pan-2-yl)-2,3,3a,4,5,9b-hexahydro-1H-benzo[e]indole-3-
carbonyl)-2-methylcyclohexane-1-carboxylate as a mixture
of diastereomers (25 mg, 83% yield). LCMS m/z 724.6
(M+H)$^+$, HPLC $t_R$ 1.23 min (method B).

Step E: (1R,2S)-4-(9b-((3-fluorophenyl)sulfonyl)-7-
(perfluoropropan-2-yl)-2,3,3a,4,5,9b-hexahydro-1H-
benzo[e]indole-3-carbonyl)-2-methylcyclohexane-1-
carboxylic Acid (2 Single Diastereomers)

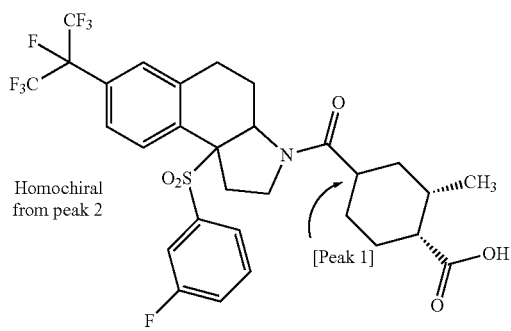

Homochiral
from peak 2

[Peak 1]

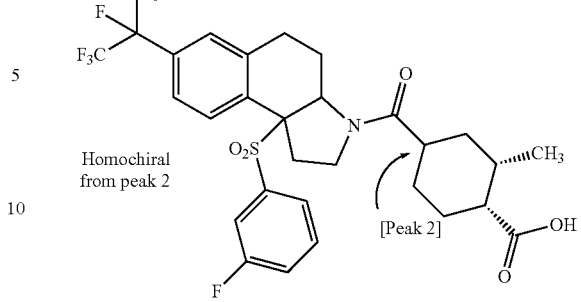

Homochiral
from peak 2

[Peak 2]

A solution of tert-butyl (1R,2S)-4-(9b-((3-fluorophenyl)
sulfonyl)-7-(perfluoropropan-2-yl)-2,3,3a,4,5,9b-hexa-
hydro-1H-benzo[e]indole-3-carbonyl)-2-methylcyclo-
hexane-1-carboxylate (25 mg, 0.035 mmol) in DCM (1mL)
was treated with TFA (3 mL) and stirred at rt for 30 min. The
mixture was concentrated and the residue was purified by
preparative HPLC (method G, gradient 20-100% B, 10 min)
to provide two homochiral diastereomers of (1R,2S)-4-(9b-
((3-fluorophenyl)sulfonyl)-7-(perfluoropropan-2-yl)-2,3,3a,
4,5,9b-hexahydro-1H-benzo[e]indole-3-carbonyl)-2-meth-
ylcyclohexane-1-carboxylic acid. Peak 1 (Example 836; $t_R$
9.3 min, 9.5 mg, 39% yield). LCMS m/z 668.4 (M+H)$^+$,
HPLC $t_R$ 1.06 min (method B). $^1$H NMR (400 MHz, MeOH-
d$_4$) δ 8.00 (d, J=8.4 Hz, 1H), 7.63 (d, J=8.6 Hz, 1H),
7.49-7.37 (m, 2H), 7.30-7.25 (m, 2H), 6.89 (dt, J=8.1, 1.9
Hz, 1H), 4.81-4.77 (m, 1H), 3.90 (dd, J=10.2, 5.4 Hz, 2H),
3.58 (dt, J=14.9, 5.2 Hz, 1H), 2.79-2.67 (m, 2H), 2.64-2.49
(m, 3H), 2.48-2.40 (m, 1H), 2.00-1.87 (m, 1H), 1.86-1.66
(m, 5H), 1.59-1.47 (m, 1H), 1.31 (qd, J=12.7, 3.2 Hz, 1H),
1.02 (d, J=7.0 Hz, 3H). Peak 2 (Example 837; $t_R$ 9.9 min, 6
mg, 25% yield). LCMS m/z 668.3 (M+H)$^+$, HPLC $t_R$ 1.08
min (method B). $^1$H NMR (400 MHz, MeOH-d$_4$) δ 8.00 (d,
J=8.4 Hz, 1H), 7.63 (d, J=8.6 Hz, 1H), 7.48-7.36 (m, 2H),
7.31-7.25 (m, 2H), 6.87 (dt, J=8.2, 2.0 Hz, 1H), 4.80-4.78
(m, 1H), 4.01-3.82 (m, 2H), 3.57 (ddd, J=14.9, 8.0, 3.1 Hz,
1H), 2.72 (dt, J=14.8, 9.5 Hz, 1H), 2.65-2.51 (m, 4H),
2.49-2.39 (m, 1H), 2.17-2.08 (m, 1H), 2.02-1.64 (m, 5H),
1.52 (d, J=13.0 Hz, 1H), 1.37-1.23 (m, 1H), 1.07 (d, J=6.8
Hz, 3H).

Examples 838 and 839

(1R,2S)-4-((3aR,9bR)-9b-((4-fluorophenyl)sulfo-
nyl)-7-(perfluoropropan-2-yl)-2,3,3a,4,5,9b-hexa-
hydro-1H-benzo[e]indole-3-carbonyl)-2-methylcy-
clohexane-1-carboxylic Acid (2 Single
Diastereomers)

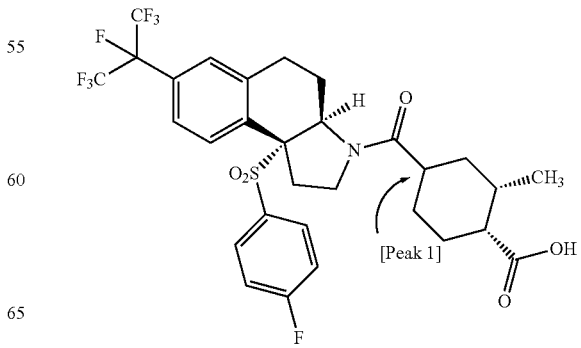

[Peak 1]

-continued

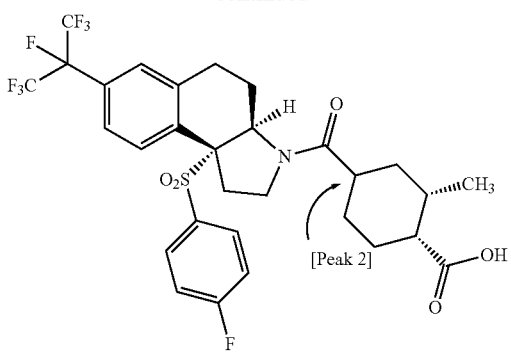

[Peak 2]

The two homochiral diastereomers of (1R,2S)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-2-methylcyclohexane-1-carboxylic acid were prepared using the procedures of Examples 836 and 837, using Intermediate 32 in place of Intermediate 43 in Step C. Peak 1 (Example 838) LCMS m/z 668.1 (M+H)+, HPLC $t_R$ 1.99 min (method D). Peak 2 (Example 839) LCMS m/z 668.2 (M+H)+, HPLC $t_R$ 2.27 min (method D).

Examples 840 and 841

(1R,2R)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-2-methylcyclohexane-1-carboxylic Acid (2 Single Diastereomers)

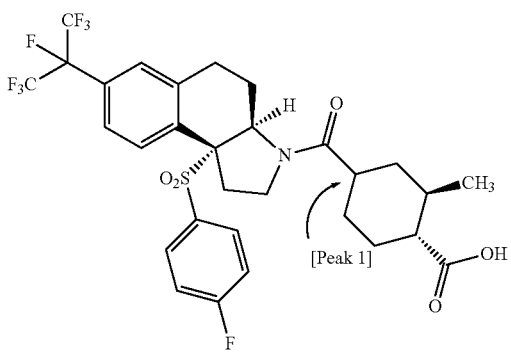

[Peak 1]

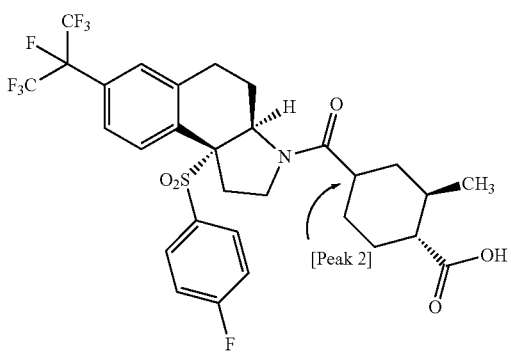

[Peak 2]

Step A. (4R,5R)-4-((R)-4-benzyl-2-oxooxazolidine-3-carbonyl)-5-methylcyclohex-1-en-1-yl Trifluoromethanesulfonate

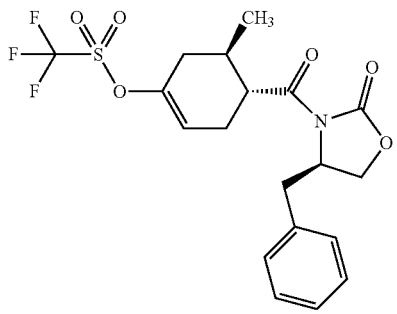 [SMILES: C[C@@H]1CC(OS(=O)(=O)C(F)(F)F)=CC[C@H]1C(=O)N1C(=O)OC[C@H]1Cc1ccccc1]

Using the procedure of Example 830 Step B, (R)-4-benzyl-3-((1R,2R)-2-methyl-4-oxocyclohexane-1-carbonyl)oxazolidin-2-one (Example 832 Step A) was converted into crude (4R,5R)-4-((R)-4-benzyl-2-oxooxazolidine-3-carbonyl)-5-methylcyclohex-1-en-1-yl trifluoromethanesulfonate in 75% yield. This material was used without purification.

Step B: (4R)-4-benzyl-3-((1R,2R)-4-((3aR,9bR)-9b-((4-fluorophenylsulfonyl)-sulfonyl)-7-(perfluoropropan-2-yl)-2,3,3a,4,5,9b-hexahydro-1H-benzo[e]indole-3-carbonyl)-2-methylcyclohexane-1-carbonyl)oxazolidin-2-one

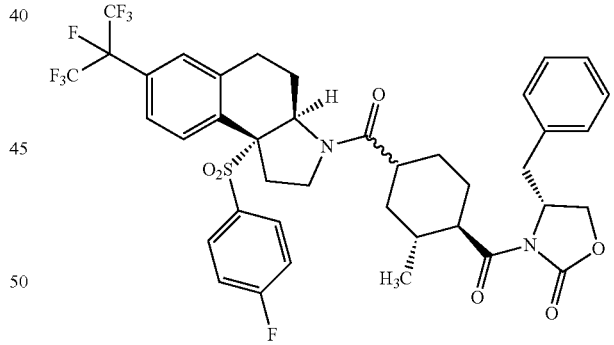

Using the procedures of Examples 836 and 837, Steps C and D, (4R,5R)-4-((R)-4-benzyl-2-oxooxazolidine-3-carbonyl)-5-methylcyclohex-1-en-1-yl trifluoromethanesulfonate and Intermediate 32 were converted into (4R)-4-benzyl-3-((1R,2R)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-2-methylcyclohexane-1-carbonyl)oxazolidin-2-one as a mixture of two diastereomers in 27% yield. LCMS m/z 827.7 (M+H)+, HPLC $t_R$ 1.17 min (method B).

Step C: (1R,2R)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-2-methylcyclohexane-1-carboxylic Acid (2 Single Diastereomers)

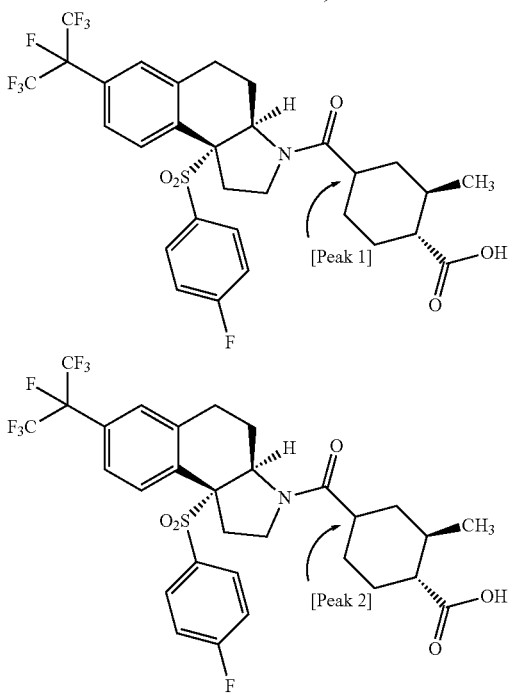

Using the procedure of Example 832 Step C, followed by preparative HPLC separation, the mixture of diastereomers of (4R)-4-benzyl-3-((1R,2R)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-2-methylcyclohexane-1-carbonyl)oxazolidin-2-one was converted into the two homochiral diastereomers of (1R,2R)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)-2-methylcyclohexane-1-carboxylic acid. Peak 1 (Example 840; 28% yield) LCMS m/z 668.5 (M+H)$^+$, HPLC t$_R$ 1.05 min (method B). Peak 2 (Example 841; 8% yield) LCMS m/z 668.5 (M+H)$^+$, HPLC t$_R$ 1.08 min (method B).

Examples 842 and 843

(1R,2R)-4-(9b-((4-fluorophenyl)sulfonyl)-7-(perfluoropropan-2-yl)-1,2,3,3a,4,9b-hexahydrochromeno[3,4-b]pyrrole-3-carbonyl)-2-methylcyclohexane-1-carboxylic Acid (2 Single Diastereomers)

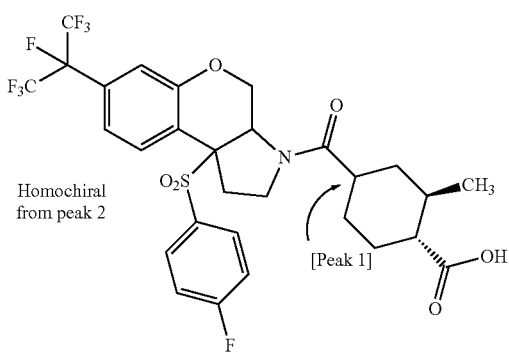

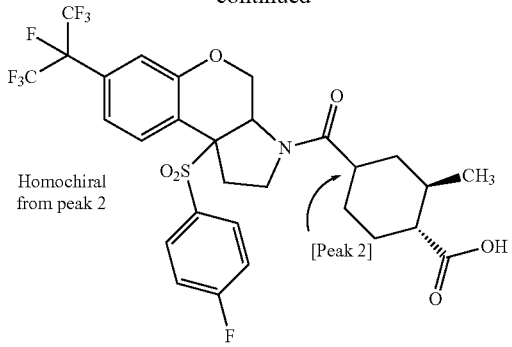

Two homochiral diastereomers of (1R,2R)-4-(9b-((4-fluorophenyl)sulfonyl)-7-(perfluoropropan-2-yl)-1,2,3,3a,4,9b-hexahydrochromeno[3,4-b]pyrrole-3-carbonyl)-2-methylcyclohexane-1-carboxylic acid were prepared using the procedures of Examples 840 and 841 but using Intermediate 38 instead of Intermediate 32 in Step B. Peak 1 (Example 842) LCMS m/z 670.0 (M+H)$^+$, HPLC t$_R$ 2.01 min (method C). Peak 2 (Example 843) LCMS m/z 670.1 (M+H)$^+$, HPLC t$_R$ 2.14 min (method C).

Example 844

(1R,4r)-4-((3aR,9bR)-8-chloro-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylic Acid

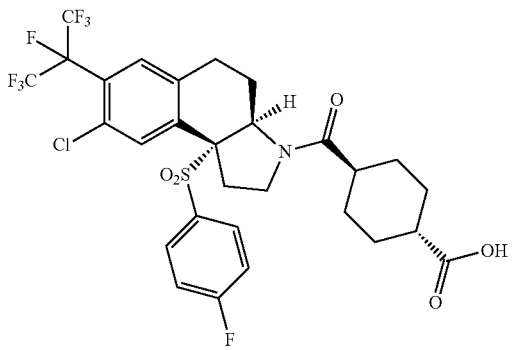

A solution of (1R,4r)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylic acid (Example 1; 124 mg, 0.190 mmol) in concentrated sulfuric acid (1 mL) was treated with N-chlorosuccinimide (50.7 mg, 0.379 mmol). The mixture was stirred at rt overnight, then was heated at 50° C. for 7 h. The mixture was cooled to −78° C. and treated dropwise with water. The mixture was warmed to rt and extracted with EtOAc. The organic phase was washed sequentially with water and brine, dried and concentrated. The residue was purified by preparative HPLC (method F, gradient 45-90% B, 27 min) to provide (1R,4r)-4-((3aR,9bR)-8-chloro-9b-((4-fluorophenyl)sulfonyl)-7-(perfluoropropan-2-yl)-2,3,3a, 4,5,9b-hexahydro-1H-benzo[e]indole-3-carbonyl)cyclohexane-1-carboxylic acid (6.5 mg, 5% yield). LCMS m/z 688.0 (M+H)$^+$, HPLC t$_R$ 2.04 min (method C).

Example 845

(1R,4r)-4-((3aR,9bR)-9b-((4-fluorophenyl)sulfonyl)-8-methyl-7-(perfluoropropan-2-yl)-2,3,3a,4,5,9b-hexahydro-1H-benzo[e]indole-3-carbonyl)cyclohexane-1-carboxylic Acid

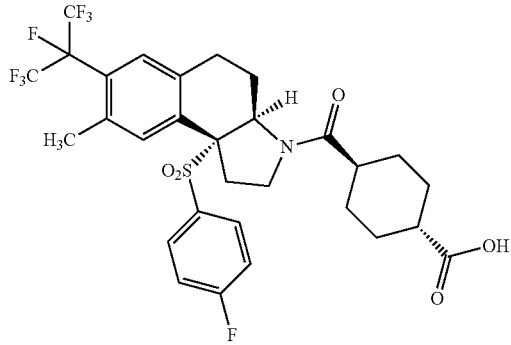 [SMILES: Cc1cc2c(cc1C(F)(C(F)(F)F)C(F)(F)F)CC[C@H]1N(C(=O)[C@H]3CC[C@H](C(=O)O)CC3)CC[C@@]21S(=O)(=O)c1ccc(F)cc1]

Step A: (1R,4r)-4-((3aR,9bR)-8-bromo-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylic Acid

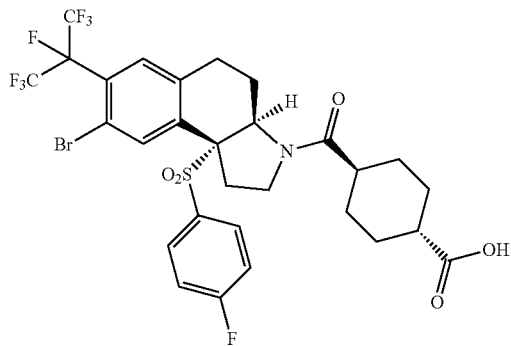

A solution of N-bromosuccinimide (40.8 mg, 0.230 mmol) in concentrated sulfuric acid (1 mL) was stirred for 10 min at rt, then was treated with (1R,4r)-4-((3 aR,9bR)-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylic acid (Example 1; 100 mg, 0.153 mmol). The mixture was stirred at rt overnight, then was cooled to −78° C. and treated dropwise with water. The mixture was warmed to rt and extracted three times with EtOAc. The combined organic phases were washed sequentially with water and brine, dried and concentrated. The residue was purified by column chromatography on silica gel (12 g), eluting with MeOH-DCM (gradient from 0-10%), to provide (1R,4r)-4-((3aR,9bR)-8-bromo-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylic acid (22 mg, 20% yield), contaminated with starting material. LCMS m/z 732.0 (M+H)$^+$, HPLC $t_R$ 1.07 min (method B). $^1$H NMR (400 MHz, CDCl$_3$) δ 8.20 (s, 1H), 7.40-7.31 (m, 2H), 7.10 (br. s., 1H), 7.04-6.96 (m, 2H), 4.77 (dd, J=12.1, 4.8 Hz, 1H), 4.10-4.01 (m, 1H), 3.93-3.80 (m, 1H), 3.66-3.56 (m, 1H), 2.65-2.39 (m, 6H), 2.28-2.06 (m, 2H), 1.98-1.45 (m, 6H), 1.26-1.11 (m, 1H).

Step B: (1R,4r)-4-((3aR,9bR)-9b-((4-fluorophenyl)sulfonyl)-8-methyl-7-(perfluoropropan-2-yl)-2,3,3a,4,5,9b-hexahydro-1H-benzo[e]indole-3-carbonyl)cyclohexane-1-carboxylic Acid

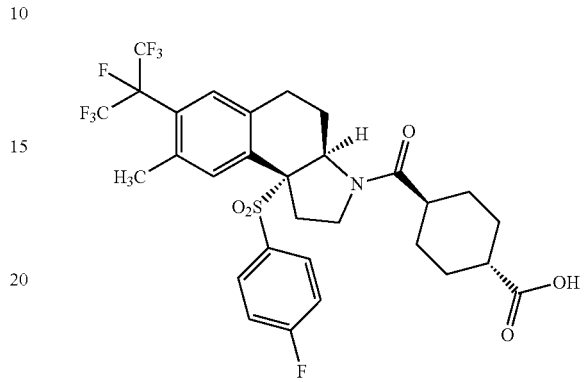

A solution of the impure (1R,4r)-4-((3aR,9bR)-8-bromo-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylic acid from Step A (22 mg, 0.030 mmol) and iron(III) acetylacetonate (2.121 mg, 6.01 µmol) in THF (1 mL) was subjected to 3 evacuate-fill cycles with nitrogen. Methylmagnesium bromide (3 M in diethyl ether; 0.015 mL, 0.045 mmol) was added dropwise. The mixture was stirred at rt for 30 min, then was diluted with EtOAc, washed sequentially with 0.5 M aqueous HCl, water and brine, and dried and concentrated. The residue was purified by preparative HPLC to provide (1R,4r)-4-((3aR,9bR)-9b-((4-fluorophenyl)sulfonyl)-8-methyl-7-(perfluoropropan-2-yl)-2,3,3a,4,5,9b-hexahydro-1H-benzo[e]indole-3-carbonyl)cyclohexane-1-carboxylic acid (3.6 mg, 18% yield). LCMS m/z 668.0 (M+H)$^+$, HPLC $t_R$ 1.96 min (method C).

Example 846

(1R,4r)-4-((3aR,9bR)-9b-((4-fluorophenyl)sulfonyl)-6,8-dimethyl(d$_6$)-7-(perfluoropropan-2-yl)-2,3,3a,4,5,9b-hexahydro-1H-benzo[e]indole-3-carbonyl)cyclohexane-1-carboxylic Acid

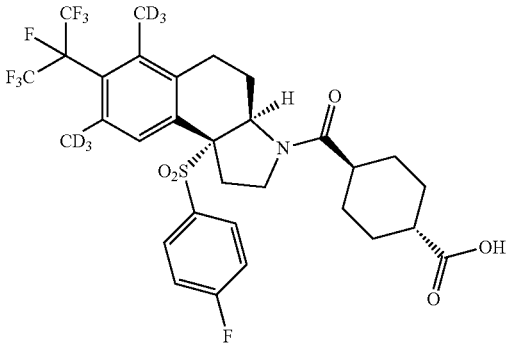 [SMILES: [2H]C([2H])([2H])c1cc2c(c(C([2H])([2H])[2H])c1C(F)(C(F)(F)F)C(F)(F)F)CC[C@H]1N(C(=O)[C@H]3CC[C@H](C(=O)O)CC3)CC[C@@]21S(=O)(=O)c1ccc(F)cc1]

Step A: (1R,4r)-4-((3aR,9bR)-6,8-dibromo-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylic Acid

Step B: (1R,4r)-4-((3aR,9bR)-9b-((4-fluorophenyl)sulfonyl)-6,8-dimethyl(d₆)-7-(perfluoropropan-2-yl)-2,3,3a,4,5,9b-hexahydro-1H-benzo[e]indole-3-carbonyl)cyclohexane-1-carboxylic Acid

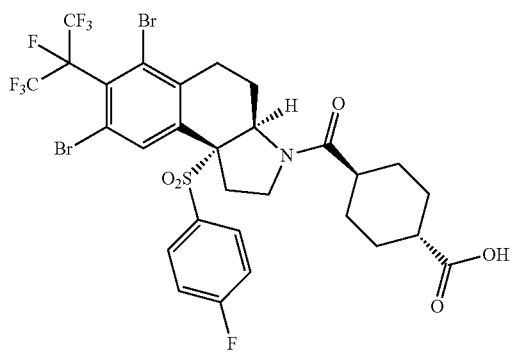 [SMILES: O=C(O)[C@H]1CC[C@H](C(=O)N2CC[C@@]3(S(=O)(=O)c4ccc(F)cc4)c4cc(Br)c(C(F)(C(F)(F)F)C(F)(F)F)c(Br)c4CC[C@@H]23)CC1]

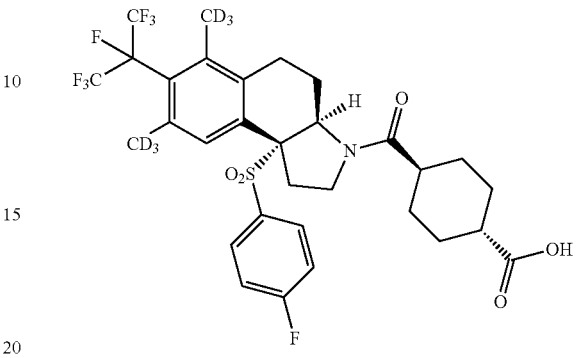

A mixture of (1R,4r)-4-((3aR,9bR)-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylic acid (Example 1; 120 mg, 0.184 mmol) and N-bromosuccinimide (98 mg, 0.551 mmol) was dissolved in concentrated sulfuric acid (1 mL). The mixture was stirred at rt overnight, then was cooled to −78° C. and treated dropwise with water. The mixture was warmed to rt and extracted with EtOAc. The organic phase was washed sequentially with water (twice) and brine, dried and concentrated. The residue was purified by column chromatography on silica gel (12 g), eluting with EtOAc-hexanes (gradient from 0-100%), to provide (1R,4r)-4-((3aR,9bR)-6,8-dibromo-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylic acid (64 mg, 43% yield). LCMS m/z 809.9 (M+H)⁺, HPLC $t_R$ 1.11 min (method B).

A solution of (1R,4r)-4-((3aR,9bR)-8-bromo-9b-((4-fluorophenyl)sulfonyl)-7-(perfluoropropan-2-yl)-2,3,3a,4,5,9b-hexahydro-1H-benzo[e]indole-3-carbonyl)cyclohexane-1-carboxylic acid (32 mg, 0.039 mmol) and iron(III) acetylacetonate (2.79 mg, 7.89 μmol) in THF (1 mL) was subjected to 3 evacuate-fill cycles with nitrogen. Methyl(d₃) magnesium bromide (1 M in diethyl ether; 0.118 mL, 0.118 mmol) was added dropwise. The mixture was stirred at rt for 30 min, then was diluted with EtOAc, washed sequentially with 0.5 M aqueous HCl, water and brine, and dried and concentrated. The residue was purified by preparative HPLC (method F, gradient 45-90% B, 27 min) to provide (1R,4r)-4-((3aR,9bR)-9b-((4-fluorophenyl)sulfonyl)-6,8-dimethyl (d₆)-7-(perfluoropropan-2-yl)-2,3,3a,4,5,9b-hexahydro-1H-benzo[e]indole-3-carbonyl)cyclohexane-1-carboxylic acid (9 mg, 17% yield). LCMS m/z 688.0 (M+H)⁺, HPLC $t_R$ 2.04 min (method C).

Additional examples prepared according to the procedures used to prepare Examples 1-846 or similar procedures are shown in Table 19.

TABLE 19

| Ex. # | Structure | LCMS m/z observed | HPLC $t_R$ (min) | HPLC method |
|---|---|---|---|---|
| 847 | 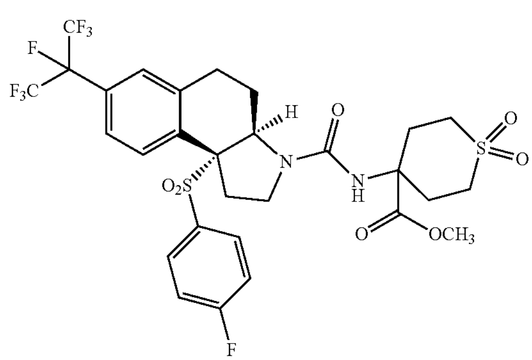 [SMILES: COC(=O)C1(NC(=O)N2CC[C@@]3(S(=O)(=O)c4ccc(F)cc4)c4ccc(C(F)(C(F)(F)F)C(F)(F)F)cc4CC[C@@H]23)CCS(=O)(=O)CC1] | 733.1 (M + H)⁺ | 2.14 | C |

TABLE 19-continued

| Ex. # | Structure | LCMS m/z observed | HPLC t_R (min) | HPLC method |
|---|---|---|---|---|
| 848 | 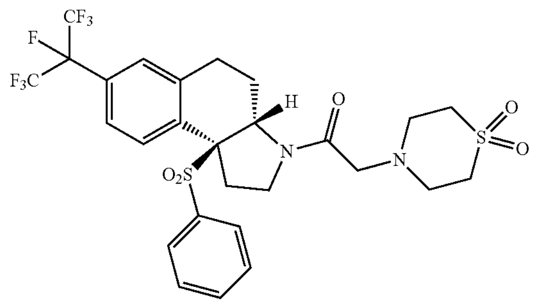 [SMILES: O=C(CN1CCS(=O)(=O)CC1)N1CC[C@]2(S(=O)(=O)c3ccccc3)c3ccc(C(F)(C(F)(F)F)C(F)(F)F)cc3CC[C@H]12] | 657.1 (M + H)+ | 2.07 | C |
| 849 | Homochiral from peak 2 | 720.8 (M + H)+ | 2.39 | C |
| 850 | 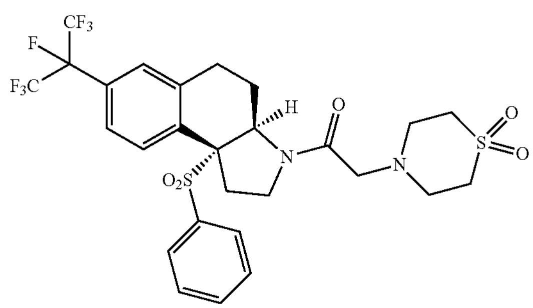 [SMILES: O=C(CN1CCS(=O)(=O)CC1)N1CC[C@@]2(S(=O)(=O)c3ccccc3)c3ccc(C(F)(C(F)(F)F)C(F)(F)F)cc3CC[C@@H]12] | 656.9 (M + H)+ | 2.07 | C |
| 851 | 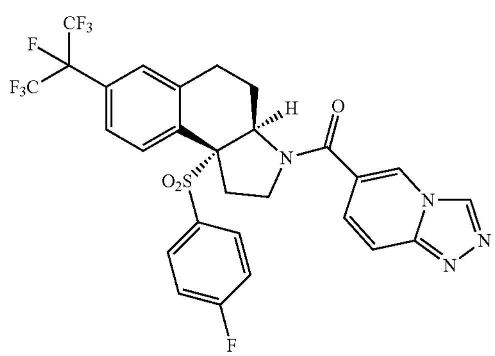 [SMILES: O=C(c1ccc2nncn2c1)N1CC[C@@]2(S(=O)(=O)c3ccc(F)cc3)c3ccc(C(F)(C(F)(F)F)C(F)(F)F)cc3CC[C@@H]12] | 645.3 (M + H)+ | 0.97 | B |

TABLE 19-continued
| Ex. # | Structure | LCMS m/z observed | HPLC t$_R$ (min) | HPLC method |
|---|---|---|---|---|
| 852 | 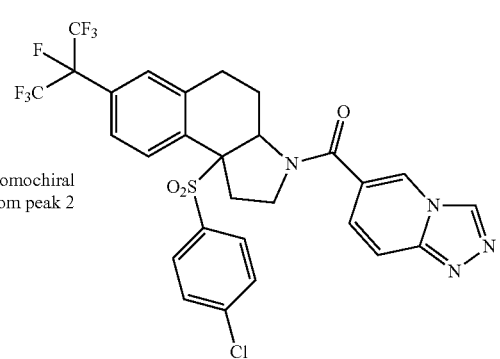 Homochiral from peak 2 | 661.1 (M + H)$^+$ | 1.00 | B |
| 853 | 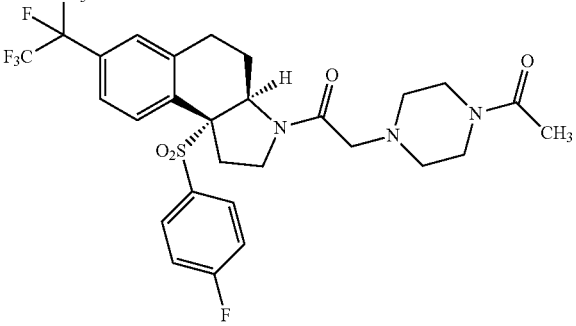 | 668.3 (M + H)$^+$ | 0.85 | B |
| 854 | 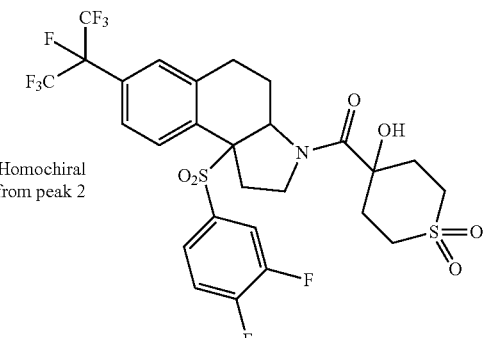 Homochiral from peak 2 | 693.3 (M + H)$^+$ | 2.17 | C |
| 855 | 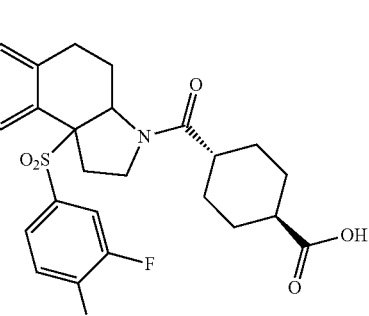 Homochiral from peak 2 | 672.1 (M + H)$^+$ | 2.02 | C |

TABLE 19-continued

| Ex. # | Structure | LCMS m/z observed | HPLC t$_R$ (min) | HPLC method |
|---|---|---|---|---|
| 856 | 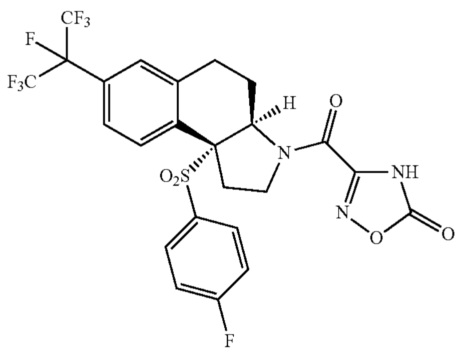 [SMILES: O=C(c1noc(=O)[nH]1)N1CC[C@@]2(S(=O)(=O)c3ccc(F)cc3)c3ccc(C(F)(C(F)(F)F)C(F)(F)F)cc3CC[C@@H]12] | 612.1 (M + H)$^+$ | 2.26 | D |
| 857 | Homochiral from peak 2 | 691.1 (M + H)$^+$ | 2.31 | C |
| 858 | 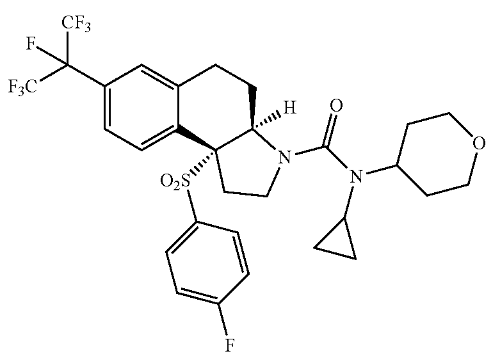 [SMILES: O=C(N(C1CCOCC1)C1CC1)N1CC[C@@]2(S(=O)(=O)c3ccc(F)cc3)c3ccc(C(F)(C(F)(F)F)C(F)(F)F)cc3CC[C@@H]12] | 667.0 (M + H)$^+$ | 2.42 | C |
| 859 | Homochiral from peak 2 | 707.0 (M + H)$^+$ | 2.29 | C |

TABLE 19-continued

| Ex. # | Structure | LCMS m/z observed | HPLC $t_R$ (min) | HPLC method |
|---|---|---|---|---|
| 860 | Homochiral from peak 2 | 628.1 (M + H)+ | 1.88 | C |
| 861 | 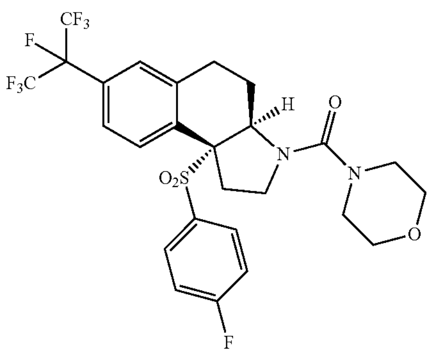 [SMILES: O=C(N1CCOCC1)N1CC[C@@]2(S(=O)(=O)c3ccc(F)cc3)c3ccc(C(F)(C(F)(F)F)C(F)(F)F)cc3CC[C@@H]12] | 612.8 (M + H)+ | 2.25 | C |
| 862 | 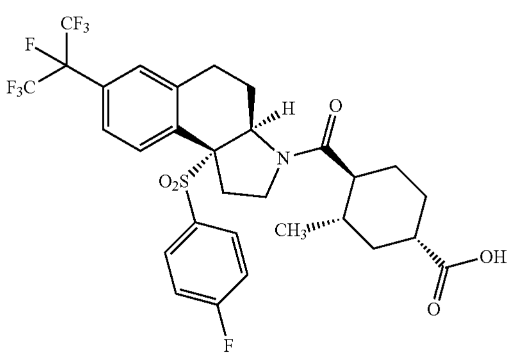 [SMILES: C[C@H]1C[C@@H](C(=O)O)CC[C@@H]1C(=O)N1CC[C@@]2(S(=O)(=O)c3ccc(F)cc3)c3ccc(C(F)(C(F)(F)F)C(F)(F)F)cc3CC[C@@H]12] | 668.2 (M + H)+ | 1.94 | C |
| 863 | 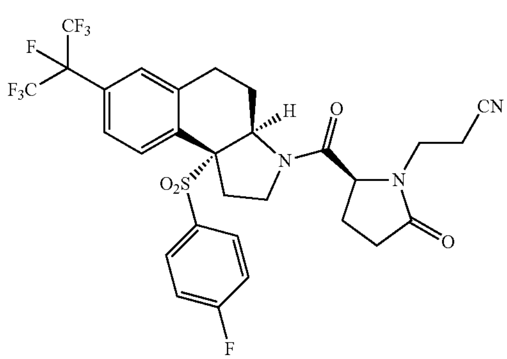 [SMILES: N#CCCN1C(=O)CC[C@H]1C(=O)N1CC[C@@]2(S(=O)(=O)c3ccc(F)cc3)c3ccc(C(F)(C(F)(F)F)C(F)(F)F)cc3CC[C@@H]12] | 663.9 (M + H)+ | 2.14 | C |

TABLE 19-continued

| Ex. # | Structure | LCMS m/z observed | HPLC t$_R$ (min) | HPLC method |
|---|---|---|---|---|
| 864 | 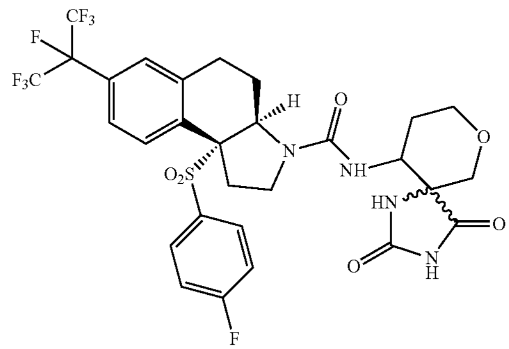 | 711.3 (M + H)$^+$ | 1.92 | C |
| 865 | 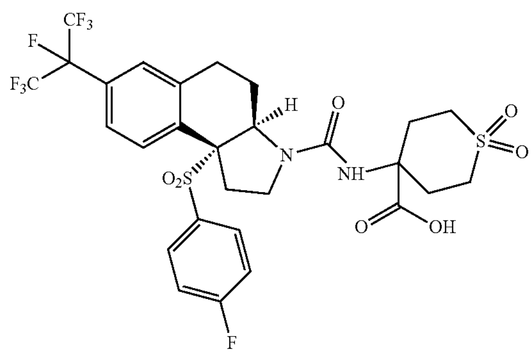 [SMILES: O=C(NC1(C(=O)O)CCS(=O)(=O)CC1)N1CC[C@@]2(S(=O)(=O)c3ccc(F)cc3)c3ccc(C(F)(C(F)(F)F)C(F)(F)F)cc3CC[C@@H]12] | 719.3 (M + H)$^+$ | 1.68 | C |
| 866 | 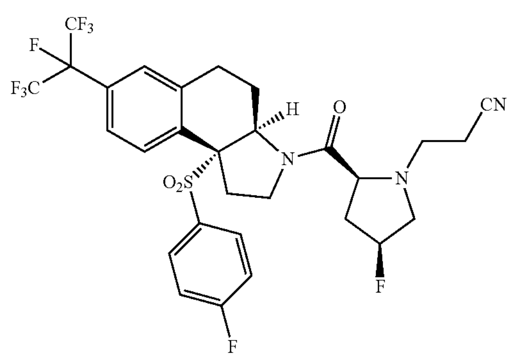 [SMILES: N#CCCN1C[C@@H](F)C[C@H]1C(=O)N1CC[C@@]2(S(=O)(=O)c3ccc(F)cc3)c3ccc(C(F)(C(F)(F)F)C(F)(F)F)cc3CC[C@@H]12] | 667.9 (M + H)$^+$ | 2.29 | C |
| 867 Homochiral from peak 2 | | 730.1 (M + H)$^+$ | 2.23 | C |

TABLE 19-continued

| Ex. # | Structure | LCMS m/z observed | HPLC t_R (min) | HPLC method |
|---|---|---|---|---|
| 868 | 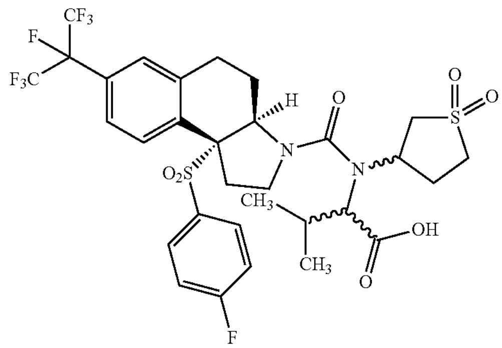 | 761.0 (M + H)+ | 1.93 | C |
| 869 | 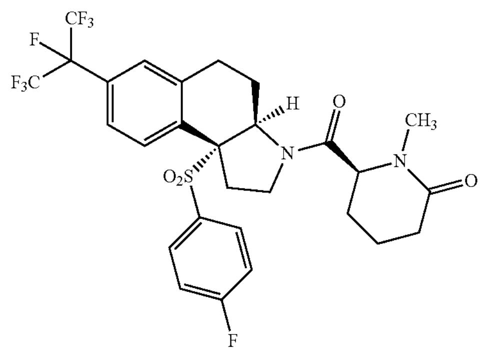 [SMILES: CN1C(=O)CCC[C@H]1C(=O)N1CC[C@@]2(S(=O)(=O)c3ccc(F)cc3)c3ccc(C(F)(C(F)(F)F)C(F)(F)F)cc3CC[C@@H]12] | 639.2 (M + H)+ | 2.18 | C |
| 870 | 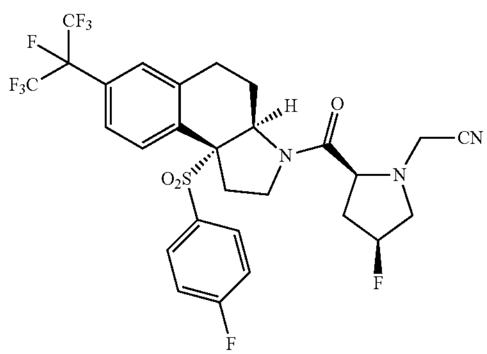 [SMILES: N#CCN1C[C@@H](F)C[C@H]1C(=O)N1CC[C@@]2(S(=O)(=O)c3ccc(F)cc3)c3ccc(C(F)(C(F)(F)F)C(F)(F)F)cc3CC[C@@H]12] | 654.1 (M + H)+ | 2.27 | C |
| 871 | 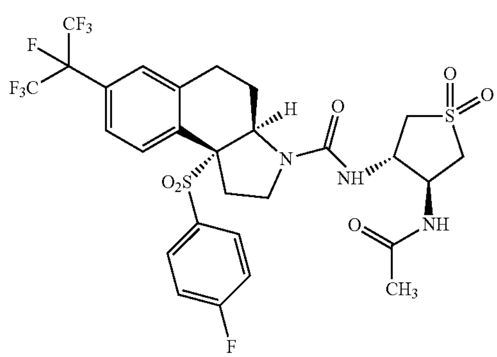 [SMILES: CC(=O)N[C@@H]1CS(=O)(=O)C[C@H]1NC(=O)N1CC[C@@]2(S(=O)(=O)c3ccc(F)cc3)c3ccc(C(F)(C(F)(F)F)C(F)(F)F)cc3CC[C@@H]12] | 718.1 (M + H)+ | 2.01 | C |

TABLE 19-continued
| Ex. # | Structure | LCMS m/z observed | HPLC t$_R$ (min) | HPLC method |
|---|---|---|---|---|
| 872 | 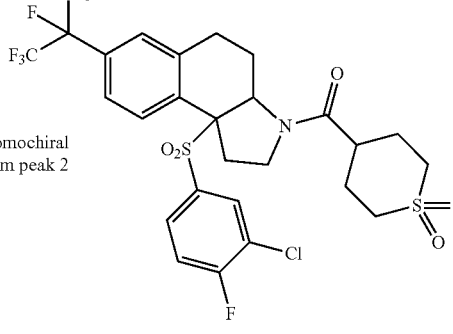 Homochiral from peak 2 | 694.1 (M + H)$^+$ | 2.29 | C |
| 873 | 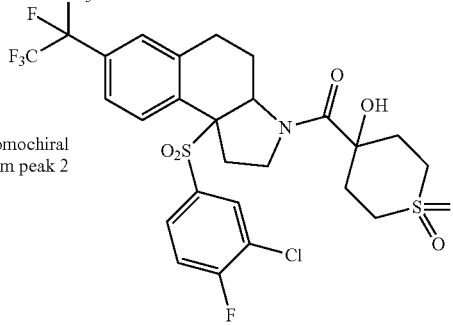 Homochiral from peak 2 | 710.1 (M + H)$^+$ | 2.26 | C |
| 874 | 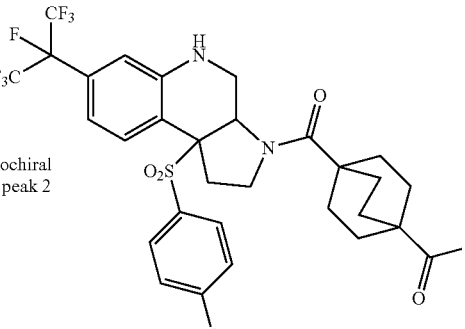 Homochiral from peak 2 | 697.0 (M + H)$^+$ | 2.28 | D |
| 875 | 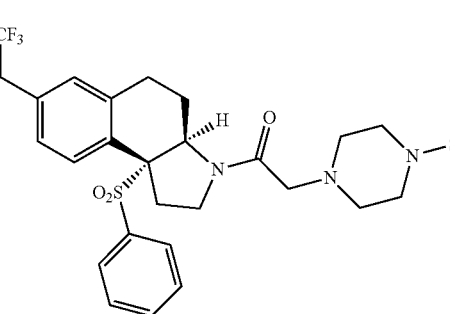 | 704.1 (M + H)$^+$ | 2.17 | C |

TABLE 19-continued

| Ex. # | Structure | LCMS m/z observed | HPLC $t_R$ (min) | HPLC method |
|---|---|---|---|---|
| 876 | Homochiral cis peak 1 | 732.2 (M + H)+ | 2.00 | C |
| 877 | 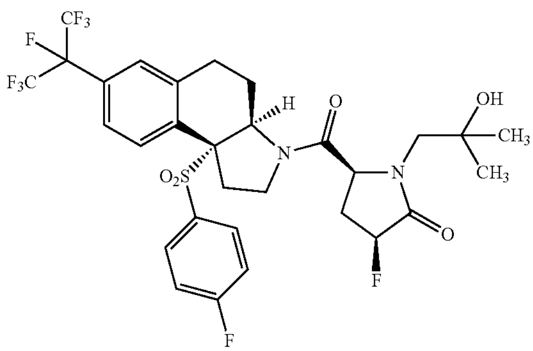 [SMILES: CC(C)(O)CN1C(=O)[C@@H](F)C[C@H]1C(=O)N1CC[C@@]2(S(=O)(=O)c3ccc(F)cc3)c3ccc(C(F)(C(F)(F)F)C(F)(F)F)cc3CC[C@@H]12] | 701.1 (M + H)+ | 2.20 | C |
| 878 | Homochiral cis peak 2 | 732.1 (M + H)+ | 1.99 | C |
| 879 | 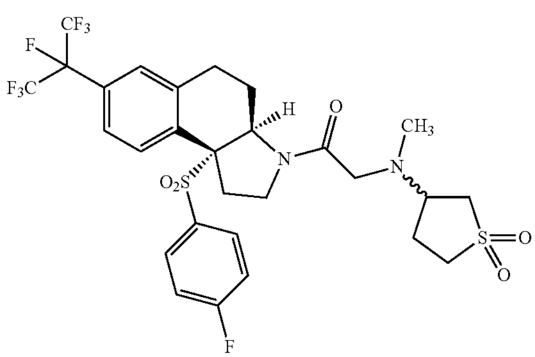 [SMILES: CN(CC(=O)N1CC[C@@]2(S(=O)(=O)c3ccc(F)cc3)c3ccc(C(F)(C(F)(F)F)C(F)(F)F)cc3CC[C@@H]12)C1CCS(=O)(=O)C1] | 689.1 (M + H)+ | 0.88 | B |

TABLE 19-continued
| Ex. # | Structure | LCMS m/z observed | HPLC $t_R$ (min) | HPLC method |
|---|---|---|---|---|
| 880 | 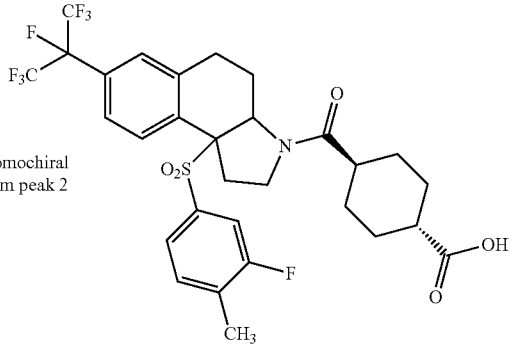 Homochiral from peak 2 | 668.1 (M + H)+ | 2.07 | C |
| 881 | 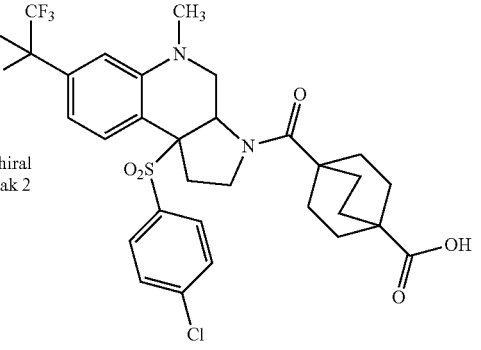 Homochiral from peak 2 | 711.2 | 2.17 | C |
| 882 | 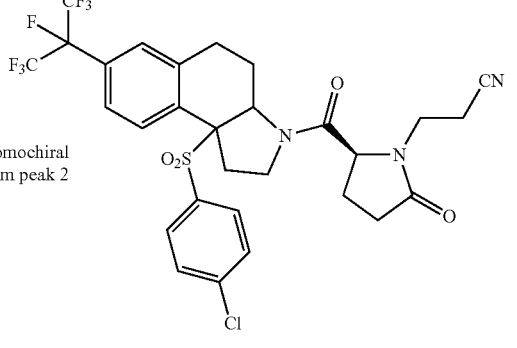 Homochiral from peak 2 | 680.0 | 2.28 | C |
| 883 | 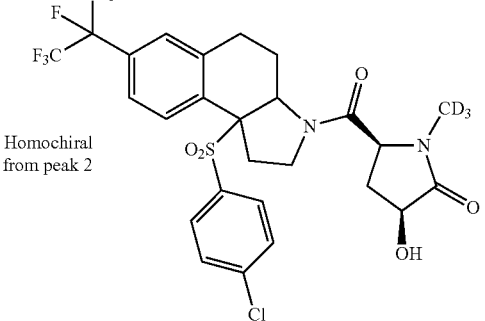 Homochiral from peak 2 | 660.2 | 2.11 | C |

TABLE 19-continued
| Ex. # | Structure | LCMS m/z observed | HPLC t$_R$ (min) | HPLC method |
|---|---|---|---|---|
| 884 | 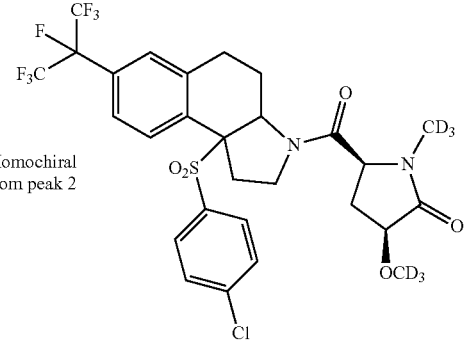 | 677.1 | 2.65 | C |
| 885 | 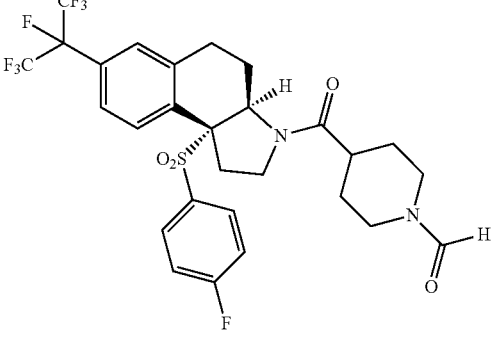 | 639.2 | 2.08 | C |
| 886 | 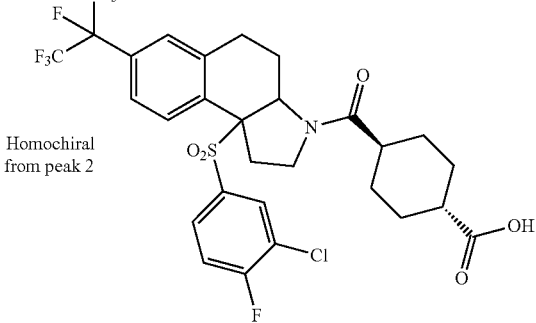 | 688.1 | 1.97 | C |
| 887 | 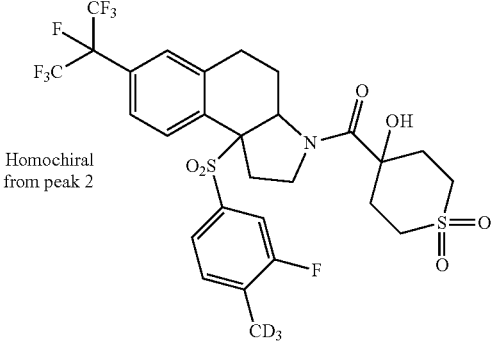 [SMILES: [2H]C([2H])([2H])c1ccc(S(=O)(=O)C23CCN(C(=O)C4(O)CCS(=O)(=O)CC4)C2CCc2cc(C(F)(C(F)(F)F)C(F)(F)F)ccc23)cc1F] | 693.1 | 2.19 | C |

TABLE 19-continued

| Ex. # | Structure | LCMS m/z observed | HPLC $t_R$ (min) | HPLC method |
|---|---|---|---|---|
| 888 | 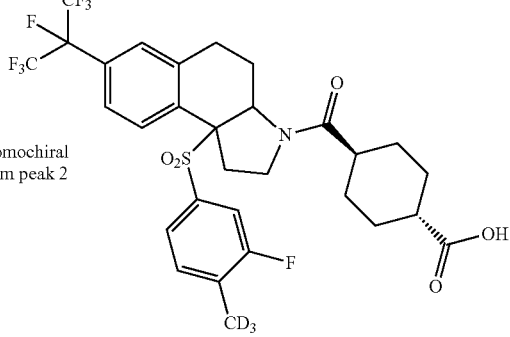 Homochiral from peak 2 | 671.2 | 2.02 | C |
| 889 | 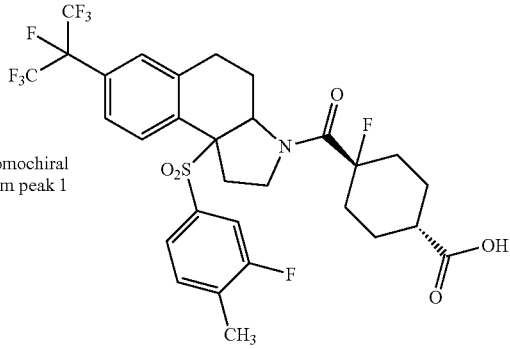 Homochiral from peak 1 | 686.2 | 2.05 | C |

General RORγ SPA Binding Assay

The binding of potential ligands to RORγ is measured by competition with [$^3$H]25-hydroxycholesterol (Perkin Elmer NET674250UC) using a scintillation proximity assay (SPA). The ligand binding domain of human RORγ (A262-S507) with an N-terminal His tag is expressed in E. coli and purified using nickel affinity chromatography. 15 μg/well RORγ (A262-S507) is incubated with test compound at varying concentrations in 3-fold serial dilution, with final concentrations ranging from 16.6 μM to 0.28 nM, for 10 min at rt in PBS buffer (Invitrogen #14190-144) containing 0.5% fatty acid free BSA (Gemini Bio-Products, Cat. #700-107P) and 0.1% glycerol (Sigma Cat # G5516). 10 nM of [$^3$H] 25-hydroxycholesterol is then added, and the reaction is incubated for 10 min. 10 mg/mL of Copper-His Tag-PVT beads (Perkin Elmer cat # RPNQ0095) are added, and the mixture is incubated for 60 min. The reaction is read on a TopCount Microplate scintillation plate reader (Perkin Elmer). The competition data of the test compound over a range of concentrations was plotted as percentage inhibition of radioligand specifically bound in the absence of test compound (percent of total signal). After correcting for non-specific binding, $IC_{50}$ values were determined. The $IC_{50}$ value is defined as the concentration of test compound needed to reduce [$^3$H] 25-hydroxycholesterol specific binding by 50% and is calculated using the four parameter logistic equation to fit the normalized data.

$IC_{50}$ values for compounds of the invention in the RORγ binding assay are provided below.

| Ex. No. | RORγ Binding $IC_{50}$, μM |
|---|---|
| 1 | 0.070 |
| 2 | 0.089 |
| 3 | 0.065 |
| 4 | 0.107 |
| 5 | 0.240 |
| 6 | 0.257 |
| 7 | 1.033 |
| 8 | 4.277 |
| 9 | 5.354 |
| 10 | 8.688 |
| 11 | 0.107 |
| 12 | 0.118 |
| 13 | 0.144 |
| 14 | 0.062 |
| 15 | 0.185 |
| 16 | 0.142 |
| 17 | 0.184 |
| 18 | 0.189 |
| 19 | 0.095 |
| 20 | 0.173 |
| 21 | 0.244 |
| 22 | 0.137 |
| 23 | 0.088 |
| 24 | 0.132 |
| 25 | 0.152 |
| 26 | 0.100 |
| 27 | 0.078 |
| 28 | 0.155 |
| 29 | 0.330 |
| 31 | 0.081 |
| 32 | 0.199 |
| 33 | 0.290 |
| 34 | 0.075 |
| 35 | 0.549 |
| 36 | 0.218 |
| 37 | 2.437 |

| Ex. No. | RORγ Binding IC$_{50}$, μM |
|---|---|
| 38 | 5.608 |
| 39 | 0.024 |
| 40 | 0.062 |
| 41 | 0.336 |
| 42 | 0.186 |
| 43 | 0.421 |
| 44 | 0.138 |
| 45 | 0.138 |
| 46 | 0.111 |
| 47 | 0.130 |
| 48 | 0.030 |
| 49 | 0.059 |
| 50 | 0.053 |
| 51 | 0.085 |
| 52 | 0.073 |
| 53 | 0.121 |
| 54 | 0.060 |
| 55 | 0.060 |
| 56 | 0.183 |
| 57 | 0.049 |
| 58 | 0.085 |
| 59 | 0.103 |
| 60 | 0.071 |
| 61 | 0.454 |
| 62 | 0.033 |
| 63 | 0.021 |
| 65 | 0.058 |
| 66 | 0.054 |
| 67 | 0.024 |
| 68 | 0.023 |
| 69 | 0.036 |
| 70 | 0.068 |
| 71 | 0.031 |
| 72 | 0.028 |
| 73 | 0.078 |
| 74 | 0.018 |
| 75 | 0.043 |
| 76 | 0.045 |
| 77 | 0.033 |
| 78 | 0.042 |
| 79 | 0.033 |
| 80 | 0.019 |
| 81 | 0.046 |
| 82 | 0.067 |
| 83 | 0.039 |
| 84 | 0.033 |
| 85 | 0.016 |
| 86 | 0.041 |
| 87 | 0.039 |
| 88 | 0.056 |
| 89 | 0.079 |
| 90 | 0.076 |
| 91 | 0.028 |
| 92 | 0.062 |
| 93 | 0.071 |
| 94 | 0.020 |
| 95 | 0.050 |
| 96 | 0.118 |
| 97 | 0.146 |
| 98 | 0.133 |
| 99 | 0.084 |
| 100 | 0.175 |
| 101 | 0.163 |
| 102 | 0.124 |
| 103 | 0.108 |
| 104 | 0.263 |
| 105 | 0.230 |
| 106 | 0.055 |
| 107 | 0.051 |
| 108 | 0.050 |
| 109 | 0.074 |
| 110 | 0.093 |
| 111 | 0.058 |
| 112 | 0.090 |
| 113 | 0.118 |
| 114 | 0.073 |
| 115 | 0.026 |
| 116 | 0.026 |
| 117 | 0.056 |
| 118 | 0.071 |
| 119 | 0.058 |
| 120 | 0.083 |
| 121 | 0.051 |
| 122 | 0.127 |
| 123 | 0.043 |
| 124 | 0.188 |
| 125 | 0.052 |
| 126 | 0.109 |
| 127 | 0.044 |
| 128 | 0.082 |
| 129 | 0.042 |
| 130 | 0.094 |
| 131 | 0.079 |
| 132 | 0.097 |
| 133 | 0.076 |
| 134 | 0.048 |
| 135 | 0.110 |
| 136 | 0.044 |
| 137 | 0.671 |
| 138 | 0.065 |
| 139 | 0.347 |
| 140 | 0.061 |
| 141 | 0.096 |
| 142 | 0.050 |
| 143 | 0.129 |
| 144 | 0.066 |
| 145 | 0.074 |
| 146 | 0.064 |
| 147 | 0.250 |
| 148 | 0.442 |
| 149 | 0.265 |
| 150 | 0.011 |
| 151 | 0.056 |
| 152 | 1.631 |
| 153 | 0.056 |
| 154 | 0.058 |
| 155 | 0.040 |
| 156 | 0.193 |
| 157 | 3.562 |
| 158 | 6.188 |
| 159 | 0.082 |
| 160 | 0.196 |
| 161 | 0.049 |
| 162 | 1.130 |
| 163 | 0.113 |
| 164 | 0.231 |
| 165 | 0.031 |
| 166 | 0.043 |
| 167 | 0.656 |
| 168 | 0.184 |
| 169 | 0.140 |
| 170 | 0.068 |
| 171 | 0.256 |
| 172 | 0.185 |
| 173 | 0.147 |
| 174 | 0.060 |
| 175 | 0.077 |
| 176 | 0.070 |
| 177 | 0.099 |
| 178 | 0.079 |
| 179 | 0.132 |
| 180 | 0.035 |
| 181 | 0.121 |
| 182 | 0.072 |
| 183 | 0.037 |
| 184 | 0.031 |
| 185 | 0.021 |
| 186 | 0.042 |
| 187 | 0.043 |
| 188 | 0.063 |
| 189 | 0.041 |
| 190 | 0.020 |
| 191 | 0.009 |
| 192 | 0.021 |

-continued

| Ex. No. | RORγ Binding IC$_{50}$, μM |
|---|---|
| 193 | 0.021 |
| 194 | 0.162 |
| 195 | 0.049 |
| 196 | 0.043 |
| 197 | 0.040 |
| 198 | 0.045 |
| 199 | 0.041 |
| 200 | 0.143 |
| 201 | 0.141 |
| 202 | 0.204 |
| 203 | 0.068 |
| 204 | 0.079 |
| 205 | 0.136 |
| 206 | 0.059 |
| 207 | 0.054 |
| 208 | 0.038 |
| 209 | 0.123 |
| 210 | 0.024 |
| 211 | 0.022 |
| 212 | 0.022 |
| 213 | 0.097 |
| 214 | 0.064 |
| 215 | 0.092 |
| 216 | 0.111 |
| 217 | 0.095 |
| 218 | 0.216 |
| 219 | 0.135 |
| 220 | 0.031 |
| 221 | 0.027 |
| 222 | 0.030 |
| 223 | 0.058 |
| 224 | 0.129 |
| 225 | 0.114 |
| 226 | 0.145 |
| 227 | 0.137 |
| 228 | 0.464 |
| 229 | 0.056 |
| 230 | 0.175 |
| 231 | 0.068 |
| 232 | 0.174 |
| 233 | 0.045 |
| 234 | 0.283 |
| 235 | 0.053 |
| 236 | 0.039 |
| 237 | 0.042 |
| 238 | 0.071 |
| 239 | 0.014 |
| 240 | 0.013 |
| 241 | 0.036 |
| 242 | 0.025 |
| 243 | 0.064 |
| 244 | 0.112 |
| 245 | 0.054 |
| 246 | 0.046 |
| 247 | 0.040 |
| 248 | 0.034 |
| 249 | 0.068 |
| 250 | 0.046 |
| 251 | 0.054 |
| 252 | 0.048 |
| 253 | 3.556 |
| 254 | 0.084 |
| 255 | 0.024 |
| 256 | 0.324 |
| 257 | 0.124 |
| 258 | 0.012 |
| 259 | 0.075 |
| 260 | 0.075 |
| 261 | 0.115 |
| 262 | 0.069 |
| 263 | 0.648 |
| 264 | 0.016 |
| 265 | 3.098 |
| 266 | 1.652 |
| 267 | 0.182 |
| 268 | 0.108 |
| 269 | 0.044 |
| 270 | 3.430 |
| 271 | 0.050 |
| 272 | 0.042 |
| 273 | 0.064 |
| 274 | 0.179 |
| 275 | 0.150 |
| 276 | 0.166 |
| 277 | 0.068 |
| 278 | 5.561 |
| 279 | 0.042 |
| 280 | 0.052 |
| 281 | 0.032 |
| 282 | 0.055 |
| 283 | 0.033 |
| 284 | 0.051 |
| 285 | 0.046 |
| 286 | 0.088 |
| 287 | 0.040 |
| 288 | 0.022 |
| 289 | 0.042 |
| 290 | 0.053 |
| 291 | 0.237 |
| 292 | 0.134 |
| 293 | 0.160 |
| 294 | 0.125 |
| 295 | 0.205 |
| 296 | 0.055 |
| 297 | 0.043 |
| 298 | 0.049 |
| 299 | 0.047 |
| 300 | 0.019 |
| 301 | 0.089 |
| 302 | 0.154 |
| 303 | 0.038 |
| 304 | 0.075 |
| 305 | 0.066 |
| 306 | 0.031 |
| 307 | 0.035 |
| 308 | 0.026 |
| 309 | 0.056 |
| 310 | 0.184 |
| 311 | 0.037 |
| 312 | 0.068 |
| 313 | 0.032 |
| 314 | 0.099 |
| 315 | 0.097 |
| 316 | 0.103 |
| 317 | 0.336 |
| 318 | 0.111 |
| 319 | 0.078 |
| 320 | 0.333 |
| 321 | 0.081 |
| 322 | 0.074 |
| 323 | 0.125 |
| 324 | 0.128 |
| 325 | 0.152 |
| 326 | 0.128 |
| 327 | 0.082 |
| 328 | 0.054 |
| 329 | 0.062 |
| 330 | 0.115 |
| 331 | 0.054 |
| 332 | 0.121 |
| 333 | 0.088 |
| 334 | 0.041 |
| 335 | 0.140 |
| 336 | 0.119 |
| 337 | 0.186 |
| 338 | 0.239 |
| 339 | 0.197 |
| 340 | 0.037 |
| 341 | 0.044 |
| 342 | 0.119 |
| 343 | 0.106 |
| 344 | 0.010 |
| 345 | 0.022 |
| 346 | 0.078 |

| Ex. No. | RORγ Binding IC$_{50}$, μM |
|---|---|
| 347 | 0.005 |
| 348 | 0.034 |
| 349 | 0.601 |
| 350 | 0.240 |
| 351 | 0.085 |
| 352 | 0.096 |
| 353 | 0.953 |
| 354 | 0.230 |
| 355 | 0.285 |
| 356 | 0.266 |
| 357 | 0.104 |
| 358 | 0.136 |
| 359 | 0.130 |
| 360 | 0.077 |
| 361 | 0.046 |
| 362 | 0.047 |
| 363 | 0.012 |
| 364 | 0.020 |
| 365 | 0.035 |
| 366 | 0.035 |
| 367 | 0.062 |
| 368 | 0.024 |
| 369 | 0.035 |
| 370 | 0.035 |
| 371 | 0.109 |
| 372 | 0.161 |
| 373 | 0.055 |
| 374 | 0.058 |
| 375 | 0.060 |
| 376 | 0.255 |
| 377 | 0.628 |
| 378 | 0.072 |
| 379 | 0.055 |
| 380 | 0.036 |
| 381 | 0.089 |
| 382 | 0.038 |
| 383 | 0.032 |
| 384 | 0.150 |
| 385 | 0.780 |
| 386 | 0.215 |
| 387 | 0.025 |
| 388 | 0.024 |
| 389 | 0.050 |
| 390 | 0.027 |
| 391 | 0.013 |
| 392 | 0.056 |
| 393 | 4.411 |
| 394 | 0.060 |
| 395 | 0.058 |
| 396 | 0.029 |
| 397 | 0.090 |
| 398 | 0.040 |
| 399 | 0.048 |
| 400 | 0.087 |
| 401 | 0.134 |
| 402 | 0.638 |
| 403 | 0.046 |
| 404 | 0.034 |
| 405 | 0.012 |
| 406 | 0.031 |
| 407 | 0.021 |
| 408 | 0.073 |
| 409 | 0.143 |
| 410 | 0.047 |
| 411 | 0.016 |
| 412 | 0.034 |
| 413 | 0.015 |
| 414 | 0.020 |
| 415 | 0.014 |
| 416 | 0.135 |
| 417 | 0.178 |
| 418 | 0.128 |
| 419 | 1.106 |
| 420 | 0.732 |
| 421 | 0.164 |
| 422 | 0.087 |
| 423 | 0.046 |
| 424 | 0.084 |
| 425 | 0.055 |
| 426 | 0.956 |
| 427 | 0.272 |
| 428 | 0.050 |
| 429 | 0.173 |
| 430 | 0.077 |
| 431 | 0.044 |
| 432 | 0.052 |
| 433 | 0.063 |
| 434 | 0.086 |
| 435 | 0.188 |
| 436 | 0.049 |
| 437 | 0.051 |
| 438 | 0.073 |
| 439 | 0.214 |
| 440 | 0.072 |
| 441 | 0.159 |
| 442 | 0.145 |
| 443 | 0.048 |
| 444 | 0.045 |
| 445 | 0.070 |
| 446 | 0.143 |
| 447 | 0.014 |
| 448 | 0.026 |
| 449 | 0.030 |
| 450 | 0.032 |
| 451 | 0.177 |
| 452 | 0.153 |
| 453 | 0.443 |
| 454 | 0.718 |
| 455 | 0.083 |
| 456 | 0.027 |
| 457 | 0.076 |
| 458 | 0.101 |
| 459 | 0.064 |
| 460 | 0.030 |
| 461 | 0.068 |
| 462 | 0.059 |
| 463 | 0.037 |
| 464 | 0.023 |
| 465 | 0.053 |
| 466 | 0.028 |
| 467 | 0.050 |
| 468 | 0.022 |
| 469 | 0.021 |
| 470 | 0.025 |
| 471 | 0.030 |
| 472 | 0.025 |
| 473 | 0.017 |
| 474 | 0.026 |
| 475 | 0.019 |
| 476 | 0.023 |
| 477 | 0.018 |
| 478 | 0.028 |
| 479 | 0.035 |
| 482 | 0.085 |
| 483 | 0.092 |
| 484 | 0.098 |
| 485 | 0.036 |
| 486 | 0.051 |
| 487 | 0.283 |
| 488 | 0.145 |
| 489 | 0.438 |
| 490 | 0.195 |
| 491 | 0.121 |
| 492 | 0.052 |
| 493 | 0.103 |
| 494 | 0.023 |
| 495 | 0.064 |
| 496 | 0.077 |
| 497 | 0.064 |
| 498 | 0.042 |
| 499 | 0.026 |
| 500 | 0.053 |
| 501 | 0.037 |
| 502 | 0.020 |

| Ex. No. | RORγ Binding IC$_{50}$, μM | Ex. No. | RORγ Binding IC$_{50}$, μM |
|---|---|---|---|
| 503 | 0.083 | 580 | 1.518 |
| 504 | 0.057 | 581 | 0.098 |
| 505 | 0.088 | 582 | 6.891 |
| 506 | 0.223 | 583 | 2.798 |
| 507 | 0.135 | 584 | 13.826 |
| 508 | 2.830 | 585 | 8.537 |
| 509 | 0.255 | 586 | 0.079 |
| 510 | 0.079 | 587 | 0.158 |
| 511 | 0.041 | 588 | 0.894 |
| 512 | 0.022 | 589 | 0.771 |
| 513 | 6.561 | 590 | 0.064 |
| 514 | 0.181 | 591 | 0.202 |
| 515 | 0.056 | 592 | 0.145 |
| 516 | 0.015 | 593 | 0.130 |
| 517 | 0.017 | 594 | 0.245 |
| 518 | 0.047 | 595 | 0.825 |
| 519 | 0.041 | 596 | 0.120 |
| 520 | 0.057 | 597 | 0.333 |
| 521 | 0.026 | 598 | 0.166 |
| 522 | 0.018 | 599 | 0.311 |
| 523 | 0.045 | 600 | 0.197 |
| 524 | 0.071 | 601 | 0.231 |
| 525 | 0.319 | 602 | 0.100 |
| 526 | 0.098 | 603 | 0.267 |
| 527 | 0.398 | 604 | 0.319 |
| 528 | 0.225 | 605 | 0.397 |
| 529 | 0.199 | 606 | 0.244 |
| 530 | 0.195 | 607 | 0.342 |
| 531 | 3.665 | 608 | 0.286 |
| 532 | 0.300 | 609 | 0.117 |
| 533 | 0.229 | 610 | 0.185 |
| 534 | 0.171 | 611 | 0.610 |
| 535 | 0.255 | 612 | 0.360 |
| 536 | 0.126 | 613 | 0.660 |
| 537 | 0.242 | 614 | 0.190 |
| 538 | 0.493 | 615 | 0.125 |
| 539 | 0.197 | 616 | 1.364 |
| 540 | 0.251 | 617 | 0.192 |
| 541 | 0.093 | 618 | 0.392 |
| 542 | 0.074 | 619 | 0.271 |
| 543 | 0.029 | 620 | 0.493 |
| 544 | 0.714 | 621 | 0.308 |
| 545 | 0.056 | 622 | 4.508 |
| 546 | 0.105 | 623 | 6.586 |
| 547 | 9.193 | 624 | 1.754 |
| 548 | 0.336 | 625 | 0.425 |
| 549 | 7.576 | 626 | 0.897 |
| 550 | 0.178 | 627 | 1.450 |
| 551 | 0.166 | 628 | 0.744 |
| 552 | 0.042 | 629 | 3.545 |
| 553 | 0.076 | 630 | 6.753 |
| 554 | 0.168 | 631 | 1.701 |
| 555 | 0.595 | 632 | 5.779 |
| 556 | 0.086 | 633 | 0.249 |
| 557 | 0.128 | 634 | 5.967 |
| 558 | 7.982 | 635 | 4.957 |
| 559 | 1.006 | 636 | 0.171 |
| 560 | 0.082 | 637 | 0.092 |
| 561 | 0.110 | 638 | 0.070 |
| 562 | 0.224 | 639 | 0.023 |
| 563 | 1.935 | 640 | 0.051 |
| 564 | 0.275 | 641 | 0.083 |
| 565 | 0.123 | 642 | 0.156 |
| 566 | 0.643 | 643 | 0.161 |
| 567 | 0.444 | 644 | 0.034 |
| 568 | 0.489 | 645 | 0.022 |
| 569 | 0.047 | 646 | 0.030 |
| 570 | 0.596 | 647 | 0.037 |
| 571 | 1.352 | 648 | 0.031 |
| 572 | 5.920 | 649 | 0.032 |
| 573 | 1.393 | 650 | 0.086 |
| 574 | 0.384 | 651 | 0.278 |
| 575 | 0.416 | 652 | 0.115 |
| 576 | 0.273 | 653 | 0.064 |
| 577 | 0.011 | 654 | 4.676 |
| 578 | 4.563 | 655 | 1.175 |
| 579 | 0.108 | 656 | 1.380 |

| Ex. No. | RORγ Binding IC$_{50}$, μM |
|---|---|
| 657 | 0.038 |
| 658 | 1.269 |
| 659 | 0.340 |
| 660 | 0.174 |
| 661 | 0.010 |
| 662 | 0.546 |
| 663 | 1.613 |
| 664 | 0.023 |
| 665 | 0.015 |
| 666 | 0.048 |
| 667 | 0.017 |
| 668 | 0.047 |
| 669 | 0.039 |
| 670 | 0.024 |
| 671 | 0.032 |
| 672 | 0.065 |
| 673 | 0.039 |
| 674 | 0.051 |
| 675 | 0.057 |
| 676 | 0.048 |
| 677 | 0.079 |
| 678 | 0.105 |
| 679 | 0.231 |
| 680 | 0.151 |
| 681 | 0.193 |
| 682 | 0.159 |
| 683 | 0.210 |
| 684 | 0.243 |
| 685 | 0.028 |
| 686 | 0.064 |
| 687 | 7.301 |
| 688 | 0.057 |
| 689 | 0.040 |
| 690 | 0.044 |
| 691 | 0.143 |
| 692 | 0.004 |
| 693 | 0.625 |
| 694 | 0.217 |
| 695 | 0.225 |
| 696 | 0.218 |
| 697 | 0.068 |
| 698 | 0.117 |
| 699 | 0.020 |
| 700 | 0.276 |
| 701 | 0.100 |
| 702 | 0.051 |
| 703 | 1.883 |
| 704 | 2.125 |
| 705 | 1.470 |
| 706 | 0.161 |
| 707 | 0.043 |
| 708 | 0.015 |
| 709 | 0.031 |
| 710 | 0.030 |
| 711 | 0.026 |
| 712 | 0.027 |
| 713 | 0.048 |
| 714 | 0.082 |
| 715 | 0.030 |
| 716 | 0.030 |
| 717 | 0.070 |
| 718 | 0.076 |
| 719 | 0.295 |
| 720 | 0.428 |
| 721 | 0.052 |
| 722 | 0.073 |
| 723 | 0.136 |
| 724 | 0.142 |
| 725 | 0.095 |
| 726 | 0.114 |
| 727 | 0.077 |
| 728 | 0.077 |
| 729 | 0.052 |
| 730 | 0.082 |
| 731 | 0.119 |
| 732 | 0.044 |
| 733 | 0.332 |
| 734 | 0.131 |
| 735 | 0.103 |
| 736 | 0.078 |
| 737 | 0.368 |
| 738 | 0.139 |
| 739 | 0.196 |
| 740 | 0.561 |
| 741 | 0.284 |
| 742 | 0.064 |
| 743 | 0.084 |
| 744 | 0.084 |
| 745 | 0.150 |
| 746 | 0.147 |
| 747 | 0.300 |
| 748 | 0.542 |
| 749 | 0.138 |
| 750 | 0.099 |
| 751 | 0.070 |
| 752 | 0.072 |
| 753 | 0.034 |
| 754 | 0.075 |
| 755 | 0.170 |
| 756 | 0.054 |
| 757 | 0.048 |
| 758 | 0.087 |
| 759 | 0.107 |
| 760 | 0.119 |
| 761 | 0.112 |
| 762 | 0.309 |
| 763 | 0.109 |
| 764 | 0.687 |
| 765 | 0.208 |
| 766 | 1.348 |
| 767 | 0.091 |
| 768 | 0.291 |
| 769 | 0.117 |
| 770 | 9.197 |
| 771 | 0.157 |
| 772 | 0.609 |
| 773 | 1.801 |
| 774 | 0.679 |
| 775 | 0.534 |
| 776 | 1.490 |
| 777 | 0.493 |
| 778 | 0.171 |
| 779 | 0.283 |
| 780 | 0.097 |
| 781 | 0.913 |
| 782 | 0.148 |
| 783 | 0.507 |
| 784 | 0.154 |
| 785 | 3.199 |
| 786 | 1.441 |
| 787 | 4.311 |
| 788 | 0.098 |
| 789 | 1.866 |
| 790 | 0.041 |
| 791 | 0.078 |
| 792 | 0.186 |
| 793 | 0.398 |
| 794 | 0.566 |
| 795 | 2.382 |
| 796 | 0.100 |
| 797 | 0.136 |
| 798 | 0.167 |
| 799 | 0.151 |
| 800 | 0.612 |
| 801 | 0.023 |
| 802 | 0.045 |
| 803 | 0.073 |
| 804 | 0.088 |
| 805 | 0.088 |
| 806 | 0.145 |
| 807 | 0.283 |
| 808 | 0.107 |
| 809 | 0.025 |
| 810 | 0.050 |

| Ex. No. | RORγ Binding IC$_{50}$, μM |
|---|---|
| 811 | 0.023 |
| 812 | 0.195 |
| 813 | 0.115 |
| 814 | 0.125 |
| 815 | 0.018 |
| 816 | 0.105 |
| 817 | 0.601 |
| 818 | 0.848 |
| 819 | 0.029 |
| 820 | 0.047 |
| 821 | 0.018 |
| 822 | 0.049 |
| 823 | 0.039 |
| 824 | 0.142 |
| 825 | 0.489 |
| 826 | 1.086 |
| 827 | 0.078 |
| 828 | 0.008 |
| 829 | 0.047 |
| 830 | 0.032 |
| 831 | 0.093 |
| 832 | 0.209 |
| 833 | 0.074 |
| 834 | 0.172 |
| 835 | 0.083 |
| 836 | 0.013 |
| 837 | 0.056 |
| 838 | 0.075 |
| 839 | 0.416 |
| 840 | 0.082 |
| 841 | 0.215 |
| 842 | 0.053 |
| 843 | 0.092 |
| 844 | 0.097 |
| 845 | 0.205 |
| 846 | 0.057 |
| 847 | 0.099 |
| 848 | 3.306 |
| 849 | 0.616 |
| 850 | 0.274 |
| 851 | 0.357 |
| 852 | 0.317 |
| 853 | 0.176 |
| 854 | 0.110 |
| 855 | 0.092 |
| 856 | 4.434 |
| 857 | 0.229 |
| 858 | 0.305 |
| 859 | 0.114 |
| 860 | 6.301 |
| 861 | 0.296 |
| 862 | 0.158 |
| 863 | 0.079 |
| 864 | 0.131 |
| 865 | 0.086 |
| 866 | 0.547 |
| 867 | 0.318 |
| 868 | 0.278 |
| 869 | 0.292 |
| 870 | 0.162 |
| 871 | 0.215 |
| 872 | 0.226 |
| 873 | 0.193 |
| 874 | 0.423 |
| 875 | 0.169 |
| 876 | 0.158 |
| 877 | 0.300 |
| 878 | 0.172 |
| 879 | 0.256 |
| 880 | 0.382 |
| 881 | 0.191 |
| 882 | 0.135 |
| 883 | 0.201 |
| 884 | 0.477 |
| 885 | 0.167 |
What is claimed is:
1. A method of treating inflammatory bowel disease, Crohn's disease and ulcerative colitis in a subject, the method comprising administering to the subject a therapeutically-effective amount of a compound of the formula
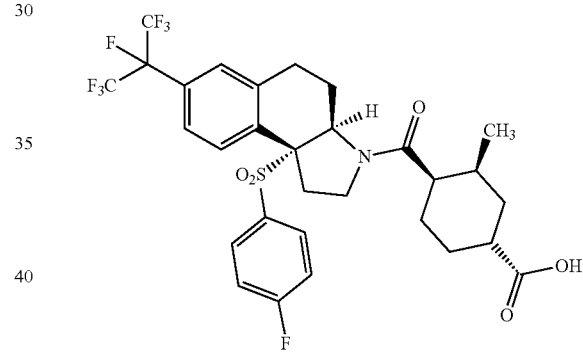
or a pharmaceutically acceptable salt, tautomer or stereoisomer thereof.
* * * * *